United States Patent
Hung et al.

(10) Patent No.: US 9,034,880 B2
(45) Date of Patent: May 19, 2015

(54) TETRACYCLIC COMPOUNDS

(71) Applicant: Medivation Technologies, Inc., San Francisco, CA (US)

(72) Inventors: David T. Hung, Redwood City, CA (US); Andrew Asher Protter, Palo Alto, CA (US); Rajendra Parasmal Jain, Pune (IN); Sundeep Dugar, San Jose, CA (US); Sarvajit Chakravarty, Mountain View, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 0 days.

(21) Appl. No.: 13/791,750

(22) Filed: Mar. 8, 2013

(65) Prior Publication Data

US 2014/0194414 A1    Jul. 10, 2014

Related U.S. Application Data

(63) Continuation of application No. 13/679,873, filed on Nov. 16, 2012, which is a continuation of application No. 12/259,234, filed on Oct. 27, 2008, now Pat. No. 8,338,408.

(Continued)

(30) Foreign Application Priority Data

Oct. 25, 2007   (RU) .................................. 2007139634

(51) Int. Cl.
*C07D 471/04*   (2006.01)
*A61K 31/506*   (2006.01)
(Continued)

(52) U.S. Cl.
CPC .......... *C07D 471/04* (2013.01); *A61K 31/5377* (2013.01); *A61K 31/4545* (2013.01); *C07D 471/14* (2013.01); *A61K 31/437* (2013.01); *A61K 31/4375* (2013.01);
(Continued)

(58) Field of Classification Search
None
See application file for complete search history.

(56) References Cited

U.S. PATENT DOCUMENTS 3,409,628 A   11/1968 Berger et al.
3,484,449 A   12/1969 Berger et al.
(Continued)

FOREIGN PATENT DOCUMENTS

CH   494 234       7/1970
EP   0 353 983 A2  2/1990
(Continued)

OTHER PUBLICATIONS

Adib, M. et al. (Apr. 24, 2006, e-pub. Mar. 10, 2006). "Microwave-Assisted Efficient, One-Pot, Three-Component Synthesis of 3,5-Disubstituted 1,2,4-Ozadiazoles Under Solvent-Free Conditions," *Tetrahedron Letters* 47(17):2965-2967.

(Continued)

*Primary Examiner* — Alicia L Otton
(74) *Attorney, Agent, or Firm* — Morrison & Foerster LLP

(57) ABSTRACT

This disclosure relates to new tetracyclic compounds that may be used to modulate a histamine receptor in an individual. The compounds in one embodiment are tetracyclic [4,3-b]indoles. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder.

42 Claims, 24 Drawing Sheets

Related U.S. Application Data

(60) Provisional application No. 60/982,678, filed on Oct. 25, 2007, provisional application No. 60/982,679, filed on Oct. 25, 2007, provisional application No. 61/062,331, filed on Jan. 25, 2008, provisional application No. 61/062,332, filed on Jan. 25, 2008, provisional application No. 61/033,754, filed on Mar. 4, 2008, provisional application No. 61/033,757, filed on Mar. 4, 2008.

(51) Int. Cl.
| | |
|---|---|
| A61K 31/437 | (2006.01) |
| A61K 31/5377 | (2006.01) |
| A61K 31/4545 | (2006.01) |
| C07D 471/14 | (2006.01) |
| A61K 31/4375 | (2006.01) |
| A61K 31/496 | (2006.01) |
| A61K 31/4985 | (2006.01) |
| A61K 31/519 | (2006.01) |
| A61K 31/541 | (2006.01) |
| C07D 471/10 | (2006.01) |

(52) U.S. Cl.
CPC .......... *A61K 31/496* (2013.01); *A61K 31/4985* (2013.01); *A61K 31/506* (2013.01); *A61K 31/519* (2013.01); *A61K 31/541* (2013.01); *C07D 471/10* (2013.01)

(56) References Cited

U.S. PATENT DOCUMENTS

| | | | |
|---|---|---|---|
| 3,502,688 | A | 3/1970 | Berger et al. |
| 3,646,045 | A | 2/1972 | Berger et al. |
| 4,754,038 | A | 6/1988 | Abou-Gharbia |
| 6,187,785 | B1 | 2/2001 | Zefirov et al. |
| 6,849,640 | B2 | 2/2005 | Ennis et al. |
| 7,071,206 | B2 | 7/2006 | Zefirov et al. |
| 8,338,408 | B2 | 12/2012 | Hung et al. |
| 8,338,447 | B2 | 12/2012 | Hung et al. |
| 8,546,381 | B2 | 10/2013 | Hung et al. |
| 8,569,287 | B2 | 10/2013 | Hung et al. |
| 8,741,919 | B2 | 6/2014 | Jain et al. |
| 8,791,132 | B2 | 7/2014 | Protter et al. |
| 2004/0014748 | A1 | 1/2004 | Grutzmann et al. |
| 2010/0022580 | A1 | 1/2010 | Hung et al. |
| 2010/0120792 | A1 | 5/2010 | Ivaschenko et al. |
| 2010/0216814 | A1 | 8/2010 | Hung et al. |
| 2010/0286188 | A1 | 11/2010 | Bachurin et al. |
| 2011/0046368 | A1 | 2/2011 | Ivaschenko et al. |
| 2011/0237582 | A1 | 9/2011 | Jain et al. |
| 2011/0245272 | A1 | 10/2011 | Jain et al. |
| 2012/0101121 | A1 | 4/2012 | Bachurin et al. |
| 2012/0136008 | A1 | 5/2012 | Jain et al. |
| 2013/0053367 | A1 | 2/2013 | Protter et al. |
| 2013/0079352 | A1 | 3/2013 | Hung et al. |
| 2013/0123277 | A1 | 5/2013 | Jain et al. |
| 2013/0131054 | A1 | 5/2013 | Hung et al. |
| 2013/0131077 | A1 | 5/2013 | Hung et al. |
| 2013/0137705 | A1 | 5/2013 | Jain et al. |
| 2013/0172320 | A1 | 7/2013 | Chakravarty et al. |
| 2013/0172366 | A1 | 7/2013 | Jain et al. |
| 2013/0184269 | A1 | 7/2013 | Hung et al. |
| 2013/0184303 | A1 | 7/2013 | Jain et al. |
| 2013/0184304 | A1 | 7/2013 | Jain et al. |
| 2013/0184306 | A1 | 7/2013 | Hung et al. |
| 2013/0190293 | A1 | 7/2013 | Chakravarty et al. |
| 2013/0190294 | A1 | 7/2013 | Protter et al. |
| 2013/0190295 | A1 | 7/2013 | Hung et al. |
| 2013/0190303 | A1 | 7/2013 | Hung et al. |
| 2013/0190304 | A1 | 7/2013 | Hung et al. |
| 2013/0190308 | A1 | 7/2013 | Jain et al. |
| 2013/0190322 | A1 | 7/2013 | Hung et al. |
| 2013/0190323 | A1 | 7/2013 | Hung et al. |
| 2013/0190328 | A1 | 7/2013 | Jain et al. |
| 2013/0190331 | A1 | 7/2013 | Jain et al. |
| 2013/0190344 | A1 | 7/2013 | Jain et al. |
| 2013/0190347 | A1 | 7/2013 | Hung et al. |
| 2013/0190348 | A1 | 7/2013 | Hung et al. |
| 2013/0190359 | A1 | 7/2013 | Jain et al. |
| 2013/0203746 | A1 | 8/2013 | Hung et al. |
| 2013/0210803 | A1 | 8/2013 | Chakravarty et al. |
| 2013/0217675 | A1 | 8/2013 | Chakravarty et al. |
| 2013/0225558 | A1 | 8/2013 | Chakravarty et al. |
| 2014/0024643 | A1 | 1/2014 | Hung et al. |
| 2014/0088086 | A1 | 3/2014 | Protter et al. |
| 2014/0088087 | A1 | 3/2014 | Hung et al. |
| 2014/0155384 | A1 | 6/2014 | Protter et al. |
| 2014/0206711 | A1 | 7/2014 | Chakravarty et al. |
| 2014/0213577 | A1 | 7/2014 | Hung et al. |

FOREIGN PATENT DOCUMENTS

| | | |
|---|---|---|
| EP | 0 353 983 A3 | 2/1990 |
| EP | 0 353 983 B1 | 2/1990 |
| EP | 2 145 887 A2 | 1/2010 |
| GB | 1253742 | 11/1971 |
| JP | 50-017480 | 2/1975 |
| JP | 9-216882 A | 8/1997 |
| WO | WO-97/15225 A1 | 5/1997 |
| WO | WO-01/97787 A2 | 12/2001 |
| WO | WO-01/97787 A3 | 12/2001 |
| WO | WO-2005/005951 A2 | 6/2005 |
| WO | WO-2005/005951 A3 | 6/2005 |
| WO | WO-2006/064355 A2 | 6/2006 |
| WO | WO-2006/064355 A3 | 6/2006 |
| WO | WO-2007/016353 A2 | 2/2007 |
| WO | WO-2007/016353 A3 | 2/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/038764 A1 | 3/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/051501 A1 | 5/2010 |
| WO | WO-2010/051503 A1 | 5/2010 |
| WO | WO-2010/127177 A1 | 11/2010 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |

(56) References Cited

FOREIGN PATENT DOCUMENTS

| WO | WO-2011/103430 A1 | 8/2011 |
|---|---|---|
| WO | WO-2011/103433 A1 | 8/2011 |
| WO | WO 2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112965 A1 | 8/2012 |
| WO | WO-2012/112966 A1 | 8/2012 |
| WO | WO 2012/154261 A1 | 11/2012 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Bartolini, L. et al. (1996). "Aniracetam Restores Object Recognition Impaired by Age, Scopolamine, and Nucleus Basalis Lesions," *Pharmacology Biochemistry Behavior* 53(2):277-283.

Berge, S.M. et al. (Jan. 1977). "Pharmaceutical Salts," *J. Pharm. Sci.* 66(1):1-19.

Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.

Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.

Brown, C.M. et al. (1990). "$\alpha_2$-Adrenoceptor Subtypes and Imidazoline-Like Binding Sites in the Rat Brain," *Br. J. Pharmacol.* 99:803-809.

Bubber, P. et al. (May 2005). "Mitochondrial Abnormalities in Alzheimer Brain: Mechanistic Implications," *Ann Neurol.* 57(5):695-703.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Dezi, C. (2007). "Modeling of 5-HT$_{2A}$ and 5-HT$_{2C}$ Receptors and of Their Complexes with Actual and Potential Antipsychotic Drugs," PhD Thesis, Pompeu Fabra University pp. 1-239.

Dodart, J.C et al. (Mar. 24, 1997). "Scopolamine-Induced Deficits in a Two-Trial Object Recognition Task in Mice," *NeuroReport* 8(5):1173-1178.

Ennaceur, A. et al. (1988). "A New One-Trial Test for Neurobiological Studies of Memory in Rats. 1: Behavioral Data," *Behav. Brain. Res.* 31:47-59.

Extended European Search Report mailed on Nov. 16, 2012 for European Patent Application No. EP 10770380.3, filed on Nov. 10, 2011, 23 pages.

Extended European Search Report mailed on Nov. 16, 2012 for European Patent Application No. EP 10808471.6, filed on Apr. 29, 2010, 15 pages.

Final Office Action mailed on Sep. 23, 2013, for U.S. Appl. No. 13/791,862, filed Mar. 8, 2013, 10 pages.

Final Office Action mailed on Oct. 25, 2013, for U.S. Appl. No. 13/318,124, filed Jan. 10, 2012, 6 pages.

Final Office Action mailed on Jul. 28, 2014, for U.S. Appl. No. 13/679,873, filed Nov. 16, 2012, 8 pages.

Gaffan, D. (1992). "Amnesia for Complex Naturalistic Scenes and for Objects Following Fornix Transection in the Rhesus Monkey," *Eur. J. Neurosci.* 4(5):381-388.

Gage, P.W. et al. (Jan. 1980). "Lifetime and Conductance of Acetylcholine-Activated Channels in Normal and Denervated Toad Sartorius Muscle," *J. Physiol.* 298:525-538.

García-Sáinz, J.A. et al. (Jul. 31, 1992). "Species Heterogeneity of Hepatic $\alpha_1$-Adrenoceptors: $\alpha 1_A$-, $\alpha 1_B$- and $\alpha 1_C$-Subtypes," *Biochemical and Biophysical Research Communications* 186(2):760-767.

Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$^{35}$S]GTP$\gamma$S Binding Assays," *Naunyn-Schmiedeberg's Archives of Pharmacology* 361:498-504.

Grandy, D.K. et al. (Dec. 1989). "Cloning of the cDNA and Gene for a Human D$_2$ Dopamine Receptor," *Proc. Natl. Acad. Sci. USA* 86:9762-9766.

Grossman, C.J. et al. (1993). "Development of a Radioligand Binding Assay for 5-HT$_4$ Receptors in Guinea-Pig and Rat Brain," *Br. J. Pharmacol.* 109:618-624.

Hamill, O.P. et al. (1981). "Improved Patch-Clamp Techniques for High-Resolution Current Recording from Cells and Cell-Free Membrane Patches," *Pflügers Arch* 391:85-100.

Hardy, J. (1996). "New Insights Into the Genetics of Alzheimer's Disease," *Annals of Medicine* 28:255-258.

Hardy, J. (1997). "Amyloid, the Presenilins and Alzheimer's Disease," *Trends Neurosci.* 20(4):154-159.

Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.

Holenz, J. et al. (Apr. 1, 2006). "Medicinal Chemistry Strategies to 5-HT$_6$ Receptor Ligands as Potential Cognitive Enhancers and Antiobesity Agents," *Drug Discovery Today* 11(7-8): 283-299.

Hoyer, D. et al. (1985). "Characterization of the 5-HT$_{1B}$ Recognition Site in Rat Brain: Binding Studies with (−)[$^{125}$I] Iodocyanopindolol," *European Journal of Pharmacology* 118:1-12.

International Search Report mailed on Feb. 13, 2009, for PCT Patent Application No. PCT/US2008/081390, filed on Oct. 27, 2008, 5 pages.

International Search Report mailed on Jul. 13, 2010, for PCT Application No. PCT/US2010/033053, filed on Apr. 29, 2010, 2 pages.

International Search Report mailed on Nov. 12, 2010, for PCT Application No. PCT/US2010/033055, filed on Apr. 29, 2010, 2 pages.

Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.

Jerman, J.C. et al. (2001). "Pharmacological Characterisation of Human 5-HT$_2$ Receptor Subtypes," *European Journal of Pharmacology* 414:23-30.

Kane, J.M. et al. (Jan. 7, 1994). "5-Aryl-3-(Alkylthio)-4H-1,2,4-Triazoles as Selective Antagonists of Strychnine-Induced Convulsions and Potential Antispastic Agents," *Journal of Medicinal Chemistry* 37(1):125-132.

Kaneda, M. et al. (Apr. 1988). "Mechanical and Enzymatic Isolation of Mammalian CNS Neurons," *Neurosci. Res.* 5(4):299-315.

Kenny, B.A. et al. (1995). "Characterization of an $\alpha 1_D$-Adrenoceptor Mediating the Contractile Response of Rat Aorta to Noradrenaline," *British Journal of Pharmacology* 115:981-986.

Khorana, N. et al. (2003). "$\gamma$-Carbolines: Binding at 5-HT$_{5A}$ Serotonin Receptors," *Bioorganic & Medicinal Chemistry* 11:717-722.

Kohen, R. et al. (1996). "Cloning, Characterization and Chromosomal Localization of a Human 5-HT$_6$ Serotonin Receptor," *J. Neurochem.* 66(1):47-56.

Kolb, B. et al. (Nov./Dec. 1994). "Dissociation of the Medial Prefrontal, Posterior Parietal, and Posterior Temporal Cortex for Spatial Navigation and Recognition Memory in the Rat," *Cereb. Cortex* 4(6):664-680.

Lohr, J.B. et al. (Aug. 28, 1995). "Motor Asymmetry, a Neurobiologic Abnormality in the Major Psychoses," *Psychiatry Research* 57(3):279-282.

Martin, G.R. (1994). "Receptors for 5-Hydroxytryptamine: Current Perspectives on Classification and Nomenclature," *Neuropharmacology* 33(3/4):261-273.

May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *J Pharmacol Exp Ther* 306(1):301-309.

(56) References Cited

OTHER PUBLICATIONS

Messier, C. (Mar. 1997). "Object Recognition in Mice: Improvement of Memory by Glucose," *Neurobiol. Learn Mem.* 67(2):172-175.
Michel, A.D. et al. (1989). "Identification of a Single $\alpha_1$-Adrenoceptor Corresponding to the $\alpha 1_A$-Subtype in Rat Submaxillary Gland," *Br. J. Pharmacol.* 98:883-889.
Miller, K et al. (1992). "Membrane-Bound and Solubilized Brain $5HT_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive $H_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Mooradian, A. et al. (Apr. 1977). "3-Aminotetrahydrocarbazoles as a New Series of Central Nervous System Agents," *Journal Medicinal Chemistry* 20(4):487-492.
Nishio, T. et al. (Aug. 15, 2001). "Thionation of ω-Acylamino Ketones with Lawesson's Reagent: Convenient Synthesis of 1,3-Thiazoles and 4*H*-1,3-Thiazines," *Helvetica Chimica Acta* 84(8):2347-2354.
Non-Final Office Action mailed on Apr. 25, 2014, for U.S. Appl. No. 13/725,909, filed Dec. 21, 2012, 27 pages.
Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.
Piercey, M.F. et al. (1988). "Dramatic Limbic and Cortical Effects Mediated by High Affinity PCP Receptors," *Life Sciences* 43(4):379-385.
Pittenger, C. et al. (Apr. 25, 2002). "Reversible Inhibition of CREB/ATF Transcription Factors in Region CA1 of the Dorsal Hippocampus Disrupts Hippocampus-Dependent Spatial Memory," *Neuron.* 34(3):447-462.
Prichep, L.S. et al. (1994). "Quantitative EEG Correlates of Cognitive Deterioration in the Elderly," *Neurobiology of Aging* 15(1):85-90.
Reddy, P.H. et al. (2005, e-pub. Apr. 19, 2005). "Are Mitochondria Critical in the Pathogenesis of Alzheimer's Disease?" *Brain Res Rev.* 49(3):618-632.
Rees, S. et al. (Oct. 11, 1994). "Cloning and Characterisation of the Human 5-HT$_{5A}$ Serotonin Receptor," *FEBS Letters* 355:242-246.
Reisberg, B. et al. (Sep. 1982). "The Global Deterioration Scale for Assessment of Primary Degenerative Dementia," *Am. J. Psychiatry* 139(9):1136-1139.
Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.
Roth, B.L. et al. (1995). "The Role of Serotonin in Schizophrenia," Chapter 102 in *Psychopharmacology—The Fourth Generation of Progress*, Raven Press, Ltd., New York, pp. 1215-1227.
Ruat, M. et al. (Mar. 1990). "Reversible and Irreversible Labeling and Autoradiographic Localization of the Cerebral Histamine $H_2$ Receptor Using [$^{125}$I]Iodinated Probes," *Proc. Natl. Acad. Sci. USA* 87(5):1658-1662.
Ryabinin, A.E. et al. (Jan.-Feb. 2002). "Effects of Acute Alcohol Administration on Object Recognition Learning in C57BL/6J Mice," *Pharmacol. Biochem. Behav.* 71(1-2):307-312.

Sargolini, F. et al. (Jan. 22, 2003). "Effects of Intra-Accumbens Focal Administrations of Glutamate Antagonists on Object Recognition Memory in Mice," *Behav. Brain. Res.* 138(2):153-163.
Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.
Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.
Seefeld, M.A. et al. (2001). "Inhibitors of Bacterial Enoyl Acyl Carrier Protein Reductase (FabI): 2,9-Disubstituted 1,2,3,4-Tetrahydropyrido[3,4-*b*]Indoles as Potential Antibacterial Agents," *Bioorganic & Medicinal Chemistry Letters* 11:2241-2244.
Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.
Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.
Sik, A. et al. (Dec. 2003). "Performance of Different Mouse Strains in an Object Recognition Task," *Behav. Brain Res.* 147(1-2):49-54.
Steckler, T. et al. (Feb. 1998). "Recognition Memory in Rats—I. Concepts and Classification," *Prog. Neurobiol.* 54(3):289-311.
Steckler, T. et al. (Feb. 1998). "Recognition Memory in Rats—II. Neuroanatomical Substrates," *Prog. Neurobiol.* 54(3):313-332.
Swerdlow, R.H. et al. (2002). "Mitochondria in Alzheimer's Disease," *International Review of Neurobiology* 53:341-385.
Tanzi, R.E. et al. (1996). "The Gene Defects Responsible for Familial Alzheimer's Disease," *Neurobiology of Disease* 3:159-168.
Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.
Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.
Wang, X-C. et al. (2005, e-pub. May 10, 2005). "Liquid-Phase Traceless Synthesis of 3,5-Disubstituted 1,2,4-Triazoles," *Synlett* 17:2595-2598.
Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.
Wolf, W.A. et al. (1997). "The Serotonin 5-HT$_{2C}$ Receptor is a Prominent Serotonin Receptor in Basal Ganglia: Evidence from Functional Studies on Serotonin-Mediated Phosphoinositide Hydrolysis," *Journal of Neurochemistry* 69(4):1449-1458.
Written Opinion of the International Searching Authority mailed on Feb. 13, 2009, for PCT Patent Application No. PCT/US2008/081390, filed on Oct. 27, 2008, 8 pages.
Written Opinion mailed on Jul. 13, 2010, for PCT Patent Application No. PCT/US2010/033053, filed on Apr. 29, 2010, 7 pages.
Written Opinion mailed on Nov. 12, 2010, for PCT Patent Application No. PCT/US2010/033055, filed on Apr. 29, 2010, 7 pages.
Yanai, K. et al. (1994). "Binding Characteristics of a Histamine $H_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.
Zhu, Y. et al. (2001). "Cloning, Expression, and Pharmacological Characterization of a Novel Human Histamine Receptor," *Molecular Pharmacology* 59(3):434-441.
U.S. Appl. No. 14/000,171, filed Aug. 16, 2013, by Protter et al.
U.S. Appl. No. 14/000,184, filed Aug. 16, 2013, by Protter et al.
U.S. Appl. No. 14/000,197, filed Aug. 16, 2013, by Protter et al.

TETRACYCLIC COMPOUNDS

CROSS-REFERENCE TO RELATED APPLICATIONS

This application is a continuation of application U.S. Ser. No. 13/679,873 filed Nov. 16, 2012, which is a continuation of application U.S. Ser. No. 12/259,234 filed Oct. 27, 2008, now issued as U.S. Pat. No. 8,338,408, which claims priority to U.S. Provisional Patent Application No. 60/982,678 filed Oct. 25, 2007, U.S. Provisional Patent Application No. 60/982,679 filed Oct. 25, 2007, U.S. Provisional Patent Application No. 61/062,332 filed Jan. 25, 2008, U.S. Provisional Patent Application No. 61/062,331 filed Jan. 25, 2008, U.S. Provisional Patent Application No. 61/033,754 filed Mar. 4, 2008, U.S. Provisional Patent Application No. 61/033,757 filed Mar. 4, 2008, and Russian Patent Application No. 2007139634 filed Oct. 25, 2007, the disclosures of each of which are incorporated herein by reference in their entireties.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barre syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., histamine antagonists may find use as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Numerous compounds have been synthesized and tested in biochemical and cell-based assays as well as in in vivo studies.

Tetracyclic compounds of the general Formula (I) are described as new histamine receptor modulators. Other compounds are also detailed herein. Compositions comprising the compounds are provided, as are kits comprising the compound as well as methods of using and making the compounds. Other tetracyclic compounds are also provided. Compounds of the invention may also find use in treating neurodegenerative diseases. Compounds of the invention may also find use in treating diseases and/or conditions in which modulation of aminergic G protein-coupled receptors and/or neurite outgrowth may be implicated in therapy. Compounds disclosed herein may find use the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

In one variation, provided are compounds of the Formula (I):

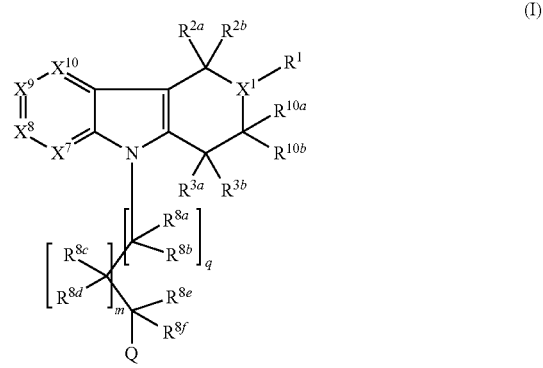

where:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano or nitro or $R^{3a}$ and $R^{3b}$ are taken together to form a carbonyl moiety;

each $X^7$, $X^8$, $X^9$ and $X^{10}$ is independently N or $CR^4$;

m and q are independently 0 or 1;

$X^1$ is N or CH;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl or is taken together with the carbon to which it is attached and a geminal $R^{8(a-f)}$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl moiety;

Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or a substituted or an unsubstituted heterocyclyl;

provided that: (i) when $X^1$ is N the compound is other than a compound in Table 1 or salt thereof; (ii) the compound is other than any of compounds 229H, 230, 241, 255, 256, 262 and 274 or a salt thereof; and (iii) the compound is other than those compounds listed in U.S. Pat. Nos. 6,187,785, 7,071,206, 3,409,628 and 6,849,640 or in PCT Publication Nos. WO 2005/055951, WO 2007/041697 and WO 2007/087425. In another variation, the compounds of the invention, pharmaceutical compositions thereof, isolated forms thereof and methods of using and administering the compounds detailed herein, encompass any of the compounds of Formula (I), including those listed in Table 1 or a salt thereof and compounds 229H, 230, 241, 255, 256, 262 and 274 or a salt thereof. In one variation, the compound is of the formula (I) wherein $R^4$ is other than a substituted or unsubstituted aryl, substituted or unsubstituted heteroaryl, an aryloxy and an aralkyl. In one variation the compound is of the formula (I) wherein $R^4$ is other than a substituted or unsubstituted aryl. In a further variation, the compound is of Formula (I) where at least one of $X^7$-$X^9$ is C—$R^4$ and $R^4$ is other than H. In one variation, the compounds listed in any of PCT publication numbers WO 2008/123800, WO 2008/123796, WO 2008/115098 and WO 2008/060190 are excluded from any compound formulae detailed herein and such publications are incorporated herein by reference in their entireties and specifically with respect to the compound species detailed therein. In one variation, the compounds listed in any of PCT publication numbers WO 2008/123800, WO 2008/123796, WO 2008/115098 and WO 2008/060190 are included in any compound formulae detailed herein and may find use in the methods provided. In another variation, the compound is of the formula (I) further provided that when Q is a substituted or unsubstituted heteroaryl, it is other than a thiazole, triazole, or oxadiazole. However, in another variation, the compound is of the formula (I) and includes compounds in which Q is a thiazole, triazole, or oxadiazole. In still another variation, the compound is of the formula (I) further provided that the compound is other than a compound of formula (G). However, in another variation, the compound is of the formula (I) and includes compounds that conform to the formula (G).

TABLE 1

| Compound No. | Compound Name |
| --- | --- |
| 1x | 1H-Pyrido[4,3-b]indole, 5-[(2,4-dimethylphenyl)methyl]-2,3,4,5-tetrahydro-2,8-dimethyl- |
| 2x | Piperidine, 1-[[5-[(2,6-difluorophenyl)methyl]-2,3,4,5-tetrahydro-2-(1-methylethyl)-1H-pyrido[4,3-b]indol-8-yl]carbonyl]-4-methoxy- |
| 3x | 2H-Pyrido[4,3-b]indole-2-carboxylic acid, 1,3,4,5-tetrahydro-8-[(4-methyl-1-piperidinyl)carbonyl]-5-[(2-methyl-4-thiazolyl)methyl]-,1,1-dimethylethyl ester |
| 4x | Piperidine, 1-[[2-cyclopentyl-2,3,4,5-tetrahydro-5-[(2-methyl-4-thiazolyl)methyl]-1H-pyrido[4,3-b]indol-8-yl]carbonyl]-4-methyl- |
| 5x | Piperidine, 4-methyl-1-[[2,3,4,5-tetrahydro-5-[(2-methyl-4-thiazolyl)methyl]-1H-pyrido[4,3-b]indol-8-yl]carbonyl]- |
| 6x | 2H-Pyrido[4,3-b]indole-2-carboxylic acid, 5-[[4-(ethylsulfonyl)phenyl]methyl]-1,3,4,5-tetrahydro-8-[(4-methyl-1-piperidinyl)carbonyl]-, 1,1-dimethylethyl ester |
| 7x | 2H-Pyrido[4,3-b]indole-2-carboxylic acid, 1,3,4,5-tetrahydro-8-[(4-methyl-1-piperidinyl)carbonyl]-5-[[4-(methylsulfonyl)phenyl]methyl]-,1,1-dimethylethyl ester |
| 8x | Piperidine, 1-[[2-cyclopentyl-2,3,4,5-tetrahydro-5-[[4-(methylsulfonyl)phenyl]methyl]-1H-pyrido[4,3-b]indol-8-yl]carbonyl]-4-methyl- |
| 9x | Piperidine, 4-methyl-1-[[2,3,4,5-tetrahydro-5-[[4-(methylsulfonyl)phenyl]methyl]-1H-pyrido[4,3-b]indol-8-yl]carbonyl]- |
| 10x | 2H-Pyrido[4,3-b]indole-2-carboxylic acid, 1,3,4,5-tetrahydro-8-[(4-methyl-1-piperidinyl)carbonyl]-5-[[4-(methylthio)phenyl]methyl]-,1,1-dimethylethyl ester |
| 11x | Piperidine, 1-[[2-cyclopentyl-2,3,4,5-tetrahydro-5-[[4-(methylthio)phenyl]methyl]-1H-pyrido[4,3-b]indol-8-yl]carbonyl]-4-methyl- |
| 12x | Piperidine, 4-methyl-1-[[2,3,4,5-tetrahydro-5-[[4-(methylthio)phenyl]methyl]-1H-pyrido[4,3-b]indol-8-yl]carbonyl]- |
| 13x | 2H-Pyrido[4,3-b]indole, 5-p-chlorobenzyl-1,3,4,5-tetrahydro-2-methyl- |
| 14x | 2H-Pyrido[4,3-b]indole, 7-chloro-5-p-chlorobenzyl-1,3,4,5-tetrahydro-2-methyl- |
| 15x | 2H-Pyrido[4,3-b]indole, 8-chloro-5-p-chlorobenzyl-1,3,4,5-tetrahydro-2-methyl- |

TABLE 1-continued

| Compound No. | Compound Name |
|---|---|
| 16x | 1H-Pyrido[4,3-b]indole, 2-(cyclobutylcarbonyl)-5-[(4-ethoxyphenyl)methyl]-2,3,4,5-tetrahydro-8-[(4-methyl-1-piperidinyl)carbonyl]- |
| 17x | 2H-Pyrido[4,3-b]indole-2-carboxylic acid, 5-[(4-ethoxyphenyl)methyl]-1,3,4,5-tetrahydro-8-[(4-methyl-1-piperidinyl)carbonyl]-,1,1-dimethylethyl ester |
| 18x | Piperidine, 1-[[2-(3,4-dihydro-2H-pyrrol-2-yl)-5-[(4-ethoxyphenyl)methyl]-2,3,4,5-tetrahydro-1H-pyrido[4,3-b]indol-8-yl]carbonyl]-4-methyl- |
| 19x | Piperidine, 1-[[2-(cyclopropylmethyl)-5-[(4-ethoxyphenyl)methyl]-2,3,4,5-tetrahydro-1H-pyrido[4,3-b]indol-8-yl]carbonyl]-4-methyl- |
| 20x | Piperidine, 1-[[2-cyclobutyl-5-[(4-ethoxyphenyl)methyl]-2,3,4,5-tetrahydro-1H-pyrido[4,3-b]indol-8-yl]carbonyl]-4-methyl- |
| 21x | Piperidine, 1-[[5-[(4-ethoxyphenyl)methyl]-2,3,4,5-tetrahydro-1H-pyrido[4,3-b]indol-8-yl]carbonyl]-4-methyl- |
| 22x | Piperidine, 1-[[5-[(4-ethoxyphenyl)methyl]-2,3,4,5-tetrahydro-2-(1-methylethyl)-1H-pyrido[4,3-b]indol-8-yl]carbonyl]-4-methoxy- |
| 23x | Piperidine, 1-[[5-[(4-ethoxyphenyl)methyl]-2,3,4,5-tetrahydro-2-(2-methylpropyl)-1H-pyrido[4,3-b]indol-8-yl]carbonyl]-4-methyl- |
| 24x | Piperidine, 1-[[5-[(4-ethoxyphenyl)methyl]-2,3,4,5-tetrahydro-2-(2-pyrimidinyl)-1H-pyrido[4,3-b]indol-8-yl]carbonyl]-4-methyl- |
| 25x | Piperidine, 1-[[5-[(4-ethoxyphenyl)methyl]-2,3,4,5-tetrahydro-2-(3,4,5,6-tetrahydro-2-pyridinyl)-1H-pyrido[4,3-b]indol-8-yl]carbonyl]-4-methyl- |
| 26x | Piperidine, 1-[[5-[(4-ethoxyphenyl)methyl]-2,3,4,5-tetrahydro-2-(tetrahydro-2H-pyran-4-yl)-1H-pyrido[4,3-b]indol-8-yl]carbonyl]-4-methyl- |
| 27x | Piperidine, 1-[[5-[(4-ethoxyphenyl)methyl]-2,3,4,5-tetrahydro-2-propyl-1H-pyrido[4,3-b]indol-8-yl]carbonyl]-4-methyl- |
| 28x | Piperidine, 4-ethoxy-1-[[5-[(4-ethoxyphenyl)methyl]-2,3,4,5-tetrahydro-2-(1-methylethyl)-1H-pyrido[4,3-b]indol-8-yl]carbonyl]- |
| 29x | 1H-Pyrido[4,3-b]indole, 8-fluoro-5-[(4-fluorophenyl)methyl]-2,3,4,5-tetrahydro-2-[2-(2-pyridinyl)ethyl]- |
| 30x | 1H-Pyrido[4,3-b]indole, 2,3,4,5-tetrahydro-2-(4-hydroxybenzoyl)-5-[(4-hydroxyphenyl)methyl]- |
| 31x | 2H-Pyrido[4,3-b]indole, 8-chloro-1,3,4,5-tetrahydro-5-p-methoxybenzyl-2-methyl- |
| 32x | Piperidine, 4-methyl-1-[[2,3,4,5-tetrahydro-5-[(4-methoxyphenyl)methyl]-2-(1-methylethyl)-1H-pyrido[4,3-b]indol-8-yl]carbonyl]- |
| 33x | 2-Furancarboxylic acid, 5-[[2-cyclopentyl-1,2,3,4-tetrahydro-8-[(4-methyl-1-piperidinyl)carbonyl]-5H-pyrido[4,3-b]indol-5-yl]methyl]-, methyl ester |
| 34x | 2-Furancarboxylic acid, 5-[[2-cyclopentyl-1,2,3,4-tetrahydro-8-[(4-methyl-1-piperidinyl)carbonyl]-5H-pyrido[4,3-b]indol-5-yl]methyl]- |
| 35x | 2H-Pyrido[4,3-b] indole-2-carboxylic acid, 1,3,4,5-tetrahydro-5-[(5-methyl-4-isoxazolyl)methyl]-8-[(4-methyl-1-piperidinyl)carbonyl]-,1,1-dimethylethyl ester |
| 36x | Piperidine, 1-[[2-cyclopentyl-2,3,4,5-tetrahydro-5-[(5-methyl-4-isoxazolyl)methyl]-1H-pyrido[4,3-b]indol-8-yl]carbonyl]-4-methyl- |
| 37x | Piperidine, 4-methyl-1-[[2,3,4,5-tetrahydro-5-[(5-methyl-4-isoxazolyl)methyl]-1H-pyrido[4,3-b]indol-8-yl]carbonyl]- |
| 38x | Piperidine, 1-[[5-[(6-chloro-1,3-benzodioxol-5-yl)methyl]-2,3,4,5-tetrahydro-2-(1-methylethyl)-1H-pyrido[4,3-b]indol-8-yl]carbonyl]-4-methoxy- |
| 39x | 1H-Pyrido[4,3-b]indole, 8-chloro-2,3,4,5-tetrahydro-2-methyl-5-[1-(6-methyl-2-pyridinyl)ethyl]- |
| 40x | 1H-Pyrido[4,3-b]indole, 8-bromo-2,3,4,5-tetrahydro-2-methyl-5-[1-(6-methyl-3-pyridinyl)ethyl]- |
| 41x | 1H-Pyrido[4,3-b]indole, 8-chloro-2,3,4,5-tetrahydro-2-methyl-5-[1-(6-methyl-3-pyridinyl)ethyl]- |
| 42x | 2H-Pyrido[4,3-b]indole-2-carboxylic acid, 5-(cyclobutylmethyl)-1,3,4,5-tetrahydro-8-[(4-methyl-1-piperidinyl)carbonyl]-, 1,1-dimethylethyl ester |
| 43x | Piperidine, 1-[[5-(cyclobutylmethyl)-2,3,4,5-tetrahydro-1H-pyrido[4,3-b]indol-8-yl]carbonyl]-4-methyl- |
| 44x | Piperidine, 1-[[5-(cyclobutylmethyl)-2-cyclopentyl-2,3,4,5-tetrahydro-1H-pyrido[4,3-b]indol-8-yl]carbonyl]-4-methyl- |
| 45x | 1H-Pyrido[4,3-b]indol-1-one, 5-(cyclopentylmethyl)-2,3,4,5-tetrahydro-2-[(5-methyl-1H-imidazol-4-yl)methyl]- |
| 46x | 1H-Pyrido[4,3-b]indol-1-one, 5-(cyclopentylmethyl)-6-fluoro-2,3,4,5-tetrahydro-2-[(5-methyl-1H-imidazol-4-yl)methyl]- |
| 47x | 2H-Pyrido[4,3-b]indole-2-carboxylic acid, 5-(cyclopropylmethyl)-1,3,4,5-tetrahydro-8-[(4-methyl-1-piperidinyl)carbonyl]-, 1,1-dimethylethyl ester |
| 48x | 2H-Pyrido[4,3-b]indole-2-carboxylic acid, 5-(cyclopropylmethyl)-9-[[(3,5-dichloro-4-pyridinyl)amino]carbonyl]-1,3,4,5-tetrahydro-6-methoxy-,1,1-dimethylethyl ester |
| 49x | Piperidine, 1-[[2-cyclopentyl-5-(cyclopropylmethyl)-2,3,4,5-tetrahydro-1H-pyrido[4,3-b]indol-8-yl]carbonyl]-4-methyl- |
| 50x | Piperidine, 1-[[5-(cyclopropylmethyl)-2,3,4,5-tetrahydro-1H-pyrido[4,3-b]indol-8-yl]carbonyl]-4-methyl- |
| 51x | 1H-Pyrido[4,3-b]indol-1-one, 2,3,4,5-tetrahydro-2-[(5-methyl-1H-imidazol-4-yl)methyl]-5-(phenylmethyl)- |
| 52x | 1H-Pyrido[4,3-b]indol-8-ol, 2,3,4,5-tetrahydro-5-(phenylmethyl)- |
| 53x | 1H-Pyrido[4,3-b]indole, 2,3,4,5-tetrahydro-1,1,3,3-tetramethyl-5-(phenylmethyl)- |
| 54x | 1H-Pyrido[4,3-b]indole, 2,3,4,5-tetrahydro-2-(3-phenoxypropyl)-5-(phenylmethyl)- |
| 55x | 1H-Pyrido[4,3-b]indole, 2,3,4,5-tetrahydro-2,5-bis(phenylmethyl)- |

TABLE 1-continued

| Compound No. | Compound Name |
|---|---|
| 56x | 1H-Pyrido[4,3-b]indole, 2,3,4,5-tetrahydro-2,8-dimethyl-5-(phenylmethyl)- |
| 57x | 1H-Pyrido[4,3-b]indole, 2,3,4,5-tetrahydro-2-methyl-5-(phenylmethyl)- |
| 58x | 1H-Pyrido[4,3-b]indole, 2,3,4,5-tetrahydro-5-(phenylmethyl)- |
| 59x | 1H-Pyrido[4,3-b]indole, 2,3,4,5-tetrahydro-8-(phenylmethoxy)-5-(phenylmethyl)- |
| 60x | 1H-Pyrido[4,3-b]indole, 2,3,4,5-tetrahydro-8-methyl-2,5-bis(phenylmethyl)- |
| 61x | 1H-Pyrido[4,3-b]indole, 2-acetyl-2,3,4,5-tetrahydro-5-(phenylmethyl)- |
| 62x | 1H-Pyrido[4,3-b]indole, 2-butyl-2,3,4,5-tetrahydro-5-(phenylmethyl)- |
| 65x | 1H-Pyrido[4,3-b]indole, 5-benzyl-2,3,4,5-tetrahydro-2-phenethyl- |
| 66x | 1H-Pyrido[4,3-b]indole, 9-bromo-2,3,4,5-tetrahydro-2-methyl-5-(phenylmethyl)- |
| 67x | 1H-Pyrido[4,3-b]indole, 9-chloro-2,3,4,5-tetrahydro-2-methyl-5-(phenylmethyl)- |
| 68x | 1H-Pyrido[4,3-b]indole-1,3(2H)-dione, 4,5-dihydro-5-(phenylmethyl)-2-[4-[4-(2-pyrimidinyl)-1-piperazinyl]butyl]- |
| 69x | 1H-Pyrido[4,3-b]indole-1,3(2H)-dione, 4,5-dihydro-8-methoxy-2-methyl-5-(phenylmethyl)- |
| 70x | 1H-Pyrido[4,3-b]indole-1-carbonitrile, 2,3,4,5-tetrahydro-2-methyl-5-(phenylmethyl)- |
| 71x | 1H-Pyrido[4,3-b]indole-6-carboxylic acid, 2-acetyl-2,3,4,5-tetrahydro-5-(phenylmethyl)- |
| 72x | 1H-Pyrido[4,3-b]indole, 2,3,4,5-tetrahydro-2-methyl-5-[2-(6-methyl-3-pyridyl)ethyl]-, N-oxide |
| 73x | 1H-Pyrido[4,3-b]indole-9-carboxamide, N-(3,5-dichloro-4-pyridinyl)-2,3,4,5-tetrahydro-6-methoxy-2-methyl-5-(phenylmethyl)- |
| 74x | 1H-Pyrido[4,3-b]indole-9-carboxamide, N-(3,5-dichloro-4-pyridinyl)-2,3,4,5-tetrahydro-6-methoxy-5-(phenylmethyl)- |
| 77x | 2,4(1H,3H)-Quinazolinedione, 3-[2-[1,3,4,5-tetrahydro-5-(phenylmethyl)-2H-pyrido[4,3-b]indol-2-yl]ethyl]- |
| 78x | 2,4(1H,3H)-Quinazolinedione, 3-[3-[1,3,4,5-tetrahydro-5-(phenylmethyl)-2H-pyrido[4,3-b]indol-2-yl]propyl]- |
| 79x | 2H-Pyrido[4,3-b]indole, 5-benzyl-1,3,4,5-tetrahydro-2,4-dimethyl- |
| 80x | 2H-Pyrido[4,3-b]indole, 5-benzyl-1,3,4,5-tetrahydro-7-methoxy-2-methyl- |
| 81x | 2H-Pyrido[4,3-b]indole, 5-benzyl-1,3,4,5-tetrahydro-8-methoxy-2-methyl- |
| 82x | 2H-Pyrido[4,3-b]indole, 5-benzyl-7-bromo-1,3,4,5-tetrahydro-2-methyl- |
| 83x | 2H-Pyrido[4,3-b]indole, 5-benzyl-7-chloro-1,3,4,5-tetrahydro-2-methyl- |
| 84x | 2H-Pyrido[4,3-b]indole, 5-benzyl-8-chloro-1,3,4,5-tetrahydro-2-methyl- |
| 85x | 2H-Pyrido[4,3-b]indole, 5-benzyl-8-ethoxy-1,3,4,5-tetrahydro-2-methyl- |
| 88x | 2H-Pyrido[4,3-b]indole-2-carbonitrile, 1,3,4,5-tetrahydro-5-(phenylmethyl)- |
| 89x | 2H-Pyrido[4,3-b]indole-2-carboxylic acid, 1,3,4,5-tetrahydro-5-(phenylmethyl)-, ethyl ester |
| 90x | 2H-Pyrido[4,3-b]indole-2-carboxylic acid, 1,3,4,5-tetrahydro-8-(phenylmethoxy)-5-(phenylmethyl)-, ethyl ester |
| 91x | 2H-Pyrido[4,3-b]indole-2-carboxylic acid, 9-[[(3,5-dichloro-4-pyridinyl)amino]carbonyl]-1,3,4,5-tetrahydro-6-methoxy-5-(phenylmethyl)-,1,1-dimethylethyl ester |
| 92x | 2H-Pyrido[4,3-b]indole-2-ethanol, 1,3,4,5-tetrahydro-5-(phenylmethyl)- |
| 93x | 4H-Pyrido[1,2-a]pyrimidin-4-one, 2-(phenylmethyl)-3-[2-[1,3,4,5-tetrahydro-5-(phenylmethyl)-2H-pyrido[4,3-b]indol-2-yl]ethyl]- |
| 94x | 4H-Pyrido[1,2-a]pyrimidin-4-one, 2-methyl-3-[2-[1,3,4,5-tetrahydro-5-(phenylmethyl)-2H-pyrido[4,3-b]indol-2-yl]ethyl]- |
| 95x | 4H-Pyrido[1,2-a]pyrimidin-4-one, 2-methyl-3-[2-[1,3,4,5-tetrahydro-8-hydroxy-5-(phenylmethyl)-2H-pyrido[4,3-b]indol-2-yl]ethyl]- |
| 96x | 4H-Pyrido[1,2-a]pyrimidin-4-one, 2-phenyl-3-[2-[1,3,4,5-tetrahydro-5-(phenylmethyl)-2H-pyrido[4,3-b]indol-2-yl]ethyl]- |
| 97x | 4H-Pyrido[1,2-a]pyrimidin-4-one, 6,7,8,9-tetrahydro-2-methyl-3-[2-[1,3,4,5-tetrahydro-5-(phenylmethyl)-2H-pyrido[4,3-b]indol-2-yl]ethyl]- |
| 98x | 4H-Pyrido[1,2-a]pyrimidin-4-one, 6,7,8,9-tetrahydro-2-methyl-3-[2-[1,3,4,5-tetrahydro-8-hydroxy-5-(phenylmethyl)-2H-pyrido[4,3-b]indol-2-yl]ethyl]- |
| 100x | 5H-Thiazolo[3,2-a]pyrimidin-5-one, 2,3-dihydro-7-methyl-6-[2-[1,3,4,5-tetrahydro-5-(phenylmethyl)-2H-pyrido[4,3-b]indol-2-yl]ethyl]- |
| 101x | 5H-Thiazolo[3,2-a]pyrimidin-5-one, 7-methyl-6-[2-[1,3,4,5-tetrahydro-5-(phenylmethyl)-2H-pyrido[4,3-b]indol-2-yl]ethyl]- |
| 102x | 5H-Thiazolo[3,2-a]pyrimidin-5-one, 7-methyl-6-[2-[1,3,4,5-tetrahydro-8-hydroxy-5-(phenylmethyl)-2H-pyrido[4,3-b]indol-2-yl]ethyl]- |
| 103x | Piperidine, 4-methyl-1-[[2,3,4,5-tetrahydro-2-(1-methylethyl)-5-(phenylmethyl)-1H-pyrido[4,3-b]indol-8-yl]carbonyl]- |
| 104x | 1H-Pyrido[4,3-b]indole, 2,3,4,5-tetrahydro-2-methyl-5-(2-pyridinylmethyl)- |
| 105x | 1H-Pyrido[4,3-b]indole, 2,3,4,5-tetrahydro-2-methyl-5-[1-(2-pyridinyl)ethyl]- |
| 106x | 1H-Pyrido[4,3-b]indole, 8-chloro-2,3,4,5-tetrahydro-2-methyl-5-(2-pyridinylmethyl)- |
| 107x | 1H-Pyrido[4,3-b]indole, 8-chloro-2,3,4,5-tetrahydro-2-methyl-5-[1-(2-pyridinyl)ethyl]- |
| 109x | 2H-Pyrido[4,3-b]indole-2-carboxylic acid, 1,3,4,5-tetrahydro-8-[(4-methyl-1-piperidinyl)carbonyl]-5-(2-pyridinylmethyl)-, 1,1-dimethylethyl ester |
| 110x | Piperidine, 4-methyl-1-[[2,3,4,5-tetrahydro-5-(2-pyridinylmethyl)-1H-pyrido[4,3-b]indol-8-yl]carbonyl]- |
| 111x | Piperidine, 4-methyl-1-[[2,3,4,5-tetrahydro-5-(2-pyridinylmethyl)-2-(tetrahydro-2H-pyran-4-yl)-1H-pyrido[4,3-b]indol-8-yl]carbonyl]- |
| 113x | 1H-Pyrido[4,3-b]indole, 2,3,4,5-tetrahydro-2,7,8-trimethyl-5-[1-(3-pyridinyl)ethyl]- |

TABLE 1-continued

| Compound No. | Compound Name |
|---|---|
| 114x | 1H-Pyrido[4,3-b]indole, 2,3,4,5-tetrahydro-2,8,9-trimethyl-5-[1-(3-pyridinyl)ethyl]- |
| 115x | 1H-Pyrido[4,3-b]indole, 2,3,4,5-tetrahydro-2,8-dimethyl-5-[1-(3-pyridinyl)ethyl]- |
| 116x | 1H-Pyrido[4,3-b]indole, 2,3,4,5-tetrahydro-8-methoxy-2-methyl-5-[1-(3-pyridinyl)ethyl]- |
| 117x | 1H-Pyrido[4,3-b]indole, 8-bromo-2,3,4,5-tetrahydro-2-methyl-5-[1-(3-pyridinyl)ethyl]- |
| 118x | 1H-Pyrido[4,3-b]indole, 8-chloro-2,3,4,5-tetrahydro-2-methyl-5-(3-pyridinylmethyl)- |
| 119x | 1H-Pyrido[4,3-b]indole, 8-chloro-2,3,4,5-tetrahydro-2-methyl-5-[1-(3-pyridinyl)ethyl]- |
| 120x | 1H-Pyrido[4,3-b]indole, 8-chloro-2,3,4,5-tetrahydro-2-methyl-5-(4-pyridinylmethyl)- |
| 121x | 1H-Pyrido[4,3-b]indole, 8-chloro-2,3,4,5-tetrahydro-2-methyl-5-[1-(4-pyridinyl)ethyl]- |
| 122x | 2H-Pyrido[4,3-b]indole-2-carboxylic acid, 1,3,4,5-tetrahydro-8-[(4-methyl-1-piperidinyl)carbonyl]-5-[(tetrahydro-2H-pyran-4-yl)methyl]-,1,1-dimethylethyl ester |
| 123x | Piperidine, 1-[[2-(cyclopropylmethyl)-2,3,4,5-tetrahydro-5-[(tetrahydro-2H-pyran-4-yl)methyl]-1H-pyrido[4,3-b]indol-8-yl]carbonyl]-4-methyl- |
| 124x | Piperidine, 4-methyl-1-[[2,3,4,5-tetrahydro-5-[(tetrahydro-2H-pyran-4-yl)methyl]-1H-pyrido[4,3-b]indol-8-yl]carbonyl]- |
| 125x | 1H-Pyrido[4,3-b]indole, 2,3,4,5-tetrahydro-2-methyl-5-[2-(2-methyl-3-pyridinyl)ethyl]- |
| 126x | 1H-Pyrido[4,3-b]indole, 2,3,4,5-tetrahydro-5-[2-[4-(2-methoxyphenyl)-1-piperazinyl]ethyl]- |
| 127x | 1H-Pyrido[4,3-b]indole, 2,3,4,5-tetrahydro-5-[2-[4-(2-methoxyphenyl)-1-piperazinyl]ethyl]-2-(phenylmethyl)- |
| 128x | 1H-Pyrido[4,3-b]indole, 2,3,4,5-tetrahydro-5-[2-[4-(2-methoxyphenyl)-1-piperazinyl]ethyl]-2-methyl- |
| 129x | 1H-Pyrido[4,3-b]indole, 2-acetyl-2,3,4,5-tetrahydro-5-[2-[4-(2-methoxyphenyl)-1-piperazinyl]ethyl]- |
| 130x | 1H-Pyrido[4,3-b]indole, 2-benzoyl-2,3,4,5-tetrahydro-5-[2-[4-(2-methoxyphenyl)-1-piperazinyl]ethyl]- |
| 131x | 1H-Pyrido[4,3-b]indole, 2,3,4,5-tetrahydro-2,7,8-trimethyl-5-[2-(6-methyl-3-pyridinyl)ethyl]- |
| 132x | 1H-Pyrido[4,3-b]indole, 2,3,4,5-tetrahydro-2,7-dimethyl-5-[2-(6-methyl-3-pyridinyl)ethyl]- |
| 133x | 1H-Pyrido[4,3-b]indole, 2,3,4,5-tetrahydro-2,8,9-trimethyl-5-[2-(6-methyl-3-pyridinyl)ethyl]- |
| 134x | 1H-Pyrido[4,3-b]indole, 2,3,4,5-tetrahydro-2,8-dimethyl-5-[2-(6-methyl-3-pyridinyl)ethyl]- |
| 135x | 1H-Pyrido[4,3-b]indole, 2,3,4,5-tetrahydro-2-isobutyl-5-[2-(6-methyl-3-pyridinyl)ethyl]- |
| 136x | 1H-Pyrido[4,3-b]indole, 2,3,4,5-tetrahydro-2-isobutyl-8-methoxy-5-[2-(6-methyl-3-pyridinyl)ethyl]- |
| 137x | 1H-Pyrido[4,3-b]indole, 2,3,4,5-tetrahydro-2-isobutyl-8-methyl-5-[2-(6-methyl-3-pyridinyl)ethyl]- |
| 138x | 1H-Pyrido[4,3-b]indole, 2,3,4,5-tetrahydro-2-isopentyl-5-[2-(6-methyl-3-pyridinyl)ethyl]- |
| 139x | 1H-Pyrido[4,3-b]indole, 2,3,4,5-tetrahydro-2-isopentyl-8-methyl-5-[2-(6-methyl-3-pyridinyl)ethyl]- |
| 140x | 1H-Pyrido[4,3-b]indole, 2,3,4,5-tetrahydro-2-methyl-5-[2-(6-methyl-3-pyridinyl)ethyl]- |
| 141x | 1H-Pyrido[4,3-b]indole, 2,3,4,5-tetrahydro-2-methyl-5-[2-(6-methyl-3-pyridinyl)ethyl]-7-(trifluoromethyl)- |
| 142x | 1H-Pyrido[4,3-b]indole, 2,3,4,5-tetrahydro-5-[2-(6-methyl-3-pyridinyl)ethyl]- |
| 143x | 1H-Pyrido[4,3-b]indole, 2,3,4,5-tetrahydro-5-[2-(6-methyl-3-pyridinyl)ethyl]-2-(phenylmethyl)- |
| 144x | 1H-Pyrido[4,3-b]indole, 2,3,4,5-tetrahydro-5-[2-(6-methyl-3-pyridinyl)ethyl]-2-pentyl- |
| 145x | 1H-Pyrido[4,3-b]indole, 2,3,4,5-tetrahydro-5-[2-(6-methyl-3-pyridinyl)ethyl]-2-phenyl- |
| 146x | 1H-Pyrido[4,3-b]indole, 2,3,4,5-tetrahydro-5-[2-(6-methyl-3-pyridinyl)ethyl]-2-propyl- |
| 148x | 1H-Pyrido[4,3-b]indole, 2,3,4,5-tetrahydro-8-methoxy-2-methyl-5-[2-(6-methyl-3-pyridinyl)ethyl]- |
| 149x | 1H-Pyrido[4,3-b]indole, 2,3,4,5-tetrahydro-8-methoxy-5-[2-(6-methyl-3-pyridinyl)ethyl]-2-propyl- |
| 150x | 1H-Pyrido[4,3-b]indole, 2,3,4,5-tetrahydro-8-methyl-5-[2-(6-methyl-3-pyridinyl)ethyl]- |
| 151x | 1H-Pyrido[4,3-b]indole, 2,3,4,5-tetrahydro-8-methyl-5-[2-(6-methyl-3-pyridinyl)ethyl]-2-(phenylmethyl)- |
| 152x | 1H-Pyrido[4,3-b]indole, 2,3,4,5-tetrahydro-8-methyl-5-[2-(6-methyl-3-pyridinyl)ethyl]-2-propyl- |
| 155x | 1H-Pyrido[4,3-b]indole, 2-benzyl-8-chloro-2,3,4,5-tetrahydro-5-[2-(6-methyl-3-pyridinyl)ethyl]- |

TABLE 1-continued

| Compound No. | Compound Name |
|---|---|
| 156x | 1H-Pyrido[4,3-b]indole, 2-butyl-2,3,4,5-tetrahydro-4-methyl-5-[2-(6-methyl-3-pyridinyl)ethyl]- |
| 157x | 1H-Pyrido[4,3-b]indole, 2-butyl-2,3,4,5-tetrahydro-5-[2-(6-methyl-3-pyridinyl)ethyl]- |
| 158x | 1H-Pyrido[4,3-b]indole, 2-butyl-2,3,4,5-tetrahydro-8-methoxy-5-[2-(6-methyl-3-pyridinyl)ethyl]- |
| 159x | 1H-Pyrido[4,3-b]indole, 2-butyl-2,3,4,5-tetrahydro-8-methyl-5-[2-(6-methyl-3-pyridinyl)ethyl]- |
| 160x | 1H-Pyrido[4,3-b]indole, 2-cyclohexyl-2,3,4,5-tetrahydro-5-[2-(6-methyl-3-pyridinyl)ethyl]- |
| 161x | 1H-Pyrido[4,3-b]indole, 2-ethyl-2,3,4,5-tetrahydro-5-[2-(6-methyl-3-pyridinyl)ethyl]- |
| 162x | 1H-Pyrido[4,3-b]indole, 2-ethyl-2,3,4,5-tetrahydro-8-methyl-5-[2-(6-methyl-3-pyridinyl)ethyl]- |
| 163x | 1H-Pyrido[4,3-b]indole, 2-heptyl-2,3,4,5-tetrahydro-5-[2-(6-methyl-3-pyridinyl)ethyl]- |
| 164x | 1H-Pyrido[4,3-b]indole, 2-heptyl-2,3,4,5-tetrahydro-8-methoxy-5-[2-(6-methyl-3-pyridinyl)ethyl]- |
| 165x | 1H-Pyrido[4,3-b]indole, 2-heptyl-2,3,4,5-tetrahydro-8-methyl-5-[2-(6-methyl-3-pyridinyl)ethyl]- |
| 166x | 1H-Pyrido[4,3-b]indole, 2-sec-butyl-2,3,4,5-tetrahydro-5-[2-(6-methyl-3-pyridinyl)ethyl]- |
| 167x | 1H-Pyrido[4,3-b]indole, 2-sec-butyl-2,3,4,5-tetrahydro-8-methyl-5-[2-(6-methyl-3-pyridinyl)ethyl]- |
| 168x | 1H-Pyrido[4,3-b]indole, 7,8-dichloro-2,3,4,5-tetrahydro-2-methyl-5-[2-(6-methyl-3-pyridinyl)ethyl]- |
| 169x | 1H-Pyrido[4,3-b]indole, 7-chloro-2,3,4,5-tetrahydro-2,8-dimethyl-5-[2-(6-methyl-3-pyridinyl)ethyl]- |
| 170x | 1H-Pyrido[4,3-b]indole, 7-chloro-2,3,4,5-tetrahydro-2-methyl-5-[2-(6-methyl-3-pyridinyl)ethyl]- |
| 171x | 1H-Pyrido[4,3-b]indole, 8-bromo-2,3,4,5-tetrahydro-2-methyl-5-[2-(6-methyl-3-pyridinyl)ethyl]- |
| 172x | 1H-Pyrido[4,3-b]indole, 8-chloro-2,3,4,5-tetrahydro-2,6-dimethyl-5-[2-(6-methyl-3-pyridinyl)ethyl]- |
| 173x | 1H-Pyrido[4,3-b]indole, 8-chloro-2,3,4,5-tetrahydro-2,7-dimethyl-5-[2-(6-methyl-3-pyridinyl)ethyl]- |
| 174x | 1H-Pyrido[4,3-b]indole, 8-chloro-2,3,4,5-tetrahydro-2-methyl-5-[2-(6-methyl-3-pyridinyl)ethyl]- |
| 175x | 1H-Pyrido[4,3-b]indole, 8-ethyl-2,3,4,5-tetrahydro-2-methyl-5-[2-(6-methyl-3-pyridinyl)ethyl]- |
| 176x | 1H-Pyrido[4,3-b]indole, 5-[2-(hexahydro-1H-azepin-1-yl)ethyl]-2,3,4,5-tetrahydro-2,8-dimethyl- |
| 177x | 2H-Pyrido[4,3-b]indole, 1,3,4,5-tetrahydro-2-methyl-5-phenethyl- |
| 178x | 1H-Pyrido[4,3-b]indole, 2,3,4,5-tetrahydro-2,8-dimethyl-5-[2-(1-piperidinyl)ethyl]- |
| 179x | 1H-Pyrido[4,3-b]indole, 2,3,4,5-tetrahydro-2-methyl-5-(2-piperidinoethyl)- |
| 180x | 1H-Pyrido[4,3-b]indole, 1-butyl-2,3,4,5-tetrahydro-5-[2-(2-pyridinyl)ethyl]- |
| 181x | 1H-Pyrido[4,3-b]indole, 2,3,4,5-tetrahydro-2-methyl-5-[2-(2-pyridinyl)ethyl]- |
| 182x | 1H-Pyrido[4,3-b]indole, 2,3,4,5-tetrahydro-2-propyl-5-[2-(2-pyridinyl)ethyl]- |
| 183x | 1H-Pyrido[4,3-b]indole, 2-butyl-2,3,4,5-tetrahydro-5-[2-(2-pyridinyl)ethyl]- |
| 184x | 1H-Pyrido[4,3-b]indole, 8-chloro-2,3,4,5-tetrahydro-2-methyl-5-[2-(3-pyridinyl)ethyl]- |
| 185x | 1H-Pyrido[4,3-b]indole, 2,3,4,5-tetrahydro-2,6-dimethyl-5-[2-(4-pyridinyl)ethyl]- |
| 186x | 1H-Pyrido[4,3-b]indole, 2,3,4,5-tetrahydro-2,7,8-trimethyl-5-[2-(4-pyridinyl)ethyl]- |
| 187x | 1H-Pyrido[4,3-b]indole, 2,3,4,5-tetrahydro-2,7-dimethyl-5-[2-(4-pyridinyl)ethyl]- |
| 188x | 1H-Pyrido[4,3-b]indole, 2,3,4,5-tetrahydro-2,8,9-trimethyl-5-[2-(4-pyridinyl)ethyl]- |
| 189x | 1H-Pyrido[4,3-b]indole, 2,3,4,5-tetrahydro-2,8-dimethyl-5-[2-(4-pyridinyl)ethyl]- |
| 190x | 1H-Pyrido[4,3-b]indole, 2,3,4,5-tetrahydro-2-methyl-5-[2-(4-pyridinyl)ethyl]- |
| 191x | 1H-Pyrido[4,3-b]indole, 2,3,4,5-tetrahydro-2-methyl-5-[2-(4-pyridinyl)ethyl]-8-(trifluoromethyl)- |
| 192x | 1H-Pyrido[4,3-b]indole, 2,3,4,5-tetrahydro-2-propyl-5-[2-(4-pyridinyl)ethyl]- |
| 193x | 1H-Pyrido[4,3-b]indole, 2,3,4,5-tetrahydro-8-methoxy-2-methyl-5-[2-(4-pyridinyl)ethyl]- |
| 194x | 1H-Pyrido[4,3-b]indole, 2-benzoyl-8-chloro-2,3,4,5-tetrahydro-5-[2-(4-pyridinyl)ethyl]- |
| 195x | 1H-Pyrido[4,3-b]indole, 2-butyl-2,3,4,5-tetrahydro-5-[2-(4-pyridinyl)ethyl]- |
| 196x | 1H-Pyrido[4,3-b]indole, 2-butyl-2,3,4,5-tetrahydro-8-methyl-5-[2-(4-pyridinyl)ethyl]- |
| 197x | 1H-Pyrido[4,3-b]indole, 7-chloro-2,3,4,5-tetrahydro-2-methyl-5-[2-(4-pyridinyl)ethyl]- |
| 198x | 1H-Pyrido[4,3-b]indole, 8-chloro-2,3,4,5-tetrahydro-2-(2-phenylethyl)-5-[2-(4-pyridinyl)ethyl]- |
| 199x | 1H-Pyrido[4,3-b]indole, 8-chloro-2,3,4,5-tetrahydro-2-methyl-5-[2-(4-pyridinyl)ethyl]- |
| 200x | 1H-Pyrido[4,3-b]indole, 8-chloro-2,3,4,5-tetrahydro-5-[2-(4-pyridinyl)ethyl]- |
| 201x | 1H-Pyrido[4,3-b]indole-8-carboxylic acid, 2,3,4,5-tetrahydro-2-methyl-5-[2-(4-pyridinyl)ethyl]- |

TABLE 1-continued

| Compound No. | Compound Name |
|---|---|
| 202x | 1H-Pyrido[4,3-b]indole, 2,3,4,5-tetrahydro-2-methyl-5-[3-(4-morpholinyl)propyl]- |
| 203x | 1H-Pyrido[4,3-b]indole-8-methanol, 2,3,4,5-tetrahydro-2-methyl-5-[2-(4-pyridinyl)ethyl]- |
| 204x | 1H-Pyrido[4,3-b]indole, 2,3,4,5-tetrahydro-2-methyl-5-[2-(1-pyrrolidinyl)ethyl]- |
| 205x | 1H-Pyrido[4,3-b]indole, 2,3,4,5-tetrahydro-5-[3-[4-(2-methoxyphenyl)-1-piperazinyl]propyl]- |
| 206x | 1H-Pyrido[4,3-b]indole, 2,3,4,5-tetrahydro-5-[3-[4-(2-methoxyphenyl)-1-piperazinyl]propyl]-2-(phenylmethyl)- |
| 207x | 1H-Pyrido[4,3-b]indole, 2,3,4,5-tetrahydro-5-[3-[4-(2-methoxyphenyl)-1-piperazinyl]propyl]-2-methyl- |
| 208x | 1H-Pyrido[4,3-b]indole, 2-acetyl-2,3,4,5-tetrahydro-5-[3-[4-(2-methoxyphenyl)-1-piperazinyl]propyl]- |
| 209x | 1H-Pyrido[4,3-b]indole, 2-benzoyl-2,3,4,5-tetrahydro-5-[3-[4-(2-methoxyphenyl)-1-piperazinyl]propyl]- |
| 210x | 1H-Pyrido[4,3-b]indole, 2,3,4,5-tetrahydro-2-methyl-5-[3-[4-(phenylmethyl)-1-piperazinyl]propyl]- |
| 211x | 1H-Pyrido[4,3-b]indole, 2,3,4,5-tetrahydro-2-methyl-5-[3-(4-methyl-1-piperazinyl)propyl]- |
| 212x | 1H-Pyrido[4,3-b]indole, 2,3,4,5-tetrahydro-5-[3-(4-methyl-1-piperazinyl)propyl]-2-(2-phenylethyl)- |
| 213x | 1H-Pyrido[4,3-b]indole, 2,3,4,5-tetrahydro-5-[3-(4-methyl-1-piperazinyl)propyl]-2-(phenylmethyl)- |
| 214x | 1H-Pyrido[4,3-b]indole, 2,3,4,5-tetrahydro-8-methoxy-2-methyl-5-[3-(4-methyl-1-piperazinyl)propyl]- |
| 216x | 1H-Pyrido[4,3-b]indol-1-one, 2,3,4,5-tetrahydro-5-(phenylmethyl)- |
| 217x | 1H-Pyrido[4,3-b]indol-1-one, 5-(cyclopentylmethyl)-2,3,4,5-tetrahydro- |
| 218x | 1H-Pyrido[4,3-b]indol-1-one, 5-(cyclopentylmethyl)-6-fluoro-2,3,4,5-tetrahydro- |
| 219x | 1H-Pyrido[4,3-b]indole, 2-benzoyl-2,3,4,5-tetrahydro-8-methoxy-5-(2-pyridinylcarbonyl)- |
| 220x | 1H-Pyrido[4,3-b]indole, 5-(4-chlorobenzoyl)-2,3,4,5-tetrahydro-8-methoxy-2-methyl- |
| 221x | 1-Propanone, 1-(2-chloro-10H-phenothiazin-10-yl)-3-(1,2,3,4-tetrahydro-2-methyl-5H-pyrido[4,3-b]indol-5-yl)- |
| 222x | Ethanone, 1-(ethyl-1-piperazinyl)-2-[1,2,3,4-tetrahydro-2-(1-methylethyl)-5H-pyrido[4,3-b]indol-5-yl]- |
| 223x | Ethanone, 1-(4-methyl-1-piperazinyl)-2-[1,2,3,4-tetrahydro-2-(1-methylethyl)-5H-pyrido[4,3-b]indol-5-yl]- |
| 224x | Ethanone, 1-(4-methyl-1-piperazinyl)-2-[1,2,3,4-tetrahydro-8-methyl-2-(1-methylethyl)-5H-pyrido[4,3-b]indol-5-yl]- |
| 225x | Ethanone, 1-[4-(2-methoxyphenyl)-1-piperazinyl]-2-[1,2,3,4-tetrahydro-2-(1-methylethyl)-5H-pyrido[4,3-b]indol-5-yl]- |
| 226x | Ethanone, 1-[4-(diphenylmethyl)-1-piperazinyl]-2-[1,2,3,4-tetrahydro-2-(1-methylethyl)-5H-pyrido[4,3-b]indol-5-yl]- |
| 227x | Ethanone, 1-[4-(phenylmethyl)-1-piperazinyl]-2-[1,2,3,4-tetrahydro-2-(1-methylethyl)-5H-pyrido[4,3-b]indol-5-yl]- |
| 228x | Ethanone, 2-[1,2,3,4-tetrahydro-2-(1-methylethyl)-5H-pyrido[4,3-b]indol-5-yl]-1-[4-[3-(trifluoromethyl)phenyl]-1-piperazinyl]- |
| 229x | Ethanone, 2-[8-ethyl-1,2,3,4-tetrahydro-2-(1-methylethyl)-5H-pyrido[4,3-b]indol-5-yl]-1-(4-methyl-1-piperazinyl)- |
| 230x | Methanone, (4-fluorophenyl)[2-[2-[3-fluoro-5-(tetrahydro-4-methoxy-2H-pyran-4-yl)phenoxy]ethyl]-1,2,3,4-tetrahydro-7-methoxy-5H-pyrido[4,3-b]indol-5-yl]- |
| 231x | Methanone, (4-methyl-1-piperidinyl)[2,3,4,5-tetrahydro-5-(4-morpholinylcarbonyl)-2-(tetrahydro-2H-pyran-4-yl)-1H-pyrido[4,3-b]indol-8-yl]- |
| 232x | Methanone, [1,1'-biphenyl]-4-yl(1,2,3,4-tetrahydro-8-methoxy-2-methyl-5H-pyrido[4,3-b]indol-5-yl)- |
| 233x | 1-(4-benzhydrylpiperazin-1-yl)-2-(7-aza-2-isopropyl-3,4-dihydro-1H-pyrido[4,3-b]indol-5(2H)-yl)ethanone |
| 234x | 1-(4-benzylpiperazin-1-yl)-2-(7-aza-2-isopropyl-3,4-dihydro-1H-pyrido[4,3-b]indol-5(2H)-yl)ethanone |
| 235x | 1-(4-ethylpiperazin-1-yl)-2-(7-aza-2-isopropyl-3,4-dihydro-1H-pyrido[4,3-b]indol-5(2H)-yl)ethanone |
| 236x | 1H-Pyrido[4,3-b]indole, 2,3,4,5-tetrahydro-2-propyl-5-(phenylmethyl)- |
| 237x | 1H-Pyrido[4,3-b]indole, 2,3,4,5-tetrahydro-5-[2-(2-methyl-3-pyridinyl)ethyl]- |
| 238x | Methanone, [1-(difluoromethyl)-1H-pyrazol-5-yl](1,2,3,4-tetrahydro-2,8-dimethyl-5H-pyrido[4,3-b]indol-5-yl)- |
| 239x | Methanone, [2-(3,4-dihydro-2H-pyrrol-5-yl)-5-[(4-ethoxyphenyl)methyl]-2,3,4,5-tetrahydro-1H-pyrido[4,3-b]indol-8-yl](4-methyl-1-piperidinyl)- |
| 243x | 2,8-dimethyl-5-phenethyl-2,3,4,5-tetrahydro-1H-pyrido[4,3-b]indole |
| 244x | 8-fluoro-2-methyl-5-phenethyl-2,3,4,5-tetrahydro-1H-pyrido[4,3-b]indole |
| 245x | 2-methyl-5-phenethyl-8-(trifluoromethyl)-2,3,4,5-tetrahydro-1H-pyrido[4,3-b]indole |
| 246x | 6-fluoro-2-methyl-5-phenethyl-2,3,4,5-tetrahydro-1H-pyrido[4,3-b]indole |
| 247x | 2-methyl-5-phenethyl-6-(trifluoromethyl)-2,3,4,5-tetrahydro-1H-pyrido[4,3-b]indole |
| 248x | 2-methyl-5-(2-(pyridin-3-yl)ethyl)-2,3,4,5-tetrahydro-1H-pyrido[4,3-b]indole |
| 249x | 2,8-dimethyl-5-(2-(pyridin-3-yl)ethyl)-2,3,4,5-tetrahydro-1H-pyrido[4,3-b]indole |
| 250x | 2,8-dimethyl-5-(2-(pyridin-2-yl)ethyl)-2,3,4,5-tetrahydro-1H-pyrido[4,3-b]indole |

TABLE 1-continued

| Compound No. | Compound Name |
|---|---|
| 251x | 2,8-dimethyl-5-(2-(pyrazin-2-yl)ethyl)-2,3,4,5-tetrahydro-1H-pyrido[4,3-b]indole |
| 252x | 8-fluoro-2-methyl-5-(2-(pyridin-4-yl)ethyl)-2,3,4,5-tetrahydro-1H-pyrido[4,3-b]indole |
| 253x | 8-fluoro-2-methyl-5-(2-pyridin-3-yl)ethyl)-2,3,4,5-tetrahydro-1H-pyrido[4,3-b]indole |
| 254x | 8-fluoro-2-methyl-5-(2-(pyridin-2-yl)ethyl)-2,3,4,5-tetrahydro-1H-pyrido[4,3-b]indole |
| 255x | 8-fluoro-2-methyl-5-(2-(6-methylpyridin-3-yl)ethyl)-2,3,4,5-tetrahydro-1H-pyrido[4,3-b]indole |
| 256x | 2-methyl-5-(2-(pyridin-3-yl)ethyl)-8-(trifluoromethyl)-2,3,4,5-tetrahydro-1H-pyrido[4,3-b]indole |
| 257x | 2-methyl-5-(2-(pyridin-3-yl)ethyl)-6-(trifluoromethyl)-2,3,4,5-tetrahydro-1H-pyrido[4,3-b]indole |
| 258x | 2-tert-butyl-8-methyl-5-(2-(pyridin-3-yl)ethyl)-2,3,4,5-tetrahydro-1H-pyrido[4,3-b]indole |
| 259x | ethyl 5-(pyridin-4-ylmethyl)-3,4-dihydro-1H-pyrido[4,3-b]indole-2(5H)-carboxylate |
| 260x | ethyl 5-(pyridin-3-ylmethyl)-3,4-dihydro-1H-pyrido[4,3-b]indole-2(5H)-carboxylate |
| 261x | ethyl 5-(pyridin-2-ylmethyl)-3,4-dihydro-1H-pyrido[4,3-b]indole-2(5H)-carboxylate |
| 262x | 5-benzyl-2-methyl-2,3,4,5-tetrahydro-1H-pyrido[4,3-b]indole-8-carboxylic acid |
| 263x | 5-(4-fluorobenzyl)-2-methyl-2,3,4,5-tetrahydro-1H-pyrido[4,3-b]indole-8-carboxylic acid |
| 264x | 2-methyl-5-(pyridin-3-ylmethyl)-2,3,4,5-tetrahydro-1H-pyrido[4,3-b]indole-8-carboxylic acid |
| 265x | 2-methyl-5-(pyridin-4-ylmethyl)-2,3,4,5-tetrahydro-1H-pyrido[4,3-b]indole-8-carboxylic acid |
| 266x | 5-(4-fluorobenzyl)-2-methyl-2,3,4,5-tetrahydro-1H-pyrido[4,3-b]indole |
| 267x | 2-methyl-5-(pyridin-3-ylmethyl)-2,3,4,5-tetrahydro-1H-pyrido[4,3-b]indole |
| 268x | 2-methyl-5-(pyridin-4-ylmethyl)-2,3,4,5-tetrahydro-1H-pyrido[4,3-b]indole |
| 269x | 5-benzyl-8-fluoro-2-methyl-2,3,4,5-tetrahydro-1H-pyrido[4,3-b]indole |
| 270x | 8-fluoro-2-methyl-5-(pyridin-2-ylmethyl)-2,3,4,5-tetrahydro-1H-pyrido[4,3-b]indole |
| 271x | 8-fluoro-2-methyl-5-(pyridin-3-ylmethyl)-2,3,4,5-tetrahydro-1H-pyrido[4,3-b]indole |
| 272x | 8-fluoro-2-methyl-5-(pyridin-4-ylmethyl)-2,3,4,5-tetrahydro-1H-pyrido[4,3-b]indole |
| 273x | 5-(4-fluorobenzyl)-2,8-dimethyl-2,3,4,5-tetrahydro-1H-pyrido[4,3-b]indole |
| 274x | 5-benzyl-2-methyl-8-(trifluoromethyl)-2,3,4,5-tetrahydro-1H-pyrido[4,3-b]indole |
| 275x | 2-methyl-5-(pyridin-3-ylmethyl)-8-(trifluoromethyl)-2,3,4,5-tetrahydro-1H-pyrido[4,3-b]indole |
| 276x | 2-methyl-5-(pyridin-4-ylmethyl)-8-(trifluoromethyl)-2,3,4,5-tetrahydro-1H-pyrido[4,3-b]indole |
| 277x | 5-benzyl-6-fluoro-2-methyl-2,3,4,5-tetrahydro-1H-pyrido[4,3-b]indole |
| 278x | 2-methyl-5-(pyridin-3-ylmethyl)-6-(trifluoromethyl)-2,3,4,5-tetrahydro-1H-pyrido[4,3-b]indole |
| 279x | 8-fluoro-2-methyl-5-(3-methylbenzyl)-2,3,4,5-tetrahydro-1H-pyrido[4,3-b]indole |
| 280x | 8-fluoro-2-methyl-5-(thiophen-2-ylmethyl)-2,3,4,5-tetrahydro-1H-pyrido[4,3-b]indole |
| 281x | 2,8-dimethyl-5-((1,2,5,6-tetrahydropyridin-3-yl)methyl)-2,3,4,5-tetrahydro-1H-pyrido[4,3-b]indole |
| 282x | 2-benzyl-5-(3-chlorobenzyl)-8-methyl-2,3,4,5-tetrahydro-1H-pyrido[4,3-b]indole |
| 283x | ethyl 2-(5-benzyl-6-fluoro-3,4-dihydro-1H-pyrido[4,3-b]indol-2(5H)-yl)acetate |
| 284x | ethyl 2-(5-(4-fluorobenzyl)-6-(trifluoromethyl)-3,4-dihydro-1H-pyrido[4,3-b]indol-2(5H)-yl)acetate |
| 285x | ethyl 3-(8-fluoro-5-(4-fluorobenzyl)-3,4-dihydro-1H-pyrido[4,3-b]indol-2(5H)-yl)propanoate |
| 286x | ethyl 3-(5-(pyridin-3-ylmethyl)-8-(trifluoromethyl)-3,4-dihydro-1H-pyrido[4,3-b]indol-2(5H)-yl)propanoate |
| 287x | ethyl 4-(8-fluoro-5-(pyridin-3-ylmethyl)-3,4-dihydro-1H-pyrido[4,3-b]indol-2(5H)-yl)butanoate |
| 288x | ethyl 4-(5-(pyridin-4-ylmethyl)-8-(trifluoromethyl)-3,4-dihydro-1H-pyrido[4,3-b]indol-2(5H)-yl)butanoate |
| 289x | 2-(5-benzyl-6-fluoro-3,4-dihydro-1H-pyrido[4,3-b]indol-2(5H)-yl)acetic acid |
| 290x | 3-(8-fluoro-5-(4-fluorobenzyl)-3,4-dihydro-1H-pyrido[4,3-b]indol-2(5H)-yl)propanoic acid |
| 291x | 3-(5-(pyridin-3-ylmethyl)-8-(trifluoromethyl)-3,4-dihydro-1H-pyrido[4,3-b]indol-2(5H)-yl)propanoic acid |
| 292x | 4-(8-fluoro-5-(pyridin-3-ylmethyl)-3,4-dihydro-1H-pyrido[4,3-b]indol-2(5H)-yl)butanoic acid |
| 293x | ethyl 4-((8-fluoro-2-methyl-3,4-dihydro-1H-pyrido[4,3-b]indol-5(2H)-yl)methyl)benzoate |
| 294x | 5-benzyl-2-methyl-2,3,4,5-tetrahydro-1H-pyrido[4,3-b]indole-8-carboxylic acid |
| 295x | 2-methyl-5-(pyridin-3-ylmethyl)-2,3,4,5-tetrahydro-1H-pyrido[4,3-b]indole-8-carboxylic acid |

TABLE 1A

| Compound No. | Compound Name |
|---|---|
| 240x | 1H-Pyrido[4,3-b]indole-6-carboxylic acid, 2-acetyl-2,3,4,5-tetrahydro-5-(phenylmethyl)-, phenylmethyl ester |
| 241x | 1H-Pyrido[4,3-b]indole-8-carboxylic acid, 2,3,4,5-tetrahydro-2-methyl-5-[2-(4-pyridinyl)ethyl]-, ethyl ester |
| 296x | ethyl 5-benzyl-2-methyl-2,3,4,5-tetrahydro-1H-pyrido[4,3-b]indole-8-carboxylate |
| 297x | ethyl 5-(4-fluorobenzyl)-2-methyl-2,3,4,5-tetrahydro-1H-pyrido[4,3-b]indole-8-carboxylate |
| 298x | ethyl 2-methyl-5-(pyridin-3-ylmethyl)-2,3,4,5-tetrahydro-1H-pyrido[4,3-b]indole-8-carboxylate |
| 299x | ethyl 2-methyl-5-(pyridin-4-ylmethyl)-2,3,4,5-tetrahydro-1H-pyrido[4,3-b]indole-8-carboxylate |
| 300x | ethyl 5-benzyl-2,3,4,5-tetrahydro-1H-pyrido[4,3-b]indole-8-carboxylate |
| 301x | ethyl 5-(4-fluorobenzyl)-2,3,4,5-tetrahydro-1H-pyrido[4,3-b]indole-8-carboxylate |
| 302x | ethyl 5-(pyridin-3-ylmethyl)-2,3,4,5-tetrahydro-1H-pyrido[4,3-b]indole-8-carboxylate |
| 303x | ethyl 5-benzyl-2-(2-(pyridin-3-yl)ethyl)-2,3,4,5-tetrahydro-1H-pyrido[4,3-b]indole-8-carboxylate |
| 304x | ethyl 5-(4-fluorobenzyl)-2-(2-(pyridin-3-yl)ethyl)-2,3,4,5-tetrahydro-1H-pyrido[4,3-b]indole-8-carboxylate |
| 305x | ethyl 2-(4-fluorobenzyl)-5-(pyridin-3-ylmethyl)-2,3,4,5-tetrahydro-1H-pyrido[4,3-b]indole-8-carboxylate |
| 306x | ethyl 2-benzyl-5-(pyridin-3-ylmethyl)-2,3,4,5-tetrahydro-1H-pyrido[4,3-b]indole-8-carboxylate |
| 307x | diethyl 5-(pyridin-3-ylmethyl)-3,4-dihydro-1H-pyrido[4,3-b]indole-2,8(5H)-dicarboxylate |
| 308x | diethyl 5-benzyl-3,4-dihydro-1H-pyrido[4,3-b]indole-2,8(5H)-dicarboxylate |
| 309x | diethyl 5-(4-fluorobenzyl)-3,4-dihydro-1H-pyrido[4,3-b]indole-2,8(5H)-dicarboxylate |
| 310x | ethyl 5-(4-fluorobenzyl)-2-(2-(pyridin-3-yl)ethyl)-2,3,4,5-tetrahydro-1H-pyrido[4,3-b]indole-6-carboxylate |
| 311x | ethyl 5-(4-fluorobenzyl)-2,3,4,5-tetrahydro-1H-pyrido[4,3-b]indole-6-carboxylate |
| 312x | ethyl 5-(pyridin-3-ylmethyl)-2,3,4,5-tetrahydro-1H-pyrido[4,3-b]indole-6-carboxylate |
| 313x | ethyl 5-(pyridin-5-ylmethyl)-2,3,4,5,-tetrahydro-1H-pyrido[4,3-b]indole-6-carboxylate |
| 314x | ethyl 5-(pyridin-4-ylmethyl)-2-(thiophen-2-ylmethyl)-2,3,4,5-tetrahydro-1H-pyrido[4,3-b]indole-6-carboxylate |
| 315x | ethyl 2-benzyl-5-(pyridin-3-ylmethyl)-2,3,4,5-tetrahydro-1H-pyrido[4,3-b]indole-6-carboxylate |
| 316x | 2-tert-butyl 6-ethyl 5-(4-fluorobenzyl)-3,4-dihydro-1H-pyrido[4,3-b]indole-2,6(5H)-dicarboxylate |
| 317x | 2-tert-butyl 6-ethyl 5-(pyridin-4-ylmethyl)-3,4-dihydro-1H-pyrido[4,3-b]indole-2,6(5H)-dicarboxylate |
| 318x | 2-tert-butyl 6-ethyl 5-(pyridin-3-ylmethyl)-3,4-dihydro-1H-pyrido[4,3-b]indole-2,6(5H)-dicarboxylate |

In one variation, the compound is of the formula (I) wherein the compound further is a type 1 compound. In another variation, the compound is of the formula (I) wherein the compound further is a type 2 compound. In yet another variation, the compound is of the formula (I) wherein the compound further is a type 3 compound. In a further variation, the compound is of the formula (I) wherein the compound further is a type 4 compound.

The invention also includes all salts of compounds referred to herein, such as pharmaceutically acceptable salts. The invention also includes any or all of the stereochemical forms, including any enantiomeric or diasteriomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, Huntington's disease, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $\alpha$1D, $\alpha$2A and/or $\alpha$2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least two of the following receptors are modulated: adrenergic receptor (e.g., $\alpha$1D, $\alpha$2A and/or $\alpha$2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least three of the following receptors are modulated: adrenergic receptor (e.g., $\alpha$1D, $\alpha$2A and/or $\alpha$2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, each of the following receptors are modulated: adrenergic receptor (e.g., $\alpha$1D, $\alpha$2A and/or $\alpha$2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least one of the following receptors is modulated: $\alpha$1D, $\alpha$2A, $\alpha$2B, 5-HT2A, 5-HT2C, 5-HT6, 5-HT7, D2L, H1, H2 and H3. In another variation, at least two or three or four or five or six or seven or eight or nine or ten or eleven of the following receptors are modulated: $\alpha$1D, $\alpha$2A, $\alpha$2B, 5-HT2A, 5-HT2C, 5-HT6, 5-HT7, D2L, H1, H2 and H3. In a particular variation, at least dopamine receptor D2L is modulated. In another particular variation, at least dopamine receptor D2L and serotonin receptor 5-HT2A are modulated. In a further particular variation, at least adrenergic receptors $\alpha$1D, $\alpha$2A, $\alpha$2B and serotonin receptor 5-HT6 are modulated. In another particular variation, at least adrenergic receptors $\alpha$1D, $\alpha$2A, $\alpha$2B, serotonin receptor 5-HT6 and one or more of serotonin receptor 5-HT7, 5-HT2A, 5-HT2C and histamine receptor H1 and H2 are modulated. In a further particular variation, histamine receptor H1 is modulated. In another variation, compounds of the invention exhibit any receptor modulation activity detailed herein and further stimulate neurite outgrowth and/or neurogenesis and/or enhance neurotrophic effects.

The invention is also directed to pharmaceutical compositions comprising a compound of the invention and a pharmaceutically acceptable carrier or excipient. Kits comprising a compound of the invention and instructions for use are also embraced by this invention.

DETAILED DESCRIPTION OF THE INVENTION

Definitions

Figure 1A:
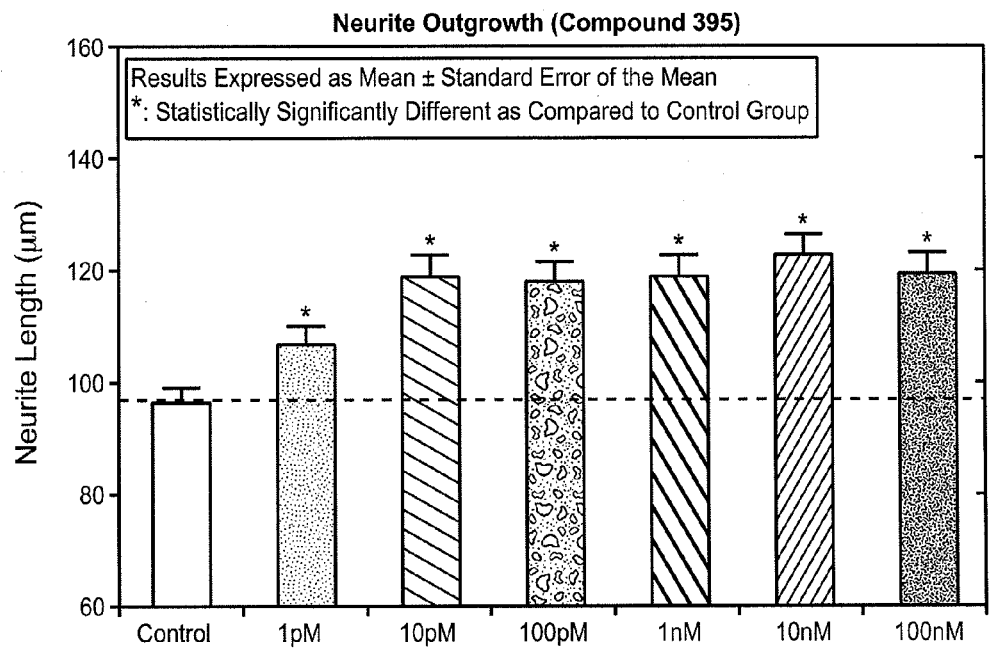
FIGS. 1A-D show the effect of compounds 395, 68, 250, and 20 at different concentrations on neurite outgrowth using cortical neurons. Asterisk (*) indicates significant difference over control group.
Figure 1B:
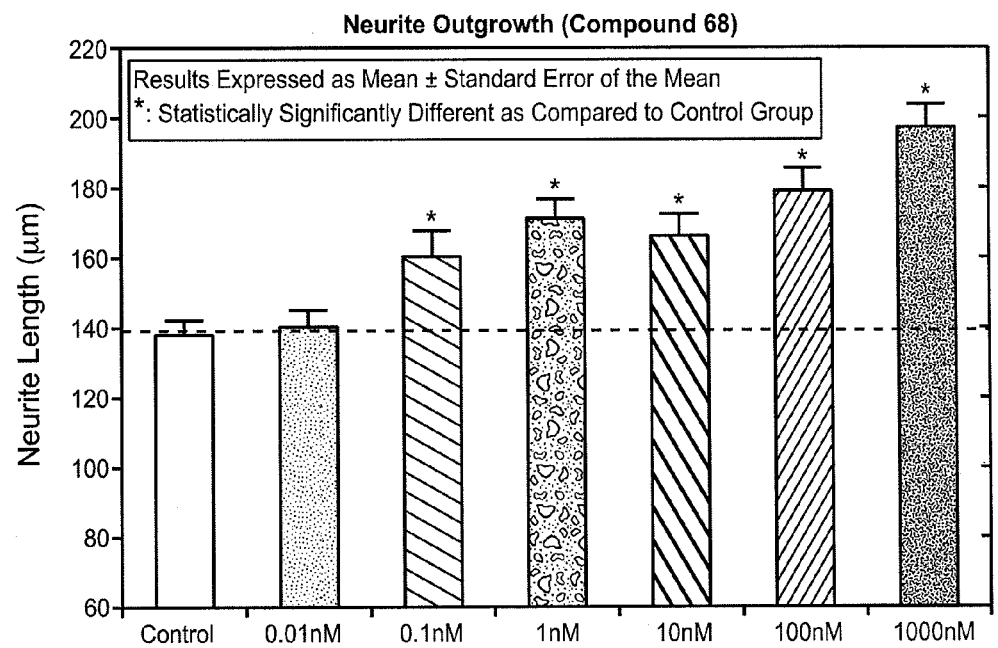
Figure 1C:
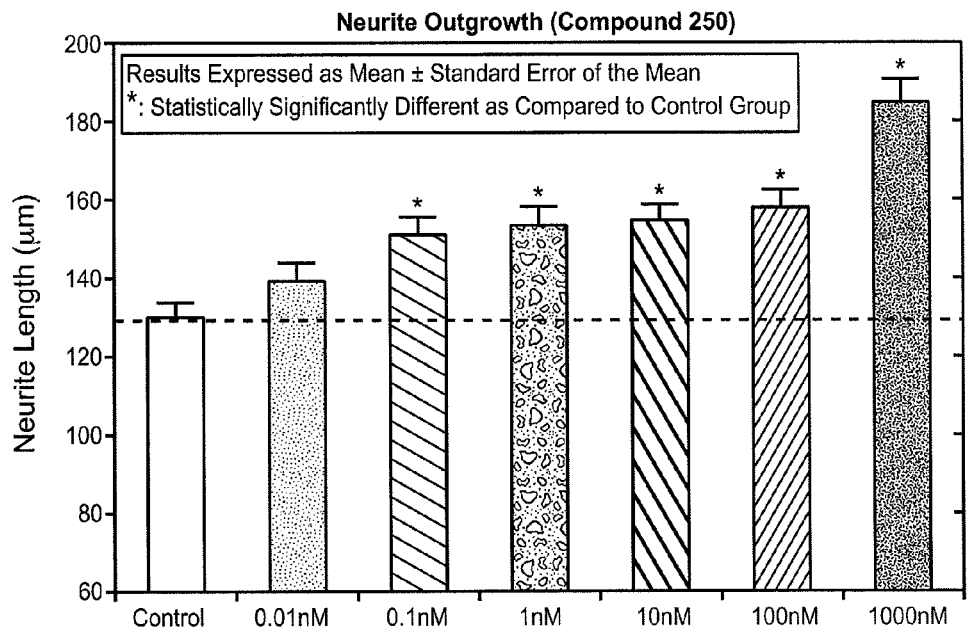
Figure 1D:
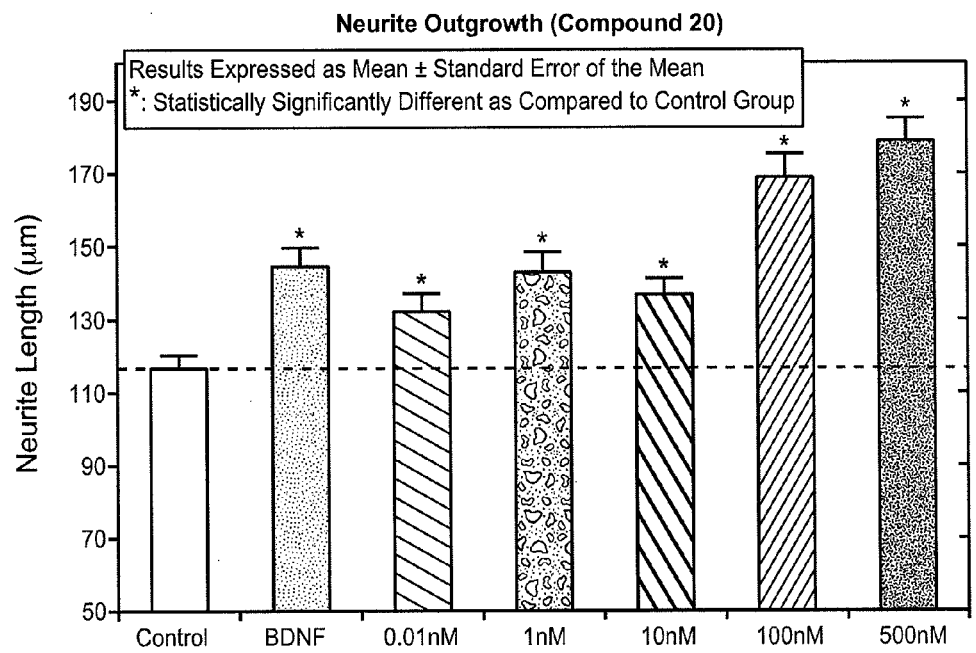

Unless clearly indicated otherwise, use of the terms "a", "an" and the like refers to one or more.

The term "about" as used herein refers to the usual range of variation for the respective value readily known to the skilled person in this technical field. Reference to "about" a value or parameter herein includes (and describes) embodiments that are directed to that value or parameter per se.

As used herein, the term "aminergic G protein-coupled receptors" refers to a family of transmembrane proteins involved in cellular communication. Aminergic G protein coupled receptors are activated by biogenic amines and represent a subclass of the superfamily of G protein coupled receptors, which are structurally characterized by seven transmembrane helices. Aminergic G protein-coupled receptors include but are not limited to adrenergic receptors, serotonin receptors, dopamine receptors, histamine receptors and imidazoline receptors.

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an α1-adrenergic receptor (e.g., α1A, α1B and/or α1D) and/or a α2-adrenergic receptor (e.g., α2A, α2B and/or α2C) and/or reduces or eliminates or increases or enhances or mimics an activity of a α1-adrenergic receptor (e.g., α1A, α1B and/or α1D) and/or a α2-adrenergic receptor (e.g., α2A, α2B and/or α2C) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 (D1) and/or a dopamine-2 (D2) receptor or reduces or eliminates or increases or enhances or mimics an activity of a dopamine-1 (D1) and/or a dopamine-2 (D2) receptor in a reversible or irreversible manner. Dopamine D2 receptors are divided into two categories, D2L and D2S, which are formed from a single gene by differential splicing. D2L receptors have a longer intracellular domain than D2S. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor or reduces or eliminates or increases or enhances or mimics an activity of a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine H1 and/or H2 and/or H3 receptor or reduces or eliminates or increases or enhances or mimics an activity of a histamine H1 and/or H2 and/or H3 receptor in a reversible or irreversible manner. In some embodiments, the histamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the histamine receptor modulator reduces an activity of a histamine receptor by at least about or about any of 10%, 20%, 30%, 40%, 50%, 60%, 70%, 80%, 90%, 95% or 100% as compared to the corresponding activity in the same subject prior to treatment with the histamine receptor modulator or compared to the corresponding activity in other subjects not receiving the histamine receptor modulator. In some embodiments, the histamine receptor modulator enhances an activity of a histamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the histamine receptor modulator or compared to the corresponding activity in other subjects not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining beneficial or desired results, including clinical results. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions.

Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, amyotrophic lateral sclerosis (ALS), autism, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barre syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic, and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. Aβ appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 1996, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: Mechanistic Implications, *Ann Neurol.*, 2005, 57(5), 695-703; Wang et al., Insights into amyloid-β-induced mitochondrial dysfunction in Alzheimer disease, *Free Radical Biology & Medicine,* 2007, 43, 1569-1573; Swerdlow et al., Mitochondria in Alzheimer's disease, *Int. Rev. Neurobiol.,* 2002, 53, 341-385; and Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntintin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" are used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) *Am. J. Psychiatry* 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep, John, Ferris, Reisberg, et al. (1994) *Neurobiol. Aging* 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. A pharmaceutically acceptable salt intends ionic interactions and not a covalent bond. As such, an N-oxide is not considered a salt. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. In fused ring systems, one or more of the rings can be aryl or heteroaryl. A cycloalkyl having more than one ring where at least one ring is aromatic may be connected to the parent structure at either a non-aromatic ring position or at an aromatic ring position. In one variation, a cycloalkyl having more than one ring where at least one ring is aromatic is connected to the parent structure at a non-aromatic ring position. A preferred cycloalkyl is a saturated cyclic hydrocarbon having from 3 to 13 annular carbon atoms. A more preferred cycloalkyl is a saturated cyclic hydrocarbon having from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Alkylene" refers to the same residues as alkyl, but having bivalency. Examples of alkylene include ethylene (—CH$_2$CH$_2$—) and propylene (—CH$_2$CH$_2$CH$_2$—).

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —CH$_2$—CH=CH—CH$_3$ and —CH$_2$—CH$_2$-cyclohexenyl, where the ethyl group of the later example can be attached to the cyclohexenyl moiety at any available position on the ring.

"Alkynyl" refers to an unsaturated hydrocarbon group having at least one site of acetylinic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents s including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like (e.g., oxide such as when an annular nitrogen is substituted with an oxide).

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. A "substituted aralkyl" refers to a residue in which an aryl moiety is attached to a substituted alkyl residue and wherein the aralkyl group may be attached to the parent structure at either the aryl or the alkyl residue.

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —NH$_2$.

"Substituted amino" refers to the group —NR$_a$R$_b$, where either (a) each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that both R$_a$ and R$_b$ groups are not H; or (b) R$_a$ and R$_b$ are joined together with the nitrogen atom to form a heterocyclic or substituted heterocyclic ring.

"Acylamino" refers to the group —C(O)NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic or R$_a$ and R$_b$ groups can be joined together with the nitrogen atom to form a heterocyclic or substituted heterocyclic ring.

"Aminoacyl" refers to the group —NR$_a$C(O)R$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic. Preferably, R$_a$ is H or alkyl.

"Aminosulfonyl" refers to the groups —NRSO$_2$-alkyl, —NRSO$_2$ substituted alkyl, —NRSO$_2$—alkenyl, —NRSO$_2$-substituted alkenyl, —NRSO$_2$-alkynyl, —NRSO$_2$-substituted alkynyl, —NRSO$_2$-aryl, —NRSO$_2$-substituted aryl, —NRSO$_2$-heteroaryl, —NRSO$_2$-substituted heteroaryl, —NRSO$_2$-heterocyclic, and —NRSO$_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$—substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic.

"Carbonylalkylenealkoxy" refers to the group —C(=O)—(CH$_2$)$_n$—OR where R is a substituted or unsubstituted alkyl and n is an integer from 1 to 100, more preferably n is an integer from 1 to 10 or from 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc., refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.
"Carboxyl" refs to the group —C(O)OH.
"Cyano" refers to the group —CN.
"Oxo" refers to the moiety =O.
"Nitro" refers to the group —NO$_2$.
"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure S compound means that the composition contains no more than 15% or no more than 10% or no more than 5% or no more than 3% or no more than 1% of the R form of the compound.

Compounds of the Invention:

Compounds according to the invention are detailed herein, including in the Brief Summary of the Invention and the appended claims. Thus, compounds of the invention include any compounds detailed herein. The invention includes the use of all of the compounds described herein, including any and all stereoisomers, salts and solvates of the compounds described as histamine receptor modulators. Further methods of using the compounds of the invention are detailed throughout.

The invention embraces compounds of the Formula (I):

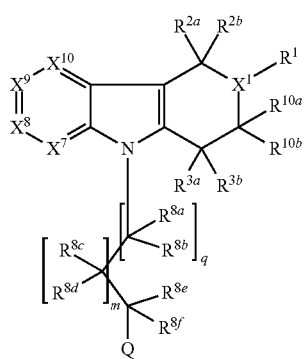

(I)

where:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$ and R$^{2b}$ is independently H, substituted or unsubstituted C$_1$-C$_8$ alkyl, halo, hydroxyl, alkoxy, cyano, nitro or R$^{2a}$ and R$^{2b}$ are taken together to form a carbonyl moiety;

each R$^{3a}$ and R$^{3b}$ is independently H, substituted or unsubstituted C$_1$-C$_8$ alkyl, halo, cyano or nitro or R$^{3a}$ and R$^{3b}$ are taken together to form a carbonyl moiety;

each X$^7$, X$^8$, X$^9$ and X$^{10}$ is independently N or CR$^4$;

m and q are independently 0 or 1;

X$^1$ is N or CH;

each R$^4$ is independently H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$ and R$^{8f}$ is independently H, hydroxyl, C$_1$-C$_8$ alkyl or is taken together with the carbon to which it is attached and a geminal R$^{8(a\text{-}f)}$ to form a cycloalkyl moiety or a carbonyl moiety;

each R$^{10a}$ and R$^{10b}$ is independently H, halo, a substituted or unsubstituted C$_1$-C$_8$ alkyl, hydroxyl, alkoxyl or R$^{10a}$ and R$^{10b}$ are taken together to form a carbonyl;

Q is a substituted or unsubstituted aryl, substituted or unsubstituted heteroaryl, substituted or unsubstituted C$_{3\text{-}8}$ cycloalkyl, substituted or unsubstituted C$_{3\text{-}8}$ cycloalkenyl or substituted or a unsubstituted heterocyclyl;

provided that: (i) when X$^1$ is N the compound is other than a compound in Table 1 or salt thereof; and (ii) the compound is other than those compounds listed in U.S. Pat. Nos. 6,187,785, 7,071,206, 3,409,628 and 6,849,640 or in PCT Publication Nos. WO 2005/05591, WO 2007/041697 and WO 2007/087425. In another variation, the compounds of the invention, and methods of using the compounds detailed herein, encompass any of the compounds of Formula (I), including those listed in Table 1 or a salt thereof. In one variation, the compound is of the formula (I) wherein R$^4$ is other than a substituted or unsubstituted aryl, substituted or unsubstituted heteroaryl, an aryloxy or an aralkyl. In one variation the compound is of the formula (I) wherein R$^4$ is other than a substituted or unsubstituted aryl. In another variation, the compound is of formula (I) wherein at least one of X$^7$, X$^8$, X$^9$ and X$^{10}$ is N, provided that the compound is other than a compound of 233x, 234x or 235x, or a salt or solvate thereof. In another variation, the compound is of the formula (I) wherein at least one of X$^7$, X$^8$, X$^9$ and X$^{10}$ is N and R$^1$ is methyl.

In one variation, when the compound is of the formula (I) and X$^1$ is CH, then the compound is of the formula (AA) where X$^7$-X$^{10}$, R$^{2a}$, R$^{2b}$, R$^{3a}$, R$^{3b}$, R$^{8a}$-R$^{8f}$, R$^{10a}$, R$^{10b}$, m, q and Q are as defined in formula (I).

In one variation, the compound is of the formula (I) wherein the compound further is a type 1 compound. In another variation, the compound is of the formula (I) wherein the compound further is a type 2 compound. In yet another variation, the compound is of the formula (I) wherein the compound further is a type 3 compound. In a further variation, the compound is of the formula (I) wherein the compound further is a type 4 compound.

In one variation, a compound is of the formula (AA):

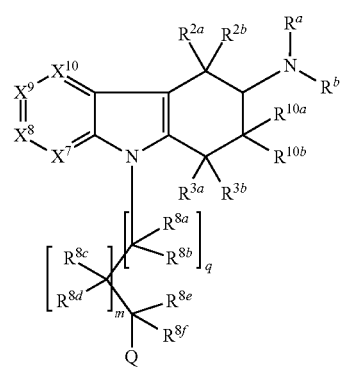

(AA)

where:

X$^7$-X$^{10}$, R$^{2a}$, R$^{2b}$, R$^{3a}$, R$^{3b}$, R$^{8a}$-R$^{8f}$, R$^{10a}$, R$^{10b}$, m, q and Q are as defined in one variation in formula (I) and in another variation in formula (E) and either:

(a) each R$^a$ and R$^b$ is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that both $R^a$ and $R^b$ groups are not H, and one or more of (i)-(iii) apply:
(i) when m and q are 0, at least one of $R^a$ and $R^b$ is other than methyl;
(ii) when m and q are 0, at least one of $X^7$-$X^{10}$ is other than CH;
(iii) when m and q are 0, either (a) Q is a other than a substituted or unsubstituted phenyl or (b) Q is a substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl; or
(b) $R^a$ and $R^b$ are joined together with the nitrogen atom to which they are attached to form a heterocyclic or substituted heterocyclic ring,
or a pharmaceutically acceptable salt thereof.

In one variation of formula (AA), at least one of m and q is 1 and either (a) each $R^a$ and $R^b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that both $R^a$ and $R^b$ groups are not H; or (b) $R^a$ and $R^b$ are joined together with the nitrogen atom to form a heterocyclic or substituted heterocyclic ring.

In another variation, a compound is of the formula (AB):

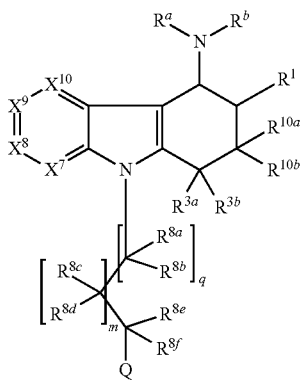

(AB)

where:
$X^7$-$X^{10}$, $R^1$, $R^{3a}$, $R^{3b}$, $R^{8b}$-$R^{8f}$, $R^{10a}$, $R^{10b}$, m, q and Q are as defined in one variation in formula (I) and in another variation in formula (E) and either:
(a) each $R^a$ and $R^b$ is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that when m and q are 0, one or more of (i)-(v) apply:
(i) at least one of $R^{8e}$ and $R^{8f}$ is hydroxyl, $C_1$-$C_8$ alkyl or $R^{8e}$ and $R^{8f}$ are taken together with the carbon to which they are attached o form a cycloalkyl moiety or a carbonyl moiety;
(ii) Q is a substituted aryl, substituted or unsubstituted heteroaryl, substituted or unsubstituted $C_{3-8}$ cycloalkyl, substituted or unsubstituted $C_{3-8}$ cycloalkenyl or a substituted or unsubstituted heterocyclyl;
(iii) $R^a$ and $R^b$ are other than a substituted alkyl;
(iv) at least one of $X^7$-$X^{10}$ is other than CH; and (v) $R^1$ is hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, acylamino, sulfonylamino, sulfonyl or carbonylalkylenealkoxy; or
(b) $R^a$ and $R^b$ are joined together with the nitrogen atom to which they are attached to form a heterocyclic or substituted heterocyclic ring,
or a pharmaceutically acceptable salt thereof.

In one variation of formula (AB), Q is other than a substituted phenyl. In another variation of formula (AB), each $R^a$ and $R^b$ is independently selected from H, alkyl, alkenyl, substituted alkenyl, alkynyl, substituted alkynyl, aryl, substituted aryl, heteroaryl, substituted heteroaryl, heterocyclic and substituted heterocyclic.

In a further variation, a compound is of the formula (AC):

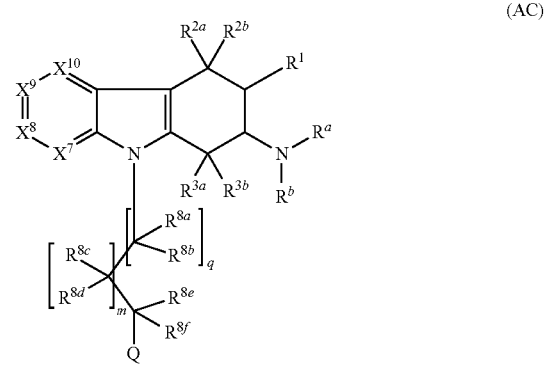

(AC)

where:
$X^7$-$X^{10}$, $R^1$, $R^{2a}$, $R^{2b}$, $R^{3a}$, $R^{3b}$, $R^{8a}$-$R^{8f}$, m, q and Q are as defined in one variation in formula (I) and in another variation in formula (E) and either:
(a) each $R^a$ and $R^b$ is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that when m and q are 0, one or more of (i)-(v) apply:
(i) $R^{8e}$ and $R^{8f}$ are independently H, hydroxyl, $C_1$-$C_8$ alkyl or $R^{8e}$ and $R^{8f}$ are taken together with the carbon to which they are attached to form a cycloalkyl moiety;
(ii) Q is a unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl;
(iii) $R^a$ and $R^b$ are other than a substituted alkyl;
(iv) at least one of $X^7$-$X^{10}$ is other than CH; and
(v) $R^1$ is hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, acylamino, sulfonylamino, sulfonyl or carbonylalkylenealkoxy; or (b) $R^a$ and $R^b$ are joined together with the nitrogen atom to which they are attached to form a heterocyclic or substituted heterocyclic ring;

or a pharmaceutically acceptable salt thereof.

In a particular variation of formula (AC), Q is other than an unsubstituted phenyl. In another variation of formula (AC), each $R^a$ and $R^b$ is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclyl and substituted heterocyclyl.

In one variation, the invention embraces compounds of the formula (H):

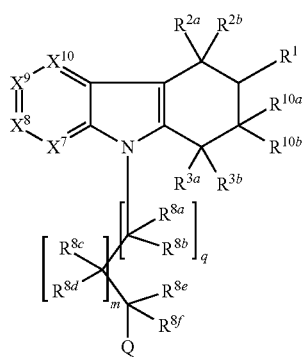

(H)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, $R^{2a}$ and $R^{2b}$ are taken together to form a carbonyl moiety or $R^{2a}$ and $R^{2b}$ are taken together with the carbon to which they are attached to form a cycloalkyl moiety;

each $R^{3a}$ and $R^{3b}$ is independently H, substituted or unsubstituted $C_1$-$C_8$ alkyl, halo, hydroxyl, alkoxy, cyano, nitro or $R^{3a}$ and $R^{3b}$ are taken together to form a carbonyl moiety or $R^{3a}$ and $R^{3b}$ are taken together with the carbon to which they are attached to form a cycloalkyl moiety;

each $X^7$, $X^8$, $X^9$ and $X^{10}$ is independently N or $CR^4$;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, or is taken together with the carbon to which it is attached and a geminal $R_8$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxy, cyano, nitro, substituted or unsubstituted amino, $R^{10a}$ and $R^{10b}$ are taken together to form a carbonyl or $R^{10a}$ and $R^{10b}$ are taken together with the carbon to which they are attached to form a cycloalkyl moiety;

Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl;

provided that exactly one of $R^1$, $R^{2a}$, $R^{2b}$, $R^{10a}$ and $R^{10b}$, is substituted or unsubstituted amino;

or a salt thereof.

In another variation, the invention embraces compounds of the formula (A):

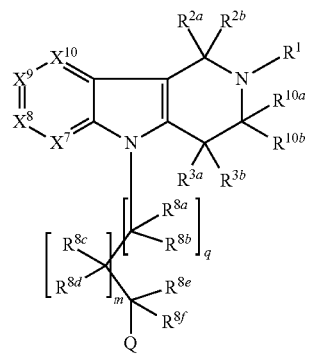

(A)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano or nitro or $R^{3a}$ and $R^{3b}$ are taken together to form a carbonyl moiety;

each $X^7$, $X^8$, $X^9$ and $X^{10}$ is independently N or $CR^4$;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl or is taken together with the carbon to which it is attached and a geminal $R^{8(a-f)}$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl;

provided that the compound is other than (i) a compound in Table 1 or salt thereof and (ii) the compound is other than any of compounds 229H, 230, 241, 255, 256, 262 and 274 or a salt thereof. In another variation, the compounds of the invention, and methods of using the compounds and administering the compounds as detailed herein, encompass any of the compounds of formula A, including those listed in Table 1 or a salt thereof and compounds 229H, 230, 241, 255, 256, 262 and 274, or a salt thereof. In a further variation, the compound is of the formula (A) provided that the compound is other than (i) a compound in Table 1 or salt thereof and (ii) the compound is other than any of compounds 229H, 230, 241, 255, 256, 262 and 274 or a salt thereof and (iii) a compound in Table 1A or salt thereof.

In one variation, the compound is of the formula (A) provided that: (i) it is other than a compound in Table 1 or salt thereof; and (ii) the compound is other than those compounds listed in U.S. Pat. Nos. 6,187,785, 7,071,206, 3,409,628 and 6,849,640 or in PCT Publication Nos. WO 2005/05591, WO 2007/041697 and WO 2007/087425. In another variation, the compounds of the invention, and methods of using the compounds detailed herein, encompass any of the compounds of formula A, including those listed in Table 1 or Table 1A or a salt thereof. In one variation, the compound is of the formula (A) wherein $R^4$ is other than a substituted or unsubstituted aryl, substituted or unsubstituted heteroaryl, an aryloxy or an aralkyl. In one variation the compound is of the formula (A) wherein $R^4$ is other than a substituted or unsubstituted aryl. In another variation, the compound is of formula (A) wherein at least one of $X^7$, $X^8$, $X^9$ and $X^{10}$ is N, provided that the compound is other than a compound of 233x, 234x or 235x, or a salt or solvate thereof. In another variation, the compound is of formula (A) wherein at least one of $X^7$, $X^8$, $X^9$ and $X^{10}$ is N and $R^1$ is methyl.

In another variation, the invention embraces compounds of the formula (E):

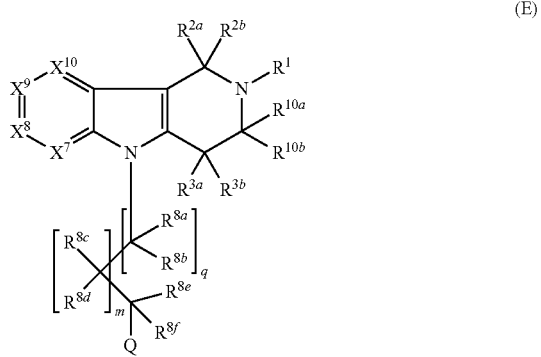

(E)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety or $R^{2a}$ and $R^{2b}$ are taken together with the carbon to which they are attached to form a cycloalkyl moiety;

each $R^{3a}$ and $R^{3b}$ is independently H, substituted or unsubstituted $C_1$-$C_8$ alkyl, halo, hydroxyl, alkoxy, cyano, nitro or $R^{3a}$ and $R^{3b}$ are taken together to form a carbonyl moiety or $R^{3a}$ and $R^{3b}$ are taken together with the carbon to which they are attached to form a cycloalkyl moiety;

each $X^7$, $X^8$, $X^9$ and $X^{10}$ is independently N or $CR^4$;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, or is taken together with the carbon to which it is attached and a geminal $R_8$ to form a cycloalkyl moiety or a carbonyl moiety;

each $R^{10a}$ and $R^{10b}$ is independently H, substituted or unsubstituted $C_1$-$C_8$ alkyl, halo, hydroxyl, alkoxy, cyano, nitro or $R^{10a}$ and $R^{10b}$ are taken together to form a carbonyl moiety or $R^{10a}$ and $R^{10b}$ are taken together with the carbon to which they are attached to form a cycloalkyl moiety; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl;

provided that (i) the compound is other than a compound in Table 1 or salt thereof; (ii) the compound is other than a compound of Table 1A or a salt thereof and (iii) the compound is other than any of compounds 229H, 230, 241, 255, 256, 262 and 274 or a salt thereof. In another variation, the compounds of the invention, and methods of using the compounds and administering the compounds as detailed herein, encompass any of the compounds of formula (E), including those listed in Table 1 and Table 1A or a salt thereof and compounds 229H, 230, 241, 255, 256, 262 and 274, or a salt thereof. In one variation, Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl. In another variation, the compound is of the formula (E) further provided that when Q is a substituted or unsubstituted heteroaryl, it is other than a thiazole, triazole, or oxadiazole. However, in another variation, the compound is of the formula (E) and includes compounds in which Q is a thiazole, triazole, or oxadiazole. In still another variation, the compound is of the formula (E) further provided that the compound is other than a compound of formula (G). However, in another variation, the compound is of the formula (E) and includes compounds that conform to the formula (G).

In one variation, the compound is of the formula (E) wherein the compound further is a type 1 compound. In another variation, the compound is of the formula (E) wherein the compound further is a type 2 compound. In yet another variation, the compound is of the formula (E) wherein the compound further is a type 3 compound. In a further variation, the compound is of the formula (E) wherein the compound further is a type 4 compound.

In another variation, the invention embraces compounds of the formula (A) or (E) where at least one of m and q is 1 and where Q is a substituted phenyl. In one variation, Q is a phenyl substituted with 0 to 6 $R^9$ moieties where each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino moiety. In another variation, Q is a phenyl substituted with at least one alkyl, perhaloalkyl, halo, hydroxyl or alkoxy moiety. In still another variation, Q is a phenyl substituted with at least one alkyl, perhaloalkyl, halo, cyano, nitro, hydroxyl, alkoxy, or perhaloalkoxy moiety. In another such variation, Q is a phenyl substituted with two or three moieties selected from methyl, perhaloalkyl, halo, hydroxyl and alkoxy. In a particular variation, at least one of m and q is 1, and Q is a phenyl substituted with at least one of: methyl, trifluoromethyl, fluoro, chloro, hydroxyl, methoxy, ethoxy and isopropoxy. When Q is a phenyl substituted with two or three moieties, the moieties may be the same or different. For example, when at least one of m and q is 1, Q in one variation is difluorophenyl, dichlorophenyl, dimethoxyphenyl, di(trifluoromethyl)phenyl, trifluorophenyl, (fluoro)(chloro)phenyl, (fluoro)(trifluoromethyl)phenyl, (chloro)(trifluoromethyl)phenyl or (fluoro)(methoxy)phenyl. In one variation, when the compound is of the formula (A) or (E) and Q is a substituted phenyl, the substituent or substituents may be positioned at any available phenyl ring position. For example, singly-substituted phenyl groups may be substituted at the ortho, meta or para-position of the phenyl group. Any available phenyl ring substitution pattern is suitable for di- or tri-substituted phenyl groups (e.g., at the ortho and para positions, at two ortho positions, at two meta positions, at the meta and para positions, at the ortho, meta and para positions, at two ortho and the para position, at two ortho and a meta position, or at two meta and a para or ortho position). In one variation, the compound is of the formula (A) or (E) where one of m and q is 1 and the other is 0 and Q is a substituted phenyl. In further variation, the compound is of the formula (A) or (E) where both m and q are 1 and Q is a substituted phenyl.

In another variation, the invention embraces compounds of the formula (A) or (E) where m and q are 0, Q is a substituted phenyl wherein the substituent is positioned at the ortho and/or meta position of the phenyl ring and the para-position bears a hydrogen and $R^1$ is methyl or ethyl. In another variation, the invention embraces compounds of the formula (A) or (E) where m and q are 0, Q is a substituted phenyl wherein the substituent is positioned at the ortho and/or meta position of the phenyl ring and the para-position bears a hydrogen and $R^1$ is methyl or ethyl, provided that Q is other than 3-methylphenyl. In one variation, Q is a mono-substituted phenyl that is substituted at the ortho or meta position. In one variation, Q is a mono-substituted phenyl that is substituted at the ortho position. Suitable phenyl substituents and substitution patterns include those detailed in the proceeding paragraph.

In another variation, the invention embraces compounds of the formula (A) or (E) where m and q are 0, Q is a substituted phenyl and $R^1$ is methyl, provided that at least one of (i)-(iii) applies: (i) when $R^{8e}$ and $R^{8f}$ are taken together with the carbon to which they are attached to form a carbonyl, $X^9$ is other than $CR^4$ where $R^4$ is methyl; (ii) Q is a substituted phenyl having at least one fluoro substituent; and (iii) when Q is 4-methoxyphenyl, $X^9$ is other than $CR^4$ where $R^4$ is chloro. In another variation, the invention embraces compounds of the formula (A) or (E) where m and q are 0, Q is a substituted phenyl and $R^1$ is methyl, provided that at least one of (i)-(iii) applies: (i) when $R^{8e}$ and $R^{8f}$ are taken together with the carbon to which they are attached to form a carbonyl, $X^9$ is other than $CR^4$ where $R^4$ is $OCH_3$; (ii) Q is a substituted phenyl having at least one fluoro substituent provided that Q is other than 4-fluorophenyl; and (iii) when Q is 4-methoxyphenyl, $X^9$ is other than $CR^4$ where $R^4$ is chloro.

In one variation, the compound is of the formula (A) or (E) where one of m and q is 1 and the other is 0 and $R^{8e}$ and $R^{8f}$ are taken together with the carbon to which they are attached to form a carbonyl. In one variation, the compound is of the formula (A) or (E) where one of m and q is 1 and the other is 0 and $R^{8e}$ and $R^{8f}$ are taken together with the carbon to which they are attached to form a carbonyl provided that (i) $R^1$ is other than isopropyl and/or (ii) Q is other than a substituted piperizinyl. In another variation, the compound is of the formula (A) or (E) where one of m and q is 1 and the other is 0, $R^{8e}$ and $R^{8f}$ are taken together with the carbon to which they are attached to form a carbonyl and $R^1$ is $CH_3$ or H. In still a further variation, the compound is of the formula (A) or (E) where one of m and q is 1 and the other is 0, $R^{8e}$ and $R^{8f}$ are taken together with the carbon to which they are attached to form a carbonyl, $R^1$ is $CH_3$ or H, $X^7$, $X^8$ and $X^{10}$ are CH and $X^9$ is $CR^4$ where $R^4$ is halo (e.g., chloro, bromo, iodo) or alkyl (e.g., methyl). In still a further such variation, $R^1$ is $CH_3$ or H, $X^7$, $X^8$ and $X^{10}$ are CH, $X^9$ is $CR^4$ where $R^4$ is halo (e.g., chloro, bromo, iodo) or alkyl (e.g., methyl) and $R^{2a}$, $R^{2b}$, $R^{3a}$, $R^{3b}$, $R^{10a}$ and $R^{10b}$ are each hydrogen. In still further such variation, where Q is substituted or unsubstituted piperazinyl, $R^1$ is other than iso-propyl. In still a further such variation, where Q is substituted or unsubstituted piperazinyl, $R^1$ is H, $CH_3$ or ethyl.

In one variation, the compound is of the formula (A) or (E) where both m and q are 1 and either: (a) at least one of $X^7$-$X^{10}$ is other than CH or (b) Q is a monocycle selected from a substituted or unsubstituted aryl, substituted or unsubstituted heteroaryl, substituted or unsubstituted $C_{3-8}$ cycloalkyl, substituted or unsubstituted $C_{3-8}$ cycloalkenyl and substituted or unsubstituted heterocyclyl. In one variation, the compound is of the formula (A) or (E) where both m and q are 1 and either: (a) at least one of $X^7$-$X^{10}$ is other than CH and $OCH_3$ or (b) Q is a monocycle selected from a substituted or unsubstituted aryl, substituted or unsubstituted heteroaryl, substituted or unsubstituted $C_{3-8}$ cycloalkyl and substituted or unsubstituted $C_{3-8}$ cycloalkenyl. In a particular variation, the compound is of the formula (A) or (E) where both m and q are 1 and at least one of $X^7$-$X^{10}$ is $CR^4$ where $R^4$ is halo or alkyl. In a still further variation, both m and q are 1; at least one of $X^7$-$X^{10}$ is $CR^4$ where $R^4$ is halo or alkyl; $R^1$ is alkyl and $R^{2a}$, $R^{2b}$, $R^{3a}$, $R^{3b}$, $R^{10a}$ and $R^{10b}$ are each hydrogen.

In one variation, the compound is of the formula (A) or (E) where at least one of $R^{8a}$-$R^{8f}$, where present, is OH. As such, when m is 0 and q is 1, at least one of $R^{8a}$, $R^{8b}$, $R^{8e}$ and $R^{8f}$ is OH. In a further variation, the compound is of the formula (A) or (E) where one of $R^{8a}$-$R^{8f}$ is OH and its geminal $R^{8(a-f)}$ moiety is alkyl or perhaloalkyl. In a further such variation, one of m and q is 1 and the other is 0; one of $R^{8a}$-$R^{8f}$ is OH and its geminal $R^{8(a-f)}$ moiety is alkyl (e.g., methyl, ethyl, cyclopropyl) or perhaloalkyl (e.g., trifluoroalkyl); $X^7$, $X^8$ and $X^{10}$ are each CH; $X^9$ is $CR^4$ where $R^4$ is alkyl (e.g., methyl) or halo (e.g., chloro, fluoro); and $R^1$ is alkyl (e.g., methyl, cyclopropyl).

In one variation, the compound is of the formula (A) or (E) where both m and q are 0 and either:
  (a) Q is phenyl and $R^1$ is ethyl;
  (b) Q is 6-methyl-3-pyridyl and $R^{8e}$ and $R^{8f}$ are both H; or
  (c) Q is 6-methyl-3-pyridyl and $X^9$ is C—$R^4$ where $R^4$ is hydroxyl, nitro, cyano, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In another variation, the compound is of the formula (A) or (E) where both m and q are 0, Q is 6-methyl-3-pyridyl and $X^9$ is C—$R^4$ where $R^4$ is hydrogen or alkyl (e.g., methyl).

In one variation, the compound is of the formula (A) or (E) where at least one of $X^7$-$X^{10}$ is N, and at least one of (i)-(iii) applies:
  (i) $R^{8e}$ and $R^{8f}$ are both H;
  (ii) $R^1$ is methyl; and
  (iii) Q is a substituted or unsubstituted pyridyl.

In one such variation, when Q is a substituted pyridyl, it is substituted with an alkyl (e.g., methyl, ethyl, isopropyl, n-propyl, cyclopropyl), perhaloalkyl (e.g., trifluoromethyl), substituted alkyl (e.g., hydroxymethyl), carboxyl, carbonylalkoxy (e.g., $CO_2CH_3$, $CO_2CH_2CH_3$), substituted amino (e.g., $NHCH_3$, $N(CH_3)_2$, $NHCH(CH_3)_2$), aminoacyl (e.g., NHC(O)$CH_3$), alkoxy (e.g., $OCH_3$, $OCH_2CH_3$), N-oxide (e.g., when the annular nitrogen of the pyridyl is substituted with an oxide), an aryl or heteroaryl fused to the pyridyl, halo (e.g., F, Cl, Br), hydroxyl, N-alkyl (e.g., where the N of the pyridyl is substituted with a methyl group or cyclopropyl group), N-perhaloalkyl (e.g., where the N of the pyridyl is substituted with a trifluoromethyl group), oxo (which may exist as a tautomer when ortho to the annular nitrogen of the pyridine ring). The substituted pyridyl is preferably substituted with one or two substituents. The substituents may be positioned at any available position on the pyridyl ring. For example, a monosubstituted 3-pyridyl may have its substituent at the 2, 4, 5 or 6 positions.

In one variation, the compound is of the formula (A) or (E) where $X^9$ is C—$R^4$ where $R^4$ is —COOH, provided that when $R^1$ is methyl, Q is other than 6-methyl-3-pyridyl or 4-pyridyl. In one variation, the compound is of the formula (A) or (E) where one of m and q is 1 and the other is 0, $X^9$ is C—$R^4$ where $R^4$ is —COOH, provided that when $R^1$ is methyl, Q is other than 6-methyl-3-pyridyl or 4-pyridyl. In another variation, when $X^9$ is C—$R^4$ and $R^1$ is H, Q is other than 6-methyl-3-pyridyl. However, in a further variation, the methods of the invention, pharmaceutical compositions, kits, and purified or isolated forms of the compounds include a compound of the formula (A) or (E) when $X^9$ is C—$R^4$, $R^1$ is H and Q is 6-methyl-3-pyridyl.

In one variation, the compound is of the formula (A) or (E) where Q is a trifluoromethylpyridyl. In a further variation, one of m and q is 1 and the other is 0, Q is a trifluoromethyl-substituted pyridyl (e.g., 4-trifluoromethyl-3-pyridyl, 5-trifluoromethyl-3-pyridyl, 6-trifluoromethyl-3-pyridyl) and $R^1$ is methyl. In still a further variation, one of m and q is 1 and the other is 0, Q is a trifluoromethyl-substituted pyridyl (e.g., 4-trifluoromethyl-3-pyridyl, 5-trifluoromethyl-3-pyridyl, 6-trifluoromethyl-3-pyridyl), $R^1$ is methyl and at least one of $X^7$-$X^{10}$ is other than CH (e.g., when one of $X^7$-$X^{10}$ is $CR^4$ where $R^4$ is alkyl (such as methyl, ethyl, isopropyl and tert-butyl), halo (such as chloro and fluoro), carboxyl (COOH) or perhaloalkoxy (such as —OCF3). In a further variation, one of m and q is 1 and the other is 0, $R^1$ is methyl, $X^9$ is $CR^4$ where $R^4$ is halo or $CH_3$ and Q is substituted or unsubstituted 6-trifluoromethyl-3-pyridyl. In a further variation, one of m and q is 1 and the other is 0, $R^1$ is methyl and $X^9$ is $CR^4$ where $R^4$ is halo or $CH_3$ and Q is a substituted 6-trifluoromethyl-3-pyridyl. In still a further variation, one of m and q is 1 and the other is 0, $R^1$ is methyl and $X^9$ is $CR^4$ where $R^4$ is halo or $CH_3$ and Q is 6-trifluoromethyl-3-pyridyl. In another such variation, Q is a 6-trifluoromethyl-3-pyridyl substituted with one, two or three moieties selected from a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino. In another such variation, Q is a 6-trifluoromethyl-3-pyridyl substituted with one, two or three moieties selected from a halo, cyano, nitro, perhaloalkyl and perhaloalkoxy.

In one variation, the compound is of the formula (A) or (E) where $R^1$ is cyclopropyl, substituted phenyl or carbonylalkoxy, provided that when $R^1$ is carbonylalkoxy, at least one of m and q is 1. In one variation, the compound is of the formula (A) or (E) where $R^1$ is cyclopropyl, $X^7$, $X^8$ and $X^{10}$ are each CH and $X^9$ is $CR^4$ where $R^4$ is alkyl or halo. In a further such variation, the compound is of the formula (A) or (E) where $R^1$ is cyclopropyl, $X^7$, $X^8$ and $X^{10}$ are each CH; $X^9$ is $CR^4$ where $R^4$ is alkyl or halo and one of m and q is 1 and the other is 0. In another variation, the compound is of the formula (A) or (E) where $R^1$ is substituted phenyl and Q is 6-methyl-3-pyridyl. In still a further variation, the compound is of the formula (A) or (E) where $R^1$ is substituted phenyl, Q is 6-methyl-3-pyridyl, $X^7$, $X^8$ and $X^{10}$ are each CH; and $X^9$ is $CR^4$ where $R^4$ is alkyl (e.g., methyl) or halo (e.g., chloro). In one aspect of this variation, one of m and q is 1 and the other is 0.

In one variation, the compound is of the formula (A) or (E) where either $R^{2a}$ and $R^{2b}$ or $R^{10a}$ and $R^{10b}$ are taken together with the carbon to which they are attached to form a carbonyl and at least one of m and q is 1. In a particular such variation, $R^{2a}$ and $R^{2b}$ are taken together with the carbon to which they are attached to form a carbonyl, $X^7$, $X^8$ and $X^{10}$ are each CH; and $X^9$ is $CR^4$ where $R^4$ is alkyl (e.g., methyl) and Q is an unsubstituted phenyl or a substituted pyridyl (e.g., 6-methyl-3-pyridyl and 6-$CO_2$H-3-pyridyl). In one variation, when $R^{2a}$ and $R^{2b}$ are taken together with the carbon to which they are attached to form a carbonyl, $X^7$, $X^8$ and $X^{10}$ are each CH, $X^9$ is $CR^4$ where $R^4$ is alkyl (e.g., methyl) and Q is other than 6-$CO_2$H-3-pyridyl. However, the methods of the invention, pharmaceutical compositions, kits, and purified or isolated forms of the compound include compounds of this variation, including those in which $R^{2a}$ and $R^{2b}$ are taken together with the carbon to which they are attached to form a carbonyl, $X^7$, $X^8$ and $X^{10}$ are each CH, $X^9$ is $CR^4$ where $R^4$ is alkyl (e.g., methyl) and Q is 6-$CO_2$H-3-pyridyl. In another such variation, $R^{10a}$ and $R^{10b}$ are taken together with the carbon to which they are attached to form a carbonyl; $X^7$, $X^8$ and $X^{10}$ are each CH or N and $X^9$ is N or $CR^4$ where $R^4$ is alkyl (e.g., methyl).

In one variation, the compound is of the formula (A) or (E) where $X^9$ is C—$R^4$ where $R^4$ is trifluoromethyl and Q is a substituted heteroaryl. In another variation, the compound is of the formula (A) or (E) where $X^9$ is C—$R^4$ where $R^4$ is trifluoromethyl, $X^7$, $X^8$ and $X^{10}$ are CH or N; and Q is a substituted or unsubstituted aryl, substituted heteroaryl or an unsubstituted heterocyclyl moiety. In another variation, the compound is of the formula (A) or (E) where $X^9$ is C—$R^4$ where $R^4$ is trifluoromethyl and Q is a substituted heteroaryl. In another variation, the compound is of the formula (A) or (E) where $X^9$ is C—$R^4$ where $R^4$ is trifluoromethyl, $X^7$, $X^8$ and $X^{10}$ are CH or N; one of m a do q is 1 and the other is 0 and Q is a substituted aryl, substituted heteroaryl or an unsubstituted heterocyclyl moiety.

In one variation, the compound is of the formula (A) or (E) where $X^9$ is C—$R^4$ where $R^4$ is isopropyl or Q is a substituted or unsubstituted pyrazinyl. In one variation, the compound is of the formula (A) or (E) where $X^9$ is C—$R^4$ where $R^4$ is isopropyl or Q is a substituted or unsubstituted pyrazinyl provided that when Q is 2-pyrazinyl, either (i) $R^9$ is other than $CR^4$ where $R^4$ is $CH_3$ or (ii) at least one of $R^{2a}$ and $R^{2b}$ is other than hydrogen. In one variation, $X^9$ is C—$R^4$ where $R^4$ is isopropyl; $X^7$, $X^8$ and $X^{10}$ are CH and $R^1$ is methyl. In another such variation, Q is a substituted or unsubstituted pyrazinyl; $X^7$, $X^8$ and $X^{10}$ are CH; $X^9$ is C—$R^4$ where $R^4$ is halo (e.g., chloro) or alkyl (e.g., methyl, ethyl, isopropyl) and $R^1$ is methyl. In still another such variation, Q is a substituted or unsubstituted pyrazinyl; $X^7$, $X^8$ and $X^{10}$ are CH; $X^9$ is C—$R^4$ where $R^4$ is halo (e.g., chloro) or $C_2$-$C_4$ alkyl (e.g., ethyl, isopropyl) and $R^1$ is methyl. In further such variations, one of m and q is 1 and the other is 0.

In one variation, the compound is of the formula (A) or (E) where one of m and q is 1 and the other is 0, $R^{8e}$ and $R^{8f}$ are both H and either: (i) Q is a substituted piperazinyl wherein the substituted piperazinyl is not 4-(2-methoxyphenyl)-piperazinyl or (ii) Q is a substituted piperazinyl and at least one of $X^7$-$X^{10}$ is other than CH. In another variation, the compound is of the formula (A) or (E) where one of m and q is 1 and the other is 0, $R^{8e}$ and $R^{8f}$ are both H and either: (i) Q is a substituted piperazinyl wherein the substituted piperazinyl is not 4-(2-methoxyphenyl)-piperazinyl or (ii) Q is a substituted piperazinyl and at least one of $X^7$-$X^{10}$ is other than CH or $CR^4$ where $R^4$ is $OCH_3$. In one such variation, one of m and q is 1 and the other is 0; $R^{8e}$ and $R^{8e}$ are both H; Q is a substituted piperazinyl; $X^7$, $X^8$ and $X^{10}$ are N or $CR^4$ where $R^4$ is H or F and $X^9$ is $CR^4$ where $R^4$ is alkyl (e.g., methyl) or halo (e.g., chloro).

In one variation, the compound is of the formula (A) or (E) where Q is 6-methyl-3-pyridyl; one of m and q is 1 and the other is 0; $R^1$ is methyl; and $X^9$ is $CR^4$ where $R^4$ is iodo or a substituted alkyl. In another variation, the compound is of the formula (A) or (E) where Q is 6-methyl-3-pyridyl; one of m and q is 1 and the other is 0; $R^1$ is methyl; and at least one of $R^{8e}$ and $R^{8f}$ is hydroxyl or alkyl, or $R^{8e}$ and $R^{8f}$ are taken together with the carbon to which they are attached to form a cycloalkyl moiety.

In one variation, the compound is of the formula (A) or (E) where Q is a carboxy substituted pyridyl, provided it is other than 6-carboxyl-3-pyridyl, or a carbonylalkoxy substituted pyridyl. However, in a further variation, the methods of the invention, pharmaceutical compositions and purified or isolated forms of the compounds include a compound of the formula (A) or (E) where Q is 6-carboxyl-3-pyridyl. In particular variations, the compounds further have one or more of the following structural features: $R^1$ is $C_2$-$C_6$ alkyl and $X^9$ other than $CR^4$ where $R^4$ is methyl. In one variation, $R^1$ is $C_2$-$C_6$ alkyl, $X^9$ other than $CR^4$ where $R^4$ is methyl and Q is a carboxy substituted pyridyl or a carbonylalkoxy substituted pyridyl.

In one variation, the compound is of the formula (A) or (E) where Q is a substituted phenyl and at least one of m and q is 1. In a particular variation, the compound further has one or more of the following structural features: $R^1$ is methyl or ethyl; $X^7$, $X^8$ and $X^{10}$ are CH; and $X^9$ is $CR^4$ where $R^4$ is halo, alkyl, H or perhaloalkyl (e.g., Cl, I, F, $CF_3$, methyl). In a further variation, Q is a substituted phenyl; at least one of m and q is 1 and $R^1$ is methyl. In yet a further variation, Q is a substituted phenyl; at least one of m and q is 1; $R^1$ is methyl and one or more of (i)-(iii) applies: (i) each of $X^7$, $X^8$ and $X^{10}$ is independently $CR^4$ where $R^4$ is hydrogen or halo (e.g., chloro); (ii) $X^9$ is $CR^4$ where $R^4$ is hydrogen, alkyl, halo, perhaloalkyl or perhaloalkoxy; and (iii) $R^{2a}$ and $R^{2b}$ are independently hydrogen, methyl or fluoro. Suitable phenyl substituents and substitution patterns include, but are not limited to, those detailed herein, e.g., at paragraph [0140]. In a particular variation, phenyl substituents are those defined as $R^9$.

In a particular variation of formula (E), one of m and q is 1 and the other is 0; $R^1$ is $CH_3$; $X^7$ is N or $CR^4$ where $R^4$ is hydrogen or chloro; $X^8$ and $X^{10}$ are independently $CR^4$ where $R^4$ is hydrogen or chloro; $X^9$ is $CR^4$ where $R^4$ is alkyl, halo, perhaloalkyl or perhaloalkoxy and Q is a substituted or unsubstituted aryl, substituted or unsubstituted cycloalkyl or a substituted or unsubstituted cycloalkenyl. In a further such variation each of $R^{2a}$, $R^{2b}$, $R^{3a}$, $R^{3b}$, $R^{10a}$ and $R^{10b}$ are hydrogen. In one variation, when Q is phenyl then at least one of $X^7$, $X^8$ and $X^{10}$ is chloro. In another variation, when Q is phenyl then at least one of $R^{2a}$, $R^{2b}$, $R^{3a}$, $R^{3b}$, $R^{10a}$, $R^{10b}$ and $R^{8a}$-$R^{8f}$ is other than hydrogen. In still another variation, when Q is phenyl then $X^9$ is $CR^4$ where $R^4$ is chloro, bromo or iodo.

In one variation, the compound is of the formula (A) or (E) where Q is an unsubstituted phenyl and at least one of m and q is 1, provided that when only one of m and q is 1, $X^9$ is $CR^4$ and $X^7$, $X^8$ and $X^{10}$ are CH, then $R^4$ is other than H. In one such variation, when Q is an unsubstituted phenyl and only one of m and q is 1, then $X^9$ is other than CH. In particular variations, the compounds further contain an $R^1$ that is alkyl (e.g., methyl, ethyl, cyclopropyl) or H. In some of these variations, $X^9$ is C—$R^4$ where $R^4$ is hydrogen, alkyl (e.g., methyl) or halo (e.g., chloro). In others, at least one of $X^7$-$X^{10}$ is C—$R^4$ where $R^4$ is halo (e.g., chloro). In still other of these variations, only one of $X^7$-$X^{10}$ is C—$R^4$ where $R^4$ is halo and the others are each CH. In another such variation, when $X^9$ is C—$R^4$ where $R^4$ is hydrogen, then at least one of $X^7$, $X^8$ or $X^{10}$ is halo (e.g., chloro). In still another variation, Q is an unsubstituted phenyl, at least one of m and q is 1 and at least one of $X^7$-$X^{10}$ is N.

In one variation, the compound is of the formula (A) or (E) where any of $R^{8a}$-$R^{8f}$, where present, is hydroxyl. In one variation, one of $R^{8e}$ and $R^{8f}$ is OH. In another variation, when one of $R^{8e}$ and $R^{8f}$ is OH, the other is methyl. In yet another variation, at least one of $R^{8a}$-$R^{8f}$, where present, is hydroxyl and one of m and q is 1 and the other is 0. In particular variations, the compounds further have one or more of the following structural features: $R^1$ is methyl; Q is a substituted or unsubstituted pyridine (e.g., 3-pyridyl, 4-pyridyl and 6-methyl-3-pyridyl); and $X^9$ is $CR^4$ where $R^4$ is halo (e.g., chloro) or alkyl (e.g., methyl). In a particular variation, one of $R^{8e}$ and $R^{8f}$ is OH; $X^7$, $X^8$ and $X^{10}$ are each C—$R^4$ where $R^4$ is hydrogen; and $X^9$ is C—$R^4$ where $R^4$ is alkyl (e.g., methyl) or halo (e.g., chloro and fluoro). In another variation, m is 1, q is 0 and any of $R^{8c}$-$R^{8f}$ is hydroxyl.

In one variation, the compound is of the formula (A) or (E) where $R^{8e}$ and $R^{8f}$ are taken together with the carbon to which they are attached to form a carbonyl and either:

(i) Q is (a) a substituted or unsubstituted piperidinyl (which in one variation, is connected via its annular nitrogen atom to the parent structure) or (b) an unsubstituted piperizinyl or a piperizinyl substituted with a branched alkyl group (e.g., isopropyl), or (ii) $X^9$ is $CR^4$ where $R^4$ is halo (e.g., chloro).

In particular variations, the compounds further have one or more of the following structural features: $R^1$ is methyl and at least one of m and q is 1.

In another variation, the compound is of the formula (A) or (E) where $R^{8e}$ and $R^{8f}$ are taken together with the carbon to which they are attached to form a carbonyl; $R^1$ is methyl or hydrogen and one of m and q is 1 and the other is 0. In another such variation, the compound further has one or more of the following structural features: $X^7$, $X^8$ and $X^{10}$ are each CH; $X^9$ is $CR^4$ where $R^4$ is halo or alkyl (e.g., methyl); and $R^{2a}$, $R^{2b}$, $R^{3a}$, $R^{3b}$, $R^{10a}$ and $R^{10b}$ are each H.

In one variation, the compound is of the formula (A) or (E) where at least one of $X^7$-$X^{10}$ is $CR^4$ where $R^4$ is halo and Q is piperidinyl. In one such variation, the compound further has the following structural features: $X^9$ is $CR^4$ where $R^4$ is halo (e.g., chloro) and Q is 1-piperidinyl. In one variation, the compound is of the formula (A) or (E) where Q is a substituted or unsubstituted piperidinyl and at least one of $X^7$-$X^{10}$ is either N or $CR^4$ where $R^4$ is halo. In one variation, the compound is of the formula (A) or (E) where Q is a substituted or unsubstituted piperidinyl and $R^{8e}$ and $R^{8f}$ are taken together with the carbon to which they are attached to form a carbonyl.

In one variation, the compound is of the formula (A) or (E) where $R^{8e}$ and $R^{8f}$ are taken together with the carbon to which they are attached to form a carbonyl, m is 1 and q is 0; and Q is a substituted or unsubstituted heteroaryl or an unsubstituted heterocyclyl; provided that when Q is an unsubstituted piperazinyl, $R^1$ is other than iso-propyl (e.g., H, $CH_3$ or ethyl). In one variation, the compound is of the formula (A) or (E) where $R^{8e}$ and $R^{8f}$ are taken together with the carbon to which they are attached to form a carbonyl, m is 1 and q is 0; and Q is a substituted or unsubstituted heteroaryl or a substituted unsubstituted heterocyclyl; provided that when Q is a substituted or unsubstituted piperazinyl, $R^1$ is other than iso-propyl (e.g., H, $CH_3$ or ethyl). In one variation, the compound is of the formula (A) or (E) where $R^{8e}$ and $R^{8f}$ are taken together with the carbon to which they are attached to form a carbonyl, m is 1 and q is 0; $R^1$ is hydrogen of methyl and Q is an unsubstituted heterocycle. In one such variation, the unsubstituted heterocycle contains no more than one annular heteroatom.

In another variation, the compound is of the formula (A) or (E) where $R^{8e}$ and $R^{8f}$ are taken together with the carbon to which they are attached to form a carbonyl; $R^1$ is methyl; Q is a substituted or unsubstituted heteroaryl or an unsubstituted heterocyclyl and one of m and q is 1 and the other is 0. In another such variation, the compound further has one or more of the following structural features: $X^9$ is $CR^4$ where $R^4$ is halo or alkyl (e.g., methyl). In another such variation, the compound further has one or more of the following structural features: $X^7$, $X^8$ and $X^{10}$ are each CH; $X^9$ is $CR^4$ where $R^4$ is halo or alkyl (e.g., methyl); and $R^{2a}$, $R^{2b}$, $R^{3a}$, $R^{3b}$, $R^{10a}$ and $R^{10b}$ are each H. In one such embodiment, Q is

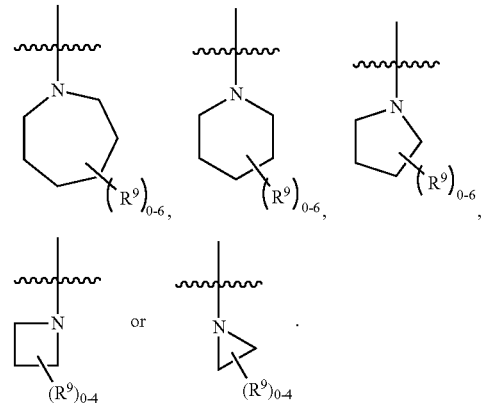

In another variation, the compound is of the formula (B-1):

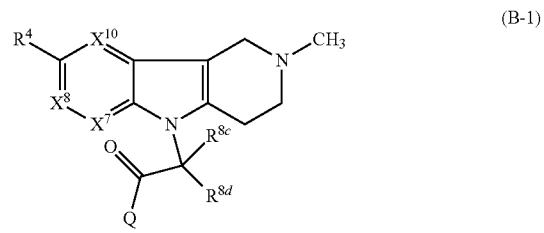

wherein:

$R^4$ is halo or $CH_3$;

Q is a substituted or unsubstituted heteroaryl or a substituted or unsubstituted heterocyclyl; and $X^7$, $X^8$, $X^{10}$, $R^{8c}$ and $R^{8d}$ are as defined in one variation for formula (B) and in another variation for formula (E).

In one variation of B-1, Q is:

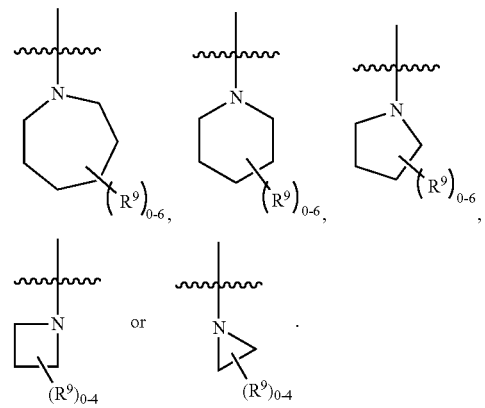

In another variation, the invention embraces compounds of the formula (B-2)

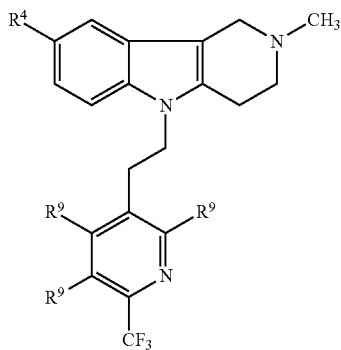

(B-2)

wherein:
R$^4$ is halo or CH$_3$; and
each R$^9$ is independently a hydrogen, halo, cyano, nitro, perhaloalkyl, or perhaloalkoxy. In another such variation, R$^4$ is halo or CH$_3$ and Q is 3Py-6CF$_3$.

In still another variation, the compound is of the formula (B) or (E), provided that when the compound is of the formula (E), m and l and q is 0 and provided that at least one of (i)-(iv) applies:
(i) when X$^7$-X$^{10}$ are each CR$^4$ where R$^4$ is hydrogen and R$^1$ is methyl or tert-butyl, then Q is other than phenyl or an unsubstituted pyridyl;
(ii) when X$^7$, X$^8$ and X$^{10}$ are each CR$^4$ where R$^4$ is hydrogen and X$^9$ is CR$^4$ where R$^4$ is methyl and R$^1$ is methyl, then Q is other than phenyl, unsubstituted pyridyl or pyrazinyl;
(iii) when X$^7$, X$^8$ and X$^{10}$ are each CR$^4$ where R$^4$ is hydrogen and X$^9$ is CR$^4$ where R$^4$ is fluoro or trifluoro and R$^1$ is methyl, then Q is other than phenyl, unsubstituted pyridyl and 6-methyl-3-pyridyl; and
(iv) when X$^8$, X$^9$ and X$^{10}$ are each CR$^4$ where R$^4$ is hydrogen and X$^7$ is CR$^4$ where R$^4$ is fluoro or trifluoro and R$^1$ is methyl, Q is other than phenyl or 3-pyridyl.

In another variation, the compound is of the formula (B) or (E) provided that when the compound is of the formula (E) then m is 1 and q is 0, and provided that at least one of (i) and (ii) applies:
(i) when X$^8$ and X$^{10}$ are both CH, one of X$^7$ and X$^9$ is CR$^4$ where R$^4$ is F or CF$_3$ and the other is CH, and R$^1$ is a substituted C$_1$-C$_3$ alkyl where the substituent is carboxy or carbonylalkoxy, then Q is other than unsubstituted phenyl, 4-fluorophenyl, and unsubstituted pyridyl; or
(ii) when each of X$^7$-X$^{10}$ is CH and R$^1$ is carbonylalkoxy, then Q is other than unsubstituted phenyl and unsubstituted pyridyl.

In one variation, the compound is of the formula (A) or (E) where at least one of X$^7$-X$^{10}$ is other than CH and Q is pyrrolidinyl. In one variation, at least one of X$^7$-X$^{10}$ is C—R$^4$ where R$^4$ is alkyl and Q is pyrrolidinyl. In a particular variation, X$^9$ is CR$^4$ where R$^4$ is methyl, Q is pyrrolidinyl and X$^9$ is CR$^4$ where R$^4$ is alkyl (e.g., methyl), perhaloalkyl (e.g., CF$_3$) or halo (e.g., chloro).

In one variation, the compound is of the formula (A) or (E) where Q is morpholino, and at least one of (i)-(iii) applies:
(i) at least one of m and q is 0;
(ii) at least one of X$^7$-X$^{10}$ is other than CH; and
(iii) at least one of X$^7$-X$^{10}$ is CR$^4$ where R$^4$ is halo.

In a particular variation, Q is morpholino, X$^9$ is CR$^4$ where R$^4$ is chloro and at least one of m and q is 1 and the other is 0. In another variation, the compound is of the formula (A) or (E) where Q is morpholino, R$^1$ is alkyl and at least one of (i)-(iii) above applies.

In one variation, the compound is of the formula (A) or (E) where Q is a perhaloalkyl substituted pyridyl (e.g., where Q is a 3-pyridyl substituted at the 5 or 6 position with CF$_3$). In particular variations, the compounds further have one or more of the following structural features: at least one of X$^7$-X$^{10}$ is CR$^4$ where each R$^4$ is independently alkyl (e.g., a C$_1$-C$_3$ alkyl such as methyl, ethyl and isopropyl) or halo (e.g., chloro or fluoro); at least one of X$^7$, X$^8$ or X$^9$ is CR$^4$ where each R$^4$ is independently alkyl (e.g., a C$_1$-C$_3$ alkyl such as methyl, ethyl and isopropyl) or halo (e.g., chloro or fluoro); two of X$^7$-X$^{10}$ are CR$^4$ where each R$^4$ is independently alkyl (e.g., a C$_1$-C$_3$ alkyl such as methyl, ethyl and isopropyl) or halo (e.g., chloro or fluoro), two of X$^7$-X$^{10}$ are CR$^4$ where each R$^4$ is independently halo (e.g., chloro or fluoro); X$^8$ and X$^9$ are both CR$^4$ where each R$^4$ is independently halo (e.g., chloro or fluoro), which halo substituents may be the same or different (e.g., X$^8$ is C—F and X$^9$ is C—Cl or X$^8$ is C—F and X$^9$ is C—Cl); and R$^1$ is methyl and at least one of m and q is 1.

In one variation, the compound is of the formula (A) or (E) where Q is a substituted or unsubstituted 6-membered heteroaryl having at least two annular N atoms. In one variation, Q is 5-pyrimidyl or 2-pyrazinyl. In another variation, when Q is pyrazinyl, X$^9$ is CR$^4$ where R$^4$ is halo or a C$_2$-C$_4$alkyl. In one variation, when Q is a substituted 6-membered heteroaryl, it is substituted with an alkyl group, e.g., methyl (e.g., 2-methyl-5-pyrimidyl or 5-methyl-2-pyrazinyl). In particular variations, the compounds further have one or more of the following structural features: R$^1$ is methyl; X$^9$ is CR$^4$ where R$^4$ is halo (e.g., chloro) or alkyl (e.g., methyl, ethyl, isopropyl); and where one of m and q is 1 and the other is 0.

In one variation, the compound is of the formula (A) or (E) where Q is cyclohexyl. In particular variations, the compounds further have one or more of the following structural features: one of m and q is 1 and the other is 0; at least one of X$^7$-X$^{10}$ is CR$^4$ where R$^4$ is halo (e.g., where X$^8$, X$^9$ or X$^{10}$ is CR$^4$ where R$^4$ is halo; e.g., where one of X$^7$-X$^{10}$ is CR$^4$ where R$^4$ is halo and the others are CH); R$^1$ is methyl; one of X$^7$-X$^{10}$ is CR$^4$ where R$^4$ is alkyl (e.g., when R$^4$ is methyl; e.g., when X$^9$ is C—CH$^3$ and X$^7$, X$^8$ and X$^{10}$ are CH).

In one variation, the compound is of the formula (A) or (E) where Q is a substituted or unsubstituted pyridyl and R$^1$ is isopropyl.

In one variation, the compound is of the formula (A) or (E) where Q is a substituted pyridyl provided that (i) the pyridyl substituent is other than methyl and (ii) when one of m and q is 1 and the other is 0, X$^9$ is CR$^4$ where R$^4$ is methyl and R$^1$ is CH$_3$, the pyridyl substituent is other than COOH. However, in a further variation, the methods of the invention, pharmaceutical compositions and purified or isolated forms of the compounds include a compound of the formula (A) or (E) when Q is a substituted pyridyl and (i) the substituent is methyl and (ii) when one of m and q is 1 and the other is 0, X$^9$ is CR$^4$ where R$^4$ is methyl and R$^1$ is CH$_3$, the substituent is COOH. In a particular variation, Q is a pyridyl substituted with at least one moiety selected from ethyl, propyl (n-propyl or isopropyl), halo (e.g., chloro) and hydroxymethyl. In another particular variation, Q is a pyridyl substituted with at least one moiety selected from ethyl, propyl (n-propyl or isopropyl), halo (e.g., chloro), perhaloalkyl (e.g., CF$_3$) and hydroxymethyl. In particular variations, the compounds further have one or more of the following structural features: R$^1$ is methyl and $X^9$ is $CR^4$ where $R^4$ is methyl or chloro (and in a particular variation, $X^7$, $X^8$ and $X^{10}$ are CH); and m and q is 1 and the other is 0.

In one variation, the compound is of the formula (A) or (E) where Q is methylpyridyl (e.g., 6-methyl-3-pyridyl); m and q are 0 and either: (i) at least one of $X^7$-$X^9$ is $CR^4$ where $R^4$ is alkyl (e.g., methyl) or (ii) both of $R^{8e}$ and $R^{8e}$ are H. In particular variations, the compounds further have one or more of the following structural features: $X^9$ is $CR^4$ where $R^4$ is methyl and $X^7$, $X^8$ and $X^{10}$ are CH and $R^1$ is methyl or ethyl.

In one variation, the compound is of the formula (A) or (E) where at least one of $X^8$ and $X^{10}$ is $CR^4$ where $R^4$ is F. In a particular variation, $X^8$ is $CR^4$ where $R^4$ is F; $X^9$ is $CR^4$ where $R^4$ is halo (e.g., chloro) or hydrogen and $R^1$ is alkyl (e.g., methyl). In another variation, $X^{10}$ is $CR^4$ where $R^4$ is F and one of m and q is 1 and the other is 0. In still a further variation, at least one of $X^8$ and $X^{10}$ is $CR^4$ where $R^4$ is F; one of m and q is 1 and the other is 0 and Q is 6-trifluoromethyl-3-pyridyl or 6-methyl-3-pyridyl.

In one variation, the compound is of the formula (A) or (E) where Q is 6-methyl-3-pyridyl; $R^1$ is methyl and one of $X^7$-$X^{10}$ is C—F. In a particular variation, Q is 6-methyl-3-pyridyl; $R^1$ is methyl; $X^8$ is C—F and $X^9$ is $CR^4$ where $R^4$ is halo (e.g., chloro).

In one variation, the compound is of the formula (A) or (E) where Q is 5-methyl-3-pyridyl. In particular variations, the compounds further have one or more of the following structural features: one of m and q is 1 and the other is 0; $R^1$ is methyl and $X^9$ is $CR^4$ where $R^4$ is alkyl (e.g., methyl).

In one variation, the compound is of the formula (A) or (E) where Q is an unsubstituted pyridyl (e.g., 2-pyridyl) and both m and q are 1. In particular variations, the compounds further have one or more of the following structural features: $R^1$ is methyl; $X^9$ is $CR^4$ where $R^4$ is alkyl (e.g., methyl).

In one variation, the compound is of the formula (A) or (E) where Q is an unsubstituted 3-pyridyl; one of m and q is 1 and the other is 0 and $X^9$ is $CR^4$ where $R^4$ is alkyl (e.g., methyl). In one variation, $R^1$ is methyl or carbonylalkoxy provided that when $R^1$ is methyl, then at least one of $R^{2a}$, $R^{2b}$, $R^{3a}$, $R^{3a}$, $R^{8a}$-$R^{8f}$ and $R^{10a}$, $R^{10b}$ is other than hydrogen. In particular variations, the compounds further have one or more of the following structural features: $R^1$ is methyl; each of $R^{2a}$, $R^{2b}$, $R^{3a}$, $R^{3a}$, $R^{8a}$-$R^{8f}$ and $R^{10a}$, $R^{10b}$ are H.

In one variation, the compound is of the formula (A) or (E) where Q is an unsubstituted 2-pyridyl; one of m and q is 1 and the other is 0 and either: (i) $R^1$ is ethyl or (ii) at least one of $X^7$-$X^9$ is $CR^4$ wherein $R^4$ is other than H (in a particular variation, $X^9$ is $CR^4$ where $R^4$ is alkyl (e.g., methyl) or halo (e.g., chloro)). In particular variations, the compounds further have one of the following structural features: $R^1$ is ethyl and $X^9$ is $CR^4$ where $R^4$ is $CH_3$ or $R^1$ is ethyl and each of $X^7$-$X^9$ is $CR^4$.

In one variation, the compound is of the formula (A) or (E) where Q is 4-pyridyl; one of m and q is 1 and the other is 0; and $R^1$ is ethyl. In particular variations, the compounds further have one of the following structural features: $X^9$ is $CR^4$ where $R^4$ is H or alkyl and $X^7$, $X^8$ and $X^{10}$ are H.

In yet another variation, the compound is of the formula (A) or (E) where at least one of $X^7$-$X^{10}$ is N and either (i) $R^1$ is methyl or (ii) $R^{8e}$ and $R^{8f}$ are both hydrogen. In one such variation, only one of $X^7$-$X^{10}$ is N, $R^1$ is methyl and the $X^7$-$X^{10}$ that are not N are $CR^4$ where $R^4$ is hydrogen, methyl or trifluoromethyl. In another variation, the compound is of the formula (A) or (E) where two of $X^7$-$X^{10}$ are N (e.g., $X^7$ and $X^{10}$ are both N or $X^7$ and $X^8$ are both N).

In still another variation, the compound is of the formula (A) or (E) where q is 0, m is 1, $R^{8e}$ and $R^{8f}$ are taken together to form a carbonyl, and at least one of (i)-(vi) applies: (i) Q is a substituted or unsubstituted heteroaryl or an unsubstituted heterocyclyl, (ii) $R^1$ is $CH_3$ or H, (iii) $X^9$ is halo or $CH_3$ provided that when $X^9$ is $CH_3$, $R^1$ is H or $CH_3$, (iv) $X^7$ and $X^8$ are both $CR^4$ (e.g. CH) and $R^1$ is H or $CH_3$, (v) each $X^7$-$X^{10}$ is CH and $R^1$ is H or $CH_3$, and (vi) each $X^7$-$X^{10}$ is CH and Q is a substituted or unsubstituted heteroaryl or an unsubstituted heterocyclyl. In another variation, the compound is of formula (A) or (E) where q is 0, m is 1, $R^{8e}$ and $R^{8f}$ are taken together to form a carbonyl, and Q is an unsubstituted or substituted piperidinyl. In a particular such variation, Q is an unsubstituted piperidinyl, $X^9$ is halo or $CH_3$ and $R^1$ is $CH_3$ or H.

The invention also embraces a compound of the formula (B):

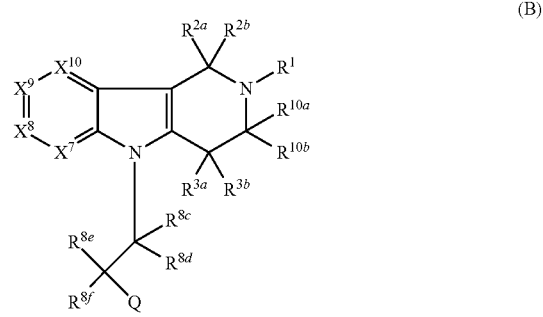

(B)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano or nitro or $R^{3a}$ and $R^{3b}$ are taken together to form a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl;

provided that (i) the compound is other than any of compounds 72x, 125x, 126x, 127x, 128x, 129x, 130x, 131x, 132x, 133x, 134x, 135x, 136x, 137x, 138x, 139x, 140x, 141x, 142x, 143x, 144x, 145x, 146x, 148x, 149x, 150x, 151x, 152x, 155x, 156x, 157x, 158x, 159x, 160x, 161x, 162x, 163x, 164x, 165x, 166x, 167x, 168x, 169x, 170x, 171x, 172x, 173x, 174x, 175x, 176x, 177x, 178x, 179x, 180x, 181x, 182x, 183x, 184x, 185x, 186x, 187x, 188x, 189x, 190x, 191x, 192x, 193x, 194x, 195x, 196x, 197x, 198x, 199x, 200x, 201x, 203x, 204x, 222x, 223x, 224x, 225x, 226x, 227x, 228x, 229x, 233x, 234x, 235x, 237x, 241x, 243x, 244x, 245x, 246x, 247x, 248x, 249x, 250x, 251x, 252x, 253x, 254x, 255x, 256x, 257x and 258x or a salt thereof and (ii) the compound is other than any of compounds 229H, 230, 241, 255, 256, 262 and 274 or a salt thereof. In another variation, the compounds of the invention, and methods of using the compounds and administering the compounds as detailed herein, encompass any of the compounds of formula B, including those listed in Table 1 or a salt thereof and compounds 229H, 230, 241, 255, 256, 262 and 274, or a salt thereof.

In one variation, the compound is of the formula (B) wherein the compound further is a type 1 compound. In another variation, the compound is of the formula (B) wherein the compound further is a type 2 compound. In yet another variation, the compound is of the formula (B) wherein the compound further is a type 3 compound. In a further variation, the compound is of the formula (B) wherein the compound further is a type 4 compound.

In one variation, the compound is of formula (B) provided that (i) Q is other than unsubstituted pyridyl or 4-substituted-1-piperazinyl; (ii) when Q is substituted pyridyl, it is substituted with at least one group that is other than methyl; and (iii) the compound is other than any of compounds 176x, 177x, 178x, 179x, 204x, 243x, 244x, 245x, 246x, 247x and 251x. In a further variation, the compound is of formula (B) provided that (i) Q is other than unsubstituted pyridyl or 4-substituted-1-piperazinyl; (ii) when Q is substituted pyridyl, it is substituted with at least one group that is other than methyl; (iii) when Q is pyrrolidinyl, piperidinyl, azepinyl, phenyl or substituted piperazinyl, at least one of $X^7$, $X^8$, $X^9$ and $X^{10}$ is other than CH; and (iv) the compound is other than any of compounds 176x, 178x, 243x, 244x, 245x, 246x, 247x and 251x. In a further variation, the compound is of formula (B) provided that (i) at least one of $R^{8c}$, $R^{8d}$, $R^{8e}$ and $R^{8f}$ is other than H; and (ii) $R^{8e}$ and $R^{8f}$ are not taken together with the carbon to which they are attached to form a carbonyl.

In another variation, the compound is of the formula B where Q is a substituted or unsubstituted $C_{3-8}$ cycloalkyl, substituted or unsubstituted $C_{3-8}$ cycloalkenyl, or substituted or a unsubstituted heterocyclyl, provided that: (i) when Q is substituted piperazin-1-yl, it is other than 4-(2-methoxyphenyl)piperazin-1-yl; (ii) when Q is pyrrolidin-1-yl, piperidin-1-yl, or azepan-1-yl, it is substituted pyrrolidin-1-yl, piperidin-1-yl, or azepan-1-yl or (iii) the compound is not 2-methyl-5-(2-(pyrrolidin-1-yl)ethyl)-2,3,4,5-tetrahydro-1H-pyrido[4,3-b]indole; 2-methyl-5-(2-(piperidin-1-yl)ethyl)-2,3,4,5-tetrahydro-1H-pyrido[4,3-b]indole; 2,8-dimethyl-5-(2-(piperidin-1-yl)ethyl)-2,3,4,5-tetrahydro-1H-pyrido[4,3-b]indole; or 5-(2-(azepan-1-yl)ethyl)-2,8-dimethyl-2,3,4,5-tetrahydro-1H-pyrido[4,3-b]indole, or a salt or solvate thereof. In one variation, the compound is of the formula B or any variation thereof detailed herein, where Q is a carbocycle, such as a 5, 6 or 7 membered carbocycle. In one variation, the compound is of the formula B or any variation thereof detailed herein, where Q is a heterocycle, such as a 3, 4, 5, 6 or 7 membered carbocycle. In one variation, the compound is of the formula B or any variation thereof detailed herein, where Q is a heterocycle, such as a 5, 6 or 7 membered heterocycle. In one variation, the compound is of the formula B or any variation thereof detailed herein, where Q is a heterocycle, such as a 3, 4, 5, 6 or 7 membered heterocycle.

In another variation, the compound is of the formula B where Q is substituted or unsubstituted aryl or a substituted or unsubstituted heteroaryl, provided that (i) at least one of $X^7$-$X^{10}$ is other than CH and at least one of (ii)-(viii) applies: (ii) when Q is 2-methylpyridin-3-yl or an unsubstituted moiety selected from phenyl and pyridin-3-yl, $R^1$ is not methyl and provided that the compound is other than 125x, 177x, 184x and 237x (iii) when Q is unsubstituted pyridin-2-yl, $R^1$ is other than H or an unsubstituted moiety selected from methyl, propyl, and butyl and provided that the compound is other than 180x-183x; (iv) when Q is unsubstituted pyridin-4-yl, $R^1$ is other than H or an unsubstituted moiety selected from methyl, propyl, butyl, phenethyl, and benzoyl provided the compound is other than 185x-241x; (v) when Q is 6-methylpyridin-3-yl, $R^1$ is other than H or an unsubstituted moiety selected from methyl, ethyl, propyl, butyl, isobutyl, sec-butyl, pentyl, isopentyl, cyclohexyl, heptyl, benzyl, and phenyl; (vi) at least one of $X^7$-$X^{10}$ is N; (vii) at least one of $R^{8c}$-$R^{8f}$ is other than H; and (viii) at least one of $R^{2a}$, $R^{2b}$, $R^{3a}$, $R^{3b}$, $R^{10a}$, or $R^{10b}$ is other than H, or a salt or solvate thereof. In another variation, the compound is of the formula B where Q is a substituted or unsubstituted heteroaryl, such as a 5, 6 or 7 membered heteroaryl, provided that at least one of provisions (ii)-(viii) above applies. In one variation, the compound is of the formula B where Q is a substituted or unsubstituted aryl, such as a 5, 6 or 7 membered aryl, provided that: (a) when Q is an unsubstituted phenyl moiety, $R^1$ is not methyl provided the compound is not 177x; (b) at least one of $X^7$-$X^{10}$ is N; (c) at least one of $R^{8c}$-$R^{8f}$ is other than H; or (d) at least one of $R^{2a}$, $R^{2b}$, $R^{3a}$, $R^{3b}$, $R^{10a}$, or $R^{10b}$ is other than H, or a salt or solvate thereof.

In another variation, the invention embraces compounds of the formula (B) where $X^7$-$X^{10}$, $R^1$, $R^{2a}$, $R^{2b}$, $R^{3a}$, $R^{3b}$, $R^{8c}$-$R^{8f}$, $R^{10a}$, $R^{10b}$, m and q a are as defined in one variation in formula (I) and in another variation in formula (E) and Q is substituted phenyl or a substituted or unsubstituted pyrrolyl, or a pharmaceutically acceptable salt thereof. In one variation of formula (B), $X^9$ is C—$R^4$ where $R^4$ is halo or H. In another variation of formula (B), $R^1$ is alkyl, such as a $C_1$-$C_8$ alkyl, e.g., methyl. Compounds of formula (B) where $X^9$ is C—$R^4$ and where $R^4$ is halo (e.g., chloro) or H and where $R^1$ is methyl are embraced. In another variation of formula (B), each of $X^7$, $X^8$ and $X^{10}$ is CH; $X^9$ is C—$R^4$ where $R^4$ is halo or H and $R^{2a}$, $R^{2b}$, $R^{3a}$, $R^{3b}$, $R^{8a}$-$R^{8f}$, $R^{10a}$, $R^{10b}$ are independently H or alkyl, e.g., methyl. In one variation, the invention embraces compounds of the formula (B) where $X^9$ is C—$R^4$ where $R^4$ is chloro; $X^7$ is N or C—$R^4$ where $R^4$ is hydrogen or halo; $X^8$ and $X^{10}$ are independently C—$R^4$ where $R^4$ is hydrogen or fluoro and at least one of (i)-(iii) applies: (i) at least one of $R^{8e}$ and $R^{8f}$ is hydroxyl, $C_1$-$C_8$alkyl, $C_1$-$C_8$perhaloalkyl or is taken together with the carbon to which it is attached and a geminal $R^{8(e-f)}$ to form a cycloalkyl moiety or a carbonyl moiety; (ii) at least one of $R^{8e}$ and $R^{8f}$ is $C_1$-$C_8$alkyl; (iii) Q is a substituted or unsubstituted aryl, substituted or unsubstituted $C_3$-$C_8$cycloalkyl, substituted or unsubstituted $C_3$-$C_8$cycloalkenyl or a substituted or unsubstituted heterocyclyl. In a particular variation, the invention embraces compounds of the formula (B) where $X^9$ is C—$R^4$ where $R^4$ is chloro; $X^7$ is N or C—$R^4$ where $R^4$ is hydrogen or halo; $X^8$ and $X^{10}$ are independently C—$R^4$ where $R^4$ is hydrogen or fluoro and Q is a substituted or unsubstituted heteroaryl, provided that when Q is an unsubstituted heteroaryl it is other than pyridyl and when Q is a substituted heteroaryl, it is other than 6-methyl-3-pyridyl.

In any variation of formula (B) detailed herein, in one variation Q is a phenyl substituted with an alkyl, perhaloalkyl, halo, hydroxyl or alkoxy moiety. In another variation, Q is a phenyl substituted with two or three moieties selected from methyl, perhaloalkyl, halo, hydroxyl and alkoxy. Particular phenyl substituents for Q are methyl, trifluoromethyl, fluoro, chloro, hydroxyl, methoxy, ethoxy and isopropoxy. When Q is a phenyl substituted with two or three moieties, the moieties may be the same or different. For example, Q may be difluorophenyl, dichlorophenyl, dimethoxyphenyl, di(trifluoromethyl)phenyl, trifluorophenyl, (fluoro)(chloro)phenyl, (fluoro)(trifluoromethyl)phenyl, (chloro)(trifluoromethyl)phenyl or (fluoro)(methoxy)phenyl.

When a compound of the formula (B) has a Q that is a substituted phenyl, the substituent or substituents may be positioned at any available phenyl ring position. For example, singly-substituted phenyl groups may be substituted at the ortho, meta or para-position of the phenyl group. Any available phenyl ring substitution pattern is suitable for di- or tri-substituted phenyl groups (e.g., at the ortho and para positions, at two ortho positions, at two meta positions, at the meta and para positions, at the ortho, meta and para positions, at two ortho and the para position, at two ortho and a meta position, or at two meta and a para or ortho position). In any variation of formula (B) detailed herein, in one variation Q is an unsubstituted pyrrolyl or a pyrrolyl substituted with an alkyl moiety (e.g., methyl, ethyl or propyl, including isopropyl). In one variation, the unsubstituted pyrrolyl or a pyrrolyl substituted with a single moiety is attached to the carbon bearing $R^{8e}$ and $R^{8f}$ via the 1, 2 or 3-positions of the unsubstituted or mono-substituted pyrrolyl moiety.

In another variation, the compound is of the formula (B) and Q is either:
(i) 4-trifluoromethyl-3-pyridyl;
(ii) unsubstituted phenyl, provided that at least one of $X^7$-$X^{10}$ is other than CH; or
(iii) Q is piperidinyl and $R^{8e}$ and $R^{8f}$ are taken together with the carbon to which they are attached to form a carbonyl.

All variations referring to Formula (A) and/or Formula (E), where applicable, may apply equally to formula B the same as if each and every variation were specifically and individually listed. Likewise, all variations referring to Formula (A) and/or Formula (E), where applicable, may apply to any other formulae detailed herein, the same as if each and every variations were specifically and individually listed.

In another variation, the compound is of the formula (E) or (B), where:
m is 1 and q is 0 (when the variation refers to formula (E));
$R^1$ is $CH_3$ or ethyl;
each of $R^{8c}$ and $R^{8d}$ are both H;
$R^{8e}$ and $R^{8f}$ are independently H, OH or $CH_3$;
$X^7$ is CH; $X^8$ is CH or C-halo; $X^{10}$ is CH or C-halo;
$X^9$ is $CR^4$ where $R^4$ is halo, $CH_3$, $CF_3$ or ethyl; and
Q is substituted or unsubstituted phenyl or substituted or unsubstituted pyridyl, provided that either:
(i) when $R^1$ is $CH_3$, both $R^{8e}$ and $R^{8f}$ and H, $X^9$ is $CR^4$ where $R^4$ is F or $CF_3$ and Q is phenyl, the compound is other than 244x and 245x; or
(ii) when $R^1$ is $CH_3$, $R^{8e}$ and $R^{8f}$ are both H; and Q is 2-pyridyl, 2-methyl-3-pyridyl or 6-methyl-3-pyridyl, the compound is other than 181x, 250x, 254x, 125x, 131x, 132x, 133x, 134x, 140x, 141x, 148x, 168x, 169x, 170x, 171x, 172x, 173x, 174x, 175x and 255x.

In one such variation, Q is a phenyl substituted with one, two or three moieties selected from halo, $C_{1-4}$ alkyl, —O—$C_{1-4}$ alkyl, perhaloalkyl and perhaloalkoxy. In one variation, Q is a phenyl substituted with one, two or three moieties selected from F, Cl, I, Br, methyl, ethyl, propyl, $CF_3$, OMe, OEt, and O—$CH(CH_3)_2$. In another such variation, Q is 2-pyridyl, 3-pyridyl or 4-pyridyl, each of which may be substituted with one, two or three moieties selected from a $C_{1-4}$ alkyl, halo, perhaloalkyl, or perhaloalkoxy. In one variation, Q is a pyridyl substituted with one, two or three moieties selected from F, Cl, I, Br, methyl, ethyl, propyl, iso-propyl and $CF_3$.

The invention also embraces compounds of the formula (C):

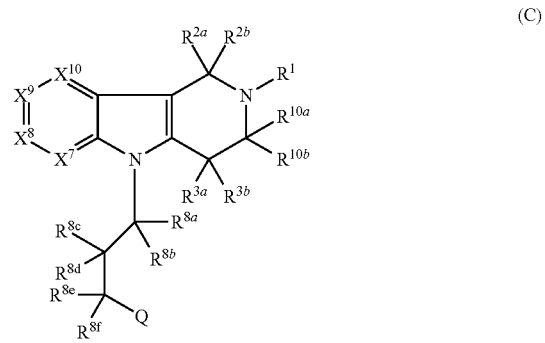

(C)

wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano or nitro or $R^{3a}$ and $R^{3b}$ are taken together to form a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl, provided that the compound is other than any of compounds 202x, 205x, 206x, 207x, 208x, 209x, 210x, 211x, 212x, 213x, 214x and 221x, or a salt thereof. In another variation, the compounds of the invention, and methods of using the compounds detailed herein, encompass any of the compounds of formula C, including those listed in Table 1, such as compounds 202x, 205x, 206x, 207x, 208x, 209x, 210x, 211x, 212x, 213x, 214x and 221x, or a salt thereof.

In one variation, the compound is of formula (C) provided that (i) when Q is a substituted piperazinyl, at least one of $X^7$, $X^8$, $X^9$ and $X^{10}$ is other than CH; and (ii) the compound is other than any of compounds 202x, 214x and 221x.

In another variation, the compound is of the formula C where Q is a substituted or unsubstituted $C_{3-8}$ cycloalkyl, substituted or unsubstituted $C_{3-8}$ cycloalkenyl, or substituted or a unsubstituted heterocyclyl, provided that: (i) when Q is 4-(2-methoxyphenyl)piperazin-1-yl, $R^1$ is not H, benzyl, methyl, acetyl, or benzoyl; or (ii) when Q is 4-benzylpiperazin-1-yl, $R^1$ is not methyl; or (iii) when Q is 4-methylpiperazin-1-yl, $R^1$ is not methyl, benzyl, or phenethyl; or (iv) the compound is not 1H-Pyrido[4,3-b]indole, 2,3,4,5-tetrahydro-2-methyl-5-[3-(4-morpholinyl)propyl]-, or a salt or solvate thereof. In one variation, the compound is of the formula C where Q is a carbocycle, such as a 5, 6 or 7 membered carbocycle. In another variation, the compound is of the formula C where Q is a heterocycle, such as a 5, 6 or 7 membered heterocycle.

In another variation, the compound is of the formula C where Q is a substituted or unsubstituted aryl, such as a 5, 6 or 7 membered aryl group. In another variation, the compound is of the formula C where Q is a substituted or unsubstituted heteroaryl, such as a 5, 6 or 7 membered heteroaryl group.

The invention also embraces compounds of the formula D:

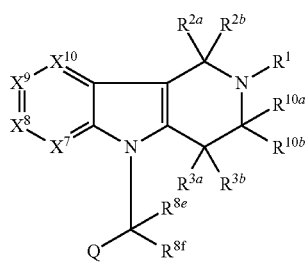

(D)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano or nitro or $R^{3a}$ and $R^{3b}$ are taken together to form a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl;

provided that the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 52x, 53x, 54x, 55x, 56x, 57x, 58x, 59x, 60x, 61x, 62x, 65x, 66x, 67x, 68x, 69x, 70x, 71x, 73x, 74x, 77x, 78x, 79x, 80x, 81x, 82x, 83x, 84x, 85x, 88x, 89x, 90x, 91x, 92x, 93x, 94x, 95x, 96x, 97x, 98x, 100x, 101x, 102x, 103x, 104x, 105x, 106x, 107x, 109x, 110x, 111x, 113x, 114x, 115x, 116x, 117x, 118x, 119x, 120x, 121x, 122x, 123x, 124x, 216x, 217x, 218x, 219x, 220x, 230x, 231x, 232x, 236x, 238x, 239x, 240x, 259x, 260x, 261x, 262x, 263x, 264x, 265x, 266x, 267x, 268x, 269x, 270x, 271x, 272x, 273x, 274x, 275x, 276x, 277x, 278x, 279x, 280x, 281x, 282x, 283x, 284x, 285x, 286x, 287x, 288x, 289x, 290x, 291x, 292x, 293x, 294x, 295x, 296x, 297x, 298x, 299x, 300x, 301x, 302x, 303x, 304x, 305x, 306x, 307x, 308x, 309x, 310x, 311x, 312x, 313x, 314x, 315x, 316x, 317x and 318x or a salt thereof. In another variation, the compounds of the invention, and methods of using the compounds detailed herein, encompass any of the compounds of formula D, including those listed in Table 1 and Table 1A, such as compounds 1x-62x, 65x-71x, 73x, 74x, 77x-85x, 88x-98x, 100x-107x, 109x-111x, 113x-124x, 216x-220x, 230x-232x, 236x, 238x-240x, 259x-295x and 296x-318x, or a salt thereof. In one variation, the compound is of the formula D where Q is a carbocycle or a heterocycle, such as a 5, 6 or 7 membered carbocycle or heterocycle.

In still another variation, the compound is of the formula D where Q is substituted or unsubstituted aryl or a substituted or unsubstituted heteroaryl provided that:

(i) when Q is a substituted or unsubstituted heteroaryl the compound is not Piperidine, 1-[[2-cyclopentyl-2,3,4,5-tetrahydro-5-[(2-methyl-4-thiazolyl)methyl]-1H-pyrido[4,3-b]indol-8-yl]carbonyl]-4-methyl-; Piperidine, 4-methyl-1-[[2,3,4,5-tetrahydro-5-[(2-methyl-4-thiazolyl)methyl]-1H-pyrido[4,3-b]indol-8-yl]carbonyl]-; 2-Furancarboxylic acid, 5-[[2-cyclopentyl-1,2,3,4-tetrahydro-8-[(4-methyl-1-piperidinyl)carbonyl]-5H-pyrido[4,3-b]indol-5-yl]methyl]-; Piperidine, 1-[[2-cyclopentyl-2,3,4,5-tetrahydro-5-[(5-methyl-4-isoxazolyl)methyl]-1H-pyrido[4,3-b]indol-8-yl]carbonyl]-4-methyl-; Piperidine, 4-methyl-1-[[2,3,4,5-tetrahydro-5-[(5-methyl-4-isoxazolyl)methyl]-1H-pyrido[4,3-b]indol-8-yl]carbonyl]-; 8-chloro-2-methyl-5-(1-(6-methylpyridin-2-yl)ethyl)-2,3,4,5-tetrahydro-1H-pyrido[4,3-b]indole; 8-bromo-2-methyl-5-(1-(6-methylpyridin-3-yl)ethyl)-2,3,4,5-tetrahydro-1H-pyrido[4,3-b]indole; 8-chloro-2-methyl-5-(1-(6-methylpyridin-3-yl)ethyl)-2,3,4,5-tetrahydro-1H-pyrido[4,3-b]indole; and (ii) when Q is a substituted or unsubstituted aryl, (a) it is other than 5-(2,4-dimethylbenzyl)-2,8-dimethyl-2,3,4,5-tetrahydro-1H-pyrido[4,3-b]indole; 5-(4-chlorobenzyl)-2-methyl-2,3,4,5-tetrahydro-1H-pyrido[4,3-b]indole; 7-chloro-5-(4-chlorobenzyl)-2-methyl-2,3,4,5-tetrahydro-1H-pyrido[4,3-b]indole; 8-chloro-5-(4-chlorobenzyl)-2-methyl-2,3,4,5-tetrahydro-1H-pyrido[4,3-b]indole; 8-fluoro-5-(4-fluorobenzyl)-2-(2-(pyridin-2-yl)ethyl)-2,3,4,5-tetrahydro-1H-pyrido[4,3-b]indole; (5-(4-hydroxybenzyl)-3,4-dihydro-1H-pyrido[4,3-b]indol-2(5H)-yl)(4-hydroxyphenyl) methanone; and 8-chloro-5-(4-methoxybenzyl)-2-methyl-2,3,4,5-tetrahydro-1H-pyrido[4,3-b]indole; or (b) it is other than an unsubstituted phenyl; and (iii) when $X^9$ is $CR^4$, $R^4$ is other than 4-methylpiperidine-1-carbonyl, 4-methoxypiperidine-1-carbonyl, 4-ethoxypiperidine-1-carbonyl; or or a salt or solvate thereof.

In one variation, the compound is of the formula (E) or (D) provided that when the compound is of the formula (E), both m and q are 0, and at least one of (i)-(vii) applies:

(i) when $X^8$ and $X^{10}$ are both CH, $X^7$ is $CR^4$ where $R^4$ is F, $CF_3$ or carbonylalkoxy, $X^9$ is $CR^4$ where $R^4$ is H, methyl, fluoro, or carbonylalkoxy, and $R^1$ is H or substituted or unsubstituted $C_1$-$C_5$alkyl, then Q is other than unsubstituted phenyl, 4-fluorophenyl, 4-ethoxycarbonylphenyl and unsubstituted pyridyl;

(ii) when $X^8$ and $X^{10}$ are both CH, $X^7$ is $CR^4$ where $R^4$ is F, $CF_3$ or carbonylalkoxy, $X^9$ is $CR^4$ where $R^4$ is H, methyl, fluoro, or carbonylalkoxy, and $R^1$ is carbonylalkoxy, then Q is other than phenyl, 4-fluorophenyl and unsubstituted pyridyl;

(iii) when each $X^7$-$X^{10}$ is CH and $R^1$ is carbonylalkoxy, then Q is other than phenyl and unsubstituted pyridyl;

(iv) when $X^8$ and $X^{10}$ are both CH, one of $X^7$ and $X^9$ is $CR^4$ where $R^4$ if fluoro, $CF_3$, carboxyl or carbonylalkoxy and the other is CH, $R^1$ is H, methyl, substituted $C_1$-$C_2$alkyl or carbonylalkoxy, then Q is other than phenyl, 4-fluorophenyl and unsubstituted pyridyl;

(v) when each of $X^7$-$X^{10}$ is CH and $R^1$ is methyl or butyl, then Q is other than phenyl, 4-fluorophenyl and unsubstituted pyridyl;

(vi) when $X^7$, $X^8$ and $X^{10}$ are each CH; $X^9$ is $CR^4$ where $R^4$ is fluoro, methyl or $CF_3$ and $R^1$ is methyl, then Q is other than phenyl, substituted phenyl, unsubstituted pyridyl, 1,2,5,6-tetrahydropyridin-3-yl and 2-thiophenyl; and (vii) when each of $X^8$-$X^{10}$ is CH, $X^7$ is $CR^4$ where $R^4$ is fluoro or $CF_3$, and $R^1$ is methyl, then Q is other than phenyl and unsubstituted pyridyl.

In one variation, a compound of the invention is of the Formula (I) where: $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; and each $R^{10a}$ and $R^{10b}$ is independently H, halo, hydroxyl or methyl or $R^{10a}$ and $R^{10b}$ are taken together to form a carbonyl. This variation of Formula (I) is referred to herein as formula "(Ia)". In one variation, the compound is of the Formula (Ia), provided that the compound is other than a compound in Table 1 or salt thereof. In another variation, the compound is of the formula Ia, provided that the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 52x, 53x, 54x, 55x, 56x, 57x, 58x, 59x, 60x, 61x, 62x, 65x, 66x, 67x, 68x, 69x, 71x, 72x, 73x, 74x, 77x, 78x, 80x, 81x, 82x, 83x, 84x, 85x, 89x, 90x, 91x, 92x, 93x, 94x, 95x, 96x, 97x, 98x, 100x, 101x, 102x, 103x, 104x, 105x, 106x, 107x, 109x, 110x, 111x, 113x, 114x, 115x, 116x, 117x, 118x, 119x, 120x, 121x, 122x, 123x, 124x, 125x, 126x, 127x, 128x, 129x, 130x, 131x, 132x, 133x, 134x, 135x, 136x, 137x, 138x, 139x, 140x, 141x, 142x, 143x, 144x, 145x, 146x, 148x, 149x, 150x, 151x, 152x, 155x, 157x, 158x, 159x, 160x, 161x, 162x, 163x, 164x, 165x, 166x, 167x, 168x, 169x, 170x, 171x, 172x, 173x, 174x, 175x, 176x, 177x, 178x, 179x, 181x, 182x, 183x, 184x, 185x, 186x, 187x, 188x, 189x, 190x, 191x, 192x, 193x, 194x, 195x, 196x, 197x, 198x, 199x, 200x, 201x, 202x, 203x, 204x, 205x, 206x, 207x, 208x, 209x, 210x, 211x, 212x, 213x, 214x, 219x, 220x, 221x, 222x, 223x, 224x, 225x, 226x, 227x, 228x, 229x, 230x, 231x, 232x, 233x, 234x, 235x, 236x, 237x, 238x, 239x, 243x, 244x, 245x, 246x, 247x, 248x, 249x, 250x, 251x, 252x, 253x, 254x, 255x, 256x, 257x, 258x, 259x, 260x, 261x, 262x, 263x, 264x, 265x, 266x, 267x, 268x, 269x, 270x, 271x, 272x, 273x, 274x, 275x, 276x, 277x, 278x, 279x, 280x, 281x, 282x, 283x, 284x, 285x, 286x, 287x, 288x, 289x, 290x, 291x, 292x, 293x, 294x and 295x or salt thereof. In another variation, the compounds of the invention, and methods of using the compounds detailed herein, encompass any of the compounds of formula Ia, including those listed in Table 1 or a salt thereof. All variations referring to Formula (I), where applicable, may apply equally to any of formula A-F the same as if each and every variation were specifically and individually listed. Similarly, all variations referring to formula (I), where applicable, apply equally to all formulations and variations detailed herein.

In a particular embodiment, the compound is of the Formula (I) or Ia where $X^7$, $X^8$, $X^9$ and $X^{10}$ are $CR^4$. In another embodiment, the compound is of the Formula (I) or Ia where at least one of $X^7$, $X^8$, $X^9$ and $X^{10}$ is N. Another variation provides a compound of the Formula (I) or Ia where at least two of $X^7$, $X^8$, $X^9$ and $X^{10}$ are N. A further variation provides a compound of the Formula (I) or Ia where twi of $X^7$, $X^8$, $X^9$ and $X^{10}$ are N and two of $X^7$, $X^8$, $X^9$ and $X^{10}$ are $CR^4$. A compound of the Formula (I) or Ia where one of $X^7$, $X^8$, $X^9$ and $X^{10}$ is N and three of $X^7$, $X^8$, $X^9$ and $X^{10}$ are $CR^4$ is also embraced by this invention.

In another variation, a compound of the invention is of the Formula (I) or Ia where $X^7$, $X^8$, $X^9$ and $X^{10}$ are taken together to provide an aromatic moiety selected from the following structures:

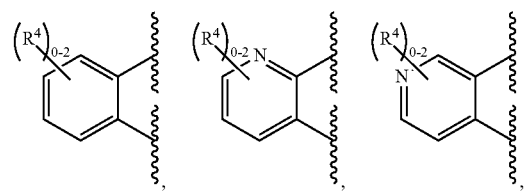

-continued

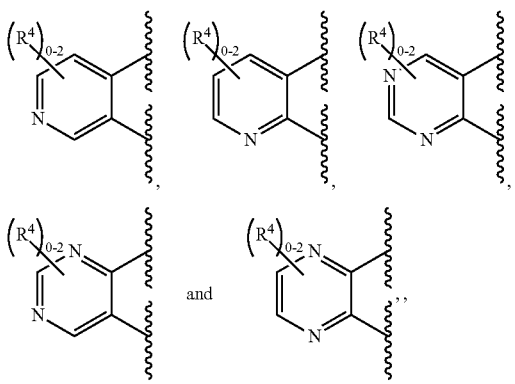

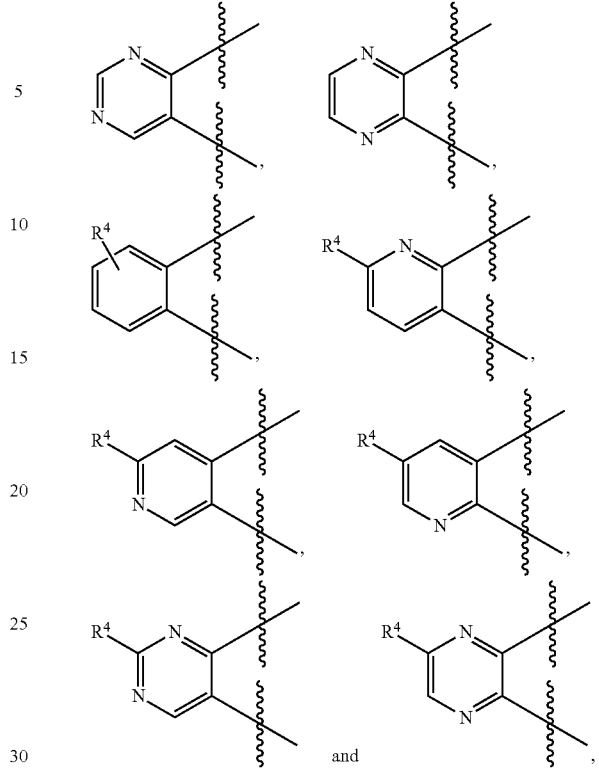

where each $R^4$ is as defined for Formula (I) or Ia; or in a particular variation, where each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where $R^4$ is independently halo, unsubstituted $C_1$-$C_4$ alkyl or $C_1$-$C_4$ perhaloalkyl. In one variation, $R^4$ is hydroxyl, carboxyl, methyl, —$CF_3$, chloro, —$OCF_3$, iso-propyl, ethyl, tert-butyl, —$CH_2OH$, bromo, iodo, fluoro, 3-pyridyl or —$CH_2CH_2CH_2NH_2$. In one variation, $R^4$ is other than hydrogen.

In still a further variation, a compound of the invention is of the Formula (I) or Ia where $X^7$, $X^8$, $X^9$ and $X^{10}$ are taken together provide an aromatic moiety selected from the following structures:

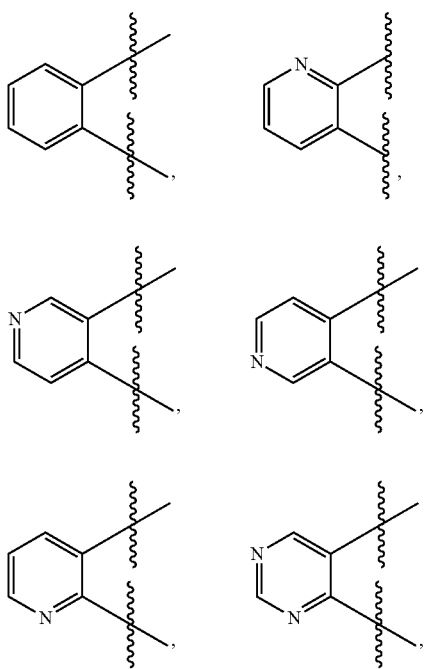

wherein $R^4$ is as defined in Formula (I); or in a particular variation, where $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where each $R^4$ is independently halo, unsubstituted $C_1$-$C_4$ alkyl or $C_1$-$C_4$ perhaloalkyl. In still another variation, $R^4$ is H, hydroxyl, carboxyl, methyl, —$CF_3$, chloro, —$OCF_3$, iso-propyl, ethyl, tert-butyl, —$CH_2OH$, bromo, iodo, fluoro, 3-pyridyl or —$CH_2CH_2CH_2NH_2$.

In another variation, a compound of the invention is of the Formula (I) or Ia or any variation herein, where $X^7$, $X^8$, $X^9$ and $X^{10}$ are taken together to form

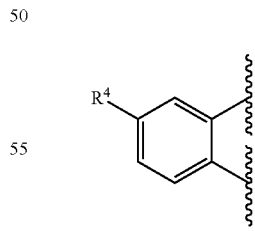

where $R^4$ is as defined in any variation herein, including where $R^4$ is H, hydroxyl, carboxyl, methyl, —$CF_3$, chloro, —$OCF_3$, iso-propyl, ethyl, tert-butyl, —$CH_2OH$, bromo, iodo, fluoro, 3-pyridyl or —$CH_2CH_2CH_2NH_2$.

In another embodiment, a compound of the invention is of the Formula (I), wherein $X^7$-$X^{10}$ are as defined in Formula (I) or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is of the Formula (I), wherein $X^7$-$X^{10}$ are as defined in Formula (I) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is of the Formula (I), wherein $X^7$-$X^{10}$ are as defined in Formula (I) or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycyclopropyl-2-yl, 1-hydroxy-1-methylcycloprop-2-yl, or 1-hydroxy-1,2,2-trimethyl-cycloprop-3-yl. In another variation of any formula or substructure herein, $R^1$ is H, carboxyl, propyl, ethoxycarbonyl, 2,2,2-trichloroethoxycarbonyl, hydroxymethyl, 3-amino-propyl, formyl, n-butyl, phenyl, or any of

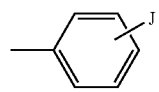

J = NH$_2$, H, CH$_3$, Br,
NO$_2$, OMe, F, Cl,
CHF$_2$, CF$_3$, I or OH.

In another variation, the compound of the invention is of the Formula (I), where $X^7$-$X^{10}$ and $R^1$ are as defined in Formula (I) or as detailed in any variation herein, where $R^{2a}$ and $R^{2b}$ are independently H, substituted or unsubstituted $C_1$-$C_8$ alkyl, halo, cyano, nitro or $R^{2a}$ and $R^{2b}$ are taken together to form a carbonyl moiety and each $R^{3a}$ and $R^{3b}$ is independently H, substituted or unsubstituted $C_1$-$C_8$ alkyl, halo, cyano or nitro. In another variation, the compound of the invention is of the Formula (I), where $X^7$-$X^{10}$ and $R^1$ are as defined in Formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is of the Formula (I), where $X^7$-$X^{10}$ and $R^1$ are as defined in Formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention according to Formula (I), where $X^7$-$X^{10}$ and $R^1$ are as defined in Formula (I) or as detailed in any variation herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety. The invention further embraces compounds of the invention according to Formula (I), where $X^7$-$X^{10}$ and $R^1$ are as defined in Formula (I) or as detailed in any variation herein, where each of $R^{2a}$, $R^{2b}$, $R^{3a}$ and $R^{3b}$ is H. In one variation, a compound of the invention is of the Formula (I) where $X^7$-$X^{10}$ and $R^1$ are as defined in Formula (I) or as detailed in any variation herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In another variation, a compound of the invention is of the Formula (I) where $X^7$-$X^{10}$ and $R^1$ are as defined in Formula (I) or as detailed in any variation herein, where at least two of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, a compound of the invention is of the Formula (I) where $X^7$-$X^{10}$ and $R^1$ are as defined in Formula (I) or as detailed in any variation herein, where at least one of $R^{2a}$, $R^{2b}$, $R^{3a}$ and $R^{3b}$ is fluoro or methyl or is taken together with a geminal $R^2$ or $R^3$ to form a carbonyl moiety. In still another variation, a compound of the invention is of the Formula (I) where $X^7$-$X^{10}$ and $R^1$ are as defined in Formula (I) or as detailed in any variation herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl. In another variation, when $X^1$ is N, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl.

The invention also embraces compounds according to Formula (I), where $X^7$-$X^{10}$, $R^1$, $R^{2a}$, $R^{2b}$, $R^{3a}$ and $R^{3b}$ are as defined in Formula (I) or as detailed in any variation herein, where each $R^{10a}$ and $R^{10b}$ is independently H, halo, an unsubstituted $C_1$-$C_8$ alkyl, hydroxyl or $R^{10a}$ and $R^{10b}$ are taken, together to form a carbonyl. Also embraced are compounds according to Formula (I), where $X^7$-$X^{10}$, $R^1$, $R^{2a}$, $R^{2b}$, $R^{3a}$ and $R^{3b}$ are as defined in Formula (I) or as detailed in any variation herein, where each $R^{10a}$ and $R^{10b}$ is independently H, halo, an unsubstituted $C_1$-$C_4$ alkyl, hydroxyl or $R^{10a}$ and $R^{10b}$ are taken together to form a carbonyl. In another variation, a compound of the invention is of the Formula (I), where $X^7$-$X^{10}$, $R^1$, $R^{2a}$, $R^{2b}$, $R^{3a}$ and $R^{3b}$ are as defined in Formula (I) or as detailed in any variation herein, where each $R^{10a}$ and $R^{10b}$ is independently H, bromo, methyl, hydroxyl or $R^{10a}$ and $R^{10b}$ are taken together to form a carbonyl. In yet another variation, a compound of the invention is of the Formula (I), where $X^7$-$X^{10}$, $R^1$, $R^{2a}$, $R^{2b}$, $R^{3a}$ and $R^{3b}$ are as defined in Formula (I) or as detailed in any variation herein, where at least one of $R^{10a}$ and $R^{10b}$ is an unsubstituted $C_1$-$C_8$ alkyl, hydroxyl, halo or $R^{10a}$ and $R^{10b}$ are taken together to form a carbonyl. In still a further variation, a compound of the invention is of the Formula (I), where $X^7$-$X^{10}$, $R^1$, $R^{2a}$, $R^{2b}$, $R^{3a}$ and $R^{3b}$ are as defined in Formula (I) or as detailed in any variation herein, where at least one of $R^{10a}$ and $R^{10b}$ is methyl, bromo, hydroxyl or $R^{10a}$ and $R^{10b}$ are taken together to form a carbonyl. In another variation, a compound of the invention is of the Formula (I), $X^7$-$X^{10}$, $R^1$, $R^{2a}$, $R^{2b}$, $R^{3a}$ and $R^{3b}$ are as defined in Formula (I) or as detailed in any variation herein, where both $R^{10a}$ and $R^{10b}$ are methyl. In another variation, a compound of the invention is of the Formula (I), where $X^7$-$X^{10}$, $R^1$, $R^{2a}$, $R^{2b}$, $R^{3a}$ and $R^{3b}$ are as defined in Formula (I) or as detailed in any variation herein, where $R^{10a}$ and $R^{10b}$ are taken together to form a carbonyl. In another variation, a compound of the invention is of the Formula (I), where $X^7$-$X^{10}$, $R^1$, $R^{2a}$, $R^{2b}$, $R^{3a}$ and $R^{3b}$ are as defined in Formula (I) or as detailed in any variation herein, where $R^{10a}$ is H and $R^{10b}$ is methyl. In another variation, a compound of the invention is of the Formula (I), where $X^7$-$X^{10}$, $R^1$, $R^{2a}$, $R^{2b}$, $R^{3a}$ and $R^{3b}$ are as defined in Formula (I) or as detailed in any variation herein, where $R^{10a}$ is H and $R^{10b}$ is bromo. When the carbon of Formula (I) bearing $R^{10a}$ and $R^{10b}$ is optically active, it may be in the S or R configuration and compositions comprising substantially pure R or S compound or mixtures thereof in any amount are embraced by this invention.

In a particular variation, a compound of the invention is of the Formula (I) where $R^{2a}$, $R^{2b}$, $X^1$, $R^{10a}$, $R^{10b}$, $R^{3a}$ and $R^{3b}$ are taken together to form a ring selected from the structures:

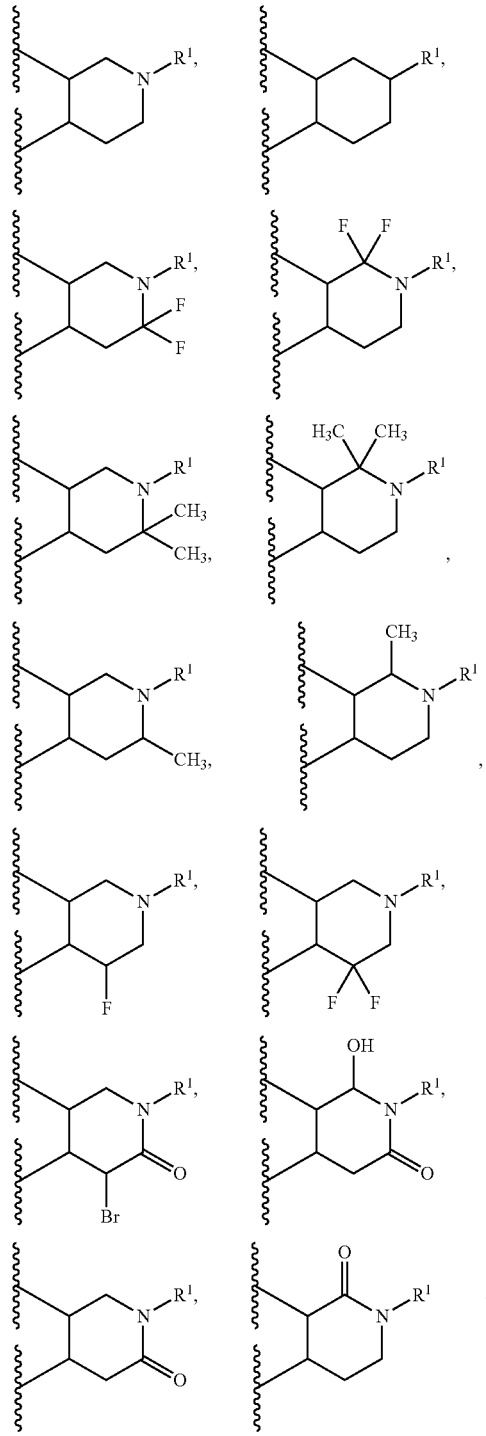

-continued

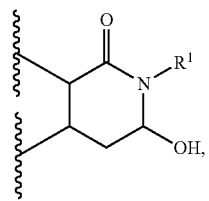

where $R^1$ in the structures above is as defined for Formula (I) or any particular variation detailed herein. In another variation, the invention embraces compounds having $R^{2a}$, $R^{2b}$, $X^1$, $R^{10a}$, $R^{10b}$, $R^{3a}$ and $R^{3b}$, wherein the substituents $R^{2a}$, $R^{2b}$, $X^1$, $R^{10a}$, $R^{10b}$, $R^{3a}$ and $R^{3b}$ are taken together to form a moiety of the formula:

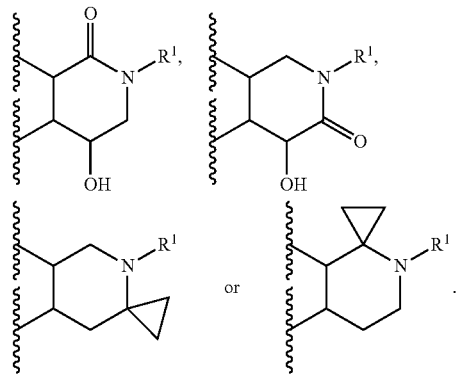

In a particular variation, $R^1$ of any structure or substructure detailed herein is methyl.

Compounds of the formulae (IIa), (IIb), (IIc), (IId), (IIe), (IIf), (IIg) and (IIh) are also embraced by this invention:

(IIa)

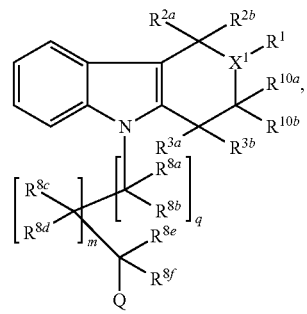

(IIb)

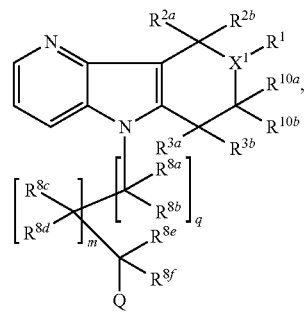

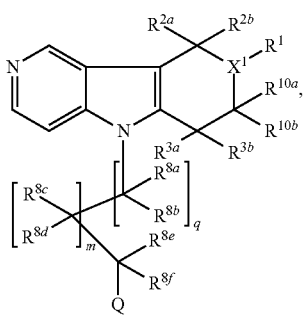

(IIc)

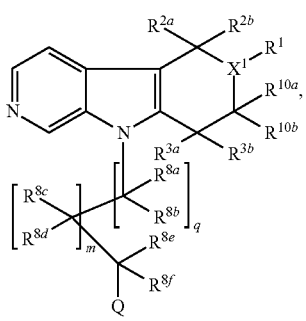

(IId)

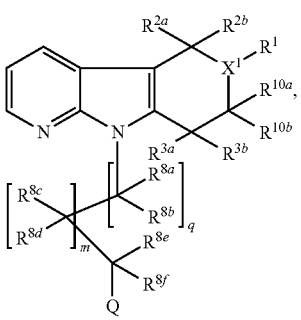

(IIe)

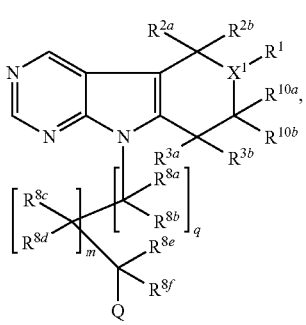

(IIf)

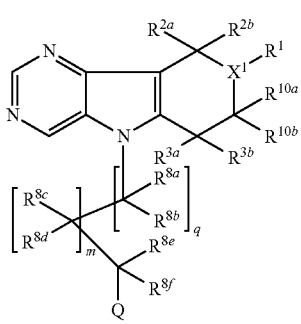

(IIg)

and

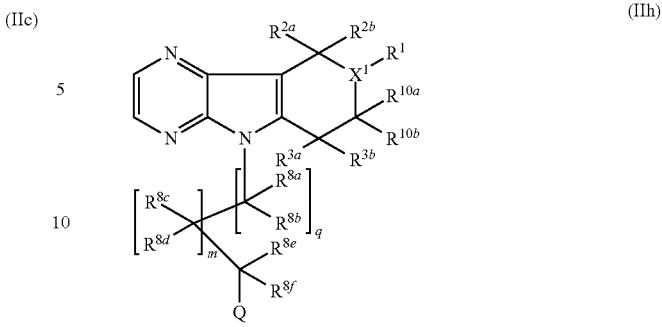

(IIh)

where in each of (IIa), (IIb), (IIc), (IId), (IIe), (IIf), (IIg) and (IIh), $R^1$, $R^{2a}$, $R^{2b}$, $R^{3a}$, $R^{3b}$, $R^{10a}$, $R^{10b}$, $R^{8a}$-$R^{8f}$, m, q and Q are as described for Formula (I) or any applicable variation thereof. Where applicable, each of (IIa), (IIb), (IIc), (IId), (IIe), (IIf), (IIg) and (IIh), $R^1$, $R^{2a}$, $R^{2b}$, $R^{3a}$, $R^{3b}$, $R^{10a}$, $R^{10b}$, $R^{8a}$-$R^{8f}$, m, q and Q may also be as described for any formulae or any applicable variation thereof detailed herein, including but not limited to formulae (A)-(G). In one variation, the compound is of the formula (IIa), provided that when $X^1$ is N, the compound is other than any of compounds 13x, 30x, 45x, 51x, 53x, 54x, 55x, 57x, 58x, 61x, 62x, 65x, 68x, 70x, 72x, 77x, 78x, 79x, 88x, 89x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 156x, 157x, 160x, 161x, 163x, 166x, 177x, 179x, 180x, 181x, 182x, 183x, 190x, 192x, 195x, 202x, 204x, 205x, 206x, 207x, 208x, 209x, 210x, 211x, 212x, 213x, 216x, 217x, 221x, 222x, 223x, 225x, 226x, 227x, 228x, 236x, 237x, 248x, 259x, 260x, 261x, 266x, 267x and 268x, or a salt thereof. In another variation, the compounds of the invention, and methods of using the compounds detailed herein, encompass any of the compounds of formula (IIa), including those listed in Table 1, such as 13x, 30x, 45x, 51x, 53x-55x, 57x, 58x, 61x, 62x, 65x, 68x, 70x, 72x, 77x-79x, 88x, 89x, 92x-94x, 96x, 97x, 100x, 101x, 104x, 105x, 125x-130x, 135x, 138x, 140x, 142x-146x, 156x, 157x, 160x, 161x, 163x, 166x, 177x, 179x-183x, 190x, 192x, 195x, 202x, 204x-213x, 216x, 217x, 221x-223x, 225x-228x, 236x, 237x, 248x, 259x, 260x, 261x, 266x, 267x and 268x, or a salt thereof. In one variation, the compound is of the formula (IIa) where q is 0, $R^1$ is methyl or ethyl and Q is a substituted phenyl.

In one variation, the compound is of the formula (IId) provided the compound is other than any of compounds 233x, 234x and 235x. In another variation, the compounds of the invention, and methods of using the compounds detailed herein, encompass any of the compounds of formula (IId), including those listed in Table 1, such as compounds 233x, 234x and 235x. In another variation, the compound is of formula (IId) provided that when Q is a substituted piperazinyl, $R^{8e}$ and $R^{8f}$ are not taken together with the carbon to which they are attached to form a carbonyl. In a further variation, the compound is of formula (IId) provided that when Q is a substituted piperazinyl and $R^{8e}$ and $R^{8f}$ are taken together with the carbon to which they are attached to form a carbonyl, $R^1$ is other than isopropyl. In a further variation, the compound is of formula (IId) where $R^1$ is methyl. In a particular variation, the compound is of formula (IId) where $R^1$ is methyl and q is 0. In still a further variation, the compound is of formula (IId) where $R^1$ is methyl and $R^{2a}$, $R^{2b}$, $R^{3a}$, $R^{3b}$, $R^{10a}$, $R^{10b}$ and each of $R^{8a}$-$R^{8f}$, where present, is hydrogen.

Compounds of the formulae (IIIa), (IIIb), (IIIc), (IIId), (IIIe), (IIIf), (IIIg), (IIIh), (IIIi), (IIIj), (IIIk), (IIIl), (IIIm) are further embraced this invention:

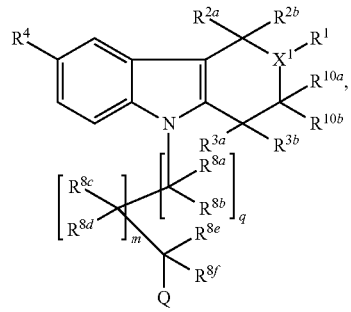 (IIIa)
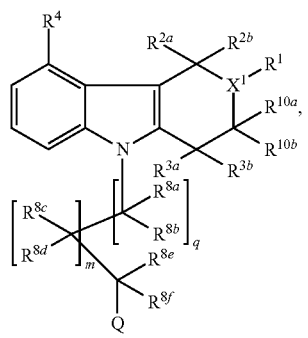 (IIIb)
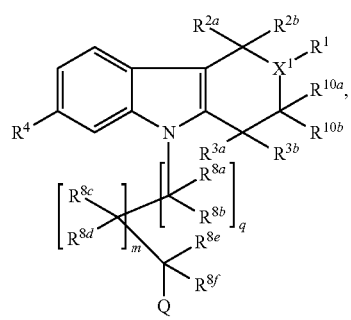 (IIIc)
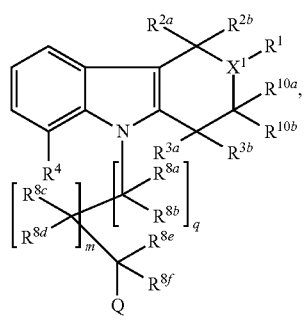 (IIId)
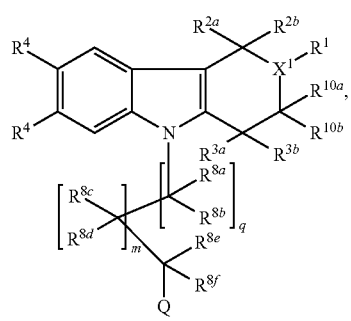 (IIIe)
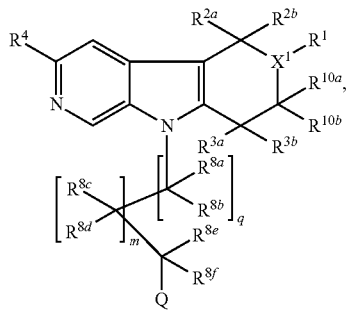 (IIIf)
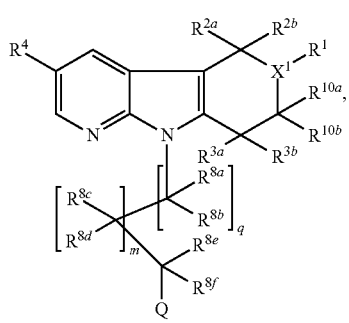 (IIIg)
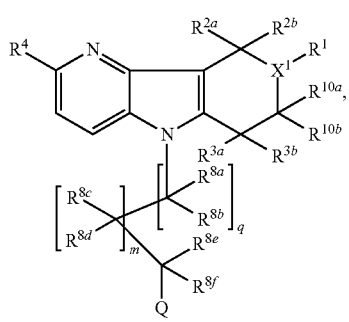 (IIIh)
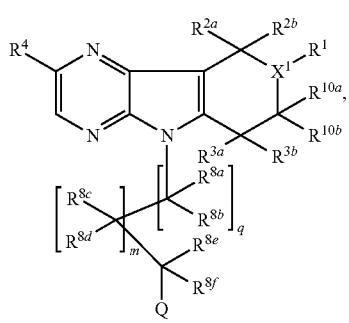 (IIIi)
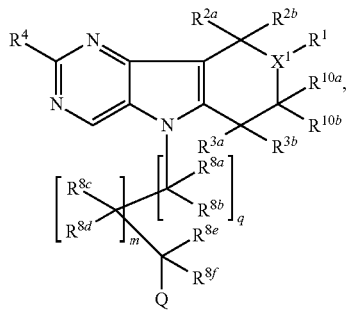 (IIIj)

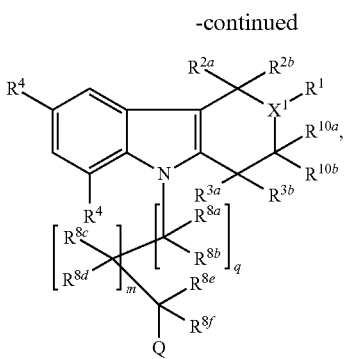

(IIIk)

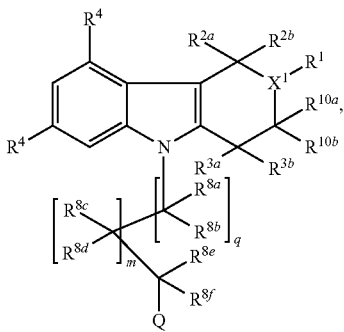

(IIIl)

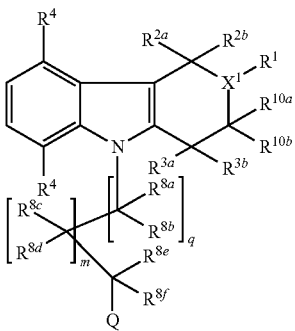

(IIIm)

where in each of (IIIa), (IIIb), (IIIc), (IIId), (IIIe), (IIIf), (IIIg), (IIIh), (IIIi), (IIIj), (IIIk), (IIIl) and (IIIm), $R^1$, $R^4$, $R^{2a}$, $R^{2b}$, $R^{3a}$, $R^{3b}$, $R^{10a}$, $R^{10b}$, $R^{8a}$-$R^{8f}$, m, q and Q are as described for Formula (I) or any applicable variation thereof. Where applicable, in each of (IIIa), (IIIb), (IIIc), (IIId), (IIIe), (IIIf), (IIIg), (IIIh), (IIIi), (IIIj), (IIIk), (IIIl) and (IIIm), $R^1$, $R^4$, $R^{2a}$, $R^{2b}$, $R^{3a}$, $R^{3b}$, $R^{10a}$, $R^{10b}$, $R^{8a}$-$R^{8f}$, m, q and Q may also be as described for any formulae or any applicable variation thereof detailed herein, including but not limited to formulae (A)-(G).

In one variation, the compound is of the formula (IIIa), provided that (i) when $X^1$ is N, the compound is other than any of compounds 1x, 2x, 3x, 4x, 5x, 6x, 7x, 8x, 9x, 10x, 11x, 12x, 13x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 47x, 49x, 50x, 51x, 52x, 53x, 54x, 55x, 56x, 57x, 58x, 59x, 60x, 61x, 62x, 65x, 68x, 69x, 70x, 72x, 77x, 78x, 79x, 81x, 84x, 85x, 88x, 89x, 90x, 92x, 93x, 94x, 95x, 96x, 97x, 98x, 100x, 101x, 102x, 103x, 104x, 105x, 106x, 107x, 109x, 110x, 111x, 115x, 116x, 117x, 118x, 119x, 120x, 121x, 122x, 123x, 124x, 125x, 126x, 127x, 128x, 129x, 130x, 134x, 135x, 136x, 137x, 138x, 139x, 140x, 142x, 143x, 144x, 145x, 146x, 148x, 149x, 150x, 151x, 152x, 155x, 156x, 157x, 158x, 159x, 160x, 161x, 162x, 163x, 164x, 165x, 166x, 167x, 171x, 174x, 175x, 176x, 177x, 178x, 179x, 180x, 181x, 182x, 183x, 184x, 189x, 190x, 191x, 192x, 193x, 194x, 195x, 196x, 198x, 199x, 200x, 201x, 202x, 203x, 204x, 205x, 206x, 207x, 208x, 209x, 210x, 211x, 212x, 213x, 214x, 216x, 217x, 219x, 220x, 221x, 222x, 223x, 224x, 225x, 226x, 227x, 228x, 229x, 231x, 232x, 236x, 237x, 238x, 239x, 243x, 244x, 245x, 248x, 249x, 250x, 251x, 252x, 253x, 254x, 255x, 256x, 258x, 259x, 260x, 261x, 262x, 263x, 264x, 265x, 266x, 267x, 268x, 269x, 270x, 271x, 272x, 273x, 274x, 275x, 276x, 279x, 280x, 281x, 282x, 285x, 286x, 287x, 288x, 290x, 291x, 292x, 293x, 294x and 295x, or a salt thereof and (ii) the compound is other than any of compounds 229H, 230, 241, 255, 256, 262 and 274 or a salt thereof. In another variation, the compounds of the invention, and methods of using the compounds and administering the compounds detailed herein, encompass any of the compounds of formula (IIIa), including those listed in Table 1, such as 1x-13x, 15x-45x, 47x, 49x-62x, 65x, 68x-70x, 72x, 77x-79x, 81x, 84x, 85x, 88x-90x, 92x-98x, 100x-107x, 109x-111x, 115x-130x, 134x-140x, 142x-146x, 148x-152x, 155x-167x, 171x, 174x-184x, 189x-196x, 198x-214x, 216x, 217x, 219x-229x, 231x, 232x, 236x-239x, 243x-245x, 248x-256x, 258x-276x, 279x-282x, 285x-288x and 290x-295x, or a salt thereof and compounds 229H, 230, 241, 255, 256, 262 and 274, or a salt thereof. In another variation, the compound is of the formula (IIIa) where $R^4$ is other than H, $R^1$ is methyl, m is 0 and q is 1 and where Q is a substituted or unsubstituted aryl, substituted or unsubstituted $C_{3-8}$ cycloalkyl or a substituted or unsubstituted $C_{3-8}$ cycloalkenyl. In a particular variation, the compound is of formula (IIIa) where $R^4$ is other than hydrogen; q is 0 and at least one of (i)-(iii) applies: (i) at least one of $R^{8c}$, $R^{8d}$, $R^{8e}$ and $R^{8f}$ is hydroxyl, $C_1$-$C_8$ alkyl, $C_1$-$C_8$ perhaloalkyl, carboxy, carbonylalkoxy, or is taken together with the carbon to which it is attached and a geminal $R^8$ to form a cycloalkyl moiety or a carbonyl moiety; (ii) at least one of $X^7$-$X^{10}$ is N; (iii) m is 0, $R^{8c}$, $R^{8d}$, $R^{8e}$ and $R^{8f}$ are each hydrogen and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl, provided that: (a) when Q is an unsubstituted heteroaryl it is other than pyridyl; (a) when Q is a substituted heteroaryl, it is other than 6-methyl-3-pyridyl; and (c) when Q is an unsubstituted heterocyclyl, it is an unsubstituted heterocyclyl having at least two annular heteroatoms.

In one variation, the compound is of the formula (IIIb), provided that when $X^1$ is N, the compound is other than any of compounds 13x, 30x, 45x, 51x, 53x, 54x, 55x, 57x, 58x, 61x, 62x, 65x, 66x, 67x, 68x, 70x, 72x, 77x, 78x, 79x, 88x, 89x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 156x, 157x, 160x, 161x, 163x, 166x, 177x, 179x, 180x, 181x, 182x, 183x, 190x, 192x, 195x, 202x, 204x, 205x, 206x, 207x, 208x, 209x, 210x, 211x, 212x, 213x, 216x, 217x, 221x, 222x, 223x, 225x, 226x, 227x, 228x, 236x, 237x, 248x, 259x, 260x, 261x, 266x, 267x and 268x, or a salt thereof. In another variation, the compounds of the invention, and methods of using the compounds detailed herein, encompass any of the compounds of formula (IIIb), including those listed in Table 1, such as 13x, 30x, 45x, 51x, 53x-55x, 57x, 58x, 61x, 62x, 65x-68x, 70x, 72x, 77x-79x, 88x, 89x, 92x-94x, 96x, 97x, 100x, 101x, 104x, 105x, 125x-130x, 135x, 138x, 140x, 142x-146x, 156x, 157x, 160x, 161x, 163x, 166x, 177x, 179x-183x, 190x, 192x, 195x, 202x, 204x-213x, 216x, 217x, 221x-223x, 225x, 226x, 236x, 237x, 248x, 259x, 260x, 261x, 266x, 267x and 268x, or a salt thereof. In one variation, the compound is of the formula (IIIb) where $R^4$ is other than hydrogen, provided the compound is other than 66x or 67x. In another variation, the compound is of the formula (IIIb) where m is 0, q is 1 and $R^4$ is hydroxyl, nitro, cyano, halo, $C_1$-$C_8$ perhaloalkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl.

In one variation, the compound is of the formula (IIIc), provided that when $X^1$ is N, the compound is other than any of compounds 13x, 14x, 30x, 45x, 51x, 53x, 54x, 55x, 57x, 58x, 61x, 62x, 65x, 68x, 70x, 72x, 77x, 78x, 79x, 80x, 82x, 83x, 88x, 89x, 92x, 93x, 94x, 96x, 97x, 100x, 101x, 104x, 105x, 125x, 126x, 127x, 128x, 129x, 130x, 132x, 135x, 138x, 140x, 141x, 142x, 143x, 144x, 145x, 146x, 156x, 157x, 160x, 161x, 163x, 166x, 170x, 177x, 179x, 180x, 181x, 182x, 183x, 187x, 190x, 192x, 195x, 197x, 202x, 204x, 205x, 206x, 207x, 208x, 209x, 210x, 211x, 212x, 213x, 216x, 217x, 221x, 222x, 223x, 225x, 226x, 227x, 228x, 230x, 236x, 237x, 248x, 259x, 260x, 261x, 266x, 267x and 268x, or a salt thereof. In another variation, the compounds of the invention, and methods of using the compounds detailed herein, encompass any of the compounds of formula (IIIc), including those listed in Table 1, such as 13x, 14x, 30x, 45x, 51x, 53x-55x, 57x, 58x, 61x, 62x, 65x, 68x, 70x, 72x, 77x-80x, 82x, 83x, 88x, 89x, 92x-94x, 96x, 97x, 100x, 101x, 104x, 105x, 125x-130x, 132x, 135x, 138x, 140x-146x, 156x, 157x, 160x, 161x, 163x, 166x, 170x, 177x, 179x-183x, 187x, 190x, 192x, 195x, 197x, 202x, 204x-213x, 216x, 217x, 221x-223x, 225x-228x, 230x, 236x, 237x, 248x, 259x-261x and 266x-268x, or a salt thereof. In one variation, the compound is of the formula (IIIc) where $X^1$ is N and $R^4$ is other than hydrogen, provided the compound is other than 14x, 80x, 82x, 83x, 132x, 141x, 170x, 187x, 197x or 230x. In one variation, the compound is of the formula (IIIc) where $X^1$ is N, $R^4$ is other than hydrogen, m is 0 and q is 1, $R^{8e}$ and $R^{8f}$ are both H and Q is other than 6-methyl-3-pyridyl or 4-pyridyl.

In one variation, the compound is of the formula (IIId), provided that when $X^1$ is N, the compound is other than any of compounds 13x, 30x, 45x, 46x, 51x, 53x, 54x, 55x, 57x, 58x, 61x, 62x, 65x, 68x, 70x, 71x, 72x, 77x, 78x, 79x, 88x, 89x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 156x, 157x, 160x, 161x, 163x, 166x, 177x, 179x, 180x, 181x, 182x, 183x, 185x, 190x, 192x, 195x, 202x, 204x, 205x, 206x, 207x, 208x, 209x, 210x, 211x, 212x, 213x, 216x, 217x, 218x, 221x, 222x, 223x, 225x, 226x, 227x, 228x, 236x, 237x, 246x, 247x, 248x, 257x, 259x, 260x, 261x, 266x, 267x, 268x, 277x, 278x, 283x, 284x and 289x, or a salt thereof. In another variation, the compounds of the invention, and methods of using the compounds detailed herein, encompass any of the compounds of formula (IIId), including those listed in Table 1, such as 13x, 30x, 45x, 46x, 51x, 53x-55x, 57x, 58x, 61x, 62x, 65x, 68x, 70x-72x, 77x-79x, 88x, 89x, 92x-94x, 96x, 97x, 100x, 101x, 104x, 105x, 125x-130x, 135x, 138x, 140x, 142x-146x, 156x, 157x, 160x, 161x, 163x, 166x, 177x, 179x-183x, 185x, 190x, 192x, 195x, 202x, 204x-213x, 216x-218x, 221x-223x, 225x-228x, 236x, 237x, 246x-248x, 257x, 259x-261x, 266x-268x, 277x, 278x, 283x, 284x and 289x, or a salt thereof. In a further variation, the compound is of the formula (IIId) where $R^4$ is other than hydrogen, provided that the compound is other than any of compounds 46x, 71x, 185x, 218x, 246x, 247x, 257x, 277x, 278x, 283x, 284x and 289x. In a further variation, the compound is of the formula (IIId) where $R^4$ is other than hydrogen, m is 0 and q is 1 and Q is other than 6-methyl-3-pyridyl and 4-pyridyl. In still a further variation, the compound is of the formula (IIId) where $R^4$ is halo or hydroxyl, m is 0 and q is 1.

In one variation, the compound is of the formula (IIIe), provided that (i) when $X^1$ is N, the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 47x, 49x, 50x, 51x, 52x, 53x, 54x, 55x, 56x, 57x, 58x, 59x, 60x, 61x, 62x, 65x, 68x, 69x, 70x, 72x, 77x, 78x, 79x, 80x, 81x, 82x, 83x, 84x, 85x, 88x, 89x, 90x, 92x, 93x, 94x, 95x, 96x, 97x, 98x, 100x, 101x, 102x, 103x, 104x, 105x, 106x, 107x, 109x, 110x, 111x, 113x, 115x, 116x, 117x, 118x, 119x, 120x, 121x, 122x, 123x, 124x, 125x, 126x, 127x, 128x, 129x, 130x, 131x, 132x, 134x, 135x, 136x, 137x, 138x, 139x, 140x, 141x, 142x, 143x, 144x, 145x, 146x, 148x, 149x, 150x, 151x, 152x, 155x, 156x, 157x, 158x, 159x, 160x, 161x, 162x, 163x, 164x, 165x, 166x, 167x, 168x, 169x, 170x, 171x, 173x, 174x, 175x, 176x, 177x, 178x, 179x, 180x, 181x, 182x, 183x, 184x, 186x, 187x, 189x, 190x, 191x, 192x, 193x, 194x, 195x, 196x, 197x, 198x, 199x, 200x, 201x, 202x, 203x, 204x, 205x, 206x, 207x, 208x, 209x, 210x, 211x, 212x, 213x, 214x, 216x, 217x, 219x, 220x, 221x, 222x, 223x, 224x, 225x, 226x, 227x, 228x, 229x, 230x, 231x, 232x, 236x, 237x, 238x, 239x, 243x, 244x, 245x, 248x, 249x, 250x, 251x, 252x, 253x, 254x, 255x, 256x, 258x, 259x, 260x, 261x, 262x, 263x, 264x, 265x, 266x, 267x, 268x, 269x, 270x, 271x, 272x, 273x, 274x, 275x, 276x, 279x, 280x, 281x, 282x, 285x, 286x, 287x, 288x, 290x, 291x, 292x, 293x, 294x and 295x, or a salt thereof and (ii) the compound is other than any of compounds 229H, 230, 241, 255, 256, 262 and 274 or a salt thereof. In another variation, the compounds of the invention, and methods of using the compounds and administering the compounds as detailed herein, encompass any of the compounds of formula (IIIe), including those listed in Table 1, such as 1x-45x, 47x, 49x-62x, 65x, 68x-70x, 72x, 77x-85x, 88x-90x, 92x-98x, 100x-107x, 109x-111x, 113x, 115x-132x, 134x-146x, 148x-152x, 155x-171x, 173x-184x, 186x, 187x, 189x-214x, 216x, 217x, 219x-232x, 236x-239x, 243x-245x, 248x-256x, 258x-276x, 279x-282x, 285x-288x and 290x-295x, or a salt thereof and compounds 229H, 230, 241, 255, 256, 262 and 274, or a salt thereof. In another variation, the compound is of the formula (IIIe) where each $R^4$ is other than hydrogen, provided that the compound is other than 113x, 131x, 168x, 169x, 173x or 186x. In another variation, the compound is of the formula (IIIe) where each $R^4$ is other than hydrogen, $R^{8e}$ and $R^{8f}$ are both hydrogen and Q is other than 4-pyridyl or 6-methyl-3-pyridyl.

In one variation, the compound is of the formula (IIIf) wherein the compound is other than any of compounds 233x, 234x and 235x. In another variation, the compounds of the invention, and methods of using the compounds and administering the compounds as detailed herein, encompass any of the compounds of formula (IIIf), including those listed in Table 1, such as 233x, 234x or 235x. In another variation, a compound of the invention is of formula (IIIf) provided that when Q is a substituted piperazinyl, $R^{8e}$ and $R^{8f}$ are not taken together with the carbon to which they are attached to form a carbonyl. In still another variation, a compound of the invention is of formula (IIIf) where $R^4$ is other than hydrogen. In still another variation, a compound of the invention is of formula (IIIf) where $R^4$ is methyl or trifluoromethyl. In another such variation, a compound of the invention is of formula (IIIf) where $R^4$ is methyl or trifluoromethyl, $R^1$ is methyl and m is 0 and q is 1.

In one variation, the compound is of the formula (IIIk) wherein the compound is other than any of compounds 1x, 2x, 3x, 4x, 5x, 6x, 7x, 8x, 9x, 10x, 11x, 12x, 13x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 49x, 50x, 51x, 52x, 53x, 54x, 55x, 56x, 57x, 58x, 59x, 60x, 61x, 62x, 65x, 68x, 69x, 70x, 71x, 72x, 77x, 78x, 79x, 81x, 84x, 85x, 88x, 89x, 90x, 92x, 93x, 94x, 95x, 96x, 97x, 98x, 100x, 101x, 102x, 103x, 104x, 105x, 106x, 107x, 109x, 110x, 111x, 115x, 116x, 117x, 118x, 119x, 120x, 121x, 122x, 123x, 124x, 125x, 126x, 127x, 128x, 129x, 130x, 134x, 135x, 136x, 137x, 138x, 139x, 140x, 142x, 143x, 144x, 145x, 146x, 148x, 149x, 150x, 151x, 152x, 155x, 156x, 157x, 158x, 159x, 160x, 161x, 162x, 163x, 164x, 165x, 166x, 167x, 171x, 172x, 174x, 175x, 176x, 177x, 178x, 179x, 180x, 181x, 182x, 183x, 184x, 185x, 189x, 190x, 191x, 192x, 193x, 194x, 195x, 196x, 198x, 199x, 200x, 201x, 202x, 203x, 204x, 205x, 206x, 207x, 208x, 209x, 210x, 211x, 212x, 213x, 214x, 216x, 217x, 218x, 219x, 220x, 221x, 222x, 223x, 224x, 225x, 226x, 227x, 228x, 229x, 231x, 232x, 236x, 237x, 238x, 239x, 243x, 244x, 245x, 246x, 247x, 248x, 249x, 250x, 251x, 252x, 253x, 254x, 255x, 256x, 257x, 258x, 259x, 260x, 261x, 262x, 263x, 264x, 265x, 266x, 267x, 268x, 269x, 270x, 271x, 272x, 273x, 274x, 275x, 276x, 277x, 278x, 279x, 280x, 281x, 282x, 283x, 284x, 285x, 286x, 287x, 288x, 289x, 290x, 291x, 292x, 293x, 294x and 295x. In another variation, the compounds of the invention, and methods of using the compounds and administering the compounds as detailed herein, encompass any of the compounds of formula (IIIk), including those listed in Table 1, such as compounds 1x-13x, 15x-47x, 49x-62x, 65x, 68x-72x, 77x-79x, 81x, 84x, 85x, 88x-90x, 92x-98x, 100x-107x, 109x-111x, 115x-130x, 134x-140x, 142x-146x, 148x-152x, 155x-167x, 171x, 172x, 174x-185x, 189x-196x, 198x, 199x-214x, 216x-229x, 231x, 232x, 236x-239x and 243x-295x. In a further variation, a compound is of the formula (IIIk) where each $R^4$ is other than hydrogen, provided that the compound is other than compound 172x. In a further variation, a compound is of the formula (IIIk) where each $R^4$ is independently alkyl, hydroxyl or halo, provided that when one $R^4$ is alkyl, the other $R^4$ is alkyl or hydroxyl. In still a further variation, a compound is of the formula (IIIk) where each $R^4$ is independently alkyl, hydroxyl or halo and Q is other than 6-methyl-3-pyridyl.

In one variation, the compound is of the formula (IIIl) wherein the compound is other than any of compounds 13x, 14x, 30x, 45x, 51x, 53x, 54x, 55x, 57x, 58x, 61x, 62x, 65x, 66x, 67x, 68x, 70x, 72x, 77x, 78x, 79x, 80x, 82x, 83x, 88x, 89x, 92x, 93x, 94x, 96x, 97x, 100x, 101x, 104x, 105x, 125x, 126x, 127x, 128x, 129x, 130x, 132x, 135x, 138x, 140x, 141x, 142x, 143x, 144x, 145x, 146x, 156x, 157x, 160x, 161x, 163x, 166x, 170x, 177x, 179x, 180x, 181x, 182x, 183x, 187x, 190x, 192x, 195x, 197x, 202x, 204x, 205x, 206x, 207x, 208x, 209x, 210x, 211x, 212x, 213x, 216x, 217x, 221x, 222x, 223x, 225x, 226x, 227x, 228x, 230x, 236x, 237x, 248x, 259x, 260x, 261x, 266x, 267x and 268x. In another variation, the compounds of the invention, and methods of using the compounds and administering the compounds as detailed herein, encompass any of the compounds of formula (IIIl), including those listed in Table 1, such as 13x, 14x, 30x, 45x, 51x, 53x-55x, 57x, 58x, 61x, 62x, 65x-68x, 70x, 72x, 77x-80x, 82x, 83x, 88x, 89x, 92x-94x, 96x, 97x, 100x, 101x, 104x, 105x, 125x-130x, 132x, 135x, 138x, 140x-146x, 156x, 157x, 160x, 161x, 163x, 166x, 170x, 177x, 179x-183x, 187x, 190x, 192x, 195x, 197x, 202x, 204x-213x, 216x, 217x, 221x-223x, 225x-228x, 230x, 236x, 237x, 248x, 259x-261x and 266x-268x. In a further variation, a compound is of the formula (IIIl) where each $R^4$ is other than hydrogen.

In one variation, the compound is of the formula (IIIm) wherein the compound is other than any of compounds 13x, 30x, 45x, 46x, 48x, 51x, 53x, 54x, 55x, 57x, 58x, 61x, 62x, 65x, 66x, 67x, 68x, 70x, 71x, 72x, 73x, 74x, 77x, 78x, 79x, 88x, 89x, 91x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 156x, 157x, 160x, 161x, 163x, 166x, 177x, 179x, 180x, 181x, 182x, 183x, 185x, 190x, 192x, 195x, 202x, 204x, 205x, 206x, 207x, 208x, 209x, 210x, 211x, 212x, 213x, 216x, 217x, 218x, 221x, 222x, 223x, 225x, 226x, 227x, 228x, 236x, 237x, 246x, 247x, 248x, 257x, 259x, 260x, 261x, 266x, 267x, 268x, 277x, 278x, 283x, 284x and 289x. In another variation, the compounds of the invention, and methods of using the compounds and administering the compounds as detailed herein, encompass any of the compounds of formula (IIIm), including those listed in Table 1, such as 13x, 30x, 45x, 46x, 48x, 51x, 53x-55x, 57x, 58x, 61x, 62x, 65x-68x, 70x-74x, 77x-79x, 88x, 89x, 91x-94x, 96x, 97x, 100x, 101x, 104x, 105x, 125x-130x, 135x, 138x, 140x, 142x-146x, 156x, 157x, 160x, 161x, 163x, 166x, 177x, 179x-183x, 185x, 190x, 192x, 195x, 202x, 204x-213x, 216x-218x, 221x-223x, 225x-228x, 236x, 237x, 246x-248x, 257x, 259x-261x, 266x-268x, 277x, 278x, 283x, 284x and 289x. In a further variation, a compound is of the formula (IIIm) where each $R^4$ is other than hydrogen, provided that the compound is other than any of compounds 48x, 73x, 74x and 91x. In still a further variation, a compound is of the formula (IIIm) where each $R^4$ is other than hydrogen, m is 0 and q is 1.

Compounds of the formulae (IVa), (IVb), (IVc), (IVd), (IVe), (IVf), (IVg), (IVh), (IVi), (IVj) and (IVk) are further embraced by this invention:

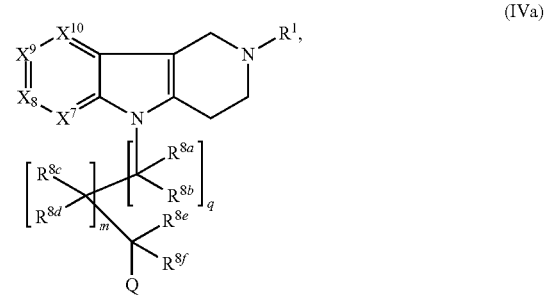

(IVa)

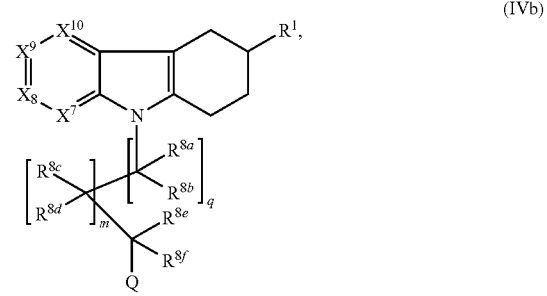

(IVb)

(IVc)
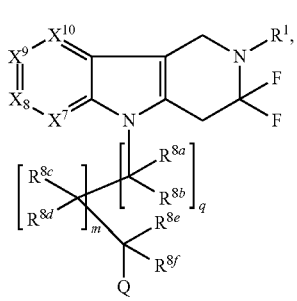

(IVd)
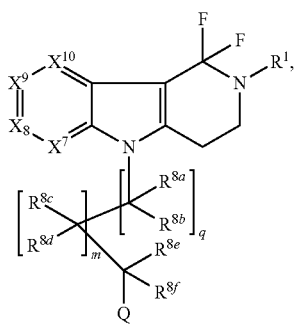

(IVe)
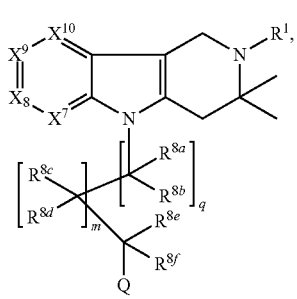

(IVf)
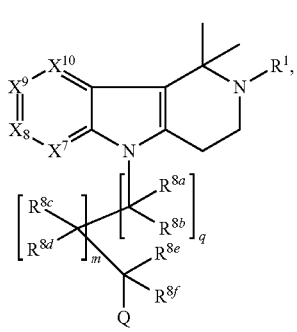

(IVg)
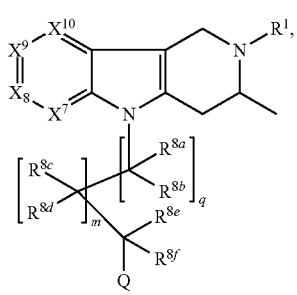

(IVh)
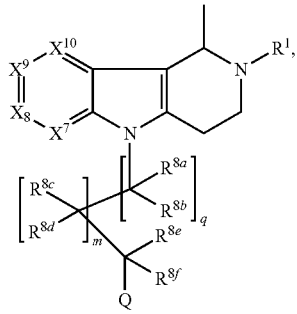

(IVi)
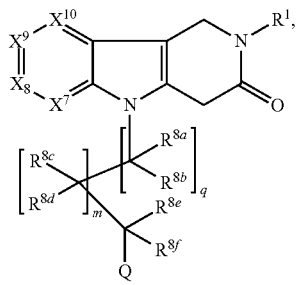

(IVj)
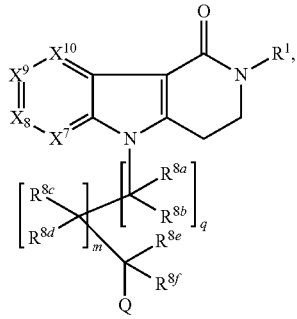

(IVk)
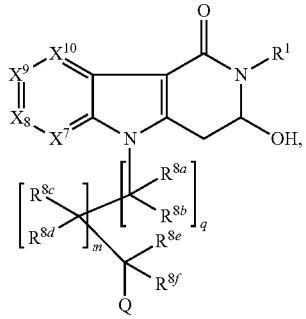

where in each of (IVa), (IVb), (IVc), (IVd), (IVe), (IVf), (IVg), (IVh), (IVi), (IVj) and (IVk), $R^1$, $X^7$, $X^8$, $X^9$, $X^{10}$, $X^{8a}$-$R^{8f}$, m, q and Q are as described for Formula (I) or any applicable variation thereof. Where applicable, in each of (IVa), (IVb), (IVc), (IVd), (IVe), (IVf), (IVg), (IVh), (IVi), (IVj) and (IVk), $R^1$, $X^7$, $X^8$, $X^9$, $X^{10}$, $R^{8a}$-$R^{8f}$, m, q and Q may also be as described for any formulae or any applicable variation thereof detailed herein, including but not limited to formulae (A)-(G).

In one variation, the compound is of the formula (IVa), provided that (i) the compound is other than any of compounds 1x-44x, 47x-50x, 52x, 54x-62x, 65x-67x, 71x-74x, 77x, 78x, 80x-85x, 88x-98x, 100x-107x, 109x-111x, 113x-146x, 148x-152x, 155x, 157x-179x, 181x-214x, 219x-239x and 243x-295x, or a salt thereof and (ii) the compound is other than any of compounds 229H, 230, 255, 256, 262 and 274 or a salt thereof. In another variation, the compounds of the invention, and methods of using the compounds and administering the compounds as detailed herein, encompass any of the compounds of formula (IVa), including those listed in Table 1, such as 1x-44x, 47x-50x, 52x, 54x-62x, 65x-67x, 71x-74x, 77x, 78x, 80x-85x, 88x-98x, 100x-107x, 109x-111x, 113x-146x, 148x-152x, 155x, 157x-179x, 181x-214x, 219x-239x and 243x-295x, or a salt thereof and compounds 229H, 230, 255, 256, 262 and 274, or a salt thereof.

In one variation, the compound is of the formula (IVb) provided that $R^1$ is $NR^aR^b$ and either:

(a) each $R^a$ and $R^b$ is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that both $R^a$ and $R^b$ groups are not H, and at least one of (i)-(iii) applies:

(i) when m and q are 0, at least one of $R^a$ and $R^b$ is other than methyl;

(ii) when m and q are 0, at least one of $X^7$-$X^{10}$ is other than CH;

(iii) when m and q are 0, either (a) Q is a other than a substituted or unsubstituted phenyl or (b) Q is a substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl; or (b) $R^a$ and $R^b$ are joined together with the nitrogen atom to form a heterocyclic or substituted heterocyclic ring. In one variation of formula (IVb), at least one of m and q is 1, $R^1$ is $NR_aR_b$ and either (a) each $R^a$ and $R^b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that both $R^a$ and $R^b$ groups are not H; or (b) $R^a$ and $R^b$ are joined together with the nitrogen atom to form a heterocyclic or substituted heterocyclic ring.

In another variation, the compound is of the (IVj), provided the compound is other than any of compounds 45x, 46x, 51x, 216x, 217x and 218x, or a salt thereof. In another variation, the compounds of the invention, and methods of using the compounds detailed herein, encompass any of the compounds of formula (IVj), including those listed in Table 1, such as 45x, 46x, 51x, 216x, 217x and 218x, or a salt thereof.

The invention also embraces compounds of the formulae (Va)-(Vzv):

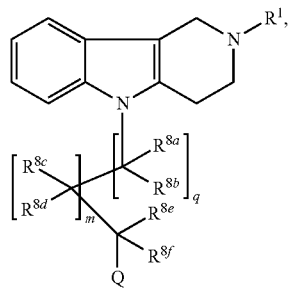

(Va)

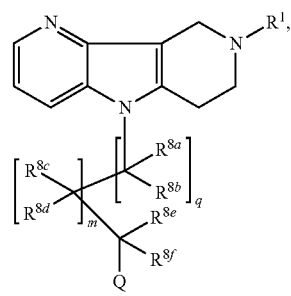

(Vb)

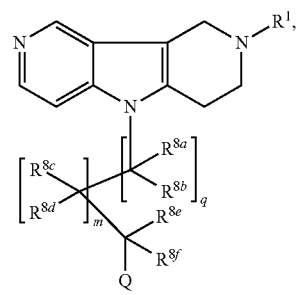

(Vc)

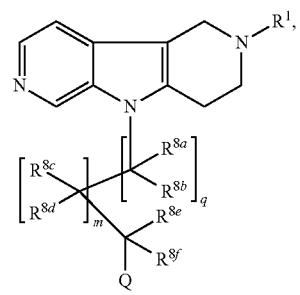

(Vd)

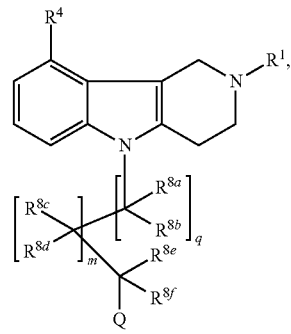

(Ve)

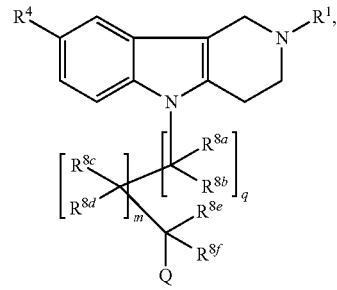

(Vf)

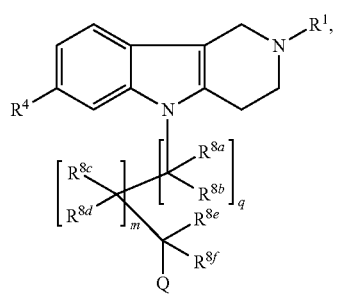 (Vg)
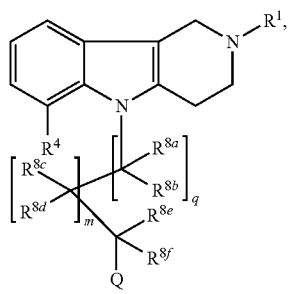 (Vh)
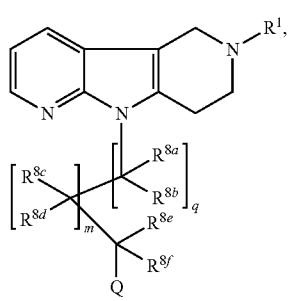 (Vi)
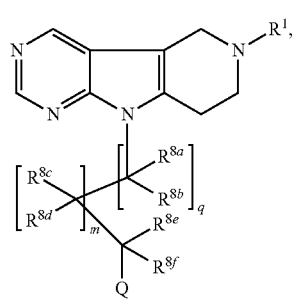 (Vj)
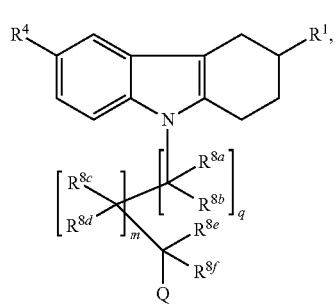 (Vk)
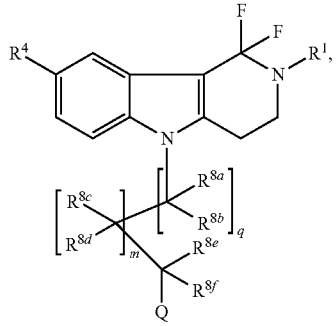 (Vl)
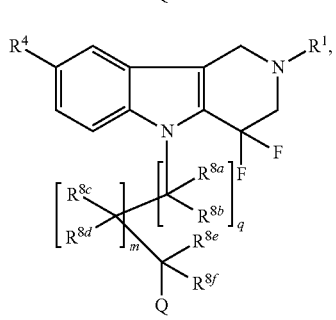 (Vm)
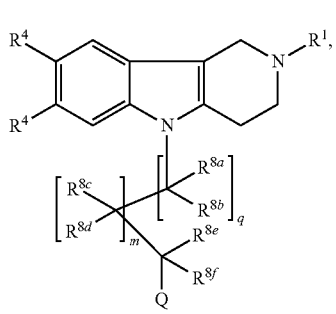 (Vn)
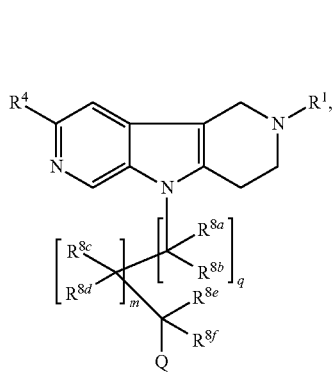 (Vo)
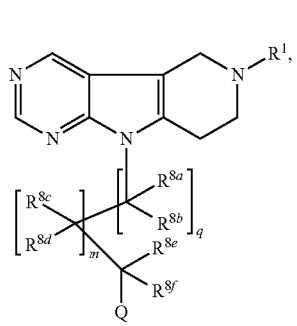 (Vp)

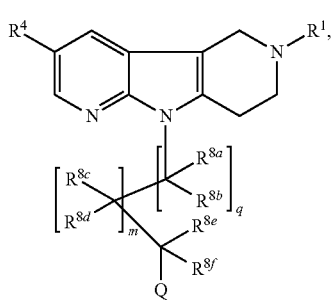
(Vq)
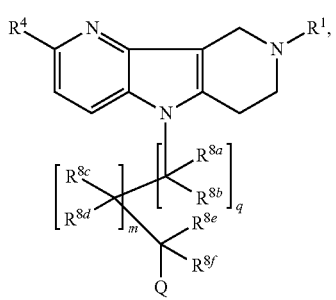
(Vr)
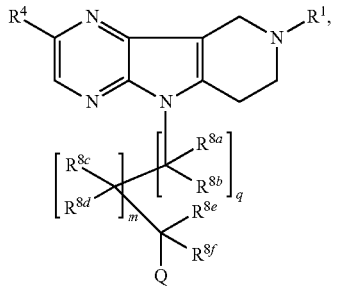
(Vs)
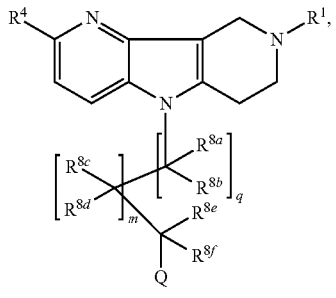
(Vt)
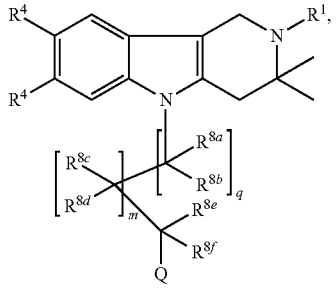
(Vu)
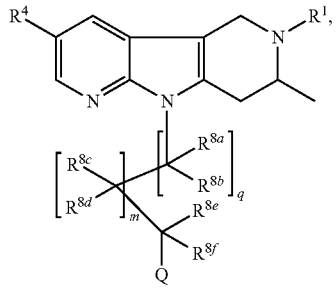
(Vv)
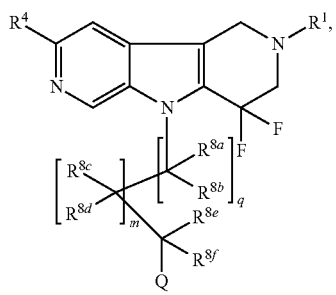
(Vw)
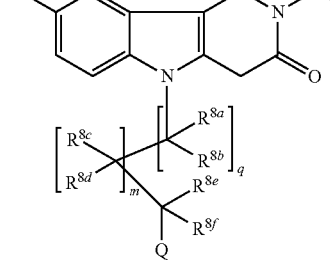
(Vx)
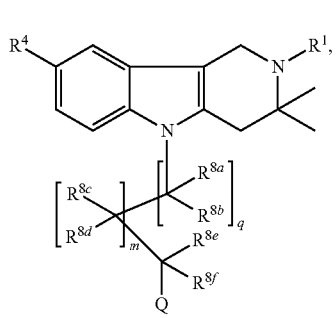
(Vy)
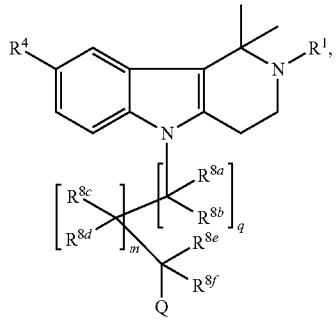
(Vz)

-continued (Vzi)
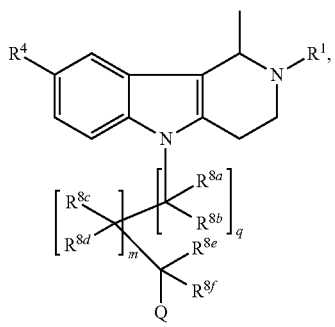

(Vzii)
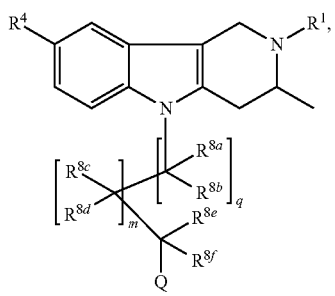

(Vziii)
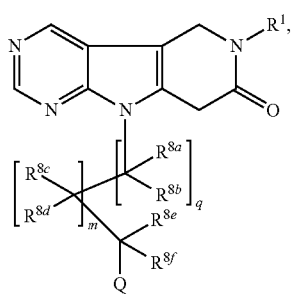

(Vziv)
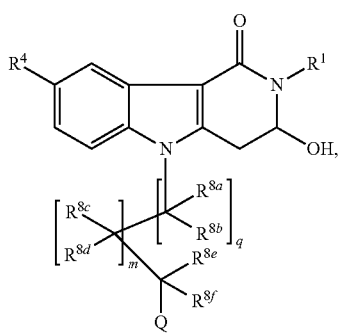

(Vzv)
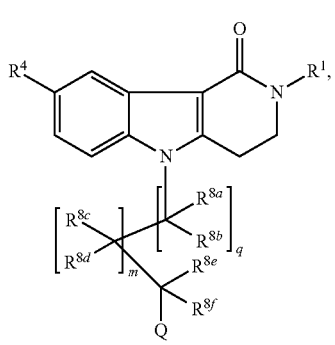

where in each of (Va)-(Vzv), $R^1$, $R^4$, $R^{8a}$-$R^{8f}$, m, q and Q are as described for Formula (I) or any applicable variation thereof. Where applicable, each of (Va)-(Vzv), $R^1$, $R^4$, $R^{8a}$-$R^{8f}$, m, q and Q may also be as described for any formulae or any applicable variation thereof detailed herein, including but not limited to formulae (A)-(G). In one variation, the compound is of the formula (Va), provided that the compound is other than any of compounds 13x, 30x, 54x, 55x, 57x, 58x, 61x, 62x, 65x, 72x, 77x, 78x, 88x, 89x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 157x, 160x, 161x, 163x, 166x, 177x, 179x, 181x, 182x, 183x, 190x, 192x, 195x, 202x, 204x, 205x, 206x, 207x, 208x, 209x, 210x, 211x, 212x, 213x, 221x, 222x, 223x, 225x, 226x, 227x, 228x, 236x, 237x, 248x, 259x, 260x, 261x, 266x, 267x and 268x, or a salt thereof. In another variation, the compounds of the invention, and methods of using the compounds detailed herein, encompass any of the compounds of formula (Va), including those listed in Table 1, such as 13x, 30x, 54x, 55x, 57x, 58x, 61x, 62x, 65x, 72x, 77x, 78x, 88x, 89x, 92x-94x, 96x, 97x, 100x, 101x, 104x, 105x, 125x-130x, 135x, 138x, 140x, 142x-146x, 157x, 160x, 161x, 163x, 166x, 177x, 179x, 181x-183x, 190x, 192x, 195x, 202x, 204x-213x, 221x-223x, 225x-228x, 236x, 237x, 248x, 259x, 260x, 261x, 266x, 267x and 268x, or a salt thereof.

In one variation, the compound is of the formula (Vd) provided the compound is other than any of compounds 233x, 234x and 235x. In another variation, the compounds of the invention, and methods of using the compounds detailed herein, encompass any of the compounds of formula (Vd), including those listed in Table 1, such as 233x, 234x and 235x. In another variation, the compound is of formula (Vd) provided that when Q is a substituted piperazinyl, $R^{8e}$ and $R^{8f}$ are not taken together with the carbon to which they are attached to form a carbonyl.

In one variation, the compound is of the formula (Ve), provided that the compound is other than any of compounds 13x, 30x, 54x, 55x, 57x, 58x, 61x, 62x, 65x, 66x, 67x, 72x, 77x, 78x, 88x, 89x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 157x, 160x, 161x, 163x, 166x, 177x, 179x, 181x, 182x, 183x, 190x, 192x, 195x, 202x, 204x, 205x, 206x, 207x, 208x, 209x, 210x, 211x, 212x, 213x, 221x, 222x, 223x, 225x, 226x, 227x, 228x, 236x, 237x, 248x, 259x, 260x, 261x, 266x, 267x and 268x, or a salt thereof. In another variation, the compounds of the invention, and methods of using the compounds detailed herein, encompass any of the compounds of formula (Ve), including those listed in Table 1, such as 13x, 30x, 54x, 55x, 57x, 58x, 61x, 62x, 65x-67x, 72x, 77x, 78x, 88x, 89x, 92x-94x, 96x, 97x, 100x, 101x, 104x, 105x, 125x-130x, 135x, 138x, 140x, 142x-146x, 157x, 160x, 161x, 163x, 166x, 177x, 179x, 181x-183x, 190x, 192x, 195x, 202x, 204x-213x, 221x-223x, 225x-228x, 236x, 237x, 248x, 259x, 260x, 261x, 266x, 267x and 268x, or a salt thereof. In another variation, the compound is of the formula (Ve) where $R^4$ is other than hydrogen, provided that the compound is other than any of compounds 66x and 67x. In another variation, the compound is of the formula (Ve) where $R^4$ is other than hydrogen (e.g., where $R^4$ is chloro), m is 0 and q is 1.

In one variation, the compound is of the formula (Vf), provided that the compound is other than any of compounds 1x, 2x, 3x, 4x, 5x, 6x, 7x, 8x, 9x, 10x, 11x, 12x, 13x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 47x, 49x, 50x, 52x, 54x, 55x, 56x, 57x, 58x, 59x, 60x, 61x, 62x, 65x, 72x, 77x, 78x, 81x, 84x, 85x, 88x, 89x, 90x, 92x, 93x, 94x, 95x, 96x, 97x, 98x, 100x, 101x, 102x, 103x, 104x, 105x, 106x, 107x, 109x, 110x, 111x, 115x, 116x, 117x, 118x, 119x, 120x, 121x, 122x, 123x, 124x, 125x, 126x, 127x, 128x, 129x, 130x, 134x, 135x, 136x, 137x, 138x, 139x, 140x, 142x, 143x, 144x, 145x, 146x, 148x, 149x, 150x, 151x, 152x, 155x, 157x, 158x, 159x, 160x, 161x, 162x, 163x, 164x, 165x, 166x, 167x, 171x, 174x, 175x, 176x, 177x, 178x, 179x, 181x, 182x, 183x, 184x, 189x, 190x, 191x, 192x, 193x, 194x, 195x, 196x, 198x, 199x, 200x, 201x, 202x, 203x, 204x, 205x, 206x, 207x, 208x, 209x, 210x, 211x, 212x, 213x, 214x, 219x, 220x, 221x, 222x, 223x, 224x, 225x, 226x, 227x, 228x, 229x, 231x, 232x, 236x, 237x, 238x, 239x, 243x, 244x, 245x, 248x, 249x, 250x, 251x, 252x, 253x, 254x, 255x, 256x, 258x, 259x, 260x, 261x, 262x, 263x, 264x, 265x, 266x, 267x, 268x, 269x, 270x, 271x, 272x, 273x, 274x, 275x, 276x, 279x, 280x, 281x, 282x, 285x, 286x, 287x, 288x, 290x, 291x, 292x, 293x, 294x and 295x, or a salt thereof. In another variation, the compounds of the invention, and methods of using the compounds and administering the compounds as detailed herein, encompass any of the compounds of formula (Vf), including those listed in Table 1, such as 1x-13x, 15x-44x, 47x, 49x, 50x, 52x, 54x-62x, 65x, 72x, 77x, 78x, 81x, 84x, 85x, 88x-90x, 92x-98x, 100x-107x, 109x-111x, 115x-130x, 134x-140x, 142x-146x, 148x-152x, 155x, 157x-167x, 171x, 174x-179x, 181x-184x, 189x-196x, 198x-214x, 219x-229x, 231x, 232x, 236x-239x, 243x-245x, 248x-256x, 258x-276x, 279x-282x, 285x-288x and 290x-295x, or a salt thereof and compounds 229H, 230, 255, 256, 262 and 274 or a salt thereof. In another variation, the compound is of the formula (Vf) where $R^4$ is other than hydrogen, m is 0 and q is 1, and at least one of (i)-(iii) applies: (i) Q is a substituted or unsubstituted aryl, a substituted or unsubstituted $C_3$-$C_8$cycloalkyl or a substituted or unsubstituted $C_3$-$C_8$cycloalkenyl; (ii) at least one of $R^{8a}$, $R^{8b}$, $R^{8e}$ and $R^{8f}$ is hydroxyl, $C_1$-$C_8$alkyl or is taken together with the carbon to which it is attached and a geminal $R^8$ to form a cycloalkyl moiety or a carbonyl moiety; and (iii) Q is other than piperidyl, azepanyl, 6-methyl-3-pyridyl or 4-pyridyl.

In one variation, the compound is of the formula (Vg), provided that the compound is other than any of compounds 13x, 14x, 30x, 54x, 55x, 57x, 58x, 61x, 62x, 65x, 72x, 77x, 78x, 80x, 82x, 83x, 88x, 89x, 92x, 93x, 94x, 96x, 97x, 100x, 101x, 104x, 105x, 125x, 126x, 127x, 128x, 129x, 130x, 132x, 135x, 138x, 140x, 141x, 142x, 143x, 144x, 145x, 146x, 157x, 160x, 161x, 163x, 166x, 170x, 177x, 179x, 181x, 182x, 183x, 187x, 190x, 192x, 195x, 197x, 202x, 204x, 205x, 206x, 207x, 208x, 209x, 210x, 211x, 212x, 213x, 221x, 222x, 223x, 225x, 226x, 227x, 228x, 230x, 236x, 237x, 248x, 259x, 260x, 261x, 266x, 267x and 268x, or a salt thereof. In another variation, the compounds of the invention, and methods of using the compounds detailed herein, encompass any of the compounds of formula (Vg), including those listed in Table 1, such as 13x, 14x, 30x, 54x, 55x, 57x, 58x, 61x, 62x, 65x, 72x, 77x, 78x, 80x, 82x, 83x, 88x, 89x, 92x-94x, 96x, 97x, 100x, 101x, 104x, 105x, 125x-130x, 132x, 135x, 138x, 140x-146x, 157x, 160x, 161x, 163x, 166x, 170x, 177x, 179x, 181x-183x, 187x, 190x, 192x, 195x, 197x, 202x, 204x-213x, 221x-223x, 225x-228x, 230x, 236x, 237x, 248x, 259x-261x and 266x-268x, or a salt thereof. In a further variation, the compound is of the formula (Vg) where $R^4$ is other than hydrogen, provided the compound is other than 14x, 80x, 82x, 83x, 132x, 141x, 170x, 187x, 197x, 216x, 217x or 230x. In a further variation, the compound is of the formula (Vg) where $R^4$ is other than hydrogen, m is 0 and q is 1 and Q is an unsubstituted or substituted aryl or an unsubstituted or substituted heteroaryl other than 4-pyridyl or 6-methyl-3-pyridyl.

In one variation, the compound is of the formula (Vh), provided that the compound is other than any of compounds 13x, 30x, 54x, 55x, 57x, 58x, 61x, 62x, 65x, 71x, 72x, 77x, 78x, 88x, 89x, 92x, 93x, 94x, 96x, 97x, 100x, 101x, 104x, 105x, 125x, 126x, 127x, 128x, 129x, 130x, 135x, 138x, 140x, 142x, 143x, 144x, 145x, 146x, 157x, 160x, 161x, 163x, 166x, 177x, 179x, 181x, 182x, 183x, 185x, 190x, 192x, 195x, 202x, 204x, 205x, 206x, 207x, 208x, 209x, 210x, 211x, 212x, 213x, 221x, 222x, 223x, 225x, 226x, 227x, 228x, 236x, 237x, 246x, 247x, 248x, 257x, 259x, 260x, 261x, 266x, 267x, 268x, 277x, 278x, 283x, 284x and 289x, or a salt thereof. In another variation, the compounds of the invention, and methods of using the compounds detailed herein, encompass any of the compounds of formula (Vh), including those listed in Table 1, such as 13x, 30x, 54x, 55x, 57x, 58x, 61x, 62x, 65x, 71x, 72x, 77x, 78x, 88x, 89x, 92x-94x, 96x, 97x, 100x, 101x, 104x, 105x, 125x-130x, 135x, 138x, 140x, 142x-146x, 157x, 160x, 161x, 163x, 166x, 177x, 179x, 181x-183x, 185x, 190x, 192x, 195x, 202x, 204x-213x, 221x-223x, 225x-228x, 236x, 237x, 246x-248x, 257x, 259x-261x, 266x-268x, 277x, 278x, 283x, 284x and 289x, or a salt thereof. In another variation, the compound is of the formula (Vh) where $R^4$ is other than hydrogen, provided the compound is other than any of compounds 71x, 185x, 246x, 247x, 257x, 277x, 278x, 283x, 284x and 289x. In still another variation, the compound is of the formula (Vh) where $R^4$ is other than hydrogen, m is 0 and q is 1 and Q is a substituted or unsubstituted aryl or a substituted heteroaryl. In still another variation, the compound is of the formula (Vh) where $R^4$ is halo or alkyl, m is 0 and q is 1 and Q is a substituted or unsubstituted phenyl or a substituted pyridyl.

In one variation, the compound is of the formula (Vk), provided that $R^1$ is $NR_aR_b$ and either: (a) each $R^a$ and $R^b$ is independently selected from the group consisting of H, alkyl, substituted alkyl, alkenyl, substituted alkenyl, alkynyl, substituted alkynyl, aryl, substituted aryl, heteroaryl, substituted heteroaryl and heterocyclic and substituted heterocyclic, provided that both $R^a$ and $R^b$ groups are not H; or (b) $R^a$ and $R^b$ are joined together with the nitrogen atom to form a heterocyclic or substituted heterocyclic ring. In one variation of (Vk) where $R^1$ is as defined immediately above and the compound further has at least one of the following structural features: (i) when m and q are 0, at least one of $R^a$ and $R^b$ is other than methyl, and (ii) when m and q are 0, either (a) Q is a other than a substituted or unsubstituted phenyl or (b) Q is a substituted or unsubstituted heteroaryl, substituted or unsubstituted $C_{3-8}$ cycloalkyl, substituted or unsubstituted $C_{3-8}$ cycloalkenyl or substituted or a unsubstituted heterocyclyl. In one variation of formula (Vk), at least one of m and q is 1, $R^1$ is $NR_aR_b$ and either (a) each $R^a$ and $R^b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that both $R^a$ and $R^b$ groups are not H; or (b) $R^a$ and $R^b$ are joined together with the nitrogen atom to form a heterocyclic or substituted heterocyclic ring.

In one variation, the compound is of the formula (Vn), provided that (i) the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 47x, 49x, 50x, 52x, 54x, 55x, 56x, 57x, 58x, 59x, 60x, 61x, 62x, 65x, 72x, 77x, 78x, 80x, 81x, 82x, 83x, 84x, 85x, 88x, 89x, 90x, 92x, 93x, 94x, 95x, 96x, 97x, 98x, 100x, 101x, 102x, 103x, 104x, 105x, 106x, 107x, 109x, 110x, 111x, 113x, 115x, 116x, 117x, 118x, 119x, 120x, 121x, 122x, 123x, 124x, 125x, 126x, 127x, 128x, 129x, 130x, 131x, 132x, 134x, 135x, 136x, 137x, 138x, 139x, 140x, 141x, 142x, 143x, 144x, 145x, 146x, 148x, 149x, 150x, 151x, 152x, 155x, 157x, 158x, 159x, 160x, 161x, 162x, 163x, 164x, 165x, 166x, 167x, 168x, 169x, 170x, 171x, 173x, 174x, 175x, 176x, 177x, 178x, 179x, 181x, 182x, 183x, 184x, 186x, 187x, 189x, 190x, 191x, 192x, 193x, 194x, 195x, 196x, 197x, 198x, 199x, 200x, 201x, 202x, 203x, 204x, 205x, 206x, 207x, 208x, 209x, 210x, 211x, 212x, 213x, 214x, 219x, 220x, 221x, 222x, 223x, 224x, 225x, 226x, 227x, 228x, 229x, 230x, 231x, 232x, 236x, 237x, 238x, 239x, 243x, 244x, 245x, 248x, 249x, 250x, 251x, 252x, 253x, 254x, 255x, 256x, 258x, 259x, 260x, 261x, 262x, 263x, 264x, 265x, 266x, 267x, 268x, 269x, 270x, 271x, 272x, 273x, 274x, 275x, 276x, 279x, 280x, 281x, 282x, 285x, 286x, 287x, 288x, 290x, 291x, 292x, 293x, 294x and 295x, or a salt thereof and (ii) the compound is other than any of compounds 229H, 230, 255, 256, 262 and 274, or a salt thereof. In another variation, the compounds of the invention, and methods of using the compounds and administering the compounds as detailed herein, encompass any of the compounds of formula (Vn), including those listed in Table 1, such as 1x-44x, 47x, 49x, 50x, 52x, 54x-62x, 65x, 72x, 77x, 78x, 80x-85x, 88x-90x, 92x-98x, 100x-107x, 109x-111x, 113x, 115x-132x, 134x-146x, 148x-152x, 155x, 157x-171x, 173x-179x, 181x-184x, 186x, 187x, 189x-214x, 219x-232x, 236x-239x, 243x-245x, 248x-256x, 258x-276x, 279x-282x, 285x-288x and 290x-295x or a salt thereof and compounds 229H, 230, 255, 256, 262 and 274, or a salt thereof. In still a further variation, the compound is of formula (Vn) where $R^4$ is other than hydrogen, provided the compound is other than 113x, 131x, 168x, 169x, 173x or 186x. In yet a further variation, the compound is of formula (Vn) where each $R^4$ is other than hydrogen and at least one $R^4$ is fluoro or hydroxyl. In still yet a further variation, the compound is of formula (Vn) where each $R^4$ is independently halo, hydroxyl or alkyl, provided that either (i) at least one $R^4$ is fluoro or hydroxyl or (ii) the $R^4$ moieties are not the same and Q is other than 6-methyl-3-pyridyl.

In one variation, the compound is of the formula (Vo), provided that the compound is other than any of compounds 233x, 234x and 235x. In another variation, the compound of the invention, and methods of using the compounds detailed herein, encompass any of the compounds of formula (Vzv), including those listed in Table 1, such as 233x, 234x and 235x. In another variation, the compound is of formula (Vo) provided that when Q is a substituted piperazinyl, $R^{8e}$ and $R^{8f}$ are not taken together with the carbon to which they are attached to form a carbonyl.

In one variation, the compound is of the formula (Vzv), provided that the compound is other than any of compounds 45x, 51x, 216x and 217x or a salt thereof. In another variation, the compounds of the invention, and methods of using the compounds detailed herein, encompass any of the compounds of formula (Vzv), including those listed in Table 1, such as 45x, 51x, 216x and 217x, or a salt thereof. In still a further variation, the compound is of the formula (Vzv) where $R^4$ is other than hydrogen. In still a further variation, the compound is of the formula (Vzv) where $R^4$ is alkyl (e.g., methyl).

In one variation, a compound of the invention is of the formula (I) or (Ia) or any variation of the foregoing detailed herein, or is of any one of the formulae (IIa)-(IIh), (IIIa)-(IIIm), (Iva)-(IVk) or (Va)-(Vzv), where each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R_8$ to form a cycloalkyl moiety. Where applicable, such variations apply equally to any formulae detailed herein, such as formula (A)-(G). In one variation, a compound of the invention is of the formula (I) or (Ia) or any variation of the foregoing detailed herein, or is of any one of the formulae (IIa)-(IIh), (IIIa)-(IIIm), (Iva)-(IVk) or (Va)-(Vzv), where at least one of $R^{8a}$, $R^{8b}$, $R^{8c}$, $R^{8d}$, $R^{8e}$ and $R^{8f}$ is taken together with the carbon to which it is attached and a geminal $R^8$ to form a carbonyl moiety. In another variation, a compound of the invention is of the formula (I) or (Ia) or any variation of the foregoing detailed herein, or is of any one of the formulae (IIa)-(IIh), (IIIa)-(IIIm), (Iva)-(IVk) or (Va)-(Vzv), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R_8$ to form a cyclopropyl moiety. Where applicable, such variations apply equally to any formulae detailed herein, such as formula (A)-(G). In yet another variation, a compound of the invention is of the formula (I) or (Ia) or any variation of the foregoing detailed herein, or is any one of the formulae (IIa)-(IIh), (IIIa)-(IIIm), (Iva)-(IVk) or (Va)-(Vzv), where wherein q is 0 and m is 1. Where applicable, such variations apply equally to any formulae detailed herein, such as formula (A)-(G). The invention also embraces a compound of the invention according to formula (I) or (Ia) or any variation of the foregoing detailed herein, or a compound according to any one of the formulae (IIa)-(IIh), (IIIa)-(IIIm), (Iva)-(IVk) or (Va)-(Vzv), where q and m are both 0. Where applicable, such variations apply equally to any formulae detailed herein, such as formula (A)-(G). The invention further embraces a compound according to formula (I) or (Ia) or any variation of the foregoing detailed herein, or a compound according to any one of the formulae (IIa)-(IIh), (IIIa)-(IIIm), (Iva)-(IVk) or (Va)-(Vzv), where q, m, $R^{8a}$, $R^{8b}$, $R^{8c}$, $R^{8d}$, $R^{8e}$ and $R^{8f}$ are taken together to form a moiety selected from the group consisting of: —$CH_2$—, —$CH_2CH_2$—, —$CH_2CH_2CH_2$—, —$CH_2$—C(H)(OH)—, —C(H)(OH)—$CH_2$—, —$CH_2$—C(OH)($CH_3$)—, —C(OH)($CH_3$)—$CH_2$—, —$CH_2$—C(H)($CH_3$)—, —C(H)($CH_3$)—$CH_2$—, —$CH_2$—C($CH_3$)($CH_3$)—, —C($CH_2CH_2$)—$CH_2$— and —$CH_2$—C($CH_2CH_2$)—. Where applicable, such variations apply equally to any formulae detailed herein, such as formula (A)-(G). For example, taking formula A, compounds of the structures listed below are embraced by the invention:

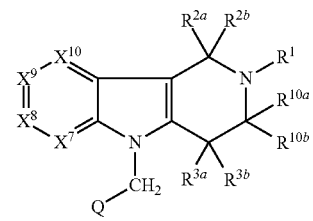
(Ab)

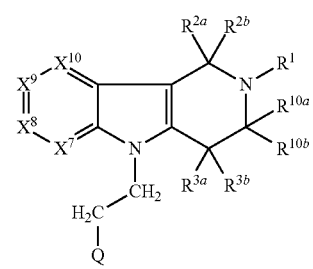
(Ac)

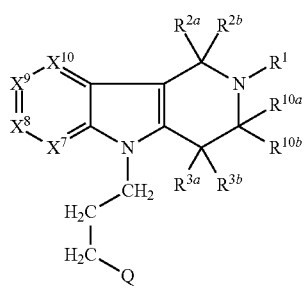 (Ad)

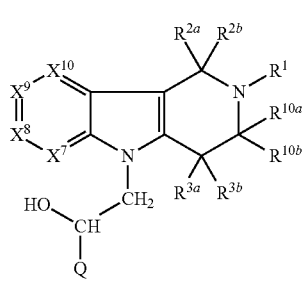 (Ae)

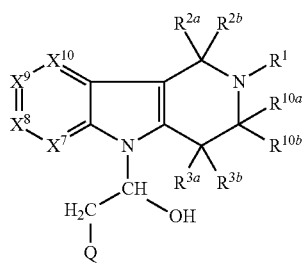 (Af)

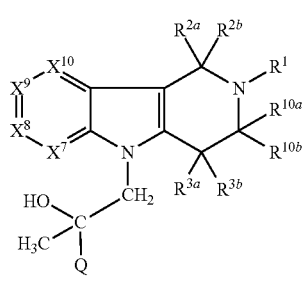 (Ag)

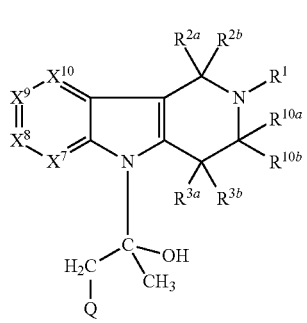 (Ah)

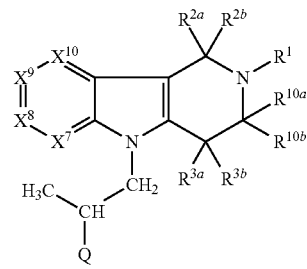 (Ai)

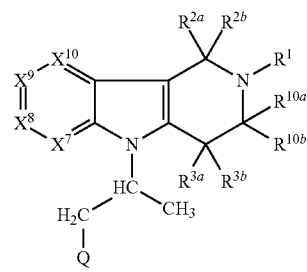 (Aj)

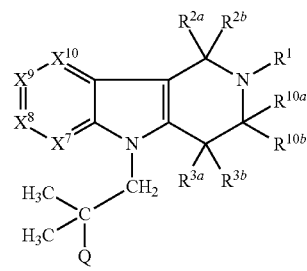 (Ak)

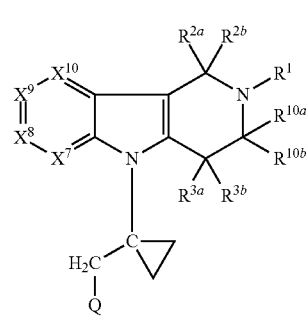 (Al)

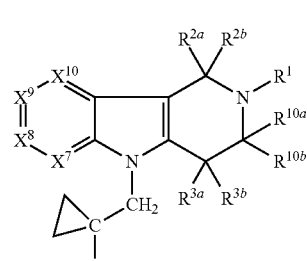 (Am)

The invention further embraces a compound according to formula (F) or any variation of the foregoing detailed herein, where q, m, $R^{8a}$, $R^{8b}$, $R^{8c}$, $R^{8d}$, $R^{8e}$ and $R^{8f}$ are taken together to form a moiety selected from the group consisting of: —C(H)(C(O)OH)—CH$_2$—, —C(H)(C(O)OEt)-CH$_2$—, —C(H)(C(O)OMe)-CH$_2$—, —CH$_2$—C(H)(C(O)OH)—, —CH$_2$—C(H)(C(O)OEt)-, —CH$_2$—C(H)(C(O)OMe)-, —C(OH)(CF$_3$)—CH$_2$— and —CH$_2$—C(OH)(CF$_3$)—.

In another variation, a compound of the invention is of the formula (I) or (Ia) or any variation of the foregoing detailed herein, or a compound according to any one of the formulae (IIIa)-(IIIm), (Iva)-(IVk) or (Va)-(Vzv), where each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl. In yet another variation, a compound of the invention is of the formula (I) or (Ia) or any variation of the foregoing detailed herein, or a compound according to any one of the formulae (IIIa)-(IIIm), (Iva)-(IVk) or (Va)-(Vzv), where each $R^4$ is independently H or a substituted or unsubstituted $C_1$-$C_8$ alkyl. In still another variation, a compound of the invention is of the formula (I) or (Ia) or any variation of the foregoing detailed herein, or a compound according to any one of the formulae (IIIa)-(IIIm), (Iva)-(IVk) or (Va)-(Vzv), where each $R^4$ is H. The invention also embraces compounds of the formula (I) or (Ia) or any variation of the foregoing detailed herein, or a compound according to any one of the formulae (IIIa)-(IIIm), (Iva)-(IVk) or (Va)-(Vzv), where each $R^4$ is independently H, halo, unsubstituted $C_1$-$C_4$ alkyl, $C_1$-$C_4$ perhaloalkyl or a substituted or unsubstituted aryl. The invention further embraces compounds of the formula (I) or (Ia) or any variation of the foregoing detailed herein, or a compound according to any one of the formulae (IIIa)-(IIIm), (Iva)-(IVk) or (Va)-(Vzv) where each $R^4$ is independently H, halo, methyl, perfluoromethyl or cyclopropyl.

The invention also embraces compounds of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a substituted or unsubstituted phenyl or pyridyl group. In a particular variation, Q is a phenyl or pyridyl group substituted with at least one methyl group. In another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In still another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a substituted or unsubstituted $C_{3-8}$ cycloalkyl or a substituted or unsubstituted heterocyclyl. In yet another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl or thiomorpholinyl group substituted with at least one methyl or halo group. In one variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is an unsubstituted $C_{3-8}$ cycloalkyl or an unsubstituted heterocyclyl. In another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a substituted or unsubstituted cyclohexyl, morpholinyl, piperizinyl, thiomorpholinyl, cyclopentyl or pyrrolidinyl moiety. In yet another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a substituted cyclohexyl, morpholinyl, piperizinyl, thiomorpholinyl, cyclopentyl or pyrrolidinyl moiety substituted with at least one carbonyl, hydroxymethyl, methyl or hydroxyl group.

In still another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a moiety selected from the structures:

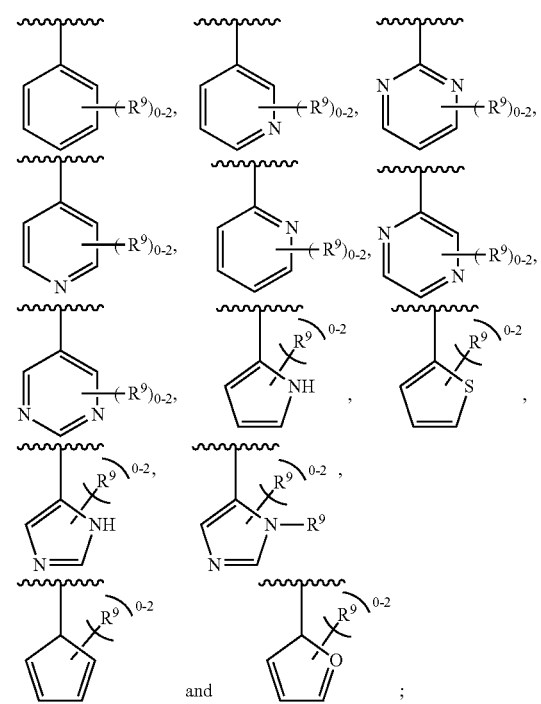

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In another variation of any Q moiety detailed herein comprising $R^9$, it is understood that variations in which greater than two $R^9$ moieties are encompassed by this invention. For example, a phenyl group having four $R^9$ moieties is provided for herein, notwithstanding the depiction in some variations of a phenyl with 0-2 $R^9$ moieties. In one variation, where applicable, a Q moiety contains from 3-5 $R^9$ moieties.

In another variation, a compound of the invention is of the formula (I), (A), (E) or (Ia) or any variation of the foregoing detailed herein, or a compound according to any one of the formulae (IIa)-(IIh), (IIIa)-(IIIm), (Iva)-(IVk) or (Va)-(Vzv) where Q is a moiety selected from the structures:

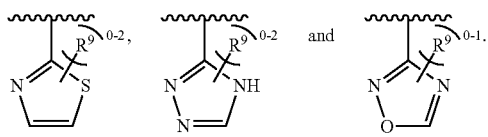

In yet another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a moiety selected from the structures:

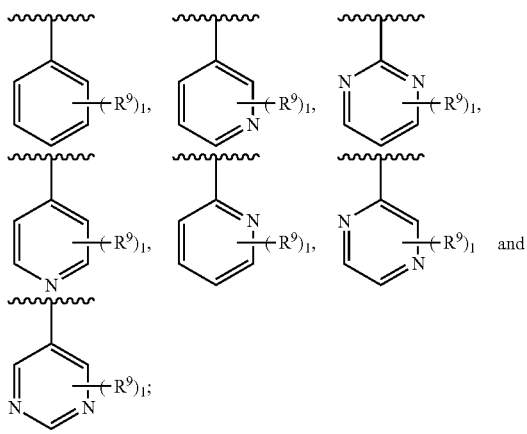

and wherein $R^9$ is connected to Q ortho or para to the position at which Q is connected to the carbon bearing $R^{8e}$ and $R^{8f}$. In a particular variation, Q is a structure of the formula:

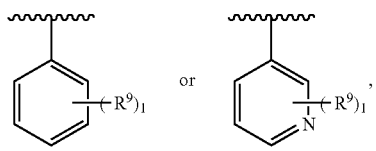

and $R^9$ is connected to Q para to the position at which Q is connected to the carbon bearing $R^{8e}$ and $R^{8f}$.

In another variation, a compound of the invention is of the formula (I) or (Ia) or any variation of the foregoing detailed herein, or a compound according to any one of the formulae (IIa)-(IIh), (IIIa)-(IIIm), (Iva)-(IVk) or (Va)-(Vzv) where Q is a moiety selected from the structures:

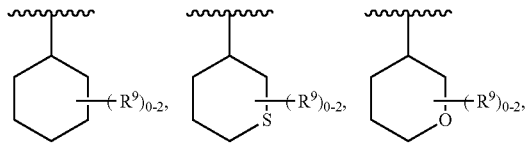

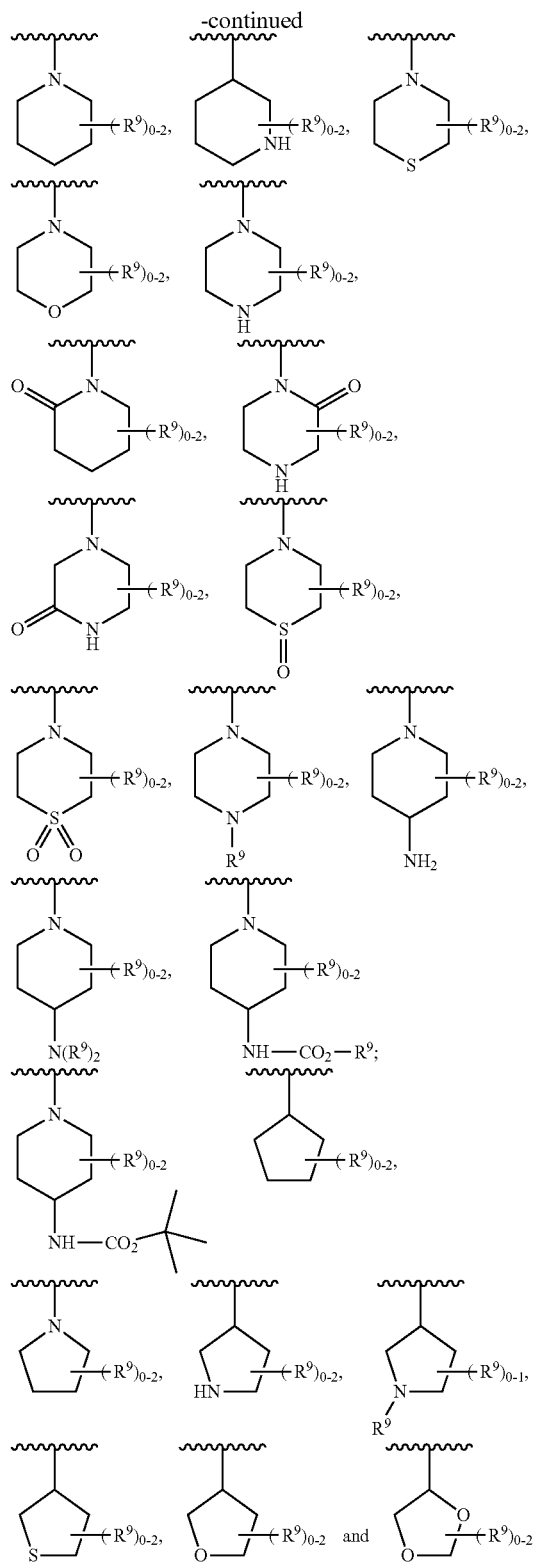

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In a particular variation, Q is selected from the carbocyclic and heterocyclic structures detailed where the residue has the moiety $(R^9)_0$ such that Q either contains no $R^9$ functionality or a moiety of the formula N—$R^9$.

In any structure or variation detailed herein, in one embodiment, Q is

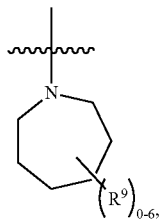

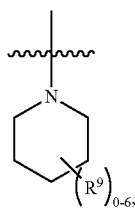

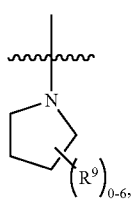

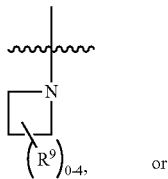

or

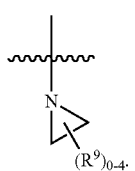

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, a compound of the invention is of the formula (I) or (Ia) or any variation of the foregoing detailed herein, or a compound according to any one of the formulae (IIa)-(IIh), (IIIa)-(IIIm), (IVa)-(IVk) or (Va)-(Vzv) where Q is a moiety selected from the structures:

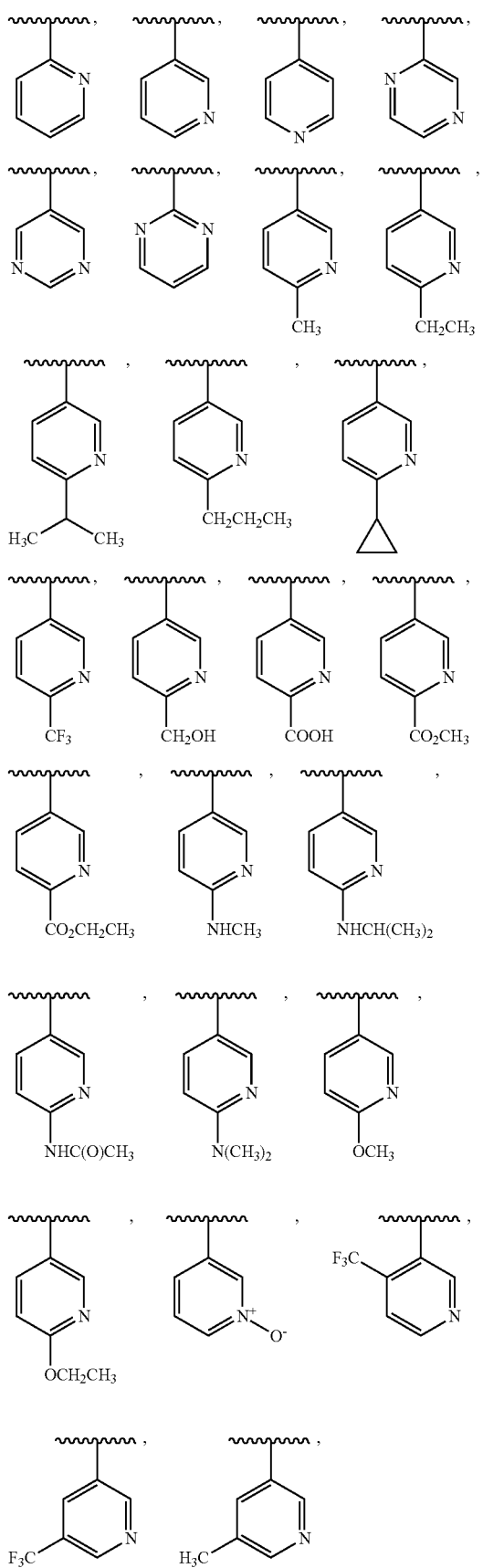

-continued
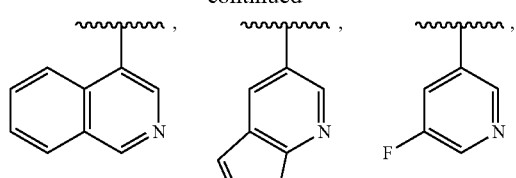
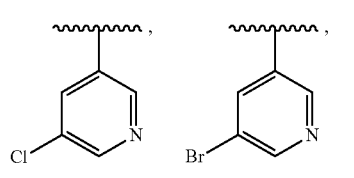
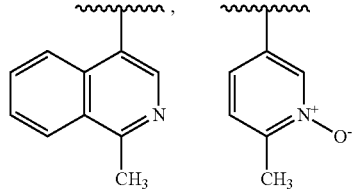
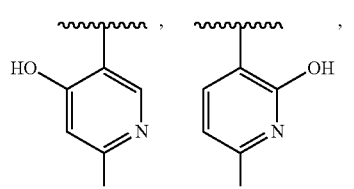
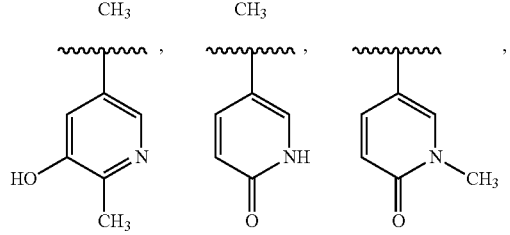
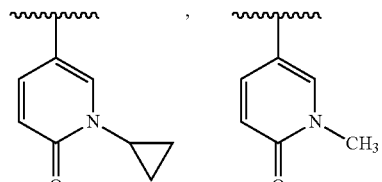
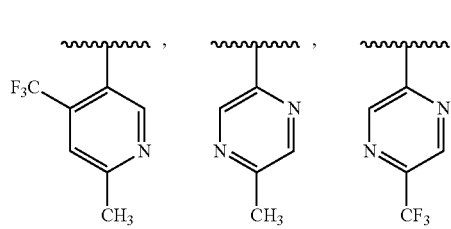
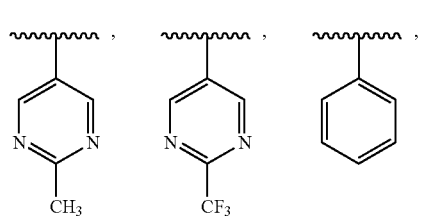
-continued
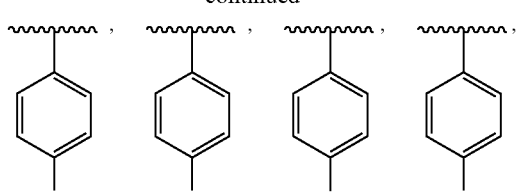
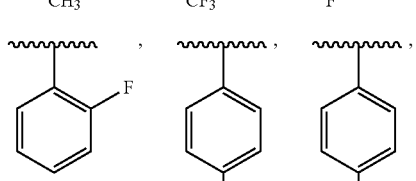
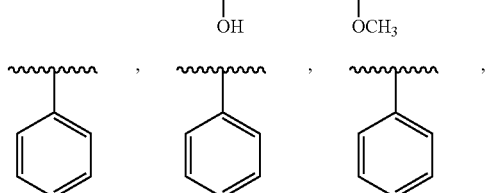
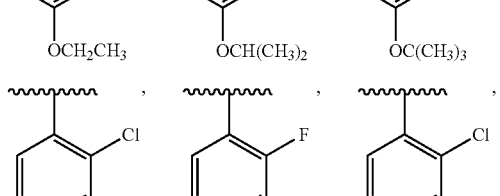
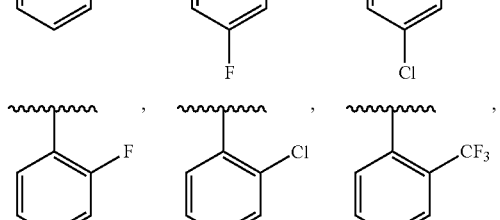
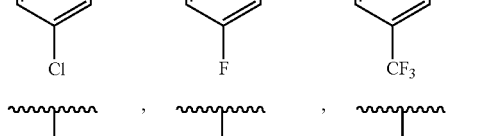
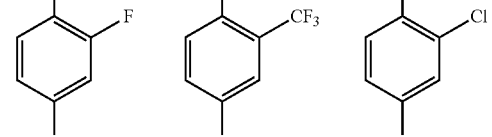
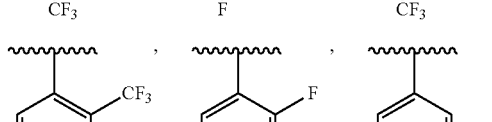
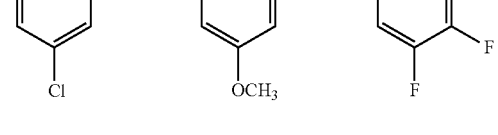
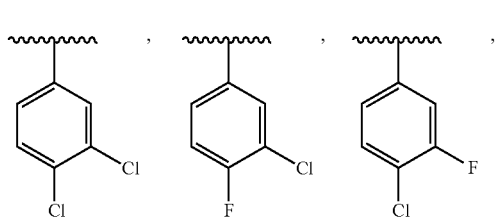

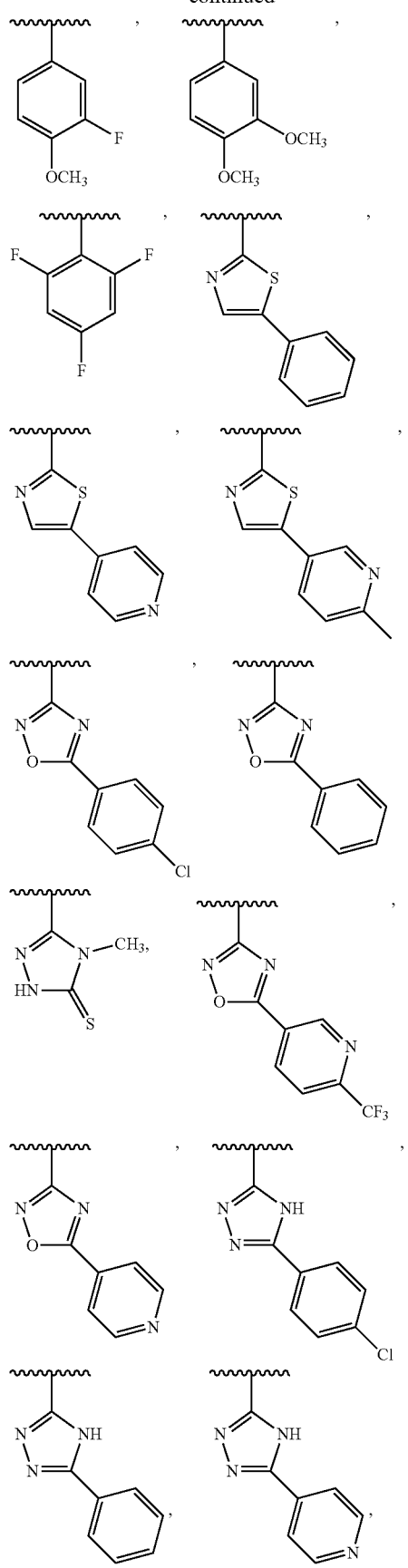
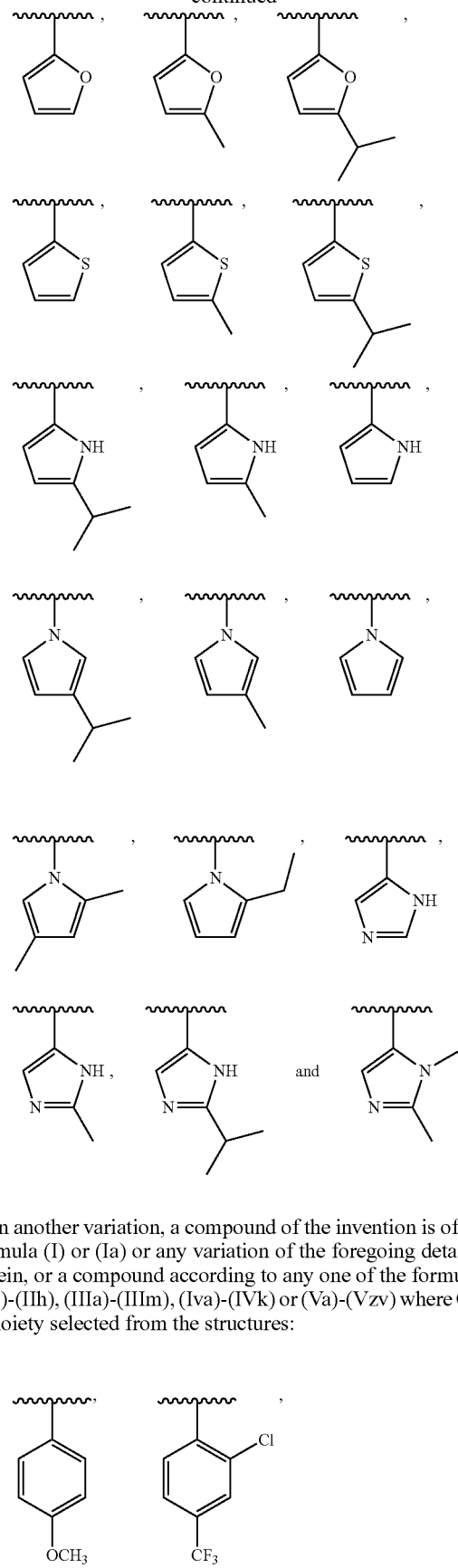
In another variation, a compound of the invention is of the formula (I) or (Ia) or any variation of the foregoing detailed herein, or a compound according to any one of the formulae (IIa)-(IIh), (IIIa)-(IIIm), (IVa)-(IVk) or (Va)-(Vzv) where Q is a moiety selected from the structures:

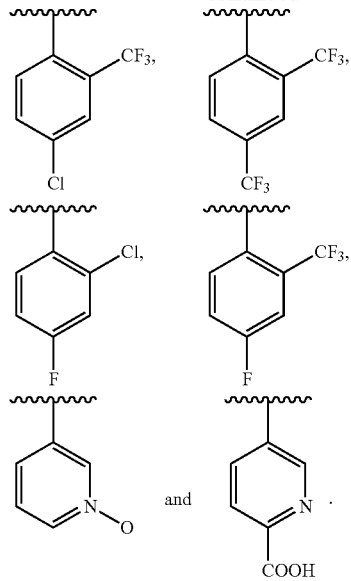
In yet another variation, a compound of the invention is of the formula (I) or (Ia) or any variation of the foregoing detailed herein, or a compound according to any one of the formulae (IIa)-(IIh), (IIIa)-(IIIm), (IVa)-(IVk) or (Va)-(Vzv) where Q is a moiety selected from the structures:
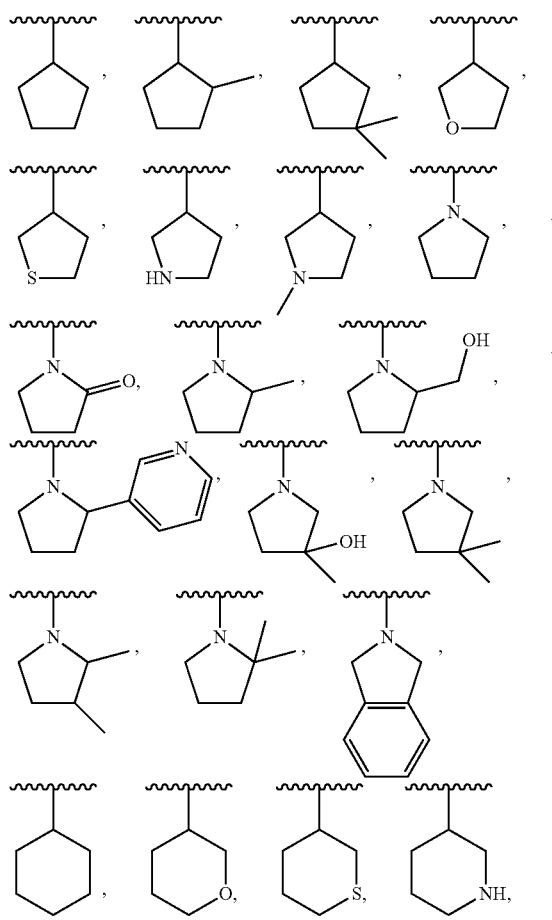
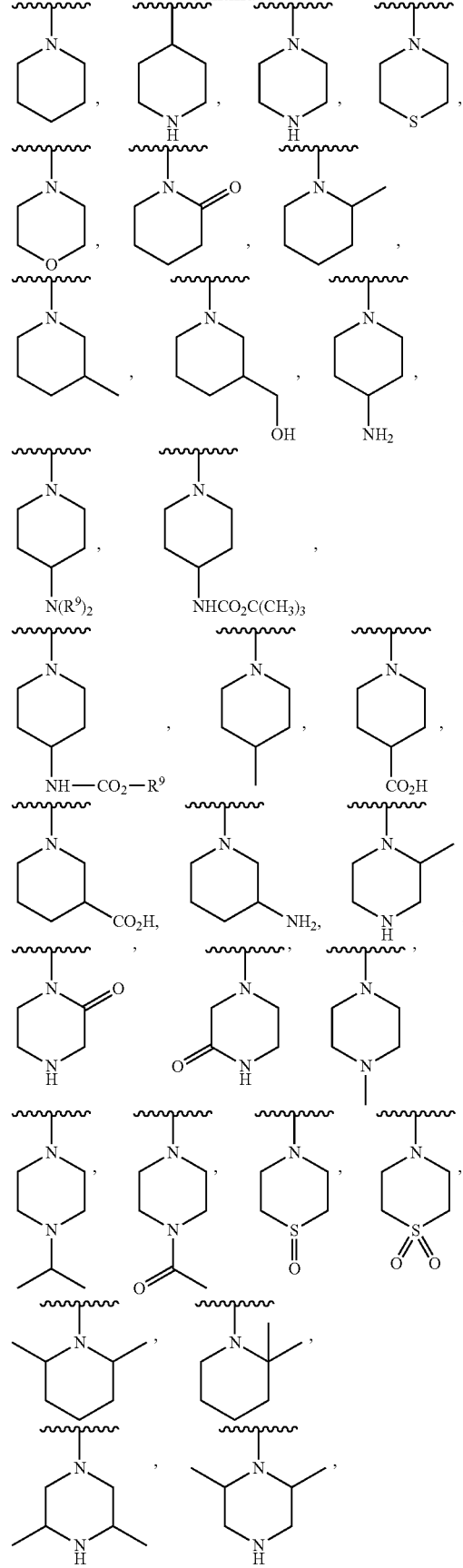

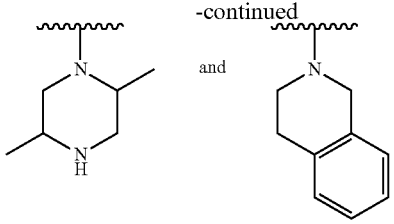

In a further variation, a compound of the invention is of the Formula (I) where $R^1$ is an unsubstituted alkyl, $R^{2a}$, $R^{2b}$, $R^{3a}$, $R^{3b}$, $R^{10a}$, $R^{10b}$ are each H, each $X^7$, $X^8$, $X^9$ and $X^{10}$ is independently N or CH, each $R^{8a}$, $R^{8b}$, $R^{8c}$, $R^{8d}$, $R^{8e}$ and $R^{8f}$ is independently H or hydroxyl, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl group.

In yet a further variation, a compound of the invention is of the Formula (I) where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$, where $R^4$ is as defined in Formula (I) or in a particular variation, $R^4$ is H, halo, pyridyl, methyl or trifluoromethyl; $R^{10a}$ and $R^{10b}$ are both H, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycyclopropo-2-yl, 1-hydroxy-1-methylcycloprop-2-yl, or 1-hydroxy-1,2,2-trimethyl-cycloprop-3-yl.

In still a further variation, a compound of the invention is of the Formula (I) where $R^1$ is a substituted or unsubstituted $C_1$-$C_8$ alkyl; each $R^{2a}$, $R^{2b}$, $R^{3a}$ and $R^{3b}$ is independently H or halo; $X^1$ is N; each $R^4$ is independently H, halo, $C_1$-$C_8$ perhaloalkyl, substituted or a unsubstituted $C_1$-$C_8$ alkyl; each $R^{8a}$, $R^{8b}$, $R^{8c}$, $R^{8e}$ and $R^{8f}$ is H; and Q is a substituted or unsubstituted cyclohexyl, morpholinyl, piperizinyl, thiomorpholinyl, cyclopentyl or pyrrolidinyl moiety. The invention also embraces a compound of the Formula (I) where $R^1$ is a methyl; at least one of $X^7$, $X^8$, $X^9$ and $X^{10}$ is $CR^4$, and each $R^4$ is independently H, halo, methyl or trifluoromethyl. The invention embraces compounds where Q in any variation detailed is substituted with at least one carbonyl, hydroxymethyl, methyl or hydroxyl group.

In a particular variation, the compound is of the Formula (I) where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; $X^1$ is N, each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl, provided that at least one of $R^{10a}$ and $R^{10b}$ is other than H. In one aspect of this variation, Q may be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In yet another aspect of this variation, $X^7$, $X^8$, $X^9$ and $X^{10}$ are $CR^4$ and each $R^4$ is independently H, halo or methyl.

In a particular variation, the invention embraces compounds of the formula (F):

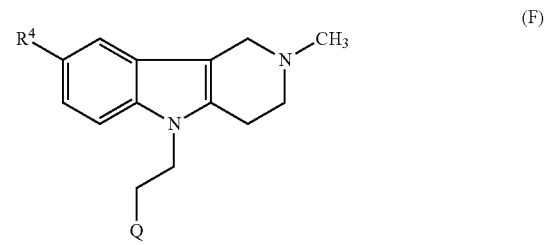

wherein:
$R^4$ is halo or $C_1$-$C_4$alkyl;
Q is

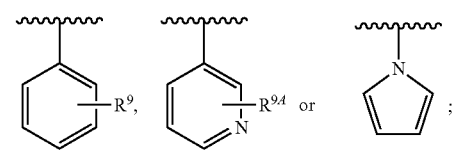

$R^9$ is halo, alkoxy or H provided that when $R^9$ is H, $R^4$ is other than fluoro or methyl; and
$R^{9A}$ is perhaloalkyl or alkyl, provided that $R^{9A}$ is other than $CH_3$,
or a salt or solvate thereof.

In one variation of formula (F), Q is

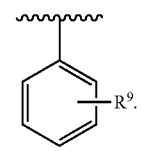

In one such variation, $R^4$ is chloro. In a further variation, $R^4$ is chloro and $R^9$ is hydrogen. In another variation of formula (F), Q is

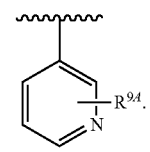

In one such variation, $R^4$ is halo. In another such variation, $R^{9A}$ is perhaloalkyl. In a still further such variation, $R^4$ is halo and $R^{9A}$ is perhaloalkyl (e.g., when $R^4$ is chloro and $R^{9A}$ is trifluoromethyl). In a still further such variation, $R^{9A}$ is a $C_1$-$C_4$ alkyl (e.g., propyl, which in one variation is n-propyl and in another is iso-propyl). In yet another variation of formula (F), Q is

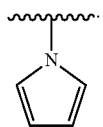

Examples of compounds according to the invention are depicted in Table 2. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2

Representative Compounds According to the Invention.

| Compound No. | Structure |
| --- | --- |
| 1 | |
| 2 | |
| 3 | 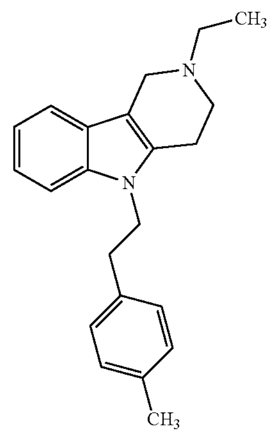 [SMILES: CCN1CCc2c(c3ccccc3n2CCc2ccc(C)cc2)C1] |
| 4 | 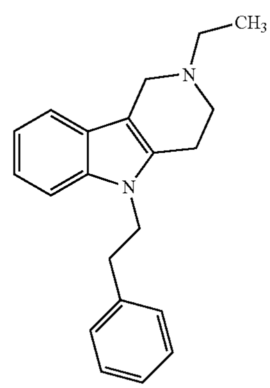 [SMILES: CCN1CCc2c(c3ccccc3n2CCc2ccccc2)C1] |
| 5 | 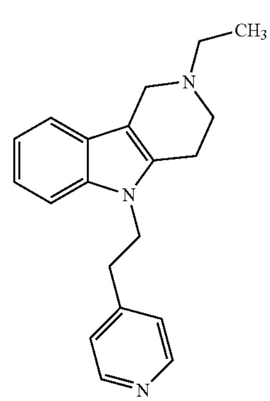 [SMILES: CCN1CCc2c(c3ccccc3n2CCc2ccncc2)C1] |

TABLE 2-continued

Representative Compounds According to the Invention.

| Compound No. | Structure |
|---|---|
| 6 | (structure) |
| 7 | (structure) |
| 8 | (structure) |
| 9H | (structure) |
| 10 | (structure) |
| 11 | (structure) |
| 12 | (structure) |

TABLE 2-continued
Representative Compounds According to the Invention.
| Compound No. | Structure |
|---|---|
| 13 | 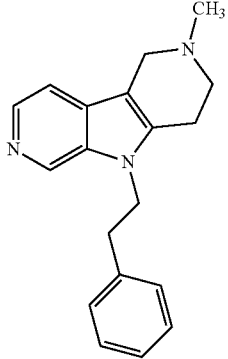 [SMILES: CN1CCc2c(c3ccncc3n2CCc2ccccc2)C1] |
| 14 | 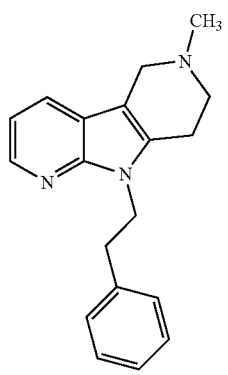 [SMILES: CN1CCc2c(c3cccnc3n2CCc2ccccc2)C1] |
| 15 | 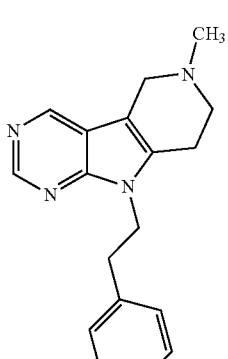 |
| 16 | 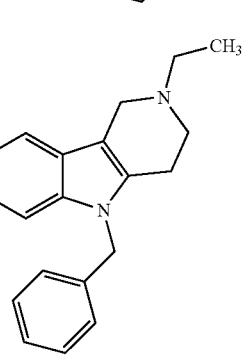 |
| 17 | 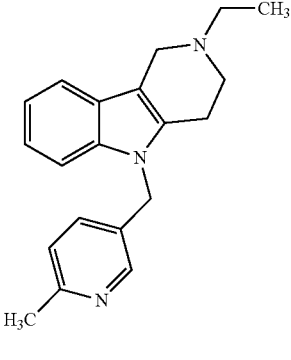 [SMILES: CCN1CCc2c(c3ccccc3n2Cc2ccc(C)nc2)C1] |
| 18 | 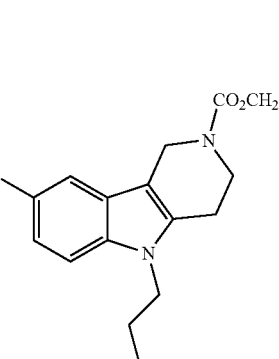 |
| 19 | 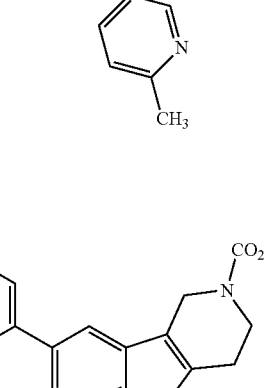 |

TABLE 2-continued

Representative Compounds According to the Invention.

| Compound No. | Structure |
|---|---|
| 20 | [structure: 8-methyl-2-methyl-5-(2-phenylethyl)-2,3,4,5-tetrahydro-1H-pyrido[4,3-b]indole] |
| 21 | [structure: 8-methyl-2-methyl-5-[2-(pyridin-2-yl)ethyl]-2,3,4,5-tetrahydro-1H-pyrido[4,3-b]indole] |
| 22 | [structure: 8-methyl-2-methyl-5-[2-(pyridin-4-yl)ethyl]-2,3,4,5-tetrahydro-1H-pyrido[4,3-b]indole] |
| 23 | [structure: 2-ethyl-8-methyl-5-[2-(pyridin-2-yl)ethyl]-2,3,4,5-tetrahydro-1H-pyrido[4,3-b]indole] |
| 24 | [structure: 2-ethoxycarbonyl-8-methyl-5-(2-phenylethyl)-2,3,4,5-tetrahydro-1H-pyrido[4,3-b]indole] |
| 25 | [structure: 8-methyl-2-methyl-5-[2-(4-methylphenyl)ethyl]-2,3,4,5-tetrahydro-1H-pyrido[4,3-b]indole] |
| 26 | [structure: 2-ethyl-8-methyl-5-[2-(4-methylphenyl)ethyl]-2,3,4,5-tetrahydro-1H-pyrido[4,3-b]indole] |

TABLE 2-continued
Representative Compounds According to the Invention.
| Compound No. | Structure |
|---|---|
| 27 | 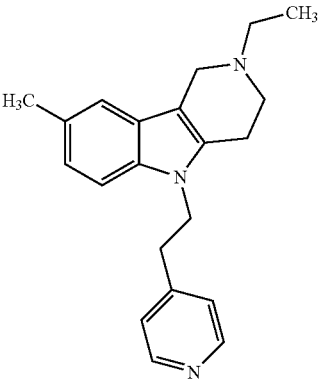 [SMILES: CCN1CCc2c(c3cc(C)ccc3n2CCc2ccncc2)C1] |
| 28 | 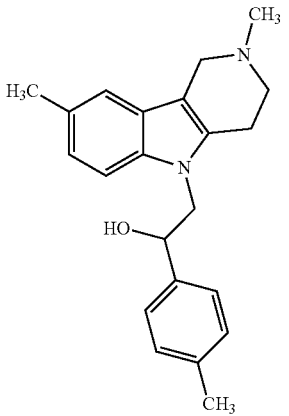 [SMILES: Cc1ccc(C(O)Cn2c3c(c4cc(C)ccc42)CN(C)CC3)cc1] |
| 29 | 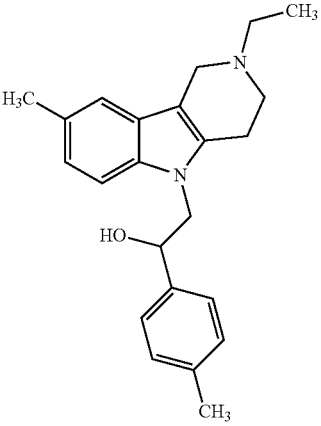 [SMILES: CCN1CCc2c(c3cc(C)ccc3n2CC(O)c2ccc(C)cc2)C1] |
| 30 | 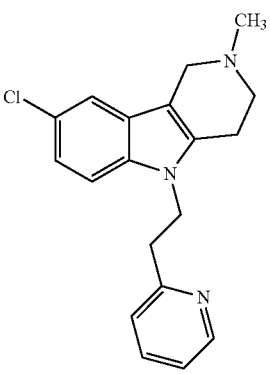 |
| 31 | 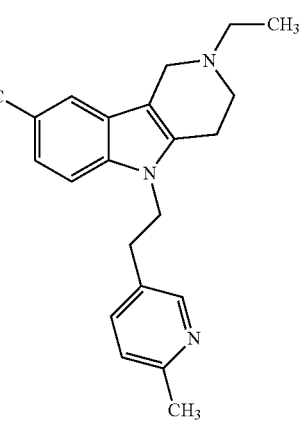 |
| 32 | 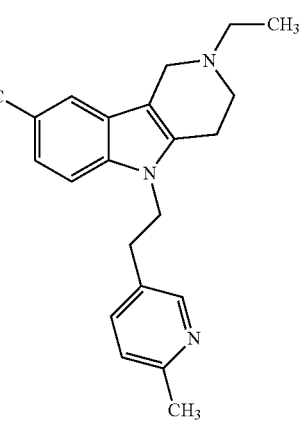 |

TABLE 2-continued
Representative Compounds According to the Invention.
| Compound No. | Structure |
|---|---|
| 33 | 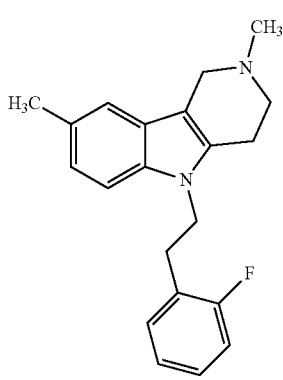 |
| 34 | 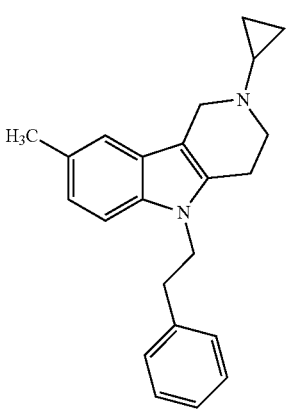 |
| 35 | 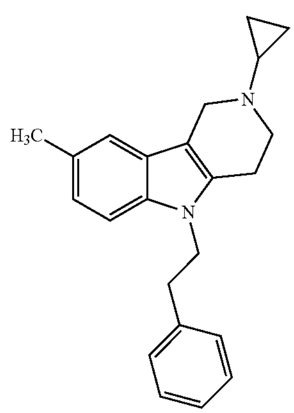 |
| 36 | 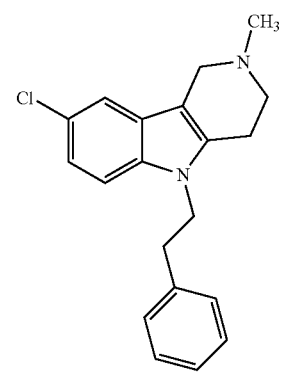 [SMILES: CN1CCc2c(c3cc(Cl)ccc3n2CCc2ccccc2)C1] |
| 37 | 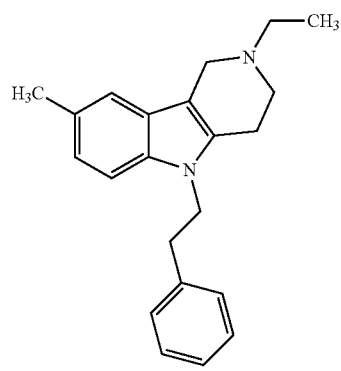 [SMILES: CCN1CCc2c(c3cc(C)ccc3n2CCc2ccccc2)C1] |
| 38H | 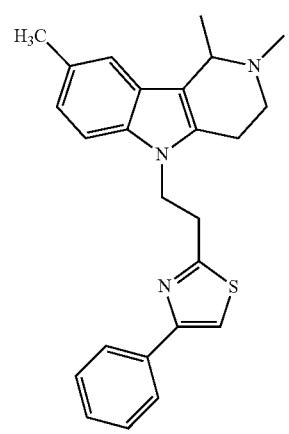 |

TABLE 2-continued
Representative Compounds According to the Invention.
| Compound No. | Structure |
|---|---|
| 39H | 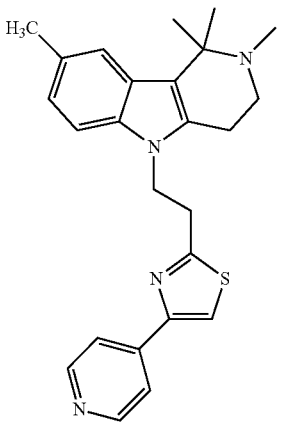 |
| 40H | 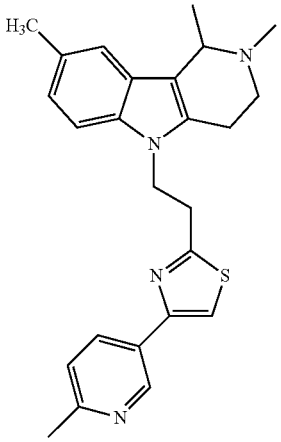 |
| 41 | 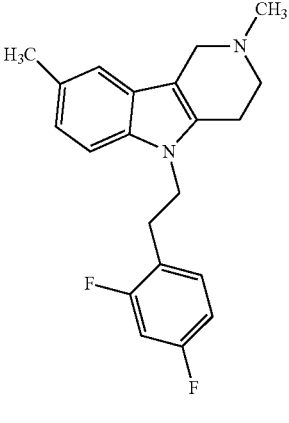 |
| 42 | 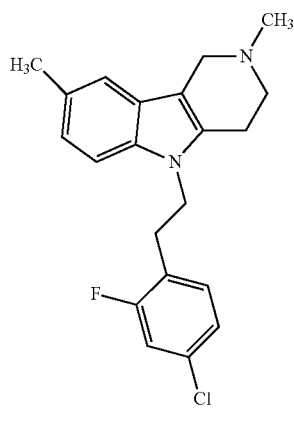 |
| 43 | 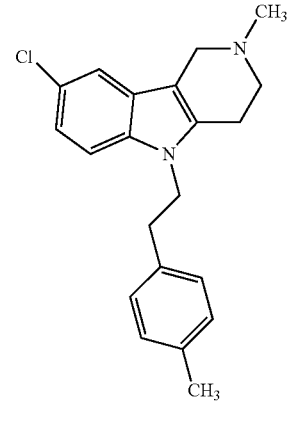 [SMILES: Cc1ccc(CCn2c3c(c4cc(Cl)ccc42)CN(C)CC3)cc1] |
| 44 | 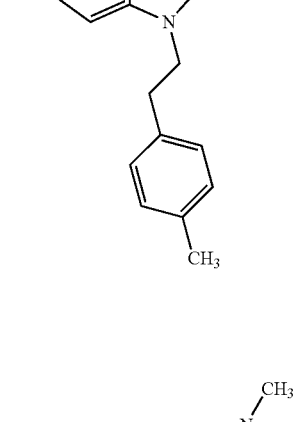 |

TABLE 2-continued
Representative Compounds According to the Invention.
| Compound No. | Structure |
|---|---|
| 45 | 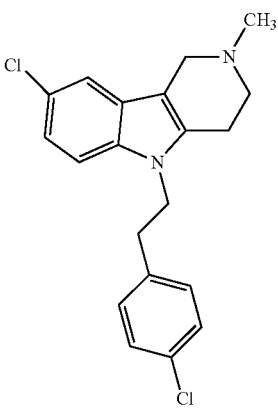 [SMILES: CN1CCc2c(c3cc(Cl)ccc3n2CCc2ccc(Cl)cc2)C1] |
| 46 | 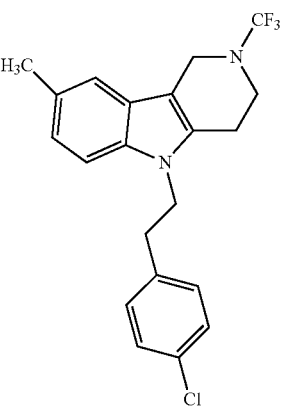 [SMILES: Cc1ccc2c(c1)c1c(n2CCc2ccc(Cl)cc2)CCN(C(F)(F)F)C1] |
| 47 | 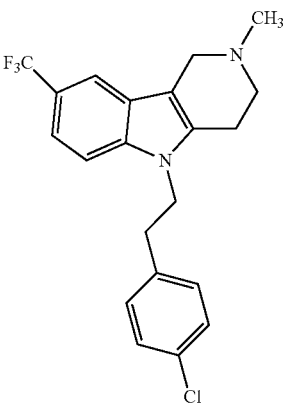 [SMILES: CN1CCc2c(c3cc(C(F)(F)F)ccc3n2CCc2ccc(Cl)cc2)C1] |
TABLE 2-continued
Representative Compounds According to the Invention.
| Compound No. | Structure |
|---|---|
| 48 | 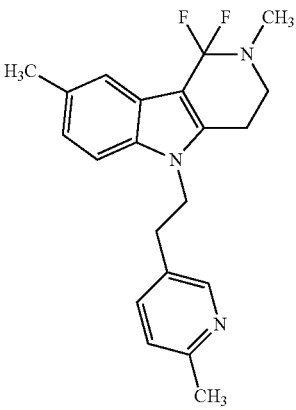 |
| 49 | 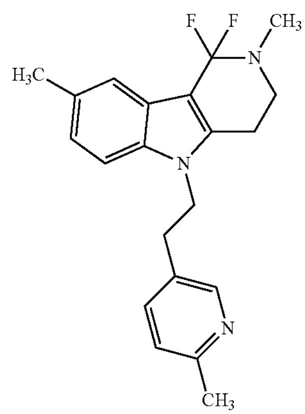 |
| 50 | 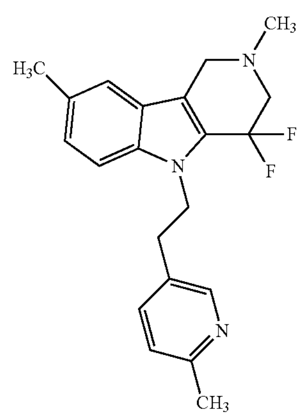 [SMILES: Cc1ccc2c(c1)c1c(n2CCc2ccc(C)nc2)C(F)(F)CN(C)C1] |

TABLE 2-continued
Representative Compounds According to the Invention.
| Compound No. | Structure |
|---|---|
| 51 | 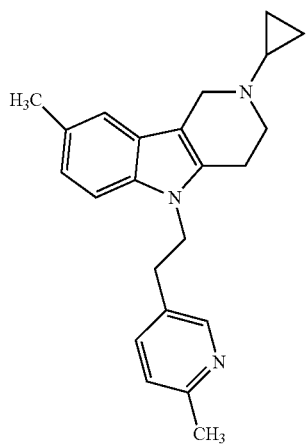 [SMILES: Cc1ccc2c(c1)c1c(n2CCc2ccc(C)nc2)CCN(C2CC2)C1] |
| 52 | 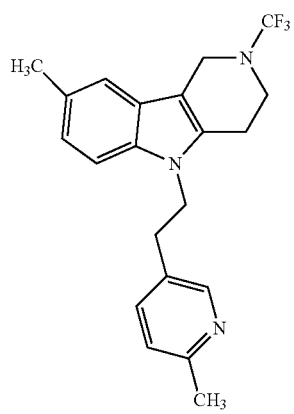 [SMILES: Cc1ccc2c(c1)c1c(n2CCc2ccc(C)nc2)CCN(C(F)(F)F)C1] |
| 53 | 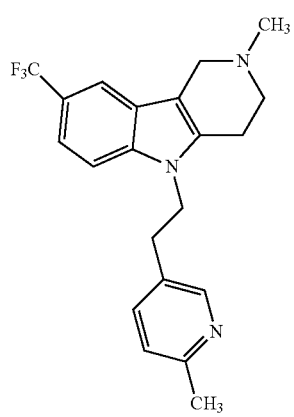 [SMILES: Cc1ccc(CCn2c3c(c4cc(C(F)(F)F)ccc42)CN(C)CC3)cn1] |
| 54 | 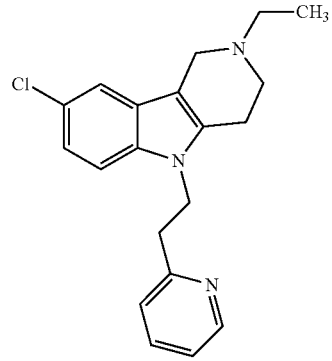 [SMILES: CCN1CCc2c(c3cc(Cl)ccc3n2CCc2ccccn2)C1] |
| 55 | 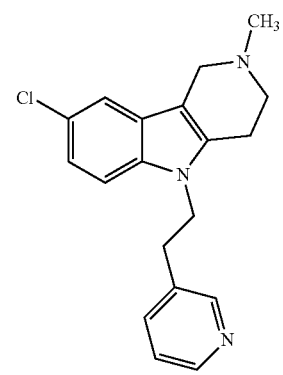 [SMILES: CN1CCc2c(c3cc(Cl)ccc3n2CCc2cccnc2)C1] |
| 56 | 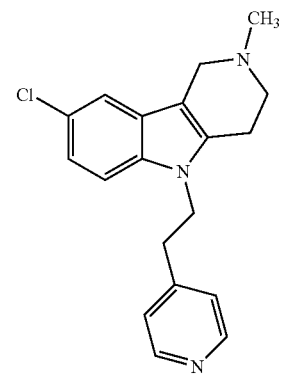 [SMILES: CN1CCc2c(c3cc(Cl)ccc3n2CCc2ccncc2)C1] |
| 57 | 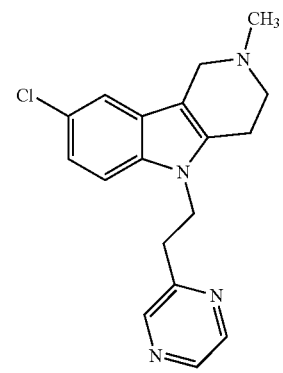 [SMILES: CN1CCc2c(c3cc(Cl)ccc3n2CCc2cnccn2)C1] |

TABLE 2-continued

Representative Compounds According to the Invention.

| Compound No. | Structure |
|---|---|
| 58 | 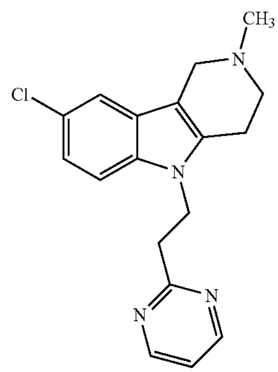 [SMILES: CN1CCc2c(c3cc(Cl)ccc3n2CCc2ncccn2)C1] |
| 59H | 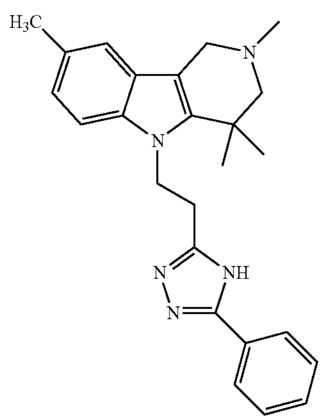 [SMILES: Cc1ccc2c(c1)c1c(n2CCc2nnc(-c3ccccc3)[nH]2)C(C)(C)CN(C)C1] |
| 60 | 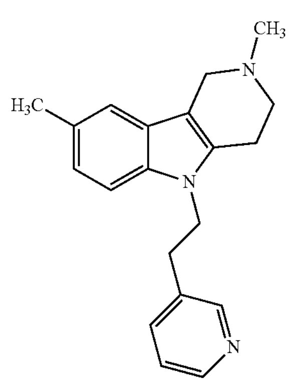 [SMILES: Cc1ccc2c(c1)c1c(n2CCc2cccnc2)CCN(C)C1] |
| 61H | 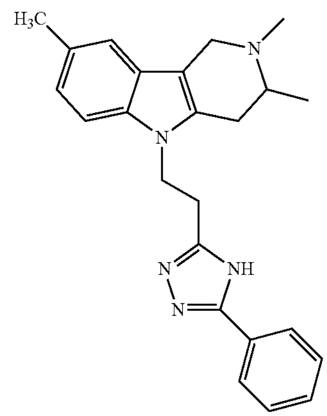 [SMILES: Cc1ccc2c(c1)c1c(n2CCc2nnc(-c3ccccc3)[nH]2)CC(C)N(C)C1] |
| 62 | 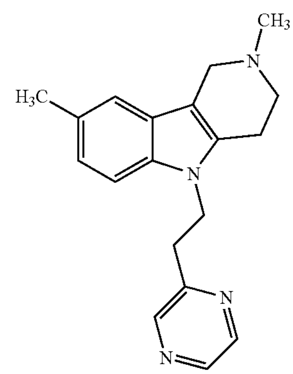 |
| 63 | 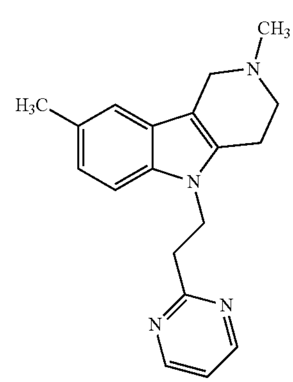 [SMILES: Cc1ccc2c(c1)c1c(n2CCc2ncccn2)CCN(C)C1] |

TABLE 2-continued
Representative Compounds According to the Invention.
| Compound No. | Structure |
|---|---|
| 64 | 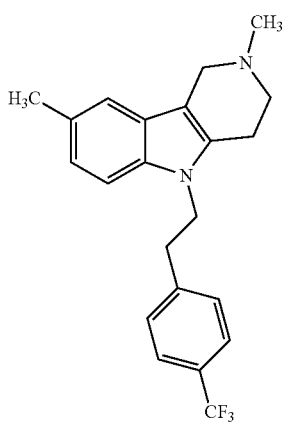 |
| 65 | 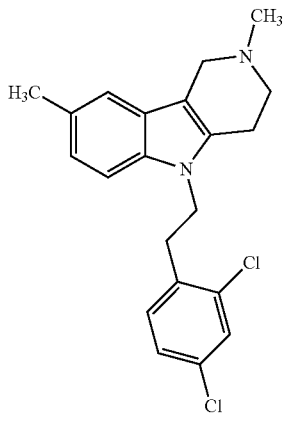 [SMILES: Cc1ccc2c(c1)c1c(n2CCc2ccc(Cl)cc2Cl)CCN(C)C1] |
| 66 | 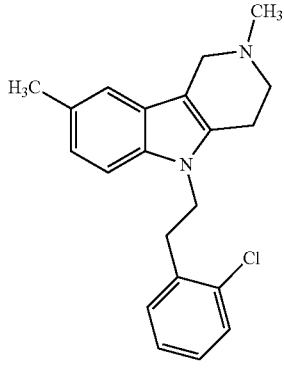 |
| 67 | 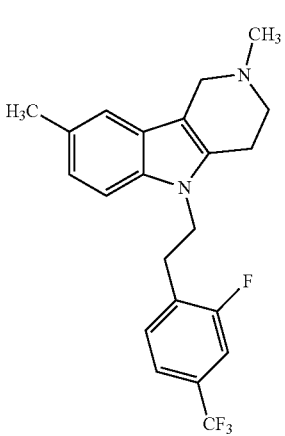 [SMILES: Cc1ccc2c(c1)c1c(n2CCc2ccc(C(F)(F)F)cc2F)CCN(C)C1] |
| 68 | 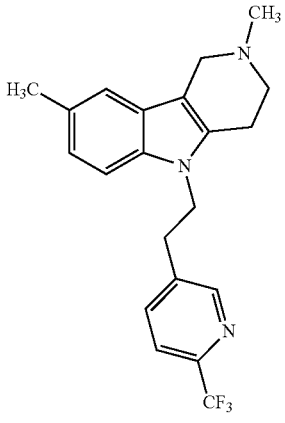 [SMILES: Cc1ccc2c(c1)c1c(n2CCc2ccc(C(F)(F)F)nc2)CCN(C)C1] |
| 69 | 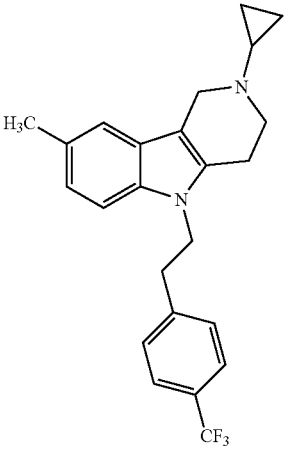 [SMILES: Cc1ccc2c(c1)c1c(n2CCc2ccc(C(F)(F)F)cc2)CCN(C2CC2)C1] |

TABLE 2-continued
Representative Compounds According to the Invention.
| Compound No. | Structure |
|---|---|
| 70 | 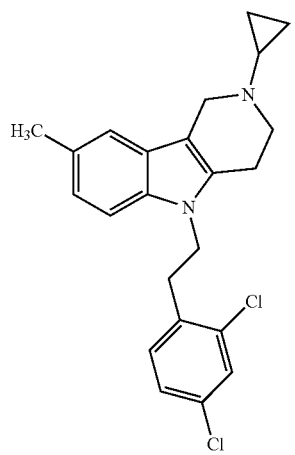 [SMILES: Cc1ccc2c(c1)c1c(n2CCc2ccc(Cl)cc2Cl)CCN(C2CC2)C1] |
| 71 | 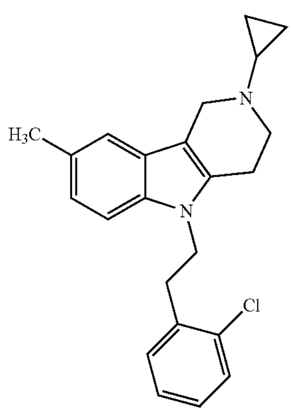 [SMILES: Cc1ccc2c(c1)c1c(n2CCc2ccccc2Cl)CCN(C2CC2)C1] |
| 72 | 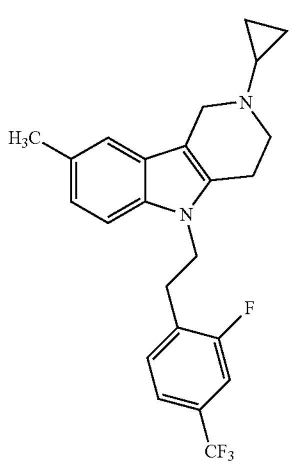 [SMILES: Cc1ccc2c(c1)c1c(n2CCc2ccc(C(F)(F)F)cc2F)CCN(C2CC2)C1] |
TABLE 2-continued
Representative Compounds According to the Invention.
| Compound No. | Structure |
|---|---|
| 73 | 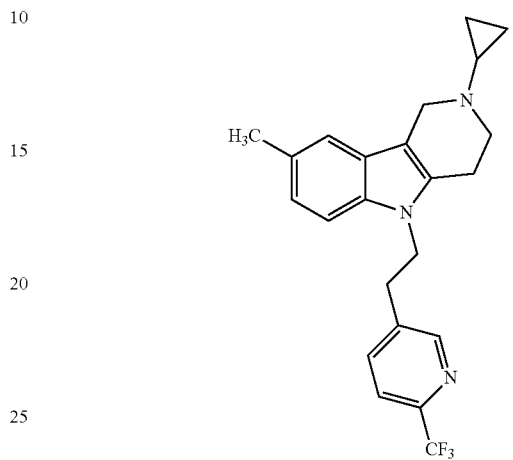 |
| 74 | 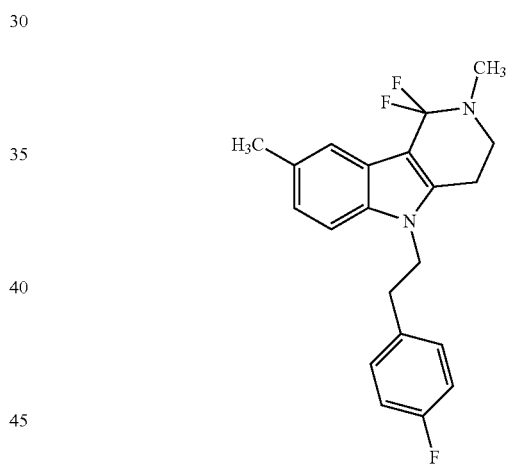 |
| 75 | 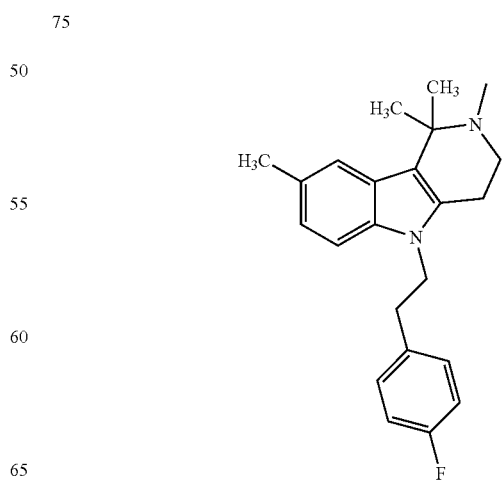 |

TABLE 2-continued

Representative Compounds According to the Invention.

| Compound No. | Structure |
|---|---|
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE 2-continued
Representative Compounds According to the Invention.
| Compound No. | Structure |
|---|---|
| 84 | 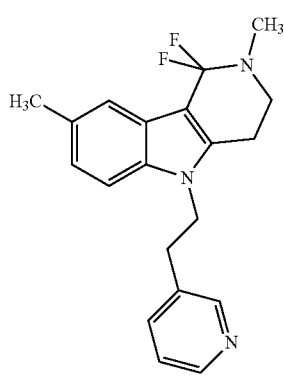 |
| 85 | 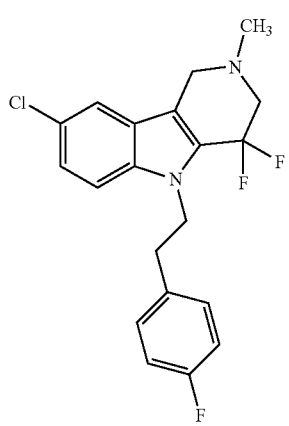 [SMILES: CN1Cc2c(n(CCc3ccc(F)cc3)c3ccc(Cl)cc23)C(F)(F)C1] |
| 86 | 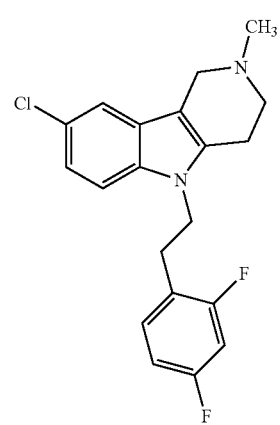 [SMILES: CN1CCc2c(c3cc(Cl)ccc3n2CCc2ccc(F)cc2F)C1] |
| 87 | 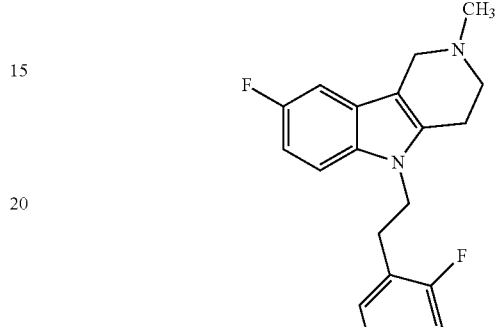 |
| 88 | 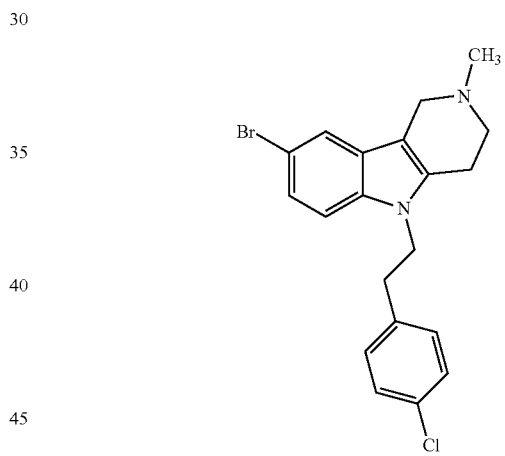 |
| 89 | 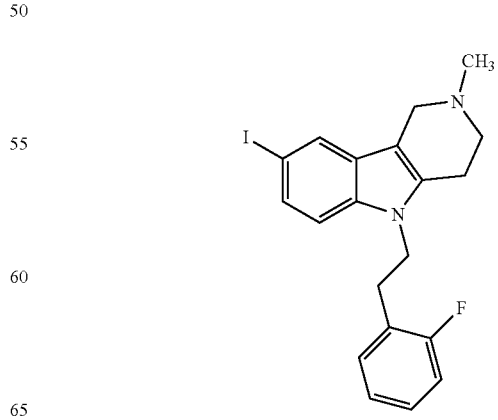 |

TABLE 2-continued

Representative Compounds According to the Invention.

| Compound No. | Structure |
|---|---|
| 90H | (structure) |
| 91 | (structure) |
| 92 | (structure) |
| 93 | (structure) |
| 94 | (structure) |
| 95 | (structure) |
| 96 | (structure) |

TABLE 2-continued

Representative Compounds According to the Invention.

| Compound No. | Structure |
|---|---|
| 97 | 2-methyl-8-methyl-tetrahydro-β-carboline N-substituted with 2-(1H-pyrrol-2-yl)ethyl |
| 98 | 2-methyl-8-methyl-tetrahydro-β-carboline N-substituted with 2-(1H-pyrrol-1-yl)ethyl |
| 99 | 2-methyl-8-methyl-tetrahydro-β-carboline N-substituted with 2-(thiophen-2-yl)ethyl |
| 100 | 2-methyl-8-methyl-tetrahydro-β-carboline N-substituted with 2-(2-methyl-1H-imidazol-4-yl)ethyl |
| 101 | 2-methyl-8-methyl-tetrahydro-β-carboline N-substituted with 2-(5-methylfuran-2-yl)ethyl |
| 102 | 2-methyl-8-methyl-tetrahydro-β-carboline N-substituted with 2-(5-methyl-1H-pyrrol-2-yl)ethyl |
| 103 | 2-methyl-8-methyl-tetrahydro-β-carboline N-substituted with 2-(3-methyl-1H-pyrrol-1-yl)ethyl |

TABLE 2-continued
Representative Compounds According to the Invention.
| Compound No. | Structure |
|---|---|
| 104 | 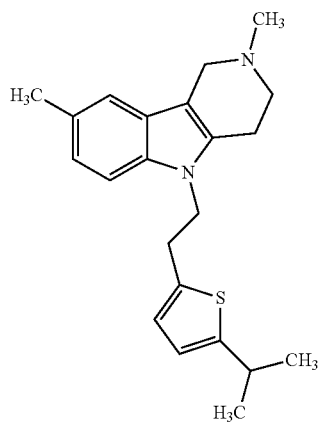 [SMILES: Cc1ccc2c(c1)c1c(n2CCc2ccc(C(C)C)s2)CCN(C)C1] |
| 105 | 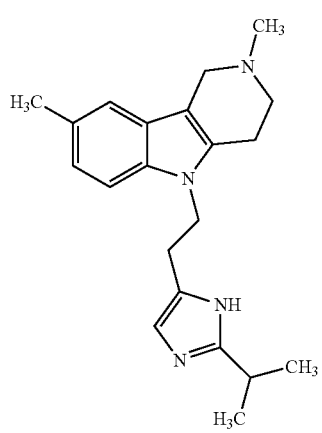 [SMILES: Cc1ccc2c(c1)c1c(n2CCc2cnc(C(C)C)[nH]2)CCN(C)C1] |
| 106 | 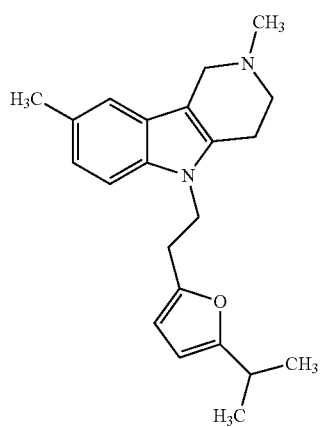 |
TABLE 2-continued
Representative Compounds According to the Invention.
| Compound No. | Structure |
|---|---|
| 107 | 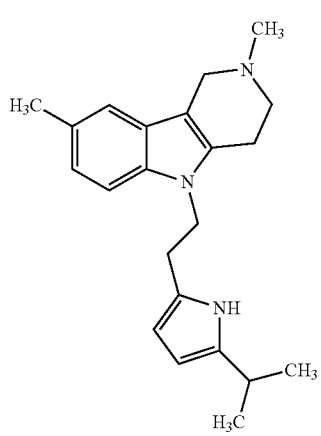 |
| 108 | 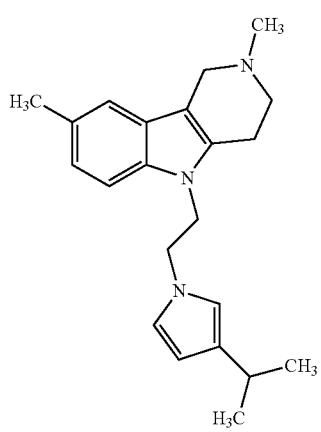 [SMILES: Cc1ccc2c(c1)c1c(n2CCn2ccc(C(C)C)c2)CCN(C)C1] |
| 109H | 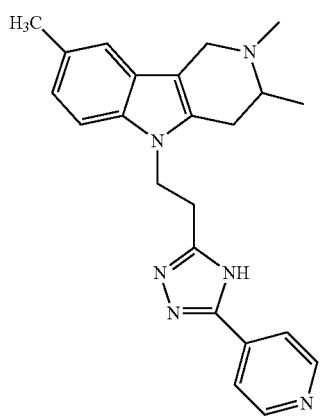 |

TABLE 2-continued
Representative Compounds According to the Invention.
| Compound No. | Structure |
|---|---|
| 110 | 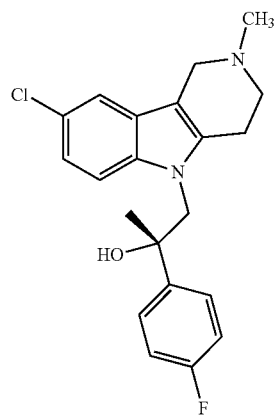 [SMILES: CN1CCc2c(c3cc(Cl)ccc3n2C[C@@](C)(O)c2ccc(F)cc2)C1] |
| 111 | 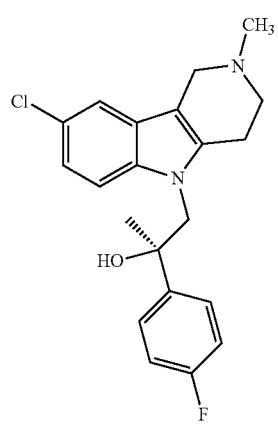 [SMILES: CN1CCc2c(c3cc(Cl)ccc3n2C[C@](C)(O)c2ccc(F)cc2)C1] |
| 112 | 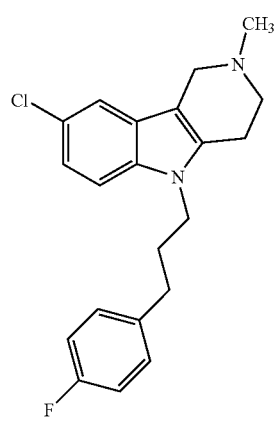 [SMILES: CN1CCc2c(c3cc(Cl)ccc3n2CCCc2ccc(F)cc2)C1] |
| 113 | 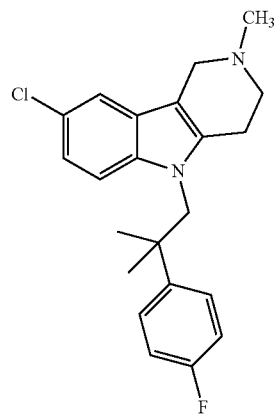 [SMILES: CN1CCc2c(c3cc(Cl)ccc3n2CC(C)(C)c2ccc(F)cc2)C1] |
| 114 | 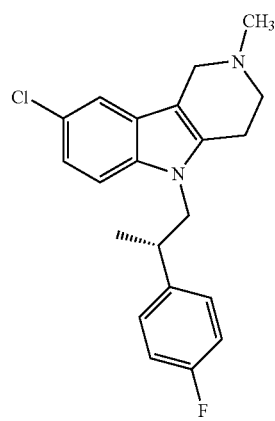 |
| 115 | 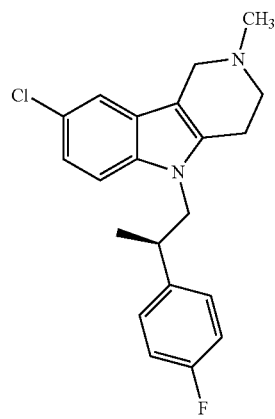 [SMILES: C[C@@H](Cn1c2c(c3cc(Cl)ccc31)CN(C)CC2)c1ccc(F)cc1] |

TABLE 2-continued

Representative Compounds According to the Invention.

| Compound No. | Structure |
|---|---|
| 116 | 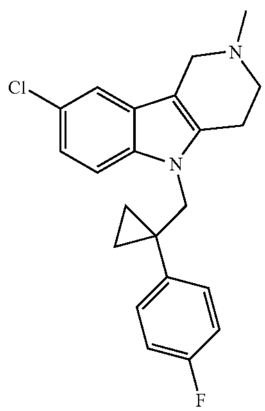 [SMILES: CN1CCc2c(c3cc(Cl)ccc3n2CC2(c3ccc(F)cc3)CC2)C1] |
| 117 | 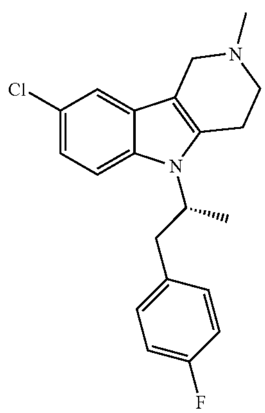 [SMILES: C[C@H](Cc1ccc(F)cc1)n1c2c(c3cc(Cl)ccc31)CN(C)CC2] |
| 118 | 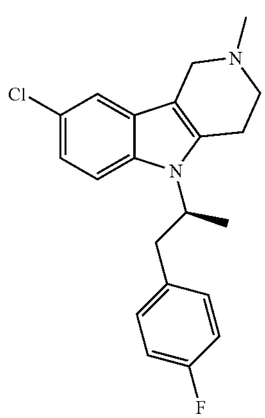 [SMILES: C[C@@H](Cc1ccc(F)cc1)n1c2c(c3cc(Cl)ccc31)CN(C)CC2] |
| 119 | 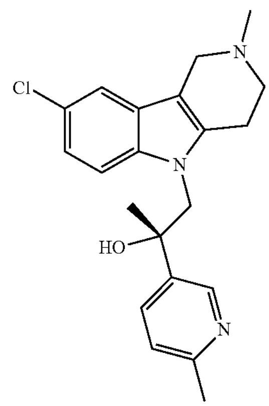 [SMILES: Cc1ccc([C@](C)(O)Cn2c3c(c4cc(Cl)ccc42)CN(C)CC3)cn1] |
| 120 | 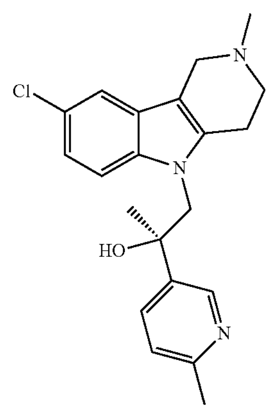 [SMILES: Cc1ccc([C@@](C)(O)Cn2c3c(c4cc(Cl)ccc42)CN(C)CC3)cn1] |
| 121 | 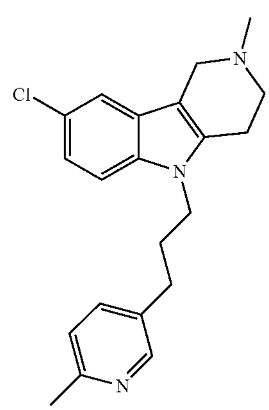 [SMILES: Cc1ccc(CCCn2c3c(c4cc(Cl)ccc42)CN(C)CC3)cn1] |

TABLE 2-continued
Representative Compounds According to the Invention.
| Compound No. | Structure |
|---|---|
| 122 | 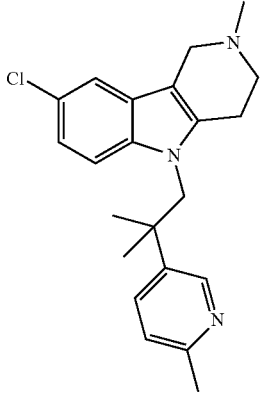 [SMILES: Cc1ccc(C(C)(C)Cn2c3c(c4cc(Cl)ccc42)CN(C)CC3)cn1] |
| 123 | 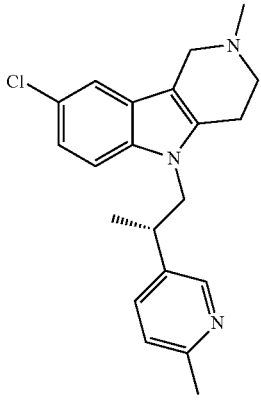 [SMILES: Cc1ccc([C@H](C)Cn2c3c(c4cc(Cl)ccc42)CN(C)CC3)cn1] |
| 124 | 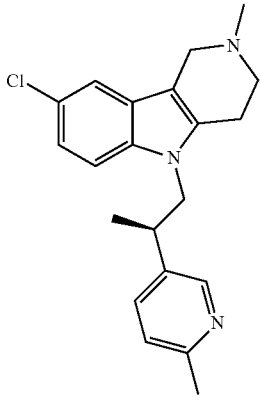 [SMILES: Cc1ccc([C@@H](C)Cn2c3c(c4cc(Cl)ccc42)CN(C)CC3)cn1] |
| 125 | 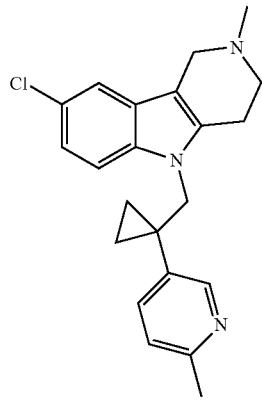 [SMILES: Cc1ccc(C2(Cn3c4c(c5cc(Cl)ccc53)CN(C)CC4)CC2)cn1] |
| 126 | 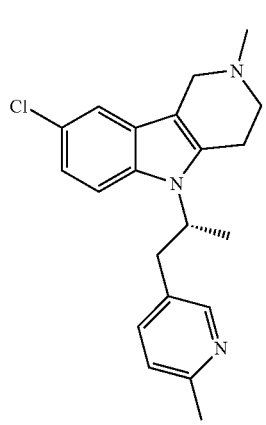 [SMILES: Cc1ccc(C[C@@H](C)n2c3c(c4cc(Cl)ccc42)CN(C)CC3)cn1] |
| 127 | 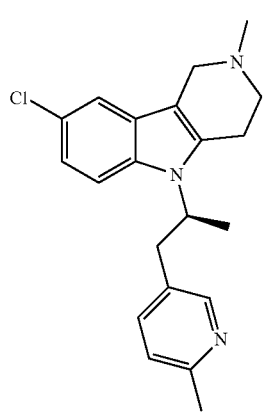 [SMILES: Cc1ccc(C[C@H](C)n2c3c(c4cc(Cl)ccc42)CN(C)CC3)cn1] |

TABLE 2-continued

Representative Compounds According to the Invention.

| Compound No. | Structure |
|---|---|
| 128 | 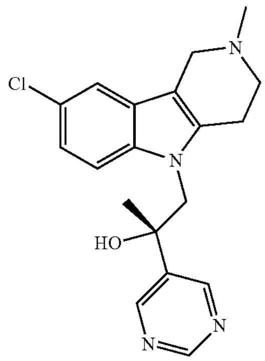 [SMILES: CN1CCc2c(c3cc(Cl)ccc3n2C[C@@](C)(O)c2cncnc2)C1] |
| 129 | 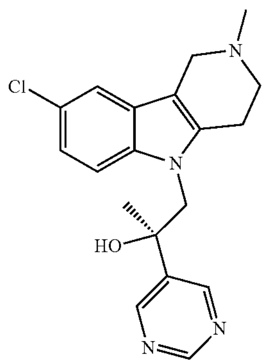 [SMILES: CN1CCc2c(c3cc(Cl)ccc3n2C[C@](C)(O)c2cncnc2)C1] |
| 130 | 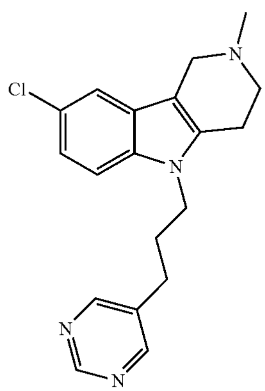 [SMILES: CN1CCc2c(c3cc(Cl)ccc3n2CCCc2cncnc2)C1] |
| 131 | 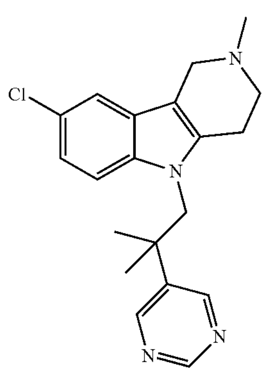 [SMILES: CN1CCc2c(c3cc(Cl)ccc3n2CC(C)(C)c2cncnc2)C1] |
| 132 | |
| 133 | |
| 134 | |
| 135 | |

TABLE 2-continued

Representative Compounds According to the Invention.

| Compound No. | Structure |
|---|---|
| 136 | 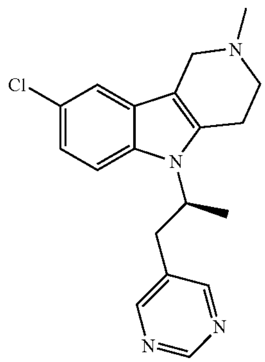 [SMILES: C[C@@H](Cc1cncnc1)n1c2c(c3cc(Cl)ccc31)CN(C)CC2] |
| 137 | 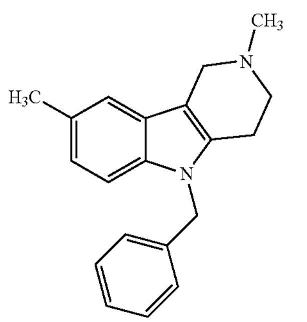 [SMILES: Cc1ccc2c(c1)c1c(n2Cc2ccccc2)CCN(C)C1] |
| 138 | 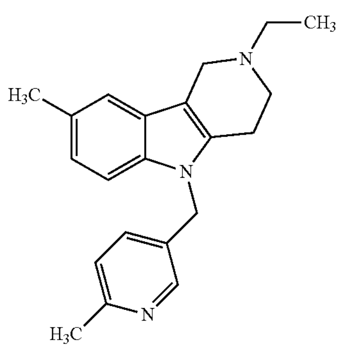 [SMILES: CCN1CCc2c(c3cc(C)ccc3n2Cc2ccc(C)nc2)C1] |
| 139 | 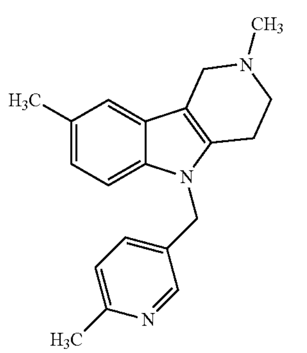 [SMILES: Cc1ccc2c(c1)c1c(n2Cc2ccc(C)nc2)CCN(C)C1] |
| 140 | |
| 141 | |
| 142 | |

TABLE 2-continued
Representative Compounds According to the Invention.
| Compound No. | Structure |
|---|---|
| 143 | 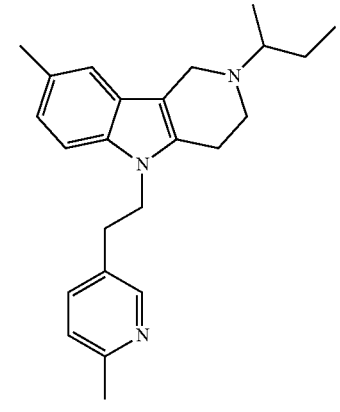 [SMILES: CCC(C)N1CCc2c(c3cc(C)ccc3n2CCc2ccc(C)nc2)C1] |
| 144 | 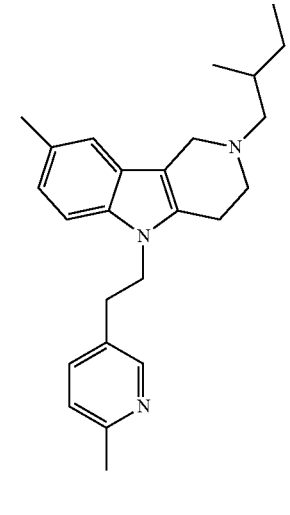 [SMILES: CCC(C)CN1CCc2c(c3cc(C)ccc3n2CCc2ccc(C)nc2)C1] |
| 145 | 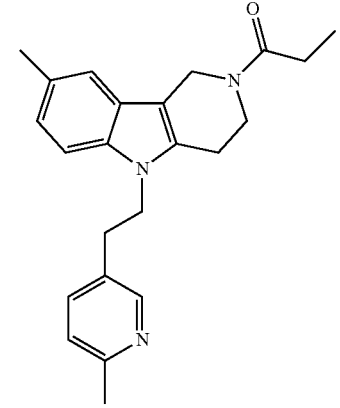 [SMILES: CCC(=O)N1CCc2c(c3cc(C)ccc3n2CCc2ccc(C)nc2)C1] |
| 146 | 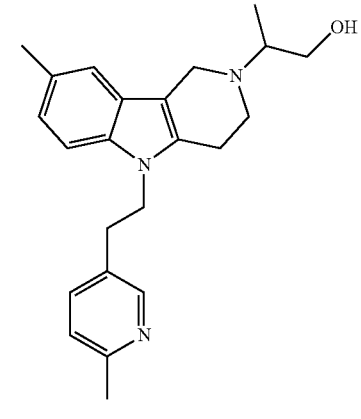 [SMILES: Cc1ccc2c(c1)c1c(n2CCc2ccc(C)nc2)CCN(C(C)CO)C1] |
| 147 | 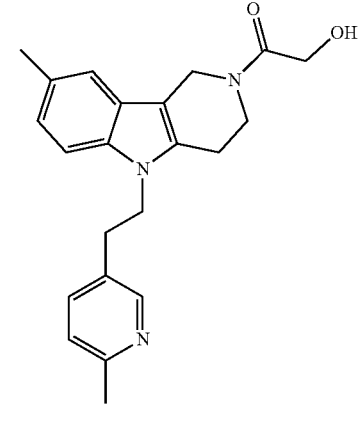 [SMILES: Cc1ccc2c(c1)c1c(n2CCc2ccc(C)nc2)CCN(C(=O)CO)C1] |
| 148 | 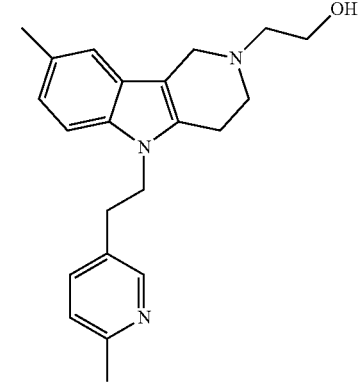 [SMILES: Cc1ccc2c(c1)c1c(n2CCc2ccc(C)nc2)CCN(CCO)C1] |

TABLE 2-continued
Representative Compounds According to the Invention.
| Compound No. | Structure |
|---|---|
| 149 | 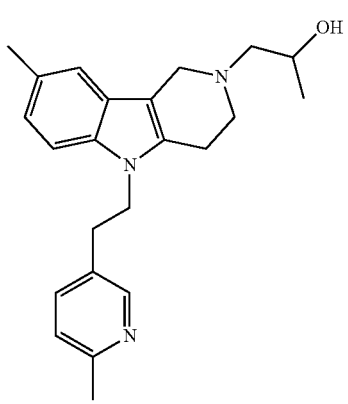 [SMILES: Cc1ccc2c(c1)c1c(n2CCc2ccc(C)nc2)CCN(CC(C)O)C1] |
| 150 | 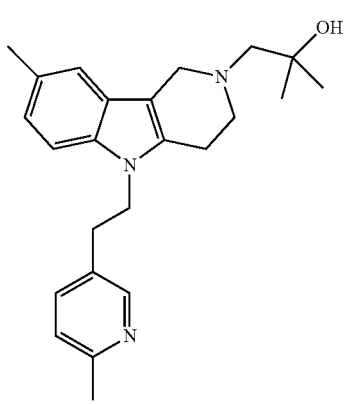 [SMILES: Cc1ccc2c(c1)c1c(n2CCc2ccc(C)nc2)CCN(CC(C)(C)O)C1] |
| 151H | 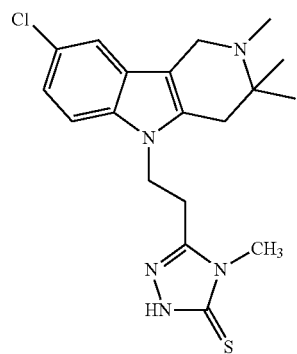 [SMILES: CN1Cc2c(n(CCc3n[nH]c(=S)n3C)c3ccc(Cl)cc23)CC1(C)C] |
TABLE 2-continued
Representative Compounds According to the Invention.
| Compound No. | Structure |
|---|---|
| 152 | 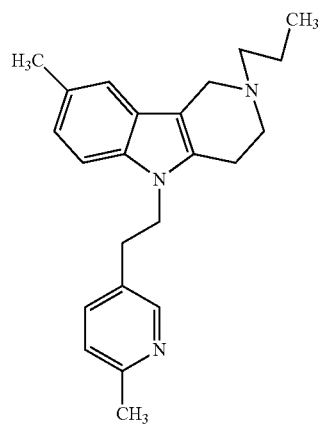 [SMILES: CCCN1CCc2c(c3cc(C)ccc3n2CCc2ccc(C)nc2)C1] |
| 153 | 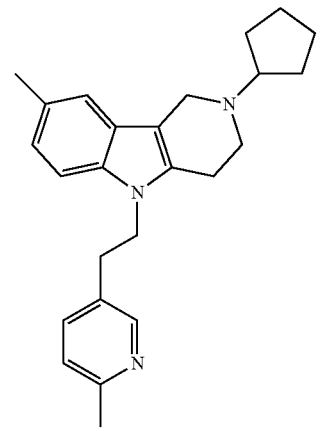 [SMILES: Cc1ccc2c(c1)c1c(n2CCc2ccc(C)nc2)CCN(C2CCCC2)C1] |
| 154 | 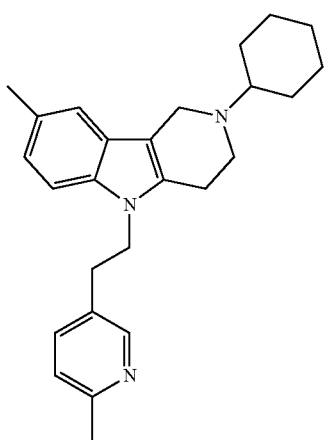 [SMILES: Cc1ccc2c(c1)c1c(n2CCc2ccc(C)nc2)CCN(C2CCCCC2)C1] |

TABLE 2-continued
Representative Compounds According to the Invention.
| Compound No. | Structure |
|---|---|
| 155 | 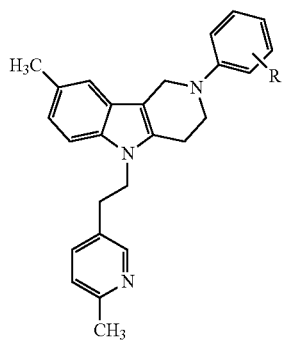 Where R is phenyl, an electron donating group or an electron withdrawing group. Examples of electron donating groups include but are not limited to: OCH₃, NH₂, OH and CH₃. Examples of electron withdrawing groups include but are not limited to: Cl, F, Br, I, NO₂, CF₃ and CHF₂. |
| 156 | 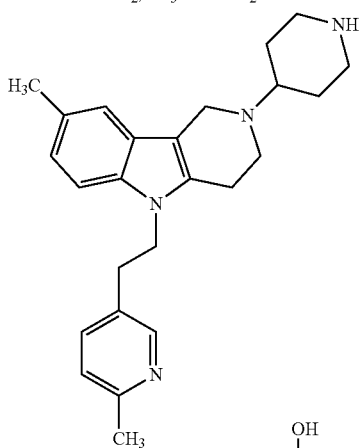 |
| 157 | 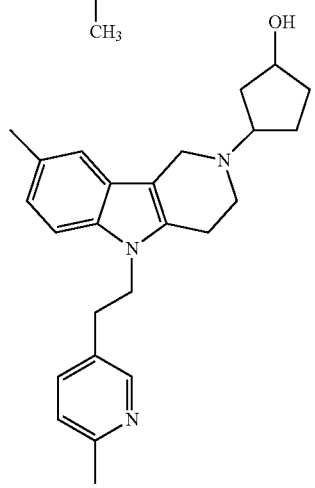 |
| 158 | 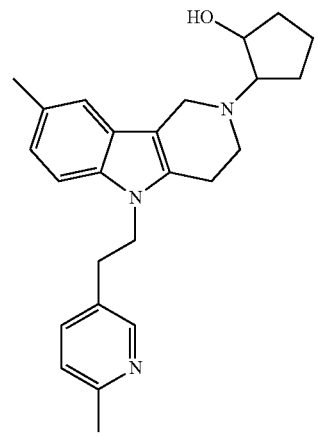 [SMILES: Cc1ccc2c(c1)c1c(n2CCc2ccc(C)nc2)CCN(C2CCCC2O)C1] |
| 159 | 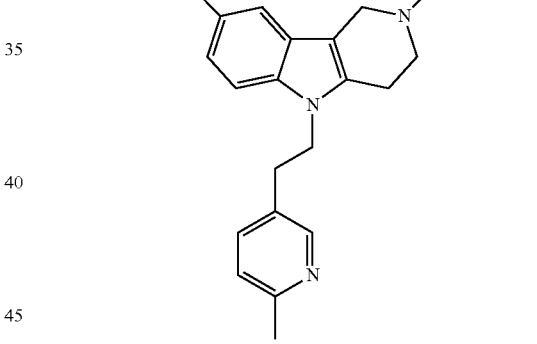 |
| 160 | 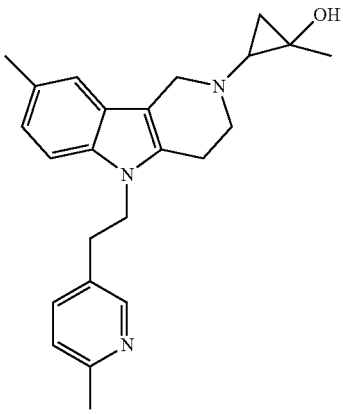 |

TABLE 2-continued
Representative Compounds According to the Invention.
| Compound No. | Structure |
|---|---|
| 161 | 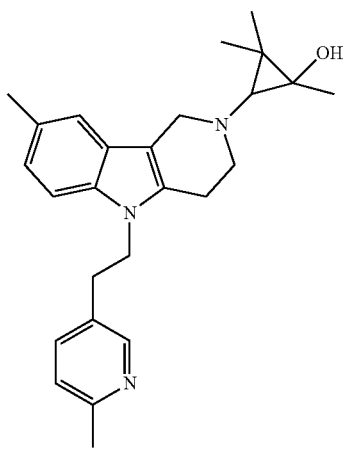 |
| 162 | 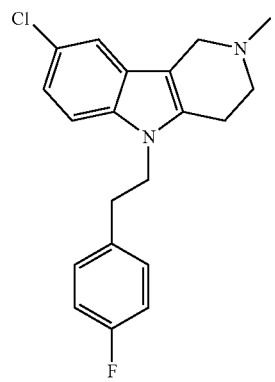 [SMILES: CN1CCc2c(c3cc(Cl)ccc3n2CCc2ccc(F)cc2)C1] |
| 163 | 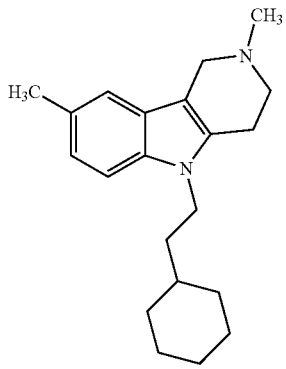 |
| 164 | 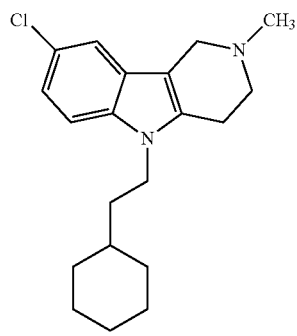 [SMILES: CN1CCc2c(c3cc(Cl)ccc3n2CCC2CCCCC2)C1] |
| 165 | 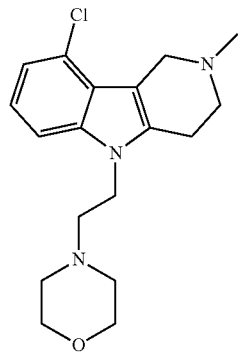 [SMILES: CN1CCc2c(c3c(Cl)cccc3n2CCN2CCOCC2)C1] |
| 166 | 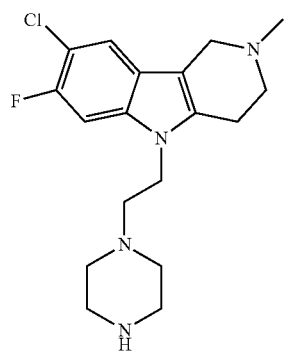 [SMILES: CN1CCc2c(c3cc(Cl)c(F)cc3n2CCN2CCNCC2)C1] |
| 167 | 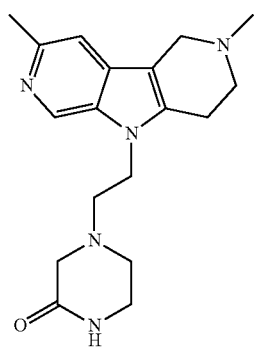 |
| 168 | 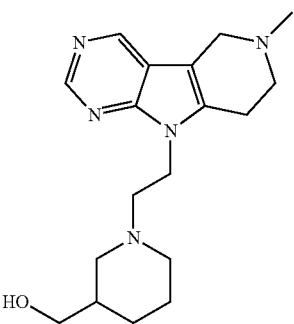 [SMILES: CN1CCc2c(c3cncnc3n2CCN2CCCC(CO)C2)C1] |

TABLE 2-continued

Representative Compounds According to the Invention.

| Compound No. | Structure |
|---|---|
| 169 | 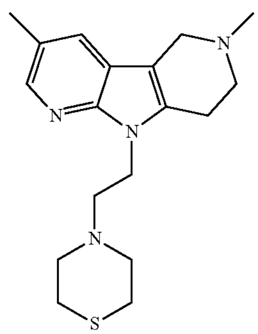 |
| 170 | 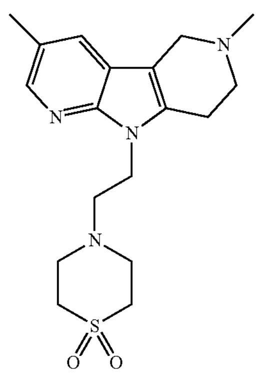 |
| 171 | 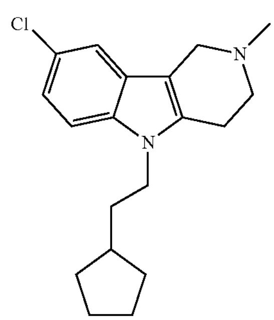 [SMILES: CN1CCc2c(c3cc(Cl)ccc3n2CCC2CCCC2)C1] |
| 172 | 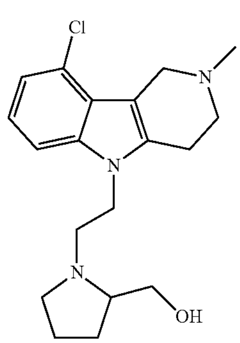 [SMILES: CN1CCc2c(c3c(Cl)cccc3n2CCN2CCCC2CO)C1] |
| 173 | |
| 174 | |
| 175 | |
| 176 | |

TABLE 2-continued
Representative Compounds According to the Invention.
| Compound No. | Structure |
|---|---|
| 177 | 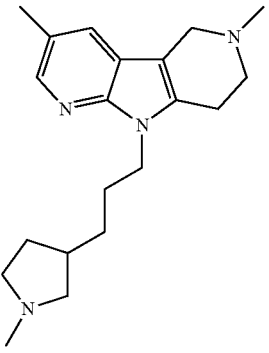 [SMILES: Cc1cnc2c(c1)c1c(n2CCCC2CCN(C)C2)CCN(C)C1] |
| 178 | 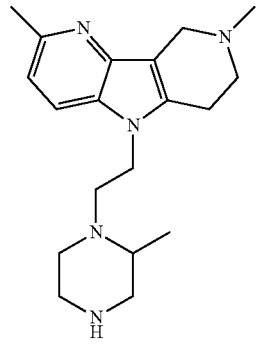 |
| 179 | 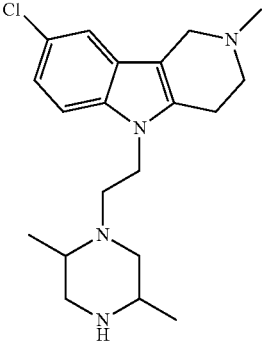 [SMILES: CC1CN(CCn2c3c(c4cc(Cl)ccc42)CN(C)CC3)C(C)CN1] |
| 180 | 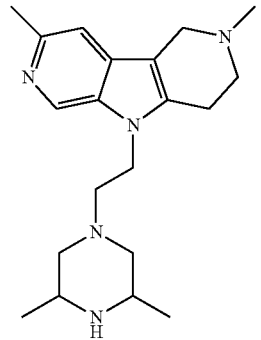 |
| 181 | 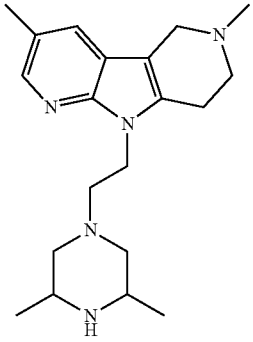 |
| 182 | 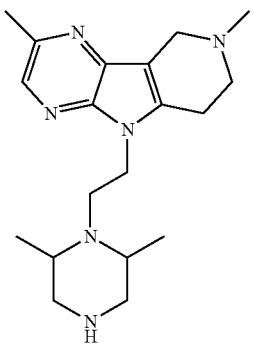 |
| 183 | 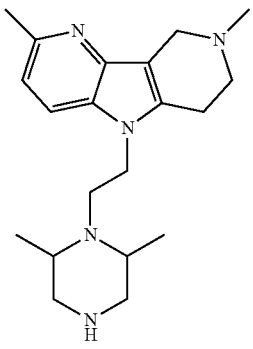 |
| 184 | 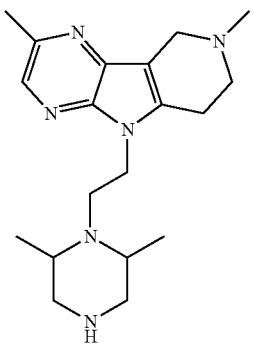 |

TABLE 2-continued
Representative Compounds According to the Invention.
| Compound No. | Structure |
|---|---|
| 185 | 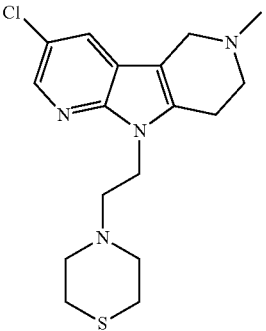 [SMILES: CN1CCc2c(c3cc(Cl)cnc3n2CCN2CCSCC2)C1] |
| 186 | 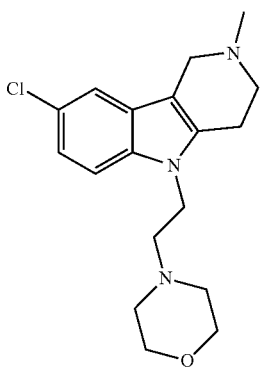 [SMILES: CN1CCc2c(c3cc(Cl)ccc3n2CCN2CCOCC2)C1] |
| 187 | 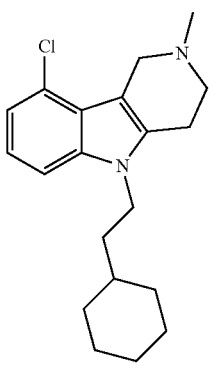 [SMILES: CN1CCc2c(c3c(Cl)cccc3n2CCC2CCCCC2)C1] |
| 188 | 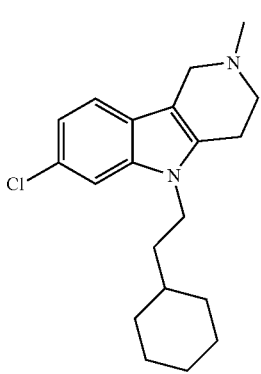 [SMILES: CN1CCc2c(c3ccc(Cl)cc3n2CCC2CCCCC2)C1] |
| 189 | 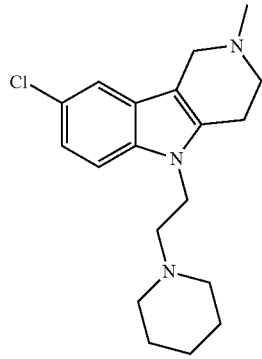 [SMILES: CN1CCc2c(c3cc(Cl)ccc3n2CCN2CCCCC2)C1] |
| 190 | 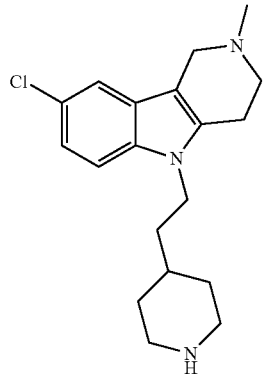 [SMILES: CN1CCc2c(c3cc(Cl)ccc3n2CCC2CCNCC2)C1] |
| 191 | 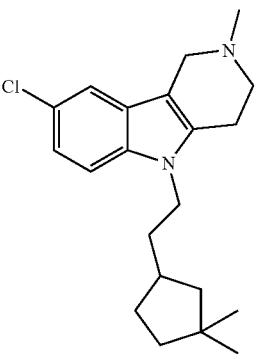 [SMILES: CN1CCc2c(c3cc(Cl)ccc3n2CCC2CCC(C)(C)C2)C1] |
| 192 | 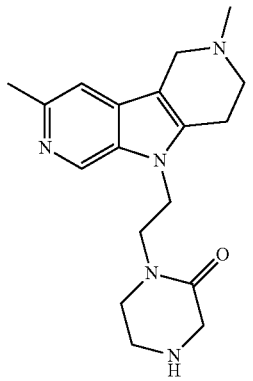 [SMILES: Cc1cc2c3c(n(CCN4CCNCC4=O)c2cn1)CCN(C)C3] |

TABLE 2-continued
Representative Compounds According to the Invention.
| Compound No. | Structure |
|---|---|
| 193 | 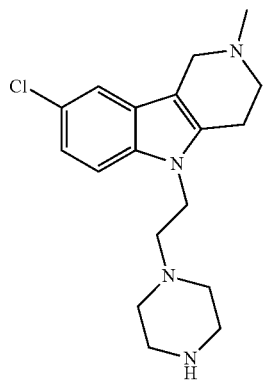 [SMILES: CN1CCc2c(c3cc(Cl)ccc3n2CCN2CCNCC2)C1] |
| 194 | 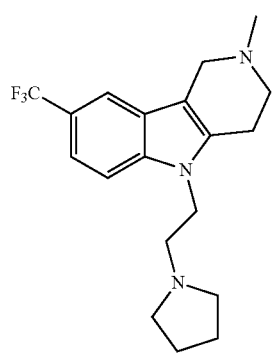 [SMILES: CN1CCc2c(c3cc(C(F)(F)F)ccc3n2CCN2CCCC2)C1] |
| 195 | 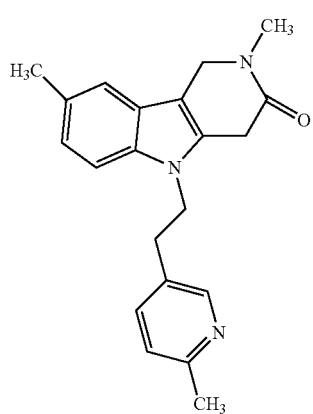 [SMILES: Cc1ccc2c(c1)c1c(n2CCc2ccc(C)nc2)CC(=O)N(C)C1] |
| 196 | 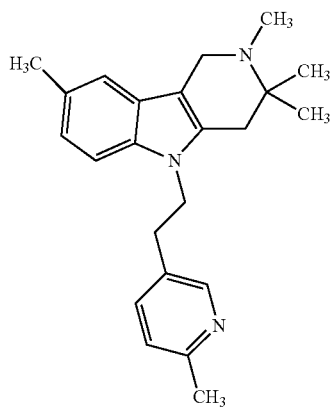 |
| 197 | 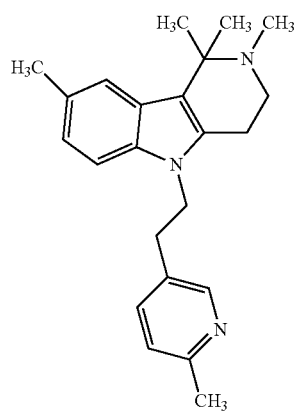 |
| 198 | 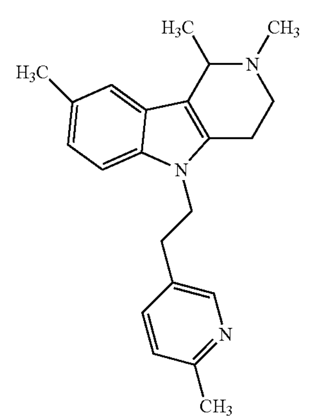 |

TABLE 2-continued

Representative Compounds According to the Invention.

| Compound No. | Structure |
|---|---|
| 199 | 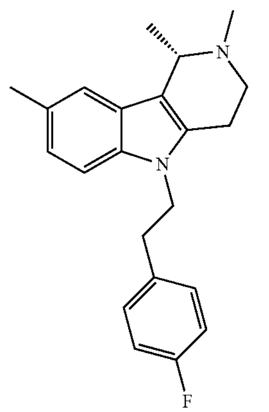 |
| 200 | 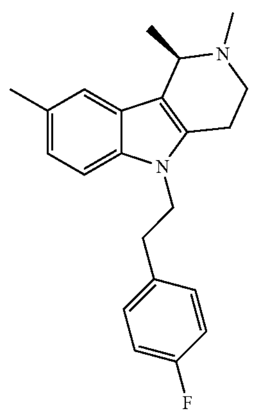 [SMILES: Cc1ccc2c(c1)c1c(n2CCc2ccc(F)cc2)CCN(C)[C@@H]1C] |
| 201 | 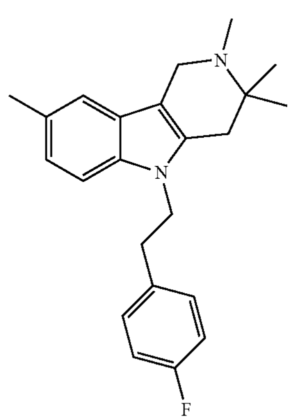 |
| 202 | |
| 203 | |
| 204 | |

TABLE 2-continued

Representative Compounds According to the Invention.

| Compound No. | Structure |
|---|---|
| 205 | 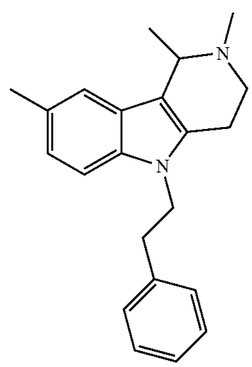 [SMILES: Cc1ccc2c(c1)c1c(n2CCc2ccccc2)CCN(C)C1C] |
| 206 | 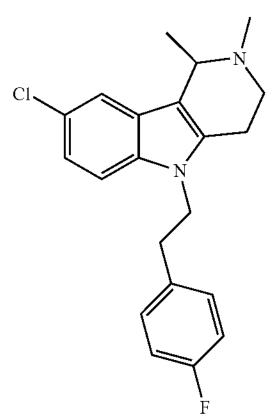 [SMILES: CC1c2c(n(CCc3ccc(F)cc3)c3ccc(Cl)cc23)CCN1C] |
| 207 | 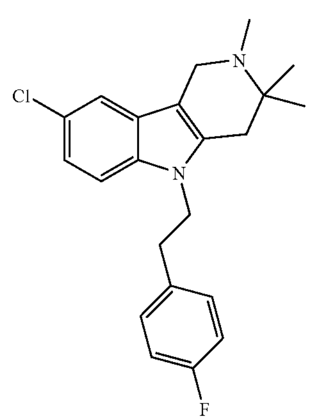 [SMILES: CN1Cc2c(n(CCc3ccc(F)cc3)c3ccc(Cl)cc23)CC1(C)C] |
| 208 | |
| 209 | |
| 210 | |

TABLE 2-continued

Representative Compounds According to the Invention.

| Compound No. | Structure |
|---|---|
| 211 | 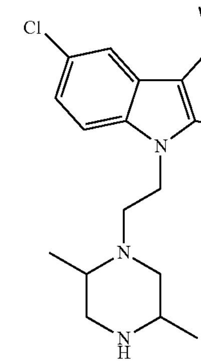 |
| 212 | 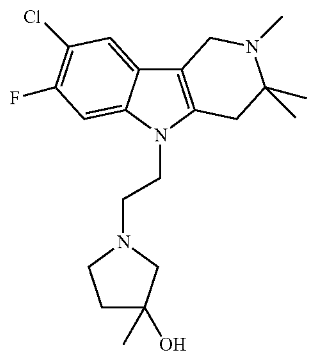 [SMILES: CN1Cc2c(n(CCN3CCC(C)(O)C3)c3cc(F)c(Cl)cc23)CC1(C)C] |
| 213 | 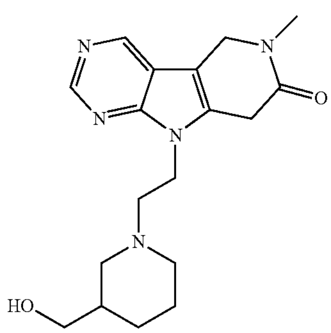 [SMILES: CN1Cc2c(n(CCN3CCCC(CO)C3)c3ncncc23)CC1=O] |
| 214 | 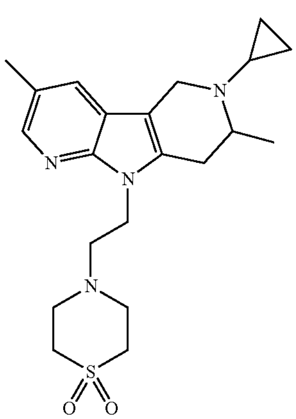 [SMILES: Cc1cnc2c(c1)c1c(n2CCN2CCS(=O)(=O)CC2)CC(C)N(C2CC2)C1] |
| 215 | |
| 216 | |
| 217 | |
| 218H | |

TABLE 2-continued
Representative Compounds According to the Invention.
| Compound No. | Structure |
|---|---|
| 219H | 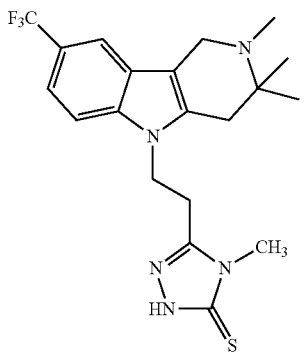 [SMILES: CN1Cc2c(n(CCc3n[nH]c(=S)n3C)c3ccc(C(F)(F)F)cc23)CC1(C)C] |
| 220H | 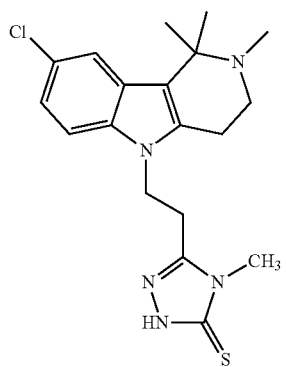 [SMILES: CN1CCc2c(c3cc(Cl)ccc3n2CCc2n[nH]c(=S)n2C)C1(C)C] |
| 221 | 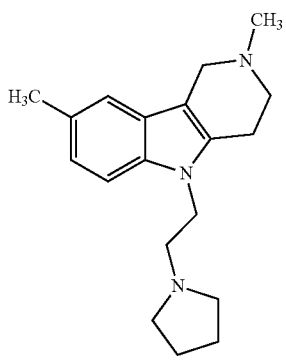 [SMILES: Cc1ccc2c(c1)c1c(n2CCN2CCCC2)CCN(C)C1] |
| 222H | 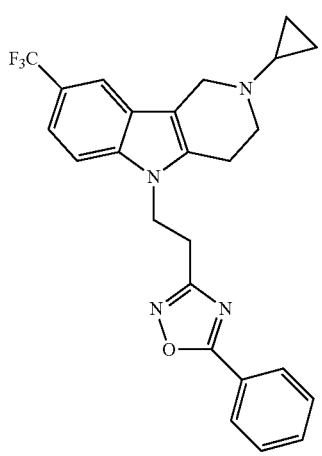 [SMILES: FC(F)(F)c1ccc2c(c1)c1c(n2CCc2noc(-c3ccccc3)n2)CCN(C2CC2)C1] |
| 223H | 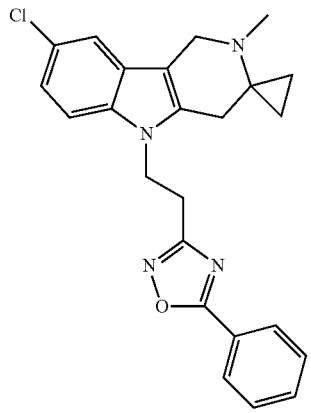 [SMILES: CN1Cc2c(n(CCc3noc(-c4ccccc4)n3)c3ccc(Cl)cc23)CC12CC2] |
| 224 | 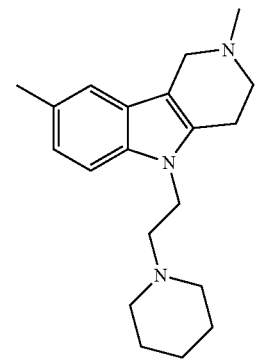 [SMILES: Cc1ccc2c(c1)c1c(n2CCN2CCCCC2)CCN(C)C1] |
| 225 | 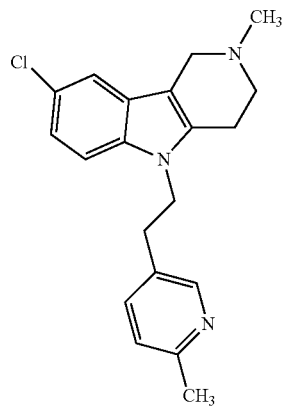 [SMILES: Cc1ccc(CCn2c3c(c4cc(Cl)ccc42)CN(C)CC3)cn1] |

TABLE 2-continued
Representative Compounds According to the Invention.
| Compound No. | Structure |
|---|---|
| 226 | 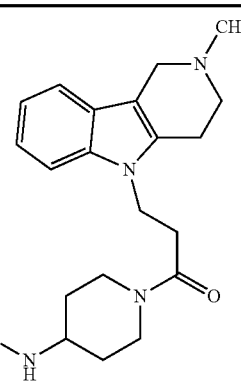 |
| 227 | 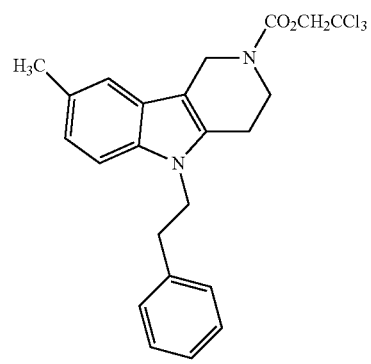 |
| 228 | 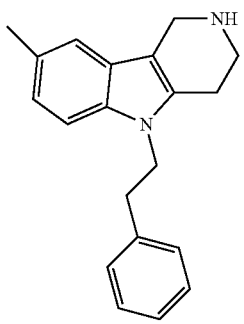 [SMILES: Cc1ccc2c(c1)c1c(n2CCc2ccccc2)CCNC1] |
| 229H | 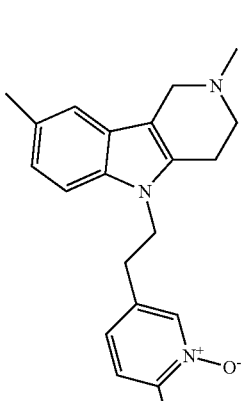 |
| 230 | 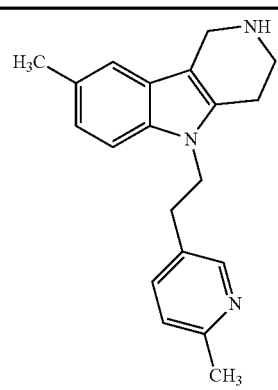 |
| 231 | 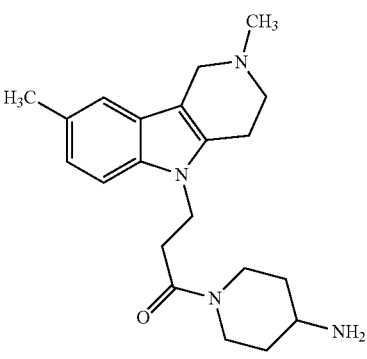 [SMILES: Cc1ccc2c(c1)c1c(n2CCC(=O)N2CCC(N)CC2)CCN(C)C1] |
| 232 | 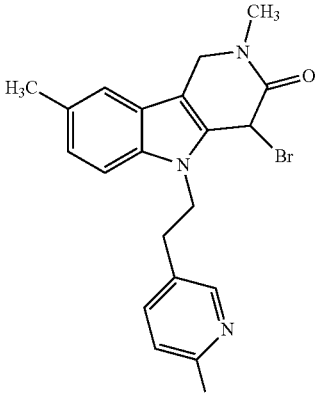 |
| 233 | 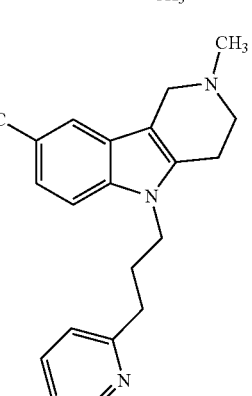 |

TABLE 2-continued

Representative Compounds According to the Invention.

| Compound No. | Structure |
|---|---|
| 234H | (structure) |
| 235 | (structure) |
| 236 | (structure) |
| 237 | (structure) |
| 238 | (structure) |
| 239 | (structure) |
| 240 | (structure) |

TABLE 2-continued
Representative Compounds According to the Invention.
| Compound No. | Structure |
|---|---|
| 241 | 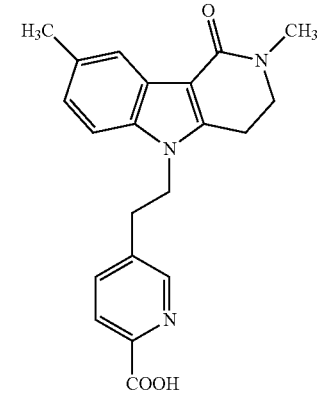 |
| 242H | 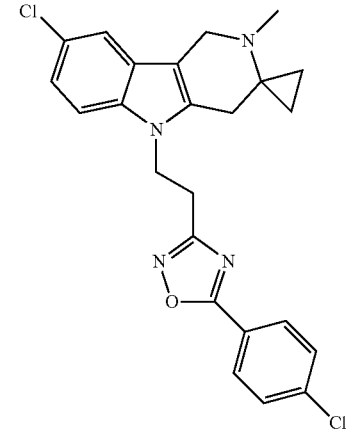 [SMILES: CN1Cc2c(n(CCc3noc(-c4ccc(Cl)cc4)n3)c3ccc(Cl)cc23)CC12CC2] |
| 243 | 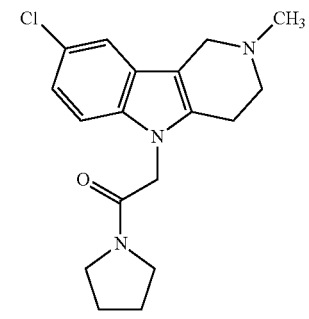 [SMILES: CN1CCc2c(c3cc(Cl)ccc3n2CC(=O)N2CCCC2)C1] |
| 244 | 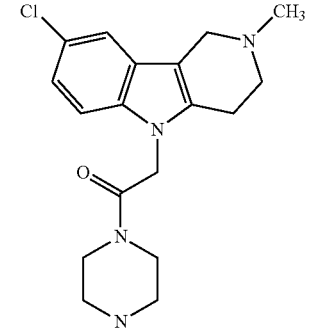 |
| 245 | 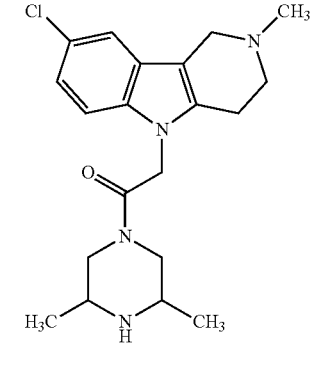 [SMILES: CC1CN(C(=O)Cn2c3c(c4cc(Cl)ccc42)CN(C)CC3)CC(C)N1] |
| 246 | 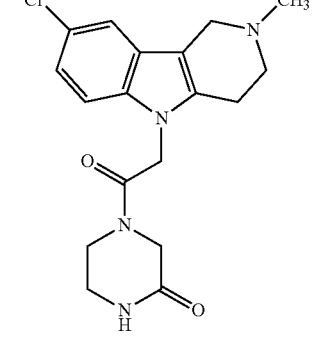 |
| 247 | 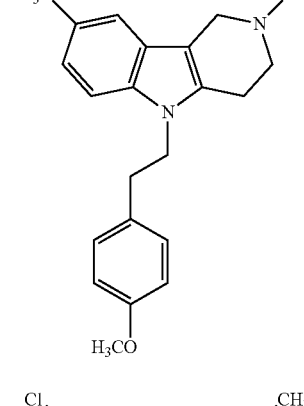 |
| 248 | 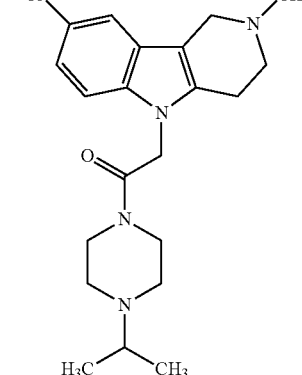 |

TABLE 2-continued
Representative Compounds According to the Invention.
| Compound No. | Structure |
|---|---|
| 249 | 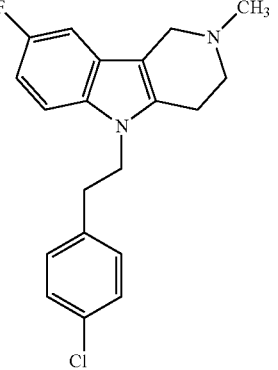 |
| 250 | 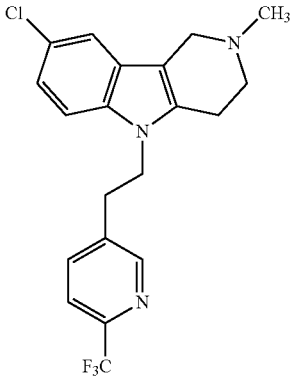 [SMILES: CN1CCc2c(c3cc(Cl)ccc3n2CCc2ccc(C(F)(F)F)nc2)C1] |
| 251 | 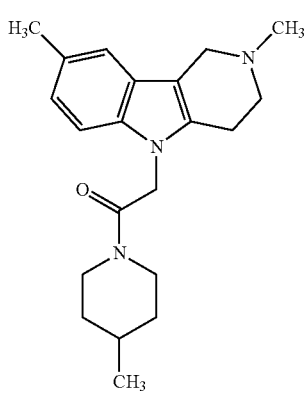 |
| 252H | 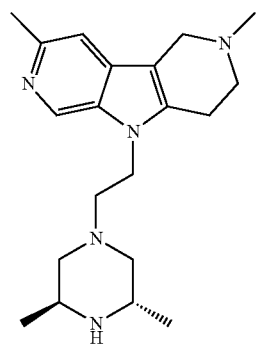 |
| 253 | 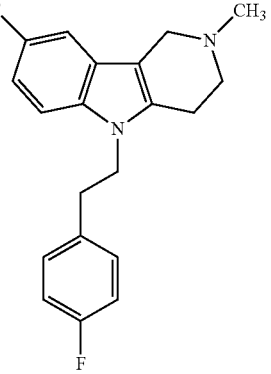 |
| 254H | 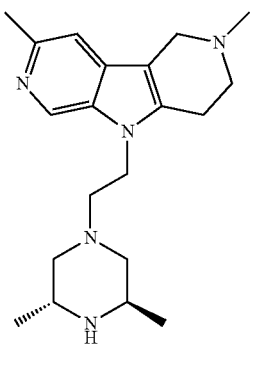 |
| 255 | 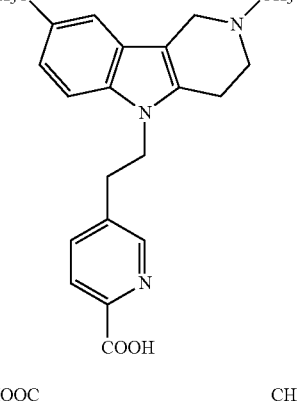 |
| 256 | 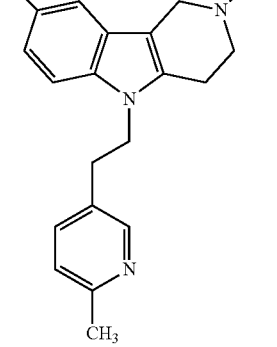 |

TABLE 2-continued

Representative Compounds According to the Invention.

| Compound No. | Structure |
|---|---|
| 257 | |
| 258H | |
| 259H | |
| 260H | |
| 261H | 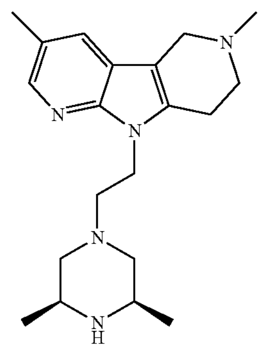 |
| 262 | 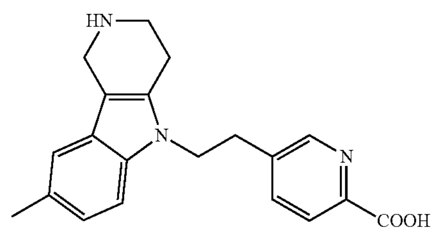 [SMILES: Cc1ccc2c(c1)c1c(n2CCc2ccc(C(=O)O)nc2)CCNC1] |
| 263 | 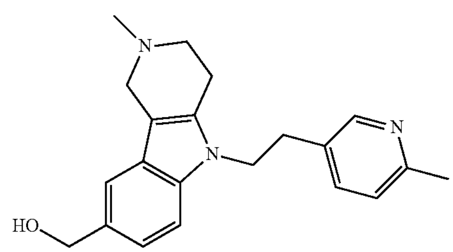 [SMILES: Cc1ccc(CCn2c3c(c4cc(CO)ccc42)CN(C)CC3)cn1] |
| 264 | 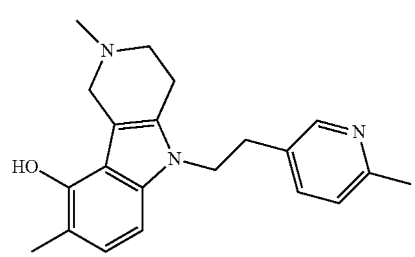 [SMILES: Cc1ccc(CCn2c3c(c4c(O)c(C)ccc42)CN(C)CC3)cn1] |
| 265 | 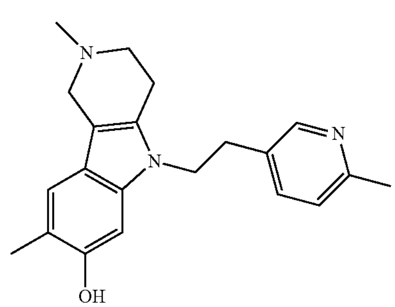 |

TABLE 2-continued
Representative Compounds According to the Invention.
| Compound No. | Structure |
|---|---|
| 266 | 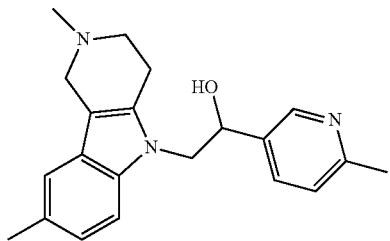 |
| 267 | 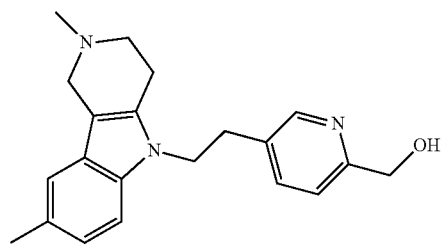 [SMILES: Cc1ccc2c(c1)c1c(n2CCc2ccc(CO)nc2)CCN(C)C1] |
| 268 | 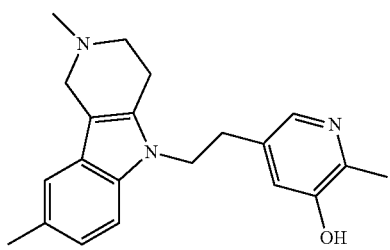 |
| 269 | 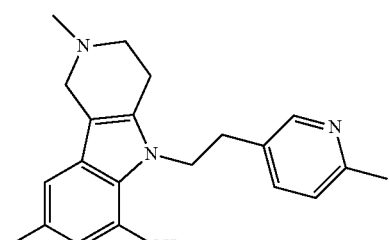 |
| 270 | 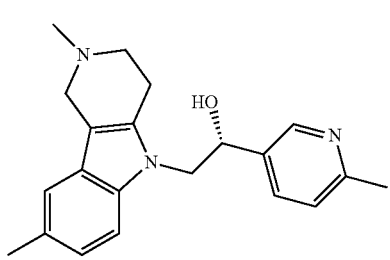 |
| 271 | 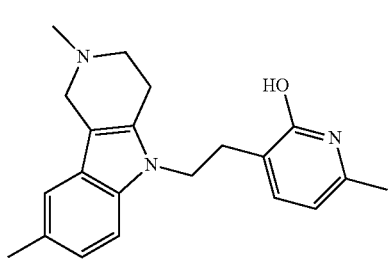 |
| 272 | 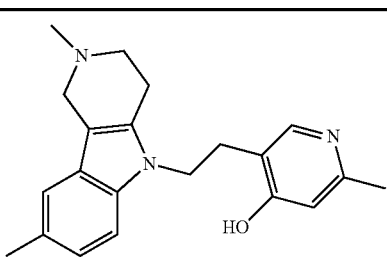 |
| 273H | 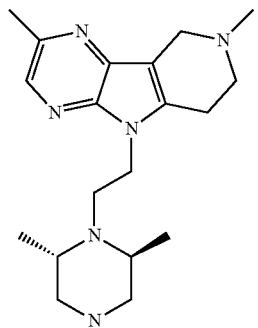 |
| 274 | 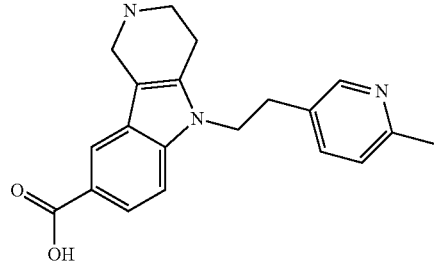 [SMILES: Cc1ccc(CCn2c3c(c4cc(C(=O)O)ccc42)CNCC3)cn1] |
| 275 | 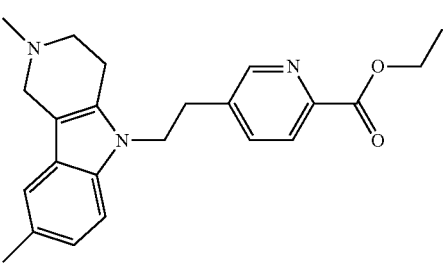 [SMILES: CCOC(=O)c1ccc(CCn2c3c(c4cc(C)ccc42)CN(C)CC3)cn1] |
| 276H | 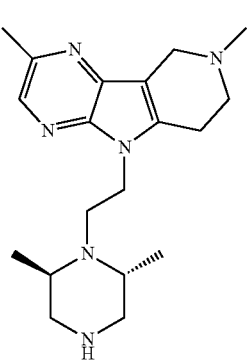 |

TABLE 2-continued
Representative Compounds According to the Invention.
| Compound No. | Structure |
|---|---|
| 277 | 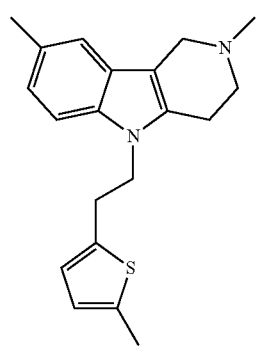 |
| 278 | 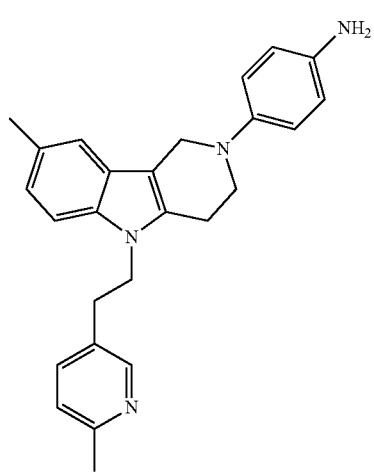 [SMILES: Cc1ccc2c(c1)c1c(n2CCc2ccc(C)nc2)CCN(c2ccc(N)cc2)C1] |
| 279 | 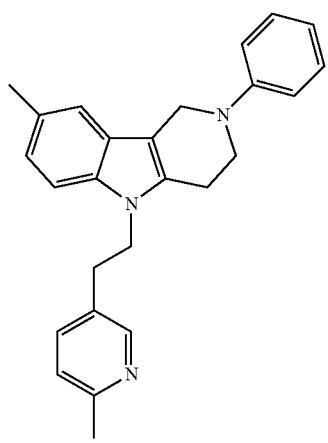 [SMILES: Cc1ccc2c(c1)c1c(n2CCc2ccc(C)nc2)CCN(c2ccccc2)C1] |
| 280 | 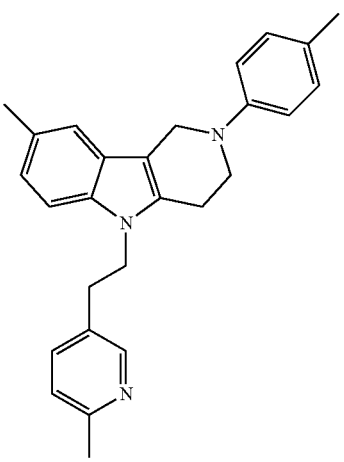 |
| 281 | 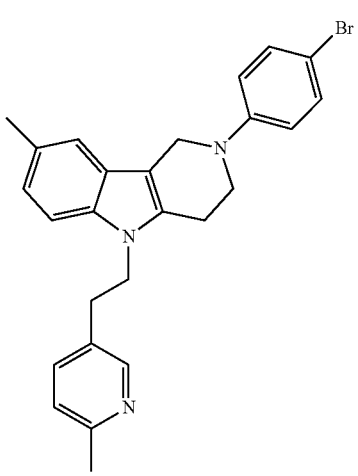 [SMILES: Cc1ccc2c(c1)c1c(n2CCc2ccc(C)nc2)CCN(c2ccc(Br)cc2)C1] |
| 282 | 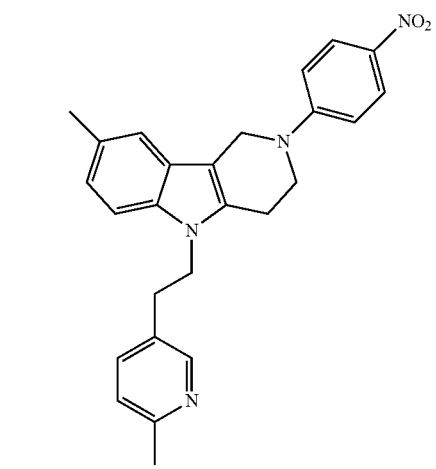 |

TABLE 2-continued
Representative Compounds According to the Invention.
| Compound No. | Structure |
|---|---|
| 283 | 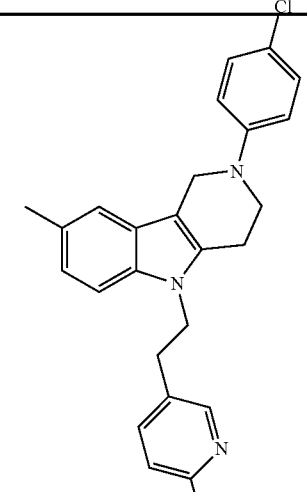 |
| 284 | 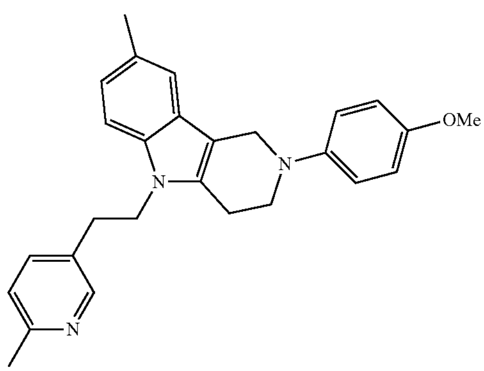 [SMILES: COc1ccc(N2CCc3c(c4cc(C)ccc4n3CCc3ccc(C)nc3)C2)cc1] |
| 285 | 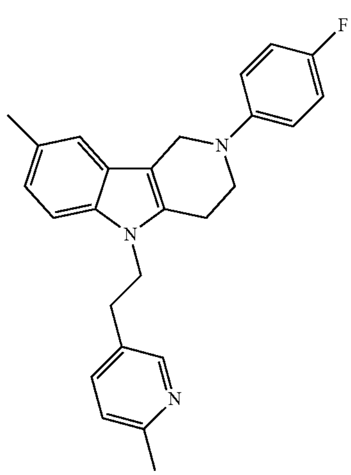 [SMILES: Cc1ccc2c(c1)c1c(n2CCc2ccc(C)nc2)CCN(c2ccc(F)cc2)C1] |
TABLE 2-continued
Representative Compounds According to the Invention.
| Compound No. | Structure |
|---|---|
| 286 | 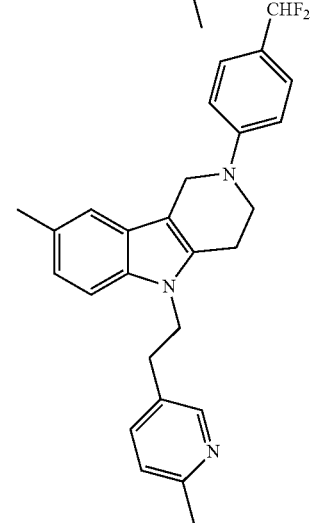 [SMILES: Cc1ccc2c(c1)c1c(n2CCc2ccc(C)nc2)CCN(c2ccc(C(F)F)cc2)C1] |
| 287 | 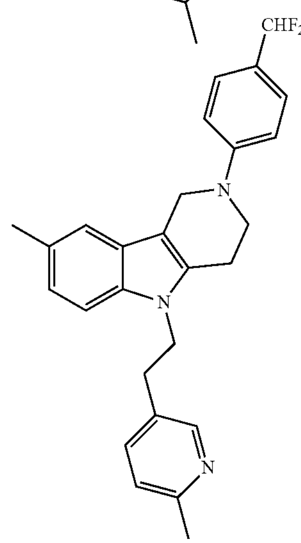 |
| 288 | 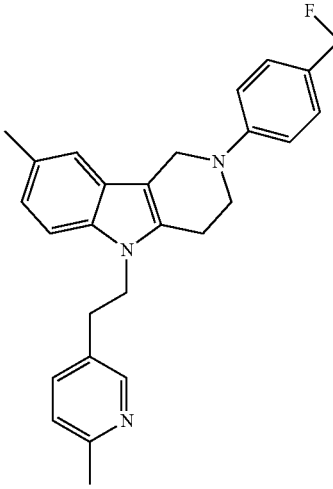 |

TABLE 2-continued
Representative Compounds According to the Invention.
| Compound No. | Structure |
|---|---|
| 289 | 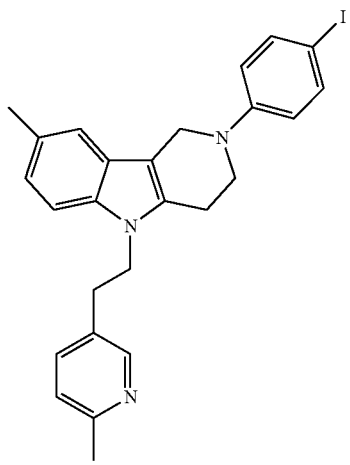 [SMILES: Cc1ccc2c(c1)c1c(n2CCc2ccc(C)nc2)CCN(c2ccc(I)cc2)C1] |
| 290 | 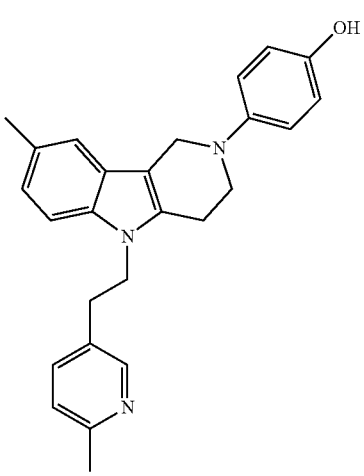 [SMILES: Cc1ccc2c(c1)c1c(n2CCc2ccc(C)nc2)CCN(c2ccc(O)cc2)C1] |
| 291 | 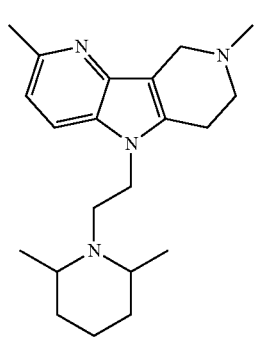 |
| 292 | 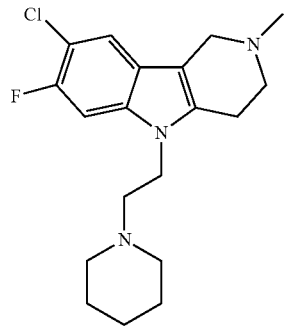 [SMILES: CN1CCc2c(c3cc(Cl)c(F)cc3n2CCN2CCCCC2)C1] |
| 293H | 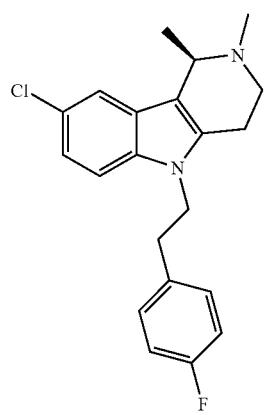 [SMILES: C[C@@H]1c2c(n(CCc3ccc(F)cc3)c3ccc(Cl)cc23)CCN1C] |
| 294 | 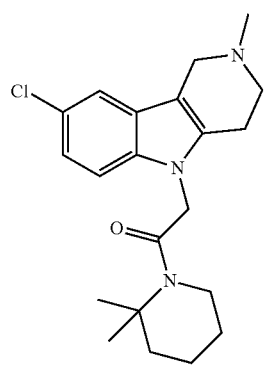 [SMILES: CN1CCc2c(c3cc(Cl)ccc3n2CC(=O)N2CCCCC2(C)C)C1] |
| 295 | 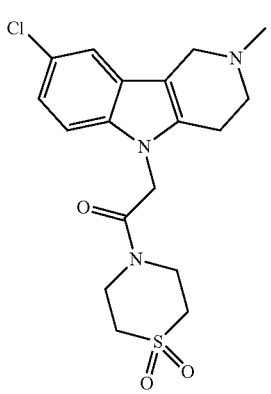 [SMILES: CN1CCc2c(c3cc(Cl)ccc3n2CC(=O)N2CCS(=O)(=O)CC2)C1] |

TABLE 2-continued
Representative Compounds According to the Invention.
| Compound No. | Structure |
|---|---|
| 296 | 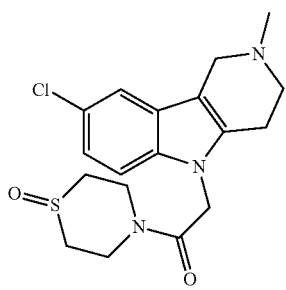 [SMILES: CN1CCc2c(c3cc(Cl)ccc3n2CC(=O)N2CCS(=O)CC2)C1] |
| 297 | 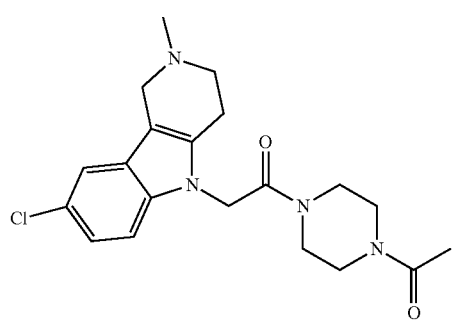 [SMILES: CC(=O)N1CCN(C(=O)Cn2c3c(c4cc(Cl)ccc42)CN(C)CC3)CC1] |
| 298 | 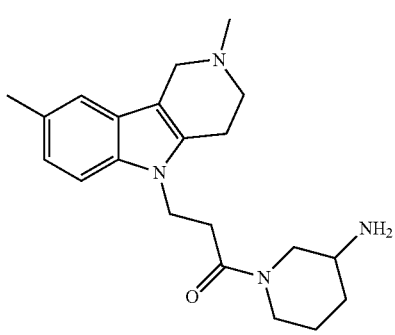 [SMILES: Cc1ccc2c(c1)c1c(n2CCC(=O)N2CCCC(N)C2)CCN(C)C1] |
| 299 | 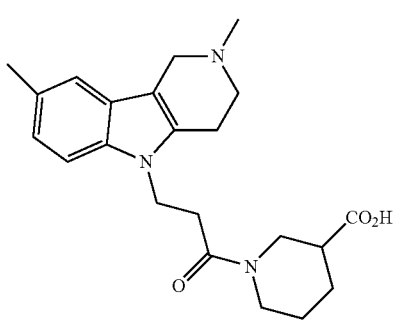 [SMILES: Cc1ccc2c(c1)c1c(n2CCC(=O)N2CCCC(C(=O)O)C2)CCN(C)C1] |
| 300 | 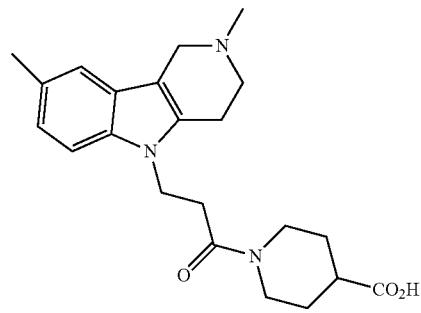 [SMILES: Cc1ccc2c(c1)c1c(n2CCC(=O)N2CCC(C(=O)O)CC2)CCN(C)C1] |
| 301 | 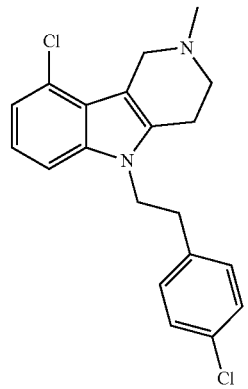 [SMILES: CN1CCc2c(c3c(Cl)cccc3n2CCc2ccc(Cl)cc2)C1] |
| 302 | 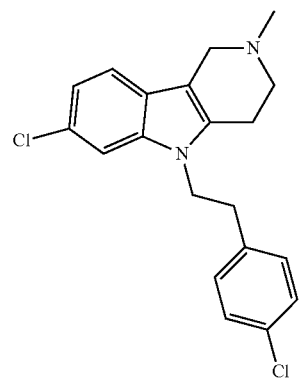 [SMILES: CN1CCc2c(c3ccc(Cl)cc3n2CCc2ccc(Cl)cc2)C1] |
| 303 | 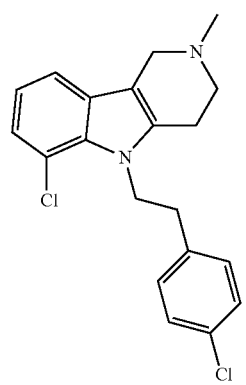 [SMILES: CN1CCc2c(c3cccc(Cl)c3n2CCc2ccc(Cl)cc2)C1] |

TABLE 2-continued

Representative Compounds According to the Invention.

| Compound No. | Structure |
|---|---|
| 304 | 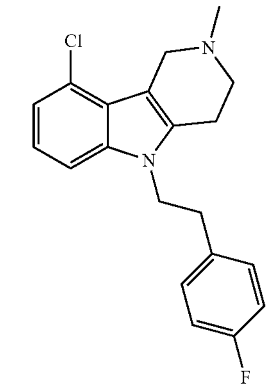 [SMILES: CN1CCc2c(c3c(Cl)cccc3n2CCc2ccc(F)cc2)C1] |
| 305 | 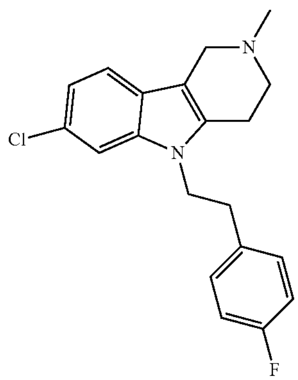 [SMILES: CN1CCc2c(c3ccc(Cl)cc3n2CCc2ccc(F)cc2)C1] |
| 306 | 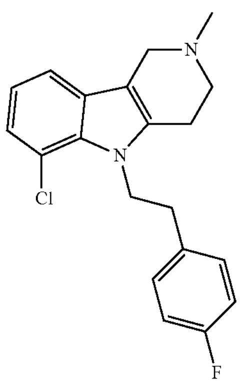 [SMILES: CN1CCc2c(c3cccc(Cl)c3n2CCc2ccc(F)cc2)C1] |
| 307 | 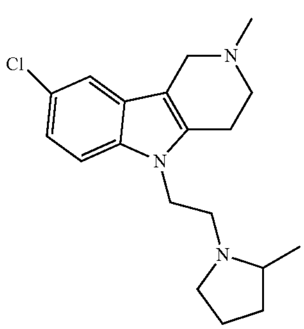 [SMILES: CC1CCCN1CCn1c2c(c3cc(Cl)ccc31)CN(C)CC2] |
| 308 | |
| 309 | |
| 310 | |
| 311 | |

TABLE 2-continued
Representative Compounds According to the Invention.
| Compound No. | Structure |
|---|---|
| 312 | 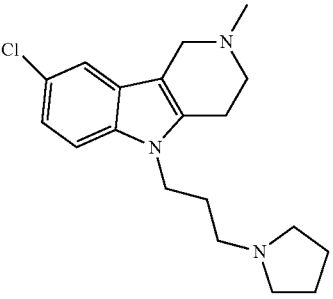 [SMILES: CN1CCc2c(c3cc(Cl)ccc3n2CCCN2CCCC2)C1] |
| 313 | 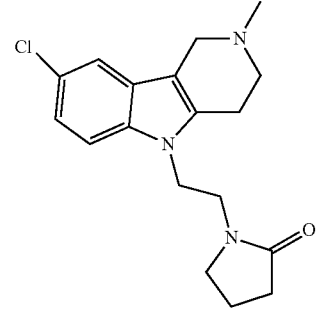 [SMILES: CN1CCc2c(c3cc(Cl)ccc3n2CCN2CCCC2=O)C1] |
| 314 | 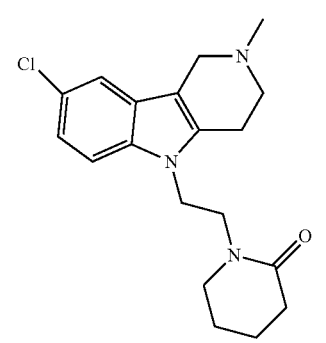 [SMILES: CN1CCc2c(c3cc(Cl)ccc3n2CCN2CCCCC2=O)C1] |
| 315 | 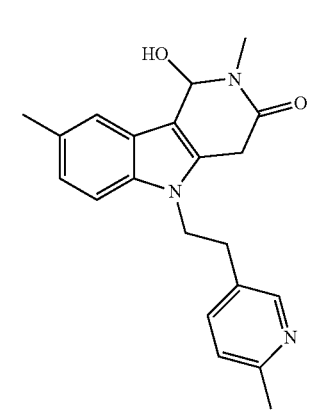 [SMILES: Cc1ccc2c(c1)c1c(n2CCc2ccc(C)nc2)CC(=O)N(C)C1O] |
| 316 | 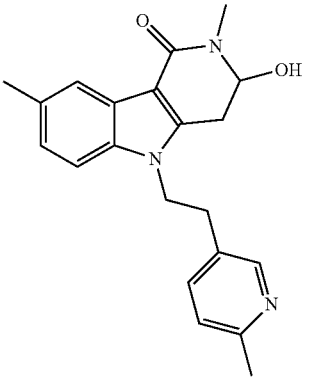 [SMILES: Cc1ccc2c(c1)c1c(n2CCc2ccc(C)nc2)CC(O)N(C)C1=O] |
| 317 | 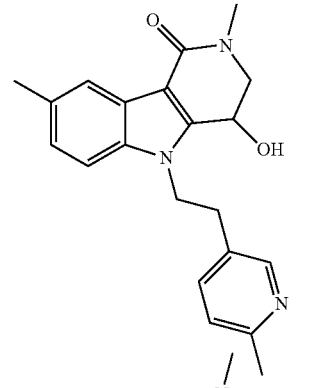 |
| 318 | 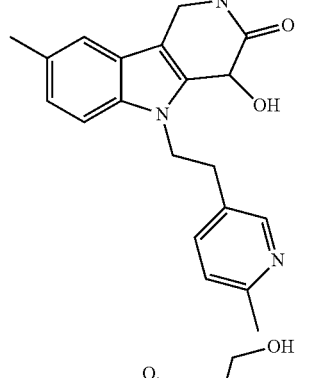 |
| 319 | 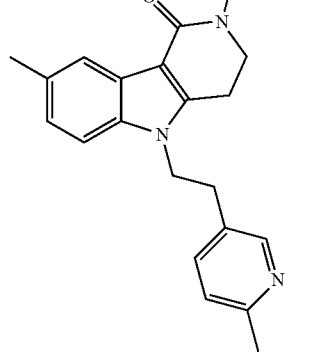 |

TABLE 2-continued
Representative Compounds According to the Invention.
| Compound No. | Structure |
|---|---|
| 320 | 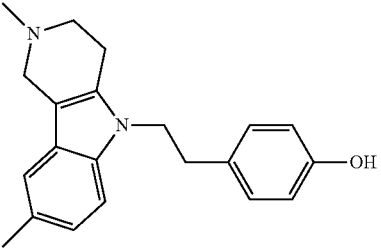 [SMILES: Cc1ccc2c(c1)c1c(n2CCc2ccc(O)cc2)CCN(C)C1] |
| 321 | 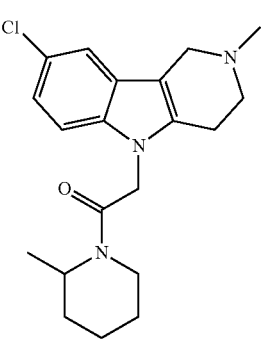 [SMILES: CC1CCCCN1C(=O)Cn1c2c(c3cc(Cl)ccc31)CN(C)CC2] |
| 322 | 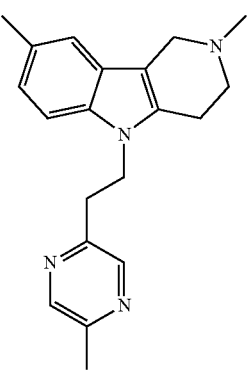 |
| 323 | 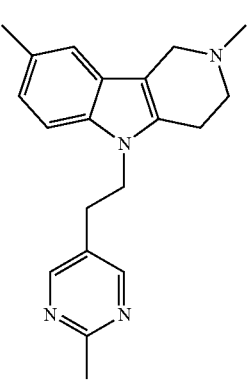 |
| 324 | 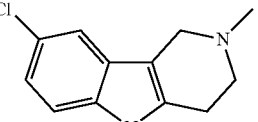 |
| 325 | 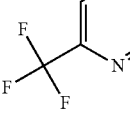 |
| 326 | 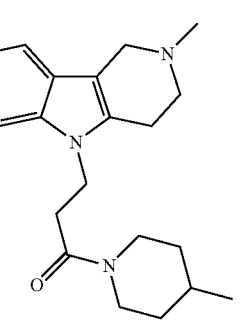 |
| 327 | 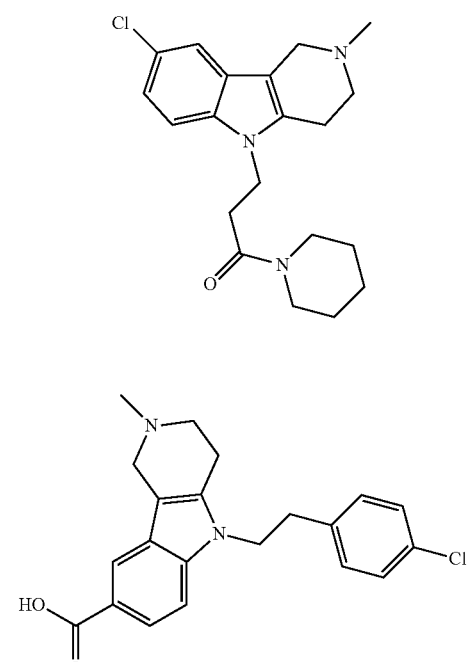 |

TABLE 2-continued

Representative Compounds According to the Invention.

| Compound No. | Structure |
|---|---|
| 328 | 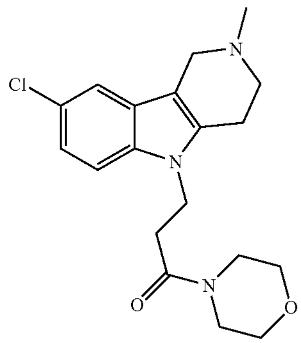 [SMILES: CN1CCc2c(c3cc(Cl)ccc3n2CCC(=O)N2CCOCC2)C1] |
| 329 | 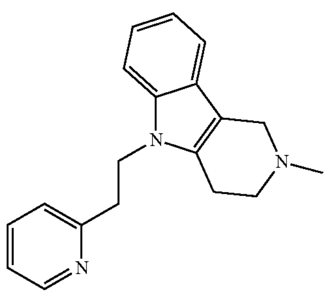 [SMILES: CN1CCc2c(c3ccccc3n2CCc2ccccn2)C1] |
| 330 | 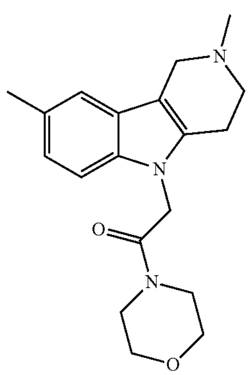 |
| 331 | 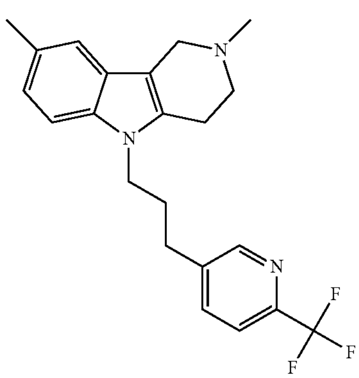 [SMILES: Cc1ccc2c(c1)c1c(n2CCCc2ccc(C(F)(F)F)nc2)CCN(C)C1] |
| 332 | 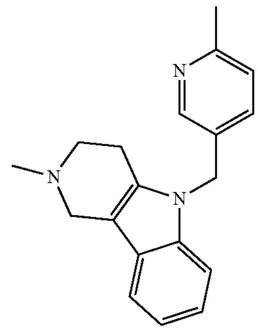 [SMILES: Cc1ccc(Cn2c3c(c4ccccc42)CN(C)CC3)cn1] |
| 333 | 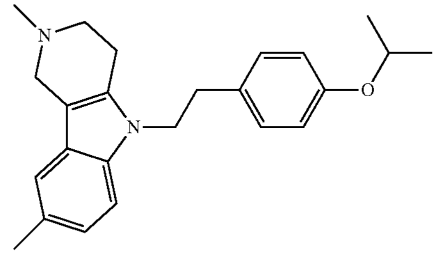 [SMILES: Cc1ccc2c(c1)c1c(n2CCc2ccc(OC(C)C)cc2)CCN(C)C1] |
| 334 | 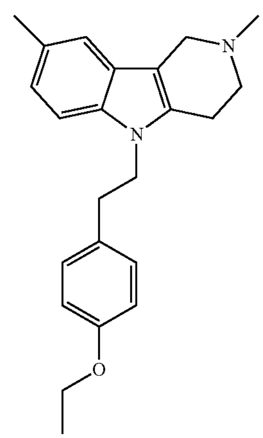 |
| 335 | 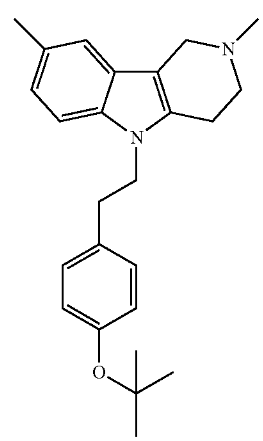 |

TABLE 2-continued

Representative Compounds According to the Invention.

| Compound No. | Structure |
|---|---|
| 336 | 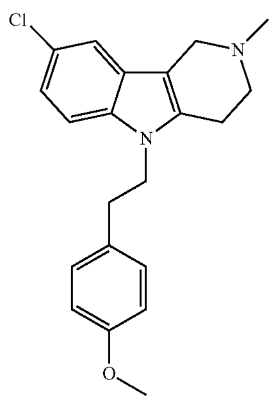 [SMILES: COc1ccc(CCn2c3c(c4cc(Cl)ccc42)CN(C)CC3)cc1] |
| 337 | 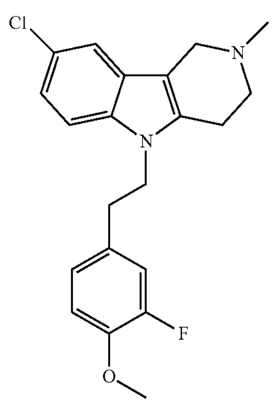 [SMILES: COc1ccc(CCn2c3c(c4cc(Cl)ccc42)CN(C)CC3)cc1F] |
| 338 | 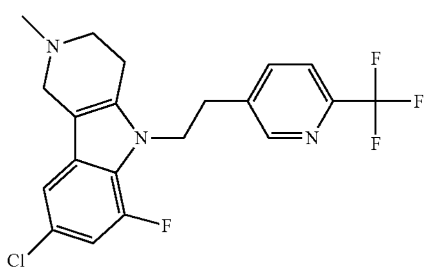 [SMILES: CN1CCc2c(c3cc(Cl)cc(F)c3n2CCc2ccc(C(F)(F)F)nc2)C1] |
| 339 | 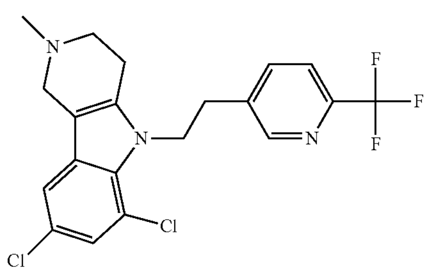 [SMILES: CN1CCc2c(c3cc(Cl)cc(Cl)c3n2CCc2ccc(C(F)(F)F)nc2)C1] |
| 340 | 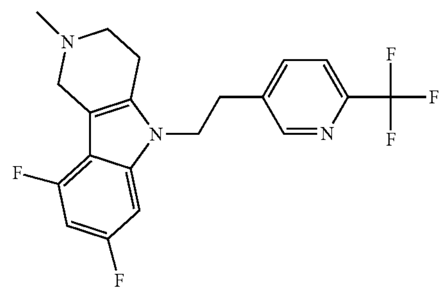 [SMILES: CN1CCc2c(c3c(F)cc(F)cc3n2CCc2ccc(C(F)(F)F)nc2)C1] |
| 341 | 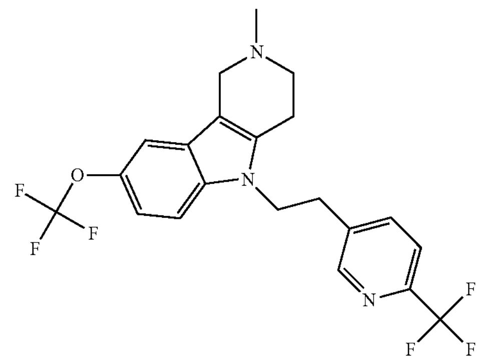 [SMILES: CN1CCc2c(c3cc(OC(F)(F)F)ccc3n2CCc2ccc(C(F)(F)F)nc2)C1] |
| 342 | 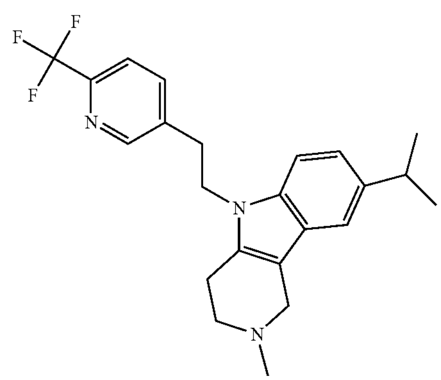 [SMILES: CC(C)c1ccc2c(c1)c1c(n2CCc2ccc(C(F)(F)F)nc2)CCN(C)C1] |
| 343 | 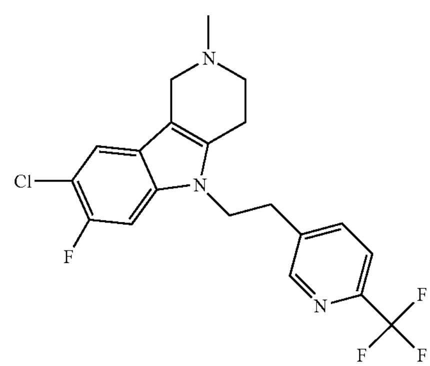 [SMILES: CN1CCc2c(c3cc(Cl)c(F)cc3n2CCc2ccc(C(F)(F)F)nc2)C1] |

TABLE 2-continued

Representative Compounds According to the Invention.

| Compound No. | Structure |
|---|---|
| 344 | 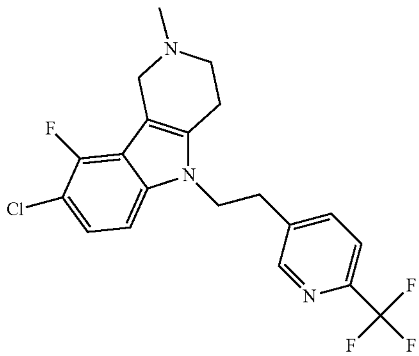 [SMILES: CN1CCc2c(c3c(F)c(Cl)ccc3n2CCc2ccc(C(F)(F)F)nc2)C1] |
| 345 | 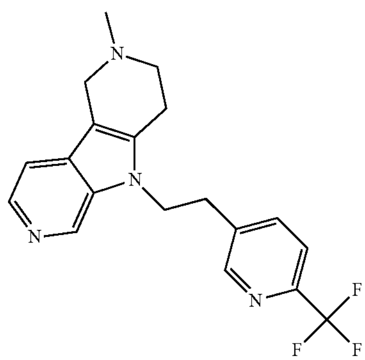 [SMILES: CN1CCc2c(c3ccncc3n2CCc2ccc(C(F)(F)F)nc2)C1] |
| 346 | 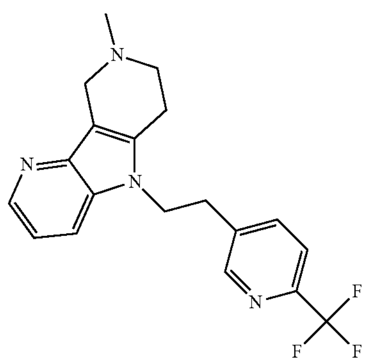 [SMILES: CN1CCc2c(c3ncccc3n2CCc2ccc(C(F)(F)F)nc2)C1] |
| 347 | 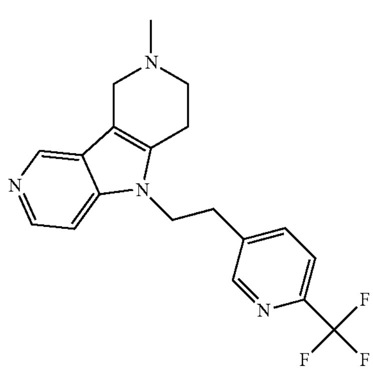 [SMILES: CN1CCc2c(c3cnccc3n2CCc2ccc(C(F)(F)F)nc2)C1] |
| 348 | |
| 349 | |
| 350 | |
| 351 | |

TABLE 2-continued

Representative Compounds According to the Invention.

| Compound No. | Structure |
|---|---|
| 352 | 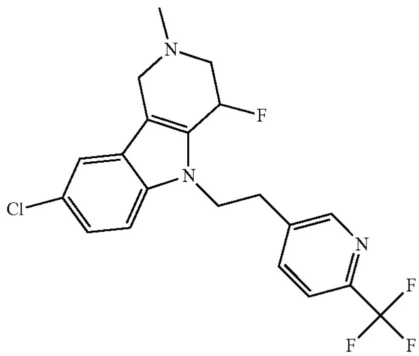 [SMILES: CN1Cc2c(n(CCc3ccc(C(F)(F)F)nc3)c3ccc(Cl)cc23)C(F)C1] |
| 353 | 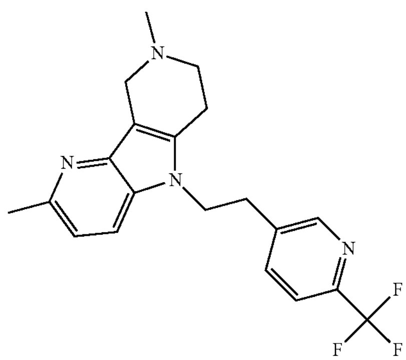 [SMILES: Cc1ccc2c(n1)c1c(n2CCc2ccc(C(F)(F)F)nc2)CCN(C)C1] |
| 354 | 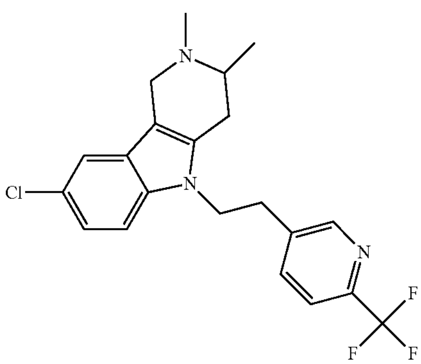 [SMILES: CC1Cc2c(c3cc(Cl)ccc3n2CCc2ccc(C(F)(F)F)nc2)CN1C] |
| 355 | 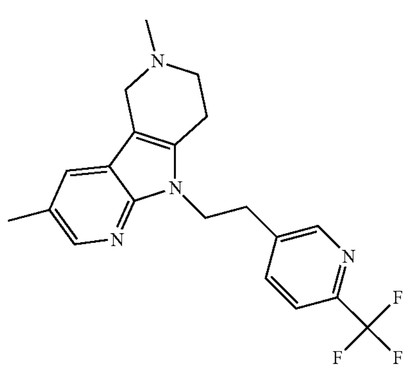 [SMILES: Cc1cnc2c(c1)c1c(n2CCc2ccc(C(F)(F)F)nc2)CCN(C)C1] |
| 356 | |
| 357 | |
| 358 | |
| 359 | |

TABLE 2-continued

Representative Compounds According to the Invention.

| Compound No. | Structure |
|---|---|
| 360 | 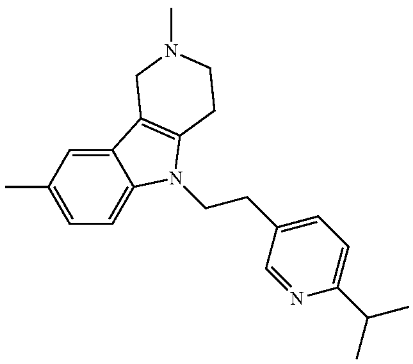 [SMILES: Cc1ccc2c(c1)c1c(n2CCc2ccc(C(C)C)nc2)CCN(C)C1] |
| 361 | 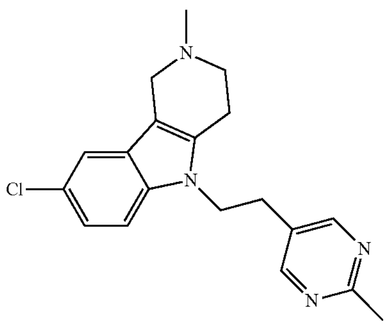 [SMILES: Cc1ncc(CCn2c3c(c4cc(Cl)ccc42)CN(C)CC3)cn1] |
| 362 | 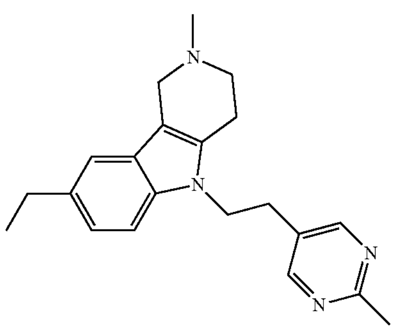 [SMILES: CCc1ccc2c(c1)c1c(n2CCc2cnc(C)nc2)CCN(C)C1] |
| 363 | 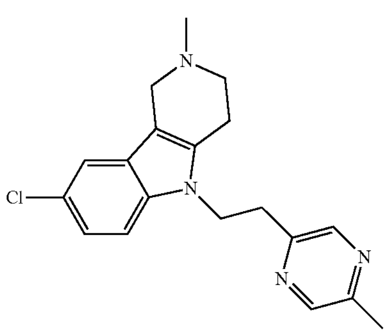 [SMILES: Cc1cnc(CCn2c3c(c4cc(Cl)ccc42)CN(C)CC3)cn1] |
| 364 | |
| 365 | |
| 366 | |
| 367 | |

TABLE 2-continued

Representative Compounds According to the Invention.

| Compound No. | Structure |
|---|---|
| 368 | 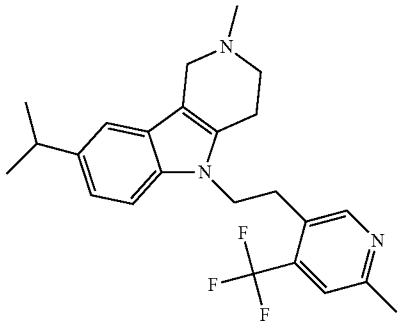 [SMILES: Cc1cc(C(F)(F)F)c(CCn2c3c(c4cc(C(C)C)ccc42)CN(C)CC3)cn1] |
| 369 | 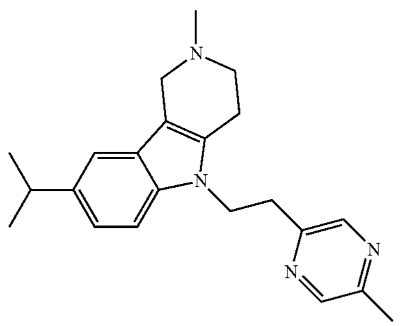 [SMILES: Cc1cnc(CCn2c3c(c4cc(C(C)C)ccc42)CN(C)CC3)cn1] |
| 370 | 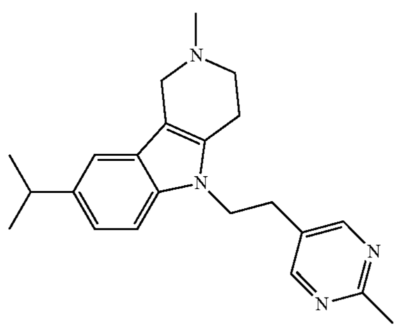 [SMILES: Cc1ncc(CCn2c3c(c4cc(C(C)C)ccc42)CN(C)CC3)cn1] |
| 371 | 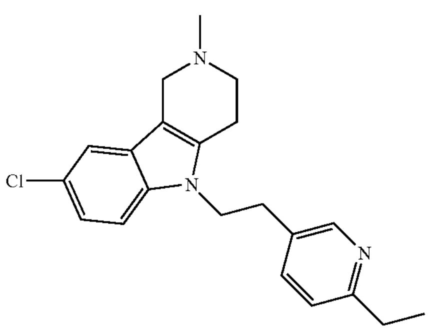 [SMILES: CCc1ccc(CCn2c3c(c4cc(Cl)ccc42)CN(C)CC3)cn1] |
| 372 | |
| 373 | |
| 374 | |
| 375 | |

TABLE 2-continued
Representative Compounds According to the Invention.
| Compound No. | Structure |
|---|---|
| 376 | 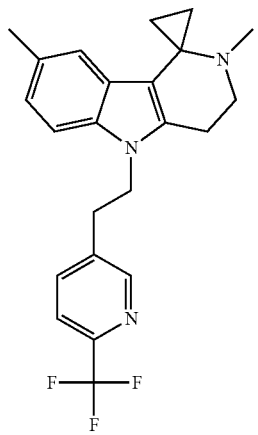 |
| 377 | 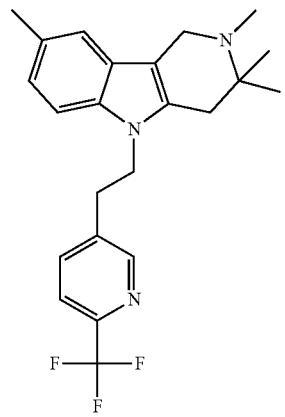 |
| 378 | 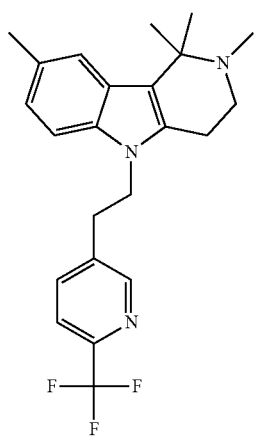 |
| 379 | 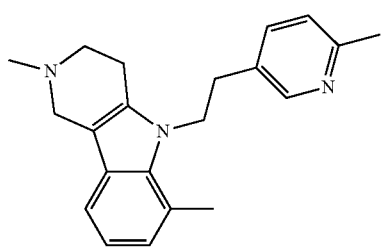 |
| 380 | 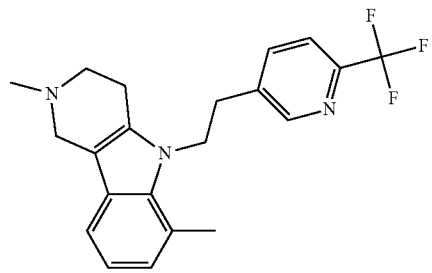 [SMILES: Cc1cccc2c3c(n(CCc4ccc(C(F)(F)F)nc4)c12)CCN(C)C3] |
| 381 | 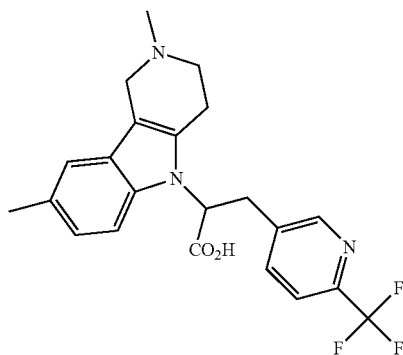 [SMILES: Cc1ccc2c(c1)c1c(n2C(Cc2ccc(C(F)(F)F)nc2)C(=O)O)CCN(C)C1] |
| 382 | 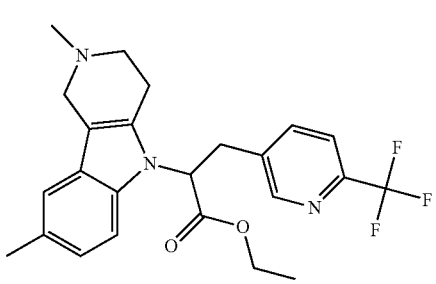 [SMILES: CCOC(=O)C(Cc1ccc(C(F)(F)F)nc1)n1c2c(c3cc(C)ccc31)CN(C)CC2] |
| 383 | 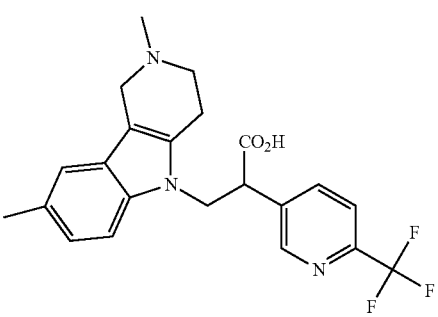 [SMILES: Cc1ccc2c(c1)c1c(n2CC(C(=O)O)c2ccc(C(F)(F)F)nc2)CCN(C)C1] |

TABLE 2-continued

Representative Compounds According to the Invention.

| Compound No. | Structure |
| --- | --- |
| 384 | 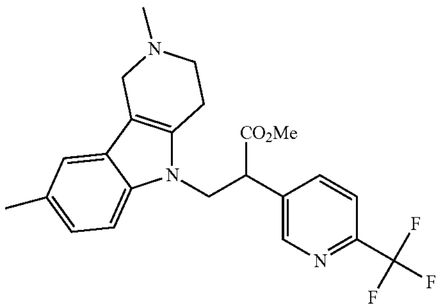 [SMILES: COC(=O)C(Cn1c2c(c3cc(C)ccc31)CN(C)CC2)c1ccc(C(F)(F)F)nc1] |
| 385 | 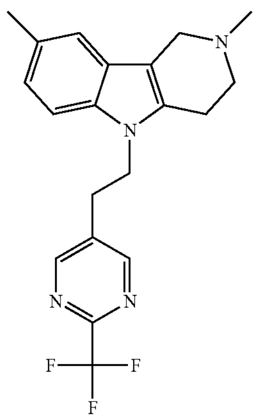 |
| 386 | 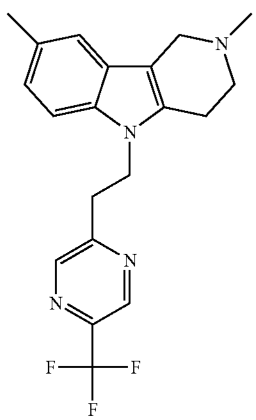 |
| 387 | 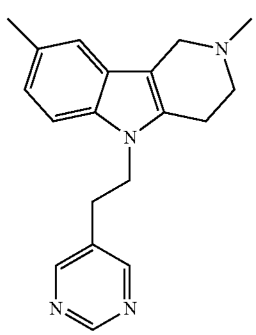 |
| 388 | |
| 389 | |
| 390 | |

TABLE 2-continued
Representative Compounds According to the Invention.
| Compound No. | Structure |
|---|---|
| 391 | 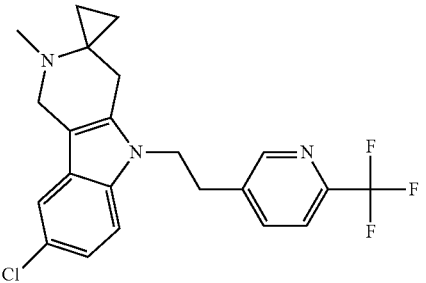 [SMILES: CN1Cc2c(n(CCc3ccc(C(F)(F)F)nc3)c3ccc(Cl)cc23)CC12CC2] |
| 392 | 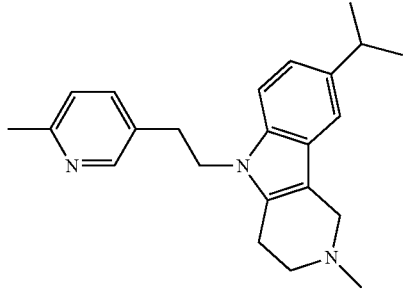 [SMILES: Cc1ccc(CCn2c3c(c4cc(C(C)C)ccc42)CN(C)CC3)cn1] |
| 393 | 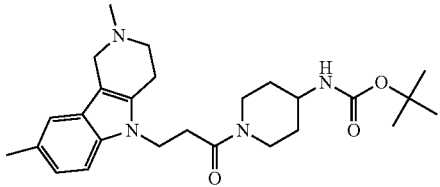 [SMILES: Cc1ccc2c(c1)c1c(n2CCC(=O)N2CCC(NC(=O)OC(C)(C)C)CC2)CCN(C)C1] |
| 394H | 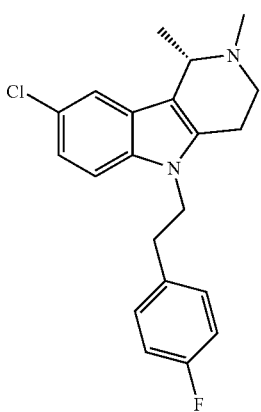 [SMILES: C[C@H]1c2c(n(CCc3ccc(F)cc3)c3ccc(Cl)cc23)CCN1C] |
TABLE 2-continued
Representative Compounds According to the Invention.
| Compound No. | Structure |
|---|---|
| 395 | 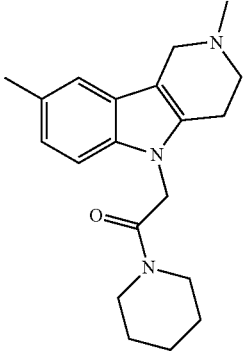 [SMILES: Cc1ccc2c(c1)c1c(n2CC(=O)N2CCCCC2)CCN(C)C1] |
| 396 | 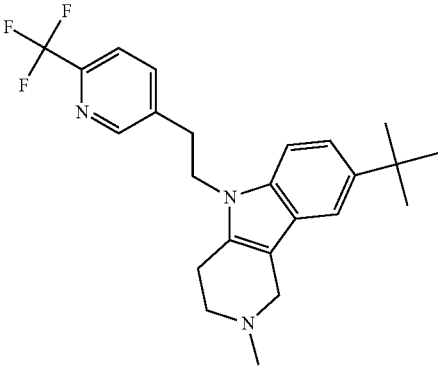 [SMILES: CN1CCc2c(c3cc(C(C)(C)C)ccc3n2CCc2ccc(C(F)(F)F)nc2)C1] |
| 397 | 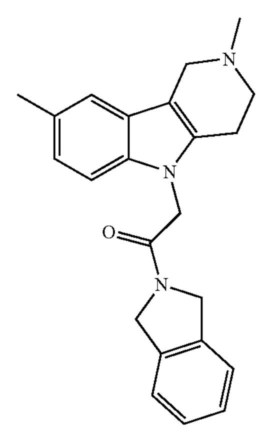 [SMILES: Cc1ccc2c(c1)c1c(n2CC(=O)N2Cc3ccccc3C2)CCN(C)C1] |

TABLE 2-continued

Representative Compounds According to the Invention.

| Compound No. | Structure |
|---|---|
| 398 | 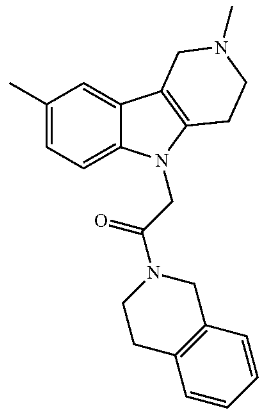 [SMILES: Cc1ccc2c(c1)c1c(n2CC(=O)N2CCc3ccccc3C2)CCN(C)C1] |
| 399 | 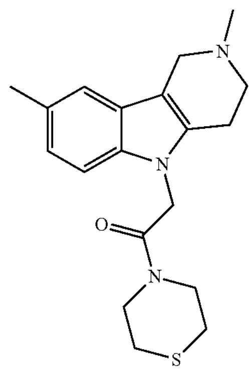 [SMILES: Cc1ccc2c(c1)c1c(n2CC(=O)N2CCSCC2)CCN(C)C1] |
| 400 | 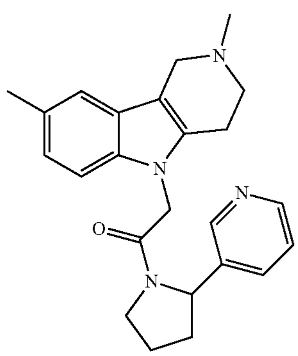 [SMILES: Cc1ccc2c(c1)c1c(n2CC(=O)N2CCCC2c2cccnc2)CCN(C)C1] |
| 401 | 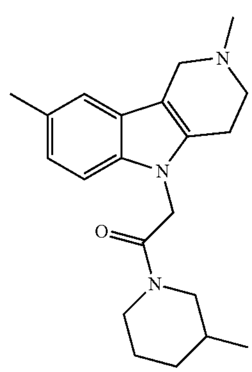 |
| 402 | |
| 403 | |
| 404 | |

TABLE 2-continued
Representative Compounds According to the Invention.
| Compound No. | Structure |
|---|---|
| 405 | 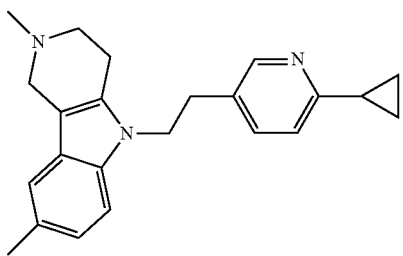 [SMILES: Cc1ccc2c(c1)c1c(n2CCc2ccc(C3CC3)nc2)CCN(C)C1] |
| 406 | 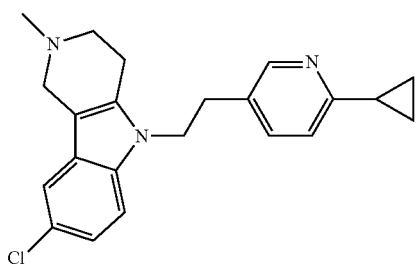 [SMILES: CN1CCc2c(c3cc(Cl)ccc3n2CCc2ccc(C3CC3)nc2)C1] |
| 407 | 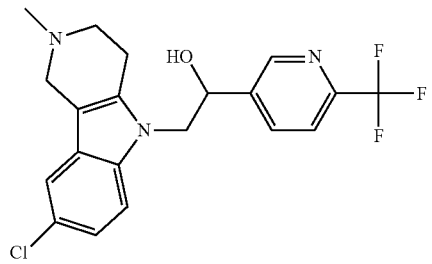 [SMILES: CN1CCc2c(c3cc(Cl)ccc3n2CC(O)c2ccc(C(F)(F)F)nc2)C1] |
| 408 | 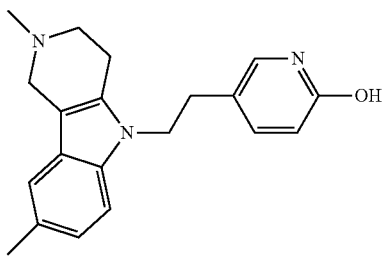 [SMILES: Cc1ccc2c(c1)c1c(n2CCc2ccc(O)nc2)CCN(C)C1] |
| 409 | 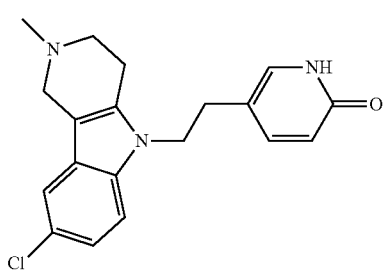 [SMILES: CN1CCc2c(c3cc(Cl)ccc3n2CCc2ccc(=O)[nH]c2)C1] |
TABLE 2-continued
Representative Compounds According to the Invention.
| Compound No. | Structure |
|---|---|
| 410 | 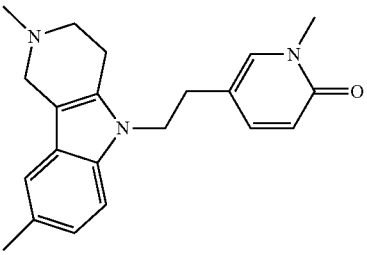 [SMILES: Cc1ccc2c(c1)c1c(n2CCc2ccc(=O)n(C)c2)CCN(C)C1] |
| 411 | 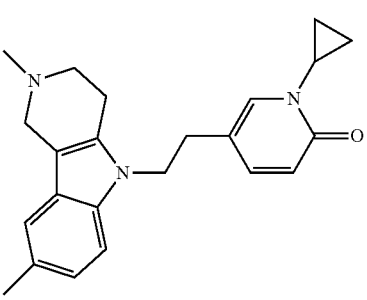 [SMILES: Cc1ccc2c(c1)c1c(n2CCc2ccc(=O)n(C3CC3)c2)CCN(C)C1] |
| 412 | 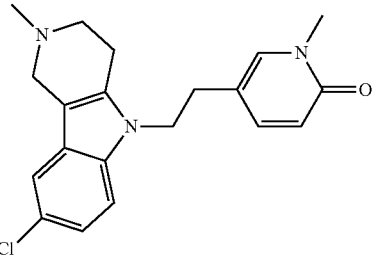 |
| 413 | 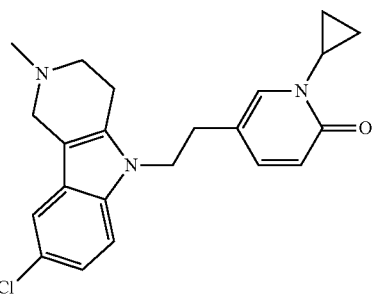 |
| 414 | 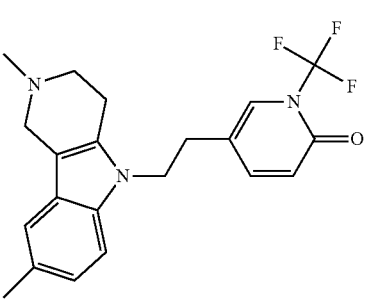 [SMILES: Cc1ccc2c(c1)c1c(n2CCc2ccc(=O)n(C(F)(F)F)c2)CCN(C)C1] |

TABLE 2-continued

Representative Compounds According to the Invention.

| Compound No. | Structure |
|---|---|
| 415 | 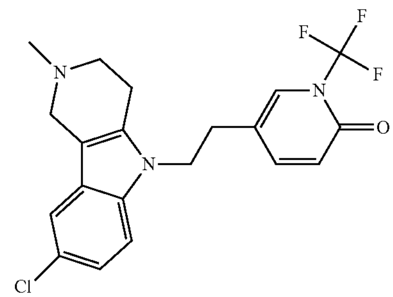 [SMILES: CN1CCc2c(c3cc(Cl)ccc3n2CCc2ccc(=O)n(C(F)(F)F)c2)C1] |
| 416 | 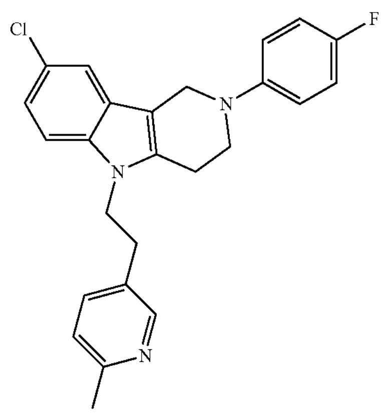 [SMILES: Cc1ccc(CCn2c3c(c4cc(Cl)ccc42)CN(c2ccc(F)cc2)CC3)cn1] |
| 417 | 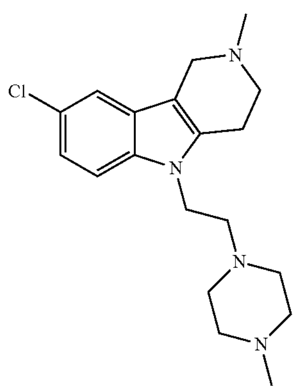 [SMILES: CN1CCN(CCn2c3c(c4cc(Cl)ccc42)CN(C)CC3)CC1] |
| 418 | 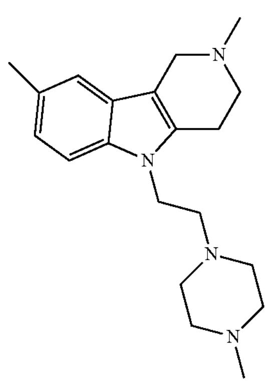 [SMILES: Cc1ccc2c(c1)c1c(n2CCN2CCN(C)CC2)CCN(C)C1] |
| 419 | 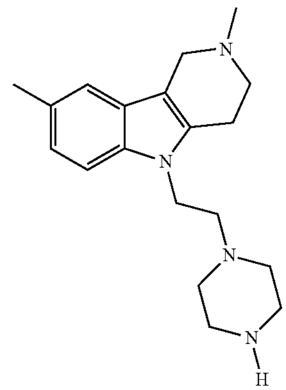 [SMILES: Cc1ccc2c(c1)c1c(n2CCN2CCNCC2)CCN(C)C1] |
| 420 | 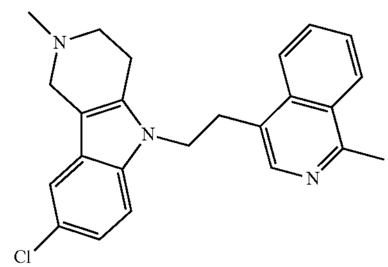 |
| 421 | 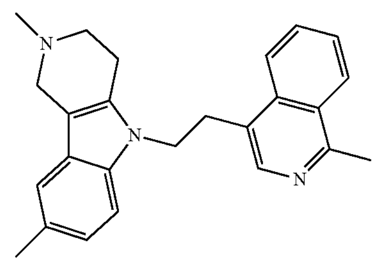 |
| 422 | 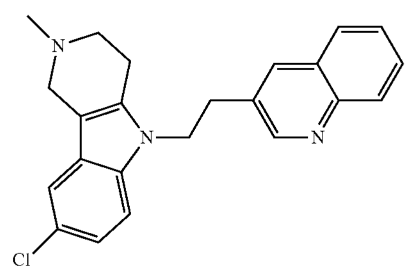 [SMILES: CN1CCc2c(c3cc(Cl)ccc3n2CCc2cnc3ccccc3c2)C1] |
| 423 | 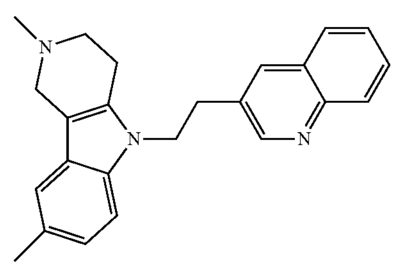 [SMILES: Cc1ccc2c(c1)c1c(n2CCc2cnc3ccccc3c2)CCN(C)C1] |

TABLE 2-continued
Representative Compounds According to the Invention.
| Compound No. | Structure |
|---|---|
| 424 | 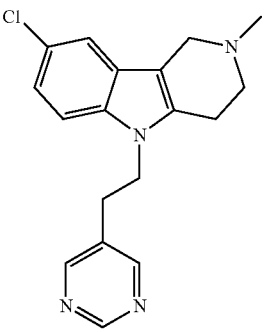 [SMILES: CN1CCc2c(c3cc(Cl)ccc3n2CCc2cncnc2)C1] |
| 425 | 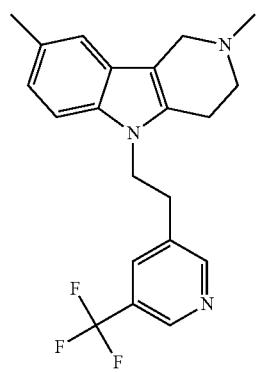 |
| 426 | 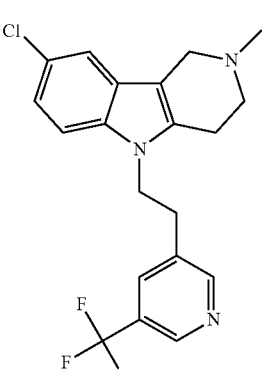 |
| 427 | 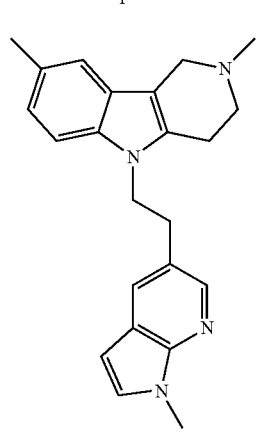 |
| 428 | 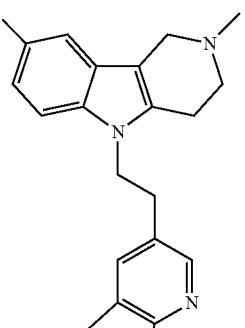 |
| 429 | 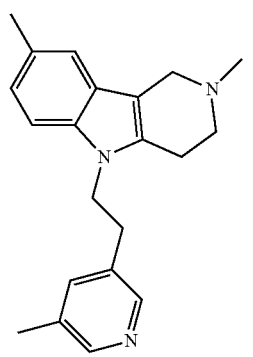 [SMILES: Cc1cncc(CCn2c3c(c4cc(C)ccc42)CN(C)CC3)c1] |
| 430 | 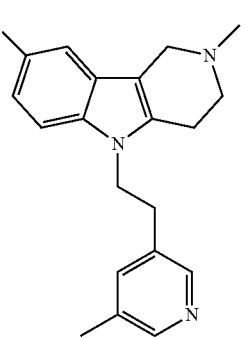 |
| 431 | 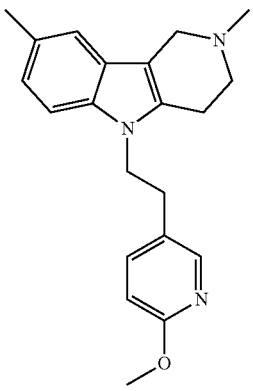 |

TABLE 2-continued

Representative Compounds According to the Invention.

| Compound No. | Structure |
|---|---|
| 432 | 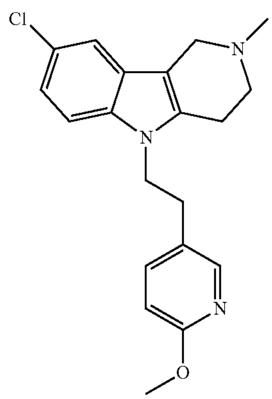 [SMILES: COc1ccc(CCn2c3c(c4cc(Cl)ccc42)CN(C)CC3)cn1] |
| 433 | 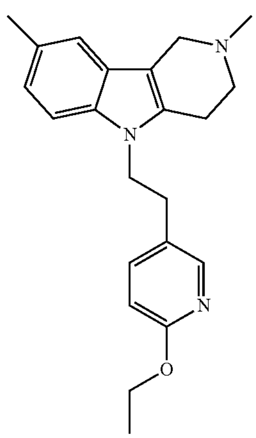 |
| 434 | 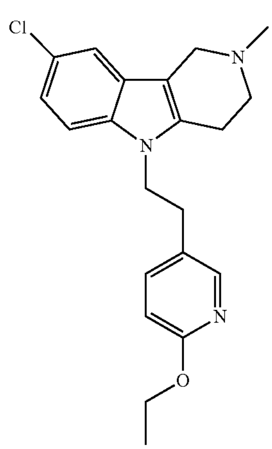 [SMILES: CCOc1ccc(CCn2c3c(c4cc(Cl)ccc42)CN(C)CC3)cn1] |
| 435 | |
| 436 | |
| 437 | |

TABLE 2-continued
Representative Compounds According to the Invention.
| Compound No. | Structure |
|---|---|
| 438 | 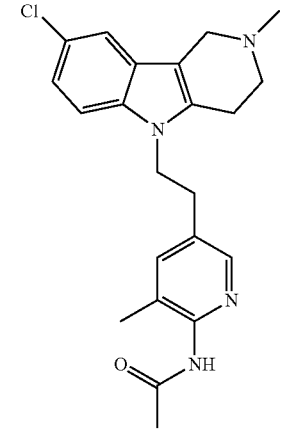 [SMILES: CC(=O)Nc1ncc(CCn2c3c(c4cc(Cl)ccc42)CN(C)CC3)cc1C] |
| 439 | 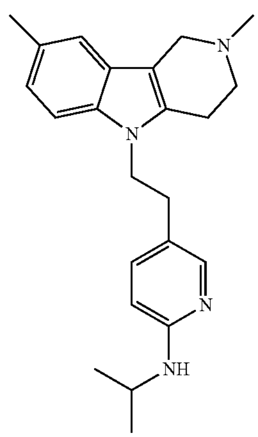 |
| 440 | 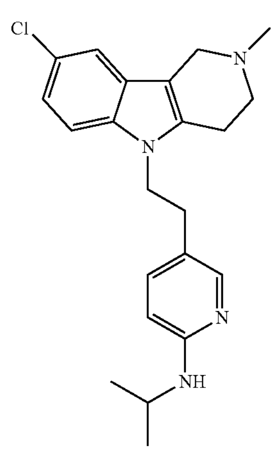 [SMILES: CC(C)Nc1ccc(CCn2c3c(c4cc(Cl)ccc42)CN(C)CC3)cn1] |
TABLE 2-continued
Representative Compounds According to the Invention.
| Compound No. | Structure |
|---|---|
| 441 | 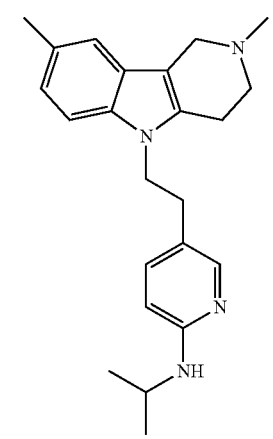 |
| 442 | 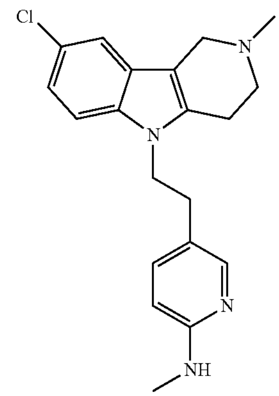 [SMILES: CNc1ccc(CCn2c3c(c4cc(Cl)ccc42)CN(C)CC3)cn1] |
| 443 | 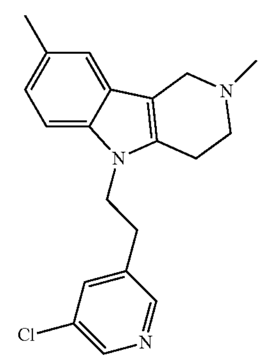 [SMILES: Cc1ccc2c(c1)c1c(n2CCc2cncc(Cl)c2)CCN(C)C1] |
| 444 | 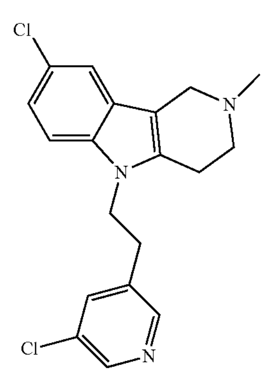 [SMILES: CN1CCc2c(c3cc(Cl)ccc3n2CCc2cncc(Cl)c2)C1] |

TABLE 2-continued
Representative Compounds According to the Invention.
| Compound No. | Structure |
|---|---|
| 445 | 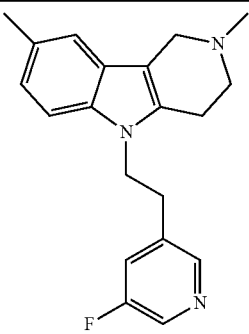 |
| 446 | 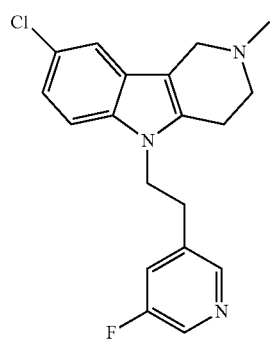 [SMILES: CN1CCc2c(c3cc(Cl)ccc3n2CCc2cncc(F)c2)C1] |
| 447 | 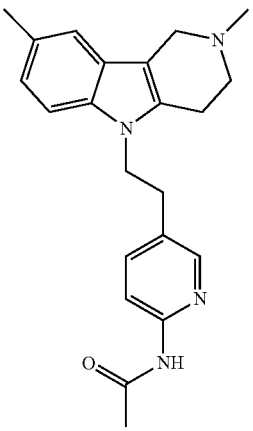 |
| 448 | 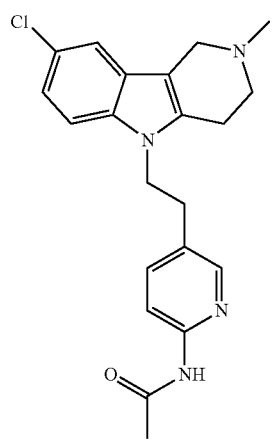 [SMILES: CC(=O)Nc1ccc(CCn2c3c(c4cc(Cl)ccc42)CN(C)CC3)cn1] |
| 449 | 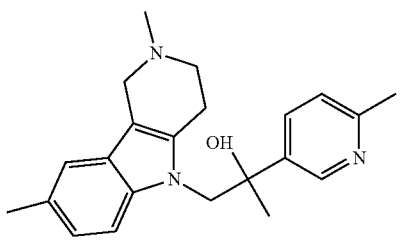 |
| 450 | 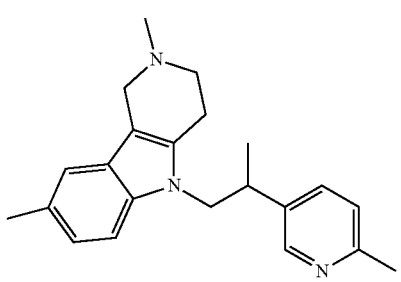 |
| 451 | 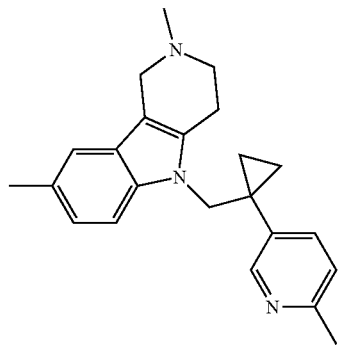 |
| 452 | 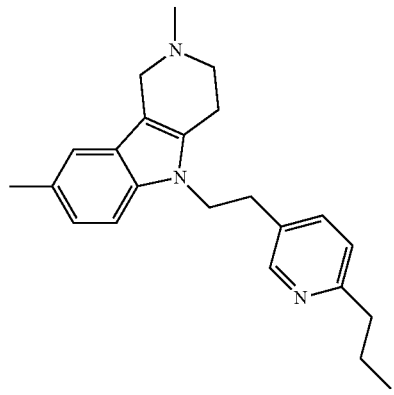 [SMILES: CCCc1ccc(CCn2c3c(c4cc(C)ccc42)CN(C)CC3)cn1] |

TABLE 2-continued
Representative Compounds According to the Invention.
| Compound No. | Structure |
|---|---|
| 453 | 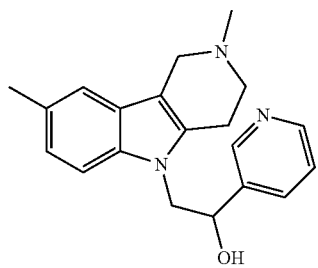 [SMILES: Cc1ccc2c(c1)c1c(n2CC(O)c2cccnc2)CCN(C)C1] |
| 454 | 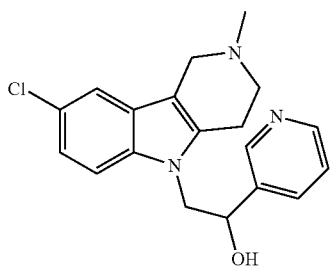 [SMILES: CN1CCc2c(c3cc(Cl)ccc3n2CC(O)c2cccnc2)C1] |
| 455 | 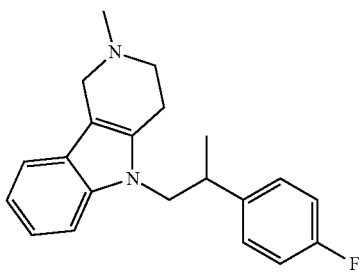 [SMILES: CC(Cn1c2c(c3ccccc31)CN(C)CC2)c1ccc(F)cc1] |
| 456 | 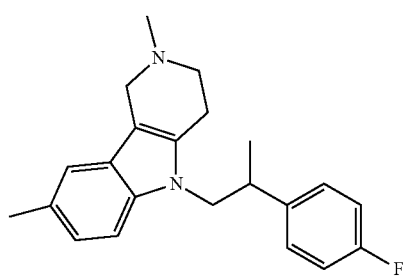 [SMILES: Cc1ccc2c(c1)c1c(n2CC(C)c2ccc(F)cc2)CCN(C)C1] |
| 457 | 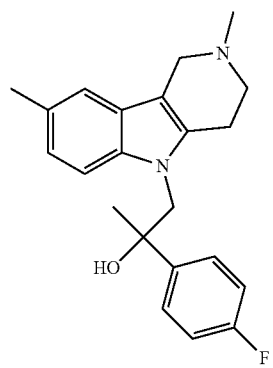 [SMILES: Cc1ccc2c(c1)c1c(n2CC(C)(O)c2ccc(F)cc2)CCN(C)C1] |
| 458 | 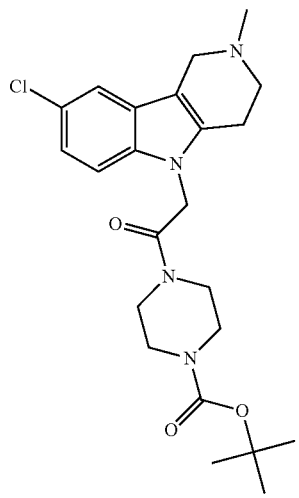 [SMILES: CN1CCc2c(c3cc(Cl)ccc3n2CC(=O)N2CCN(C(=O)OC(C)(C)C)CC2)C1] |
| 459 | 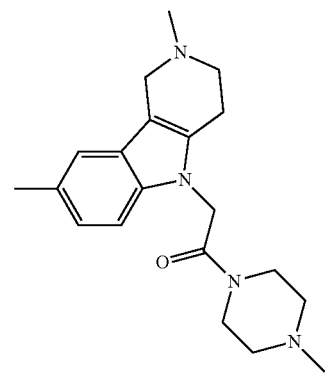 |
| 460 | 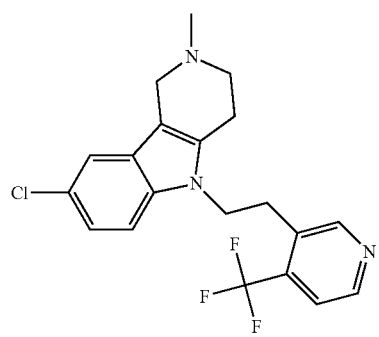 [SMILES: CN1CCc2c(c3cc(Cl)ccc3n2CCc2cnccc2C(F)(F)F)C1] |
| 461 | 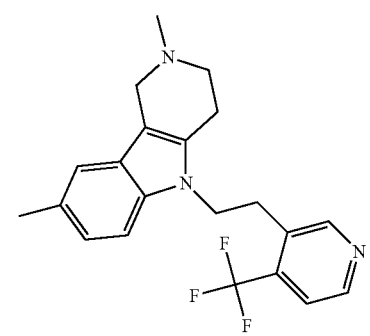 [SMILES: Cc1ccc2c(c1)c1c(n2CCc2cnccc2C(F)(F)F)CCN(C)C1] |

TABLE 2-continued
Representative Compounds According to the Invention.
| Compound No. | Structure |
|---|---|
| 462 | 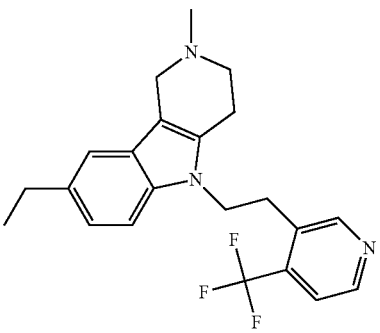 [SMILES: CCc1ccc2c(c1)c1c(n2CCc2cnccc2C(F)(F)F)CCN(C)C1] |
| 463 | 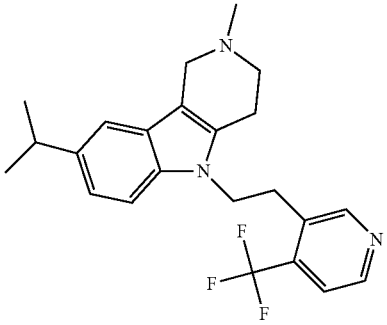 [SMILES: CC(C)c1ccc2c(c1)c1c(n2CCc2cnccc2C(F)(F)F)CCN(C)C1] |
| 464 | 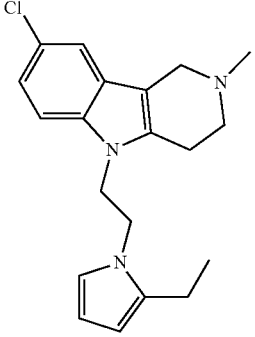 [SMILES: CCc1cccn1CCn1c2c(c3cc(Cl)ccc31)CN(C)CC2] |
| 465 | 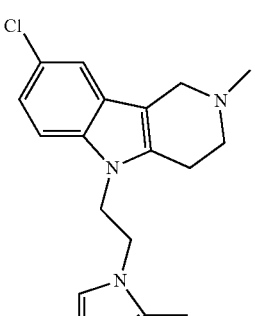 |
| 466 | 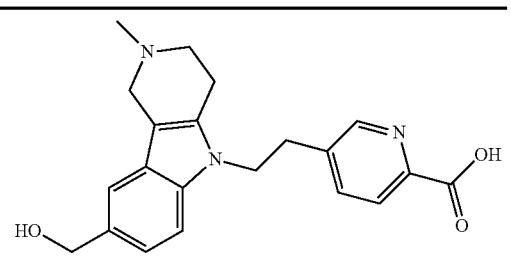 |
| 467 | 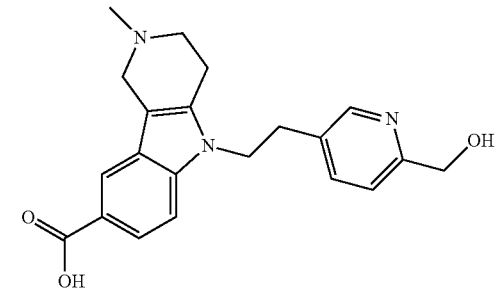 [SMILES: CN1CCc2c(c3cc(C(=O)O)ccc3n2CCc2ccc(CO)nc2)C1] |
| 468 | 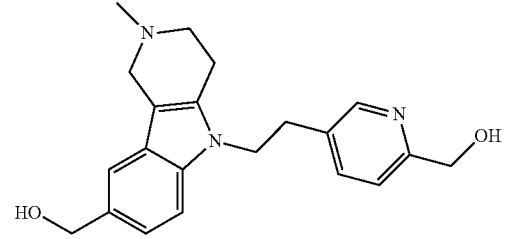 [SMILES: CN1CCc2c(c3cc(CO)ccc3n2CCc2ccc(CO)nc2)C1] |
| 469 | 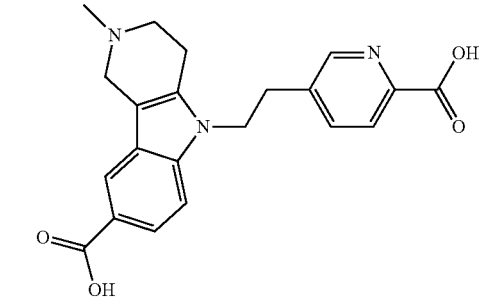 [SMILES: CN1CCc2c(c3cc(C(=O)O)ccc3n2CCc2ccc(C(=O)O)nc2)C1] |
| 470 | 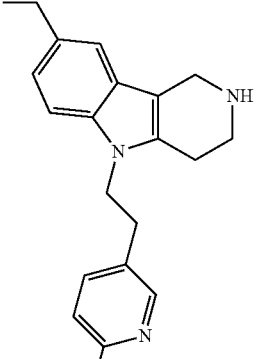 |

TABLE 2-continued
Representative Compounds According to the Invention.
| Compound No. | Structure |
|---|---|
| 471 | 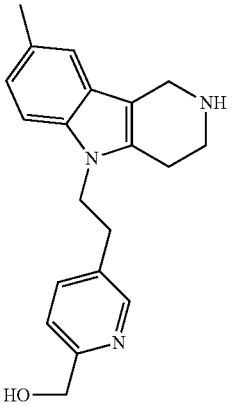 [SMILES: Cc1ccc2c(c1)c1c(n2CCc2ccc(CO)nc2)CCNC1] |
| 472 | 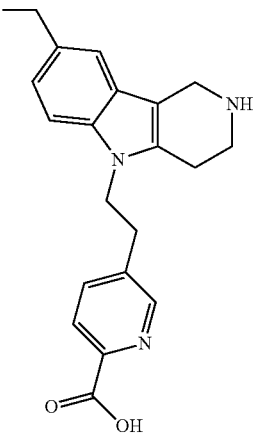 |
| 473 | 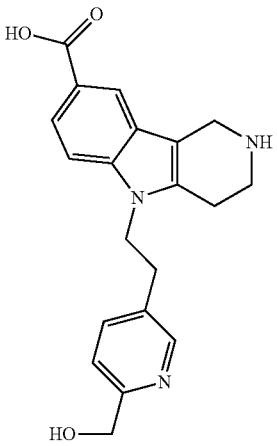 [SMILES: O=C(O)c1ccc2c(c1)c1c(n2CCc2ccc(CO)nc2)CCNC1] |
| 474 | 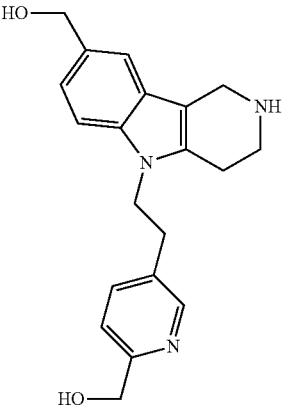 [SMILES: OCc1ccc2c(c1)c1c(n2CCc2ccc(CO)nc2)CCNC1] |
| 475 | 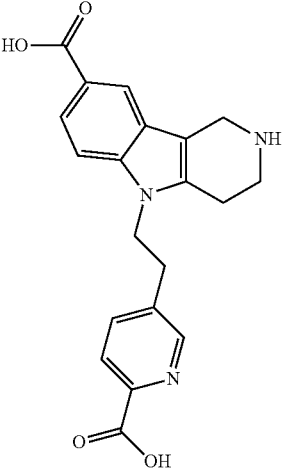 [SMILES: O=C(O)c1ccc2c(c1)c1c(n2CCc2ccc(C(=O)O)nc2)CCNC1] |
| 476 | 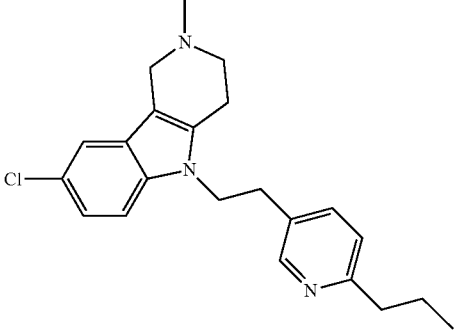 [SMILES: CCCc1ccc(CCn2c3c(c4cc(Cl)ccc42)CN(C)CC3)cn1] |

TABLE 2-continued
Representative Compounds According to the Invention.
| Compound No. | Structure |
|---|---|
| 477 | 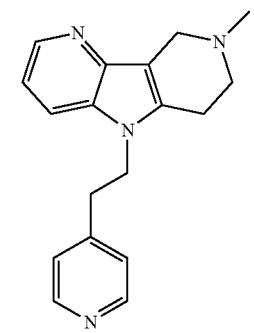 |
| 478 | 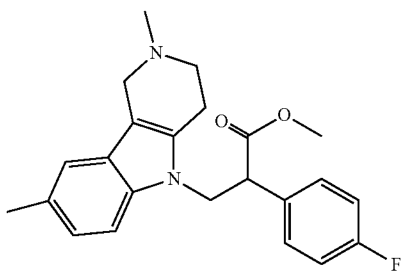 [SMILES: COC(=O)C(Cn1c2c(c3cc(C)ccc31)CN(C)CC2)c1ccc(F)cc1] |
| 479 | 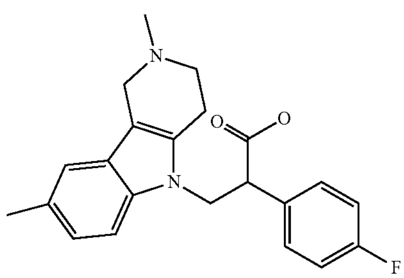 [SMILES: Cc1ccc2c(c1)c1c(n2CC(C(=O)O)c2ccc(F)cc2)CCN(C)C1] |
| 480 | 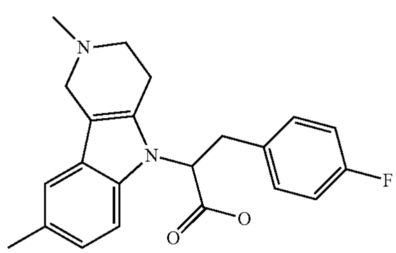 [SMILES: Cc1ccc2c(c1)c1c(n2C(Cc2ccc(F)cc2)C(=O)O)CCN(C)C1] |
| 481 | 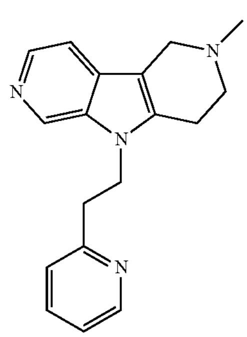 [SMILES: CN1CCc2c(c3ccncc3n2CCc2ccccn2)C1] |
| 482 | 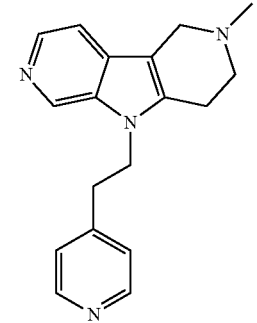 [SMILES: CN1CCc2c(c3ccncc3n2CCc2ccncc2)C1] |
| 483 | |
| 484 | |
| 485 | |

TABLE 2-continued
Representative Compounds According to the Invention.
| Compound No. | Structure |
|---|---|
| 486 | 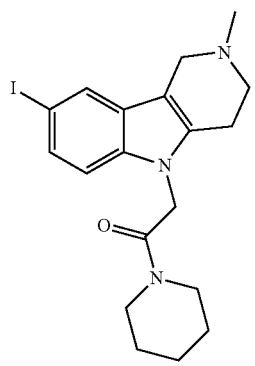 [SMILES: CN1CCc2c(c3cc(I)ccc3n2CC(=O)N2CCCCC2)C1] |
| 487 | 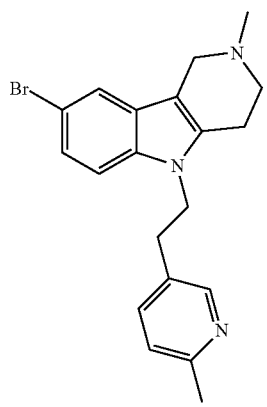 |
| 488 | 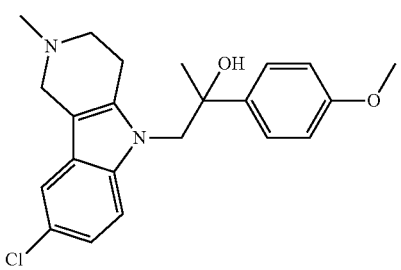 [SMILES: COc1ccc(C(C)(O)Cn2c3c(c4cc(Cl)ccc42)CN(C)CC3)cc1] |
| 489 | 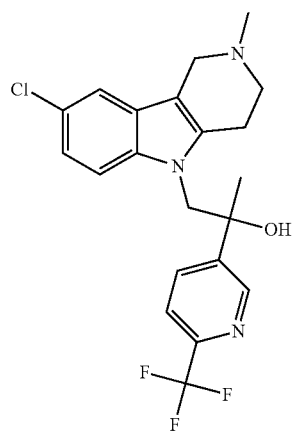 [SMILES: CN1CCc2c(c3cc(Cl)ccc3n2CC(C)(O)c2ccc(C(F)(F)F)nc2)C1] |
| 490 | 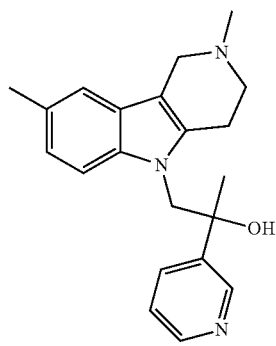 [SMILES: Cc1ccc2c(c1)c1c(n2CC(C)(O)c2cccnc2)CCN(C)C1] |
| 491 | 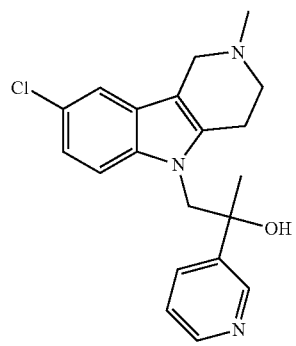 [SMILES: CN1CCc2c(c3cc(Cl)ccc3n2CC(C)(O)c2cccnc2)C1] |
| 492 | 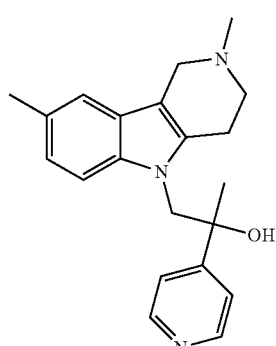 |
| 493 | 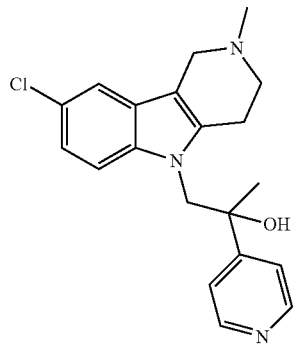 [SMILES: CN1CCc2c(c3cc(Cl)ccc3n2CC(C)(O)c2ccncc2)C1] |

TABLE 2-continued
Representative Compounds According to the Invention.
| Compound No. | Structure |
|---|---|
| 494 | 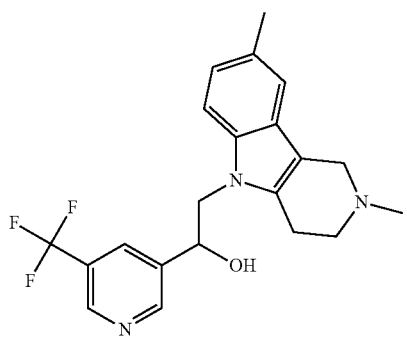 [SMILES: Cc1ccc2c(c1)c1c(n2CC(O)c2cncc(C(F)(F)F)c2)CCN(C)C1] |
| 495 | 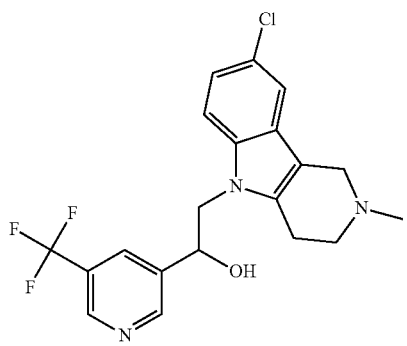 [SMILES: CN1CCc2c(c3cc(Cl)ccc3n2CC(O)c2cncc(C(F)(F)F)c2)C1] |
| 496 | 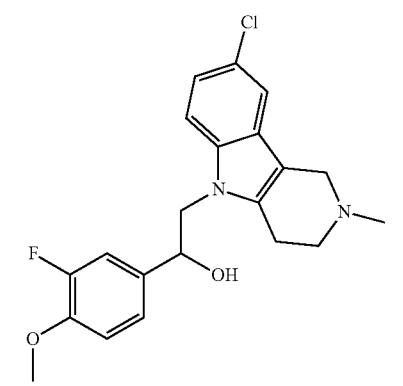 [SMILES: COc1ccc(C(O)Cn2c3c(c4cc(Cl)ccc42)CN(C)CC3)cc1F] |
| 497 | 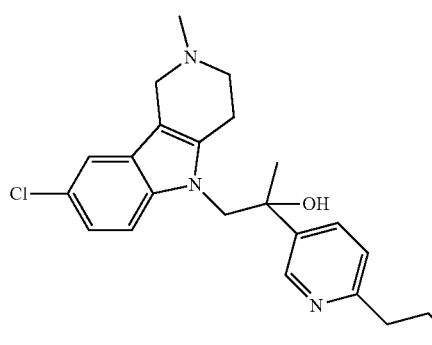 |
| 498 | 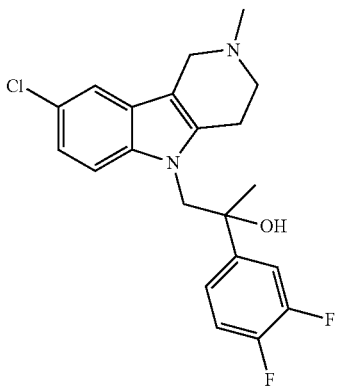 [SMILES: CN1CCc2c(c3cc(Cl)ccc3n2CC(C)(O)c2ccc(F)c(F)c2)C1] |
| 499 | 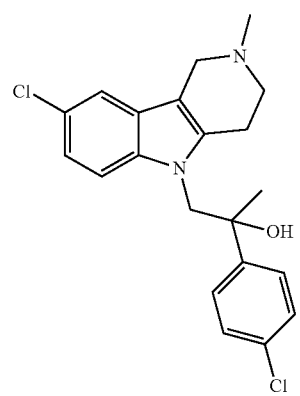 [SMILES: CN1CCc2c(c3cc(Cl)ccc3n2CC(C)(O)c2ccc(Cl)cc2)C1] |
| 500 | 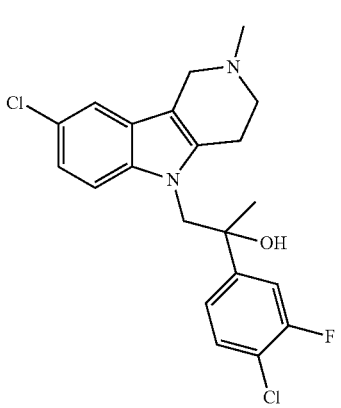 [SMILES: CN1CCc2c(c3cc(Cl)ccc3n2CC(C)(O)c2ccc(Cl)c(F)c2)C1] |

TABLE 2-continued
Representative Compounds According to the Invention.
| Compound No. | Structure |
|---|---|
| 501 | 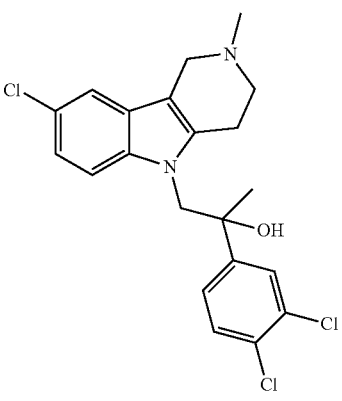 [SMILES: CN1CCc2c(c3cc(Cl)ccc3n2CC(C)(O)c2ccc(Cl)c(Cl)c2)C1] |
| 502 | 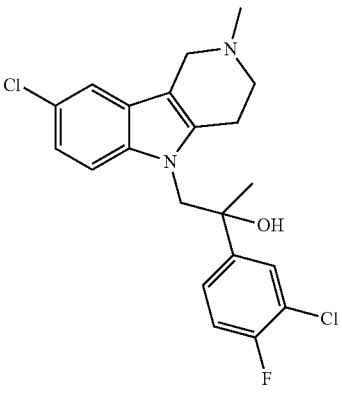 [SMILES: CN1CCc2c(c3cc(Cl)ccc3n2CC(C)(O)c2ccc(F)c(Cl)c2)C1] |
| 503 | 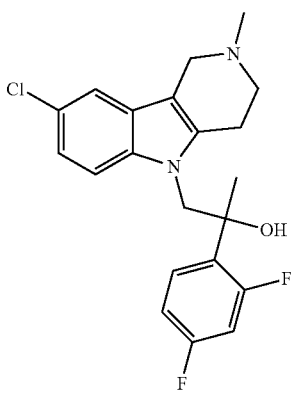 [SMILES: CN1CCc2c(c3cc(Cl)ccc3n2CC(C)(O)c2ccc(F)cc2F)C1] |
| 504 | 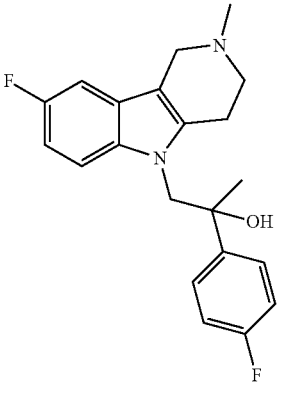 [SMILES: CN1CCc2c(c3cc(F)ccc3n2CC(C)(O)c2ccc(F)cc2)C1] |
| 505 | 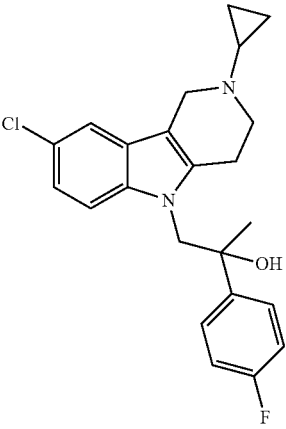 [SMILES: CC(O)(Cn1c2c(c3cc(Cl)ccc31)CN(C1CC1)CC2)c1ccc(F)cc1] |
| 506 | 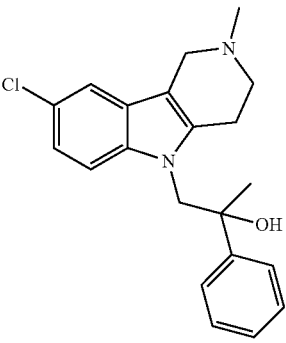 [SMILES: CN1CCc2c(c3cc(Cl)ccc3n2CC(C)(O)c2ccccc2)C1] |
| 507 | 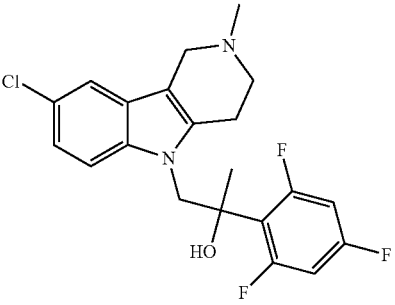 [SMILES: CN1CCc2c(c3cc(Cl)ccc3n2CC(C)(O)c2c(F)cc(F)cc2F)C1] |

TABLE 2-continued
Representative Compounds According to the Invention.
| Compound No. | Structure |
|---|---|
| 508 | 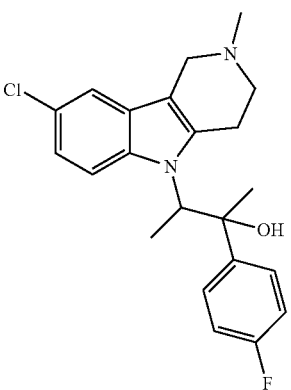 [SMILES: CC(n1c2c(c3cc(Cl)ccc31)CN(C)CC2)C(C)(O)c1ccc(F)cc1] |
| 509 | 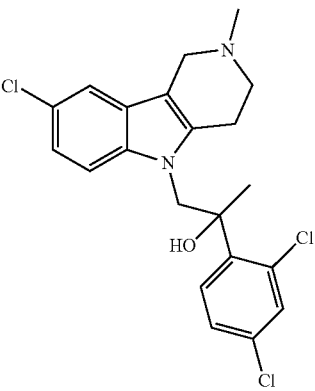 [SMILES: CN1CCc2c(c3cc(Cl)ccc3n2CC(C)(O)c2ccc(Cl)cc2Cl)C1] |
| 510 | 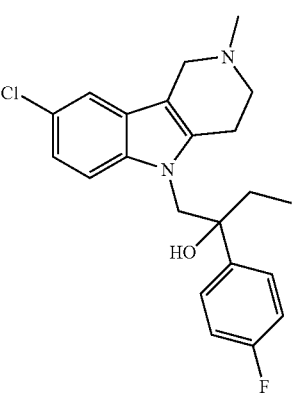 [SMILES: CCC(O)(Cn1c2c(c3cc(Cl)ccc31)CN(C)CC2)c1ccc(F)cc1] |
| 511 | 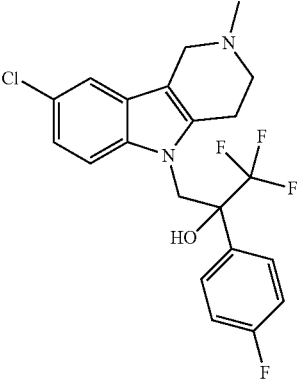 [SMILES: CN1CCc2c(c3cc(Cl)ccc3n2CC(O)(c2ccc(F)cc2)C(F)(F)F)C1] |
| 512 | 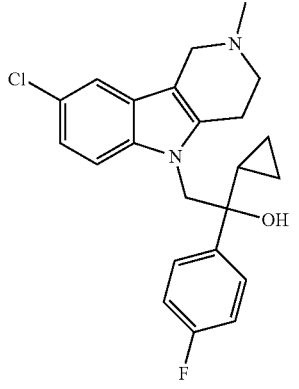 [SMILES: CN1CCc2c(c3cc(Cl)ccc3n2CC(O)(c2ccc(F)cc2)C2CC2)C1] |
| 513 | 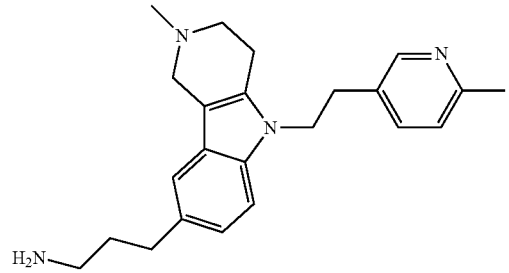 [SMILES: Cc1ccc(CCn2c3c(c4cc(CCCN)ccc42)CN(C)CC3)cn1] |
| 514 | 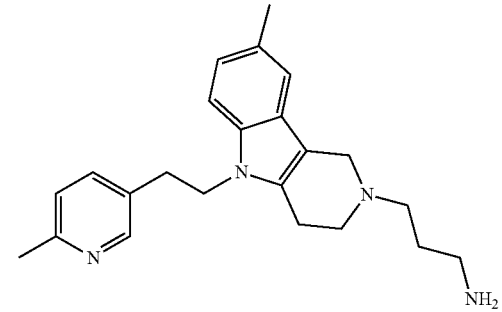 [SMILES: Cc1ccc2c(c1)c1c(n2CCc2ccc(C)nc2)CCN(CCCN)C1] |

TABLE 2-continued

Representative Compounds According to the Invention.

| Compound No. | Structure |
|---|---|
| 515 | 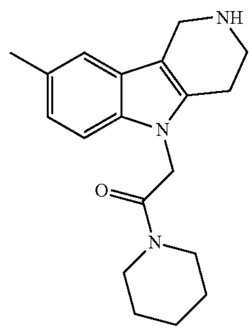 [SMILES: Cc1ccc2c(c1)c1c(n2CC(=O)N2CCCCC2)CCNC1] |
| 516 | 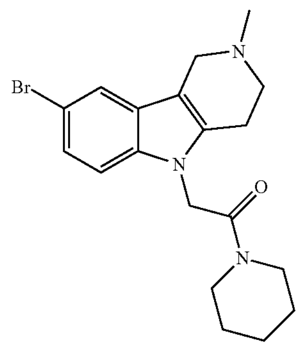 [SMILES: CN1CCc2c(c3cc(Br)ccc3n2CC(=O)N2CCCCC2)C1] |
| 517 | 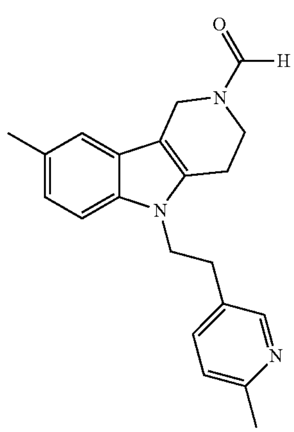 [SMILES: Cc1ccc2c(c1)c1c(n2CCc2ccc(C)nc2)CCN(C=O)C1] |
| 518 | 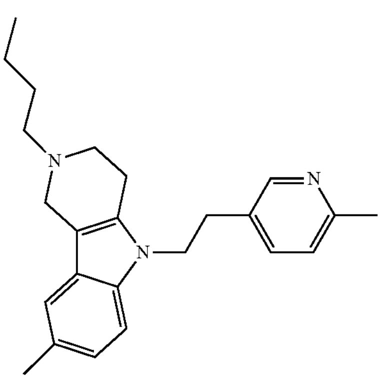 [SMILES: CCCCN1CCc2c(c3cc(C)ccc3n2CCc2ccc(C)nc2)C1] |
| 519 | 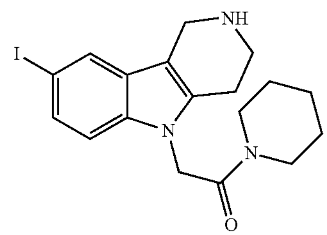 [SMILES: O=C(Cn1c2c(c3cc(I)ccc31)CNCC2)N1CCCCC1] |
| 520 | 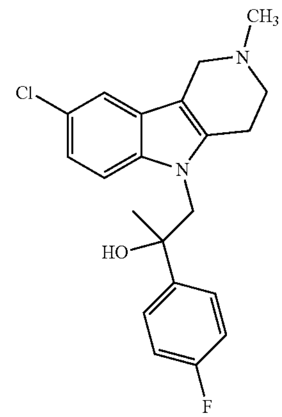 [SMILES: CN1CCc2c(c3cc(Cl)ccc3n2CC(C)(O)c2ccc(F)cc2)C1] |
| 521 | 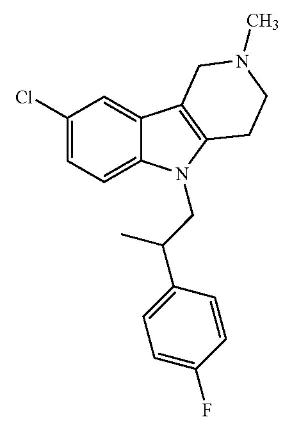 [SMILES: CC(Cn1c2c(c3cc(Cl)ccc31)CN(C)CC2)c1ccc(F)cc1] |
| 522 | 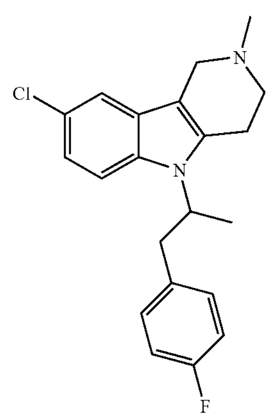 [SMILES: CC(Cc1ccc(F)cc1)n1c2c(c3cc(Cl)ccc31)CN(C)CC2] |

TABLE 2-continued

Representative Compounds According to the Invention.

| Compound No. | Structure |
|---|---|
| 523 | 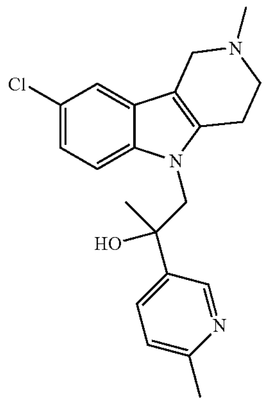 [SMILES: Cc1ccc(C(C)(O)Cn2c3c(c4cc(Cl)ccc42)CN(C)CC3)cn1] |
| 524 | 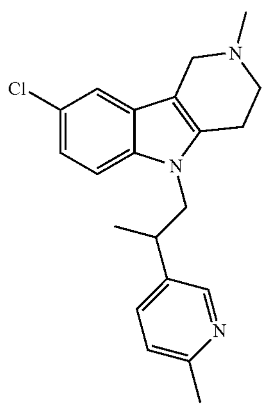 [SMILES: Cc1ccc(C(C)Cn2c3c(c4cc(Cl)ccc42)CN(C)CC3)cn1] |
| 525 | 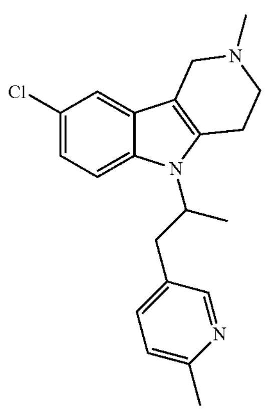 |
| 526 | 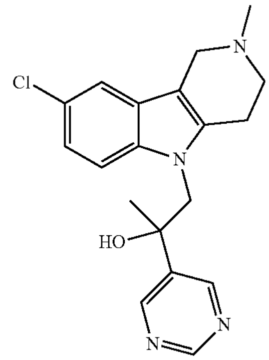 [SMILES: CN1CCc2c(c3cc(Cl)ccc3n2CC(C)(O)c2cncnc2)C1] |
| 527 | 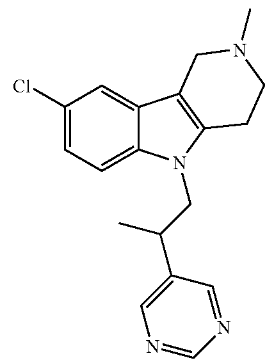 [SMILES: CC(Cn1c2c(c3cc(Cl)ccc31)CN(C)CC2)c1cncnc1] |
| 528 | 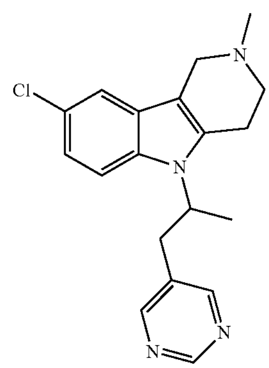 [SMILES: CC(Cc1cncnc1)n1c2c(c3cc(Cl)ccc31)CN(C)CC2] |
| 529 | 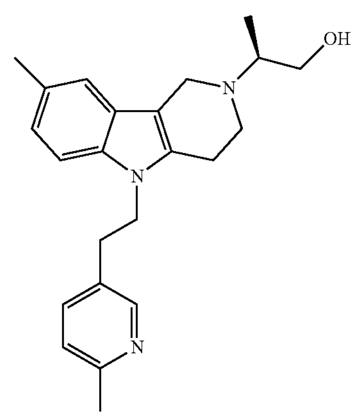 [SMILES: Cc1ccc2c(c1)c1c(n2CCc2ccc(C)nc2)CCN([C@@H](C)CO)C1] |

TABLE 2-continued

Representative Compounds According to the Invention.

| Compound No. | Structure |
|---|---|
| 530 | 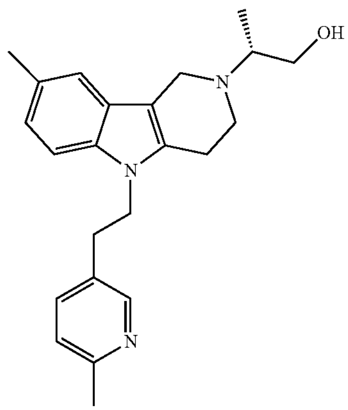 [SMILES: Cc1ccc2c(c1)c1c(n2CCc2ccc(C)nc2)CCN([C@H](C)CO)C1] |
| 531 | 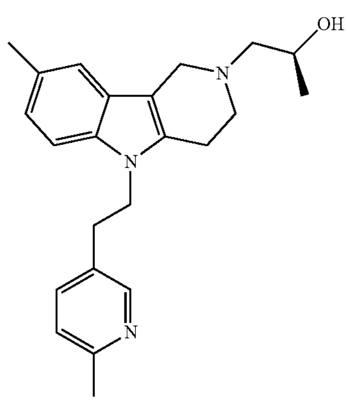 [SMILES: Cc1ccc2c(c1)c1c(n2CCc2ccc(C)nc2)CCN(C[C@H](C)O)C1] |
| 532 | 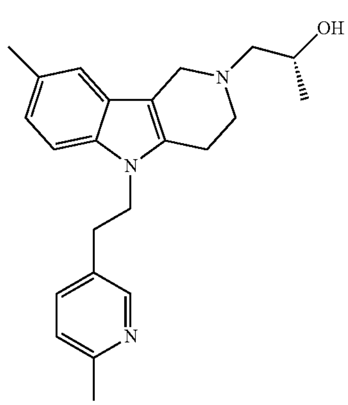 [SMILES: Cc1ccc2c(c1)c1c(n2CCc2ccc(C)nc2)CCN(C[C@@H](C)O)C1] |
| 533 | 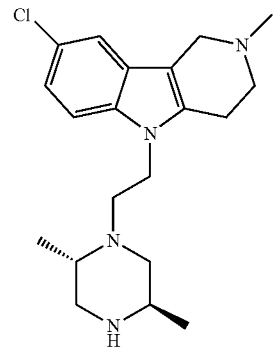 [SMILES: C[C@@H]1CN(CCn2c3c(c4cc(Cl)ccc42)CN(C)CC3)[C@@H](C)CN1] |
| 534 | 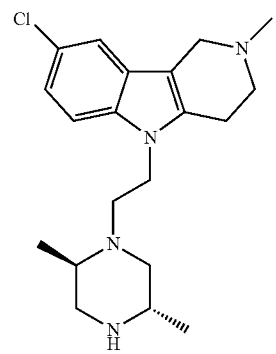 [SMILES: C[C@@H]1CN[C@@H](C)CN1CCn1c2c(c3cc(Cl)ccc31)CN(C)CC2] |
| 535 | 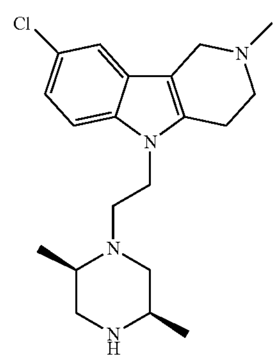 [SMILES: C[C@@H]1CN(CCn2c3c(c4cc(Cl)ccc42)CN(C)CC3)[C@H](C)CN1] |
| 536 | 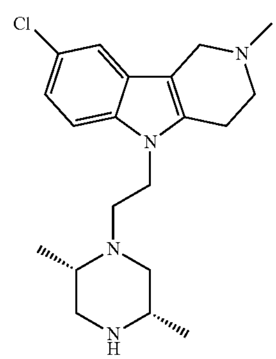 [SMILES: C[C@H]1CN(CCn2c3c(c4cc(Cl)ccc42)CN(C)CC3)[C@@H](C)CN1] |

TABLE 2-continued

Representative Compounds According to the Invention.

| Compound No. | Structure |
|---|---|
| 537 | 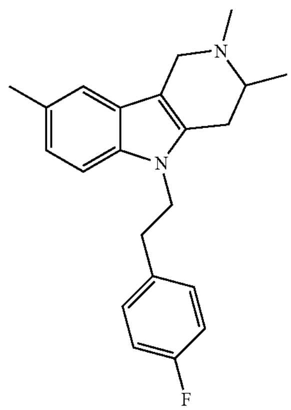 |
| 538 | 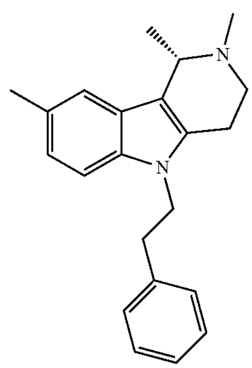 |
| 539 | 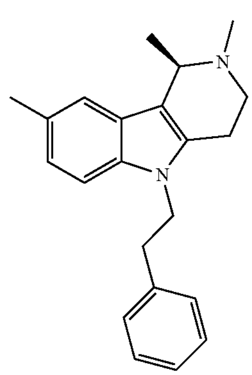 [SMILES: Cc1ccc2c(c1)c1c(n2CCc2ccccc2)CCN(C)[C@@H]1C] |
| 540 | 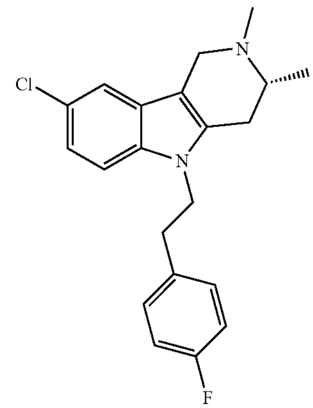 [SMILES: C[C@@H]1Cc2c(c3cc(Cl)ccc3n2CCc2ccc(F)cc2)CN1C] |
| 541 | 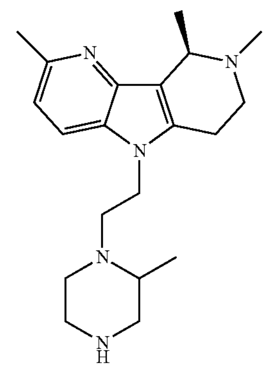 |
| 542 | 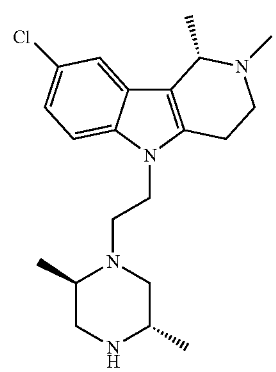 [SMILES: C[C@@H]1CN[C@@H](C)CN1CCn1c2c(c3cc(Cl)ccc31)[C@H](C)N(C)CC2] |
| 543 | 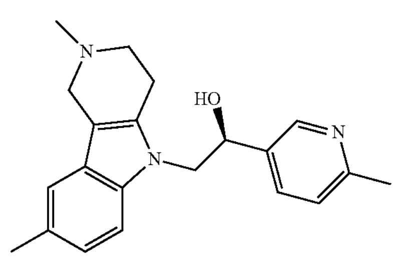 |

TABLE 2-continued

Representative Compounds According to the Invention.

| Compound No. | Structure |
|---|---|
| 544 | 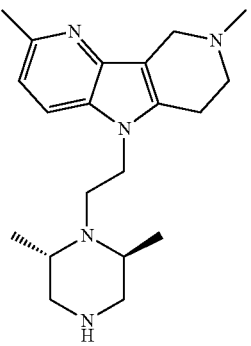 |
| 545 | 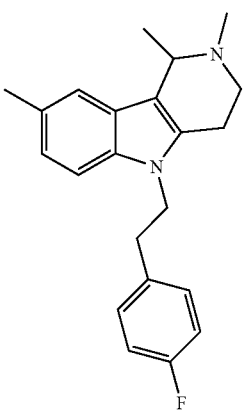 [SMILES: Cc1ccc2c(c1)c1c(n2CCc2ccc(F)cc2)CCN(C)C1C] |
| 546 | 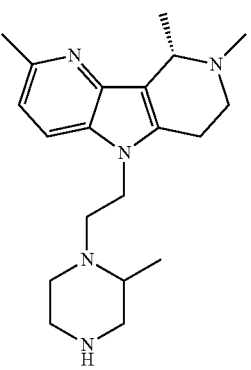 |
| 547 | 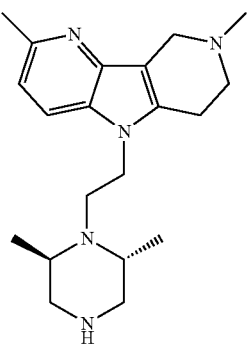 |
| 548 | 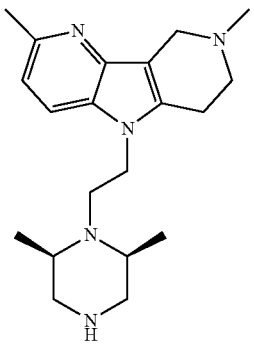 |

Additional compounds of the invention include compounds of the formula (G):

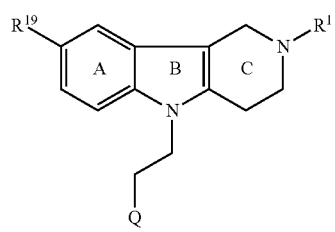

(G)

where:

R$^1$ is selected from unsubstituted alkyl and unsubstituted aralkyl or heteroaralkyl;

R$^{19}$ is selected from hydrogen, unsubstituted alkyl, unsubstituted alkoxy, and halo; and Q is selected from substituted thiazolyl, triazolyl, and oxadiazolyl, or a pharmaceutically acceptable salt thereof. In one variation, Q is a triazolo-thione.

In some embodiments of formula (G) or any variation herein, such as compounds of the formula (Ga)-(Gd), R$^{19}$ is selected from hydrogen, unsubstituted C$_1$-C$_8$ alkyl, unsubstituted C$_1$-C$_8$ alkoxy, and halo. In some embodiments, R$^{19}$ is selected from hydrogen, unsubstituted C$_1$-C$_4$ alkyl, unsubstituted C$_1$-C$_4$ alkoxy, and halo. In some embodiments, R$^{19}$ is selected from hydrogen, methyl, methoxy, fluoro, and chloro.

In another variation, a compound of the invention is of the formula G or any variation herein, such as compounds of the formula (Ga)-(Gd), wherein the A-ring is selected from the following structures:

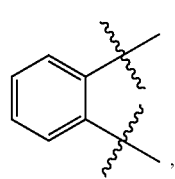

,

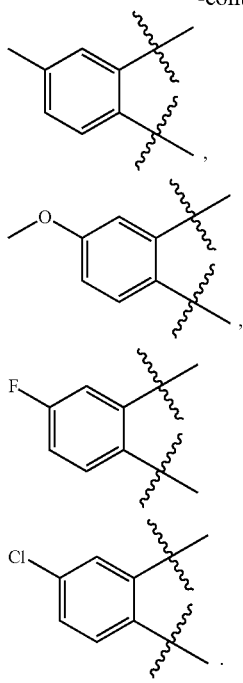

In some embodiments the compound is of formula (G) or any variation herein, such as compounds of the formula (Ga)-(Gd), where $R^1$ is selected from unsubstituted $C_1$-$C_8$ alkyl and unsubstituted $C_1$-$C_8$ aralkyl or heteroaralkyl. In some embodiments, $R^1$ is selected from unsubstituted $C_1$-$C_4$ alkyl and unsubstituted $C_1$-$C_4$ aralkyl or heteroaralkyl. In some embodiments, $R^1$ is selected from methyl and benzyl. It is further understood that any $R^1$ detailed herein may be combined with any variation for $R^{19}$. In one variation, both $R^1$ and $R^{19}$ are methyl.

In still a further variation, a compound of the invention is of the formula G or any variation herein, such as compounds of the formula (Ga)-(Gd), wherein the C-ring is selected from the following structures:

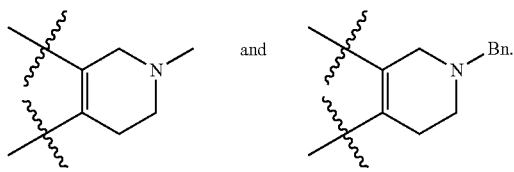

In some embodiments, Q is selected from thiazol-2-yl, 1,2,4-triazol-3-yl, 5-thioxo-4,5-dihydro-1H-1,2,4-triazol-3-yl, and 1,2,4-oxadiazol-3-yl. In some embodiments, Q is thiazol-2-yl, 1,2,4-triazol-3-yl, 5-thioxo-4,5-dihydro-1H-1,2,4-triazol-3-yl, or 1,2,4-oxadiazol-3-yl, substituted with a group selected from unsubstituted $C_1$-$C_8$ alkyl and unsubstituted aryl or heteroaryl. In some embodiments, Q is thiazol-2-yl, 1,2,4-triazol-3-yl, 5-thioxo-4,5-dihydro-1H-1,2,4-triazol-3-yl, or 1,2,4-oxadiazol-3-yl, substituted with a group selected from unsubstituted $C_1$-$C_4$ alkyl and unsubstituted aryl or heteroaryl. In some embodiments, Q is thiazol-2-yl, 1,2,4-triazol-3-yl, 5-thioxo-4,5-dihydro-1H-1,2,4-triazol-3-yl, or 1,2,4-oxadiazol-3-yl, substituted with a group selected from methyl, phenyl, and pyridin-4-yl.

In another variation, the compound of the invention is of the formula G where rings A and C are as detailed in any variation herein and Q is selected from the following structures:

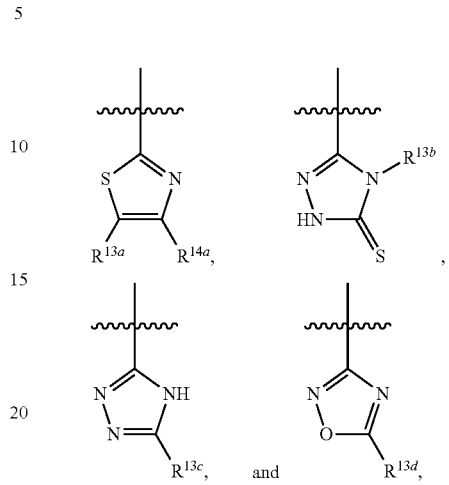

where $R^{13a}$ is selected from hydrogen and alkyl; $R^{14a}$ is selected from aryl and heteroaryl; $R^{13b}$ is alkyl; $R^{13c}$ is selected from alkyl, aryl, and heteroaryl; and $R^{13d}$ is selected from aryl and heteroaryl. In another variation, Q is selected from the structures above and $R^{13a}$ is selected from hydrogen and methyl; $R^{14a}$ is selected from phenyl and pyridin-4-yl; $R^{13b}$ is methyl; $R^{13c}$ is selected from methyl, phenyl, and pyridin-4-yl; and $R^{13d}$ is selected from phenyl and pyridin-4-yl.

Thus, compounds of Formula (Ga)-(Gd) are embraced by this invention:

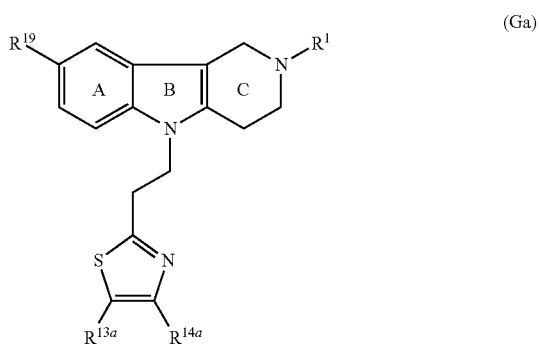

(Ga)

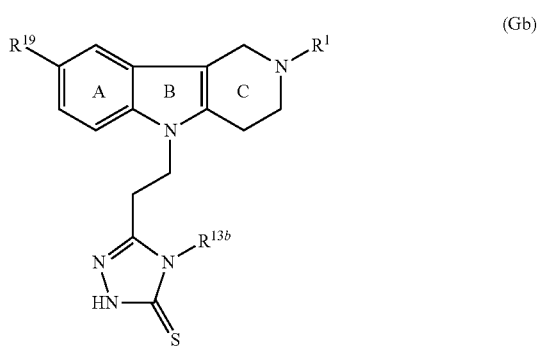

(Gb)

267
-continued

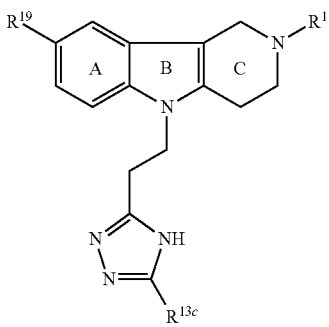

(Gc)

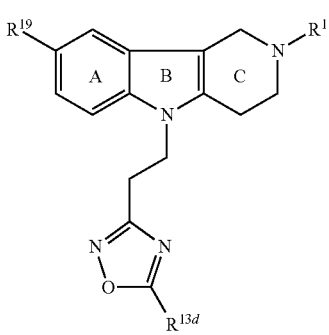

(Gd)

In some embodiments, the compound is of Formula Ga, wherein $R^1$ is selected from methyl and benzyl; $R^{19}$ is selected from hydrogen, methyl, methoxy, chloro, and fluoro; $R^{13a}$ is selected from hydrogen and methyl; and $R^{14a}$ is selected from phenyl and pyridin-4-yl.

In some embodiments, the compound is of Formula Gb, wherein $R^1$ is selected from methyl and benzyl; $R^{19}$ is selected from hydrogen, methyl, methoxy, chloro, and fluoro; and $R^{13b}$ is methyl.

In some embodiments, the compound is of Formula Gc, wherein $R^1$ is selected from methyl and benzyl; $R^{19}$ is selected from hydrogen, methyl, methoxy, chloro, and fluoro; and $R^{13c}$ is selected from methyl, phenyl, and pyridin-4-yl.

In some embodiments, the compound is of Formula Gd, wherein $R^1$ is selected from methyl and benzyl; $R^{19}$ is selected from hydrogen, methyl, methoxy, chloro, and fluoro; and $R^{13d}$ is selected from phenyl and pyridin-4-yl.

Certain examples of compounds according to the invention are depicted in Table 3. The compounds depicted may be present as salts even if salts are not depicted and it is understood that the invention embraces all salts, hydrates and solvates of the compounds depicted here, as well as the non-salt, non-hydrate, non-solvate form of the compound, as is well understood by the skilled artisan. It is thus understood that pharmaceutically acceptable salts of compounds according the invention are intended.

268
TABLE 3

Representative Compounds According to the Invention

| No. | Structure |
|---|---|
| G6-a | 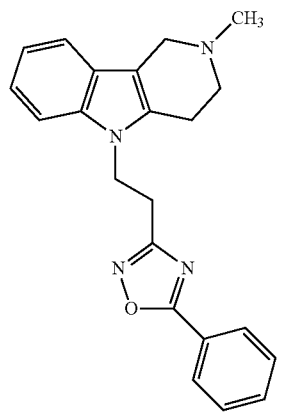 [SMILES: CN1CCc2c(c3ccccc3n2CCc2noc(-c3ccccc3)n2)C1] |
| G6-b | 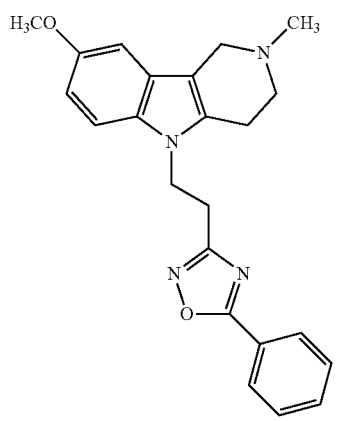 [SMILES: COc1ccc2c(c1)c1c(n2CCc2noc(-c3ccccc3)n2)CCN(C)C1] |
| G6-c | 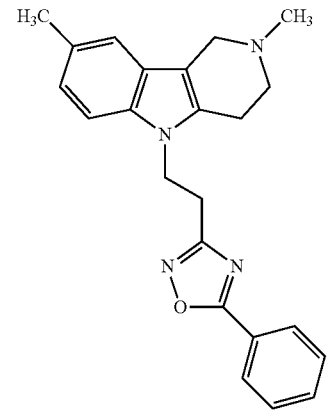 [SMILES: Cc1ccc2c(c1)c1c(n2CCc2noc(-c3ccccc3)n2)CCN(C)C1] |

TABLE 3-continued
Representative Compounds According to the Invention
| No. | Structure |
|---|---|
| G6-d | 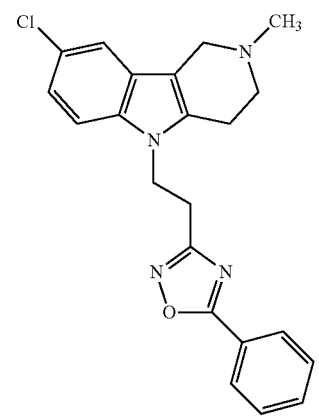 [SMILES: CN1CCc2c(c3cc(Cl)ccc3n2CCc2noc(-c3ccccc3)n2)C1] |
| G6-e | 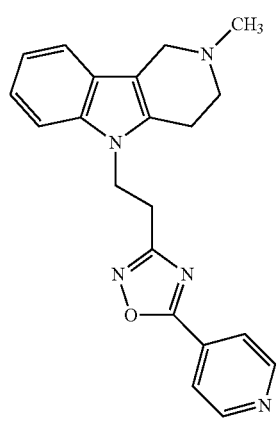 [SMILES: CN1CCc2c(c3ccccc3n2CCc2noc(-c3ccncc3)n2)C1] |
| G6-f | 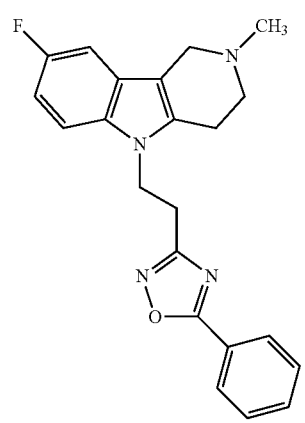 [SMILES: CN1CCc2c(c3cc(F)ccc3n2CCc2noc(-c3ccccc3)n2)C1] |
TABLE 3-continued
Representative Compounds According to the Invention
| No. | Structure |
|---|---|
| G8-a | 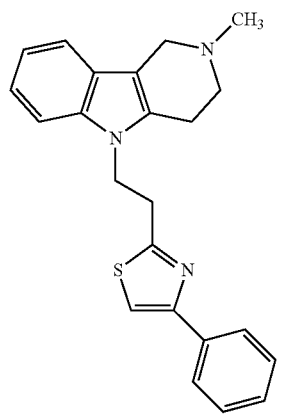 [SMILES: CN1CCc2c(c3ccccc3n2CCc2nc(-c3ccccc3)cs2)C1] |
| G8-b | 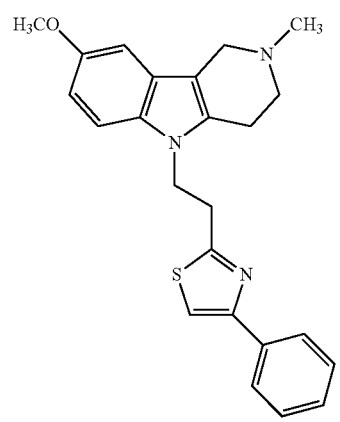 [SMILES: COc1ccc2c(c1)c1c(n2CCc2nc(-c3ccccc3)cs2)CCN(C)C1] |
| G8-c | 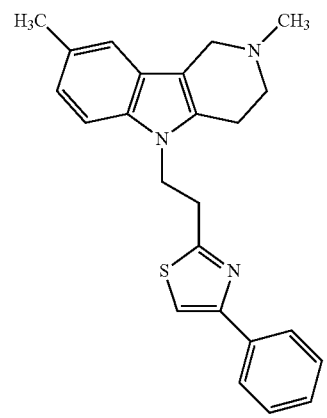 [SMILES: Cc1ccc2c(c1)c1c(n2CCc2nc(-c3ccccc3)cs2)CCN(C)C1] |

TABLE 3-continued

Representative Compounds According to the Invention

| No. | Structure |
|---|---|
| G8-d | (structure) |
| G8-e | (structure) |
| G8-f | (structure) |
| G11-a | (structure) |
| G11-b | (structure) |
| G11-c | (structure) |
| G11-d | (structure) |

Compounds according to the invention as listed in Table 3 are also referred to as follows in the Biological Examples 16B to 19B: G6-a (C4-1); G6-b (C4-5); G6-c (C4-4); G6-d (C4-6); G6-e (C4-3); G6-f (C4-7); G8-a (C1-1); G8-b (C1-6); G8-c (C1-5); G8-d (C1-4); G8-e (C1-8); G8-f (C1-7); G11-a (C2-1); G11-b (C2-5); G11-c (C2-6); and G11-d (C2-4).

Pharmaceutical compositions comprising any of the compounds detailed herein are embraced by this invention. Thus, the invention includes pharmaceutical compositions comprising a compound of the invention or a pharmaceutically acceptable salt thereof and a pharmaceutically acceptable carrier or excipient. Provided are pharmaceutical compositions comprising a compound disclosed herein or a pharmaceutically acceptable salt thereof (e.g., an oxalate salt or a TFA salt or a hydrochloride salt or dihydrochloride salt) and a pharmaceutically acceptable carrier or excipient. Pharmaceutical compositions according to the invention may take a form suitable for oral, buccal, parenteral, nasal, topical or rectal administration, or a form suitable for administration by inhalation.

In one variation, compounds of the invention are synthetic compounds prepared for administration to an individual. In another variation, compositions are provided containing compounds of the invention in substantially pure form. In another variation, the invention embraces pharmaceutical compositions comprising a compound of the invention and a pharmaceutically acceptable carrier. In another variation, methods of administering a compound of the invention are provided. The purified forms, pharmaceutical compositions and methods of administering the compounds are suitable for any compound or form thereof detailed herein, such as compound 229H, 230, 241, 255, 256, 262 and 274. In particular, where applicable, metabolites of dimebon are in one variation excluded from the formulae provided. In another variation, metabolites of dimebon are encompassed by the methods, pharmaceutical compositions, isolated and purified forms of the compounds of the invention. Such metabolites are believed to include compounds 229H, 230, 241, 255, 256, 262, 274 and the compound of Example 93. Compounds substituted with an O-Glu are likewise excluded in one variation from the compounds of the formulae provided.

In one variation, a compound of the invention is according to any of the formulae detailed herein, wherein the compound further is a type 1 compound according to the invention. In one variation, a compound of the invention is according to any of the formulae detailed herein, wherein the compound further is a type 2 compound according to the invention. In one variation, a compound of the invention is according to any of the formulae detailed herein, wherein the compound further is a type 3 compound according to the invention. In one variation, a compound of the invention is according to any of the formulae detailed herein, wherein the compound further is a type 4 compound according to the invention.

Classification of Compounds

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha 1D$, $\alpha 2A$ and $\alpha 2B$), inhibition of binding of a ligand to a serotonin receptor (e.g., 5-HT2A, 5-HT2C, 5-HT6 and 5-HT7), inhibition of binding of a ligand to a dopamine receptor (e.g., D2L), and inhibition of binding of a ligand to a histamine receptor (e.g., H1, H2 and H3); agonist/antagonist activity to a serotonin receptor (e.g., 5-HT2A, 5-HT6); agonist/antagonist activity to a dopamine receptor (e.g., D2L, D2S); agonist/antagonist activity to a histamine receptor (e.g., H1); activity in a neurite outgrowth assay; efficacy in a preclinical model of memory dysfunction associated with cholinergic hyperfunction; and efficacy in a preclinical model of schizophrenia. In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85-95% or between about 90-100% as determined in a suitable assay known in the art such as the assays described herein. In one variation, binding of a ligand to a receptor is inhibited by at least about 80%±20% as determined in an assay known in the art. In one variation, a compound of the invention inhibits binding of a ligand to at least one and as many as eleven receptors detailed herein (e.g. $\alpha 1D$, $\alpha 2A$, $\alpha 2B$, 5-HT2A, 5-HT2C, 5-HT6, 5-HT7, D2L, H1, H2, H3) and further displays agonist or antagonist activity to one or more receptors detailed herein (e.g., 5-HT2A, 5-HT6, D2L, D2S, H1). In one variation, a compound of the invention inhibits binding of a ligand to at least one receptor and as many as eleven as detailed herein and further stimulates neurite outgrowth, e.g. as measured by the assays described herein. In another variation, a compound of the invention inhibits binding of a ligand to at least one receptor and as many as eleven as detailed herein, further displays agonist or antagonist activity to one or more receptors detailed herein and further stimulates neurite outgrowth. In a further variation, a compound of the invention inhibits binding of a ligand to at least one and as many as eleven receptors as detailed herein and further shows efficacy in a preclinical model of memory dysfunction associated with cholinergic hyperfunction. In another variation, a compound of the invention inhibits at least one and as many as eleven receptors as detailed herein, further shows efficacy in a preclinical model of memory dysfunction associated with cholinergic hyperfunction and further displays agonist or antagonist activity to one or more receptors detailed herein. In a further variation, a compound of the invention inhibits binding of a ligand to at least one and as many as eleven receptors as detailed herein, further shows efficacy in a preclinical model of memory dysfunction associated with cholinergic hyperfunction and further stimulates neurite outgrowth. In another variation, a compound of the invention inhibits at least one and as many as eleven receptors as detailed herein, further shows efficacy in a preclinical model of memory dysfunction associated with cholinergic hyperfunction, further displays agonist or antagonist activity to one or more receptor detailed herein and further stimulates neurite outgrowth. In a further variation, a compound of the invention inhibits binding of a ligand to at least one and as many as eleven receptors and further shows efficacy in a preclinical model of schizophrenia. In another variation, a compound of the invention inhibits binding of a ligand to at least one and as many as eleven receptors, further shows efficacy in a preclinical model of schizophrenia and further displays agonist or antagonist activity to one or more receptors detailed herein. In a further variation, a compound of the invention inhibits binding of a ligand to at least one and as many as eleven receptors, further shows efficacy in a preclinical model of schizophrenia and further stimulates neurite outgrowth. In a further variation, a compound of the invention inhibits binding of a ligand to at least one and as many as eleven receptors, further shows efficacy in a preclinical model of memory dysfunction associated with cholinergic hyperfunction and further shows efficacy in a preclinical model of schizophrenia. In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic hyperfunction. In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic hyperfunction. In a further variation, a compound of the invention inhibits binding to at least one and as many as eleven receptors detailed herein, further displays agonist or antagonist activity to one ore more receptors detailed herein, further stimulates neurite outgrowth and further shows efficacy in a preclinical model of schizophrenia. In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic hyperfunction.

In one aspect, compounds of the invention inhibit binding of a ligand to adrenergic receptors α1D, α2A, α2B and inhibit binding of a ligand to serotonin receptor 5-HT6. In another variation, compounds of the invention inhibit binding of a ligand to adrenergic receptors α1D, α2A, α2B, to serotonin receptor 5-HT6 and to any one or more of the following receptors: serotonin receptor 5-HT7, 5-HT2A and 5-HT2C. In another variation, compounds of the invention inhibit binding of a ligand to adrenergic receptors α1D, α2A, α2B, to serotonin receptor 5-HT6 and to any one or more of the following receptors: serotonin receptor 5-HT7, 5-HT2A and 5-HT2C and further show weak inhibition of binding of a ligand to histamine receptor H1 and/or H2. In another variation, compounds of the invention inhibit binding of a ligand to adrenergic receptors α1D, α2A, α2B, to serotonin receptor 5-HT6 and further show weak inhibition of binding of a ligand to histamine receptor H1 and/or H2. In another variation, compounds of the invention inhibit binding of a ligand to dopamine receptor D2L. In another variation, compounds of the invention inhibit binding of a ligand to dopamine receptor D2L and to serotonin receptor 5-HT2A. In another variation, compounds of the invention inhibit binding of a ligand to histamine receptor H1. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85-95% or about 90-100% as determined in a suitable assay known in the art such as the assays described herein. In one variation, compounds of the invention show any of the receptor binding aspects detailed herein and further display agonist/antagonist activity to one or more of the following receptors: serotonin receptor 5-HT2A, serotonin receptor 5-HT6, dopamine receptor D2L, dopamine receptor D2S and histamine receptor H1. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic hyperfunction. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT2A, 5-HT6, dopamine receptor D2L, dopamine receptor D2S and histamine receptor H1), neurite outgrowth, a preclinical model of memory dysfunction associated with cholinergic hyperfunction and a preclinical model of schizophrenia.

Compounds of the invention that inhibit binding of a ligand to adrenergic receptors α1D, α2A, α2B and serotonin receptor 5-HT6 by at least about 80% as determined in a suitable assay such as the assays described herein can be classified as Type 1 compounds. In one variation, binding of a ligand to adrenergic receptors α1D, α2A, α2B and serotonin receptor 5-HT6 is inhibited by greater than about any of 80%, 85%, 90%, 95%, 100%, between about 85-95% or between about 90-100%, as determined in a suitable assay known in the art such as the assays described herein. Type 1 compounds that also display strong inhibition of binding of a ligand to the serotonin receptor 5-HT7 are particularly desired. In one variation, binding of a ligand to serotonin receptor 5-HT7 is at least about 80%. In another variation, binding of a ligand to serotonin receptor 5-HT7 is inhibited by greater than about any of 80%, 85%, 90%, 95%, 100%, between about 85-95% or between about 90-100%, as determined in a suitable assay known in the art such as the assays described herein. Weak inhibition of binding of a ligand to the histamine H1 receptor is permitted as agonists of this receptor have been implicated in stimulating memory as well as weight gain. In one variation, binding to histamine receptor H1 is inhibited by less than about 80%. In another variation, binding of a ligand to histamine receptor H1 is inhibited by less than about any of 75%, 70%, 65%, 60%, 55%, or 50% as determined by a suitable assay known in the art such as the assays described herein. Compounds that inhibit binding of a ligand to the dopamine D2L receptor by at least about 80% as determined in a suitable assay such as the assay described herein can be classified as Type 2 compounds. Compounds of the invention that do not inhibit binding of a ligand to adrenergic receptors α1D, α2A, α2B; serotonin receptor 5-HT6 and to the dopamine receptor D2L by at least about 80% as determined in a suitable assay such as the assays described herein, but show activity in neurite outgrowth assays, can be classified as Type 3 compounds. Compounds of the invention that do not inhibit binding of a ligand to adrenergic receptors α1D, α2A, α2B; serotonin receptor 5-HT6 and to the dopamine receptor D2L by at least about 80% as determined in a suitable assay such as the assays described herein, and do not show activity in neurite outgrowth assays or if the concentration required for neurite outgrowth is greater than 1 µM are referred to as Type 4 compounds.

Type 1 Compounds

Type 1 compounds inhibit binding of a ligand to adrenergic receptors α1D, α2A, α2B and serotonin receptor 5-HT6 by at least about 80% as determined by a suitable assay known in the art such as the assays described herein. In one variation, Type 1 compounds inhibit binding of Prozosin, MK-912 or Rauwolscine to adrenergic receptors α1D, α2A, and α2B, respectively and binding of LSD to serotonin receptor 5-HT6 by at least about 80% as determined in the assays described herein. In another variation, binding is inhibited by greater than about any of 80%, 85%, 90%, 95%, 100%, between about 85-95% or between about 90-100%, as determined in a suitable assay known in the art such as the assays described herein. In another variation, inhibition of binding of a ligand is at least about 80%±20% as measured by an assay known to a person skilled in the art. In one variation, Type 1 compounds further inhibit binding of a ligand to dopamine receptor D2L by less than about 80% as determined in a suitable assay known in the art such as the assay described herein. In certain aspects, Type 1 compounds further show one or more of the following properties: strong inhibition of binding of a ligand to the serotonin 5-HT7 receptor, strong inhibition of binding of a ligand to the serotonin 5-HT2A receptor, strong inhibition of binding of a ligand to the serotonin 5-HT2C receptor, weak inhibition of binding of a ligand to the histamine H1 receptor, weak inhibition of binding of ligands to the histamine H2 receptor, and antagonist activity to serotonin receptor 5-HT2A. In one variation, binding of a ligand to serotonin receptor 5-HT7, 5-HT2A and/or 5-HT2C is inhibited by at least about 80% as determined in a suitable assay such as the assays described herein. In another variation, binding of a ligand to serotonin receptor 5-HT7, 5-HT2A and/or 5-HT2C is inhibited by greater than about any of 80%, 85%, 90%, 95%, 100%, between about 85-95% or between about 90-100%, as determined in a suitable assay known in the art such as the assays described herein. In one variation, binding of a ligand to histamine receptor H1 and/or H2 is inhibited by less than about 80% as determined by a suitable assay known in the art such as the assays described herein. In another variation, binding of a ligand to histamine receptor H1 and/or H2 is inhibited by less than about any of 75%, 70%, 65%, 60%, 55%, or 50% as determined by a suitable assay known in the art such as the assays described herein. In one variation, agonist response of serotonin receptor 5-HT2A is inhibited by a Type 1 compound by at least about any one of 50%, 60%, 70%, 80%, 90%, 100%, 110%, 120%, 130%, 140%, 150% as determined in a suitable assay such as the assay described herein.

In some aspects, Type 1 compounds display the above described neurotransmitter receptor binding profile and further show agonist or antagonist activity one or more of the following receptors: serotonin receptor 5-HT2A, serotonin receptor 5-HT6, dopamine receptor D2L, and dopamine receptor D2S, histamine receptor H1 as measured in the assays described herein. In one variation, agonist response of serotonin receptor 5-HT2A is inhibited by a Type 1 compounds by at least about any one of 50%, 50%, 70%, 80%, 90%, 100%, 110%, 120%, 130%, 140%, 150% as determined in a suitable assay such as the assay described herein.

In some aspects, Type 1 compounds display the above described neurotransmitter receptor binding profile and further stimulate neurite outgrowth as determined in a suitable assay such as the assays described herein. Certain Type 1 compounds showed activity in neurite outgrowth assays using primary neurons in culture (see Example 11B). Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In certain aspects, Type 1 compounds display the above described neurotransmitter receptor binding profile and further show pro-cognitive effects in a preclinical model of memory dysfunction. Type 1 compounds have been shown to be effective in a preclinical model of memory dysfunction associated with cholinergic hypofunction (see Example 12B). As H1 antagonism may contribute to sedation, weight gain and reduced cognition, low affinity (less than about 80% inhibition of binding of Pyrilamine at 1 uM in the assay described herein) for this receptor may be associated with pro-cognitive effects and a more desirable side effect profile. Furthermore, Type 1 compounds with increased potency as a 5-HT6 antagonist may have cognition-enhancing effects as serotonin acting through this receptor may impair memory.

In another aspect, Type 1 compounds display the above described neurotransmitter receptor binding profile and further possess anti-psychotic effects as measured in a preclinical model of schizophrenia. In another variation, Type 1 compounds display the above described neurotransmitter receptor binding profile and do not possess anti-psychotic effects as measured in a preclinical model of schizophrenia.

In one variation, Type 1 compounds display the above described neurotransmitter binding profile, display agonist or antagonist activity to at least one receptor detailed herein and further stimulate neurite outgrowth. In a further variation, Type 1 compounds display the above described neurotransmitter binding profile, further display agonist or antagonist activity to at least one receptor detailed herein and further show pro-cognitive effects in a preclinical model of memory dysfunction. In a further variation, Type 1 compounds display the above described neurotransmitter binding profile, further display agonist or antagonist activity to at least one receptor detailed herein, and further possess anti-psychotic effects as measured in a preclinical model of schizophrenia. In a further variation, Type 1 compounds display the above described neurotransmitter binding profile, further stimulate neurite outgrowth and further show pro-cognitive effects in a preclinical model of memory dysfunction. In a further variation, Type 1 compounds display the above described neurotransmitter binding profile, further stimulate neurite outgrowth and further possess anti-psychotic effects as measured in a preclinical model of schizophrenia. In a further variation, Type 1 compounds display the above described neurotransmitter binding profile, further show pro-cognitive effects in a preclinical model of memory dysfunction and further possess anti-psychotic effects as measured in a preclinical model of schizophrenia. In one variation, Type 1 compounds display the above described neurotransmitter binding profile, further display agonist or antagonist activity to at least one receptor detailed herein, further stimulate neurite outgrowth and further show pro-cognitive effects in a preclinical model of memory dysfunction. In one variation, Type 1 compounds display the above described neurotransmitter binding profile, further display agonist or antagonist activity to at least one receptor detailed herein, further stimulate neurite outgrowth and further possess anti-psychotic effects as measured in a preclinical model of schizophrenia. In one variation, Type 1 compounds display the above described neurotransmitter binding profile, further stimulate neurite outgrowth, further show pro-cognitive effects in a preclinical model of memory dysfunction and further possess anti-psychotic effects as measured in a preclinical model of schizophrenia. In one variation, Type 1 compounds display the above described neurotransmitter binding profile, display agonist or antagonist activity to at least one receptor detailed herein, further stimulate neurite outgrowth, further show pro-cognitive effects in a preclinical model of memory dysfunction and further possess anti-psychotic effects as measured in a preclinical model of schizophrenia.

Accordingly, in one aspect, Type 1 compounds are particularly useful for the treatment of cognition and memory-related disorders, including but not limited to: Alzheimer's Disease, Huntington's Disease, Parkinson's Disease, amyotrophic, lateral sclerosis (ALS), autism, mild cognitive impairment (MCI), cognitive impairment associated with schizophrenia or other psychotic disorders, stroke, traumatic brain injury (TBI) and age-associated memory impairment (AAMI) and pathogen-induced cognitive dysfunction, e.g. HIV associated cognitive dysfunction, Lyme disease associated cognitive dysfunction. In another aspect, Type 1 compounds are particularly useful for the treatment of neurotransmitter-mediated disorders including, but not limited to spinal cord injury, diabetic neuropathy, and diseases involving geroprotective activity such as age-associated hair loss (alopecia), age-associated weight loss and age-associated vision disturbances (cataracts).

Type one compounds of the invention include compound 37, 26, 28, 29, 32, 43, 47, 45, 83, 162, 89, 250, 68, 357, 55, 60, 404, 371, 452, 56, 333, 334, 360, 372, 443, 444, 456, 476, 487, and 225.

Type 2 Compounds

Type 2 compounds inhibit binding of a ligand to the dopamine receptor D2L by at least about 80% as determined in a suitable assay known in the art such as the assay described herein. In one variation, Type 2 compounds inhibit binding of Spiperone to the dopamine receptor D2L by at least about 80% as determined in the assay described herein. In another variation, binding is inhibited by greater than about any of 80%, 85%, 90%, 95%, 100%, between about 85-95% or between about 90-100%, as determined in a suitable assay known in the art such as the assay described herein. In another variation, inhibition of binding of a ligand is at least about 80%±20% as measured by an assay known to a person skilled in the art. In certain aspects, Type 2 compounds further show strong inhibition of binding of a ligand to serotonin receptor 5-HT2A as determined in the assay described herein. In one variation, biding to serotonin receptor 5-HT2A is inhibited by at least about 80% as determined in a suitable assay know in the art such as the assay described herein. In another variation, binding is inhibited by greater than about any of 80%, 85%, 90%, 95%, 100%, between about 85-95% or between about 90-100%, as determined in a suitable assay known in the art such as the assay described herein. In some aspects, Type 2 compounds inhibit binding of a ligand to adrenergic receptors α1D, α2A, α2B, serotonin receptor 5-HT6 and dopamine receptor D2L by at least about 80% as determined in a suitable assay known in the art such as the assays described herein. In one variation, Type 2 compounds inhibit binding of a ligand to adrenergic receptors α1D, α2A, α2B, serotonin receptor 5-HT6 and dopamine receptor D2L by at least about 80% as determined in a suitable assay known in the art such as the assays described herein. In another variation, Type 2 compounds inhibit binding of a ligand to adrenergic receptors α1D, α2A, α2B, serotonin receptor 5-HT6 and dopamine receptor D2L by greater than about any of 80%, 85%, 90%, 95%, 100%, between about 85-95%, or between about 90-100%, as determined in a suitable assay known in the art such as the assays described herein. As H1 antagonism may contribute to sedation, weight gain and reduced cognition, low affinity (less than about 80% inhibition of binding of Pyrilamine at 1 uM in the assay described herein) for this receptor may be associated with pro-cognitive effects and a more desirable side effect profile.

In some aspects, Type 2 compounds display the above described neurotransmitter receptor binding profile and further show agonist or antagonist activity one or more of the following receptors: serotonin receptor 5-HT2A, serotonin receptor 5-HT6, dopamine receptor D2L, dopamine receptor D2S and histamine receptor H1 as measured in a suitable assay such as the assays described herein. In one variation, Type 2 compounds inhibit agonist response to serotonin receptor 5-HT2A by at least about any one of 50%, 60%, 70%, 80%, 90%, 100%, 110%, 120%, 130%, 140%, 150% as determined in a suitable assay such as the assay described herein. In one variation, Type 2 compounds inhibit agonist response to dopamine receptor D2L by at least about any one of 50%, 60%, 70%, 80%, 90%, 100%, 110%, 120%, 130%, 140%, 150% as determined in a suitable assay such as the assay described herein. In one variation, Type 2 compounds inhibit agonist response to dopamine receptor D2S by at least about any one of 50%, 60%, 70%, 80%, 90%, 100%, 110%, 120%, 130%, 140%, 150% as determined in a suitable assay such as the assay described herein.

In some aspects, Type 2 compounds display the above described neurotransmitter receptor binding profile and further show antipsychotic effects. It is recognized that Type 2 compounds have binding profiles similar to compounds with antipsychotic activity and several Type 2 compounds have been shown to be effective in a preclinical model of schizophrenia (see Example 13B). In addition, Type 2 compounds might possess the cognitive enhancing properties of dimebon and thus add to the beneficial pharmacology profile of these antipsychotic molecules. In one variation, Type 2 compounds display the above described neurotransmitter receptor binding profile and further show pro-cognitive effects in a preclinical model of memory dysfunction. In another variation, Type 2 compounds display the above described neurotransmitter receptor binding profile and do not show pro-cognitive effects in a preclinical model of memory dysfunction.

In some aspects, Type 2 compounds display the above described neurotransmitter receptor binding profile and further stimulate neurite outgrowth as determined in a suitable assay such as the assays described herein. Certain Type 2 compounds showed activity in neurite outgrowth assays using primary neurons in culture (see Example 11B). In one variation, neurite outgrowth is observed with a potency of about 1 μM. In another variation, neurite outgrowth is observed with a potency of about 500 nM. In a further variation, neurite outgrowth is observed with a potency of about 50 nM. In another variation, neurite outgrowth is observed with a potency of about 5 nM.

In one variation, Type 2 compounds display the above described neurotransmitter binding profile, display agonist or antagonist activity to at least one receptor detailed herein and further stimulate neurite outgrowth. In a further variation, Type 2 compounds display the above described neurotransmitter binding profile, further display agonist or antagonist activity to at least one receptor detailed herein and further show pro-cognitive effects in a preclinical model of memory dysfunction. In a further variation, Type 2 compounds display the above described neurotransmitter binding profile, further display agonist or antagonist activity to at least one receptor detailed herein, and further possess anti-psychotic effects as measured in a preclinical model of schizophrenia. In a further variation, Type 2 compounds display the above described neurotransmitter binding profile, further stimulate neurite outgrowth and further show pro-cognitive effects in a preclinical model of memory dysfunction. In a further variation, Type 2 compounds display the above described neurotransmitter binding profile, further stimulate neurite outgrowth and further possess anti-psychotic effects as measured in a preclinical model of schizophrenia. In a further variation, Type 2 compounds display the above described neurotransmitter binding profile, further show pro-cognitive effects in a preclinical model of memory dysfunction and further possess anti-psychotic effects as measured in a preclinical model of schizophrenia. In one variation, Type 2 compounds display the above described neurotransmitter binding profile, further display agonist or antagonist activity to at least one receptor detailed herein, further stimulate neurite outgrowth and further show pro-cognitive effects in a preclinical model of memory dysfunction. In one variation, Type 2 compounds display the above described neurotransmitter binding profile, further display agonist or antagonist activity to at least one receptor detailed herein, further stimulate neurite outgrowth and further possess anti-psychotic effects as measured in a preclinical model of schizophrenia. In one variation, Type 2 compounds display the above described neurotransmitter binding profile, further stimulate neurite outgrowth, further show pro-cognitive effects in a preclinical model of memory dysfunction and further possess anti-psychotic effects as measured in a preclinical model of schizophrenia. In one variation, Type 2 compounds display the above described neurotransmitter binding profile, display agonist or antagonist activity to at least one receptor detailed herein, further stimulate neurite outgrowth, further show pro-cognitive effects in a preclinical model of memory dysfunction and further possess anti-psychotic effects as measured in a preclinical model of schizophrenia.

Accordingly, in one aspect, Type 2 compounds are particularly useful for the treatment of psychotic indications such as schizophrenia, bipolar disorder, psychosis, depression and anxiety.

Type 2 compounds include compound 25, 20, 34, 32, 33, 36, 247, 253, 336, 349, 337, and 455.

Type 3 Compounds

Type 3 compounds do not inhibit binding of a ligand to adrenergic receptors α1D, α2A, α2B; serotonin receptor 5-HT6 and to the dopamine receptor D2L by at least about 80% as determined in a suitable assay such as the assays described herein, but are active in neurite outgrowth assays, e.g., in the assays described herein. Certain Type 3 compounds showed activity in neurite outgrowth assays using primary neurons in culture (see Example 11B). In one variation, neurite outgrowth is observed with a potency of less than or equal to about 1 µM. In another variation, neurite outgrowth is observed with a potency of about 500 nM. In a further variation, neurite outgrowth is observed with a potency of about 50 nM. In another variation, neurite outgrowth is observed with a potency of about 5 nM.

In some aspects, Type 3 compounds display the above described neurotransmitter receptor binding profile and further show pro-cognitive effects. As H1 antagonism may contribute to sedation, weight gain and reduced cognition, low affinity (less than about 80% inhibition of binding of Pyrilamine at 1 uM in the assay described herein) for this receptor may be associated with pro-cognitive effects and a more desirable side effect profile. In a further variation, Type 3 compounds display the above described neurotransmitter receptor binding profile and further possess anti-psychotic effects. In another variation, Type 3 compounds display the above described neurotransmitter receptor binding profile and do not possess anti-psychotic effects.

In one variation, Type 3 compounds display the above described neurotransmitter binding profile, further stimulate neurite outgrowth and further show pro-cognitive effects in a preclinical model of memory dysfunction. In another variation, Type 3 compounds display the above described neurotransmitter binding profile, further stimulate neurite outgrowth and further possess anti-psychotic effects as measured in a preclinical model of schizophrenia. In a further variation, Type 3 compounds display the above described neurotransmitter binding profile, further stimulate neurite outgrowth, further show pro-cognitive effects in a preclinical model of memory dysfunction and further possess anti-psychotic effects as measured in a preclinical model of schizophrenia.

Accordingly, in one aspect, Type 3 compounds are particularly useful for the treatment of neuronal disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder and adjuvant chemotherapy, traumatic brain injury, (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety and depression. In another aspect, Type 3 compounds are particularly suitable for the treatment of neurotransmitter-mediated disorders including, but not limited to spinal cord injury, diabetic neuropathy, allergic diseases and diseases involving geroprotective activity such as age-associated hair loss (alopecia), age-associated weight loss and age-associated vision disturbances (cataracts).

Type 3 compounds include compound 395.

Type 4 Compounds

Type 4 compounds do not inhibit binding of a ligand to adrenergic receptors α1D, α2A, α2B; serotonin receptor 5-HT6 and to the dopamine receptor D2L by at least about 80% as determined in a suitable assay such as the assays described herein and are effective in a neurite outgrowth assay only with a potency of greater than about 1 µM. In one variation, Type 4 compounds are not active in a neurite outgrowth assay.

In one variation, Type 4 compounds show pro-cognitive effects in a preclinical model of memory dysfunction. In another variation, Type 4 compounds do not show pro-cognitive effects in a preclinical model of memory dysfunction. In a further variation, Type 4 compounds possess anti-psychotic effects in a preclinical model of schizophrenia. In another variation, Type 4 compounds do not possess anti-psychotic effects in a preclinical model of schizophrenia. In a further variation, Type 4 compounds show pro-cognitive effects in a preclinical model of memory dysfunction and further possess anti-psychotic effects in a preclinical model of schizophrenia.

Accordingly, in one aspect, Type 4 compounds are particularly useful for the treatment of neuronal disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder and adjuvant chemotherapy, traumatic brain injury, (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety and depression. In another aspect, Type 4 compounds are particularly suitable for the treatment of neurotransmitter-mediated disorders including, but not limited to spinal cord injury, diabetic neuropathy, allergic diseases and diseases involving geroprotective activity such as age-associated hair loss (alopecia), age-associated weight loss and age-associated vision disturbances (cataracts).

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In another aspect, the compounds described herein may be used to treat, prevent, delay the onset and/or delay the development of a psychotic disorder. In yet another aspect, the compounds described herein may be used to treat, prevent, delay the onset and/or delay the development of a neurotransmitter-mediated disorders disorder. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barre syndrome, mild cognitive impairment, multiple sclerosis, stroke and traumatic brain injury. In yet another embodiment, the neurotransmitter-mediated disorder includes schizophrenia, anxiety, bipolar disorders, psychosis and depression. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha1D$, $\alpha2A$, $\alpha2B$, serotonin receptor 5-HT2A, 5-HT6, 5HT7, histamine receptor H1 and/or H2 is expected to be or is beneficial for the cognitive disorders, psychotic disorders, neurotransmitter-mediated disorders and/or neuronal disorders. In some variations, modulation of adrenergic receptor $\alpha1D$, $\alpha2A$, $\alpha2B$ and a serotonin receptor 5-HT6 receptor is expected to be or is beneficial for the cognitive disorders, psychotic disorders, neurotransmitter-mediated disorders and/or neuronal disorders. In some variations, modulation of adrenergic receptor $\alpha1D$, $\alpha2A$, $\alpha2B$, and a serotonin receptor 5-HT6 receptor and modulation of one or more of the following receptors serotonin 5-HT7, 5-HT2A, 5-HT2C and histamine H1 and H2 is expected to be or is beneficial for the cognitive disorders, psychotic disorders, neurotransmitter-mediated disorders and/or neuronal disorders. In some variations, modulation of dopamine receptor D2L is expected to be or is beneficial for the cognitive disorders, psychotic disorders, neurotransmitter-mediated disorders and/or neuronal disorders. In certain variations, modulation of a dopamine D2L receptor and serotonin receptor 5-HT2A is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a Type 1 compound. In some variations, the cognitive disorders, psychotic disorders, neurotransmitter-mediated disorders and/or neuronal disorders are treated, prevented and/or their onset or development is delayed by administering a Type 2 compound. In some variations, the cognitive disorders, psychotic disorders, neurotransmitter-mediated disorders and/or neuronal disorders are treated, prevented and/or their onset or development is delayed by administering a Type 3 compound. In some variations, the cognitive disorders, psychotic disorders, neurotransmitter-mediated disorders and/or neuronal disorders are treated, prevented and/or their onset or development is delayed by administering a Type 4 compound.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor α1D, α2A, α2B, serotonin receptor 5-HT2A, 5-HT6, 5HT7, histamine receptor H1 and/or H2 is desirable or expected to be desirable to improve cognitive functions. In some variations modulation of α1D, α2A, α2B adrenergic receptors and a serotonin 5-HT6 receptor is desirable or expected to be desirable to improve cognitive functions. In some variations, modulation of α1D, α2A, α2B adrenergic receptors and serotonin receptor 5-HT6 and modulation of one or more of the following receptors: serotonin receptor 5-HT7, 5-HT2A, 5-HT2C and histamine receptor H1 and H2, is desirable or expected to be desirable to improve cognitive functions. In another aspect, the invention encompasses methods to reduce psychotic effects by administering a compound of the invention to an individual in need thereof. In some embodiments, modulation of a dopamine D2L receptor is expected to be or is desirable to reduce psychotic effects. In some embodiments, modulation of a dopamine D2L receptor and a serotonin 5-HT2A receptor is expected to be or is desirable to reduce psychotic effects. In some variations, a Type 1 compound is administered to an individual in need thereof. In some variations, a Type 2 compound is administered to an individual in need thereof. In some variations, Type 3 compounds are administered to an individual in need thereof. In some variations, Type 4 compounds are administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein. In some variations, the compound of the invention is a Type 1 compound. In some variations, the compound of the invention is a Type 2 compound. In some variations, the compound of the invention is a Type 3 compound. In some variations, the compound of the invention is a Type 4 compound.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the compound of the invention is a Type 1 compound. In some variations, the compound of the invention is a Type 2 compound. In some variations, the compound of the invention is a Type 3 compound. In some variations, the compound of the invention is a Type 4 compound. In some variations, the aminergic G protein-coupled receptor is a α1D, α2A, α2B adrenergic receptor and a serotonin 5-HT6 receptor. In some variations, the aminergic G protein-coupled receptor is a α1D, α2A, α2B adrenergic receptor and a serotonin 5-HT6 and 5-HT7 receptor. In some variations, the aminergic G protein-coupled receptor is a α1D, α2A, α2B adrenergic receptor, a serotonin 5-HT6 and one or more of the following receptors: serotonin 5-HT-7, 5-HT2A and 5-HT2C and histamine H1 and H2 receptor. In some variations, the aminergic G protein-coupled receptor is a dopamine D2L receptor. In some variations, the aminergic G protein-coupled receptor is a dopamine D2L receptor and a serotonin 5-HT2A receptor. In some variations, the aminergic G protein-coupled receptor is a histamine H1 receptor.

Additional Methods

In one aspect, compounds 162x, 177x, 150x, 174x, 155x, 184x, 171x, 133x, 131x, 132x, 170x, 151x, 141x, 169x, 172x, 173x, or 168x are used to treat, prevent, delay the onset and/or delay the development of cognitive disorders. In one variation, compounds 162x, 177x, 150x, 174x, 155x, 184x, 171x, 133x, 131x, 132x, 170x, 151x, 141x, 169x, 172x, 173x, or 168x are used to treat, prevent, delay the onset and/or delay the development of psychotic disorders. In a further variation, compounds 162x, 177x, 150x, 174x, 155x, 184x, 171x, 133x, 131x, 132x, 170x, 151x, 141x, 169x, 172x, 173x, or 168x are used to treat, prevent, delay the onset and/or delay the development of neuronal indications. In a further variation, compounds 162x, 177x, 150x, 174x, 155x, 184x, 171x, 133x, 131x, 132x, 170x, 151x, 141x, 169x, 172x, 173x, or 168x are used to treat, prevent, delay the onset and/or delay the development of spinal cord injury, diabetic neuropathy, and diseases involving geroprotective activity.

In another aspect, compounds 152x, 137x, 139x, 159x or 165x are used to treat, prevent, delay the onset and/or delay the development of cognitive disorders. In one variation, compounds 152x, 137x, 139x, 159x and 165x are used to treat, prevent, delay the onset and/or delay the development of psychotic disorders. In a further variation, compounds 152x, 137x, 139x, 159x and 165x are used to treat, prevent, delay the onset and/or delay the development of neuronal indications. In a further variation, compounds 152x, 137x, 139x, 159x and 165x are used to treat, prevent, delay the onset and/or delay the development of spinal cord injury, diabetic neuropathy, and/or diseases involving geroprotective activity.

In a further aspect, compound 167 is used to treat, prevent, delay the onset and/or delay the development of cognitive disorders. In one variation, compound 167 is used to treat, prevent, delay the onset and/or delay the development of psychotic disorders. In a further variation, compound 167 is used to treat, prevent, delay the onset and/or delay the development of neuronal indications. In a further variation, compound 167 is used to treat, prevent, delay the onset and/or delay the development of neurotransmitter-mediated diseases except diseases mediated via serotonin.

In a further aspect, compounds 188x, 190x or 199x are used to treat, prevent, delay the onset and/or delay the development of cognitive disorders. In one variation, compounds 188x, 190x and 199x are used to treat, prevent, delay the onset and/or delay the development of psychotic disorders. In a further variation, compounds 188x, 190x and 199x are used to treat, prevent, delay the onset and/or delay the development of neurotransmitter-mediated disorders. In another variation, compounds 188x, 190x and 199x are used to treat, prevent, delay the onset and/or delay the development of neuronal indications.

In a further aspect, compound 134x is used to treat, prevent, delay the onset and/or delay the development of spinal cord injury, diabetic neuropathy, neuropathy associated with nerve injury, avulsion injury, myasthenia gravis, Guillain-Barre syndrome, multiple sclerosis, and fibromyalgia.

In another aspect, compound 178x is used to treat, prevent, delay the onset and/or delay the development of spinal cord injury, allergic diseases and diseases involving geroprotective activity. In one variation, compound 178x is used to treat, prevent, delay the onset and/or delay the development of avulsion injury, myasthenia gravis, Guillain-Barre syndrome, multiple sclerosis, and fibromyalgia.

In another aspect, compound 140x is used to treat, prevent, delay the onset and/or delay the development of spinal cord injury, diseases involving geroprotective activity, avulsion injury, myasthenia gravis, Guillain-Barre syndrome, multiple sclerosis, and/or fibromyalgia.

In a further aspect, compound 56x is used to treat, prevent, delay the onset and/or delay the development of spinal cord injury, allergic diseases, avulsion injury, myasthenia gravis, Guillain-Barre syndrome, multiple sclerosis, and fibromyalgia.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); Hour (h); Ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); Retention factor (Rf).

While certain solvents, temperatures and reaction times are shown herein by way of example, other variations are possible and one skilled in the art would optimize the conditions, for example, based on the choice of starting materials.

A method of synthesizing an intermediate used in the synthesis of compounds of the invention is shown as General Method 1.

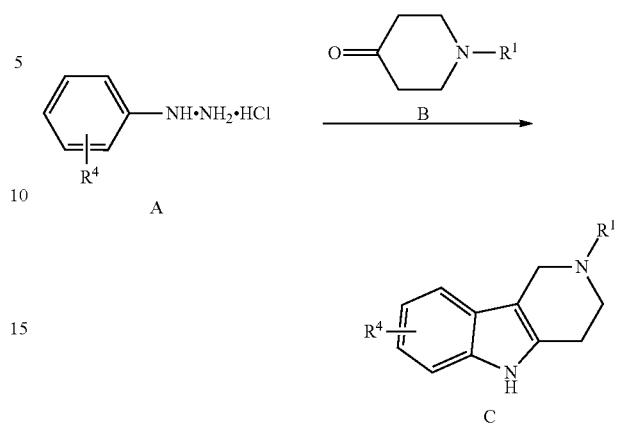

General Method 1.

Compound A (1 equiv) and compound B (0.76-1.4 equiv) are mixed in a suitable solvent such as EtOH and heated at 80° C. for 16 h (overnight) after which the solvent is removed in vacuo. The remaining residue is basified, e.g., with saturated aq. $NaHCO_3$. The aqueous layer is extracted with dichloromethane and the combined organic layers are dried over $Na_2SO_4$, concentrated in vacuo, and purified, e.g., by silica gel chromatography (230-400 mesh) using a suitable solvent gradient such as either a methanol-dichloromethane gradient or an ethyl acetate-hexane gradient.

A method of synthesizing certain compounds of the invention is shown in General Method 2.

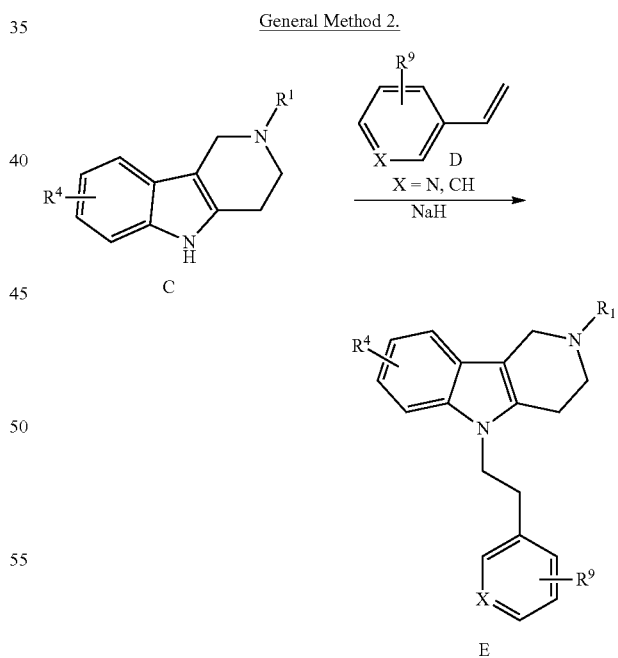

General Method 2.

Compound C (1 equiv), compound D (2-20 equiv) and NaH (1-20 equiv) are heated either in DMSO at 100-120° C. for 72 h or in DMF at 120-200° C. for 5-24 h. Contents are cooled to 25° C., quenched by careful addition of methanol or water, and evaporated to dryness under vacuo. The resulting crude product is purified, e.g., by silica gel chromatography (100-200 mesh or 230-400 mesh) by using methanol-dichloromethane gradient and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

A method of synthesizing compounds of the invention is shown in General Method 3.

General Method 3.

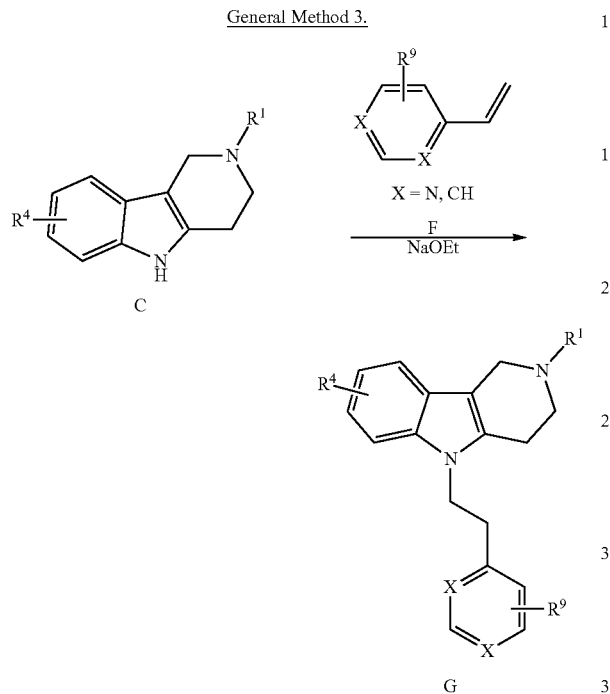

Compound C (1 equiv), compound F (2-20), sodium (0.2-0.8 equiv), and $CuSO_4$ (catalytic) are heated in EtOH at 120° C. for 16 h. The contents are evaporated to dryness under vacuo. Water is added and the contents are extracted with ethyl acetate, dried over anhydrous sodium sulfate, and concentrated. The resulting crude product is purified by reverse-phase chromatography (C-18, 500 mm×50 mm, Mobile Phase A=0.05% TFA in water, B=0.05% TFA in acetonitrile, Gradient: 10% B to 80% B in 30 min, injection vol: 5 mL) and/or silica gel (230-400 mesh) chromatography eluting with methanol-dichloromethane gradient.

A method of synthesizing certain compounds of the invention is shown in General Method 4.

General Method 4.

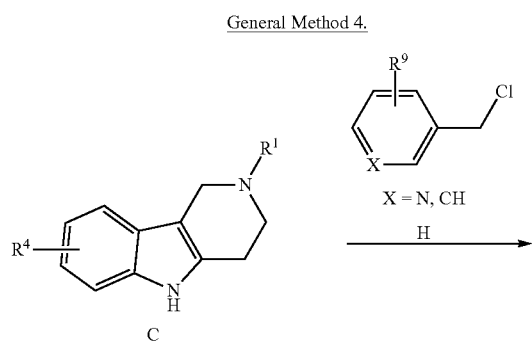

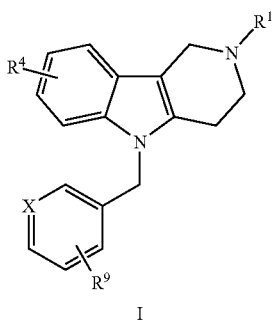

Compound C (1 equiv), compound H (2-10 equiv) and NaH (3 equiv) are heated in DMF 120° C. for 16 h. Contents are cooled to 25° C., quenched by careful addition of methanol or water and evaporated to dryness under vacuo. The resulting crude product is purified by silica gel chromatography (100-200 mesh or 230-400 mesh) by using methanol-dichloromethane gradient and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

A method of synthesizing certain compounds of the invention is shown in General Method 5.

General Method 5.

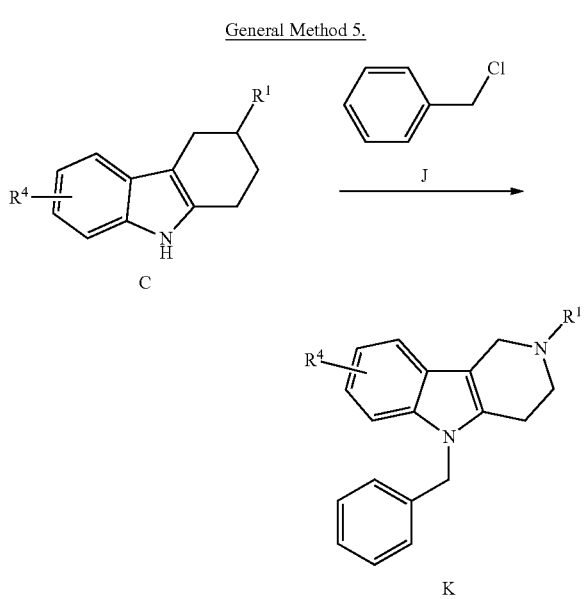

Compound C (1 equiv) and compound J (1.8-2.5 equiv) in diisopropylamine are heated at 80° C. for 12 h. The contents are basified with 1N NaOH and extracted with ethyl acetate. The organic layer was dried over sodium sulfate and concentrated. The resulting crude product is purified by silica gel chromatography (230-400 mesh) using methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

A method of synthesizing certain compounds of the invention is shown in General Method 6.

General Method 6.

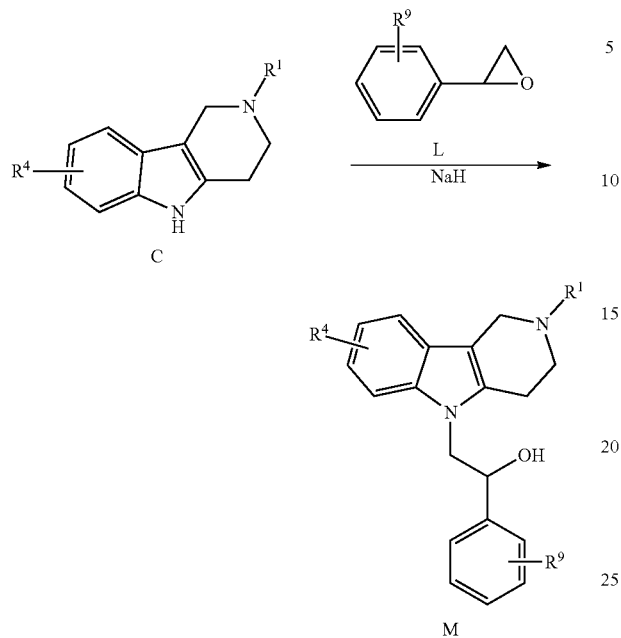

Compound C (1 equiv), compound L (4-7.5 equiv) and NaH (3 equiv) are heated in DMF at 120° C. for 16 h. The contents are quenched by methanol and evaporated to dryness. The resulting crude product is purified by silica gel chromatography (230-400 mesh) using methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

A method of synthesizing certain compounds of the invention is shown in General Method 7.

General Method 7.

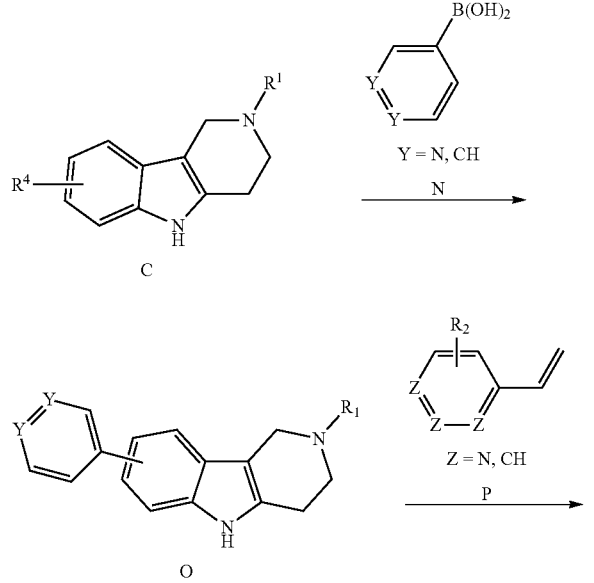

Compound C (1 equiv), compound N (2.05 equiv) and $K_3PO_4$ (1.9 equiv) in $DMF:H_2O$ (2:1) are purged with nitrogen for 30 minutes after which $PdCl_2(PPh_3)_2$ (25 mg, 0.04 mmol) is added and the contents are heated at 100° C. for 4 h. The contents are concentrated in vacuo and the crude product is purified by silica gel chromatography (230-400 mesh) to obtain compound O. The compound O (1 equiv), 2-methyl-5-vinylpyridine (12-15 equiv) and NaH (3-4 equiv) are heated in DMSO at 100° C. for 48 h. The contents are quenched by methanol and evaporated to dryness. The resulting crude product is purified by silica gel chromatography (230-400 mesh) using methanol-dichloromethane gradient to obtain compound Q.

A method of synthesizing compounds of the invention is shown in General Method 8.

General Method 8.

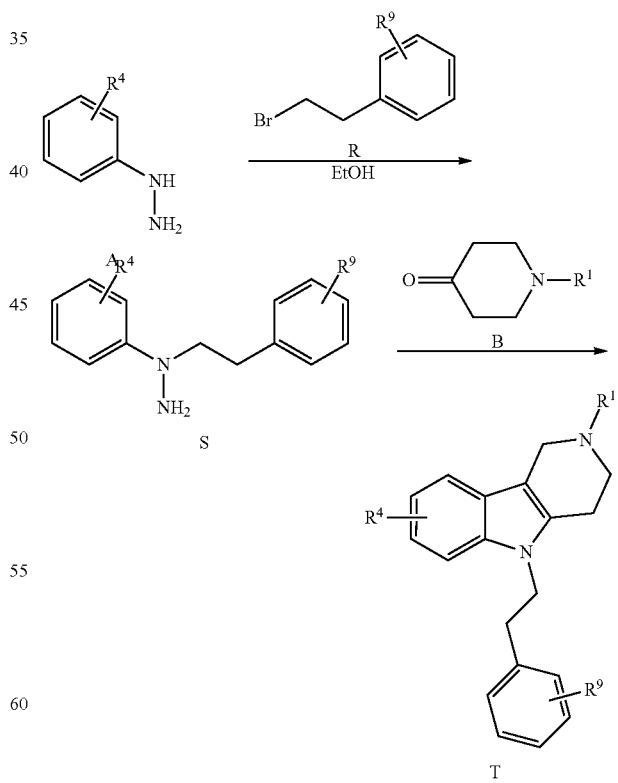

Compound A (1 equiv), triethyl amine (1 equiv) and compound R (1 equiv) are dissolved in EtOH and heated at 80° C. for 2 h after which compound B (1 to 1.5 equiv) is added and the contents are heated at 80° C. for additional 16 h. Solvent is removed in vacuo. The remaining residue is diluted with EtOAc and washed with saturated aq. NaHCO$_3$. The aqueous layer is extracted twice with ethyl acetate and combined organic layer is dried over Na$_2$SO$_4$, and concentrated. The resulting crude product was purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

A method of synthesizing compounds of the invention is shown in General Method 9.

A method of synthesizing certain compounds of the invention is shown in General Method 10.

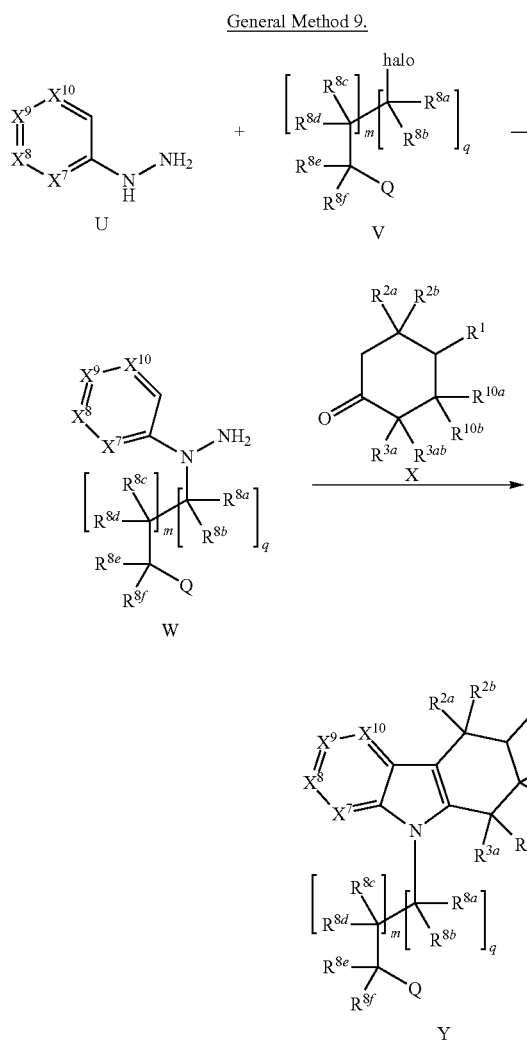

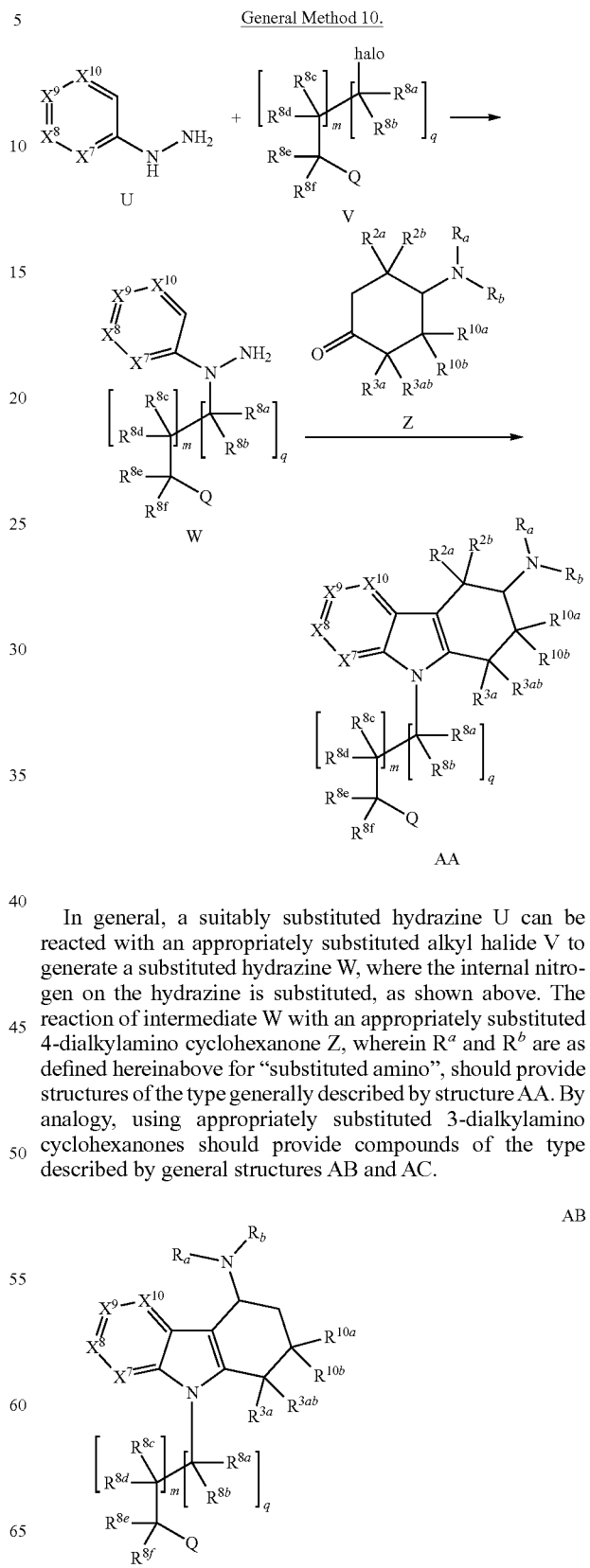

In general, a suitably substituted hydrazine U can be reacted with an appropriately substituted alkyl halide V to generate a substituted hydrazine W, where the internal nitrogen on the hydrazine is substituted, as shown above. The reaction of intermediate W with an appropriately substituted cyclohexanone X should provide structures of the type generally described by structure Y.

In general, a suitably substituted hydrazine U can be reacted with an appropriately substituted alkyl halide V to generate a substituted hydrazine W, where the internal nitrogen on the hydrazine is substituted, as shown above. The reaction of intermediate W with an appropriately substituted 4-dialkylamino cyclohexanone Z, wherein R$^a$ and R$^b$ are as defined hereinabove for "substituted amino", should provide structures of the type generally described by structure AA. By analogy, using appropriately substituted 3-dialkylamino cyclohexanones should provide compounds of the type described by general structures AB and AC.

-continued

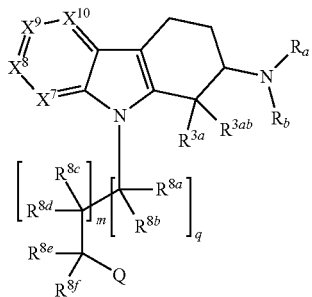

Reference: Journal of Medicinal Chemistry, 1977, Volume 20, Number 4, page 487-492.

A method of synthesizing an intermediate used in the synthesis of certain compounds of the invention is shown as General Method 11.

General Method 11.

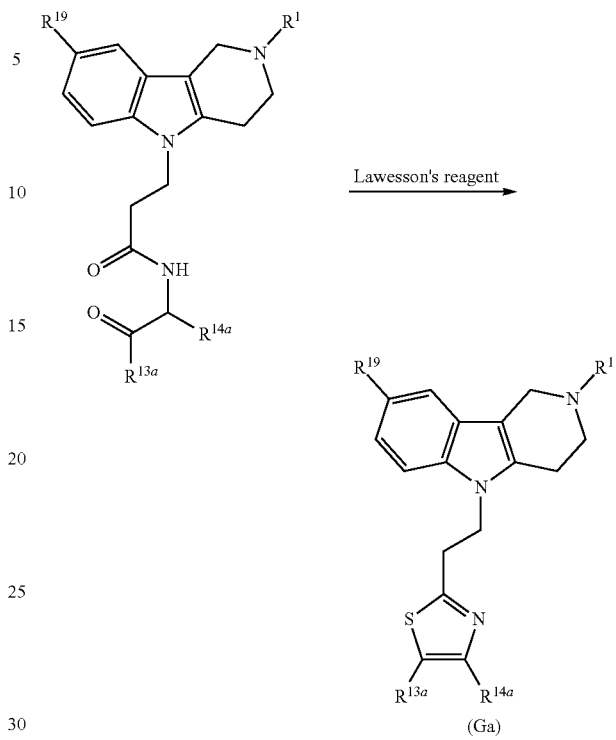

General Method 12.

Reaction of the N-(2-oxoethyl)amide shown above with Lawesson's reagent (2,4-bis(4-methoxyphenyl)-1,3,2,4-dithiadiphosphetane-2,4-disulfide) should provide entry into compounds of Formula Ga.

See: Helvetica Chimica Acta, 2001, Volume 84, page 2347-2354.

A method of synthesizing certain compounds of the invention is shown in General Method 13.

General Method 13.

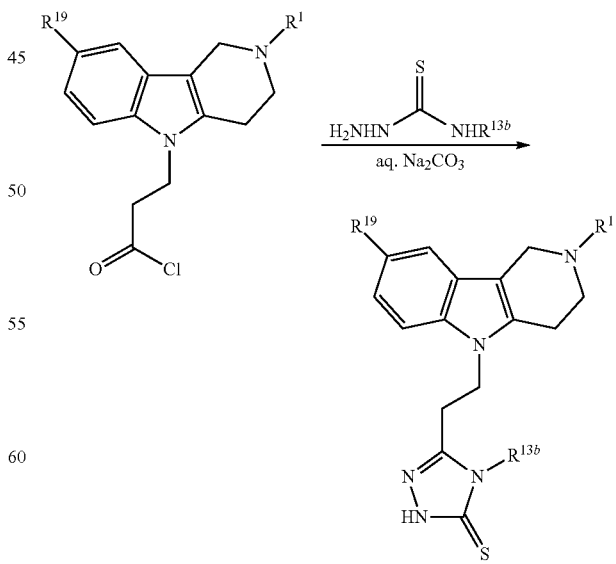

See: Helvetica Chimica Acta, 2001, Volume 84, page 2347-2354.

A method of synthesizing certain compounds of the invention is shown in General Method 12.

Reaction of the acid chloride shown above with thiosemi-carbazides (containing R[13b]) followed by heating in the presence of aqueous sodium bicarbonate should allow for entry into compounds of Formula Gb.

A method of synthesizing certain compounds of the invention is shown in General Method 14.

General Method 14.

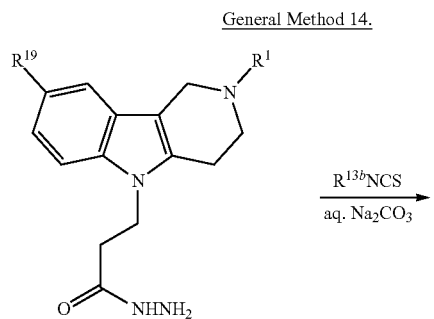

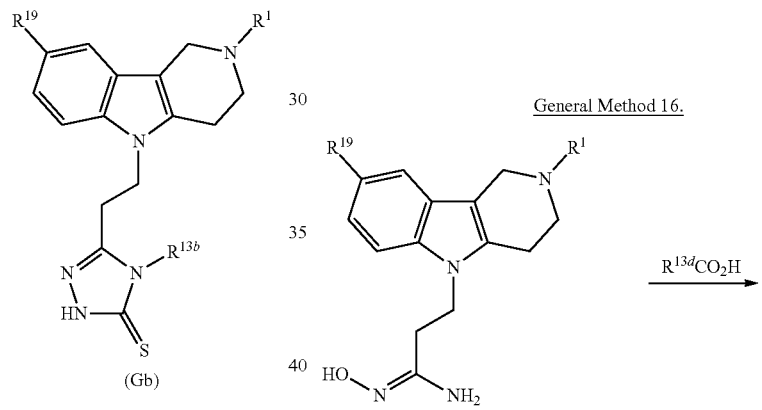

(Gb)

Reaction of the acyl hydrazine shown above with different alkyl isothiocyanates (containing R[13b]), followed by heating in the presence of aqueous sodium bicarbonate should allow for entry into compounds of Formula Gb.

See: Journal of Medicinal Chemistry, 1994, Volume 37, pp 125-132.

A method of synthesizing certain compounds of the invention is shown in General Method 15.

General Method 15.

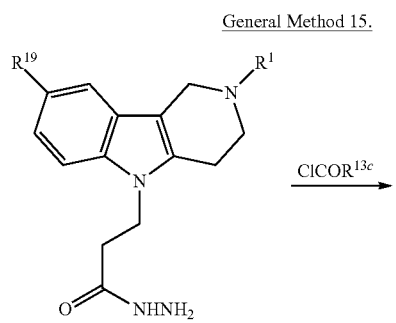

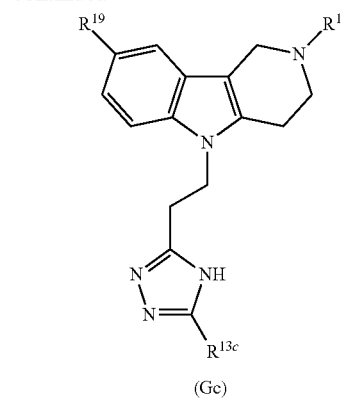

(Gc)

Reaction of the acyl hydrazine shown above with acid chlorides, either alkyl, aryl or heteroaryl, should allow for entry into compounds of Formula Gc.

See: Synlett, 2005, No. 17, pp 2595-2598.

A method of synthesizing certain compounds of the invention is shown in General Method 16.

General Method 16.

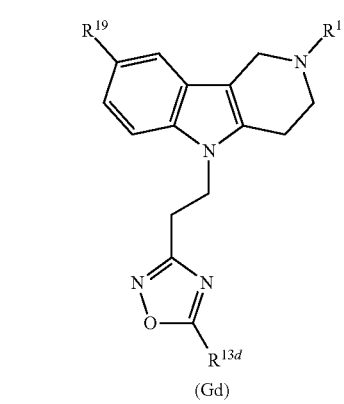

(Gd)

Reaction of the hydroxyamidine shown above with different aromatic and heteroaromatic acids, should allow for entry into compounds of Formula Gd.

See: Tetrahedron Letters, 2006, 47, pp 2965-2967.

A method of synthesizing certain compounds of the invention is shown in General Method 17.

General Method 17.

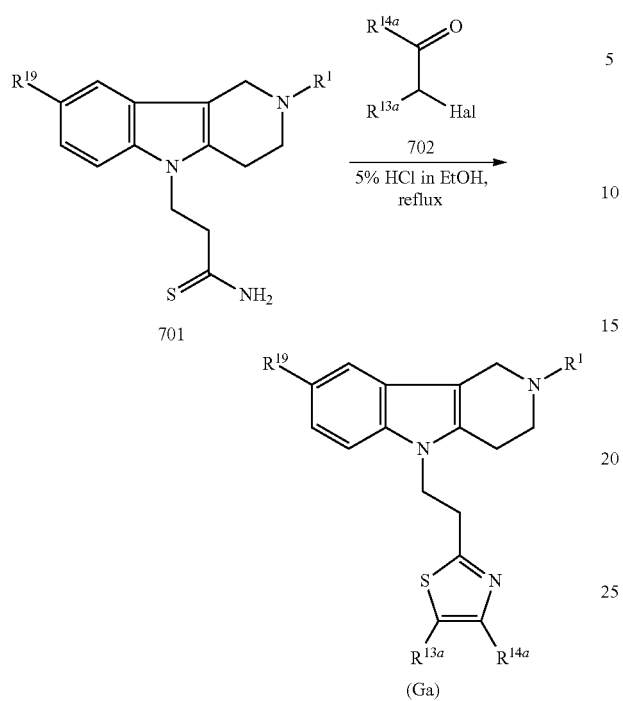

Reaction of about a 1:1 mixture of starting materials 701 and 702 in an alcohol solvent, for example, ethanol, containing an acid, for example, 5% hydrogen chloride in ethanol, at reflux should allow entry into compounds of Formula Ga. Hal is halo, for example, chloro or bromo, and $R^1$, $R^{19}$, $R^{13a}$, and $R^{14a}$, are defined as hereinabove.

A method of synthesizing certain compounds of the invention is shown in General Method 18.

General Method 18.

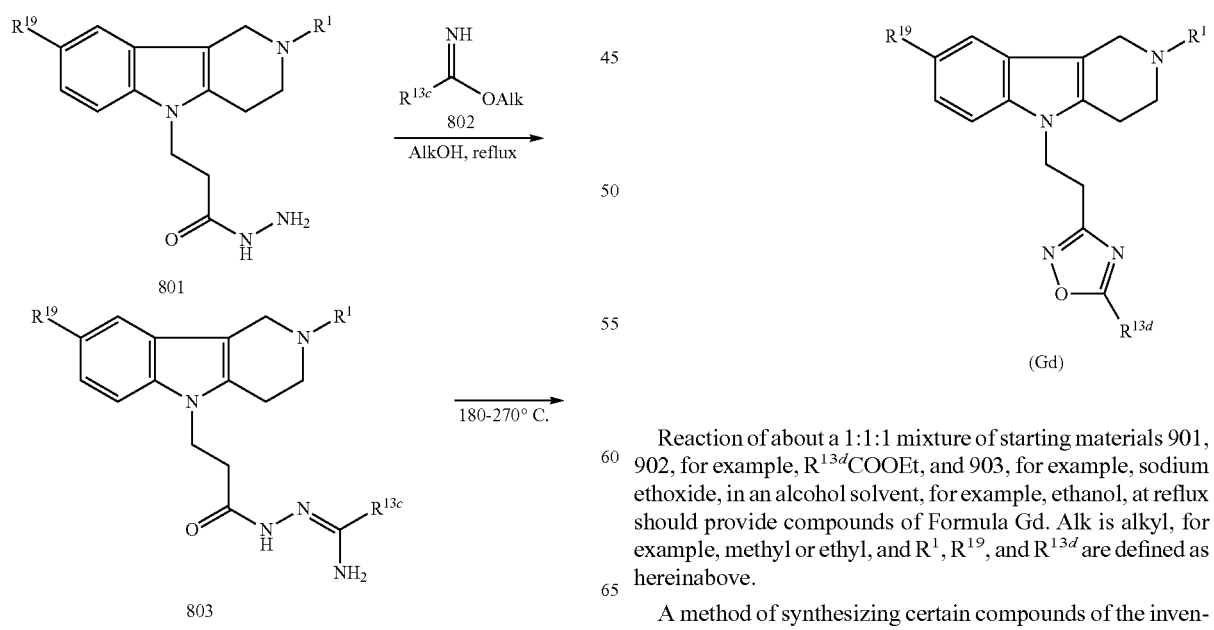

Reaction of about a 1:1 mixture of starting materials 801 and 802 in an alcohol solvent, for example, methanol or ethanol, at reflux should provide intermediate compounds such as 803. Subsequent heating of 803 at about 180-270° C. should allow entry into compounds of Formula Gc. Alk is alkyl, for example, methyl or ethyl, and $R^1$, $R^{19}$, and $R^{13c}$ are defined as hereinabove.

A method of synthesizing certain compounds of the invention is shown in General Method 19.

General Method 19.

Reaction of about a 1:1:1 mixture of starting materials 901, 902, for example, $R^{13d}$COOEt, and 903, for example, sodium ethoxide, in an alcohol solvent, for example, ethanol, at reflux should provide compounds of Formula Gd. Alk is alkyl, for example, methyl or ethyl, and $R^1$, $R^{19}$, and $R^{13d}$ are defined as hereinabove.

A method of synthesizing certain compounds of the invention is shown in General Method 20.

General Method 20.

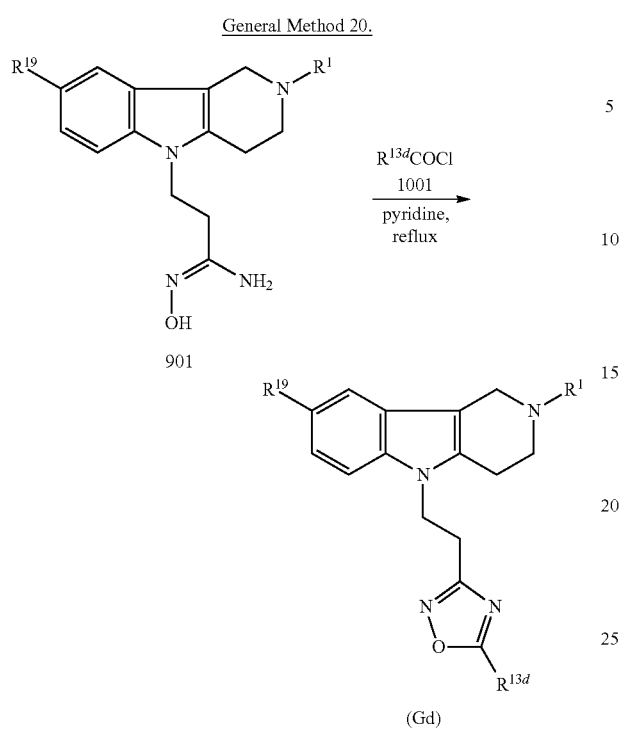

Reaction of about a 1:1-1.3 mixture of starting materials 901 and 1001 in a basic organic solvent, for example, pyridine, at reflux should provide compounds of Formula Gd. $R^1$, $R^{19}$, and $R^{13d}$ are defined as hereinabove.

A method of synthesizing certain compounds of the invention is shown in General Method 21.

General Method 21.

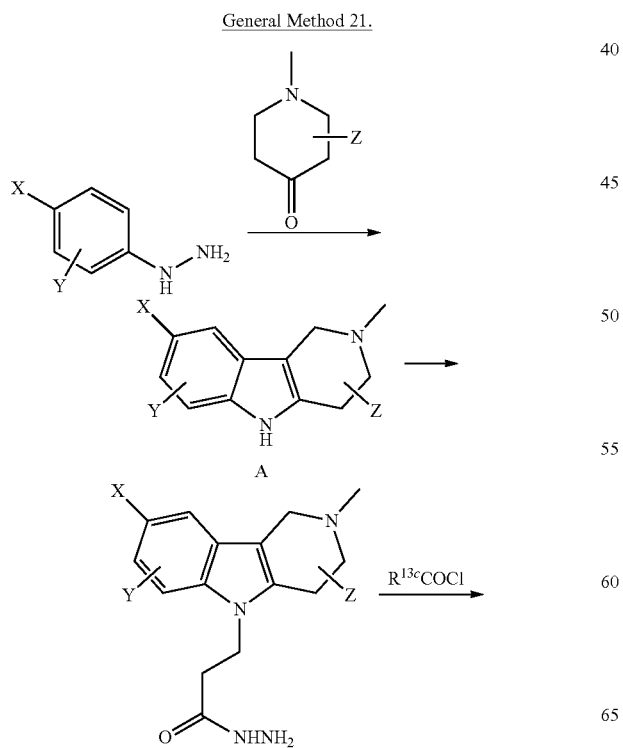

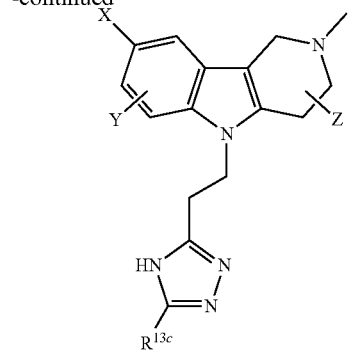

Compounds 59H, 61H, 90H and 109H are synthesized according to General Method 21.

A method of synthesizing certain compounds of the invention is shown in General Method 22.

General Method 22.

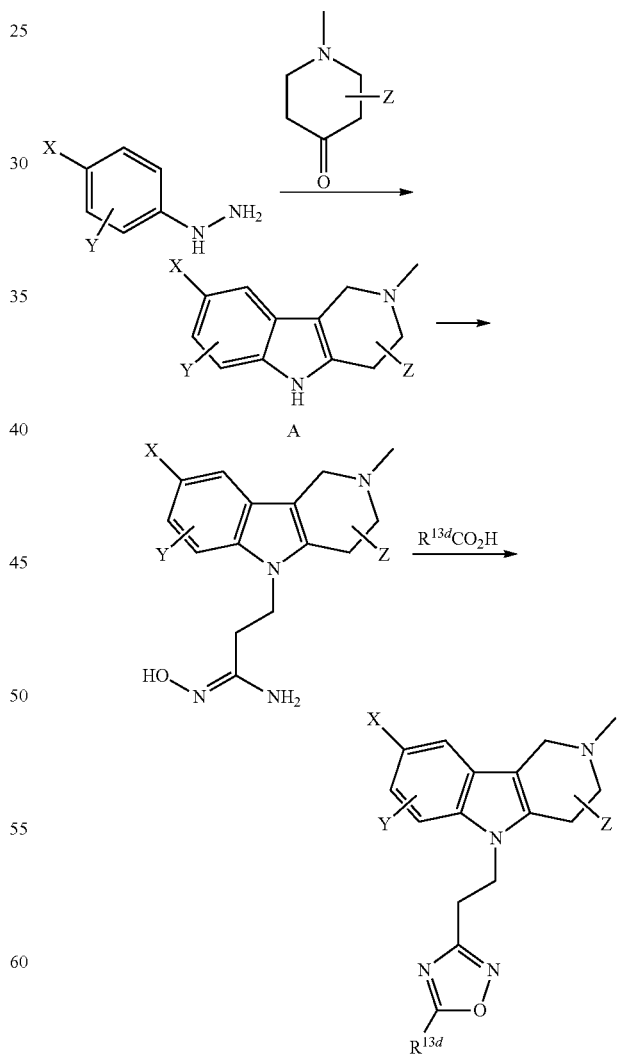

Compounds 222H, 223H, 234H and 242H are synthesized according to General Method 22.

A method of synthesizing certain compounds of the invention is shown in General Method 23.

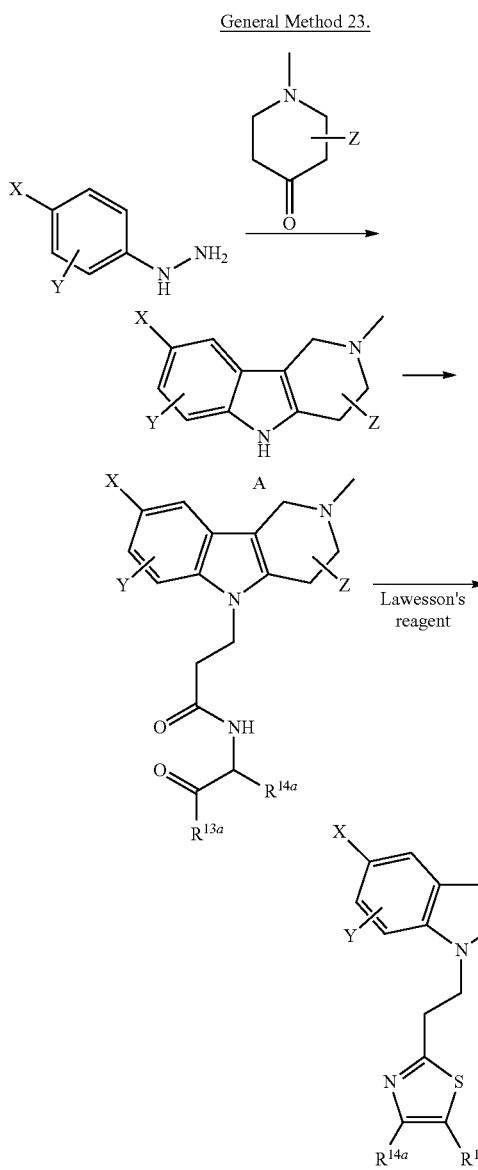

Compounds 9H, 38H, 39H and 40H are synthesized according to General Method 23.

A method of synthesizing certain compounds of the invention is shown in General Method 24.

General Method 24.

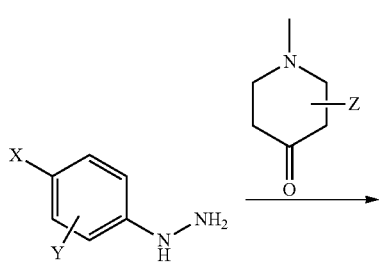

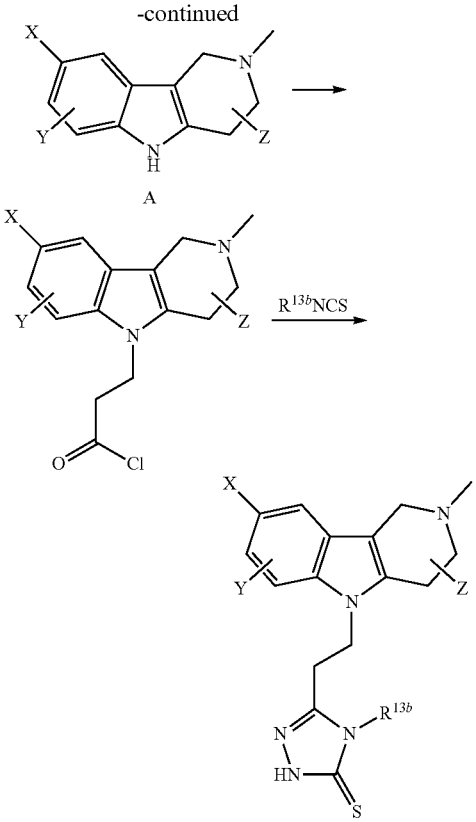

Compounds 151H, 218H, 219H and 220H are synthesized according to General Method 24.

The methods detailed above may be adapted as known by those of skill in the art. Particular examples of each General Method are provided in the Examples below.

The following Examples are provided to illustrate but not limit the invention.

All references disclosed herein are incorporated by reference in their entireties.

EXAMPLES

Example 1

Preparation of 2,3,4,5-tetrahydro-2,8-dimethyl-1H-pyrido[4,3-b]indole

Preparation of 2,3,4,5-tetrahydro-2,8-dimethyl-1H-pyrido [4,3-b]indole was carried out according to General Method 1. Specifically, 4-methylphenylhydrazine hydrochloride (5 g, 31.5 mmol) and N-methyl-4-piperidone hydrochloride (3.6 g, 24 mmol) were mixed in EtOH (150 mL) and heated at 80° C. for 16 h (overnight) after which the solvent was removed in vacuo. The remaining residue was basified with saturated aq. NaHCO$_3$. The aqueous layer was extracted with dichloromethane and the combined organic layers were dried over Na$_2$SO$_4$, concentrated in vacuo, and purified by silica gel chromatography (230-400 mesh) using a methanol-dichloromethane gradient to obtain the 4.1 g (65% yield) of 2,3,4,5-tetrahydro-2,8-dimethyl-1H-pyrido[4,3-b]indole. TLC (Merck silica gel 60F-254) Rf=0.1 (10% MeOH in DCM).

Example 2

Preparation of 8-bromo-2,3,4,5-tetrahydro-2-methyl-1H-pyrido[4,3-b]indole

Preparation of 8-bromo-2,3,4,5-tetrahydro-2-methyl-1H-pyrido[4,3-b]indole was carried out according to General Method 1 using 4-bromophenylhydrazine hydrochloride (10 g, 44.7 mmol) and N-methyl-4-piperidone hydrochloride (9.3 g, 62.6 mmol) in EtOH (400 mL) to obtain 2.5 g (21% yield) of 8-bromo-2,3,4,5-tetrahydro-2-methyl-1H-pyrido[4,3-b]indole after purification.

Example 3

Preparation of 2,3,4,5-tetrahydro-2-methyl-1H-pyrido[4,3-b]indole

Preparation of 2,3,4,5-tetrahydro-2-methyl-1H-pyrido[4,3-b]indole was carried out according to General Method 1 using phenylhydrazine hydrochloride (5 g, 34.6 mmol) and N-methyl-4-piperidone hydrochloride (7.2 g, 48.4 mmol) in EtOH (200 mL) to obtain 3.75 g (58.3% yield) of 2,3,4,5-tetrahydro-2-methyl-1H-pyrido[4,3-b]indole after purification.

Example 4

Preparation of 8-chloro-2,3,4,5-tetrahydro-2-methyl-1H-pyrido[4,3-b]indole

Preparation of 8-chloro-2,3,4,5-tetrahydro-2-methyl-1H-pyrido[4,3-b]indole was carried out according to General Method 1 using 4-chlorophenylhydrazine hydrochloride (10 g, 55.8 mmol) and N-methyl-4-piperidone hydrochloride (11.68 g, 78.19 mmol) in EtOH (400 mL) to obtain 3.1 g (25% yield) of 8-chloro-2,3,4,5-tetrahydro-2-methyl-1H-pyrido[4,3-b]indole after purification.

Example 5

Preparation of 2-ethyl-2,3,4,5-tetrahydro-1H-pyrido[4,3-b]indole

Preparation of 2-ethyl-2,3,4,5-tetrahydro-1H-pyrido[4,3-b]indole was carried out according to General Method 1, using phenylhydrazine hydrochloride (3.4 g, 23.5 mmol) and N-ethyl-4-piperidone hydrochloride (5.3 g, 32.9 mmol) in EtOH (150 mL) to obtain 1.4 g (30% yield) of 2-ethyl-2,3,4,5-tetrahydro-1H-pyrido[4,3-b]indole after purification.

Example 6

Preparation of 2-ethyl-2,3,4,5-tetrahydro-8-methyl-1H-pyrido[4,3-b]indole

Preparation of 2-ethyl-2,3,4,5-tetrahydro-8-methyl-1H-pyrido[4,3-b]indole was carried out according to General Method 1, using 4-methylphenylhydrazine hydrochloride (5 g, 31.5 mmol) and N-ethyl-4-piperidone hydrochloride (4 g, 24.5 mmol) in EtOH (150 mL) to obtain 4.8 g (71% yield) of 2-ethyl-2,3,4,5-tetrahydro-8-methyl-1H-pyrido[4,3-b]indole after purification.

Example 7

Preparation of ethyl 8-bromo-3,4-dihydro-1H-pyrido[4,3-b]indole-2(5H)-carboxylate Preparation of ethyl 8-bromo-3,4-dihydro-1H-pyrido[4,3-b]indole-2(5H)-carboxylate was carried out according to General Method 1 using 4-bromophenylhydrazine hydrochloride (447 mg, 2 mmol) and N-carbethoxy-4-piperidone (342 mg, 2 mmol) in EtOH (10 mL) to obtain 423 mg (65% yield) of ethyl 8-bromo-3,4-dihydro-1H-pyrido[4,3-b]indole-2(5H)-carboxylate after purification.

Example 8

Preparation of ethyl 8-methyl-3,4-dihydro-1H-pyrido[4,3-b]indole-2(5H)-carboxylate Preparation of ethyl 8-methyl-3,4-dihydro-1H-pyrido[4,3-b]indole-2(5H)-carboxylate was carried out according to General Method 1 using 4-methylphenylhydrazine hydrochloride (317 mg, 2 mmol) and N-carbethoxy-4-piperidone (342 mg, 2 mmol) in EtOH (10 mL) to obtain 340 mg (65% yield) of 8-methyl-3,4-dihydro-1H-pyrido[4,3-b]indole-2(5H)-carboxylate after purification.

Example 9

Preparation of 2,3,4,5-tetrahydro-2,8-dimethyl-5-(4-methylphenethyl)-1H-pyrido[4,3-b]indole. (Compound 25)

Preparation of 2,3,4,5-tetrahydro-2,8-dimethyl-5-(4-methylphenethyl)-1H-pyrido[4,3-b]indole was carried out according to General Method 2. 2,3,4,5-tetrahydro-2,8-dimethyl-1H-pyrido[4,3-b]indole (See Example 1) (200 mg, 1 mmol), 4-methylstyrene (239 mg, 2.3 mmol) and NaH (120 mg, 60% dispersion in oil, 3 mmol) were heated in DMSO (4 ml) at 120° C. overnight (16 h) after which methanol was added and the contents were concentrated to dryness. The resulting crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol: 5 mL) and/or silica gel (230-400 mesh) chromatography eluting with methanol-dichloromethane gradient to obtain 20 mg (6.2% yield) of 2,3,4,5-tetrahydro-2,8-dimethyl-5-(4-methylphenethyl)-1H-pyrido[4,3-b]indole as a trifluoroacetate salt.

Example 10

Preparation of ethyl 8-bromo-3,4-dihydro-5-(2-(6-methylpyridin-3-yl)ethyl)-1H-pyrido[4,3-b]indole-2(5H)-carboxylate. (Compound 18)

Preparation of ethyl 8-bromo-3,4-dihydro-5-(2-(6-methylpyridin-3-yl)ethyl)-1H-pyrido[4,3-b]indole-2(5H)-carboxylate was carried out according to General Method 2. The title compound was prepared from ethyl 8-bromo-3,4-dihydro-1H-pyrido[4,3-b]indole-2(5H)-carboxylate (See Example 7) (25 mg, 0.056 mmol), 2-methyl-5-vinyl pyridine (0.12 mL) and NaH (10 mg, 60% dispersion in oil, 0.25 mmol) in DMSO (0.3 ml) to obtain 4.5 mg of ethyl 8-bromo-3,4-dihydro-5-(2-(6-methylpyridin-3-yl)ethyl)-1H-pyrido[4,3-b]indole-2(5H)-carboxylate after purification.

Example 11

Preparation of ethyl 3,4-dihydro-8-methyl-5-phenethyl-1H-pyrido[4,3-b]indole-2(5H)-carboxylate. (Compound 24)

The title compound was prepared according to General Method 2. Ethyl 3,4-dihydro-8-methyl-5-phenethyl-1H-pyrido[4,3-b]indole-2(5H)-carboxylate was prepared from ethyl 8-methyl-3,4-dihydro-1H-pyrido[4,3-b]indole-2(5H)-carboxylate (See Example 8) (257 mg, 1 mmol), styrene (239 mg, 2.3 mmol) and NaH (120 mg, 60% dispersion in oil, 3 mmol) in DMSO (5 ml) at 120° C. for overnight (16 h) to obtain 15 mg of ethyl 3,4-dihydro-8-methyl-5-phenethyl-1H-pyrido[4,3-b]indole-2(5H)-carboxylate after purification.

Example 12

Preparation of 2-ethyl-2,3,4,5-tetrahydro-8-methyl-5-phenethyl-1H-pyrido[4,3-b]indole. (Compound 37)

The title compound was prepared according to General Method 2. 2-Ethyl-2,3,4,5-tetrahydro-8-methyl-5-phenethyl-1H-pyrido[4,3-b]indole was prepared from 2-ethyl-2,3,4,5-tetrahydro-8-methyl-1H-pyrido[4,3-b]indole (See Example 6) (100 mg, 0.46 mmol), styrene (1 mL, 8.41 mmol) and NaH (200 mg, 60% dispersion in oil, 8.30 mmol) in DMF (3 ml) at 200° C. for 5 h to obtain 15 mg (4.7% yield) of 2-ethyl-2,3,4,5-tetrahydro-8-methyl-5-phenethyl-1H-pyrido[4,3-b]indole.

Example 13

Preparation of 2-ethyl-2,3,4,5-tetrahydro-8-methyl-5-(4-methylphenethyl)-1H-pyrido[4,3-b]indole. (Compound 26)

The title compound was prepared according to General Method 2. 2-Ethyl-2,3,4,5-tetrahydro-8-methyl-5-(4-methylphenethyl)-1H-pyrido[4,3-b]indole was prepared from 2-ethyl-2,3,4,5-tetrahydro-8-methyl-1H-pyrido[4,3-b]indole (See Example 6) (100 mg, 0.4 mmol), 4-methylstyrene (1 mL, 7.6 mmol) and NaH (100 mg, 60% dispersion in oil, 2.5 mmol) in DMF (2 ml) at 180° C. for 24 h to obtain 13 mg of 2-ethyl-2,3,4,5-tetrahydro-8-methyl-5-(4-methylphenethyl)-1H-pyrido[4,3-b]indole after purification.

Example 14

Preparation of 2,3,4,5-tetrahydro-2-methyl-5-(4-methylphenethyl)-1H-pyrido[4,3-b]indole. (Compound 1)

The title compound was prepared according to General Method 2. 2,3,4,5-tetrahydro-2-methyl-5-(4-methylphenethyl)-1H-pyrido[4,3-b]indole was prepared from 2,3,4,5-tetrahydro-2-methyl-1H-pyrido[4,3-b]indole (See Example 3) (200 mg, 1.07 mmol), 4-methylstyrene (1.41 mL, 10.7 mmol) and NaH (250 mg, 60% dispersion in oil, 6.25 mmol) in DMF (6 ml) at 200° C. for 16 h to obtain 7 mg of 2,3,4,5-tetrahydro-2-methyl-5-(4-methylphenethyl)-1H-pyrido[4,3-b]indole after purification.

Example 15

Preparation of 2,3,4,5-tetrahydro-2-methyl-5-phenethyl-1H-pyrido[4,3-b]indole. (Compound 2)

The title compound was prepared according to General Method 2. 2,3,4,5-Tetrahydro-2-methyl-5-phenethyl-1H-pyrido[4,3-b]indole was prepared from 2,3,4,5-tetrahydro-2-methyl-1H-pyrido[4,3-b]indole (200 mg, 1.07), styrene (1.23 mL mmol, 10.65) and NaH (250 mg, 6.25 mmol) in DMF (6 ml) at 200° C. for 16 h to obtain 15 mg of 2,3,4,5-tetrahydro-2-methyl-5-phenethyl-1H-pyrido[4,3-b]indole after purification.

Example 16

Preparation of 2-ethyl-2,3,4,5-tetrahydro-5-phenethyl-1H-pyrido[4,3-b]indole. (Compound 4)

The title compound was prepared according to General Method 2. 2-Ethyl-2,3,4,5-tetrahydro-5-phenethyl-1H-pyrido[4,3-b]indole was prepared from 2-ethyl-2,3,4,5-tetrahydro-1H-pyrido[4,3-b]indole (See Example 5) (100 mg, 0.5 mmol), styrene (1 mL, 8.64 mmol) and NaH (200 mg, 5 mmol) in DMF (4 ml) at 150° C. for 16 h to obtain 15 mg of 2-ethyl-2,3,4,5-tetrahydro-5-phenethyl-1H-pyrido[4,3-b]indole after purification.

Example 17

Preparation of 2-ethyl-2,3,4,5-tetrahydro-5-(4-methylphenethyl)-1H-pyrido[4,3-b]indole. (Compound 3)

The title compound was prepared according to General Method 2. 2-Ethyl-2,3,4,5-tetrahydro-5-(4-methylphenethyl)-1H-pyrido[4,3-b]indole was prepared from 2-ethyl-2,3,4,5-tetrahydro-1H-pyrido[4,3-b]indole (See Example 5) (100 mg, 0.5 mmol), 4-methylstyrene (1 mL, 6.72 mmol) and NaH (200 mg, 5 mmol) in DMF (4 ml) at 150° C. for 16 h to obtain 16 mg of 2-ethyl-2,3,4,5-tetrahydro-5-(4-methylphenethyl)-1H-pyrido[4,3-b]indole after purification.

Example 18

Preparation of 2-ethyl-2,3,4,5-tetrahydro-8-methyl-5-(2-(6-methylpyridin-3-yl)ethyl)-1H-pyrido[4,3-b]indole. (Compound 31)

Preparation of the title compound was carried out according to General Method 2. 2-Ethyl-2,3,4,5-tetrahydro-8-methyl-5-(2-(6-methylpyridin-3-yl)ethyl)-1H-pyrido[4,3-b]indole was prepared from 2-ethyl-2,3,4,5-tetrahydro-8-methyl-1H-pyrido[4,3-b]indole (See Example 6) (214 mg, 1 mmol), 2-methyl-5-vinylpyridine (1 mL, 2.3 mmol) and NaH (120 mg, 3 mmol) in DMSO (4 ml) at 120° C. for 48 h to obtain 10 mg of 2-ethyl-2,3,4,5-tetrahydro-8-methyl-5-(2-(6-methylpyridin-3-yl)ethyl)-1H-pyrido[4,3-b]indole after purification.

Example 19

Preparation of 5-(4-chlorophenethyl)-2,3,4,5-tetrahydro-2,8-dimethyl-1H-pyrido[4,3-b]indole. (Compound 32)

The title compound was prepared according to General Method 2. 5-(4-Chlorophenethyl)-2,3,4,5-tetrahydro-2,8- dimethyl-1H-pyrido[4,3-b]indole was prepared from 2,3,4,5-tetrahydro-2,8-dimethyl-1H-pyrido[4,3-b]indole (See Example 1) (500 mg, 2.5 mmol), 4-chlorostyrene (3.18 mL, 25 mmol) and NaH (300 mg, 7.5 mmol) in DMF (10 ml) at 180° C. for overnight (16 h) to obtain 15 mg of 5-(4-chlorophenethyl)-2,3,4,5-tetrahydro-2,8-dimethyl-1H-pyrido[4,3-b]indole after purification.

Example 20

Preparation of 2,3,4,5-tetrahydro-2,8-dimethyl-5-(2-(pyridin-2-yl)ethyl)-1H-pyrido[4,3-b]indole. (Compound 21)

The title compound was prepared according to General Method 3. 2,3,4,5-Tetrahydro-2,8-dimethyl-1H-pyrido[4,3-b]indole (See Example 1) (400 mg, 2 mmol), 2-vinylpyridine (500 mg, 5 mmol), sodium (30 mg, 1.3 g atom), and CuSO$_4$ (20 mg, catalytic) were heated in EtOH (8 mL) at 150° C. overnight (16 h). The contents were evaporated to dryness under vacuo. Water was added and the contents were extracted with ethyl acetate, dried over anhydrous sodium sulfate, and concentrated. The resulting crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 15 mg of 2,3,4,5-tetrahydro-2,8-dimethyl-5-(2-(pyridin-2-yl)ethyl)-1H-pyrido[4,3-b]indole as a trifluoroacetate salt.

Example 21

Preparation of 2,3,4,5-tetrahydro-2,8-dimethyl-5-(2-(pyridin-4-yl)ethyl)-1H-pyrido[4,3-b]indole. (Compound 22)

The title compound was prepared according to General Method 3. 2,3,4,5-Tetrahydro-2,8-dimethyl-5-(2-(pyridin-4-yl)ethyl)-1H-pyrido[4,3-b]indole was prepared from 2,3,4,5-tetrahydro-2,8-dimethyl-1H-pyrido[4,3-b]indole (See Example 1) (100 mg, 0.5 mmol), 4-vinylpyridine (120 mg, 1.14 mmol) and sodium (5 mg, 0.21 g atom) in ethanol (1 mL) at 120° C. for 16 h to obtain 4.5 mg of 2,3,4,5-tetrahydro-2,8-dimethyl-5-(2-(pyridin-4-yl)ethyl)-1H-pyrido[4,3-b]indole after purification on silica gel (230-400 mesh) chromatography eluting with methanol-dichloromethane gradient.

Example 22

Preparation of 2-ethyl-2,3,4,5-tetrahydro-8-methyl-5-(2-(pyridin-2-yl)ethyl)-1H-pyrido[4,3-b]indole. (Compound 23)

The title compound was prepared according to General Method 3. 2-Ethyl-2,3,4,5-tetrahydro-8-methyl-5-(2-(pyridin-2-yl)ethyl)-1H-pyrido[4,3-b]indole was prepared from 2-ethyl-2,3,4,5-tetrahydro-8-methyl-1H-pyrido[4,3-b]indole (See Example 6) (214 mg, 1 mmol), 2-vinylpyridine (0.25 ml, 2.3 mmol), sodium (15 mg, 0.65 g atom) and CuSO$_4$ (10 mg, catalytic) in ethanol (2 mL) at 120° C. for 48 h to obtain 15 mg of 2-ethyl-2,3,4,5-tetrahydro-8-methyl-5-(2-(pyridin-2-yl)ethyl)-1H-pyrido[4,3-b]indole as a trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 23

Preparation of 2-ethyl-2,3,4,5-tetrahydro-8-methyl-5-(2-(pyridin-4-yl)ethyl)-1H-pyrido[4,3-b]indole. (Compound 27)

The title compound was prepared according to General Method 3. 2-Ethyl-2,3,4,5-tetrahydro-8-methyl-5-(2-(pyridin-4-yl)ethyl)-1H-pyrido[4,3-b]indole was prepared from 2-ethyl-2,3,4,5-tetrahydro-8-methyl-1H-pyrido[4,3-b]indole (See Example 6) (214 mg, 1 mmol), 4-vinylpyridine (0.25 ml, 2.3 mmol), sodium (15 mg, 0.65 g atom) and CuSO$_4$ (10 mg, catalytic) in ethanol (2 mL) at 120° C. for overnight (16 h) to obtain 6 mg of 2-ethyl-2,3,4,5-tetrahydro-8-methyl-5-(2-(pyridin-4-yl)ethyl)-1H-pyrido[4,3-b]indole as a trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 24

Preparation of 2-ethyl-2,3,4,5-tetrahydro-5-(4-pyridyl)-1H-pyrido[4,3-b]indole. (Compound 5)

The title compound was prepared according to General Method 3. 2-Ethyl-2,3,4,5-tetrahydro-5-(4-pyridyl)-1H-pyrido[4,3-b]indole was prepared from 2-ethyl-2,3,4,5-tetrahydro-1H-pyrido[4,3-b]indole (See Example 5) (200 mg, 1 mmol), 4-vinylpyridine (0.26 mg, 2.5 mmol), and sodium (15 mg, 0.65 g atom) in ethanol (2 mL) at 150° C. overnight (16 h) to obtain 10 mg of 2-ethyl-2,3,4,5-tetrahydro-5-(4-pyridyl)-1H-pyrido[4,3-b]indole as a trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 25

Preparation of 2-ethyl-2,3,4,5-tetrahydro-5-(2-pyridyl)-1H-pyrido[4,3-b]indole. (Compound 6)

The title compound was prepared according to General Method 3. 2-Ethyl-2,3,4,5-tetrahydro-5-(2-pyridyl)-1H-pyrido[4,3-b]indole was prepared from 2-ethyl-2,3,4,5-tetrahydro-1H-pyrido[4,3-b]indole (See Example 5) (200 mg, 1 mmol), 2-vinylpyridine (0.26 mg, 2.5 mmol), sodium (15 mg, 0.65 g atom) and CuSO$_4$ (10 mg, catalytic) in ethanol (2 mL) at 150° C. for 16 h to obtain 8 mg of 2-ethyl-2,3,4,5-tetrahydro-5-(2-pyridyl)-1H-pyrido[4,3-b]indole as a trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 26

Preparation of 2,3,4,5-tetrahydro-2-methyl-5-(2-(pyridin-2-yl)ethyl)-1H-pyrido[4,3-b]indole. (Compound 26)

The title compound was prepared according to General Method 3. 2,3,4,5-Tetrahydro-2-methyl-5-(2-(pyridin-2-yl) ethyl)-1H-pyrido[4,3-b]indole was prepared from 2,3,4,5-tetrahydro-2-methyl-1H-pyrido[4,3-b]indole (See Example 3) (200 mg, 1 mmol), 2-vinylpyridine (0.26 mg, 2.5 mmol), sodium (5 mg, 0.21 g atom) and CuSO$_4$ (5 mg, catalytic) in ethanol (4 mL) at 120° C. for 16 h (overnight) to obtain 60 mg of 2,3,4,5-tetrahydro-2-methyl-5-(2-(pyridin-2-yl)ethyl)-1H-pyrido[4,3-b]indole as a trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 27

Preparation of 8-chloro-2,3,4,5-tetrahydro-2-methyl-5-(2-(pyridin-2-yl)ethyl)-1H-pyrido[4,3-b]indole. (Compound 30)

The title compound was prepared according to General Method 3. 8-Chloro-2,3,4,5-tetrahydro-2-methyl-5-(2-(pyridin-2-yl)ethyl)-1H-pyrido[4,3-b]indole was prepared from 8-chloro-2,3,4,5-tetrahydro-2-methyl-1H-pyrido[4,3-b]indole (See Example 4) (220 mg, 1 mmol), 2-vinylpyridine (1 ml, 18 mmol), sodium (20 mg, 0.87 g atom) and CuSO$_4$ (20 mg, catalytic) in ethanol (5 mL) at 150° C. for 16 h (overnight) to obtain 38 mg of 8-chloro-2,3,4,5-tetrahydro-2-methyl-5-(2-(pyridin-2-yl)ethyl)-1H-pyrido[4,3-b]indole after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) followed by purification on silica gel (230-400 mesh) chromatography eluting with methanol-dichloromethane gradient.

Compound 54 is prepared according to the process described in Example 27 using the appropriately substituted reagents: 8-chloro-2,3,4,5-tetrahydro-2-ethyl-1H-pyrido[4,3-b]indole, 2-vinylpyridine, sodium and CuSO$_4$ in ethanol.

Example 28

Preparation of 2,3,4,5-tetrahydro-2-methyl-5-(2-(pyridin-4-yl)ethyl)-1H-pyrido[4,3-b]indole. (Compound 10)

The title compound was prepared according to General Method 3. 2,3,4,5-Tetrahydro-2-methyl-5-(2-(pyridin-4-yl)ethyl)-1H-pyrido[4,3-b]indole was prepared from 2,3,4,5-tetrahydro-2-methyl-1H-pyrido[4,3-b]indole (See Example 3) (200 mg, 1.07 mmol), 4-vinylpyridine (0.26 mL, 2.41 mmol), sodium (5 mg, 0.21 g atom) and CuSO$_4$ (5 mg, catalytic) in ethanol (4 mL) at 120° C. for 16 h (overnight) to obtain 60 mg of 2,3,4,5-tetrahydro-2-methyl-5-(2-(pyridin-4-yl)ethyl)-1H-pyrido[4,3-b]indole as trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 29

Preparation of 2,3,4,5-tetrahydro-2,8-dimethyl-5-((6-methylpyridin-3-yl)methyl)-1H-pyrido[4,3-b]indole. (Compound 139)

The title compound was prepared according to General Method 4. 2,3,4,5-Tetrahydro-2,8-dimethyl-5-((6-methylpyridin-3-yl)methyl)-1H-pyrido[4,3-b]indole was prepared from 2,3,4,5-tetrahydro-2,8-dimethyl-1H-pyrido[4,3-b]indole (See Example 1) (200 mg, 1 mmol), 5-(chloromethyl)-2-methylpyridine (324 mg, 2.3 mmol) and NaH (120 mg, 3 mmol) were heated in DMF (4 ml) at 120° C. for 16 h. The reaction was quenched by careful addition of methanol or water and the contents were evaporated to dryness under vacuo. The resulting crude product was purified by silica gel chromatography (100-200 mesh or 230-400 mesh) by using methanol-dichloromethane gradient and by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 12.4 mg of 2,3,4,5-tetrahydro-2,8-dimethyl-5-((6-methylpyridin-3-yl)methyl)-1H-pyrido[4,3-b]indole as trifluoroacetate salt.

Example 30

Preparation of 2-ethyl-2,3,4,5-tetrahydro-8-methyl-5-((6-methylpyridin-3-yl)methyl)-1H-pyrido[4,3-b]indole. (Compound 138)

Preparation of the title compound was carried out according to General Method 4. 2-Ethyl-2,3,4,5-tetrahydro-8-methyl-1H-pyrido[4,3-b]indole (See Example 6) (214 mg, 1 mmol), 5-(chloromethyl)-2-methylpyridine (324 mg, 2.3 mmol) and NaH (120 mg, 3 mmol) were heated in DMF (4 ml) at 120° C. for 16 h to obtain 50 mg of 2-ethyl-2,3,4,5-tetrahydro-8-methyl-5-((6-methylpyridin-3-yl)methyl)-1H-pyrido[4,3-b]indole after purification by silica gel chromatography (100-200 mesh or 230-400 mesh) using methanol-dichloromethane gradient Example 31

Preparation of 2,3,4,5-tetrahydro-2-methyl-5-((6-methylpyridin-3-yl)methyl)-1H-pyrido[4,3-b]indole. (Compound 17)

Preparation of the title compound was carried out according to General Method 4. 2,3,4,5-Tetrahydro-2-methyl-1H-pyrido[4,3-b]indole (See Example 3) (186 mg, 1 mmol), 5-(chloromethyl)-2-methylpyridine (324 mg, 2.3 mmol) and NaH (120 mg, 3 mmol) were heated in DMF (3 ml) at 120° C. for 16 h to obtain 30 mg of 2,3,4,5-tetrahydro-2-methyl-5-((6-methylpyridin-3-yl)methyl)-1H-pyrido[4,3-b]indole after purification by silica gel chromatography (230-400 mesh) using methanol-dichloromethane gradient.

Example 32

Preparation of 5-benzyl-2,3,4,5-tetrahydro-2,8-dimethyl-1H-pyrido[4,3-b]indole. (Compound 137)

Preparation of the title compound was carried out according to General Method 5. 2,3,4,5-Tetrahydro-2,8-dimethyl-1H-pyrido[4,3-b]indole (Example 1) (100 mg, 0.5 mmol) and benzyl chloride (0.11 ml, 0.9 mmol) in diisopropylamine (2 mL) were heated at 80° C. for 12 h. The contents were basified with 1N NaOH and extracted with ethyl acetate. The organic layer was dried over sodium sulfate and concentrated. The resulting crude product was purified by silica gel chromatography (230-400 mesh) using methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 20 mg of 5-benzyl-2,3,4,5-tetrahydro-2,8-dimethyl-1H-pyrido[4,3-b]indole as a trifluoroacetate salt.

Example 33

Preparation of 5-benzyl-2-ethyl-2,3,4,5-tetrahydro-8-methyl-1H-pyrido[4,3-b]indole. (Compound 140)

Preparation of the title compound was carried out according to General Method 5. 2-Ethyl-2,3,4,5-tetrahydro-8-methyl-1H-pyrido[4,3-b]indole (See Example 6) (100 mg, 0.46 mmol) and benzyl chloride (0.11 ml, 0.9 mmol) in diisopropylamine (2 mL) were heated at 80° C. for 12 h to obtain 40 mg of 5-benzyl-2-ethyl-2,3,4,5-tetrahydro-8-methyl-1H-pyrido[4,3-b]indole as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 34

Preparation of 5-benzyl-2-ethyl-2,3,4,5-tetrahydro-1H-pyrido[4,3-b]indole. (Compound 16)

Preparation of the title compound was carried out according to General Method 5. 2-Ethyl-2,3,4,5-tetrahydro-1H-pyrido[4,3-b]indole (See Example 5) (100 mg, 0.5 mmol), benzyl chloride (158 mg, 1.25 mmol) in diisopropylamine (2 mL) were heated at 80° C. for 12 h to obtain 50 mg of 5-benzyl-2-ethyl-2,3,4,5-tetrahydro-1H-pyrido[4,3-b]indole as trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 35

Preparation of racemic-2-(1,2,3,4-tetrahydro-2,8-dimethylpyrido[4,3-b]indol-5-yl)-1-p-tolylethanol. (Compound 28)

Preparation of the title compound was carried out according to General Method 6. 3,4,5-Tetrahydro-2,8-dimethyl-1H-pyrido[4,3-b]indole (See Example 1) (2.2 g, 11 mmol), 4-methylstyrene oxide (5.8 g, 44 mmol) and NaH (1.3 g, 32.5 mmol) were heated in DMF (70 mL) at 120° C. for 16 h (overnight). The contents were quenched by methanol and evaporated to dryness. The resulting crude product was purified by silica gel chromatography (230-400 mesh) using ethyl acetate-hexane gradient to obtain 1.3 g of racemic-2-(1,2,3,4-tetrahydro-2,8-dimethylpyrido[4,3-b]indol-5-yl)-1-p-tolylethanol. The free base was converted into its hydrochloride salt by treatment of ethanolic HCl.

Example 36

Preparation of racemic-2-(2-ethyl-1,2,3,4-tetrahydro-8-methylpyrido[4,3-b]indol-5-yl)-1-p-tolylethanol. (Compound 29)

Preparation of the title compound was carried out according to General Method 6. 2-Ethyl-2,3,4,5-tetrahydro-8-methyl-1H-pyrido[4,3-b]indole (See Example 6) (214 mg, 1 mmol), 4-methylstyrene oxide (1 mL, 7.5 mmol) and NaH (120 mg, 3 mmol) were heated in DMF (4 mL) at 120° C. for 16 h (overnight) to obtain 50 mg of racemic-2-(2-ethyl-1,2,3,4-tetrahydro-8-methylpyrido[4,3-b]indol-5-yl)-1-p-tolylethanol as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 37

Preparation of racemic-2-(1,2,3,4-tetrahydro-2-methylpyrido[4,3-b]indol-5-yl)-1-p-tolylethanol. (Compound 37)

Preparation of the title compound was carried out according to General Method 6. 2,3,4,5-Tetrahydro-2-methyl-1H-pyrido[4,3-b]indole (See Example 3) (400 mg, 2.1 mmol), 4-methylstyrene oxide (2.1 g, 15.7 mmol) and NaH (252 mg, 6.3 mmol) were heated in DMF (5 mL) at 120° C. for 16 h to obtain 75 mg of racemic-2-(1,2,3,4-tetrahydro-2-methylpyrido[4,3-b]indol-5-yl)-1-p-tolylethanol as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 38

Preparation of racemic-2-(2-ethyl-1,2,3,4-tetrahydropyrido[4,3-b]indol-5-yl)-1-p-tolylethanol. (Compound 8)

Preparation of the title compound was carried out according to General Method 6. 2-Ethyl-2,3,4,5-tetrahydro-1H-pyrido[4,3-b]indole (See Example 5) (400 mg, 2.0 mmol), 4-methylstyrene oxide (2.01 g, 15 mmol) and NaH (240 mg, 6 mmol) were heated in DMF (6 mL) at 120° C. for 16 h to obtain 120 mg of racemic-2-(2-ethyl-1,2,3,4-tetrahydropyrido[4,3-b]indol-5-yl)-1-p-tolylethanol as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 39

Preparation of ethyl 3,4-dihydro-5-(2-(6-methylpyridin-3-yl)ethyl)-8-(pyridin-3-yl)-1H-pyrido[4,3-b]indole-2(5H)-carboxylate. (Compound 19)

Preparation of the title compound was carried out according to General Method 7. A mixture of ethyl 8-bromo-3,4-dihydro-1H-pyrido[4,3-b]indole-2(5H)-carboxylate (See Example 7) (100 mg, 0.3 mmol), pyridine-3-boronic acid (76 mg, 0.62 mmol) and $K_3PO_4$ (120 mg, 0.57 mmol) in DMF:$H_2O$ (2:1, 3 ml) was purged with nitrogen for 30 minutes. $PdCl_2(PPh_3)_2$ (25 mg, 0.04 mmol) was added and the reaction was heated at 100° C. for 4 h. The contents were concentrated in vacuo and the crude product was purified by silica gel chromatography (230-400 mesh) using ethyl acetate-hexane gradient to obtain 62 mg of ethyl 3,4-dihydro-8-(pyridin-3-yl)-1H-pyrido[4,3-b]indole-2(5H)-carboxylate. This intermediate (25 mg, 0.078 mmol), 2-methyl-5-vinylpyridine (0.120 ml, 1 mmol) and NaH (10 mg, 60% dispersion in oil, 0.02 mmol) were heated in DMSO (0.3 ml) at 100° C. for 48 h, after which methanol was added and the contents were concentrated to dryness. The resulting crude product was purified by silica gel chromatography (100-200 mesh or 230-400 mesh) using methanol-dichloromethane gradient to obtain 7 mg of 3,4-dihydro-5-(2-(6-methylpyridin-3-yl)ethyl)-8-(pyridin-3-yl)-1H-pyrido[4,3-b]indole-2(5H)-carboxylate.

Example 40

Preparation of 2,3,4,5-tetrahydro-2,8-dimethyl-5-phenethyl-1H-pyrido[4,3-b]indole. (Compound 20)

Preparation of the title compound was carried out according to General Method 8. p-Tolylhydrazine hydrochloride (2 g, 12.6 mmol), 2-phenyl ethyl bromide (1.7 ml, 12.6 mmol) and triethyl amine (1.7 mL, 12.6 mmol) in ethanol (6 ml) were stirred at 25° C. for 1 h after which the contents were heated at 80° C. for 2 h. The contents were cooled to 25° C., N-methyl-4-piperidone hydrochloride (2.87 g, 18.9 mmol) was added and heating was continued at 80° C. for 16 h. The contents were concentrated in vacuo, basified by adding saturated aqueous NaHCO$_3$, and extracted with ethyl acetate. The organic layer was dried over anhydrous sodium sulfate and concentrated. The crude product was purified by silica gel chromatography (230-400 mesh) using ethyl acetate-hexane gradient to obtain 150 mg of 2,3,4,5-tetrahydro-2,8-dimethyl-5-phenethyl-1H-pyrido[4,3-b]indole. The free base was converted into its oxalate salt by treatment of oxalic acid (1 equiv) in anhydrous THF.

Example 41

Preparation of 5-(2-fluorophenethyl)-2,3,4,5-tetrahydro-2,8-dimethyl-1H-pyrido[4,3-b]indole. (Compound 34)

Preparation of the title compound was carried out according to General Method 8. p-Tolylhydrazine hydrochloride (500 mg, 3.1 mmol), 2-fluorophenyl ethyl bromide (639 mg, 3.1 mmol), triethyl amine (313 mg, 3.1 mmol) and N-methyl-4-piperidone hydrochloride (692 mg, 4.6 mmol) were combined in ethanol (2 ml) to obtain 30 mg of 5-(2-fluorophenethyl)-2,3,4,5-tetrahydro-2,8-dimethyl-1H-pyrido[4,3-b]indole after purification on neutral alumina using ethyl acetate-hexane gradient. The free base was converted into its oxalate salt by treatment of oxalic acid (1 equiv) in anhydrous THF.

Example 42

Preparation of 5-(2-cyclohexylethyl)-2,3,4,5-tetrahydro-2,8-dimethyl-1H-pyrido[4,3-b]indole. (Compound 163)

Preparation of the title compound was carried out according to General Method 8. p-Tolylhydrazine hydrochloride (500 mg, 3.1 mmol), 1-bromo-2-cyclohexylethane (602 mg, 3 mmol), triethyl amine (303 mg, 3 mmol) and N-methyl-4-piperidone hydrochloride (589 mg, 4.5 mmol) were combined in ethanol (3 ml) to obtain 150 mg of 5-(2-cyclohexylethyl)-2,3,4,5-tetrahydro-2,8-dimethyl-1H-pyrido[4,3-b]indole after purification on neutral alumina using ethyl acetate-hexane gradient.

Example 43

Preparation of 5-(4-fluorophenethyl)-2,3,4,5-tetrahydro-2,8-dimethyl-1H-pyrido[4,3-b]indole. (Compound 33)

Preparation of the title compound was carried out according to General Method 8. p-Tolylhydrazine hydrochloride (312 mg, 1.9 mmol), 4-fluorophenyl ethyl bromide (400 mg, 1.9 mmol), triethyl amine (0.264 ml, 1.9 mmol) and N-methyl-4-piperidone hydrochloride (424 mg, 2.8 mmol) were combined in ethanol (3 ml) to obtain 10 mg of 5-(4-fluorophenethyl)-2,3,4,5-tetrahydro-2,8-dimethyl-1H-pyrido[4,3-b]indole after purification by silica gel chromatography (100-200 mesh or 230-400 mesh) using ethyl acetate-hexane gradient. The free base was converted into its oxalate salt by treatment of oxalic acid (1 equiv) in anhydrous THF.

Example 44

Preparation of 2-cyclopropyl-2,3,4,5-tetrahydro-8-methyl-5-phenethyl-1H-pyrido[4,3-b]indole. (Compound 35)

Preparation of the title compound was carried out according to General Method 8. p-Tolylhydrazine hydrochloride (500 mg, 3.1 mmol), 2-phenyl ethyl bromide (0.43 ml, 3.1 mmol), triethyl amine (0.43 ml, 3.1 mmol) and N-cyclopropyl-4-piperidone hydrochloride (650 mg, 4.72 mmol) were combined in ethanol (3 ml) to obtain 62 mg of 2-cyclopropyl-2,3,4,5-tetrahydro-8-methyl-5-phenethyl-1H-pyrido[4,3-b]indole after purification on neutral alumina using ethyl acetate-hexane gradient. The free base was converted into its oxalate salt by treatment of oxalic acid (1 equiv) in anhydrous THF.

Compound 51 was synthesized according to General Method 8 and as described in Example 44 using appropriately substituted reagents: p-Tolylhydrazine hydrochloride, 5-(2-bromoethyl)-2-methylpyridine, triethyl amine and N-cyclopropyl-4-piperidone hydrochloride were combined in ethanol.

Example 45

Preparation of 8-chloro-2,3,4,5-tetrahydro-2-methyl-5-phenethyl-1H-pyrido[4,3-b]indole. (Compound 36)

Preparation of the title compound was carried out according to General Method 8. 4-Chlorophenylhydrazine hydrochloride (500 mg, 2.79 mmol), 2-phenyl ethyl bromide (0.38 ml, 2.79 mmol), triethyl amine (0.39 ml, 2.79 mmol) and N-methyl-4-piperidone hydrochloride (623 mg, 4.18 mmol) were combined in ethanol (2 ml) to obtain 15 mg of 8-chloro-2,3,4,5-tetrahydro-2-methyl-5-phenethyl-1H-pyrido[4,3-b]indole as a trifluoroacetate salt after purification on neutral alumina using ethyl acetate-hexane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Compound 43, Compound 81, Compound 82 and Compound 83 were synthesized according to General Method 8 and as described in Example 45 using appropriately substituted reagents. Compound 43 Reagents: 4-Chlorophenylhydrazine hydrochloride, 1-(2-bromoethyl)-4-methylbenzene, triethyl amine and N-methyl-4-piperidone hydrochloride were combined in ethanol. Compound 81 Reagents: 3-Chlorophenylhydrazine hydrochloride, 1-(2-bromoethyl)-4-methylbenzene, triethyl amine and N-methyl-4-piperidone hydrochloride were combined in ethanol. Compound 82 Reagents: 3-Chlorophenylhydrazine hydrochloride, 1-(2-bromoethyl)-4-methylbenzene, triethyl amine and N-methyl-4-piperidone hydrochloride were combined in ethanol. Compound 83 Reagents: 2-Chlorophenylhydrazine hydrochloride, 1-(2-bromoethyl)-4-methylbenzene, triethyl amine and N-methyl-4-piperidone hydrochloride were combined in ethanol.

Example 46

Preparation of 8-chloro-2,3,4,5-tetrahydro-2-methyl-5-(2-morpholinoethyl)-1H-pyrido[4,3-b]indole. (Compound 186)

Preparation of the title compound was carried out according to General Method 8. 4-Chlorophenylhydrazine hydrochloride (2 g, 11 mmol), 4-(2-bromoethyl)morpholine (2.1 g, 11 mmol), triethyl amine (4.6 ml, 33 mmol) and N-methyl-4-piperidone hydrochloride (1.6 g, 11 mmol) were combined in ethanol (20 ml) to obtain 180 mg of -chloro-2,3,4,5-tetrahydro-2-methyl-5-(2-morpholinoethyl)-1H-pyrido[4,3-b]indole after purification on silica gel (230-400 mesh) chromatography eluting with acetone-hexane gradient. The free base was converted into its dioxalate salt by treatment of oxalic acid (2 equiv) in anhydrous THF.

Example 47

Preparation of 8-chloro-5-(2-cyclohexylethyl)-2,3,4,5-tetrahydro-2-methyl-1H-pyrido[4,3-b]indole. (Compound 164)

Preparation of the title compound was carried out according to General Method 8. 4-Chlorophenylhydrazine hydrochloride (1 g, 5.5 mmol), 1-bromo-2-cyclohexylethane (0.87 ml, 5.5 mmol), triethyl amine (2.31 ml, 16.6 mmol) and N-methyl-4-piperidone hydrochloride (810 mg, 5.5 mmol) were combined in ethanol (10 ml) to obtain 16 mg of 8-chloro-5-(2-cyclohexylethyl)-2,3,4,5-tetrahydro-2-methyl-1H-pyrido[4,3-b]indole after purification on silica gel (230-400 mesh) chromatography eluting with acetone-hexane gradient. The free base was converted into its oxalate salt by treatment of oxalic acid (1 equiv.) in anhydrous THF.

Example 48

Preparation of 9-chloro-5-(2-cyclohexylethyl)-2,3,4,5-tetrahydro-2-methyl-1H-pyrido[4,3-b]indole (Compound 187) and 7-chloro-5-(2-cyclohexylethyl)-2,3,4,5-tetrahydro-2-methyl-1H-pyrido[4,3-b]indole. (Compound 188)

Preparation of the title compounds was carried out according to General Method 8. 3-Chlorophenylhydrazine hydrochloride (5 g, 27.9 mmol), 1-bromo-2-cyclohexylethane (4.37 ml, 27.9 mmol), triethyl amine (11.66 ml, 83.7 mmol) and N-methyl-4-piperidone hydrochloride (4 g, 27.9 mmol) were combined in ethanol (30 ml) to obtain 9-chloro-5-(2-cyclohexylethyl)-2,3,4,5-tetrahydro-2-methyl-1H-pyrido[4,3-b]indole and 7-chloro-5-(2-cyclohexylethyl)-2,3,4,5-tetrahydro-2-methyl-1H-pyrido[4,3-b]indole after on purification on silica gel (230-400 mesh) chromatography eluting with acetone-hexane gradient. The free base was converted into its oxalate salt by treatment of oxalic acid (1 equiv.) in anhydrous THF.

Example 49

Preparation of 2,3,4,5-tetrahydro-2,8-dimethyl-5-(2-(pyrrolidin-1-yl)ethyl)-1H-pyrido[4,3-b]indole. (Compound 221)

Preparation of the title compound was carried out according to General Method 8. 4-Methylphenylhydrazine hydrochloride (2 g, 12.6 mmol), 1-(2-bromoethyl)pyrrolidine hydrobromide (8.1 g, 31.5 mmol), triethyl amine (17.5 ml, 126 mmol) and N-methyl-4-piperidone hydrochloride (1.87 g, 12.6 mmol) were combined in ethanol (15 ml) to obtain 180 mg of 2,3,4,5-tetrahydro-2,8-dimethyl-5-(2-(pyrrolidin-1-yl)ethyl)-1H-pyrido[4,3-b]indole after on purification on silica gel (230-400 mesh) chromatography eluting with acetone-hexane gradient. The free base was converted into its dioxalate salt by treatment of oxalic acid (2 equiv.) in anhydrous THF.

Example 50

Preparation of 3,4-dihydro-3-hydroxy-2,8-dimethyl-5-phenethyl-2H-pyrido[4,3-b]indol-1(5H)-one. (Compound 215)

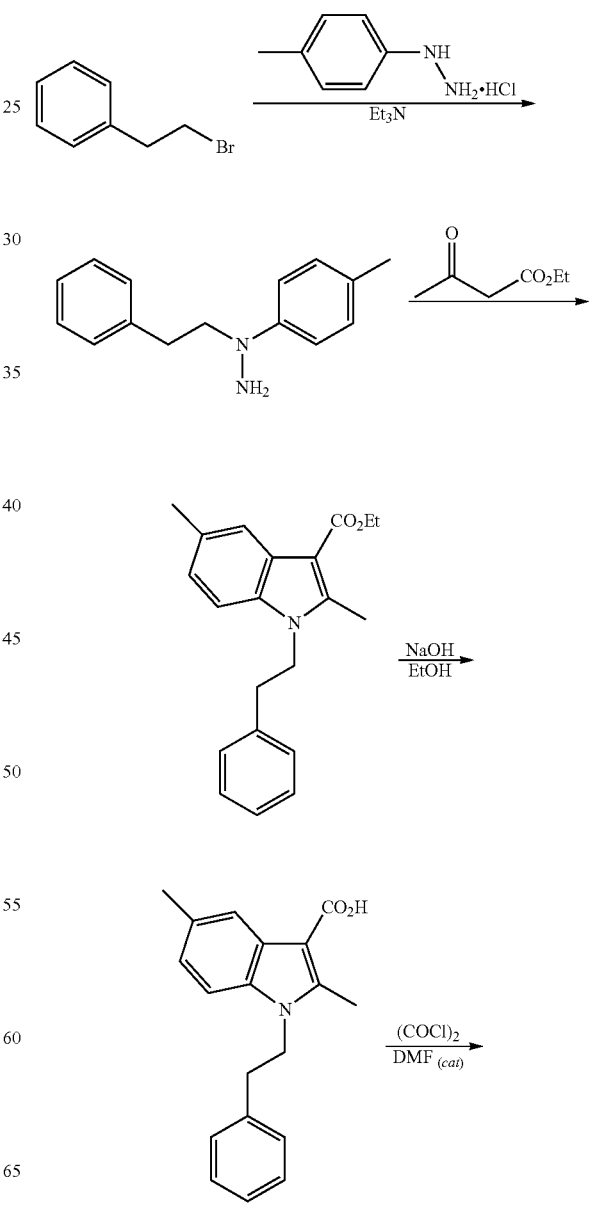

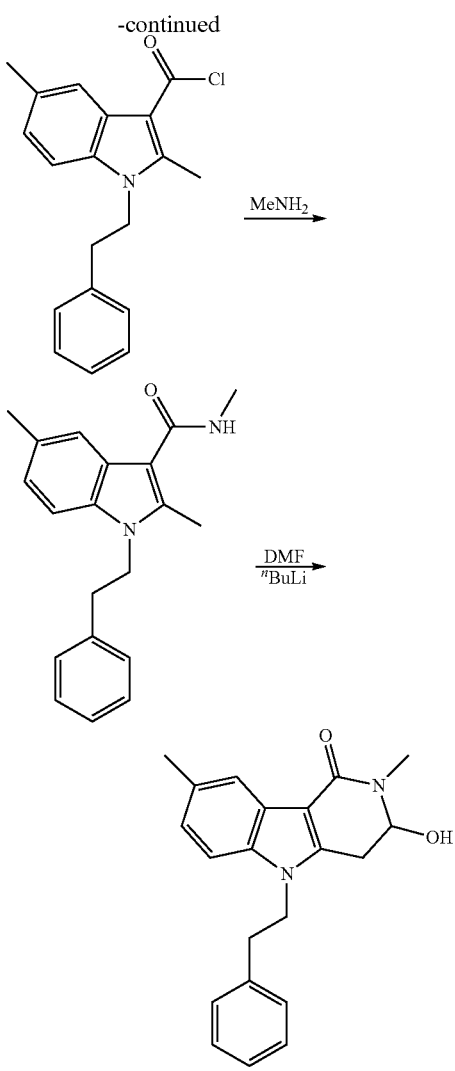

The title compound was prepared according to the synthetic scheme outlined above and detailed below.

Example 50A

Preparation of 1-phenethyl-1-p-tolylhydrazine p-Tolylhydrazine hydrochloride (10.0 g, 63 mmol) was suspended in EtOH (45 mL). To this suspension was added triethylamine (9.0 mL, 63 mmol) drop-wise over a period of 5-10 minutes. The reaction mixture was stirred for additional 10 minutes. Phenethyl bromide (9 mL, 63 mmol) was added drop-wise at 25° C. over a period of 10 to 15 minutes. The reaction mixture was heated at 80° C. for 2 h at which point the reaction was found complete by TLC and LC-MS. The reaction mixture was concentrated under reduced pressure, the residue was suspended in saturated aqueous NaHCO$_3$ (pH 9) and extracted with ethyl acetate (100 mL×2). The organic layer was separated, dried (Na$_2$SO$_4$) and concentrated to obtain crude product as a dark brown oil (14 g). Purification of crude product by flash column chromatography (silica gel, 230-400 mesh, eluent: 8-10% ethyl acetate-hexanes) furnished 3.7 g of pure product as yellow oil. Yield: 26% (unoptimized).

Example 50B

Preparation of ethyl 2,5-dimethyl-1-phenethyl-1H-indole-3-carboxylate 1-phenethyl-1-p-tolylhydrazine (3.7 g, 16.3 mmol) was dissolved in ethanolic HCl (40 mL, pH of the solution was acidic) and ethyl acetoacetate (2.0 mL, 16.3 mmol) was added to it. The reaction mixture was heated at 110° C. for 1.5 h at which point the reaction was found complete by TLC and LC-MS. The reaction mixture was concentrated under reduced pressure, the residue was suspended in saturated aqueous NaHCO$_3$ (pH 9) and extracted with ethyl acetate (100 mL×2). The organic layer was separated, dried (Na$_2$SO$_4$) and concentrated to obtain a crude product as dark brown oil. Purification of crude product by flash column chromatography (silica gel, 230-400 mesh, eluent: 5-10% ethyl acetate-hexanes) furnished 3.2 g of pure product as yellow solid.

Example 50C

Preparation of 2,5-dimethyl-1-phenethyl-1H-indole-3-carboxylic acid

A mixture of ethyl 2,5-dimethyl-1-phenethyl-1H-indole-3-carboxylate (500 mg) and NaOH (500 mg) in ethanol (15 mL) was heated at 100° C. for 3 h at which point the reaction was found complete by TLC and LC-MS. The reaction mixture was acidified to pH 4-5 by adding ethanolic HCl and evaporated under reduced pressure. The residue (1 g), that also contained NaCl generated during NaOH neutralization, was carried forward to next reaction without any purification.

Example 50D

Preparation of 2,5-dimethyl-1-phenethyl-1H-indole-3-carbonyl chloride

To a stirring solution of the carboxylate acid (1.6 g crude product over previous two examples, considered as approx. 2.5 mmol) in anhydrous CH$_2$Cl$_2$ (15 ml) at 0° C. was added a drop of DMF, followed by oxalyl chloride (0.6 mL, 6.9 mmol) via syringe. After stirring at 0° C. for 15 minutes, the ice bath was removed and the mixture was stirred at ambient temperature for 55 minutes. The mixture is concentrated to dryness under reduced pressure (protected from moisture) to obtain the crude acid chloride that was stored under nitrogen, and used in the next example without any purification.

Example 50E

Preparation of N,2,5-trimethyl-1-phenethyl-1H-indole-3-carboxamide

The acid chloride from example 50D was dissolved in CH$_2$Cl$_2$ (10 ML) and cooled to 0° C. To this was added in excess, a solution of methylamine in DCM (50 ml). The reaction was slowly warmed to and stirred at 25° C. for additional 1 h at which point the reaction was found complete by TLC and LC-MS. The solution was partitioned between CH$_2$Cl$_2$ and water. The organic layer was separated, dried over Na$_2$SO$_4$ and concentrated under reduced pressure to obtain 650 mg of light brown solid.

Example 50F

Preparation of 3,4-dihydro-3-hydroxy-2,8-dimethyl-5-phenethyl-2H-pyrido[4,3-b]indol-1(5H)-one A solution of amide (125 mg, 0.41 mmol) in 3 mL of tetrahydrofuran was cooled to −25 to −30° C. (under $N_2$) and a solution of n-BuLi in hexanes (1 mL of 1.6 M, 1.6 mmol) was added at such a rate as to maintain the internal temperature between −25 to −30° C. The resulting deep red solution was stirred at −25 to −30° C. for 40 minutes and DMF (0.1 mL) was added at −25 to −30° C. After the addition was complete, the solution was stirred at −25 to −30° C. for 30 minutes. Hydrochloric acid (0.3 mL of 6 N) was slowly added, keeping the temperature below 5° C. (pH 3-4). The mixture was concentrated in vacuo to obtain 90 mg of yellow semi-solid. The product was triturated with diethyl ether-hexanes, followed by diethyl ether and filtered to obtain 30 mg of yellow solid.

Compound 216 was prepared according General Method 8 by following an analogous procedure described for Preparation of 2,3,4,5-tetrahydro-2,8-dimethyl-5-phenethyl-1H-pyrido[4,3-b]indole (Example 47) using p-tolylhydrazine hydrochloride, 5-(2-bromoethyl)-2-methylpyridine and 1-methylpiperidine-2,4-dione.

Example 51

Preparation of (Compound 47) and (Compound 53)

The title compounds were prepared according to General Method 8 using the appropriately substituted reagents: (Compound 47) Reagents: 4-(trifluoromethyl)phenylhydrazine hydrochloride, 1-(2-bromoethyl)-4-methylbenzene, triethyl amine and N-methyl-4-piperidone hydrochloride in ethanol and (Compound 53). Reagents: 4-(trifluoromethyl)phenylhydrazine hydrochloride, 5-(2-bromoethyl)-2-methylpyridine, triethyl amine and N-methyl-4-piperidone hydrochloride in ethanol.

Example 52

Preparation of 2,3,4,5-tetrahydro-2,8-dimethyl-5-(2-(piperidin-1-yl)ethyl)-1H-pyrido[4,3-b]indole. (Compound 224)

Preparation of the title compound was carried out according to General Method 8. p-Tolylhydrazine hydrochloride (2.0 g, 12.6 mmol), 1-(2-chloroethyl)-piperidine monohydrochloride (2.32 g, 12.6 mmol), triethyl amine (5.3 ml, 37.8 mmol) and N-methyl-4-piperidone hydrochloride (1.87 g, 2.1 mmol) were taken in ethanol (30 ml) to obtain 180 mg of 2,3,4,5-tetrahydro-2,8-dimethyl-5-(2-(piperidin-1-yl)ethyl)-1H-pyrido[4,3-b]indole after purification on silica gel (230-400 mesh) chromatography eluting with acetone-hexane gradient. The free base was converted into bis(oxalate) salt by treatment of oxalic acid (2 equiv) in anhydrous THF.

Example 53

Preparation of 8-chloro-2,3,4,5-tetrahydro-2-methyl-5-(2-(6-methylpyridin-3-yl)ethyl)-1H-pyrido[4,3-b]indole. (Compound 225)

Preparation of the title compound was carried out according to General Method 8. 4-Chlorophenylhydrazine hydrochloride (9 g, 50 mmol), 5-(2-bromoethyl)-2-methylpyridine (10 g, 50 mmol), triethyl amine (21 ml, 150 mmol) and N-methyl-4-piperidone hydrochloride (7.5 g, 50 mmol) were taken in ethanol (100 ml) to obtain 390 mg of 8-chloro-2,3,4,5-tetrahydro-2-methyl-5-(2-(6-methylpyridin-3-yl)ethyl)-1H-pyrido[4,3-b]indole after on purification on silica gel (230-400 mesh) chromatography eluting with methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 54

Preparation of tert-butyl 1-(3-(1,2,3,4-tetrahydro-2,8-dimethylpyrido[4,3-b]indol-5-yl)propanoyl)piperidin-4-ylcarbamate. (Compound 226)

Example 54A

Preparation of 3-(1,2,3,4-tetrahydro-2,8-dimethylpyrido[4,3-b]indol-5 yl)propanoic acid Preparation of ethyl 3-(1,2,3,4-tetrahydro-2,8-dimethylpyrido[4,3-b]indol-5-yl)propanoate was accomplished using tolylhydrazine hydrochloride (20 g, 126 mmol), 3-bromoethyl propionate (22.8 g, 126 mmol), triethyl amine (38.1 g, 378 mmol) and N-methyl-4-piperidone hydrochloride (18.77 g, 126 mmol) in ethanol (200 ml) to obtain 1.5 g of ethyl 3-(1,2,3,4-tetrahydro-2,8-dimethylpyrido[4,3-b]indol-5-yl)propanoate after purification on neutral alumina chromatography eluting with dichloromethane-hexane gradient.

Example 54B

Preparation of 3-(1,2,3,4-tetrahydro-2,8-dimethylpyrido[4,3-b]indol-5-yl)propanoic acid A mixture of ethyl 3-(1,2,3,4-tetrahydro-2,8-dimethylpyrido[4,3-b]indol-5-yl)propanoate (See Example 54A) (1.5 g) and NaOH (3N, 30 ml) in ethanol (30 ml) was stirred at 50° C. for 3 h after which it was cooled to room temperature and neutralized with concentrated HCl. The solvent was removed under reduced pressure to obtain crude 3-(1,2,3,4-tetrahydro-2,8-dimethylpyrido[4,3-b]indol-5-yl)propanoic acid.

Example 54C

The title compound, tert-butyl 1-(3-(1,2,3,4-tetrahydro-2,8-dimethylpyrido[4,3-b]indol-5-yl)propanoyl)piperidin-4-ylcarbamate, was obtained as follows. 3-(1,2,3,4-tetrahydro-2,8-dimethylpyrido[4,3-b]indol-5-yl)propanoic acid (500 mg, 1.8 mmol) (See Example 54B) was stirred with tert-butyl piperidin-4-ylcarbamate (0.366 ml, 1.8 mmol), EDCI-HCl (0.35 g, 1.8 mmol) and triethyl amine (0.253 ml, 1.8 mmol) in dichloromethane (20 ml) to obtain 50 mg of tert-butyl 1-(3-(1,2,3,4-tetrahydro-2,8-dimethylpyrido[4,3-b]indol-5-yl)propanoyl)piperidin-4-ylcarbamate as a trifluoroacetate salt after purification on neutral alumina chromatography eluting with methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 55

Preparation of 2,2,2-trichloroethyl 3,4-dihydro-8-methyl-5-phenethyl-1H-pyrido[4,3-b]indole-2(5H)-carboxylate. (Compound 227)

Preparation of the title compound was carried out according to General Method 8. p-Tolylhydrazine hydrochloride (10 g, 63 mmol), 2-phenyl ethyl bromide (11.6 g, 63 mmol), triethyl amine (19.4 g, 189 mmol) and 2,2,2-trichloroethyl 4-oxopiperidine-1-carboxylate (452 mg, 2 mmol) were taken in ethanol (10 ml) at 90° C. for 3 h to obtain 200 mg of 2,2,2-trichloroethyl 3,4-dihydro-8-methyl-5-phenethyl-1H-pyrido[4,3-b]indole-2(5H)-carboxylate after purification on silica gel (230-400 mesh) chromatography eluting with methanol-dichloromethane gradient.

Compound 235 can be made according to the procedure described in Example 55 using appropriately substituted reagents. 1-(2-(6-methylpyridin-3-yl)ethyl)-1-p-tolylhydrazine (500 mg) and N-Troc-piperidone (560 mg) were mixed in 15 mL ethanolic HCl and stirred for 20 min. The volatiles were removed under reduced pressure, the residue was taken in ethanol (5 mL) and the solution was heated at 90° C. for 3 h (the reaction was monitored by LCMS and TLC). The reaction mixture was cooled to 25° C. and evaporated under reduced pressure. The residue was basified with satd. aq. NaHCO$_3$ and extracted with ethyl acetate. The combined ethyl acetate layer was dried over Na$_2$SO$_4$ and concentrated under reduced pressure to obtain the crude product. The crude product was purified by flash chromatography on silica gel (eluent: hexane to 10% acetonehexane gradient) to obtain 100 mg of product as light yellow oil. TLC Rf 0.2 in 20% acetone-hexane.

Example 56

Preparation of 2,3,4,5-tetrahydro-8-methyl-5-phenethyl-1H-pyrido[4,3-b]indole. (Compound 228)

A mixture of 2,2,2-trichloroethyl 3,4-dihydro-8-methyl-5-phenethyl-1H-pyrido[4,3-b]indole-2(5H)-carboxylate (100 mg, 0.2 mmol) and Zn dust (120 mg, 1.9 mmol) in acetic acid (1.2 ml) was stirred at 25° C. for 2 h. The reaction mixture was basified with saturated aqueous NaHCO$_3$ and extracted with ethyl acetate. The organic layer was dried over anhydrous sodium sulfate and evaporated to obtain 30 mg of 2,3,4,5-tetrahydro-8-methyl-5-phenethyl-1H-pyrido[4,3-b]indole after purification on silica gel (230-400 mesh) chromatography eluting with methanol-dichloromethane gradient.

Example 57

Preparation of 2,3,4,5-tetrahydro-2,8-dimethyl-5-(2-(6-methylpyridin-3-yl)ethyl)-1H-pyrido[4,3-b]indole N'-oxide. (Compound 229)

2,3,4,5-tetrahydro-2,8-dimethyl-5-(2-(6-methylpyridin-3-yl)ethyl)-1H-pyrido[4,3-b]indole (98 mg, 3.1 mmol) was stirred with hydrogen peroxide (30% in water, 0.2 ml) in glacial acetic acid (1.2 ml) at 865-70° C. for 20 h to obtain 76 mg of corresponding N,N'-dioxide. To this intermediate (76 mg, 0.21 mmol) in acetic acid (0.3 ml) and methanol (2 ml) was added sodium bisulphate (40% in water, 0.2 ml) and the reaction mixture was stirred at 0° C. for 0.5 h. The reaction mixture was basified with saturated aqueous NaHCO$_3$ and extracted with ethyl acetate to obtain 50 mg of 2,3,4,5-tetrahydro-2,8-dimethyl-5-(2-(6-methylpyridin-3-yl)ethyl)-1H-pyrido[4,3-b]indole N'-oxide.

Example 58A

Preparation of 2,2,2-trichloroethyl 3,4-dihydro-8-methyl-5-(2-(6-methylpyridin-3-yl)ethyl)-1H-pyrido[4,3-b]indole-2(5H)-carboxylate Preparation of the title compound was carried out according to General Method 8. p-Tolylhydrazine hydrochloride (5 g, 31.5 mmol), 5-(2-bromoethyl)-2-methylpyridine (6.3 g, 31.5 mmol), triethyl amine (13 ml, 94.5 mmol) and 2,2,2-trichloroethyl 4-oxopiperidine-1-carboxylate (563 mg, 2 mmol) were taken in ethanol (15 ml) to obtain 100 mg of 2,2,2-trichloroethyl 3,4-dihydro-8-methyl-5-(2-(6-methylpyridin-3-yl)ethyl)-1H-pyrido[4,3-b]indole-2(5H)-carboxylate after purification on silica gel (230-400 mesh) chromatography eluting with acetone-hexane gradient.

Example 58B

Preparation of 2,3,4,5-tetrahydro-8-methyl-5-(2-(6-methylpyridin-3-yl)ethyl)-1H-pyrido[4,3-b]indole A mixture of 2,2,2-trichloroethyl 3,4-dihydro-8-methyl-5-(2-(6-methylpyridin-3-yl)ethyl)-1H-pyrido[4,3-b]indole-2(5H)-carboxylate (100 mg, 0.2 mmol) and Zn dust (120 mg, 1.9 mmol) in acetic acid (1.2 ml) was stirred at 25° C. for 12 h. The reaction mixture was basified with saturated aqueous ammonia and extracted with ethyl acetate. The organic layer was dried over anhydrous sodium sulfate and evaporated to obtain 75 mg of 2,3,4,5-tetrahydro-8-methyl-5-(2-(6-methylpyridin-3-yl)ethyl)-1H-pyrido[4,3-b]indole after purification on silica gel (230-400 mesh) chromatography eluting with methanol-dichloromethane gradient. The free base was converted into its oxalate salt by treatment of oxalic acid (1 equiv.) in anhydrous THF.

Example 59

Preparation of 1-(4-aminopiperidin-1-yl)-3-(1,2,3,4-tetrahydro-2,8dimethylpyrido[4,3-b]indol-5-yl)propan-1-one. (Compound 231)

Tert-butyl 1-(3-(1,2,3,4-tetrahydro-2,8-dimethylpyrido[4,3-b]indol-5-yl)propanoyl)piperidin-4-ylcarbamate (See Example 54) (50 mg) was stirred with trifluoroacetic acid (2 ml) in dichloromethane (2 ml) for 16 h at 25° C. to obtain 10 mg of 1-(4-aminopiperidin-1-yl)-3-(1,2,3,4-tetrahydro-2,8-dimethylpyrido[4,3-b]indol-5-yl)propan-1-one as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 60

Preparation of 4-bromo-1,2-dihydro-2,8-dimethyl-5-(2-(6-methylpyridin-3-yl)ethyl)-4H-pyrido[4,3-b]indol-3(5H)-one. (Compound 232)

Preparation of the title compound was carried out according to General Method 8. p-Tolylhydrazine hydrochloride (1.27 g, 8 mmol), 5-(2-bromoethyl)-2-methylpyridine (1.6 g, 8 mmol), triethyl amine (3.5 ml, 24 mmol) and 1-methylpiperidine-2,4-dione (4.2 g, 8 mmol) were taken in ethanol (25 ml) to obtain 40 mg of 1,2-dihydro-2,8-dimethyl-5-(2-(6-methylpyridin-3-yl)ethyl)-4H-pyrido[4,3-b]indol-3(5H)-one after purification on silica gel (230-400 mesh) chromatography eluting with methanol-dichloromethane gradient. To this intermediate (25 mg, 0.07 mmol) was added N-bromo succinamide (26 mg, 0.1), and azobisisobutyronitrile (1 mg) in carbon tetrachloride (10 ml) and the reaction mixture was heated at 80° C. for 12 h to obtain 5 mg of 4-bromo-1,2-dihydro-2,8-dimethyl-5-(2-(6-methylpyridin-3-yl)ethyl)-4H-pyrido[4,3-b]indol-3(5H)-one as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 61

Preparation of 2,3,4,5-tetrahydro-2,8-dimethyl-5-(3-(pyridin-2-yl)propyl)-1H-pyrido[4,3-b]indole. (Compound 233)

Example 61A

Preparation of 2,3,4,5-tetrahydro-2,8-dimethyl-5-(3-(pyridin-2-yl)prop-2-ynyl)-1H-pyrido[4,3-b]indole A mixture of 2,3,4,5-tetrahydro-2,8-dimethyl-5-(prop-2-ynyl)-1H-pyrido[4,3-b]indole (obtained by General Method 8; p-tolylhydrazine hydrochloride (600 mg, 3.7 mmol), propargyl bromide (80 wt % solution in toluene, 0.34 ml, 3.7 mmol), triethyl amine (1.5 ml, 11.3 mmol) and N-methyl-4-piperidone hydrochloride (316 mg, 2.1 mmol) were taken in ethanol (15 ml) to obtain 80 mg of 2,3,4,5-tetrahydro-2,8-dimethyl-5-(prop-2-ynyl)-1H-pyrido[4,3-b]indole after purification on silica gel (230-400 mesh) chromatography eluting with methanol-dichloromethane gradient) (150 mg, 0.6 mmol), 2-bromopyridine (0.06 ml, 0.6 mmol), dichlorobis(triphenylphosphine) palladium (8 mg, 0.012 mmol), CuI (1 mg, 0.006 mmol), and triethylamine (0.01 ml 0.071 mmol) in acetonitrile (5 ml) was heated at 80° C. for 1.5 h to obtain 108 mg of 2,3,4,5-tetrahydro-2,8-dimethyl-5-(3-(pyridin-2-yl)prop-2-ynyl)-1H-pyrido[4,3-b]indole after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 61B 2,3,4,5-tetrahydro-2,8-dimethyl-5-(3-(pyridin-2-yl)prop-2-ynyl)-1H-pyrido[4,3-b]indole (See Example 61A) (20 mg, 0.06 mmol) was hydrogenated in methanol (2 ml) with 10% Pd—C (10 mg) at 1 atm of hydrogen to obtain 5 mg of 2,3,4,5-tetrahydro-2,8-dimethyl-5-(3-(pyridin-2-yl)propyl)-1H-pyrido[4,3-b]indole after purification on neutral alumina chromatography eluting with methanol-dichloromethane gradient. The free base was converted into its diHCl salt by treatment of ethanolic HCl.

Example 62

Preparation of 5-(2-fluorophenethyl)-2,3,4,5-tetrahydro-8-iodo-2-methyl-1H-pyrido[4,3-b]indole. (Compound 89)

Preparation of the title compound was carried out according to General Method 8. 4-Iodophenylhydrazine hydrochloride (500 mg, 2.1 mmol), 2-fluorophenethylbromide (0.3 ml, 2.1 mmol), triethyl amine (0.8 ml, 6.3 mmol) and N-methyl-4-piperidone hydrochloride (312 mg, 2.1 mmol) were taken in ethanol (10 ml) to obtain 5 mg of 5-(2-fluorophenethyl)-2,3,4,5-tetrahydro-8-iodo-2-methyl-1H-pyrido[4,3-b]indole as a trifluoroacetate salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 63

Preparation of 1,2-dihydro-2,8-dimethyl-5-(2-(6-methylpyridin-3-yl)ethyl)-4H-pyrido[4,3-b]indol-3(5H)-one. (Compound 195)

Preparation of the title compound was carried out according to General Method 8 by following an analogous procedure described for Preparation of 2,3,4,5-tetrahydro-2,8-dimethyl-5-phenethyl-1H-pyrido[4,3-b]indole (Example 47) using p-tolylhydrazine hydrochloride, 5-(2-bromoethyl)-2-methylpyridine and 1-methylpiperidine-2,4-dione.

Example 64

Preparation of 8-(trifluoromethyl)-2,3,4,5-tetrahydro-2-methyl-5-phenethyl-1H-pyrido[4,3-b]indole. (Compound 80)

Preparation of the title compound was carried out according to General Method 8 by following an analogous procedure described for Preparation of 2,3,4,5-tetrahydro-2,8-dimethyl-5-phenethyl-1H-pyrido[4,3-b]indole (See Example 47) using 4-(trifluoromethyl)phenylhydrazine, 2-phenyl ethyl bromide and N-methyl-4-piperidone hydrochloride.

Example 65

Preparation of 5-(4-chlorophenethyl)-8-chloro-2,3,4,5-tetrahydro-2-methyl-1H-pyrido[4,3-b]indole. (Compound 45)

Preparation of the title compound was carried out according to General Method 8 by following an analogous procedure described for Preparation of 2,3,4,5-tetrahydro-2,8-dimethyl-5-phenethyl-1H-pyrido[4,3-b]indole (See Example 47) using 4-chlorophenylhydrazine hydrochloride, 4-chlorophenethyl bromide and N-methyl-4-piperidone hydrochloride.

Example 66

Preparation of 5-(4-fluorophenethyl)-8-chloro-2,3,4,5-tetrahydro-2-methyl-1H-pyrido[4,3-b]indole. (Compound 162)

Preparation of the title compound was carried out according to General Method 8 by following an analogous procedure described for Preparation of 2,3,4,5-tetrahydro-2,8-dimethyl-5-phenethyl-1H-pyrido[4,3-b]indole (See Example 47) using 4-chlorophenylhydrazine hydrochloride, 4-fluorophenethyl bromide and N-methyl-4-piperidone hydrochloride.

Example 67

Preparation of 2-(8-chloro-1,2,3,4-tetrahydro-2-methylpyrido[4,3-b]indol-5-yl)-1-(piperidin-1-yl)ethanone (Compound 236)

A mixture of ethyl 2-(8-chloro-1,2,3,4-tetrahydro-2-methylpyrido[4,3-b]indol-5-yl)acetate (200 mg) and piperidine (2 ml) was heated at 120° C. for 8 h to obtain 5 mg of 2-(8-chloro-1,2,3,4-tetrahydro-2-methylpyrido[4,3-b]indol-5-yl)-1-(piperidin-1-yl)ethanone as TFA salt after purification on silica gel (230-400 mesh) chromatography eluting with methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 68

Preparation of 2-(8-chloro-1,2,3,4-tetrahydro-2-methylpyrido[4,3-b]indol-5-yl)-1-(4-methylpiperidin-1-yl)ethanone (Compound 237)

A mixture of ethyl 2-(8-chloro-1,2,3,4-tetrahydro-2-methylpyrido[4,3-b]indol-5-yl)acetate (200 mg) and 4-methylpiperidine (2 ml) was heated at 120° C. for 8 h to obtain 40 mg of 2-(8-chloro-1,2,3,4-tetrahydro-2-methylpyrido[4,3-b]indol-5-yl)-1-(4-methylpiperidin-1-yl)ethanone after purification on neutral alumina chromatography eluting with methanol-dichloromethane gradient. The free base was converted into its oxalate salt by treatment of oxalic acid (1 equiv) in anhydrous THF.

Example 69

Preparation of 2-(8-chloro-1,2,3,4-tetrahydro-2-methylpyrido[4,3-b]indol-5-yl)-1-morpholinoethanone (Compound 238)

A mixture of ethyl 2-(8-chloro-1,2,3,4-tetrahydro-2-methylpyrido[4,3-b]indol-5-yl)acetate (200 mg) and morpholine (2 ml) was heated at 120° C. for 15 h to obtain 27 mg of 2-(8-chloro-1,2,3,4-tetrahydro-2-methylpyrido[4,3-b]indol-5-yl)-1-morpholinoethanone after purification on neutral alumina chromatography eluting with methanol-dichloromethane gradient. The free base was converted into its oxalate salt by treatment of oxalic acid (1 equiv) in anhydrous THF.

Example 70

Preparation of 2-(8-chloro-1,2,3,4-tetrahydro-2-methylpyrido[4,3-b]indol-5-yl)-1-thiomorpholinoethanone (Compound 239)

A mixture of ethyl 2-(8-chloro-1,2,3,4-tetrahydro-2-methylpyrido[4,3-b]indol-5-yl)acetate (200 mg) and thiomorpholine (2 ml) was heated at 120° C. for 15 h to obtain 38 mg of 2-(8-chloro-1,2,3,4-tetrahydro-2-methylpyrido[4,3-b]indol-5-yl)-1-thiomorpholinoethanone after purification on neutral alumina chromatography eluting with methanol-dichloromethane gradient. The free base was converted into its oxalate salt by treatment of oxalic acid (1 equiv) in anhydrous THF.

Example 71

Preparation of 3-(8-chloro-1,2,3,4-tetrahydro-2-methylpyrido[4,3-b]indol-5-yl)-1-(pyrrolidin-1-yl)propan-1-one (Compound 240)

A mixture of ethyl 3-(8-chloro-1,2,3,4-tetrahydro-2-methylpyrido[4,3-b]indol-5-yl)propanoate (100 mg) and pyrrolidine (2 ml) was heated at 120° C. for 3 h to obtain 39 mg of 3-(8-chloro-1,2,3,4-tetrahydro-2-methylpyrido[4,3-b]indol-5-yl)-1-(pyrrolidin-1-yl)propan-1-one after purification on neutral alumina chromatography eluting with methanol-dichloromethane gradient. The free base was converted into its oxalate salt by treatment of oxalic acid (1 equiv) in anhydrous THF.

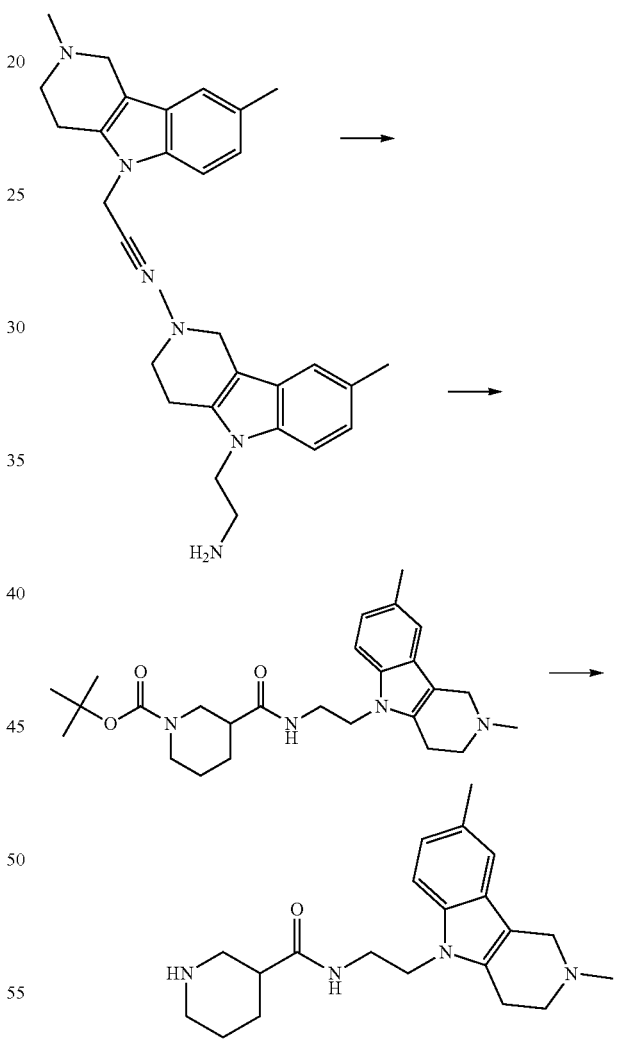

Example 72

Preparation of 1-(4-aminopiperidin-1-yl)-3-(1,2,3,4-tetrahydro-2,8-dimethylpyrido[4,3-b]indol-5-yl)propan-1-one (Compound 231)

tert-butyl 1-(3-(1,2,3,4-tetrahydro-2,8-dimethylpyrido[4,3-b]indol-5-yl)propanoyl)piperidin-4-ylcarbamate (50 mg)

was stirred with trifluoroacetic acid (2 ml) in dichloromethane (2 ml) for 16 h at 25° C. to obtain 10 mg of 1-(4-aminopiperidin-1-yl)-3-(1,2,3,4-tetrahydro-2,8-dimethylpyrido[4,3-b]indol-5-yl)propan-1-one as di-TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 76

Preparation of Compound 241

Dimebon dihydrochloride (100 mg) was mixed with $SeO_2$ (138 mg) in pyridine (1 mL) and the reaction mixture was heated at 80° C. for 48 h. The reaction mixture was concentrated under reduced pressure and the resulting crude product was purified by reverse phase chromatography to obtain 28 mg of product.

Example 77

Preparation of Compound 189

The title compound was prepared according to General Method 8 using the following reagents: 4-chlorophenylhydrazine, 1-(2-chloroethyl)piperidine hydrochloride, N-methyl-4-piperidone.

Example 78

Preparation of 2-(8-chloro-1,2,3,4-tetrahydro-2-methylpyrido[4,3-b]indol-5-yl)-1-(pyrrolidin-1-yl)ethanone (Compound 243)

A mixture of ethyl 2-(8-chloro-1,2,3,4-tetrahydro-2-methylpyrido[4,3-b]indol-5-yl)acetate (100 mg) and pyrrolidine (1 ml) was heated at 120° C. for 15 h to obtain 59 mg of 2-(8-chloro-1,2,3,4-tetrahydro-2-methylpyrido[4,3-b]indol-5-yl)-1-(pyrrolidin-1-yl)ethanone after purification on neutral alumina chromatography eluting with methanol-dichloromethane gradient. The free base was converted into its oxalate salt by treatment of oxalic acid (1 equiv) in anhydrous THF.

Example 79

Preparation of Compound 244

The title compound was prepared using the following reagents: 4-chlorophenylhydrazine hydrochloride, N-methyl-4-piperidone, ethyl bromoacetate, piperazine.

Example 80

Preparation of Compound 245

The title compound was prepared using the following reagents: 4-chlorophenylhydrazine hydrochloride, N-methyl-4-piperidone, ethyl bromoacetate, 2,6-dimethylpiperazine.

Example 81

Preparation of Compound 246

The title compound was prepared using the following reagents: 4-chlorophenylhydrazine hydrochloride, N-methyl-4-piperidone, ethyl bromoacetate, 2-oxopiperazine.

Example 82

Preparation of Compound 247

The title compound was prepared according to General Method 8 using the following reagents: p-Tolylhydrazine hydrochloride, N-methyl-4-piperidone, 4-methoxyphenethyl bromide.

Example 83

Preparation of Compound 248

The title compound was prepared using the following reagents: 4-chlorophenylhydrazine hydrochloride, N-methyl-4-piperidone, ethyl bromoacetate, 1-isopropylpiperazine

Example 84

Preparation of Compound 249

The title compound was prepared according to General Method 8 using the following reagents: 4-fluorophenylhydrazine hydrochloride, N-methyl-4-piperidone, 4-chlorophenethyl bromide.

Example 85

Preparation of Compound 250

The title compound was prepared according to General Method 1 using the following reagents: 4-chlorophenylhydrazine hydrochloride, N-methyl-4-piperidone, 2-(trifluoromethyl)-5-vinylpyridine.

2 g of 5-bromo-2-(trifluoromethyl)pyridine was dissolved in DMF:THF (3:1, 12 mL). vinyltributyltin (3 g) and tetrakis (triphenylphosphine)palladium (135 mg) were added to this solution. The reaction mixture was degassed and purged with nitrogen for 5 min and then heated at 100° C. for 2 h. at which point the reaction was found complete (monitored by TLC). The reaction mixture was diluted with water and extracted with ethyl acetate. The combined organic layer was dried over anhydrous sodium sulfate and evaporated under reduced pressure (Caution: product may be volatile) and the residue was purified by $SiO_2$ chromatography (100-200 mesh, eluent: hexane-ethyl acetate gradient). The requisite fractions were concentrated below 40° C. under reduced pressure to obtain 20.3 g of 2-(trifluoromethyl)-5-vinylpyridine as oil.

222 mg 8-chloro-2,3,4,5-tetrahydro-2-methyl-1H-pyrido[4,3-b]indole was dissolved in NMP (0.6 mL). Powdered KOH (196 mg) was added to this solution, and the reaction mixture was stirred for 10 min at 25° C. Finally, 2-(trifluoromethyl)-5-vinylpyridine (190 mg) was added and the reaction mixture was heated in sealed tube at 45° C. for 30 min. The reaction was monitored by LCMS. After this period, the reaction mixture was cooled to 25° C. and diluted with satd. aqueous NaCl (5 mL). The product was extracted with ethyl acetate. The combined organic layer was dried over anhydrous sodium sulfate and evaporated under reduced pressure and the residue was purified by SiO$_2$ chromatography (100-200 mesh, eluent: dichloromethane-methanol gradient). The requisite fractions were concentrated below 40° C. under reduced pressure to obtain 160 mg of product. The free base was converted into its oxalate salt by treatment of oxalic acid (1 equiv) in anhydrous THF.

Example 86

Preparation of Compound 251

The title compound was prepared using the following reagents: p-Tolylhydrazine hydrochloride, N-methyl-4-piperidone, ethyl bromoacetate, 4-methylpiperidine.

Example 87

Preparation of Compound 252

The title compound was prepared according to General Method 1 using the following reagents: p-Tolylhydrazine hydrochloride, N-methyl-4-piperidone, 2-(trifluoromethyl)-5-vinylpyridine.

2,8-dimethyl-2,3,4,5-tetrahydro-1H-pyrido[4,3-b]indole dihydrochloride (203 mg) was dissolved in NMP (2.5 mL). Powdered KOH (463 mg) was added to this solution, and the reaction mixture was stirred for 10 min at 25° C. Finally, 2-(trifluoromethyl)-5-vinylpyridine (300 mg) was added and the reaction mixture was stirred at 25° C. for 4 h. The reaction was monitored by LCMS. After this period, the reaction mixture was cooled to 25° C. and diluted with satd. aqueous NaCl (5 mL). The product was extracted with ethyl acetate. The combined organic layer was dried over anhydrous sodium sulfate and evaporated under reduced pressure and the residue was purified by SiO$_2$ chromatography (100-200 mesh, eluent: dichloromethane-methanol gradient). The requisite fractions were concentrated below 40° C. under reduced pressure to obtain 140 mg of product. The free base was converted into its oxalate salt by treatment of oxalic acid (1 equiv) in anhydrous THF.

Example 88

Preparation of Compound 253

The title compound was prepared according to General Method 8 using the following reagents: 4-fluorophenylhydrazine hydrochloride, N-methyl-4-piperidone, 4-fluorophenethyl bromide.

Example 89

Preparation of 2,3,4,5-tetrahydro-2,8-dimethyl-5-(3-(pyridin-2-yl)prop-2-ynyl)-1H-pyrido[4,3-b]indole A mixture of 2,3,4,5-tetrahydro-2,8-dimethyl-5-(prop-2-ynyl)-1H-pyrido[4,3-b]indole (150 mg, 0.6 mmol), 3-bromopyridine (0.6 ml, 0.6 mmol), dichlorobis(triphenyl-phosphine) palladium (8 mg, 0.012 mmol), CuI (1 mg, 0.006 mmol), and triethylamine (0.01 ml 0.071 mmol) in acetonitrile (5 ml) was heated at 80° C. to obtain 108 mg of 2,3,4,5-tetrahydro-2,8-dimethyl-5-(3-(pyridin-2-yl)prop-2-ynyl)-1H-pyrido[4,3-b]indole after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Preparation of 2,3,4,5-tetrahydro-2,8-dimethyl-5-(3-(pyridin-2-yl)propyl)-1H-pyrido[4,3-b]indole 2,3,4,5-tetrahydro-2,8-dimethyl-5-(3-(pyridin-2-yl)prop-2-ynyl)-1H-pyrido[4,3-b]indole (20 mg, 0.06 mmol) was hydrogenated in methanol (2 ml) with 10% Pd—C (10 mg) at 1 atm of hydrogen to obtain 5 mg of 2,3,4,5-tetrahydro-2,8-dimethyl-5-(3-(pyridin-2-yl)propyl)-1H-pyrido[4,3-b]indole after purification on neutral alumina chromatography eluting with methanol-dichloromethane gradient. The free base was converted into its HCl salt by treatment of ethanolic HCl.

Example 90

Preparation of Compound 255

2,5-Dibromopyridine (5 g) was dissolved in toluene (30 mL) and the solution was cooled to −75° C. BuLi was added drop wise to this solution over a period of 20 min. The reaction was maintained at −75° C. for 2 h. Dry ice (200 g) was added and the reaction mixture was slowly allowed to warm to 25° C. The reaction mixture was evaporated to dryness, the residue was dissolved in water (25 mL) and the pH was adjusted to 7 by adding conc. HCl. The solid product was filtered and washed with water followed by diethyl ether. Yield 3 g. TLC Rf 0.1 in 50% ethyl acetate-hexane.

5-Bromopyridine-2-carboxylic acid (10 g) was dissolved in 260 mL MeOH. SOCl$_2$ (26 mL) was added dropwise to this solution over a period of 10 min (Caution: Exothermic reaction). The reaction mixture was heated to 65° C. for 2 h at which point the reaction was found complete by TLC (an aliquot was evaporated to dryness, the residue taken up in satd. aq. NaHCO$_3$ and extracted with ethyl acetate). The reaction mixture was evaporated to dryness. The residue was basified with satd. aq. NaHCO$_3$ and extracted with ethyl acetate. The combined ethyl acetate layer was dried (Na$_2$SO$_4$) and evaporated under reduced pressure to obtain 9.2 g of the solid product. TLC Rf 0.5 (40% Ethyl acetate-hexane).

4 g of methyl 5-bromopyridine-2-carboxylate was dissolved in 160 mL dioxane. vinyltributyltin (11.7 g) was added to this solution at 25° C., followed by addition of dichlorobis (triphenylphosphine)palladium (1.5 g). The reaction mixture was degassed and purged with nitrogen for 5 min and then heated at 100° C. for 2 h. at which point the reaction was found complete (monitored by TLC). The reaction mixture was evaporated under reduced pressure (Caution: product may be volatile) and the residue was purified by SiO$_2$ chromatography (100-200 mesh, eluent: hexane-50% ethyl acetate hexane gradient). The requisite fractions were concentrated below 40° C. under reduced pressure to obtain 2 g of product as pale yellow oil (solid at −20° C.). TLC Rf 0.3 in 40% EA-Hexane.

2,8-dimethyl-2,3,4,5-tetrahydro-1H-pyrido[4,3-b]indole dihydrochloride (710 mg) was dissolved in NMP (7.5 mL). Powdered KOH (1.62 g) was added to this solution, and the reaction mixture was stirred for 10 min at 25° C. Finally, 5-vinyl pyridine-2-carboxylic acid methyl ester (977 mg) was added dropwise over 5 min and the reaction mixture was heated in sealed tube at 100° C. for 24 h. The reaction was monitored by LCMS. After this period, the reaction mixture was cooled to 25° C. and diluted with water (7 mL). The pH of the resulting solution was adjusted to 4-5 by addition of formic acid. The resulting solution was directly subjected to purification by reverse-phase HPLC. The requisite fractions containing product were pooled and lyophilized (Caution: compound may be heat sensitive) to obtain 370 mg of product as TFA salt with 84% HPLC purity (with 16% contamination of unreacted carboline). The purity was enhanced to 98.5 by a second purification on reverse phase HPLC.

Example 91

Preparation of Compound 256

Methyl 4-aminobenzoate (5.0 g, 0.0331 moles) was taken up in conc. HCl (50 mL) and cooled to 0° C. Sodium nitrite (2.5 g, 0.0331 moles) solution in water was added at 0° C. over 30 minutes and stirred at RT for 90 min. Tin chloride (19.40 g, 0.0927 moles) in HCl (100 mL) was added drop wise at 0° C. and stirred at RT for 2 hr. The reaction was filtered and the solid obtained was washed with diethyl ether and dried on a rotary evaporator to give 6.2 g, 92.53% yield of Methyl 4-hydrazinylbenzoate as a white solid.

Methyl 4-hydrazinylbenzoate (1 g, 0.005 moles) and 5-(2-bromoethyl)-2-methylpyridine (1 g, 0.005 moles) was taken up in triethylamine (2.1 mL) and stirred at RT for 1 hr. The reaction was heated at 100° C., overnight. LCMS analysis of the reaction mixtures shows the formation of product. The reaction mixture was concentrated, water (20 mL) was added to the reaction mixture and the mixture extracted with ethyl acetate. The crude product was dissolved in ethyl acetate and purified by column chromatography using neutral alumina, using 100% ethyl acetate as the eluent. After chromatography 400 mg of Methyl 4-(1-(2-(6-methylpyridin-3-yl)ethyl)hydrazinyl)benzoate was obtained, 28.5% yield.

Methyl 4-(1-(2-(6-methylpyridin-3-yl)ethyl)hydrazinyl) benzoate (0.1 g, 0.350 mmoles) and 1-methylpiperidin-4-one (0.052 g, 0.350 mmoles) was taken up in 1M HCl (4 mL) and heated at 100° C. for 18 hr. LCMS of the reaction mixture shows the formation of the product. The reaction mixture was concentrated and purified by reverse phase HPLC to give 5 mg of 2-Methyl-5-(2-(6-methylpyridin-3-yl)ethyl)-2,3,4,5-tetrahydro-1H-pyrido[4,3-b]indole-8-carboxylic acid, as a white solid, 4% yield.

Example 92

Preparation of 2-(1,2,3,4-tetrahydro-2,8-dimethylpyrido[4,3-b]indol-5-yl)-1-(pyrrolidin-1-yl)ethanone (Compound 257)

A mixture of ethyl 2-(1,2,3,4-tetrahydro-2,8-dimethylpyrido[4,3-b]indol-5-yl)acetate (100 mg) and pyrrolidine (1 ml) was heated at 100° C. for 15 h to obtain 60 mg of 2-(1,2,3,4-tetrahydro-2,8-dimethylpyrido[4,3-b]indol-5-yl)-1-(pyrrolidin-1-yl)ethanone as off white solid after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 93

Preparation of 2,8-dimethyl-5-(2-(6-methylpyridin-3-yl)ethyl)-2,3,4,5-tetrahydro-1H-pyrido[4,3-b]indole 2-oxide Dimebon (500 mg) was dissolved in 10 mL dichloromethane. To this was added a solution of mCPBA (65%, 536 mg) in 5 mL dichloromethane drop wise at 25 deg C. The reaction mixture was stirred at 25 deg C. for 24 h at which point it was found complete (by TLC and LCMS). The solvent was removed under reduced pressure (below 30 deg C.) and the residue was purified by column chromatography on neutral alumina eluting with methanol-dichloromethane gradient to obtain 220 mg of product as light brown oil. TLC Rf 0.5 in 5% MeOH-DCM. This compound also exhibited the following inhibition profile:

| Adren. alpha1D | Adren. alpha2A | Adren. alpha2B | Dop. D2L | Hist. H1 | Hist. H2 | Ser. 5-HT2A | Ser. 5-HT2C | Ser. 5-HT6 | Ser. 5-HT7 |
|---|---|---|---|---|---|---|---|---|---|
| 19 | 1 | 36 |  | 68 | 19 | 4 | 9 | 11 | 35 |

Example 94

Preparation of 2,2,2-trichloroethyl 3,4-dihydro-8-methyl-5-(2-(6-methylpyridin-3-yl)ethyl)-1H-pyrido[4,3-b]indole-2(5H)-carboxylate (Compound 259)

1-(2-(6-methylpyridin-3-yl)ethyl)-1-p-tolylhydrazine (500 mg) and N-Troc-piperidone (560 mg) were mixed in 15 mL ethanolic HCl and stirred for 20 min. The volatiles were removed under reduced pressure, the residue was taken in ethanol (5 mL) and the solution was heated at 90 deg C. for 3 h (the reaction was monitored by LCMS and TLC). The reaction mixture was cooled to 25 deg C. and evaporated under reduced pressure. The residue was basified with satd. aq. NaHCO3 and extracted with ethyl acetate. The combined ethyl acetate layer was dried over Na2SO4 and concentrated under reduced pressure to obtain the crude product. The crude product was purified by flash chromatography on silica gel (eluent: hexane to 10% acetonehexane gradient) to obtain 100 mg of product as light yellow oil. TLC Rf 0.2 in 20% acetone-hexane.

Example 95

Preparation of 2,3,4,5-tetrahydro-8-methyl-5-(2-(6-methylpyridin-3-yl)ethyl)-1H-pyrido[4,3-b]indole (Compound 230)

2,2,2-trichloroethyl 3,4-dihydro-8-methyl-5-(2-(6-methylpyridin-3-yl)ethyl)-1Hpyrido[4,3-b]indole 2(5H)-carboxylate (100 mg) was dissolved in glacial AcOH (1.2 mL) and the solution was stirred at 25 deg C. for 10 min. To this solution Zn dust (121 mg) was added in portions at 25 deg C. after which the reaction mixture was stirred at 25 deg C. overnight. The reaction mixture was cooled to 0 deg C. and pH was adjusted to 8 with aq. NH3. The reaction mixture was extracted with ethyl acetate, the combined ethyl acetate layer was dried over sodium sulfate and concentrated to obtain 75 mg of product with 87% HPLC purity. The product (free base) was converted into oxalate salt by treatment of 30 mg oxalic acid in 2 mL THF. Filtration of the resulting suspension furnished product.

Example 96

Preparation of 2-Methyl-5-(2-(6-methylpyridin-3-yl)ethyl)-2,3,4,5-tetrahydro-1H-pyrido[4,3-b]indole-8-carboxylic acid Compound 261

Methyl 4-hydrazinylbenzoate (5.0 g, 0.0331 moles) was taken up in 50 mL of conc. HCl and cooled to 0 degrees C. Sodium nitrite (2.5 g, 0.0331 moles) solution in water, was added at 0 degrees C. over 30 minutes and stirred at RT for 90 min. Tin chloride (19.40 g, 0.0927 moles) in 100 mL HCl was added drop wise at 0 degrees C. and stirred at RT for 2 hr. The reaction was filtered and the solid obtained was washed with diethyl ether and dried on a rotary evaporator to give 6.2 g, 92.53% yield of Methyl 4-hydrazinylbenzoate as a white solid.

Methyl 4-hydrazinylbenzoate (1 g, 0.005 moles) and 5-(2-bromoethyl)-2-methylpyridine (1 g, 0.005 moles) was taken up in 2.1 mL of triethylamine and stirred at RT for 1 hr. The reaction was then heated at 100 degrees C., overnight. LCMS analysis of the reaction mixtures shows the formation of product. Reaction mixture was concentrated, water (20 mL) was added to the reaction mixture and the mixture extracted with ethyl acetate. The crude product was dissolved in ethyl acetate and purified by column chromatography using neutral alumina, using 100% ethyl acetate as the eluent. After chromatography 400 mg of Methyl 4-(1-(2-(6-methylpyridin-3-yl)ethyl)hydrazinyl)benzoate was obtained, 28.5% yield.

Methyl 4-(1-(2-(6-methylpyridin-3-yl)ethyl)hydrazinyl) benzoate (0.1 g, 0.350 mmoles) and 1-methylpiperidin-4-one (0.052 g, 0.350 mmoles) was taken up in 4 mL 1M HCl and heated at 100 degrees C. for 18 hr. LCMS of the reaction mixture shows the formation of the product. The reaction mixture was concentrated and purified by reverse phase HPLC.[1] to give 5 mg of 2-Methyl-5-(2-(6-methylpyridin-3-yl)ethyl)-2,3,4,5-tetrahydro-1H-pyrido[4,3-b]indole-8-carboxylic acid, as a white solid, 4% yield.

Batch Size—800 mg, Purity:—~3% Since the compound is highly Polar First Purification Was carried on prep HPLC using Water (0.05% TFA) as eluent. Method Details: Sample preparation: Compound dissolved in Milli-Q Water (4.0 mL) Clear Brown solution Column: YMC ODS A, 500 mm×30 mm×10µ Flow: 30 mL/min Wavelength: monitored at 220 nm & 254 nm. Mobile Phase Mobile Phase A: 0.05% TFA in water Mobile Phase B: 0.05% TFA in Acetonitrile Gradient Program 0% B for 15 min 0% B to 50% B in 27 min. Column Washed with 100% methanol. Collected fractions were lyophilized. Lyophilized solid having purity 80% were dissolved in 250 µL and analyzed by following method. (Method details for analysis: Column Zorbax cyano, 150 mm×4.6×3.50, Flow: 1.2 mL/min, inj. Vol: 10.0 µL, Wavelength: 220 nm & 254 nm, Gradient Program: 0% B to 50% B in 5 min hold for 2 min 7.01 min to 10.0 min 0% B Second purification Total Vol: 250 µL Column: Zorbax cyano, 150 mm×4.6×3.5µ), Flow: 1.2 mL/min, inj. Vol: 10.0 µL, Wavelength: 220 nm & 254 nm, Mobile Phase Mobile Phase A: 0.05% TFA in water Mobile Phase B: 0.05% TFA in Acetonitrile Isocratic program 8% B for 5 min. number of injections: 25 Purity of pooled fraction: 98% Collected fractions were lyophilized Purity after lyophilization: 92.07%

Example 97

Preparation of 2,3,4,5-tetrahydro-5-(2-(6-methylpyridin-3-yl)ethyl)-1H-pyrido[4,3-b]indole-8-carboxylic acid (Compound 274)

A mixture of Methyl 4-(1-(2-(6-methylpyridin-3-yl)ethyl) hydrazinyl)benzoate hydrochloride (0.15 gm, 0.447 mol), piperidone (0.13 gm, 1.34 mol) and 7% sulfuric acid in dioxane (5 mL) was heated at 100 deg C. for 2 h. Reaction mass was cooled and concentrated under reduced pressure to give crude 2,3,4,5-tetrahydro-5-(2-(6-methylpyridin-3-yl)ethyl)-1H-pyrido[4,3-b]indole-8-carboxylic acid (LCMS; 44% of desired peak) as a brown colored oil which is submitted for purification by preparative HPLC.

Example 98

Preparation of ethyl 5-(2-(1,2,3,4-tetrahydro-2,8-dimethylpyrido[4,3-b]indol-5-yl)ethyl)pyridine-2-carboxylate (Compound 275)

Ethanolic HCl was add to the compound of (2-(2,8-dimethyl-3,4-dihydro-1H-pyrido[4,3-b]indol-5(2H)-yl)ethyl)picolinic acid (0.750 gm, 2.14 mmol) and refluxed for 7 h. The reaction mixture was concentrated, basified with Sat. NaHCO₃, extracted with ethylacetate (2×100 mL), dried over sodium sulfate and concentrated to get crude product. The crude was purified by Silica Gel (100-200) Chromatography (10% Me-OH in DCM) to get ethyl 5-(2-(2,8-dimethyl-3,4-dihydro-1H-pyrido[4,3-b]indol-5(2H)-yl)picolinate as a free base. Ethanolic HCl was add to the compound of ethyl 5-(2-(2,8-dimethyl-3,4-dihydro-1H-pyrido[4,3-b]indol-5 (2H)-yl)ethyl)picolinate (free base, 0.07 g, 0.185 mmol) and then allow to keep at for some time then concentrated to get stick compound which was washed with ether two to three times to get ethyl 5-(2-(2,8-dimethyl-3,4-dihydro-1H-pyrido [4,3-b]indol-5(2H)-yl)ethyl)picolinate. HCl Salt. (50 mg).

Example 99

Preparation of 2,3,4,5-tetrahydro-2,8-dimethyl-5-(2-(5-methylthiophen-2-yl)ethyl)-1H-pyrido[4,3-b]indole (Compound 277)

The title compound is prepared from a mixture of 2,3,4,5-tetrahydro-2,8-dimethyl-1H-pyrido[4,3-b]indole, 2-methyl-5-vinylthiophene and KOH (5-7 equiv) in NMP at a temperature ranging between 25 deg C. to 100 deg C. The product obtained is isolated by preparative HPLC.

Example 100

Preparation of 4-(3,4-dihydro-8-methyl-5-(2-(6-methylpyridin-3-yl)ethyl)-1H-pyrido[4,3-b]indol-2 (5H)-yl)benzenamine (Compound 278)

The title compound is prepared from a mixture of 4-(3,4-dihydro-8-methyl-1H-pyrido[4,3-b]indol-2(5H)-yl)benzenamine, 2-methyl-5-vinylpyridine and KOH (5-7 equiv) in NMP at a temperature ranging between 25 deg C. to 100 deg C. The product obtained is isolated by preparative HPLC.

Example 101

Preparation of 2,3,4,5-tetrahydro-8-methyl-5-(2-(6-methylpyridin-3-yl)ethyl)-2-phenyl-1H-pyrido[4,3-b]indole (Compound 279)

The title compound is prepared from a mixture of 2,3,4,5-tetrahydro-8-methyl-2-phenyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 102

Preparation of 2,3,4,5-tetrahydro-8-methyl-5-(2-(6-methylpyridin-3-yl)ethyl)-2-p-tolyl-1H-pyrido[4,3-b] indole (Compound 280)

The title compound is prepared from a mixture of 2,3,4,5-tetrahydro-8-methyl-2-p-tolyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 103

Preparation of 2-(4-bromophenyl)-2,3,4,5-tetrahydro-8-methyl-5-(2-(6-methylpyridin-3-yl)ethyl)-1H-pyrido[4,3-b]indole (Compound 281)

The title compound is prepared from a mixture of 2-(4-bromophenyl)-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 104

Preparation of 2,3,4,5-tetrahydro-8-methyl-5-(2-(6-methylpyridin-3-yl)ethyl)-2-(4-nitrophenyl)-1H-pyrido[4,3-b]indole (Compound 282)

The title compound is prepared from a mixture of 2,3,4,5-tetrahydro-8-methyl-2-(4-nitrophenyl)-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 105

Preparation of 2-cyclobutyl-2,3,4,5-tetrahydro-8-methyl-5-(2-(6-methylpyridin-3-yl)ethyl)-1H-pyrido[4,3-b]indole (Compound 283)

The title compound is prepared from a mixture of 2-cyclobutyl-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 106

Preparation of 2,3,4,5-tetrahydro-2-(4-methoxyphenyl)-8-methyl-5-(2-(6-methylpyridin-3-yl)ethyl)-1H-pyrido[4,3-b]indole (Compound 284)

The title compound is prepared from a mixture of 2,3,4,5-tetrahydro-2-(4-methoxyphenyl)-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 107

Preparation of 2-(4-fluorophenyl)-2,3,4,5-tetrahydro-8-methyl-5-(2-(6-methylpyridin-3-yl)ethyl)-1H-pyrido[4,3-b]indole (Compound 285)

The title compound is prepared from a mixture of 2-(4-fluorophenyl)-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 108

Preparation of 2-(4-chlorophenyl)-2,3,4,5-tetrahydro-8-methyl-5-(2-(6-methylpyridin-3-yl)ethyl)-1H-pyrido[4,3-b]indole (Compound 286)

The title compound is prepared from a mixture of 2-(4-chlorophenyl)-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 109

Preparation of 2-(4-(difluoromethyl)phenyl)-2,3,4,5-tetrahydro-8-methyl-5-(2-(6-methylpyridin-3-yl)ethyl)-1H-pyrido[4,3-b]indole (Compound 287)

The title compound is prepared from a mixture of 2-(4-(difluoromethyl)phenyl)-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 110

Preparation of 2-(4-(trifluoromethyl)phenyl)-2,3,4,5-tetrahydro-8-methyl-5-(2-(6-methylpyridin-3-yl)ethyl)-1H-pyrido[4,3-b]indole (Compound 288)

The title compound is prepared from a mixture of 2-(4-(trifluoromethyl)phenyl)-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 111

Preparation of 2,3,4,5-tetrahydro-2-(4-iodophenyl)-8-methyl-5-(2-(6-methylpyridin-3-yl)ethyl)-1H-pyrido[4,3-b]indole (Compound 289)

The title compound is prepared from a mixture of 2,3,4,5-tetrahydro-2-(4-iodophenyl)-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 112

Preparation of 4-(3,4-dihydro-8-methyl-5-(2-(6-methylpyridin-3-yl)ethyl)-1H-pyrido[4,3-b]indol-2(5H)-yl)phenol (Compound 290)

The title compound is prepared from a mixture of 4-(3,4-dihydro-8-methyl-1H-pyrido[4,3-b]indol-2(5H)-yl)phenol, 2-methyl-5-vinylpyridine and KOH (5-7 equiv) in NMP at a temperature ranging between 25 deg C. to 100 deg C. The product obtained is isolated by preparative HPLC.

Example 113

Preparation of 8-chloro-7-fluoro-2,3,4,5-tetrahydro-2-methyl-5-(2-(piperidin-1-yl)ethyl)-1H-pyrido[4,3-b]indole (Compound 292)

The title compound is prepared by following General Method 8 by using 1-(bromomethyl)piperidine, 4-chloro-3-fluorophenylhydrazine hydrochloride, triethylamine and N-methyl-4-piperidone.

Example 114

Preparation of 2,8-dimethyl-5-(2-(6-methyl-1-oxidopyridin-3-yl)ethyl)-2,3,4,5-tetrahydro-1H-pyrido[4,3-b]indole 2-oxide (Compound 293)

2,3,4,5-tetrahydro-2,8-dimethyl-5-(2-(6-methylpyridin-3-yl)ethyl)-1H-pyrido[4,3-b]indole (98 mg, 3.1 mmol) was stirred with hydrogen peroxide (30% in water, 0.2 ml) in glacial acetic acid (1.2 ml) at 865-70° C. for 20 h to obtain 76 mg of corresponding N,N'-dioxide.

Example 115

Preparation of 2-(8-chloro-1,2,3,4-tetrahydro-2-methylpyrido[4,3-b]indol-5-yl)-1-(2,2-dimethylpiperidin-1-yl)ethanone (Compound 294)

The title compound is prepared by following Method 8 by using 2-bromo-1-(2,2-dimethylpiperidin-1-yl)ethanone, 4-chlorophenylhydrazine hydrochloride, triethylamine and N-methyl-4-piperidone.

Example 116

Preparation of 2-(8-Chloro-2-methyl-1,2,3,4-tetrahydro-pyrido[4,3-b]indol-5-yl)-1-(1-oxo-1,4-thiomorpholin-4-yl)-ethanone (Compound 295)

A mixture of 2-(8-chloro-1,2,3,4-tetrahydro-2-methylpyrido[4,3-b]indol-5-yl)acetic acid (100 mg, 0.35 mmol), Thiomorpholine-1,1-dioxide (48 mg, 0.35 mmol), DCC (81 mg, 0.39 mmol), and DMAP (48 mg, 0.39 mmol) in dry DCM (2.5 mL) was stirred at room temperature for 3 h. The reaction mixture was filtered through Celite and concentrated by rotary evaporation to obtain 10 mg of 2-(8-Chloro-2-methyl-1,2,3,4-tetrahydro-pyrido[4,3-b]indol-5-yl)-1-(1-oxo-1,4-thiomorpholin-4-yl)-ethanone as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 117

Preparation of 2-(8-Chloro-2-methyl-1,2,3,4-tetrahydro-pyrido[4,3-b]indol-5-yl)-1-(1-oxo-1λ4-thiomorpholin-4-yl)-ethanone (Compound 296)

A mixture of 2-(8-chloro-1,2,3,4-tetrahydro-2-methylpyrido[4,3-b]indol-5-yl)acetic acid (100 mg, 0.35 mmol), Thiomorpholine-1,1-dioxide (48 mg, 0.35 mmol), DCC (81 mg, 0.39 mmol), and DMAP (48 mg, 0.39 mmol) in dry DCM (2.5 mL) was stirred at room temperature for 3 h. The reaction mixture was filtered through Celite and concentrated by rotary evaporation to obtain 10 mg of 2-(8-Chloro-2-methyl-1,2,3,4-tetrahydro-pyrido[4,3-b]indol-5-yl)-1-(1-oxo-1,4-thiomorpholin-4-yl)-ethanone as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 118

Preparation of 1-(4-Acetyl-piperazin-1-yl)-2-(8-chloro-2-methyl-1,2,3,4-tetrahydro-pyrido[4,3-b]indol-5-yl)-ethanone (Compound 297)

A mixture of 2-(8-chloro-1,2,3,4-tetrahydro-2-methylpyrido[4,3-b]indol-5-yl)acetic acid (125 mg, 0.45 mmol) and oxalyl chloride (2 ml) in dichloromethane (6.0 ml) was stirred at 25 deg C. for 3 h. The reaction mixture was concentrated to dryness. The resulting crude was dissolved in dichloromethane (6.0 ml) and DMAP (64 mg, 0.52 mmol) was added followed by addition of acetyl piperazine (56 mg, 0.43 mmol). The resulting mixture was stirred at 25 deg C. for 14 h. The solvent was removed in vacuo and purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 20 mg of 1-(4-Acetyl-piperazin-1-yl)-2-(8-chloro-2-methyl-1,2,3,4-tetrahydro-pyrido[4,3-b]indol-5-yl)-ethanone as trifluoroacetic acid salt.

Example 119

Preparation of 1-(3-aminopiperidin-1-yl)-3-(1,2,3,4-tetrahydro-2,8-dimethylpyrido[4,3-b]indol-5-yl)propan-1-one (Compound 298)

The title compound is prepared by following Method 8 by using 1-(3-aminopiperidin-1-yl)-3-bromopropan-1-one, 4-methylphenylhydrazine hydrochloride, triethylamine and N-methyl-4-piperidone.

Example 120

Preparation of 1-(3-(1,2,3,4-tetrahydro-2,8-dimethylpyrido[4,3-b]indol-5-yl)propanoyl)piperidine-3-carboxylic acid (Compound 299)

The title compound is prepared by following Method 8 by using 1-(3-bromopropanoyl)piperidine-3-carboxylic acid, 4-methylphenylhydrazine hydrochloride, triethylamine and N-methyl-4-piperidone.

Example 121

Preparation of 1-(3-(1,2,3,4-tetrahydro-2,8-dimethylpyrido[4,3-b]indol-5-yl)propanoyl)piperidine-4-carboxylic acid (Compound 300)

The title compound is prepared by following Method 8 by using 1-(3-bromopropanoyl)piperidine-4-carboxylic acid, 4-methylphenylhydrazine hydrochloride, triethylamine and N-methyl-4-piperidone.

Example 122

Preparation of 5-(4-chlorophenethyl)-9-chloro-2,3,4,5-tetrahydro-2-methyl-1H-pyrido[4,3-b]indole (Compound 301)

The title compound is prepared by following Method 8 by using 1-(2-bromoethyl)-4-chlorobenzene, 3-chlorophenylhydrazine hydrochloride, triethylamine and N-methyl-4-piperidone

Example 123

Preparation of 5-(4-chlorophenethyl)-7-chloro-2,3,4,5-tetrahydro-2-methyl-1H-pyrido[4,3-b]indole (Compound 302)

The title compound is prepared by following Method 8 by using 1-(2-bromoethyl)-4-chlorobenzene, 3-chlorophenylhydrazine hydrochloride, triethylamine and N-methyl-4-piperidone

Example 124

Preparation of 5-(4-chlorophenethyl)-6-chloro-2,3,4,5-tetrahydro-2-methyl-1H-pyrido[4,3-b]indole (Compound 303)

The title compound is prepared by following Method 8 by using 1-(2-bromoethyl)-4-chlorobenzene, 2-chlorophenylhydrazine hydrochloride, triethylamine and N-methyl-4-piperidone

Example 125

Preparation of 5-(4-fluorophenethyl)-9-chloro-2,3,4,5-tetrahydro-2-methyl-1H-pyrido[4,3-b]indole (Compound 304)

The title compound is prepared by following Method 8 by using 1-(2-bromoethyl)-4-fluorobenzene, 3-chlorophenylhydrazine hydrochloride, triethylamine and N-methyl-4-piperidone

Example 126

Preparation of 5-(4-fluorophenethyl)-7-chloro-2,3,4,5-tetrahydro-2-methyl-1H-pyrido[4,3-b]indole (Compound 305)

The title compound is prepared by following Method 8 by using 1-(2-bromoethyl)-4-fluorobenzene, 3-chlorophenylhydrazine hydrochloride, triethylamine and N-methyl-4-piperidone

Example 127

Preparation of 5-(4-fluorophenethyl)-6-chloro-2,3,4,5-tetrahydro-2-methyl-1H-pyrido[4,3-b]indole (Compound 306)

The title compound is prepared by following Method 8 by using 1-(2-bromoethyl)-4-fluorobenzene, 2-chlorophenylhydrazine hydrochloride, triethylamine and N-methyl-4-piperidone

Example 128

Preparation of 8-chloro-2,3,4,5-tetrahydro-2-methyl-5-(2-(2-methylpyrrolidin-1-yl)ethyl)-1H-pyrido[4,3-b]indole (Compound 307)

The title compound is prepared by following Method 8 by using 1-(2-bromoethyl)-2-methylpyrrolidine, 4-chlorophenylhydrazine hydrochloride, triethylamine and N-methyl-4-piperidone

Example 129

Preparation of 8-chloro-2,3,4,5-tetrahydro-2-methyl-5-(2-(3-methylpyrrolidin-1-yl)ethyl)-1H-pyrido[4,3-b]indole (Compound 308)

The title compound is prepared by following Method 8 by using 1-(2-bromoethyl)-3-methylpyrrolidine, 4-chlorophenylhydrazine hydrochloride, triethylamine and N-methyl-4-piperidone

Example 130

Preparation of 8-chloro-2,3,4,5-tetrahydro-2-methyl-5-(2-(2,3-dimethylpyrrolidin-1-yl)ethyl)-1H-pyrido[4,3-b]indole (Compound 309)

The title compound is prepared by following Method 8 by using 1-(2-bromoethyl)-2,3-dimethylpyrrolidine, 4-chlorophenylhydrazine hydrochloride, triethylamine and N-methyl-4-piperidone

Example 131

Preparation of 8-chloro-2,3,4,5-tetrahydro-2-methyl-5-(2-(2,2-dimethylpyrrolidin-1-yl)ethyl)-1H-pyrido[4,3-b]indole (Compound 310)

The title compound is prepared by following Method 8 by using 1-(2-bromoethyl)-2,2-dimethylpyrrolidine, 4-chlorophenylhydrazine hydrochloride, triethylamine and N-methyl-4-piperidone

Example 132

Preparation of 8-chloro-2,3,4,5-tetrahydro-2-methyl-5-(2-(3,3-dimethylpyrrolidin-1-yl)ethyl)-1H-pyrido[4,3-b]indole (Compound 311)

The title compound is prepared by following Method 8 by using 1-(2-bromoethyl)-3,3-dimethylpyrrolidine, 4-chlorophenylhydrazine hydrochloride, triethylamine and N-methyl-4-piperidone

Example 133

Preparation of 8-chloro-2,3,4,5-tetrahydro-2-methyl-5-(3-(pyrrolidin-1-yl)propyl)-1H-pyrido[4,3-b]indole (Compound 312)

The title compound is prepared by following Method 8 by using 1-(3-bromopropyl)pyrrolidine, 4-chlorophenylhydrazine hydrochloride, triethylamine and N-methyl-4-piperidone

Example 134

Preparation of 1-(2-(8-chloro-1,2,3,4-tetrahydro-2-methylpyrido[4,3-b]indol-5-yl)ethyl)pyrrolidin-2-one (Compound 313)

The title compound is prepared by following Method 8 by using 1-(2-bromoethyl)pyrrolidin-2-one, 4-chlorophenylhydrazine hydrochloride, triethylamine and N-methyl-4-piperidone

Example 135

Preparation of 1-(2-(8-chloro-1,2,3,4-tetrahydro-2-methylpyrido[4,3-b]indol-5-yl)ethyl)piperidin-2-one (Compound 314)

The title compound is prepared by following Method 8 by using 1-(2-bromoethyl)piperidin-2-one, 4-chlorophenylhydrazine hydrochloride, triethylamine and N-methyl-4-piperidone

Example 136

Preparation of 1,2-dihydro-1-hydroxy-2,8-dimethyl-5-(2-(6-methylpyridin-3-yl)ethyl)-4H-pyrido[4,3-b]indol-3(5H)-one (Compound 315)

The title compound is prepared from a mixture of 1,2-dihydro-1-hydroxy-2,8-dimethyl-4H-pyrido[4,3-b]indol-3(5H)-one, 2-methyl-5-vinylpyridine and KOH (5-7 equiv) in NMP at a temperature ranging between 25 deg C. to 100 deg C. The product obtained is isolated by preparative HPLC.

Example 137

Preparation of 3,4-dihydro-4-hydroxy-2,8-dimethyl-5-(2-(6-methylpyridin-3-yl)ethyl)-2H-pyrido[4,3-b]indol-1(5H)-one (Compound 317)

The title compound is prepared from a mixture of 3,4-dihydro-4-hydroxy-2,8-dimethyl-2H-pyrido[4,3-b]indol-1(5H)-one, 2-methyl-5-vinylpyridine and KOH (5-7 equiv) in NMP at a temperature ranging between 25 deg C. to 100 deg C. The product obtained is isolated by preparative HPLC.

Example 138

Preparation of 1,2-dihydro-4-hydroxy-2,8-dimethyl-5-(2-(6-methylpyridin-3-yl)ethyl)-4H-pyrido[4,3-b]indol-3(5H)-one (Compound 318)

The title compound is prepared from a mixture of 1,2-dihydro-4-hydroxy-2,8-dimethyl-4H-pyrido[4,3-b]indol-3(5H)-one, 2-methyl-5-vinylpyridine and KOH (5-7 equiv) in NMP at a temperature ranging between 25 deg C. to 100 deg C. The product obtained is isolated by preparative HPLC.

Example 139

Preparation of 3,4-dihydro-2-(hydroxymethyl)-8-methyl-5-(2-(6-methylpyridin-3-yl)ethyl)-2H-pyrido[4,3-b]indol-1(5H)-one (Compound 319)

The title compound is prepared from a mixture of 3,4-dihydro-2-(hydroxymethyl)-8-methyl-2H-pyrido[4,3-b]indol-1(5H)-one, 2-methyl-5-vinylpyridine and KOH (5-7 equiv) in NMP at a temperature ranging between 25 deg C. to 100 deg C. The product obtained is isolated by preparative HPLC.

Example 140

Preparation of 2-(8-chloro-1,2,3,4-tetrahydro-2-methylpyrido[4,3-b]indol-5-yl)-1-(2-methylpiperidin-1-yl)ethanone (Compound 321)

A mixture of 2-(8-chloro-1,2,3,4-tetrahydro-2-methylpyrido[4,3-b]indol-5-yl)acetic acid (125 mg, 0.45 mmol) and oxalyl chloride (2 ml) in dichloromethane (6.0 ml) was stirred at 25 deg C. for 3 h. After completion of the reaction (monitored by TLC), the reaction mixture was concentrated to dryness. To the resulting crude dichloromethane (6.0 ml) and DMAP (64 mg, 0.52 mmol) was added followed by addition of 2-methylpiperidine (43 mg, 0.43 mmol). The resulting mixture was stirred at 25 deg C. for 14 h. After completion of the reaction (monitored by LCMS), solvent was removed in vacuo and purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 30 mg of 2-(8-chloro-1,2,3,4-tetrahydro-2-methylpyrido[4,3-b]indol-5-yl)-1-(2-methylpiperidin-1-yl)ethanone as trifluoroacetic acid salt.

Example 141

Preparation of 2,8-dimethyl-5-(2-(5-methylpyrazin-2-yl)ethyl)-2,3,4,5-tetrahydro-1H-pyrido[4,3-b]indole (Compound 322)

To a solution of 2,8-Dimethyl-2,3,4,5-tetrahydro-1H-pyrido[4,3-b]indole (0.1 g, 0.5 mmol) in N-methyl 2-pyrolidone (0.75 mL) was added powdered potassium hydroxide (0.281 g, 5.0 mmol) and allowed to stir for 10 min at RT. 2-methyl-5-vinyl pyrazine (0.151 g, 1.2 mmol) was added and stirred for further 2 h. at 60 deg C. After completion (TLC), reaction mixture was diluted with water (25 mL) and extracted with ethyl acetate (3×100 mL). The organic layer was dried over anhydrous sodium sulphate and concentrated under reduced pressure. The crude was purified through column chromatography (6% MeOH:DCM in silica 100-200 mesh, Diameter of column—2.5 cm, Height of silica—approx. 5 inch) to provide the desired compound as yellow oil (0.05 g, 31% yield). 2,8-Dimethyl-5-[2-(5-methyl-pyrazin-2-yl)-ethyl]-2,3,4,5-tetrahydro-1H-pyrido[4,3-b]indole (0.05 g, 0.156 mmol) was dissolved in THF (2.0 mL). A solution of oxalic acid dihydrate (0.015 g, 0.000119 mol) in THF (1.0 mL) was added and stirred for 30 min at RT. Precipitate obtained was filtered and dried to give oxalate salt as white solid (0.03 g, 47% yield).

Example 142

Preparation of 2,3,4,5-tetrahydro-2,8-dimethyl-5-(2-(2-methylpyrimidin-5-yl)ethyl)-1H-pyrido[4,3-b]indole (Compound 323)

To a solution of 2,8-Dimethyl-2,3,4,5-tetrahydro-1H-pyrido[4,3-b]indole (0.1 g, 0.0005 mol) in N-methyl 2-pyrolidone (1.0 mL) was added powdered potassium hydroxide (0.14 g, 0.0025 mol) and allowed to stir r for 10 min at RT. 2-methyl-5-vinyl pyrimidine (0.151 g, 0.0012 mol) was added and stirred for further 3 h at 80 deg C. After completion (TLC), reaction mixture was diluted with water (15 mL) and extracted with ethyl acetate (3×50 mL). The organic layer was dried over anhydrous sodium sulphate and concentrated under reduced pressure using rotary evaporator. The crude was purified through column chromatography (7% MeOH:DCM in silica 100-200 mesh, Diameter of column—2.5 cm, Height of silica—approx. 5 inch) then purified through preparative TLC. to get the desired compound as yellow oil (0.025 g, 16% yield). 2,8-Dimethyl-5-[2-(2-methyl-pyrimidin-5-yl)-ethyl]-2,3,4,5-tetrahydro-1H-pyrid[4,3-b]indole (0.025 g, 0.000078 mol) was dissolved in THF (1.0 mL). A solution of oxalic acid dihydrate (0.0098 g, 0.000078 mol) in THF (1.0 mL) was added and stirred for 30 min at RT, Precipitate obtained was filtered and dried to give oxalate salt as off white solid (0.015 g, 47% yield).

Example 143

Preparation of 8-chloro-5-(3-(6-(trifluoromethyl)pyridin-3-yl)propyl)-2,3,4,5-tetrahydro-2-methyl-1H-pyrido[4,3-b]indole (Compound 324)

To a suspension of sodium hydride (0.014 g, 0.00054 mol) in dry DMF (3 mL), 8-Chloro-2-methyl-2,3,4,5-tetrahydro-1H-pyrido[4,3-b]indole (0.1 g, 0.00045 mol) was added at ice cold temp and stirred for 2 h at room temperature. Reaction mix was cooled to −20° c. and 5-(3-Bromo-propyl)-2-trifluoromethyl-pyridine (0.183 g, 0.00068 mol) was added, stirred for 1 h at 15° c., Reaction was monitor by TLC. After completion (TLC), reaction mix was cooled to 0° C. and water (10 mL) was added, extracted with ethyl acetate (3×100 mL). The organic layer was dried over anhydrous sodium sulphate and concentrated under reduced pressure using rotary evaporator. The crude was purified through column chromatography (4% Methanol:DCM in silica 100-200 mesh, Diameter of column—2.5 cm, Height of silica—approx. 5 inch) to provide desired compound as brown oil (0.06 g, 32% yield). 8-Chloro-2-methyl-5-[3-(6-trifluoromethyl-pyridin-3-yl)-propyl]-2,3,4,5-tetrahydro-1H-pyrido[4,3-b]indole (0.06 g, 0.000147 mol) was dissolved in THF (1.0 mL), A solution of oxalic acid dihydrate (0.016 g, 0.000126 mol) in THF (1.0 mL) was added and stirred for 30 min at RT. The precipitate was filtered and dried to give oxalate salt as off white solid (0.050 g, 68% yield).

Example 144

Preparation of 3-(8-chloro-1,2,3,4-tetrahydro-2-methylpyrido[4,3-b]indol-5-yl)-1-(4-methylpiperidin-1-yl)propan-1-one (Compound 325)

A mixture of 3-(8-chloro-1,2,3,4-tetrahydro-2-methylpyrido[4,3-b]indol-5-yl)propanoic acid (50 mg, 0.17 mmol), 4-methyl Piperidine (0.02 mL, 0.17 mmol), DCC (38 mg, 0.18 mmol), and DMAP (23 mg, 0.18 mmol) in dry DCM (2 mL) was stirred at room temperature for 3 h. The reaction mixture was filtered through Celite and concentrated to obtain 12 mg of 3-(8-chloro-1,2,3,4-tetrahydro-2-methylpyrido[4,3-b]indol-5-yl)-1-(4-methylpiperidin-1-yl)propan-1-one as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 145

Preparation of 3-(8-chloro-1,2,3,4-tetrahydro-2-methylpyrido[4,3-b]indol-5-yl)-1-(piperidin-1-yl)propan-1-one (Compound 326)

3-(8-chloro-1,2,3,4-tetrahydro-2-methylpyrido[4,3-b]indol-5-yl)propanoic acid (0.1 g, 0.34 mmol) was taken in dichloromethane (3 mL) and was cooled to 0 deg C. Oxalyl chloride (0.04 mL, 0.41 mmol) was added drop-wise to the reaction mixture. A catalytic amount (1 drop) of dimethyl formamide was added to the reaction mixture. Reaction mixture was stirred for 1 h at room temperature. Excess oxalyl chloride was distilled away under reduced pressure. To this residue, a solution of Piperidine (0.036 mL, 0.374 mmol) in 2 mL DCM and DMAP (0.055 g, 0.45 mmol) was added under nitrogen at room temperature and reaction mass was stirred for 30 min at room temperature. Reaction mixture was quenched with water and neutralized with 10% NaHCO3, extracted with Ethyl acetate (10 ml×2). Combined organic layers dried over sodium sulphate and concentrated under reduced pressure to obtain crude product which was further purified by flash column chromatography using Methanol:DCM (5:95) to afford 12 mg of product. This product was stirred in THF (2 mL) and oxalic acid (9 mg, 0.06 mmol) for 15 min and mixture was concentrated under vacuo to afford 11 mg of 3-(8-chloro-1,2,3,4-tetrahydro-2-methylpyrido[4,3-b]indol-5-yl)-1-(piperidin-1-yl)propan-1-one as oxalate Salt.

Example 146

Preparation of 5-(4-chlorophenethyl)-2,3,4,5-tetrahydro-2-methyl-1H-pyrido[4,3-b]indole-8-carboxylic acid (Compound 327)

The title compound is prepared by following Method 8 by using 1-(2-bromoethyl)-4-chlorobenzene, methyl 4-hydrazinobenzoate, triethylamine and N-methyl-4-piperidone Example 147

Preparation of 3-(8-chloro-1,2,3,4-tetrahydro-2-methylpyrido[4,3-b]indol-5-yl)-1-morpholinopropan-1-one (Compound 328)

A mixture of 3-(8-chloro-1,2,3,4-tetrahydro-2-methylpyrido[4,3-b]indol-5-yl)propanoic acid (100 mg, 0.34 mmol), morpholine (29 mg, 0.34 mmol), DCC (77 mg, 0.37 mmol), and DMAP (46 mg, 0.37 mmol) in dry DCM (2.5 mL) was stirred at room temperature for 3 h. The reaction mixture was filtered through Celite and concentrated by rota vapor to obtain 10 mg of 3-(8-chloro-1,2,3,4-tetrahydro-2-methylpyrido[4,3-b]indol-5-yl)-1-morpholinopropan-1-one as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 148

Preparation of 2,3,4,5-tetrahydro-2-methyl-5-(2-(pyridin-2-yl)ethyl)-1H-pyrido[4,3-b]indole (Compound 329)

2,3,4,5-tetrahydro-2-methyl-1H-pyrido[4,3-b]indole (200 mg, 1 mmol), 2-vinylpyridine (0.26 mg, 2.5 mmol), sodium (5 mg, 0.21 mmol) and CuSO4 (5 mg, catalytic) in ethanol (4 mL) was at 120° C. for 16 h to obtain 60 mg of 2,3,4,5-tetrahydro-2-methyl-5-(2-(pyridin-2-yl)ethyl)-1H-pyrido[4,3-b]indole as a trifluoroacetate salt after purification on reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 149

Preparation of 2-(1,2,3,4-tetrahydro-2,8-dimethylpyrido[4,3-b]indol-5-yl)-1-morpholinoethanone (Compound 330)

To a solution of 2-(1,2,3,4-tetrahydro-2,8-dimethylpyrido[4,3-b]indol-5-yl) acetic acid (100 mg, 0.38 mmol) in DCM (10 ml) was added DCC (95 mg, 0.46 mmol), DMAP (56 mg, 0.46 mmol), and stirred for 5 min at RT, morpholine (1 ml, 11.5 mmol) was added and stirred at 25 deg C. for 14 h. The reaction mixture was concentrated to dryness and The resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 10 mg (Yield 5.8%) of 2-(1,2,3,4-tetrahydro-2,8-dimethylpyrido[4,3-b]indol-5-yl)-1-morpholino ethanone as TFA salt.

Example 150

Preparation of 5-(3-(6-(trifluoromethyl)pyridin-3-yl)propyl)-2,3,4,5-tetrahydro-2,8-dimethyl-1H-pyrido[4,3-b]indole (Compound 331)

To a suspension of DMF (5 mL) and sodium hydride (0.024 g, 0.0006 mol) at 0° c., 2,8-Dimethyl-2,3,4,5-tetrahydro-1H-pyrido[4,3-b]indole (0.1 g, 0.0005 mol) was added and stirred for 2 h at room temperature, Reaction mix was cooled to −20° c. and 5-(3-Bromo-propyl)-2-trifluoromethyl-pyridine (0.2 g, 0.00075 mol) was added, stirred for 1 h at 15° C. After completion (TLC), reaction mass was cooled to 0° c. and water (10 mL) was added, and extracted with ethyl acetate (3×100 mL). The organic layer was dried over anhydrous sodium sulphate and concentrated under reduced pressure using rotary evaporator. The crude was purified through column chromatography (3-4% methanol:DCM in silica 100-200 mesh, Diameter of column—2.5 cm, Height of silica—approx. 5 inch) to provide desired compound as brown oil (0.04 g, 20% yield). 2,8-Dimethyl-5-[3-(6-trifluoromethyl-pyridin-3-yl)-propyl]-2,3,4,5-tetrahydro-1H-pyrido[4,3-b]indole (0.04 g, 0.000103 mol) was dissolved in THF (1.0 mL). A solution of oxalic acid dihydrate (0.012 g, 0.0000952 mol) in THF (1.0 mL) was added and stirred for 30 min at RT. The precipitate was filtered and dried to give oxalate salt as off white solid (0.030 g, 61% yield).

Example 151

Preparation of 2,3,4,5-tetrahydro-2-methyl-5-((6-methylpyridin-3-yl)methyl)-1H-pyrido[4,3-b]indole (Compound 332)

A solution of 2,3,4,5-Tetrahydro-2-methyl-1H-pyrido[4,3-b]indole (186 mg, 1 mmol), 5-(chloromethyl)-2-methylpyridine (324 mg, 2.3 mmol) and 60% NaH (120 mg, 3 mmol) in DMF (3 ml) were heated at 120° C. for 16 h to obtain 30 mg of 2,3,4,5-tetrahydro-2-methyl-5-(((6-methylpyridin-3-yl)methyl)-1H-pyrido[4,3-b]indole after purification by silica gel chromatography (230-400 mesh) using methanol-dichloromethane gradient.

Example 152

Preparation of 5-[2-(4-Ethoxy-phenyl)-ethyl]-2,8-dimethyl-2,3,4,5-tetrahydro-1H-pyrido[4,3-b]indole (Compound 333)

2,8-Dimethyl-2,3,4,5-tetrahydro-1H-pyrido[4,3-b]indole (0.2 g, 0.001 mol) was dissolved in N-methyl 2-pyrolidone (3.0 mL). Powdered potassium hydroxide (0.448 g, 0.008 mol) was added and heated at 120° C. for 2 h. 1-(2-Bromo-ethyl)-4-ethoxy-benzene (0.228 g, 0.001 mol) was added at the same temperature and stir for 3 h. at RT (TLC showed incomplete reaction). Reaction mixture was diluted with water (30 mL) and extracted with ethyl acetate (3×100 mL). Organic layer was dried over anhydrous sodium sulfate and concentrated under reduced pressure using rotary evaporator. The crude was purified through column chromatography (4% MeOH:DCM in silica 100-200 mesh, Diameter of column—2.5 cm, Height of silica—approx. 5 inch) to provide the desired compound as light yellow oil (0.035 g, 10% yield). 5-[2-(4-Ethoxy-phenyl)-ethyl]-2,8-dimethyl-2,3,4,5-tetrahydro-1H-pyrido[4,3-b]indole (0.035 g, 0.0001 mol) was dissolved in THF (0.5 mL), A solution of oxalic acid dihydrate (0.013 g, 0.0001 mol) in THF (0.5 mL) was added and stirred for 30 min at RT. The precipitate was filtered and dried to give oxalate salt as off white solid (0.015 g, 34% yield).

Example 153

Preparation of 5-[2-(4-Ethoxy-phenyl)-ethyl]-2,8-dimethyl-2,3,4,5-tetrahydro-1H-pyrido[4,3-b]indole (Compound 334)

2,8-Dimethyl-2,3,4,5-tetrahydro-1H-pyrido[4,3-b]indole (0.2 g, 0.001 mol) was dissolved in N-methyl 2-pyrolidone (3.0 mL), powdered potassium hydroxide (0.448 g, 0.008 mol) was added and heated at 120° C. for 2 h. 1-(2-Bromo-ethyl)-4-ethoxy-benzene (0.228 g, 0.001 mol) was added at the same temperature and stir for 3 h. at RT (TLC showed incomplete reaction). Reaction mixture was diluted with water (30 mL) and extracted with ethyl acetate (3×100 mL). Organic layer was dried over anhydrous sodium sulfate and concentrated under reduced pressure using rotary evaporator. The crude was purified through column chromatography (4% MeOH:DCM in silica 100-200 mesh, Diameter of column—2.5 cm, Height of silica—approx. 5 inch) to provide the desired compound as light yellow oil (0.035 g, 10% yield). 5-[2-(4-Ethoxy-phenyl)-ethyl]-2,8-dimethyl-2,3,4,5-tetrahydro-1H-pyrido[4,3-b]indole (0.035 g, 0.0001 mol) was dissolved in THF (0.5 mL), A solution of oxalic acid dihydrate (0.013 g, 0.0001 mol) in THF (0.5 mL) was added and stirred for 30 min at RT. The precipitate was filtered and dried to give oxalate salt as off white solid (0.015 g, 34% yield).

Example 154

Preparation of 5-(4-tert-butoxyphenethyl)-2,3,4,5-tetrahydro-2,8-dimethyl-1H-pyrido[4,3-b]indole (Compound 335)

2,8-Dimethyl-2,3,4,5-tetrahydro-1H-pyrido[4,3-b]indole (0.2 g, 0.001 mol) was dissolved in N-methyl 2-pyrolidone (2.0 mL). Powdered potassium hydroxide (0.5 g, 0.0089 mol) was added and heated at 100° C. for 3 h. Reaction mass was cooled to RT and 1-(2-Bromo-ethyl)-4-tert-butoxy-benzene (0.245 g, 0.001 mol) was added at the same temperature and stir for 2 h at RT (TLC showed incomplete reaction). Reaction mixture was diluted with water (50 mL) and extracted with ethyl acetate (2×100 mL). Organic layer was dried over anhydrous sodium sulfate and concentrated under reduced pressure using rotary evaporator. The crude was purified through column chromatography (0.5% MeOH:DCM in neutral alumina, Diameter of column—2.5 cm, Height of alumina—approx. 5 inch) then further purified by preparative TLC to provide the desired compound as light yellow oil (0.024 g, 6% yield). 5-[2-(4-tert-Butoxy-phenyl)-ethyl]-2,8-dimethyl-2,3,4,5-tetrahydro-1H-pyrido[4,3-b]indole (0.024 g, 0.000063 mol) was dissolved in THF (1.0 mL), A solution of oxalic acid dihydrate (0.008 g, 0.000063 mol) in THF (1.0 mL) was added and stirred for 30 min at RT. The precipitate was filtered and dried to give oxalate salt as off white solid (0.020 g, 67% yield).

Example 155

Preparation of 8-Chloro-5-[2-(4-methoxy-phenyl)-ethyl]-2-methyl-2,3,4,5-tetrahydro-1H pyrido[4,3-b]indole (Compound 336)

8-Chloro-2-methyl-2,3,4,5-tetrahydro-1H-pyrido[4,3-b]indole (0.22 g, 0.001 mol) was dissolved in N-methyl 2-pyrolidone (3.0 mL). Powdered potassium hydroxide (0.224 g, 0.004 mol) was added and heated at 100 deg C. for 3 h. 1-(2-Bromo-ethyl)-4-methoxy-benzene (0.214 g, 0.001 mol) was added at the same temperature and stir for 6 h. at RT. Reaction mixture was diluted with water (30 mL) and extracted with ethyl acetate (3×50 mL). Organic layer was dried over anhydrous sodium sulfate and concentrated under reduced pressure using rotary evaporator. The crude was purified through column chromatography (4% MeOH:DCM in silica 100-200 mesh, Diameter of column—2.5 cm, Height of silica—approx. 5 inch) to provide the desired compound as light yellow oil (0.02 g, 6% yield). 8-Chloro-5-[2-(4-methoxy-phenyl)-ethyl]-2-methyl-2,3,4,5-tetrahydro-1H-pyrido[4,3-b]indole (0.020 g, 0.0564 mol) was dissolved in THF (1.0 mL), A solution of oxalic acid dihydrate (0.007 g, 0.0564 mol) in 1.5 mL THF was added and stirred for 30 min at RT. The precipitate was filtered and dried to give oxalate salt as white solid (0.01 g, 40% yield).

Example 156

Preparation of 5-(3-fluoro-4-methoxyphenethyl)-8-chloro-2,3,4,5-tetrahydro-2-methyl-1H-pyrido[4,3-b]indole (Compound 337)

8-Chloro-2-methyl-2,3,4,5-tetrahydro-1H-pyrido[4,3-b]indole (0.5 g, 0.0022 mol) was dissolved in N-methyl 2-pyrolidone (4.0 mL). Powdered potassium hydroxide (1 g, 0.008 mol) was added and heated at 100° C. for 2 h. 4-(2-Bromo-ethyl)-2-fluoro-1-methoxy-benzene (0.520 g, 0.0022 mol) was added at the room temperature and stir for 0.5 h at RT (TLC showed incomplete reaction). Reaction mixture was diluted with water (200 mL) and extracted with ethyl acetate (3×100 mL). Organic layer was dried over anhydrous sodium sulfate and concentrated under reduced pressure using rotary evaporator. The crude was purified through column chromatography (4% MeOH:DCM in silica 100-200 mesh, Diameter of column—2.5 cm, Height of silica—approx. 5 inch) to provide the desired compound as light yellow oil (0.038 g, 4% yield). 8-Chloro-5-[2-(3-fluoro-4-methoxy-phenyl)-ethyl]-2-methyl-2,3,4,5-tetrahydro-1H-pyrido[4,3-b]indole (0.038 g, 0.00010 mol) was dissolved in THF (1.0 mL). A solution of oxalic acid dihydrate (0.012 g, 0.00010 mol) in THF (1.0 mL) was added and stirred for 30 min at RT. The precipitate was filtered and dried to give oxalate salt as off white solid (0.016 g, 34% yield).

Example 157

Preparation of 8-chloro-6-fluoro-5-(2-(6-(trifluoromethyl) pyridin-3-yl)ethyl)-2,3,4,5-tetrahydro-2-methyl-1H-pyrido[4,3-b]indole (Compound 338)

To a solution of 8-chloro-6-fluoro-2,3,4,5-tetrahydro-2-methyl-1H-pyrido[4,3-b]indole (300 mg, 1.26 mmol) in NMP (3.0 ml), powdered KOH (705 mg, 12.57 mmol) was added and stirred for 10 min at 25 deg C. After which 2-(trifluoromethyl)-5-vinylpyridine (435 mg, 2.5 mmol) was added slowly to the above solution and stirred for 24 h at 25 deg C. After completion of the reaction (monitored by LCMS), DM water was added to the crude and extracted with the ethylacetate. The organic layer was separated, dried and concentrated. The resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 15 mg of 8-chloro-6-fluoro-5-(2-(6-(trifluoromethyl)pyridin-3-yl)ethyl)-2,3,4,5-tetrahydro-2-methyl-1H-pyrido[4,3-b]indole as TFA salt.

Example 158

Preparation of 6,8-dichloro-5-(2-(6-(trifluoromethyl) pyridin-3-yl)ethyl)-2,3,4,5-tetrahydro-2-methyl-1H-pyrido[4,3-b]indole (Compound 339)

The title compound is prepared from a mixture of 6,8-dichloro-2,3,4,5-tetrahydro-2-methyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 159

Preparation of 7,9-difluoro-5-(2-(6-(trifluoromethyl) pyridin-3-yl)ethyl)-2,3,4,5-tetrahydro-2-methyl-1H-pyrido[4,3-b]indole (Compound 340)

The title compound is prepared from a mixture of 7,9-difluoro-2,3,4,5-tetrahydro-2-methyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 160

Preparation of 5-(2-(6-(trifluoromethyl)pyridin-3-yl) ethyl)-2,3,4,5-tetrahydro-2-methyl-8-(trifluoromethoxy)-1H-pyrido[4,3-b]indole (Compound 341)

To a solution of 5-(2-(6-(trifluoromethyl)pyridin-3-yl)ethyl)-2,3,4,5-tetrahydro-2-methyl-8-(trifluoromethoxy)-1H-pyrido[4,3-b]indole (200 mg, 0.74 mmol) in NMP (1.5 ml), powdered KOH (415 mg 7.4 mmol) was added and stirred for 10 min at 25 deg C. after which 2-(trifluoromethyl)-5-vinylpyridine (256 mg, 1.48 mmol) was added slowly to the above solution and stirred at 25 deg C. for 2 h. After completion of the reaction (monitored by LCMS), DM water was added to the crude and extracted with the ethyl acetate. The organic layer was dried and concentrated. The resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 50 mg (Yield 15.24%) of 5-(2-(6-(trifluoromethyl)pyridin-3-yl)ethyl)-2,3,4,5-tetrahydro-2-methyl-8-(trifluoromethoxy)-1H-pyrido[4,3-b]indole as TFA salt.

Example 161

Preparation of 8-Isopropyl-2-methyl-5-[2-(6-trifluoromethyl-pyridin-3-yl)-ethyl]-2,3,4,5-tetrahydro-1H-pyrido[4,3-b]indole (Compound 342)

To a solution of 8-Isopropyl-2-methyl-2,3,4,5-tetrahydro-1H-pyrido[4,3-b]indole (0.1 g, 0.43 mmol) in N-methyl 2-pyrolidone (0.5 mL) was added powdered potassium hydroxide (0.096 g, 1.72 mmol) and allowed to stir for 10 min at RT. 2-trifluoromethyl-5-vinyl pyridine (0.19 g, 1.1 mmol) was added and stirred for further at 35 deg C. for 3 h. Reaction mixture was diluted with brine (5 mL) and extracted with ethyl acetate (3×50 mL). The organic layer was dried over anhydrous sodium sulphate and concentrated under reduced pressure. The crude was purified through column chromatography (5% MeOH:DCM in silica 100-200 mesh, Diameter of column—2.5 cm, Height of silica—approx. 5 inch) to provide the desired compound as brown oil (0.17 g, 45% yield). Isopropyl-2-methyl-5-[2-(6-trifluoromethyl-pyridin-3-yl)-ethyl]-2,3,4,5-tetrahydro-1H-pyrido[4,3-b]indole (0.080 g, 0.19 mmol) was dissolved in THF (2.0 mL). A solution of oxalic acid dihydrate (0.017 g, 0.19 mmol) in THF (2 mL) was added and stirred for 30 min at RT, Precipitate obtained was filtered and dried to give oxalate salt as white solid (0.045 g, 46% yield).

Example 162

Preparation of Chloro-7-fluoro-2-methyl-5-[2-(6-trifluoromethyl-pyridin-3-yl)-ethyl]-2,3,4,5-tetrahydro-1H-pyrido[4,3-b]indole (Compound 343)

To a solution of 8-Chloro-7-fluoro-2-methyl-2,3,4,5-tetrahydro-1H-pyrido[4,3-b]indole (0.1 g. 0.0041 mol) in N-methyl 2-pyrolidone (0.5 mL) was added powdered potassium hydroxide (0.08 g, 0.00143 mol) and allowed to stir for 10 min at RT. 2-trifluoromethyl-5-vinyl pyridine (0.079 g, 0.00046 mol) was added and stirred for further 15 h. at rt, After completion (TLC), reaction mixture was diluted with water (5 mL) and extracted with ethyl acetate (3×50 mL). The organic layer was dried over anhydrous sodium sulphate and concentrated under reduced pressure using rotary evaporator. The crude was purified through preparative HPLC to give the desired compound 10 as light yellow solid (0.02 g, 12% yield). 8-Chloro-7-fluoro-2-methyl-5-[2-(6-trifluoromethyl-pyridin-3-yl)-ethyl]-2,3,4,5-tetrahydro-1H-pyrido[4,3-b]indole (0.02 g, 0.0000485 mol) was dissolved in THF (1.0 mL). A solution of oxalic acid dihydrate (0.006 g, 0.0000485 mol) in THF (1.0 mL) was added and stirred for 30 min at RT, Precipitate obtained was filtered and dried to give oxalate salt as white solid (0.015 g, 62% yield).

Example 163

Preparation of 8-chloro-9-fluoro-5-(2-(6-(trifluoromethyl)pyridin-3-yl)ethyl)-2,3,4,5-tetrahydro-2-methyl-1H-pyrido[4,3-b]indole (Compound 344)

The title compound is prepared from a mixture of 8-chloro-9-fluoro-2,3,4,5-tetrahydro-2-methyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 164

Preparation of 7-aza-5-(2-(6-(trifluoromethyl)pyridin-3-yl)ethyl)-2,3,4,5-tetrahydro-2-methyl-1H-pyrido[4,3-b]indole (Compound 345)

The title compound is prepared from a mixture of 9-aza-2-methyl-2,3,4,5-tetrahydro-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 165

Preparation of 9-aza-2-methyl-5-(2-(6-(trifluoromethyl)pyridin-3-yl)ethyl)-2,3,4,5-tetrahydro-1H-pyrido[4,3-b]indole (Compound 346)

The title compound is prepared from a mixture of 9-aza-2-methyl-2,3,4,5-tetrahydro-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 166

Preparation of 8-aza-2-methyl-5-(2-(6-(trifluoromethyl)pyridin-3-yl)ethyl)-2,3,4,5-tetrahydro-1H-pyrido[4,3-b]indole (Compound 347)

The title compound is prepared from a mixture of 8-aza-2-methyl-2,3,4,5-tetrahydro-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 167

Preparation of 6,8-diaza-2-methyl-5-(2-(6-(trifluoromethyl)pyridin-3-yl)ethyl)-2,3,4,5-tetrahydro-1H-pyrido[4,3-b]indole (Compound 348)

The title compound is prepared from a mixture of 6,8-diaza-2-methyl-2,3,4,5-tetrahydro-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 168

Preparation of 8-Chloro-2-methyl-5-(2-pyrrol-1-yl-ethyl)-2,3,4,5-tetrahydro-1H-pyrido[4,3-b]indole (Compound 349)

8-Chloro-2-methyl-2,3,4,5-tetrahydro-1H-pyrido[4,3-b]indole (0.1 g, 0.45 mmol) was dissolved in N-methyl 2-pyrolidone (3.0 mL). Powdered potassium hydroxide (0.224 g, 4 mmol) was added and heated at 100 deg C. for 3 h. 2-(2-Bromo-ethyl)pyridine (0.09 g, 0.51 mol) was added at the same temperature and stir for 3 h at RT Reaction mixture was diluted with water (30 mL) and extracted with ethyl acetate (3×50 mL). Organic layer was dried over anhydrous sodium sulfate and concentrated under reduced pressure using rotary evaporator. The crude was purified through column chromatography (4% MeOH:DCM in silica 100-200 mesh, Diameter of column—2.5 cm, Height of silica—approx. 5 inch) to provide the desired compound as light yellow oil (0.01 g, 7% yield). 8-Chloro-2-methyl-5-(2-pyrrol-1-yl-ethyl)-2,3,4,5-tetrahydro-1H-pyrido[4,3-b]indole (0.010 g, 0.0319 mmol) was dissolved in THF (0.5 mL), A solution of oxalic acid dihydrate (0.004 g, 0.0319 mol) in THF (0.5 mL) was added and stirred for 30 min at RT. The precipitate was filtered and dried to give oxalate salt as white solid (0.01 g, 78% yield).

Example 169

Preparation of 8-chloro-5-(2-(6-(trifluoromethyl)pyridin-3-yl)ethyl)-2,3,4,5-tetrahydro-1,2-dimethyl-1H-pyrido[4,3-b]indole (Compound 350)

The title compound is prepared from a mixture of 8-chloro-2,3,4,5-tetrahydro-1,2-dimethyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 170

Preparation of 3-(8-chloro-5-(2-(6-(trifluoromethyl)pyridin-3-yl)ethyl)-3,4-dihydro-1H-pyrido[4,3-b]indol-2(5H)-yl)cyclopentanol (Compound 351)

3-(8-chloro-3,4-dihydro-1H-pyrido[4,3-b]indol-2(5H)-yl)cyclopentanol (300 mg, 1.03 mmol), 2-trifluoromethyl-5-vinylpyridine (140 mg, 0.809 mmol) and potassium hydroxide (310 mg, 5.5 mmol) in 0.6 ml of NMP was heated to 60 deg C. for 2 h. The reaction mass was cooled at RT and diluted with 20 ml of ethyl acetate. The organic layer was washed with brine and dried over sodium sulphate and concentrated under vacuum. It was purified on 230-400 silica gel (flash) deactivated with triethylamine using ethyl acetate/methanol (5-10%) as eluant, followed by isolation of 3-(8-chloro-5-(2-(6-(trifluoromethyl)pyridin-3-yl)ethyl)-3,4-dihydro-1H-pyrido[4,3-b]indol-2(5H)-yl)cyclopentanol by PREP HPLC. Yield: 70 mg as TFA salt.

Example 171

Preparation of 8-chloro-4-fluoro-5-(2-(6-(trifluoromethyl)pyridin-3-yl)ethyl)-2,3,4,5-tetrahydro-2-methyl-1H-pyrido[4,3-b]indole (Compound 352)

The title compound is prepared from a mixture of 8-chloro-4-fluoro-2,3,4,5-tetrahydro-2-methyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 172

Preparation of 9-aza-2,8-dimethyl-5-(2-(6-(trifluoromethyl)pyridin-3-yl)ethyl)-2,3,4,5-tetrahydro-1H-pyrido[4,3-b]indole (Compound 353)

Carboline (150 mg, 0.746 mmol, 1 equiv), 2-trifluoromethyl-5-vinylpyridine (142 mg, 0.82 mmol, 1.1 equiv) and KOH (146 mg, 2.61 mmol, 3.5 equiv) were stirred with 0.45 ml of NMP at 50° C. for 3.5 h. Reaction mixture was then diluted with ethyl acetate (15 ml) and washed with brine. Organic part was evaporated under vacuum and column purified over neutral alumina using a gradient of ethyl acetate/MeOH (0-100%). Preparative HPLC was used to further purify the fraction containing the desired mass by LC-MS. Yield: 35 mg as TFA Salt.

Example 173

Preparation of 8-chloro-5-(2-(6-(trifluoromethyl)pyridin-3-yl)ethyl)-2,3,4,5-tetrahydro-2,3-dimethyl-1H-pyrido[4,3-b]indole (Compound 354)

The title compound is prepared from a mixture of 8-chloro-2,3,4,5-tetrahydro-2,3-dimethyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 174

Preparation of 6-aza-2,8-dimethyl-5-(2-(6-(trifluoromethyl)pyridin-3-yl)ethyl)-2,3,4,5-tetrahydro-1H-pyrido[4,3-b]indole (Compound 355)

The title compound is prepared from a mixture of 6-aza-2,8-dimethyl-2,3,4,5-tetrahydro-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 175

Preparation of 7-aza-2,8-dimethyl-5-(2-(6-(trifluoromethyl)pyridin-3-yl)ethyl)-2,3,4,5-tetrahydro-1H-pyrido[4,3-b]indole (Compound 356)

The title compound is prepared from a mixture of 7-aza-2,8-dimethyl-2,3,4,5-tetrahydro-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 176

Preparation of 8-Ethyl-2-methyl-5-[2-(6-methyl-pyridin-3-yl)-ethyl]-2,3,4,5-tetrahydro-1H-pyrido[4,3-b]indole (Compound 357)

To a solution of 8-Ethyl-2-methyl-2,3,4,5-tetrahydro-1H-pyrido[4,3-b]indole (0.107 g, 0.5 mmol) in N-methyl 2-pyrolidone (2 mL) was added powdered potassium hydroxide (0.224 g, 4.0 mmol) and allowed to stir for 10 min at RT. 2-methyl-5-vinyl pyridine (0.065 g, 0.55 mmol) was added and stirred for further 24 h. at 120 deg C., After completion of TLC, Reaction mixture was diluted with water (30 mL) and extracted with ethyl acetate (3×50 mL). The organic layer was dried over anhydrous sodium sulphate and concentrated under reduced pressure. The crude was purified through column chromatography (8% MeOH:DCM in silica 100-200 mesh, Diameter of column—2.5 cm, Height of silica—approx. 5 inch) to provide the desired compound as brown oil (0.034 g, 20% yield). 8-Ethyl-2-methyl-5-[2-(6-methyl-pyridin-3-yl)-ethyl]-2,3,4,5-tetrahydro-1H-pyrido[4,3-b]indole (0.034 g, 0.102 mmol) was dissolved in THF (0.5 mL). A solution of oxalic acid dihydrate (0.013 g, 0.102 mol) in THF (0.5 mL) was added and stirred for 30 min at RT, Precipitate obtained was filtered and dried to give oxalate salt as off white solid (0.015 g, 32% yield).

Example 177

Preparation of 8-Ethyl-2-methyl-5-[2-(6-trifluoromethyl-pyridin-3-yl)-ethyl]-2,3,4,5-tetrahydro-1H-pyrido[4,3-b]indole (Compound 358)

To a solution of 8-Ethyl-2-methyl-2,3,4,5-tetrahydro-1H-pyrido[4,3-b]indole (0.107 g. 0.0005 mol) in N-methyl 2-pyrolidone (2.0 mL) was added powdered potassium hydroxide (0.224 g, 0.004 mol) and allowed to stir for 10 min at RT. 2-trifluoromethyl-5-vinyl pyridine (0.095 g, 0.00055 mol) was added and stirred for further 1 h. at 60 deg C., After completion of TLC, Reaction mixture was diluted with brine (5 mL) and extracted with ethyl acetate (3×50 mL). The organic layer was dried over anhydrous sodium sulphate and concentrated under reduced pressure using rotary evaporator. The crude was purified through column chromatography (4% MeOH:DCM in silica 100-200 mesh, Diameter of column—2.5 cm, Height of silica—approx. 5 inch) to provide the desired compound as brown oil (0.11 g, 57% yield). 8-Ethyl-2-methyl-5-[2-(6-trifluoromethyl-pyridin-3-yl)-ethyl]-2,3,4,5-tetrahydro-1H-pyrido[4,3-b]indole (0.1 g, 0.000258 mol) was dissolved in THF (2.0 mL). A solution of oxalic acid dihydrate (0.032 g, 0.000258 mol) in THF (2 mL) was added and stirred for 30 min at RT, Precipitate obtained was filtered and dried to give oxalate salt as white solid (0.080 g, 65% yield).

Example 178

Preparation of 5-[2-(6-Ethyl-pyridin-3-yl)-ethyl]-2,8-dimethyl-2,3,4,5-tetrahydro-1H-pyrido[4,3-b]indole (Compound 359)

To a solution of 2,8-Dimethyl-2,3,4,5-tetrahydro-1H-pyrido[4,3-b]indole (0.15 g. 0.749 mmol) in N-methyl 2-pyrolidone (1.2 mL) was added powdered potassium hydroxide (0.42 g, 7.49 mmol) and allowed to stir for 10 min at RT. 2-Ethyl-5-vinyl-pyridine (0.299 g, 2.24 mmol) was added and stirred for further 18 h. at 100 deg C. After completion (TLC), reaction mixture was diluted with water (15 mL) and extracted with ethyl acetate (3×50 mL). The organic layer was dried over anhydrous sodium sulphate and concentrated under reduced pressure. The crude was purified through column chromatography (7% MeOH:DCM in silica 100-200 mesh, Diameter of column 2.5 cm, Height of silica—approx. 5 inch), Then further purified by preparative TLC, to give the desired compound as yellow oil (0.045 g, 18% yield). 5-[2-(6-Ethyl-pyridin-3-yl)-ethyl]-2,8-dimethyl-2,3,4,5-tetrahydro-1H-pyrido[4,3-b]indole (0.040 g, 0.12 mol) was dissolved in THF (1.0 mL). A solution of oxalic acid dihydrate (0.012 g, 0.096 mol) in THF (1.0 mL) was added and stirred for 30 min at RT, Precipitate obtained was filtered and dried to give oxalate salt as off white solid (0.030 g, 60% yield).

Example 179

Preparation of 5-[2-(6-Isopropyl-pyridin-3-yl)-ethyl]-2,8-dimethyl-2,3,4,5-tetrahydro-1H-pyrido[4,3-b]indole (Compound 360)

To a solution of 2,8-Dimethyl-2,3,4,5-tetrahydro-1H-pyrido[4,3-b]indole (0.1 g. 0.5 mmol) in N-methyl 2-pyrolidone (1.0 mL) was added powdered potassium hydroxide (0.140 g, 2.5 mmol) and allowed to stir for 10 min at RT. 2-Isopropyl-5-vinyl-pyridine (0.185 g, 1.25 mol) was added and stirred for further 4 h at 100 deg C. After completion (TLC), reaction mixture was diluted with water (15 mL) and extracted with ethyl acetate (3×50 mL). The organic layer was dried over anhydrous sodium sulphate and concentrated under reduced pressure. The crude was purified through column chromatography (7% MeOH:DCM in silica 100-200 mesh, Diameter of column—2.5 cm, Height of silica—approx. 5 inch), Then further purified by preparative TLC, to give the desired compound as yellow oil (0.025 g, 14% yield). 5-[2-(6-Isopropyl-pyridin-3-yl)-ethyl]-2,8-dimethyl-2,3,4,5-tetrahydro-1H-pyrido[4,3-b]indole (0.025 g, 0.00007 mol) was dissolved in THF (1.0 mL). A solution of oxalic acid dihydrate (0.0095 g, 0.00007 mol) in THF (0.5 mL) was added and stirred for 30 min at RT, Precipitate obtained was filtered and dried to give oxalate salt as off white solid (0.024 g, 77% yield).

Example 180

Preparation of 8-Chloro-2-methyl-5-[2-(2-methyl-pyrimidin-5-yl)-ethyl]-2,3,4,5-tetrahydro-1H-pyrido[4,3-b]indole (Compound 361)

To a solution of 8-Chloro-2-methyl-2,3,4,5-tetrahydro-1H-pyrido[4,3-b]indole (0.075 g, 0.34 mmol) in N-methyl 2-pyrolidone (0.5 mL) was added powdered potassium hydroxide (0.095 g, 1.7 mmol) and allowed to stir for 10 min at RT. 2-methyl-5-vinyl pyrimidine (0.102 g, 0.85 mmol) was added and stirred for further at 80 deg C. 3 h. After completion (TLC), reaction mixture was diluted with water (15 mL) and extracted with ethyl acetate (3×50 mL). The organic layer was dried over anhydrous sodium sulphate and concentrated under reduced pressure. The crude was purified through column chromatography (7% MeOH:DCM in silica 100-200 mesh, Diameter of column—2.5 cm, Height of silica—approx. 5 inch) then purified through preparative TLC to get the desired compound as yellow oil (0.020 g, 13% yield). 8-Chloro-2-methyl-5-[2-(2-methyl-pyrimidin-5-yl)-ethyl]-2,3,4,5-tetrahydro-1H-pyrido[4,3-b]indole (0.020 g, 0.06 mmol) was dissolved in THF (1.0 mL). A solution of oxalic acid dihydrate (0.008 g, 0.06 mmol) in THF (0.5 mL) was added and stirred for 30 min at RT, Precipitate obtained was filtered and dried to give oxalate salt as off white solid (0.008 g, 32% yield).

Example 181

Preparation of 8-Ethyl-2-methyl-5-[2-(2-methyl-pyrimidin-5-yl)-ethyl]-2,3,4,5-tetrahydro-1H-pyrido[4,3-b]indole (Compound 362)

To a solution of 8-Ethyl-2-methyl-2,3,4,5-tetrahydro-1H-pyrido[4,3-b]indole (0.1 g. 0.00046 mol) in N-methyl 2-pyrolidone (1.0 mL) was added powdered potassium hydroxide (0.13 g, 0.0023 mol) and allowed to stir for 10 min at RT. 2-methyl-5-vinyl pyrimidine (0.14 g, 0.00116 mol) was added and stirred for further 3 h. At 80 deg C. After completion (TLC), reaction mixture was diluted with water (15 mL) and extracted with ethyl acetate (3×50 mL). The organic layer was dried over anhydrous sodium sulphate and concentrated under reduced pressure using rotary evaporator. The crude was purified through column chromatography (7% MeOH:DCM in silica 100-200 mesh, Diameter of column—2.5 cm, Height of silica—approx. 5 inch) then purified through preparative TLC. to get the desired compound as yellow oil (0.032 g, 20% yield). 8-Ethyl-2-methyl-5-[2-(2-methyl-pyrimidin-5-yl)-ethyl]-2,3,4,5-tetrahydro-1H-pyrido[4,3-b]indole (0.032 g, 0.000095 mol) was dissolved in THF (1.0 mL). A solution of oxalic acid dihydrate (0.012 g, 0.000095 mol) in THF (1.0 mL) was added and stirred for 30 min at RT, Precipitate obtained was filtered and dried to give oxalate salt as off white solid (0.030 g, 75% yield).

Example 182

Preparation of 8-Chloro-2-methyl-5-[2-(5-methyl-pyrazin-2-yl)-ethyl]-2,3,4,5-tetrahydro-1H-pyrido[4,3-b]indole (Compound 363)

To a solution of 8-Chloro-2-methyl-2,3,4,5-tetrahydro-1H-pyrido[4,3-b]indole (0.11 g, 5.0 mmol) in N-methyl 2-pyrolidone (2.0 mL) was added powdered potassium hydroxide (0.224 g, 4.0 mmol) and allowed to stir for 10 min at RT. 2-methyl-5-vinyl pyrazine (0.065 g, 0.55 mmol) was added and stirred for further 2 h at 60 deg C. After completion (TLC), reaction mixture was diluted with water (20 mL) and extracted with ethyl acetate (3×100 mL). The organic layer was dried over anhydrous sodium sulphate and concentrated under reduced pressure. The crude was purified through column chromatography (6% MeOH:DCM in silica 100-200 mesh, Diameter of column—2.5 cm, Height of silica—approx. 5 inch) to provide the desired compound as yellow oil (0.09 g, 54% yield). 8-Chloro-2-methyl-5-[2-(5-methyl-pyrazin-2-yl)-ethyl]-2,3,4,5-tetrahydro-1H-pyrido[4,3-b]indole (0.09 g, 0.26 mmol) was dissolved in THF (1.0 mL). A solution of oxalic acid dihydrate (0.034 g, 0.26 mmol) in THF (1.0 mL) was added and stirred for 30 min at RT, Precipitate obtained was filtered and dried to give oxalate salt as white solid (0.08 g, 68% yield).

Example 183

Preparation of 8-Ethyl-2-methyl-5-[2-(5-methyl-pyrazin-2-yl)-ethyl]-2,3,4,5-tetrahydro-1H-pyrido[4,3-b]indole (Compound 364)

To a solution of 8-Ethyl-2-methyl-2,3,4,5-tetrahydro-1H-pyrido[4,3-b]indole (0.054 g. 0.25 mmol) in N-methyl 2-pyrolidone (2.0 mL) was added powdered potassium hydroxide (0.112 g, 0.002 mol) and allowed to stir for 10 min at RT. 2-methyl-5-vinyl pyrazine (0.033 g, 0.75 mmol) was added and stirred for further 1 h. at 60 deg C. After completion (TLC), reaction mixture was diluted with water (20 mL) and extracted with ethyl acetate (3×50 mL). The organic layer was dried over anhydrous sodium sulphate and concentrated under reduced pressure using rotary evaporator. The crude was purified through column chromatography (7% MeOH:DCM in silica 100-200 mesh, Diameter of column—2.5 cm, Height of silica—approx. 5 inch) to provide the desired compound as yellow oil (0.05 g, 60% yield). 8-Ethyl-2-methyl-5-[2-(5-methyl-pyrazin-2-yl)-ethyl]-2,3,4,5-tetrahydro-1H-pyrido[4,3-b]indole (0.05 g, 0.000149 mol) was dissolved in THF (1.0 mL). A solution of oxalic acid dihydrate (0.019 g, 0.000149 mol) in THF (1.0 mL) was added and stirred for 30 min at RT, Precipitate obtained was filtered and dried to give oxalate salt as off white solid (0.035 g, 50% yield).

Example 184

Preparation of 8-chloro-5-(2-(4-(trifluoromethyl)-6-methylpyridin-3-yl)ethyl)-2,3,4,5-tetrahydro-2-methyl-1H-pyrido[4,3-b]indole (Compound 365)

The title compound is prepared from a mixture of 8-chloro-2,3,4,5-tetrahydro-2-methyl-1H-pyrido[4,3-b]indole, 4-(trifluoromethyl)-2-methyl-5-vinylpyridine and KOH (5-7 equiv) in NMP at a temperature ranging between 25 deg C. to 100 deg C. The product obtained is isolated by preparative HPLC.

Example 185

Preparation of 8-ethyl-5-(2-(4-(trifluoromethyl)-6-methylpyridin-3-yl)ethyl)-2,3,4,5-tetrahydro-2-methyl-1H-pyrido[4,3-b]indole (Compound 366)

The title compound is prepared from a mixture of 8-ethyl-2,3,4,5-tetrahydro-2-methyl-1H-pyrido[4,3-b]indole, 4-(trifluoromethyl)-2-methyl-5-vinylpyridine and KOH (5-7 equiv) in NMP at a temperature ranging between 25 deg C. to 100 deg C. The product obtained is isolated by preparative HPLC.

Example 186

Preparation of 5-(2-(4-(trifluoromethyl)-6-methylpyridin-3-yl)ethyl)-2,3,4,5-tetrahydro-2,8-dimethyl-1H-pyrido[4,3-b]indole (Compound 367)

The title compound is prepared from a mixture of 2,3,4,5-tetrahydro-2,8-dimethyl-1H-pyrido[4,3-b]indole, 4-(trifluoromethyl)-2-methyl-5-vinylpyridine and KOH (5-7 equiv) in NMP at a temperature ranging between 25 deg C. to 100 deg C. The product obtained is isolated by preparative HPLC.

Example 187

Preparation of 5-(2-(4-(trifluoromethyl)-6-methylpyridin-3-yl)ethyl)-2,3,4,5-tetrahydro-8-isopropyl-2-methyl-1H-pyrido[4,3-b]indole (Compound 368)

The title compound is prepared from a mixture of 2,3,4,5-tetrahydro-8-isopropyl-2-methyl-1H-pyrido[4,3-b]indole, 4-(trifluoromethyl)-2-methyl-5-vinylpyridine and KOH (5-7 equiv) in NMP at a temperature ranging between 25 deg C. to 100 deg C. The product obtained is isolated by preparative HPLC.

Example 188

Preparation of 8-Isopropyl-2-methyl-5-[2-(5-methyl-pyrazin-2-yl)-ethyl]-2,3,4,5-tetrahydro-1H-pyrido[4,3-b]indole (Compound 369)

To a solution of 8-Isopropyl-2-methyl-2,3,4,5-tetrahydro-1H-pyrido[4,3-b]indole (0.2 g. 0.87 mmol) in N-methyl 2-pyrolidone (1.0 mL) was added powdered potassium hydroxide (0.5 g, 8.7 mmol) and allowed to stir for 10 min at RT. 2-methyl-5-vinyl pyrazine (0.25 g, 2.1 mmol) was added and stirred for further 5 h. at 60 deg C. After completion (TLC), reaction mixture was diluted with water (20 mL) and extracted with ethyl acetate (3×100 mL). The organic layer was dried over anhydrous sodium sulphate and concentrated under reduced pressure using rotary evaporator. The crude was purified through column chromatography (6% MeOH:DCM in silica 100-200 mesh, Diameter of column 2.5 cm, Height of silica—approx. 5 inch) then further purified through preparative TLC to provide the desired compound as yellow solid (0.05 g, 16% yield). 8-Isopropyl-2-methyl-5-[2-(5-methyl-pyrazin-2-yl)-ethyl]-2,3,4,5-tetrahydro-1H-pyrido[4,3-b]indole (0.05 g, 0.143 mmol) was dissolved in THF (2.0 mL). A solution of oxalic acid dihydrate (0.018 g, 0.143 mmol) in THF (1.0 mL) was added and stirred for 30 min at RT, Precipitate obtained was filtered and dried to give oxalate salt as off white solid (0.02 g, 32% yield).

Example 189

Preparation of 8-Isopropyl-2-methyl-5-[2-(2-methyl-pyrimidin-5-yl)-ethyl]-2,3,4,5-tetrahydro-1H-pyrido[4,3-b]indole (Compound 370)

To a solution of 8-Isopropyl-2-methyl-2,3,4,5-tetrahydro-1H-pyrido[4,3-b]indole (0.1 g. 0.000438 mol) in N-methyl 2-pyrolidone (1.0 mL) was added powdered potassium hydroxide (0.122 g, 0.00021 mol) and allowed to stir for 10 min at RT. 2-methyl-5-vinyl pyrimidine (0.13 g, 0.00109 mol) was added and stirred for further 3 h. At 80 deg C. After completion (TLC), reaction mixture was diluted with water (15 mL) and extracted with ethyl acetate (3×50 mL). The organic layer was dried over anhydrous sodium sulphate and concentrated under reduced pressure using rotary evaporator. The crude was purified through column chromatography (7% MeOH:DCM in silica 100-200 mesh, Diameter of column—2.5 cm, Height of silica—approx. 5 inch) then purified through preparative TLC. To get the desired compound as yellow oil (0.036 g, 24% yield). 8-Isopropyl-2-methyl-5-[2-(2-methyl-pyrimidin-5-yl)-ethyl]-2,3,4,5-tetrahydro-1H-pyrido[4,3-b]indole 0.036 g, 0.000103 mol) was dissolved in THF (1.0 mL). A solution of oxalic acid dihydrate (0.013 g, 0.000103 mol) in THF (1.0 mL) was added and stirred for 30 min at RT, Precipitate obtained was filtered and dried to give oxalate salt as off white solid (0.022 g, 49% yield).

Example 190

Preparation of 8-Chloro-5-[2-(6-ethyl-pyridin-3-yl)-ethyl]-2-methyl-2,3,4,5-tetrahydro-1H-pyrido[4,3-b]indole (Compound 371)

To a solution of 8-Chloro-2-methyl-2,3,4,5-tetrahydro-1H-pyrido[4,3-b]indole (0.15 g, 0.68 mmol) in N-methyl 2-pyrolidone (1.0 mL) was added powdered potassium hydroxide (0.4 g, 6.8 mmol) and allowed to stir for 10 min at RT. 2-Ethyl-5-vinyl-pyridine (0.28 g, 2.04 mmol) was added and stirred for further at 100 deg C. for 18 h. After completion (TLC), reaction mixture was diluted with water (15 mL) and extracted with ethyl acetate (3×100 mL). The organic layer was dried over anhydrous sodium sulphate and concentrated under reduced pressure. The crude was purified through column chromatography (7% MeOH:DCM in silica 100-200 mesh, Diameter of column—2.5 cm, Height of silica—approx. 5 inch), Then further purified by preparative TLC, to give the desired compound as yellow oil (0.025 g, 10% yield). 8-Chloro-5-[2-(6-ethyl-pyridin-3-yl)-ethyl]-2-methyl-2,3,4,5-tetrahydro-1H-pyrido[4,3-b]indole (0.025 g, 0.07 mmol) was dissolved in THF (1.0 mL). A solution of oxalic acid dihydrate (0.009 g, 0.07 mmol) in THF (1.0 mL) was added and stirred for 30 min at RT, Precipitate obtained was filtered and dried to give oxalate salt as off white solid (0.010 g, 32% yield).

Example 191

Preparation of 8-Chloro-5-[2-(6-isopropyl-pyridin-3-yl)-ethyl]-2-methyl-2,3,4,5-tetrahydro-1H-pyrido[4,3-b]indole (Compound 372)

To a solution of 8-Chloro-2-methyl-2,3,4,5-tetrahydro-1H-pyrido[4,3-b]indole (0.1 g. 0.00045 mol) in N-methyl 2-pyrolidone (1.0 mL) was added powdered potassium hydroxide (0.140 g, 0.0025 mol) and allowed to stir for 10 min at RT. 2-Isopropyl-5-vinyl-pyridine (0.185 g, 0.00125 mol) was added and stirred for further 4 h. at 100 deg C. After completion (TLC), reaction mixture was diluted with water (15 mL) and extracted with ethyl acetate (3×50 mL). The organic layer was dried over anhydrous sodium sulphate and concentrated under reduced pressure using rotary evaporator. The crude was purified through column chromatography (7% MeOH:DCM in silica 100-200 mesh, Diameter of column—2.5 cm, Height of silica—approx. 5 inch), Then further purified by preparative TLC, to give the desired compound as yellow oil (0.027 g, 15% yield). 8-Chloro-5-[2-(6-isopropyl-pyridin-3-yl)-ethyl]-2-methyl-2,3,4,5-tetrahydro-1H-pyrido[4,3-b]indole (0.027 g, 0.00007 mol) was dissolved in THF (1.0 mL). A solution of oxalic acid dihydrate (0.009 g, 0.00007 mol) in THF (0.5 mL) was added and stirred for 30 min at RT, Precipitate obtained was filtered and dried to give oxalate salt as off white solid (0.027 g, 81% yield).

Example 192

Preparation of 8-chloro-5-(2-(2-(trifluoromethyl)pyrimidin-5-yl)ethyl)-2,3,4,5-tetrahydro-2-methyl-1H-pyrido[4,3-b]indole (Compound 373)

The title compound is prepared from a mixture of 8-chloro-2,3,4,5-tetrahydro-2-methyl-1H-pyrido[4,3-b]indole, 2-(trifluoromethyl)-5-vinylpyrimidine and KOH (5-7 equiv) in NMP at a temperature ranging between 25 deg C. to 100 deg C. The product obtained is isolated by preparative HPLC.

Example 193

Preparation of 8-chloro-5-(2-(5-(trifluoromethyl)pyrazin-2-yl)ethyl)-2,3,4,5-tetrahydro-2-methyl-1H-pyrido[4,3-b]indole (Compound 374)

The title compound is prepared from a mixture of 8-chloro-2,3,4,5-tetrahydro-2-methyl-1H-pyrido[4,3-b]indole, 2-(trifluoromethyl)-5-vinylpyrimidine and KOH (5-7 equiv) in NMP at a temperature ranging between 25 deg C. to 100 deg C. The product obtained is isolated by preparative HPLC.

Example 194

Preparation of 2',8'-dimethyl-5'-(2-(6-(trifluoromethyl)pyridin-3-yl)ethyl)-1',2',4',5'-tetrahydrospiro[cyclopropane-1,3'-pyrido[4,3-b]indole] (Compound 375)

The title compound is prepared from a mixture of 2',8'-dimethyl-1',2',4',5'-tetrahydrospiro[cyclopropane-1,3'-pyrido[4,3-b]indole], 2-(trifluoromethyl)-5-vinylpyridine and KOH (5-7 equiv) in NMP at a temperature ranging between 25 deg C. to 100 deg C. The product obtained is isolated by preparative HPLC.

Example 195

Preparation of 2',8'-dimethyl-5'-(2-(6-(trifluoromethyl)pyridin-3-yl)ethyl)-2',3',4',5'-tetrahydrospiro[cyclopropane-1,1'-pyrido[4,3-b]indole] (Compound 376)

The title compound is prepared from a mixture of 2',8'-dimethyl-2',3',4',5'-tetrahydrospiro[cyclopropane-1,1'-pyrido[4,3-b]indole], 2-(trifluoromethyl)-5-vinylpyridine and KOH (5-7 equiv) in NMP at a temperature ranging between 25 deg C. to 100 deg C. The product obtained is isolated by preparative HPLC.

Example 196

Preparation of 5-(2-(6-(trifluoromethyl)pyridin-3-yl) ethyl)-2,3,4,5-tetrahydro-2,3,3,8-tetramethyl-1H-pyrido[4,3-b]indole (Compound 377)

The title compound is prepared from a mixture of 2,3,4,5-tetrahydro-2,3,3,8-tetramethyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 197

Preparation of 5-(2-(6-(trifluoromethyl)pyridin-3-yl) ethyl)-2,3,4,5-tetrahydro-1,1,2,8-tetramethyl-1H-pyrido[4,3-b]indole (Compound 378)

The title compound is prepared from a mixture of 2,3,4,5-tetrahydro-1,1,2,8-tetramethyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 198

Preparation of 2,3,4,5-tetrahydro-2,6-dimethyl-5-(2-(6-methylpyridin-3-yl)ethyl)-1H-pyrido[4,3-b]indole (Compound 379)

The title compound is prepared from a mixture of 2,3,4,5-tetrahydro-2,6-dimethyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 199

Preparation of 5-(2-(6-(trifluoromethyl)pyridin-3-yl) ethyl)-2,3,4,5-tetrahydro-2,6-dimethyl-1H-pyrido[4,3-b]indole (Compound 380)

To a solution of 2,3,4,5-tetrahydro-2,6-dimethyl-1H-pyrido[4,3-b]indole (200 mg, 1.0 mmol) in NMP (2.5 ml), powdered KOH (561 mg, 10 mmol) was added and stirred for 10 min at 25 deg C. After which 2-(trifluoromethyl)-5-vinylpyridine (346 mg, 2.0 mmol) was added slowly to the above solution and stirred for 16 h at 25 deg C. After completion of the reaction (monitored by LCMS), water (5 mL) was added to the crude and extracted with the ethyl acetate. The organic layer was dried and concentrated. The resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 40 mg (8.2%) of 5-(2-(6-(trifluoromethyl)pyridin-3-yl)ethyl)-2,3,4,5-tetrahydro-2,6-dimethyl-1H-pyrido[4,3-b]indole as TFA salt.

Example 200

Preparation of 3-(6-(trifluoromethyl)pyridin-3-yl)-2-(1,2,3,4-tetrahydro-2,8-dimethylpyrido[4,3-b]indol-5-yl)propanoic acid (Compound 381)

The title compound is prepared from a mixture of 2,3,4,5-tetrahydro-2,8-dimethyl-1H-pyrido[4,3-b]indole, (Z)-3-(6-(trifluoromethyl)pyridin-3-yl)acrylic acid and KOH (5-7 equiv) in NMP at a temperature ranging between 25 deg C. to 100 deg C. The product obtained is isolated by preparative HPLC.

Example 201

Preparation of ethyl 3-(6-(trifluoromethyl)pyridin-3-yl)-2-(1,2,3,4-tetrahydro-2,8-dimethylpyrido[4,3-b] indol-5-yl)propanoate (Compound 382)

The title compound is prepared from a mixture of 2,3,4,5-tetrahydro-2,8-dimethyl-1H-pyrido[4,3-b]indole, (Z)-ethyl 3-(6-(trifluoromethyl)pyridin-3-yl)acrylate and KOH (5-7 equiv) in NMP at a temperature ranging between 25 deg C. to 100 deg C. The product obtained is isolated by preparative HPLC.

Example 202

Preparation of 2-(6-(trifluoromethyl)pyridin-3-yl)-3-(1,2,3,4-tetrahydro-2,8-dimethylpyrido[4,3-b]indol-5-yl)propanoic acid (Compound 383)

The title compound is prepared from a mixture of 2,3,4,5-tetrahydro-2,8-dimethyl-1H-pyrido[4,3-b]indole, 2-(6-(trifluoromethyl)pyridin-3-yl)acrylic acid and KOH (5-7 equiv) in NMP at a temperature ranging between 25 deg C. to 100 deg C. The product obtained is isolated by preparative HPLC.

Example 203

Preparation of methyl 2-(6-(trifluoromethyl)pyridin-3-yl)-3-(1,2,3,4-tetrahydro-2,8-dimethylpyrido[4,3-b]indol-5-yl)propanoate (Compound 384)

The title compound is prepared from a mixture of 2,3,4,5-tetrahydro-2,8-dimethyl-1H-pyrido[4,3-b]indole, methyl 2-(6-(trifluoromethyl)pyridin-3-yl)acrylate and KOH (5-7 equiv) in NMP at a temperature ranging between 25 deg C. to 100 deg C. The product obtained is isolated by preparative HPLC.

Example 204

Preparation of 5-(2-(2-(trifluoromethyl)pyrimidin-5-yl)ethyl)-2,3,4,5-tetrahydro-2,8-dimethyl-1H-pyrido [4,3-b]indole (Compound 385)

The title compound is prepared from a mixture of 2,3,4,5-tetrahydro-2,8-dimethyl-1H-pyrido[4,3-b]indole, 2-(trifluoromethyl)-5-vinylpyrimidine and KOH (5-7 equiv) in NMP at a temperature ranging between 25 deg C. to 100 deg C. The product obtained is isolated by preparative HPLC.

Example 205

Preparation of 5-(2-(5-(trifluoromethyl)pyrazin-2-yl) ethyl)-2,3,4,5-tetrahydro-2,8-dimethyl-1H-pyrido[4,3-b]indole (Compound 386)

The title compound is prepared from a mixture of 2,3,4,5-tetrahydro-2,8-dimethyl-1H-pyrido[4,3-b]indole, 2-(trifluoromethyl)-5-vinylpyrazine and KOH (5-7 equiv) in NMP at a temperature ranging between 25 deg C. to 100 deg C. The product obtained is isolated by preparative HPLC.

Example 206

Preparation of 2,8-Dimethyl-5-(2-pyrimidin-5-yl-ethyl)-2,3,4,5-tetrahydro-1H-pyrido[4,3-b]indole (Compound 387)

To a solution of 2,8-Dimethyl-2,3,4,5-tetrahydro-1H-pyrido[4,3-b]indole (0.1 g. 0.49 mmol) in N-methyl 2-pyrolidone (1.0 mL) was added powdered potassium hydroxide (0.14 g, 2.5 mmol) and allowed to stir for 10 min at RT. 5-vinyl pyrimidine (0.132 g, 1.25 mmol) was added and stirred for further 5 h at 60 deg C. After completion (TLC), reaction mixture was diluted with water (15 mL) and extracted with ethyl acetate (3×50 mL). The organic layer was dried over anhydrous sodium sulphate and concentrated under reduced pressure. The crude was purified through column chromatography (7% MeOH:DCM in silica 100-200 mesh, Diameter of column—2.5 cm, Height of silica approx. 5 inch), Then further purified by preparative TLC, to give the desired compound as yellow oil (0.050 g, 32.6% yield). 2,8-Dimethyl-5-(2-pyrimidin-5-yl-ethyl)-2,3,4,5-tetrahydro-1H-pyrido[4,3-b]indole (0.040 g, 0.13 mol) was dissolved in THF (1.0 mL). A solution of oxalic acid dihydrate (0.015 g, 0.119 mol) in THF (1.0 mL) was added and stirred for 30 min at RT, Precipitate obtained was filtered and dried to give oxalate salt as off white solid (0.046 g, 90% yield).

Example 207

Preparation of 8-chloro-5-(2-(6-(trifluoromethyl) pyridin-3-yl)ethyl)-2,3,4,5-tetrahydro-2,3,3-trimethyl-1H-pyrido[4,3-b]indole (Compound 388)

The title compound is prepared from a mixture of 8-chloro-2,3,4,5-tetrahydro-2,3,3-trimethyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 208

Preparation of 8-chloro-5-(2-(6-(trifluoromethyl) pyridin-3-yl)ethyl)-2,3,4,5-tetrahydro-1,1,2-trimethyl-1H-pyrido[4,3-b]indole (Compound 389)

The title compound is prepared from a mixture of 8-chloro-2,3,4,5-tetrahydro-1,1,2-trimethyl-1H-pyrido[4,3-b]indole, 2-(trifluoromethyl)-5-vinylpyridine and KOH (5-7 equiv) in NMP at a temperature ranging between 25 deg C. to 100 deg C. The product obtained is isolated by preparative HPLC.

Example 209

Preparation of 8'-chloro-2'-methyl-5'-(2-(6-(trifluoromethyl)pyridin-3-yl)ethyl)-2',3',4',5'-tetrahydrospiro[cyclopropane-1,1'-pyrido[4,3-b]indole] (Compound 390)

The title compound is prepared from a mixture of 8'-chloro-2'-methyl-2',3',4',5'-tetrahydrospiro[cyclopropane-1,1'-pyrido[4,3-b]indole], 2-(trifluoromethyl)-5-vinylpyridine and KOH (5-7 equiv) in NMP at a temperature ranging between 25 deg C. to 100 deg C. The product obtained is isolated by preparative HPLC.

Example 210

Preparation of 8'-chloro-2'-methyl-5'-(2-(6-(trifluoromethyl)pyridin-3-yl)ethyl)-1',2',4',5'-tetrahydrospiro[cyclopropane-1,3'-pyrido[4,3-b]indole] (Compound 391)

The title compound is prepared from a mixture of 8'-chloro-2'-methyl-1',2',4',5'-tetrahydrospiro[cyclopropane-1,3'-pyrido[4,3-b]indole],2-(trifluoromethyl)-5-vinylpyridine and KOH (5-7 equiv) in NMP at a temperature ranging between 25 deg C. to 100 deg C. The product obtained is isolated by preparative HPLC.

Example 211

Preparation of 8-Isopropyl-2-methyl-5-[2-(6-methyl-pyridin-3-yl)-ethyl]-2,3,4,5-tetrahydro-1H-pyrido[4,3-b]indole (Compound 392)

To a solution of 8-Isopropyl-2-methyl-2,3,4,5-tetrahydro-1H-pyrido[4,3-b]indole (0.2 g, 0.877 mmol) in N-methyl 2-pyrolidone (2 mL) was added powdered potassium hydroxide (0.2 g, 3.5 mmol) and allowed to stir for 10 min at RT. 2-methyl-5-vinyl pyridine (0.104 g, 0.877 mmol) was added and stirred for further at 120 deg C. for 20 h. Reaction mixture was diluted with water (30 mL) and extracted with ethyl acetate (3×50 mL). The organic layer was dried over anhydrous sodium sulphate and concentrated under reduced pressure. The crude was purified through column chromatography (5% Me OH:DCM in silica 100-200 mesh, Diameter of column—2.5 cm, Height of silica—approx. 5 inch) and further purified with preparative TLC to provide the desired compound as brown oil (0.045 g, 15% yield). 8-Isopropyl-2-methyl-5-[2-(6-methyl-pyridin-3-yl)-ethyl]-2,3,4,5-tetrahydro-1H-pyrido[4,3-b]indole (0.045 g, 0.129 mmol) was dissolved in THF (2.0 mL). A solution of oxalic acid dihydrate (0.016 g, 0.129 mmol) in THF (2 mL) was added and stirred for 30 min at RT, Precipitate obtained was filtered and dried to give oxalate salt as off white solid (0.045 g, 80% yield).

Example 212

Preparation of tert-butyl 1-(3-(1,2,3,4-tetrahydro-2,8-dimethylpyrido[4,3-b]indol-5-yl)propanoyl)piperidin-4-ylcarbamate (Compound 393)

3-(1,2,3,4-tetrahydro-2,8-dimethylpyrido[4,3-b]indol-5-yl)propanoic acid (500 mg, 1.8 mmol) was stirred with tert-butyl piperidin-4-ylcarbamate (0.366 ml, 1.8 mmol), EDCI-HCl (0.35 g, 1.8 mmol) and triethyl amine (0.253 ml, 1.8 mmol) in dichloromethane (20 ml) to obtain 50 mg of tert-butyl 1-(3-(1,2,3,4-tetrahydro-2,8-dimethylpyrido[4,3-b]indol-5-yl)propanoyl)piperidin-4-yl carbamate as a trifluoroacetate salt after purification on neutral alumina chromatography eluting with methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 213

Preparation of 5-(2-(2,8-dimethyl-3,4-dihydro-1H-pyrido[4,3-b]indol-5(2H)-yl)ethyl)-2-methylpyridine 1-oxide (Compound 394)

To the N,N'-dioxide intermediate (76 mg, 0.21 mmol) in acetic acid (0.3 ml) and methanol (2 ml) sodium bisulphite (40% in water, 0.2 ml) was added and the reaction mixture was stirred at 0 deg C. for 0.5 h. The reaction mixture was basified with saturated aqueous NaHCO₃ and extracted with ethyl acetate to obtain 50 mg of 2,3,4,5-tetrahydro-2,8-dimethyl-5-(2-(6-methylpyridin-3-yl)ethyl)-1H-pyrido[4,3-b]indole N'-oxide.

Example 214

Preparation of 2-(1,2,3,4-tetrahydro-2,8-dimethylpyrido[4,3-b]indol-5-yl)-1-(piperidin-1-yl)ethanone (Compound 395)

2-(2,8-dimethyl-3,4-dihydro-1H-pyrido[4,3-b]indol-5 (2H)-yl) acetic acid (1.5 g, 5.8 mmol) was taken in dichloromethane (15 mL) and was cooled to 0° C. using an ice-bath; oxalyl chloride (0.61 mL, 6.9 mmol) was added drop-wise, catalytic amount (2 drop) of dimethyl formamide was added to the reaction mixture. After the addition, reaction mixture was stirred for 1 h at room temperature. Excess oxalyl chloride was distilled away under reduced pressure. To this residue, solution of Piperidine (0.68 mL, 6.9 mmol) in 4 mL DCM and DMAP (0.71 g, 5.8 mmol) was added under nitrogen at room temperature and reaction mass was stirred for 0.5 h at room temperature. The reaction mixture was quenched by ice water and extracted with Dichloromethane and purified by column chromatography to gives 0.8 g of desired compound as free base. The free base was converted into HCl salt by treatment with ethanolic HCl. Sodium hydride (0.8 g, 20 mmol) washed with hexane for removal of oil and dried under vacuum. Then sodium hydride was taken in THF. To this solution 2,8-dimethyl-2,3,4,5-tetrahydro-1H-pyrido[4,3-b]indole (2 g, 10 mmol) in THF was added drop wise at 0° C. Then reaction mixture stirred for 0.5 h. The solution of 2-chloro-1-(piperidin-1-yl)ethanone (1.9 g, 12 mmol) in THF was added drop wise in react ion mixture. Then reaction mixture stirred at RT for 2 h. Reaction monitored by TLC. After completion of reaction, reaction mixture quench with ice-water. THF was evaporated and aqueous layer was extracted with ethyl acetate. Organic layer was dried over anhydrous sodium sulphate. The crude compound was washed with hexane and diethyl ether for removal of color impurities then recrystallized by using methanol to give 1 g of desired compound then it was stirred with ethanolic HCl to give HCl salt of 2-(2,8-dimethyl-3,4-dihydro-1H-pyrido[4,3-b]indol-5(2H)-yl)-1-(piperidin-1-yl)ethanone.

Example 215

Preparation of 8-tert-butyl-2,3,4,5-tetrahydro-2-methyl-5-(2-(6-methylpyridin-3-yl)ethyl)-1H-pyrido[4,3-b]indole (Compound 396)

To a solution of 8-tert-butyl-2,3,4,5-tetrahydro-2-methyl-1H-pyrido[4,3-b]indole (200 mg, 0.82 mmol) in NMP (3.0 ml), powdered KOH (462 mg, 8.23 mmol) was added and stirred for 10 min at 25 deg C. After which 2-(trifluoromethyl)-5-vinylpyridine (286 mg, 1.65 mmol) was added slowly to the above solution and stirred for 14 h at 25 deg C. After completion of the reaction (monitored by LCMS), water (5 mL) was added to the crude and extracted with the ethylacetate. The organic layer was dried and concentrated. The resulting crude was purified by reverse-phase chromatography (C-18, 500 mm×50 mm, Mobile Phase A=0.05% TFA in water, B=0.05% TFA in acetonitrile, gradient: 10% B to 80% B in 30 min, injection vol. 5 mL) to obtain 30 mg of 8-tert-butyl-2,3,4,5-tetrahydro-2-methyl-5-(2-(6-methylpyridin-3-yl)ethyl)-1H-pyrido[4,3-b]indole as TFA salt Example 216

Preparation of 2-(1,2,3,4-tetrahydro-2,8-dimethylpyrido[4,3-b]indol-5-yl)-1-(isoindolin-2-yl)ethanone (Compound 397)

A mixture of 2-(1,2,3,4-tetrahydro-2,8-dimethylpyrido[4,3-b]indol-5-yl)acetic acid (50 mg, 0.205 mmol), Isoindoline (23 mg, 0.205 mmol), DCC (46 mg, 0.22 mmol), and DMAP (27 mg, 0.22 mmol) in dry DCM (2.0 mL) was stirred at room temperature for 3 h. The reaction mixture was filtered through Celite and concentrated using rotary evaporator afforded 16.3 mg of 2-(1,2,3,4-tetrahydro-2,8-dimethylpyrido[4,3-b]indol-5-yl)-1-(isoindolin-2-yl)ethanone as TFA Salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 217

Preparation of 2-(1,2,3,4-tetrahydro-2,8-dimethylpyrido[4,3-b]indol-5-yl)-1-(3,4-dihydroisoquinolin-2 (1H)-yl)ethanone (Compound 398)

A mixture of 2-(1,2,3,4-tetrahydro-2,8-dimethylpyrido[4,3-b]indol-5-yl) acetic acid (50 mg, 0.205 mmol), 1,2,3,4 Tetrahydroisoquinoline (25 mg, 0.205 mmol), DCC (46 mg, 0.22 mmol), and DMAP (27 mg, 0.22 mmol) in dry DCM (2.0 mL) was stirred at room temperature for 3 h. The reaction mixture was filtered through Celite and concentrated using rotary evaporator afforded 7.9 mg of 2-(1,2,3,4-tetrahydro-2,8-dimethylpyrido[4,3-b]indol-5-yl)-1-(3,4-dihydroisoquinolin-2 (1H)-yl)ethanone as TFA Salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 218

Preparation of 2-(1,2,3,4-tetrahydro-2,8-dimethylpyrido[4,3-b]indol-5-yl)-1-thiomorpholinoethanone (Compound 399)

A mixture of 2-(1,2,3,4-tetrahydro-2,8-dimethylpyrido[4,3-b]indol-5-yl)acetic acid (50 mg, 0.205 mmol), Thiomorpholine (19 mg, 0.205 mmol), DCC (46 mg, 0.22 mmol), and DMAP (27 mg, 0.22 mmol) in dry DCM (2.0 mL) was stirred at room temperature for 3 h. The reaction mixture was filtered through Celite and concentrated using rotary evaporator afforded 34.2 mg of 2-(1,2,3,4-tetrahydro-2,8-dimethylpyrido[4,3-b]indol-5-yl)-1-thiomorpholinoethanone as TFA Salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 219

Preparation of 2-(1,2,3,4-tetrahydro-2,8-dimethylpyrido[4,3-b]indol-5-yl)-1-(2-(pyridin-3-yl)pyrrolidin-1-yl)ethanone (Compound 400)

The title compound is prepared by following Method 8 by using 2-bromo-1-(2-(pyridin-3-yl)pyrrolidin-1-yl)ethanone, (2,3,4,5-tetrahydro-2,8-dimethyl-1H-pyrido[4,3-b]indole), triethylamine and N-methyl-4-piperidone.

Example 220

Preparation of 2-(1,2,3,4-tetrahydro-2,8-dimethylpyrido[4,3-b]indol-5-yl)-1-(3-methylpiperidin-1-yl)ethanone (Compound 401)

A mixture of 2-(1,2,3,4-tetrahydro-2,8-dimethylpyrido[4,3-b]indol-5-yl)acetic acid (50 mg, 0.205 mmol), 3-methyl piperidine (19 mg, 0.205 mmol), DCC (46 mg, 0.22 mmol), and DMAP (27 mg, 0.22 mmol) in dry DCM (2.0 mL) was stirred at room temperature for 3 h. The reaction mixture was filtered through Celite and concentrated using rotary evaporator afforded 34.2 mg of 2-(1,2,3,4-tetrahydro-2,8-dimethylpyrido[4,3-b]indol-5-yl)-1-(3-methylpiperidin-1-yl)ethanone as TFA Salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 221

Preparation of 2,3,4,5-tetrahydro-2-methyl-5-(2-(6-methylpyridin-3-yl)ethyl)-1H-pyrido[4,3-b]indole-8-carboxylic acid (Compound 402)

To a solution of 2,3,4,5-tetrahydro-2-methyl-5-(2-(6-methylpyridin-3-yl)ethyl)-1H-pyrido[4,3-b]indole-8-carboxylic acid (1.0 g, 4.09 mmol) in NMP (7.8 ml), powdered KOH (2.3 g, 40.9 mmol) was added and stirred for 10 min at 25 deg C. After which 2-(trifluoromethyl)-5-vinylpyridine (1.4 g, 8.1 mmol) was added slowly to the above solution and stirred for 14 h at 45 deg C. After completion of the reaction (monitored by LCMS), DM water was added to the crude and extracted with the ethyl acetate. The organic layer was separated, dried and concentrated. The resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL) to obtain 15 mg of 2,3,4,5-tetrahydro-2-methyl-5-(2-(6-methylpyridin-3-yl)ethyl)-1H-pyrido[4,3-b]indole-8-carboxylic acid as a TFA salt.

Example 222

Preparation of 8-Chloro-5-[2-(6-methyl-pyridin-3-yl)-ethyl]-2-(3-trifluoromethyl-phenyl)-2,3,4,5-tetrahydro-1H-pyrido[4,3-b]indole (Compound 403)

To a stirred solution of N-(4-Chloro-phenyl)-N-[2-(6-methyl-pyridin-3-yl)-ethyl]-hydrazine hydrochloride (0.13 g, 0.5 mmol) in absolute ethanol (5 mL) was added 1-(3-Trifluoromethyl-phenyl)-piperidin-4-one (0.122 g, 0.5 mmol) at RT and then refluxed for 1 h. After completion (TLC), ethanol was evaporated. The crude was purified by preparative HPLC to provide desired compound as brown colored solid (0.02 g, 10% yield) 8-Chloro-5-[2-(6-methyl-pyridin-3-yl)-ethyl]-2-(3-trifluoromethyl-phenyl)-2,3,4,5-tetrahydro-1H-pyrido[4,3-b]indole (0.020 g, 0.0425 mmol) was dissolved in THF (1.0 mL). A solution of oxalic acid dihydrate (0.0053 g, 0.0425 mmol) in 1.5 mL THF was added and stirred for 30 min at RT. Precipitate was filtered and dried to give oxalate salt as brown solid (0.01 g, 43% yield).

Example 223

Preparation of 8-Chloro-7-fluoro-2-methyl-5-[2-(6-methyl-pyridin-3-yl)-ethyl]-2,3,4,5-tetrahydro-1H-pyrido[4,3-b]indole (Compound 404)

To a solution of 8-Chloro-7-fluoro-2-methyl-2,3,4,5-tetrahydro-1H-pyrido[4,3-b]indole (0.3 g, 1.25 mmol) in N-methyl 2-pyrolidone (1.5 mL) was added powdered potassium hydroxide (0.7 g, 12.5 mmol) and allowed to stir for 10 min at RT. 2-trifluoromethyl-5-vinyl pyridine (0.44 g, 3.7 mmol) was added and stirred at 120 deg C. for further 24 h. After completion (TLC), reaction mixture was diluted with water (15 mL) and extracted with ethyl acetate (3×150 mL). The organic layer was dried over anhydrous sodium sulphate and concentrated under reduced pressure. The crude was purified through column chromatography (6% Methanol:DCM in silica 100-200 mesh, Diameter of column—2.5 cm, Height of silica—approx. 5 inch) then further purified through preparative HPLC to give the desired compound 10 as light yellow solid (0.080 g, 21% yield). 8-Chloro-7-fluoro-2-methyl-5-[2-(6-methyl-pyridin-3-yl)-ethyl]-2,3,4,5-tetrahydro-1H-pyrido[4,3-b]indole (0.08 g, 0.22 mmol) was dissolved in THF (2.0 mL). A solution of oxalic acid dihydrate (0.028 g, 0.22 mmol) in THF (1.0 mL) was added and stirred for 30 min at RT, Precipitate obtained was filtered and dried to give oxalate salt as white solid (0.070 g, 70% yield).

Example 224

Preparation of 5-(2-(6-cyclopropylpyridin-3-yl)ethyl)-2,3,4,5-tetrahydro-2,8-dimethyl-1H-pyrido[4,3-b]indole (Compound 405)

The title compound is prepared from a mixture of 2,3,4,5-tetrahydro-2,8-dimethyl-1H-pyrido[4,3-b]indole, 2-cyclopropyl-5-vinylpyridine and KOH (5-7 equiv) in NMP at a temperature ranging between 25 deg C. to 100 deg C. The product obtained is isolated by preparative HPLC.

Example 225

Preparation of 8-chloro-5-(2-(6-cyclopropylpyridin-3-yl)ethyl)-2,3,4,5-tetrahydro-2-methyl-1H-pyrido[4,3-b]indole (Compound 406)

The title compound is prepared from a mixture of 8-chloro-2,3,4,5-tetrahydro-2-methyl-1H-pyrido[4,3-b]indole, 2-cyclopropyl-5-vinylpyridine and KOH (5-7 equiv) in NMP at a temperature ranging between 25 deg C. to 100 deg C. The product obtained is isolated by preparative HPLC.

Example 226

Preparation of 2-(8-chloro-1,2,3,4-tetrahydro-2-methylpyrido[4,3-b]indol-5-yl)-1-(6-(trifluoromethyl)pyridin-3-yl)ethanol (Compound 407)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(4-fluorophenyl)-2-methyloxirane (400 mg, 2.1 mmol, 1.6 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 227

Preparation of 5-(2-(1,2,3,4-tetrahydro-2,8-dimethylpyrido[4,3-b]indol-5-yl)ethyl)pyridin-2(1H)-one (Compound 408)

The title compound is prepared from a mixture of 2,3,4,5-tetrahydro-2,8-dimethyl-1H-pyrido[4,3-b]indole, 5-vinylpyridin-2(1H)-one and KOH (5-7 equiv) in NMP at a temperature ranging between 25 deg C. to 100 deg C. The product obtained is isolated by preparative HPLC.

Example 228

Preparation of 5-(2-(8-chloro-1,2,3,4-tetrahydro-2-methylpyrido[4,3-b]indol-5-yl)ethyl)pyridin-2(1H)-one (Compound 409)

The title compound is prepared from a mixture of 8-chloro-2,3,4,5-tetrahydro-2-methyl-1H-pyrido[4,3-b]indole, 5-vinylpyridin-2(1H)-one and KOH (5-7 equiv) in NMP at a temperature ranging between 25 deg C. to 100 deg C. The product obtained is isolated by preparative HPLC.

Example 229

Preparation of 5-(2-(1,2,3,4-tetrahydro-2,8-dimethylpyrido[4,3-b]indol-5-yl)ethyl)-1-methylpyridin-2(1H)-one (Compound 410)

The title compound is prepared from a mixture of 2,3,4,5-tetrahydro-2,8-dimethyl-1H-pyrido[4,3-b]indole, 1-methyl-5-vinylpyridin-2(1H)-one and KOH (5-7 equiv) in NMP at a temperature ranging between 25 deg C. to 100 deg C. The product obtained is isolated by preparative HPLC.

Example 230

Preparation of 1-cyclopropyl-5-(2-(1,2,3,4-tetrahydro-2,8-dimethylpyrido[4,3-b]indol-5-yl)ethyl)pyridin-2(1H)-one (Compound 411)

The title compound is prepared from a mixture of 2,3,4,5-tetrahydro-2,8-dimethyl-1H-pyrido[4,3-b]indole, 1-cyclopropyl-5-vinylpyridin-2(1H)-one and KOH (5-7 equiv) in NMP at a temperature ranging between 25 deg C. to 100 deg C. The product obtained is isolated by preparative HPLC.

Example 231

Preparation of 5-(2-(8-chloro-1,2,3,4-tetrahydro-2-methylpyrido[4,3-b]indol-5-yl)ethyl)-1-methylpyridin-2(1H)-one (Compound 412)

The title compound is prepared from a mixture of 8-chloro-2,3,4,5-tetrahydro-2-methyl-1H-pyrido[4,3-b]indole, 1-methyl-5-vinylpyridin-2(1H)-one and KOH (5-7 equiv) in NMP at a temperature ranging between 25 deg C. to 100 deg C. The product obtained is isolated by preparative HPLC.

Example 232

Preparation of 5-(2-(8-chloro-1,2,3,4-tetrahydro-2-methylpyrido[4,3-b]indol-5-yl)ethyl)-1-cyclopropylpyridin-2(1H)-one (Compound 413)

The title compound is prepared from a mixture of 8-chloro-2,3,4,5-tetrahydro-2-methyl-1H-pyrido[4,3-b]indole, 1-cyclopropyl-5-vinylpyridin-2(1H)-one and KOH (5-7 equiv) in NMP at a temperature ranging between 25 deg C. to 100 deg C. The product obtained is isolated by preparative HPLC.

Example 233

Preparation of 1-(trifluoromethyl)-5-(2-(1,2,3,4-tetrahydro-2,8-dimethylpyrido[4,3-b]indol-5-yl)ethyl)pyridin-2(1H)-one (Compound 414)

The title compound is prepared from a mixture of 2,3,4,5-tetrahydro-2,8-dimethyl-1H-pyrido[4,3-b]indole, 1-(trifluoromethyl)-5-vinylpyridin-2(1H)-one and KOH (5-7 equiv) in NMP at a temperature ranging between 25 deg C. to 100 deg C. The product obtained is isolated by preparative HPLC.

Example 234

Preparation of 5-(2-(8-chloro-1,2,3,4-tetrahydro-2-methylpyrido[4,3-b]indol-5-yl)ethyl)-1-(trifluoromethyl)pyridin-2(1H)-one (Compound 415)

The title compound is prepared from a mixture of 8-chloro-2,3,4,5-tetrahydro-2-methyl-1H-pyrido[4,3-b]indole, 1-(trifluoromethyl)-5-vinylpyridin-2(1H)-one and KOH (5-7 equiv) in NMP at a temperature ranging between 25 deg C. to 100 deg C. The product obtained is isolated by preparative HPLC.

Example 235

Preparation of 8-chloro-2-(4-fluorophenyl)-2,3,4,5-tetrahydro-5-(2-(6-methylpyridin-3-yl)ethyl)-1H-pyrido[4,3-b]indole (Compound 416)

The title compound is prepared from a mixture of 8-chloro-2-(4-fluorophenyl)-2,3,4,5-tetrahydro-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 236

Preparation of 8-chloro-2,3,4,5-tetrahydro-2-methyl-5-(2-(4-methylpiperazin-1-yl)ethyl)-1H-pyrido[4,3-b]indole (Compound 417)

The title compound is prepared by following Method 8 by using 1-(2-bromoethyl)-4-methylpiperazine, 4-chlorophenylhydrazine hydrochloride, triethylamine and N-methyl-4-piperidone Example 237

Preparation of 2,3,4,5-tetrahydro-2,8-dimethyl-5-(2-(4-methylpiperazin-1-yl)ethyl)-1H-pyrido[4,3-b]indole (Compound 418)

LAH (0.022 g, 0.58 mmol) was charged in dry THF (3 mL) and cooled to 0 deg C., 2-(2,8-dimethyl-3,4-dihydro-1H-pyrido[4,3-b]indol-5(2H)-yl)-1-(4-methylpiperazin-1-yl)ethanone (0.05 g, 0.147 mmol) was added to it portion wise. The reaction mixture was refluxed for 4 h. The reaction mixture was cooled to 0 deg C. and quenched with sat. Na2SO4. The solid formed was filtered through celite, washed with THF, dried over Na2SO4 and concentrated under reduced pressure to obtain 11 mg of 2,8-dimethyl-5-(2-(4-methylpiperazin-1-yl)ethyl)-2,3,4,5-tetrahydro-1H-pyrido[4,3-b]indole as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 238

Preparation of 8-chloro-2,3,4,5-tetrahydro-2-methyl-5-(2-(1-methylisoquinolin-4-yl)ethyl)-1H-pyrido[4,3-b]indole (Compound 420)

The title compound is prepared from a mixture of 8-chloro-2,3,4,5-tetrahydro-2-methyl-1H-pyrido[4,3-b]indole, 1-methyl-4-vinylisoquinoline and KOH (5-7 equiv) in NMP at a temperature ranging between 25 deg C. to 100 deg C. The product obtained is isolated by preparative HPLC.

Example 239

Preparation of 2,3,4,5-tetrahydro-2,8-dimethyl-5-(2-(1-methylisoquinolin-4-yl)ethyl)-1H-pyrido[4,3-b]indole (Compound 421)

The title compound is prepared from a mixture of 2,3,4,5-tetrahydro-2,8-dimethyl-1H-pyrido[4,3-b]indole, 1-methyl-4-vinylisoquinoline and KOH (5-7 equiv) in NMP at a temperature ranging between 25 deg C. to 100 deg C. The product obtained is isolated by preparative HPLC.

Example 240

Preparation of 8-chloro-2,3,4,5-tetrahydro-2-methyl-5-(2-(quinolin-3-yl)ethyl)-1H-pyrido[4,3-b]indole (Compound 422)

The title compound is prepared from a mixture of 8-chloro-2,3,4,5-tetrahydro-2-methyl-1H-pyrido[4,3-b]indole, 3-vinylquinoline and KOH (5-7 equiv) in NMP at a temperature ranging between 25 deg C. to 100 deg C. The product obtained is isolated by preparative HPLC.

Example 241

Preparation of 2,3,4,5-tetrahydro-2,8-dimethyl-5-(2-(quinolin-3-yl)ethyl)-1H-pyrido[4,3-b]indole (Compound 423)

The title compound is prepared from a mixture of 2,3,4,5-tetrahydro-2,8-dimethyl-1H-pyrido[4,3-b]indole, 3-vinylquinoline and KOH (5-7 equiv) in NMP at a temperature ranging between 25 deg C. to 100 deg C. The product obtained is isolated by preparative HPLC.

Example 242

Preparation of 8-Chloro-2-methyl-5-(2-pyrimidin-5-yl-ethyl)-2,3,4,5-tetrahydro-1H-pyrido[4,3-b]indole (Compound 424)

To a solution of 8-Chloro-2-methyl-2,3,4,5-tetrahydro-1H-pyrido[4,3-b]indole (0.15 g, 0.68 mmol) in N-methyl 2-pyrolidone (1.0 mL) was added powdered potassium hydroxide (0.19 g, 3.4 mmol) and allowed to stir for 10 min at RT. 5-vinyl pyrimidine (0.177 g, 1.7 mmol) was added and stirred for further 5 h at 60 deg C. After completion (TLC), reaction mixture was diluted with water (15 mL) and extracted with ethyl acetate (3×100 mL). The organic layer was dried over anhydrous sodium sulphate and concentrated under reduced pressure. The crude was purified through column chromatography (7% MeOH:DCM in silica 100-200 mesh, Diameter of column—2.5 cm, Height of silica—approx. 5 inch), Then further purified by preparative TLC, to give the desired compound as yellow oil (0.030 g, 14% yield). 8-Chloro-2-methyl-5-(2-pyrimidin-5-yl-ethyl)-2,3,4,5-tetrahydro-1H-pyrido[4,3-b]indole (0.025 g, 0.076 mmol) was dissolved in THF (1.0 mL). A solution of oxalic acid dihydrate (0.0096 g, 0.076 mol) in THF (1.0 mL) was added and stirred for 30 min at RT, precipitate obtained was filtered and dried to give oxalate salt as off white solid (0.025 g, 78% yield).

Example 243

Preparation of 5-(2-(5-(trifluoromethyl)pyridin-3-yl) ethyl)-2,3,4,5-tetrahydro-2,8-dimethyl-1H-pyrido[4, 3-b]indole (Compound 425)

2,8-dimethyl-2,3,4,5-tetrahydro-1H-pyrido[4,3-b]indole (0.15 g, 0.75 mmole), 3-(trifluoromethyl)-5-vinylpyridine (0.13 g, 0.75 mmole) and, tetra butyl ammonium chloride (2 mg, 0.0375 mmole) were charged in 5 ml, 50% aqueous NaOH. The reaction mixture at 100° C. for 8 hrs. The reaction mass was cool at RT, added 5 ml water and extracted with ethyl acetate. The organic layer was dried over anhydrous sodium sulphate, concentrated and purified by Prep HPLC to get 2,8-dimethyl-5-(2-(5-(trifluoromethyl) pyridin-3-yl) ethyl)-2,3,4,5-tetrahydro-1H-pyrido[4,3-b]indole (35 mg).

Example 244

Preparation of 8-chloro-5-(2-(5-(trifluoromethyl) pyridin-3-yl)ethyl)-2,3,4,5-tetrahydro-2-methyl-1H-pyrido[4,3-b]indole (Compound 426)

8-chloro-2-methyl-2,3,4,5-tetrahydro-1H-pyrido[4,3-b] indole (0.165 g, 0.75 mmol), 3-(trifluoromethyl)-5-vinylpyridine (0.13 g, 0.75 mmol) and tetra butyl ammonium chloride (2 mg, 0.0375 mmol) in 5 ml, 50% aqueous NaOH was heated at 100° C. for 8 hrs. The reaction mixture was cooled at RT, added 5 ml water and extracted with ethyl acetate. Dried on anhydrous sodium sulphate and concentrated and submitted for Prep HPLC to get 8-chloro-2-methyl-5-(2-(5-(trifluoromethyl)pyridin-3-yl)ethyl)-2,3,4,5-tetrahydro-1H-pyrido[4,3-b]indole.

Example 245

Preparation of 2,3,4,5-tetrahydro-2,8-dimethyl-5-(2-(1-methyl-1H-pyrrolo[2,3-b]pyridin-5-yl)ethyl)-1H-pyrido[4,3-b]indole (Compound 427)

The title compound is prepared from a mixture of 2,3,4,5-tetrahydro-2,8-dimethyl-1H-pyrido[4,3-b]indole, 1-methyl-5-vinyl-1H-pyrrolo[2,3-b]pyridine and KOH (5-7 equiv) in NMP at a temperature ranging between 25 deg C. to 100 deg C. The product obtained is isolated by preparative HPLC.

Example 246

Preparation of 8-chloro-2,3,4,5-tetrahydro-2-methyl-5-(2-(1-methyl-1H-pyrrolo[2,3-b]pyridin-5-yl)ethyl)-1H-pyrido[4,3-b]indole (Compound 428)

The title compound is prepared from a mixture of 8-chloro-2,3,4,5-tetrahydro-2-methyl-1H-pyrido[4,3-b]indole, 1-methyl-5-vinyl-1H-pyrrolo[2,3-b]pyridine and KOH (5-7 equiv) in NMP at a temperature ranging between 25 deg C. to 100 deg C. The product obtained is isolated by preparative HPLC.

Example 247

Preparation of 2,3,4,5-tetrahydro-2,8-dimethyl-5-(2-(5-methylpyridin-3-yl)ethyl)-1H-pyrido[4,3-b]indole (Compound 429)

Tetra butyl ammonium chloride (0.013 g, 0.0469 mmol) was taken in 2 ml of 50% aq. NaOH solution, stirred for 15 min at RT. Then added 2,8-dimethyl-2,3,4,5-tetrahydro-1H-pyrido[4,3-b]indole (0.5 g, 2.49 mmol) in it, stirred for 10 min at RT, then added 3-methyl-5-vinylpyridine (0.13 g, 1.1 mmol). Reaction mixture was stirred at 120° C. for overnight. Reaction mixture cooled to RT, quenched with water and extracted with ethyl acetate. Organic layer was dried over anhydrous sodium sulfate, concentrated and purified by reverse phase chromatography to afford 5 mg of, (2,8-dimethyl-5-(2-(5-methylpyridin-3-yl)ethyl)-2,3,4,5-tetrahydro-1H-pyrido[4,3-b]indole) as TFA salt.

Example 248

Preparation of 8-chloro-2,3,4,5-tetrahydro-2-methyl-5-(2-(5-methylpyridin-3-yl)ethyl)-1H-pyrido[4,3-b]indole (Compound 430)

The title compound is prepared from a mixture of 8-chloro-2,3,4,5-tetrahydro-2-methyl-1H-pyrido[4,3-b]indole, 3-methyl-5-vinylpyridine and KOH (5-7 equiv) in NMP at a temperature ranging between 25 deg C. to 100 deg C. The product obtained is isolated by preparative HPLC.

Example 249

Preparation of 2,3,4,5-tetrahydro-5-(2-(6-methoxypyridin-3-yl)ethyl)-2,8-dimethyl-1H-pyrido[4,3-b]indole (Compound 431)

The title compound is prepared from a mixture of 2,3,4,5-tetrahydro-2,8-dimethyl-1H-pyrido[4,3-b]indole, 2-methoxy-5-vinylpyridine and KOH (5-7 equiv) in NMP at a temperature ranging between 25 deg C. to 100 deg C. The product obtained is isolated by preparative HPLC.

Example 250

Preparation of 8-chloro-2,3,4,5-tetrahydro-5-(2-(6-methoxypyridin-3-yl)ethyl)-2-methyl-1H-pyrido[4,3-b]indole (Compound 432)

The title compound is prepared from a mixture of 8-chloro-2,3,4,5-tetrahydro-2-methyl-1H-pyrido[4,3-b]indole, 2-methoxy-5-vinylpyridine and KOH (5-7 equiv) in NMP at a temperature ranging between 25 deg C. to 100 deg C. The product obtained is isolated by preparative HPLC.

Example 251

Preparation of 5-(2-(6-ethoxypyridin-3-yl)ethyl)-2,3,4,5-tetrahydro-2,8-dimethyl-1H-pyrido[4,3-b]indole (Compound 433)

The title compound is prepared from a mixture of 2,3,4,5-tetrahydro-2,8-dimethyl-1H-pyrido[4,3-b]indole, 2-methoxy-5-vinylpyridine and KOH (5-7 equiv) in NMP at a temperature ranging between 25 deg C. to 100 deg C. The product obtained is isolated by preparative HPLC.

Example 252

Preparation of 8-chloro-5-(2-(6-ethoxypyridin-3-yl)ethyl)-2,3,4,5-tetrahydro-2-methyl-1H-pyrido[4,3-b]indole (Compound 434)

The title compound is prepared from a mixture of 8-chloro-2,3,4,5-tetrahydro-2-methyl-1H-pyrido[4,3-b]indole, 2-methoxy-5-vinylpyridine and KOH (5-7 equiv) in NMP at a temperature ranging between 25 deg C. to 100 deg C. The product obtained is isolated by preparative HPLC.

Example 253

Preparation of 5-(2-(1,2,3,4-tetrahydro-2,8-dimethylpyrido[4,3-b]indol-5-yl)ethyl)-N,N-dimethylpyridin-2-amine (Compound 435)

The title compound is prepared from a mixture of 2,3,4,5-tetrahydro-2,8-dimethyl-1H-pyrido[4,3-b]indole, N,N-dimethyl-5-vinylpyridin-2-amine and KOH (5-7 equiv) in NMP at a temperature ranging between 25 deg C. to 100 deg C. The product obtained is isolated by preparative HPLC.

Example 254

Preparation of 5-(2-(8-chloro-1,2,3,4-tetrahydro-2-methylpyrido[4,3-b]indol-5-yl)ethyl)-N,N-dimethylpyridin-2-amine (Compound 436)

The title compound is prepared from a mixture of 8-chloro-2,3,4,5-tetrahydro-2-methyl-1H-pyrido[4,3-b]indole, N,N-dimethyl-5-vinylpyridin-2-amine and KOH (5-7 equiv) in NMP at a temperature ranging between 25 deg C. to 100 deg C. The product obtained is isolated by preparative HPLC.

Example 255

Preparation of N-(5-(2-(1,2,3,4-tetrahydro-2,8-dimethylpyrido[4,3-b]indol-5-yl)ethyl)-3-methylpyridin-2-yl)acetamide (Compound 437)

The title compound is prepared from a mixture of 2,3,4,5-tetrahydro-2,8-dimethyl-1H-pyrido[4,3-b]indole, N-(3-methyl-5-vinylpyridin-2-yl)acetamide and KOH (5-7 equiv) in NMP at a temperature ranging between 25 deg C. to 100 deg C. The product obtained is isolated by preparative HPLC.

Example 256

Preparation of N-(5-(2-(8-chloro-1,2,3,4-tetrahydro-2-methylpyrido[4,3-b]indol-5-yl)ethyl)-3-methylpyridin-2-yl)acetamide (Compound 438)

The title compound is prepared from a mixture of 8-chloro-2,3,4,5-tetrahydro-2-methyl-1H-pyrido[4,3-b]indole, N-(3-methyl-5-vinylpyridin-2-yl)acetamide and KOH (5-7 equiv) in NMP at a temperature ranging between 25 deg C. to 100 deg C. The product obtained is isolated by preparative HPLC.

Example 257

Preparation of 5-(2-(1,2,3,4-tetrahydro-2,8-dimethylpyrido[4,3-b]indol-5-yl)ethyl)-N-isopropylpyridin-2-amine (Compound 439)

The title compound is prepared from a mixture of 2,3,4,5-tetrahydro-2,8-dimethyl-1H-pyrido[4,3-b]indole, N-isopropyl-5-vinylpyridin-2-amine and KOH (5-7 equiv) in NMP at a temperature ranging between 25 deg C. to 100 deg C. The product obtained is isolated by preparative HPLC.

Example 258

Preparation of 5-(2-(8-chloro-1,2,3,4-tetrahydro-2-methylpyrido[4,3-b]indol-5-yl)ethyl)-N-isopropylpyridin-2-amine (Compound 440)

The title compound is prepared from a mixture of 8-chloro-2,3,4,5-tetrahydro-2-methyl-1H-pyrido[4,3-b]indole, N-isopropyl-5-vinylpyridin-2-amine and KOH (5-7 equiv) in NMP at a temperature ranging between 25 deg C. to 100 deg C. The product obtained is isolated by preparative HPLC.

Example 259

Preparation of 5-(2-(1,2,3,4-tetrahydro-2,8-dimethylpyrido[4,3-b]indol-5-yl)ethyl)-N-methylpyridin-2-amine (Compound 441)

The title compound is prepared from a mixture of 2,3,4,5-tetrahydro-2,8-dimethyl-1H-pyrido[4,3-b]indole, N-methyl-5-vinylpyridin-2-amine and KOH (5-7 equiv) in NMP at a temperature ranging between 25 deg C. to 100 deg C. The product obtained is isolated by preparative HPLC.

Example 260

Preparation of 5-(2-(8-chloro-1,2,3,4-tetrahydro-2-methylpyrido[4,3-b]indol-5-yl)ethyl)-N-methylpyridin-2-amine (Compound 442)

The title compound is prepared from a mixture of 8-chloro-2,3,4,5-tetrahydro-2-methyl-1H-pyrido[4,3-b]indole, N-methyl-5-vinylpyridin-2-amine and KOH (5-7 equiv) in NMP at a temperature ranging between 25 deg C. to 100 deg C. The product obtained is isolated by preparative HPLC.

Example 261

Preparation of 5-(2-(5-chloropyridin-3-yl)ethyl)-2,3,4,5-tetrahydro-2,8-dimethyl-1H-pyrido[4,3-b]indole (Compound 443)

Tetra butyl ammonium chloride (0.034 g, 0.124 m mole) was taken in 15 ml, 50% aq. NaOH solution. Stir for 15 min. at RT, Then added 2,8-dimethyl-2,3,4,5-tetrahydro-1H-pyrido[4,3-b]indole (0.500 gm, 2.49 mmole) in it. Stir for 10 min. at RT. 3-chloro-5-vinylpyridine (0.381 gm, 2.74 mmole) was added heated the reaction mixture at 100 deg C. for 12-15 hrs. The reaction mixture allowed to cool at RT, extracted with ethyl acetate, dried on anhydrous sodium sulphate, concentrated and purified by Reverse Phase to get pure compound TFA Salt (510 mg). This TFA Salt Convert into Oxalate Salt (345 mg).

Example 262

Preparation of 8-chloro-5-(2-(5-chloropyridin-3-yl)ethyl)-2,3,4,5-tetrahydro-2-methyl-1H-pyrido[4,3-b]indole (Compound 444)

Tetra butyl ammonium chloride (0.044 g, 0.159 mmol) was taken in 10 ml, 50% aq. NaOH solution and stirred for 15 minutes at RT. 8-chloro-2-methyl-2,3,4,5-tetrahydro-1H-pyrido[4,3-b]indole (0.700 gm, 3.18 mmole) was added and further stirred for 10 minutes at RT. 3-chloro-5-vinylpyridine (0.486 gm, 3.49 mmole) was added and reaction mixture was heated at 100° C. for 12-15 hrs. The reaction mixture was cooled at RT, extracted with ethyl acetate dried over anhydrous sodium sulphate, concentrated and purified by Reverse Phase to get TFA Salt (750 mg). TFA Salt was converted into Oxalate Salt (485 mg).

Example 263

Preparation of 5-(2-(5-fluoropyridin-3-yl)ethyl)-2,3,4,5-tetrahydro-2,8-dimethyl-1H-pyrido[4,3-b]indole (Compound 445)

The title compound is prepared from a mixture of 2,3,4,5-tetrahydro-2,8-dimethyl-1H-pyrido[4,3-b]indole, 3-fluoro-5-vinylpyridine and KOH (5-7 equiv) in NMP at a temperature ranging between 25 deg C. to 100 deg C. The product obtained is isolated by preparative HPLC.

Example 264

Preparation of 8-chloro-5-(2-(5-fluoropyridin-3-yl)ethyl)-2,3,4,5-tetrahydro-2-methyl-1H-pyrido[4,3-b]indole (Compound 446)

The title compound is prepared from a mixture of 8-chloro-2,3,4,5-tetrahydro-2-methyl-1H-pyrido[4,3-b]indole, 3-fluoro-5-vinylpyridine and KOH (5-7 equiv) in NMP at a temperature ranging between 25 deg C. to 100 deg C. The product obtained is isolated by preparative HPLC.

Example 265

Preparation of N-(5-(2-(1,2,3,4-tetrahydro-2,8-dimethylpyrido[4,3-b]indol-5-yl)ethyl)pyridin-2-yl)acetamide (Compound 447)

The title compound is prepared from a mixture of 2,3,4,5-tetrahydro-2,8-dimethyl-1H-pyrido[4,3-b]indole, N-(5-vinylpyridin-2-yl)acetamide and KOH (5-7 equiv) in NMP at a temperature ranging between 25 deg C. to 100 deg C. The product obtained is isolated by preparative HPLC.

Example 266

Preparation of N-(5-(2-(8-chloro-1,2,3,4-tetrahydro-2-methylpyrido[4,3-b]indol-5-yl)ethyl)pyridin-2-yl)acetamide (Compound 448)

The title compound is prepared from a mixture of 8-chloro-2,3,4,5-tetrahydro-2-methyl-1H-pyrido[4,3-b]indole, N-(5-vinylpyridin-2-yl)acetamide and KOH (5-7 equiv) in NMP at a temperature ranging between 25 deg C. to 100 deg C. The product obtained is isolated by preparative HPLC.

Example 267

Preparation of 1-(1,2,3,4-tetrahydro-2,8-dimethylpyrido[4,3-b]indol-5-yl)-2-(6-methylpyridin-3-yl)propan-2-ol (Compound 449)

A mixture of compound 2,3,4,5-tetrahydro-2,8-dimethyl-1H-pyrido[4,3-b]indole (1.5 g, 7.5 mmol, 1 equiv.) and NaH (252 mg, 10.5 mmol, 1.4 equiv) in 30 ml of DMF were heated to 12° C., 1 h. It was cooled to RT and compound 2-methyl-5-(2-methyloxiran-2-yl)pyridine (2.46 g, 16.5 mmol, 2.2 equiv) in 17 ml DMF was added dropwise over 12 min. The temperature was again raised to 120 deg C. and stirred for 3 h. The reaction mixture was cooled to RT and 5 ml of water was added to it, diluted with 700 ml of ethyl acetate and the organic part was washed with water (100 ml×3) and then with brine. It was dried over sodium sulphate and concentrated under vacuum. Column purified over 230-400 silica gel using a gradient of 10-20% methanol in ethyl acetate. Yield: 2.3 g (87%)

Example 268

Preparation of 2,3,4,5-tetrahydro-2,8-dimethyl-5-(2-(6-methylpyridin-3-yl)propyl)-1H-pyrido[4,3-b]indole (Compound 450)

The title compound is prepared from a mixture of 2,3,4,5-tetrahydro-2,8-dimethyl-1H-pyrido[4,3-b]indole, 2-methyl-5-(prop-1-en-2-yl)pyridine and KOH (5-7 equiv) in NMP at a temperature ranging between 25 deg C. to 100 deg C. The product obtained is isolated by preparative HPLC.

Example 269

Preparation of 2,3,4,5-tetrahydro-2,8-dimethyl-5-((1-(6-methylpyridin-3-yl)cyclopropyl)methyl)-1H-pyrido[4,3-b]indole (Compound 451)

The title compound is prepared by following Method 8 by using 5-(1-(bromomethyl)cyclopropyl)-2-methylpyridine, (4-methylphenylhydrazine hydrochloride), triethylamine and N-methyl-4-piperidone.

Example 270

Preparation of 2,8-Dimethyl-5-[2-(6-propyl-pyridin-3-yl)-ethyl]-2,3,4,5-tetrahydro-1H-pyrido[4,3-b]indole (Compound 452)

To a solution of 2,8-Dimethyl-2,3,4,5-tetrahydro-1H-pyrido[4,3-b]indole (0.1 g, 0.5 mmol) in N-methyl 2-pyrolidone (1.0 mL) was added powdered potassium hydroxide (0.14 g, 2.5 mmol) and allowed to stir for 10 min at RT. 2-Propyl-5-vinyl-pyridine (0.18 g, 0.5 mol) was added and stirred for further 15 h. at 100 deg C. After completion (TLC), reaction mixture was diluted with water (15 mL) and extracted with ethyl acetate (3×50 mL). The organic layer was dried over anhydrous sodium sulphate and concentrated under reduced pressure. The crude was purified through column chromatography (7% MeOH:DCM in silica 100-200 mesh, Diameter of column—2.5 cm, Height of silica—approx. 5 inch), Then further purified by preparative TLC, to give the desired compound as yellow oil (0.015 g, 9% yield). 2,8-Dimethyl-5-[2-(6-propyl-pyridin-3-yl)-ethyl]-2,3,4,5-tetrahydro-1H-pyrido[4,3-b]indole (0.015 g, 0.043 mmol) was dissolved in THF (1.0 mL). A solution of oxalic acid dihydrate (0.006 g, 0.043 mmol) in THF (1.0 mL) was added and stirred for 30 min at RT, Precipitate obtained was filtered and dried to give oxalate salt as off white solid (0.008 g, 42% yield).

Example 271

Preparation of 2-(1,2,3,4-tetrahydro-2,8-dimethylpyrido[4,3-b]indol-5-yl)-1-(pyridin-3-yl)ethanol (Compound 453)

Carboline (500 mg, 2.5 mmol) was dissolved in DMF (5 mL). To this solution was added NaH (60%, 180 mg, 4.5 mmol) at RT and the reaction mixture was stirred for 10-15 min after which 3-(oxiran-2-yl)pyridine (450 mg, 3.7 mmol) was added. The reaction mixture was stirred at RT for 4 h (monitored by LCMS). Work up: The reaction mixture was poured on ice water and extracted with ethyl acetate. The organic layer was dried on sodium sulfate and concentrated under reduced pressure. The residue was purified by reverse phase HPLC to obtain 420 mg of product as white solid (TFA salt). TLC (silica gel) 5:95 MeOH:DCM, Rf 0.1 was observed.

Example 272

Preparation of 2-(8-chloro-1,2,3,4-tetrahydro-2-methylpyrido[4,3-b]indol-5-yl)-1-(pyridin-3-yl)ethanol (Compound 454)

Chloro carboline (500 MG, 2.27 mmol) was taken in DMF. NaH (180 mg, 4.5 mmol) was added at RT and stirred for 10-15 min. Neat epoxide (450 mg, 3.7 mmol) was added to it drop wise at RT. Reaction was stirred at RT for 4 h (monitored by LCMS). RM was poured on ice water and extracted with ethyl acetate. dried and concentrated and residue was purified by RP-HPLC. 465 mg of product as white solid (TFA salt). TLC 5% MeOH-DCM Rf 0.1 was observed.

Example 273

Preparation of 5-(2-(4-fluorophenyl)propyl)-2,3,4,5-tetrahydro-2,8-dimethyl-1H-pyrido[4,3-b]indole (Compound 456)

A mixture of compound 5-((Z)-2-(4-fluorophenyl)prop-1-enyl)-2,3,4,5-tetrahydro-2,8-dimethyl-1H-pyrido[4,3-b]indole and 5-(2-(4-fluorophenyl)allyl)-2,3,4,5-tetrahydro-2,8-dimethyl-1H-pyrido[4,3-b]indole (of ratio 1:3, 1.8 g, 5.38 mmol, 1 equiv) were shaken in a 250 ml Parr Shaker vessel with 180 mg of Pd/C in 50 ml of Methanol/acetic acid (10:1) mixture for 18 hours under 60 psi H2. It was filtered over a celite bed with methanol and evaporated under vacuum. The residue was diluted with ethyl acetate (500 ml) and washed with 50 ml of satd. sodium bicarbonate solution and then brine. The organic part was concentrated under reduced pressure and column purified over 100-200 silica gel using 0 to 50% ethyl acetate in hexanes as eluant, at an interval of 5%. Yield: 685 mg (38%).

Example 274

Preparation of 2-(4-fluorophenyl)-1-(1,2,3,4-tetrahydro-2,8-dimethylpyrido[4,3-b]indol-5-yl)propan-2-ol (Compound 457)

A mixture of compound 2,3,4,5-tetrahydro-2,8-dimethyl-1H-pyrido[4,3-b]indole (2.6 g, 13.1 mmol, 1 equiv.) and NaH (55%, 750 mg, 17.2 mmol, 1.3 equiv.) in 60 ml of THF was heated to 120 deg C. for 1 h. It was then cooled to RT and compound 2-(4-fluorophenyl)-2-methyloxirane (4 g, 26 mmol, 2 equiv.) in 25 ml of DMF was added dropwise for 5 mins at RT followed by heating at 120 deg C. for 2 h. It was cooled to RT and 10 ml of water was added followed by dilution with 800 ml of ethyl acetate, which was first washed with water (150 ml×3) and then brine, dried over sodium sulphate and concentrated under vacuum. Column purified over 230-400 Silica gel (flash) using 15% methanol in ethyl acetate as eluent. Yield: 3 g (66%).

Example 275

Preparation of tert-butyl 4-(2-(8-chloro-1,2,3,4-tetrahydro-2-methylpyrido[4,3-b]indol-5-yl)acetyl)piperazine-1-carboxylate (Compound 458)

2-(8-chloro-2-methyl-3,4-dihydro-1H-pyrido[4,3-b]indol-5(2H)-yl)acetic acid (0.2 g, 0.719 mmol) in 10 mL of DCM was taken, EDCI.HCl (137 mg, 0.719 mmol) was added and stirred for 10 min at RT. N-Boc piperazine (133 mg, 0.719 mmol) was added to the reaction mixture and stirred for 24 h at RT. Reaction was monitored by TLC & LCMS. After completion of the reaction, reaction mixture was concentrated and purified by column chromatography (neutral alumina; 2% Methanol-DCM) then purified by reverse phase chromatography to afford 90 mg of tert-butyl 4-(2-(8-chloro-2-methyl-3,4-dihydro-1H-pyrido[4,3-b]indol-5(2H)-yl)acetyl)piperazine-1-carboxylate.

Example 276

Preparation of 2-(1,2,3,4-tetrahydro-2,8-dimethylpyrido[4,3-b]indol-5-yl)-1-(4-methylpiperazin-1-yl)ethanone (Compound 459)

2-(2,8-dimethyl-3,4-dihydro-1H-pyrido[4,3-b]indol-5(2H)-yl)acetic acid (0.57 g, 2.2 mmol) was taken in DCM, cooled to 0° C., oxalyl chloride (0.228 mL, 2.6 mmol) was added, followed by the addition of DMAP (catalytic amount) and stirred for 1 h at RT. Solvent was evaporated under nitrogen, N-methyl piperazine (0.269 mg, 2.4 mmol) and DMAP (80 mg) in DCM was added slowly drop wise at RT (under nitrogen) and stirred at RT for 30 min. Reaction mixture was quenched with water, neutralized with 10% NaHCO3 solution and extracted with ethyl acetate. Organic layer was dried over anhydrous sodium sulfate and evaporated to dryness. Crude product was purified by reverse phase chromatography to afford 100 mg of 2-(2,8-dimethyl-3,4-dihydro-1H-pyrido[4,3-b]indol-5(2H)-yl)-1-(4-methylpiperazin-1-yl)ethanone as TFA salt.

Example 277

Preparation of 8-chloro-5-(2-(4-(trifluoromethyl)pyridin-3-yl)ethyl)-2,3,4,5-tetrahydro-2-methyl-1H-pyrido[4,3-b]indole (Compound 460)

The title compound is prepared from a mixture of 8-chloro-2,3,4,5-tetrahydro-2-methyl-1H-pyrido[4,3-b]indole, 4-(trifluoromethyl)-3-vinylpyridine and KOH (5-7 equiv) in NMP at a temperature ranging between 25 deg C. to 100 deg C. The product obtained is isolated by preparative HPLC.

Example 278

Preparation of 5-(2-(4-(trifluoromethyl)pyridin-3-yl)ethyl)-2,3,4,5-tetrahydro-2,8-dimethyl-1H-pyrido[4,3-b]indole (Compound 461)

The title compound is prepared from a mixture of 2,3,4,5-tetrahydro-2,8-dimethyl-1H-pyrido[4,3-b]indole, 4-(trifluoromethyl)-3-vinylpyridine and KOH (5-7 equiv) in NMP at a temperature ranging between 25 deg C. to 100 deg C. The product obtained is isolated by preparative HPLC.

Example 279

Preparation of 8-ethyl-5-(2-(4-(trifluoromethyl)pyridin-3-yl)ethyl)-2,3,4,5-tetrahydro-2-methyl-1H-pyrido[4,3-b]indole (Compound 462)

The title compound is prepared from a mixture of 8-ethyl-2,3,4,5-tetrahydro-2-methyl-1H-pyrido[4,3-b]indole, 4-(trifluoromethyl)-3-vinylpyridine and KOH (5-7 equiv) in NMP at a temperature ranging between 25 deg C. to 100 deg C. The product obtained is isolated by preparative HPLC.

Example 280

Preparation of 5-(2-(4-(trifluoromethyl)pyridin-3-yl) ethyl)-2,3,4,5-tetrahydro-8-isopropyl-2-methyl-1H-pyrido[4,3-b]indole (Compound 463)

The title compound is prepared from a mixture of 2,3,4,5-tetrahydro-8-isopropyl-2-methyl-1H-pyrido[4,3-b]indole, 4-(trifluoromethyl)-3-vinylpyridine and KOH (5-7 equiv) in NMP at a temperature ranging between 25 deg C. to 100 deg C. The product obtained is isolated by preparative HPLC.

Example 281

Preparation of 8-chloro-5-(2-(2-ethyl-1H-pyrrol-1-yl)ethyl)-2,3,4,5-tetrahydro-2-methyl-1H-pyrido[4,3-b]indole (Compound 464)

The title compound is prepared by following Method 8 by using 1-(2-bromoethyl)-2-ethyl-1H-pyrrole,(4-chlorophenylhydrazine hydrochloride), triethylamine and N-methyl-4-piperidone

Example 282

Preparation of 8-chloro-2,3,4,5-tetrahydro-2-methyl-5-(2-(2,4-dimethyl-1H-pyrrol-1-yl)ethyl)-1H-pyrido[4,3-b]indole (Compound 465)

The title compound is prepared by following Method 8 by using 1-(2-bromoethyl)-2,4-dimethyl-1H-pyrrole,(4-chlorophenylhydrazine hydrochloride), triethylamine and N-methyl-4-piperidone

Example 283

Preparation of 5-(2-(1,2,3,4-tetrahydro-8-(hydroxymethyl)-2-methylpyrido[4,3-b]indol-5-yl)ethyl)pyridine-2-carboxylic acid (Compound 466)

The title compound is prepared from a mixture of (2,3,4,5-tetrahydro-2-methyl-1H-pyrido[4,3-b]indol-8-yl)methanol, 5-vinylpyridine-2-carboxylic acid and KOH (5-7 equiv) in NMP at a temperature ranging between 25 deg C. to 100 deg C. The product obtained is isolated by preparative HPLC.

Example 284

Preparation of 2,3,4,5-tetrahydro-5-(2-(6-(hydroxymethyl)pyridin-3-yl)ethyl)-2-methyl-1H-pyrido[4,3-b]indole-8-carboxylic acid (Compound 467)

The title compound is prepared from a mixture of 2,3,4,5-tetrahydro-2-methyl-1H-pyrido[4,3-b]indole-8-carboxylic acid, (5-vinylpyridin-2-yl)methanol and KOH (5-7 equiv) in NMP at a temperature ranging between 25 deg C. to 100 deg C. The product obtained is isolated by preparative HPLC.

Example 285

Preparation of (5-(2-(8-(hydroxymethyl)-2-methyl-3,4-dihydro-1H-pyrido[4,3-b]indol-5(2H)-yl)ethyl)pyridin-2-yl)methanol (Compound 468)

The title compound is prepared from a mixture of (2,3,4,5-tetrahydro-2-methyl-1H-pyrido[4,3-b]indol-8-yl)methanol, (5-vinylpyridin-2-yl)methanol and KOH (5-7 equiv) in NMP at a temperature ranging between 25 deg C. to 100 deg C. The product obtained is isolated by preparative HPLC.

Example 286

Preparation of 5-(2-(6-carboxypyridin-3-yl)ethyl)-2,3,4,5-tetrahydro-2-methyl-1H-pyrido[4,3-b]indole-8-carboxylic acid (Compound 469)

The title compound is prepared from a mixture of 2,3,4,5-tetrahydro-2-methyl-1H-pyrido[4,3-b]indole-8-carboxylic acid, 5-vinylpyridine-2-carboxylic acid and KOH (5-7 equiv) in NMP at a temperature ranging between 25 deg C. to 100 deg C. The product obtained is isolated by preparative HPLC.

Example 287

Preparation of 8-chloro-2,3,4,5-tetrahydro-2-methyl-5-(2-(6-propylpyridin-3-yl)ethyl)-1H-pyrido[4,3-b]indole (Compound 476)

To a solution of 8-Chloro-2-methyl-2,3,4,5-tetrahydro-1H-pyrido[4,3-b]indole (0.1 g. 0.00045 mol) in N-methyl 2-pyrolidone (1.0 mL) was added powdered potassium hydroxide (0.20 g, 0.0036 mol) and allowed to stir for 10 min at RT. 2-propyl-5-vinyl-pyridine (0.2 g, 0.00136 mol) was added and stirred for further 24 h. at 100° C. After completion (TLC), reaction mixture was diluted with water (10 mL) and extracted with ethyl acetate (3×50 mL). The organic layer was dried over anhydrous sodium sulphate and concentrated under reduced pressure using rotary evaporator. The crude was semi-purified through column chromatography (7% MeOH:DCM in silica 100-200 mesh, Diameter of column—2.5 cm, Height of silica—approx. 5 inch), Then further purified by preparative TLC, to give the desired compound as yellow oil (0.016 g, 9.6% yield). 8-Chloro-5-[2-(6-isopropyl-pyridin-3-yl)-ethyl]-2-methyl-2,3,4,5-tetrahydro-1H-pyrido [4,3-b]indole (0.016 g, 0.0000435 mol) was dissolved in THF (1.0 mL). A solution of oxalic acid dihydrate (0.005 g, 0.00007 mol) in THF (0.5 mL) was added and stirred for 30 min at RT. Precipitate obtained was filtered and dried to give oxalate salt as off white solid (0.010 g, 52% yield).

Example 288

Preparation of 7-aza-2-methyl-5-(2-(pyridin-2-yl)ethyl)-2,3,4,5-tetrahydro-1H-pyrido[4,3-b]indole (Compound 481)

To a solution of tetra n-butyl ammonium chloride (0.0075 g, 0.04 mmole) in 50% aq NaOH (3 mL) was added 7-aza-2-methyl-2,3,4,5-tetrahydro-1H-pyrido[4,3-b]indole (0.075 g, 0.4 mmole) and 2-vinyl pyridine (0.047 g, 0.44 mmole). Then heated at 90 deg C. for 7 h. Reaction was monitored by LCMS, TLC. After complete reaction, mixture was quenched with water and extracted with Ethyl acetate. Combined organic layers dried over sodium sulphate and concentrated under reduced pressure afforded 4 mg of the product as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 289

Preparation of 9-aza-2-methyl-5-(2-(pyridin-4-yl)ethyl)-2,3,4,5-tetrahydro-1H-pyrido[4,3-b]indole (Compound 482)

To a solution of tetra n-butyl ammonium chloride (0.017 g, 0.09 mmole) in 50% aq NaOH (5 mL) was added 9-aza-2-methyl-2,3,4,5-tetrahydro-1H-pyrido[4,3-b]indole (0.17 g, 0.9 mmole) and 4-vinyl pyridine (0.107 g, 1 mmole). Then heated at 90 deg C. for 7 h. Reaction was monitored by LCMS, TLC. After complete reaction, mixture was quenched with water and extracted with Ethyl acetate. Combined organic layers dried over sodium sulphate and concentrated under reduced pressure afforded 3 mg of the product as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 290

Preparation of 7-aza-2-methyl-5-(2-(pyridin-4-yl)ethyl)-2,3,4,5-tetrahydro-1H-pyrido[4,3-b]indole (Compound 483)

To a solution of tetra n-butyl ammonium chloride (0.017 g, 0.09 mmole) in 50% aq NaOH (5 mL), 7-aza-2-methyl-2,3,4,5-tetrahydro-1H-pyrido[4,3-b]indole (0.17 g, 0.9 mmole) and 4-vinyl pyridine (0.107 g, 1 mmole) was added then heated at 90 deg C. for 7 h. Reaction was monitored by LCMS, TLC. After complete reaction, mixture was quenched with water and extracted with Ethyl acetate. Combined organic layers dried over sodium sulphate and concentrated under reduced pressure afforded 5 mg of product as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 291

Preparation of 9-aza-2-methyl-5-(2-(pyridin-2-yl)ethyl)-2,3,4,5-tetrahydro-1H-pyrido[4,3-b]indole (Compound 484)

To a solution of tetra n-butyl ammonium chloride (0.0075 g, 0.04 mmole) in 50% aq NaOH (3 mL) 9-aza-2-methyl-2,3,4,5-tetrahydro-1H-pyrido[4,3-b]indole (0.075 g, 0.4 mmole) and 2-vinyl pyridine (0.047 g, 0.44 mmole) was added then heated at 90 deg C. for 7 h. Reaction was monitored by LCMS, TLC. After complete reaction, mixture was quenched with water and extracted with Ethyl acetate. Combined organic layers dried over sodium sulphate and concentrated under reduced pressure afforded 2 mg of product as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 292

Preparation of 2,3,4,5-tetrahydro-8-iodo-2-methyl-5-(2-(6-methylpyridin-3-yl)ethyl)-1H-pyrido[4,3-b]indole (Compound 485)

To a solution of 8-Iodo-2-methyl-2,3,4,5-tetrahydro-1H-pyrido[4,3-b]indole (0.5 g. 0.0016 mol) in N-methyl 2-pyrolidone (5 mL) was added powdered potassium hydroxide (0.9 g, 0.016 mol) and allowed to stir for 10 min at RT. 2-Methyl-5-vinyl-pyridine (0.969 g, 0.0048 mol) was added and stirred for further 24 hours at 100° C., after completion (TLC), reaction mixture was diluted with water (50 mL) and extracted with ethyl acetate (3×150 mL). The organic layer was dried over anhydrous sodium sulphate and concentrated under reduced pressure using rotary evaporator. The crude was semi-purified through column chromatography (6% Methanol:DCM in silica 100-200 mesh, Diameter of column—2.5 cm, Height of silica—approx. 5 inch), then further purified by preparative HPLC to get the desired compound as brown solid (0.105 g, 15.2% yield). 8-Iodo-2-methyl-5-[2-(6-methyl-pyridin-3-yl)-ethyl]-2,3,4,5-tetrahydro-1H-pyrido[4,3-b]indole (0.095 g, 0.00022 mol) was dissolved in THF (2.0 mL). A solution of oxalic acid dihydrate (0.0277 g, 0.00022 mol) in THF (2.0 mL) was added and stirred for 30 min at RT. The precipitate was filtered and dried to give oxalate salt as off white solid (0.09 g, 79% yield).

Example 292

Preparation of 2-(1,2,3,4-tetrahydro-8-iodo-2-methylpyrido[4,3-b]indol-5-yl)-1-(piperidin-1-yl)ethanone (Compound 486)

Sodium hydride was washed with hexane for removal of oil and dried under vacuum. Then sodium hydride was taken in THF. To this solution 8-iodo-2-methyl-2,3,4,5-tetrahydro-1H-pyrido[4,3-b]indole (100 mg, 0.32 mmol) in THF was added drop wise at 0° C. Then reaction mixture stirred for 0.5 h. The solution of 2-chloro-1-(piperidin-1-yl)ethanone in THF was added drop wise in reaction mixture. Then reaction mixture stirred at rt for 2 h. Reaction monitored by TLC, after completion of reaction, reaction mixture quench with ice-water. THF was evaporated and aqueous layer was extracted with ethyl acetate. Organic layer was dried over anhydrous sodium sulphate. The crude compound was purified by column chromatography to gives 25 mg of desired compound. Out of that 5 mg was stirred with ethanolic HCl to give HCl salt of 2-(8-iodo-2-methyl-3,4-dihydro-1H-pyrido[4,3-b]indol-5(2H)-yl)-1-(piperidin-1-yl)ethanone.

Example 294

Preparation of 8-bromo-2-methyl-5-(2-(6-methylpyridin-3-yl)ethyl)-2,3,4,5-tetrahydro-1H-pyrido[4,3-b]indole (Compound 487)

Tetra butyl ammonium chloride (0.026 g, 0.094 mmol) was taken in 15 ml, 50% aq. NaOH solution (7 ml) and stirred for 15 minutes at RT. 8-bromo-2-methyl-2,3,4,5-tetrahydro-1H-pyrido[4,3-b]indole (0.500 gm, 1.89 mmole) was added and further stirred for 10 min. at RT. 2-methyl-5-vinylpyridine (0.247 gm, 2.08 mmole) was added and reaction mixture was heated at 100° C. for 12-15 hrs. The reaction mixture was cooled at RT, extracted with ethyl acetate, dried over anhydrous sodium sulphate, concentrated and purified by Reverse Phase HPLC to get 63 mg 8-bromo-2-methyl-5-(2-(6-methylpyridin-3-yl)ethyl)-2,3,4,5-tetrahydro-1H-pyrido[4,3-b]indole as TFA Salt.

Example 295

Preparation of 1-(8-chloro-1,2,3,4-tetrahydro-2-methylpyrido[4,3-b]indol-5-yl)-2-(4-methoxyphenyl)propan-2-ol (Compound 488)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(4-methoxyphenyl)-2-methyloxirane (400 mg, 2.43 mmol, 1.85 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dihydrate Example 296

Preparation of 1-(8-chloro-1,2,3,4-tetrahydro-2-methylpyrido[4,3-b]indol-5-yl)-2-(6-(trifluoromethyl) pyridin-3-yl)propan-2-ol (Compound 489)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(trifluoromethyl)-5-(2-methyloxiran-2-yl)pyridine (400 mg, 1.97 mmol, 1.5 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 297

Preparation of 1-(1,2,3,4-tetrahydro-2,8-dimethylpyrido[4,3-b]indol-5-yl)-2-(pyridin-3-yl)propan-2-ol (Compound 490)

Sodium hydride (38 mg, 1.6 mmol, 1.14 equiv.) was added to a solution of 2,3,4,5-tetrahydro-2,8-dimethyl-1H-pyrido[4,3-b]indole (290 mg, 1.4 mmol, 1.0 equiv.) in DMF (6 ml), and heated to 120° C. for 1 hour with stirring. The reaction mixture was cooled to 0° C. and 3-(2-methyloxiran-2-yl) pyridine (400 mg, 2.96 mmol, 2.1 equiv) was added drop wise over 5 minutes. The temperature was raised to 120° C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 298

Preparation of 1-(8-chloro-1,2,3,4-tetrahydro-2-methylpyrido[4,3-b]indol-5-yl)-2-(pyridin-3-yl)propan-2-ol (Compound 491)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.3 mmol, 1.0 equiv.) in DMF (6 ml), and heated to 120 deg C. for 1 hour with stirring. The reaction mixture was cooled to 0 deg C. and 3-(2-methyloxiran-2-yl)pyridine (400 mg, 2.96 mmol, 2.3 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 299

Preparation of 1-(1,2,3,4-tetrahydro-2,8-dimethylpyrido[4,3-b]indol-5-yl)-2-(pyridin-4-yl)propan-2-ol (Compound 492)

Sodium hydride (38 mg, 1.6 mmol, 1.14 equiv.) was added to a solution of 2,3,4,5-tetrahydro-2,8-dimethyl-1H-pyrido[4,3-b]indole (290 mg, 1.4 mmol, 1.0 equiv.) in DMF (6 ml), and heated to 120 deg C. for 1 hour with stiffing. The reaction mixture was cooled to 0 deg C. and 4-(2-methyloxiran-2-yl) pyridine (400 mg, 2.96 mmol, 2.1 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 300

Preparation of 1-(8-chloro-1,2,3,4-tetrahydro-2-methylpyrido[4,3-b]indol-5-yl)-2-(pyridin-4-yl)propan-2-ol (Compound 493)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.3 mmol, 1.0 equiv.) in DMF (6 ml), and heated to 120° C. for 1 hour with stiffing. The reaction mixture was cooled to 0° C. and 4-(2-methyloxiran-2-yl)pyridine (400 mg, 2.96 mmol, 2.3 equiv) was added drop wise over 5 minutes. The temperature was raised to 120° C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 301

Preparation of 1-(5-(trifluoromethyl)pyridin-3-yl)-2-(1,2,3,4-tetrahydro-2,8-dimethylpyrido[4,3-b]indol-5-yl)ethanol (Compound 494)

Sodium hydride (38 mg, 1.6 mmol, 1.1 equiv.) was added to a solution of 2,3,4,5-tetrahydro-2,8-dimethyl-1H-pyrido[4,3-b]indole (290 mg, 1.44 mmol, 1.0 equiv.) in DMF (6 ml), and heated to 120 deg C. for 1 hour with stirring. The reaction mixture was cooled to 0 deg C. and 3-(trifluoromethyl)-5-(oxiran-2-yl)pyridine (400 mg, 2.11 mmol, 1.5 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 302

Preparation of 2-(8-chloro-1,2,3,4-tetrahydro-2-methylpyrido[4,3-b]indol-5-yl)-1-(5-(trifluoromethyl)pyridin-3-yl)ethanol (Compound 495)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120° C. for 1 hour with stiffing. The reaction mixture was cooled to 0° C. and 3-(trifluoromethyl)-5-(oxiran-2-yl)pyridine (400 mg, 2.1 mmol, 1.6 equiv) was added drop wise over 5 minutes. The temperature was raised to 120° C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 303

Preparation of 2-(8-chloro-1,2,3,4-tetrahydro-2-methylpyrido[4,3-b]indol-5-yl)-1-(3-fluoro-4-methoxyphenyl)ethanol (Compound 496)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(3-fluoro-4-methoxyphenyl)oxirane (400 mg, 2.37 mmol, 1.8 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 304

Preparation of 1-(8-chloro-1,2,3,4-tetrahydro-2-methylpyrido[4,3-b]indol-5-yl)-2-(6-propylpyridin-3-yl)propan-2-ol (Compound 497)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120° C. for 1 hour with stiffing. The reaction mixture was cooled to 0° C. and 5-(2-methyloxiran-2-yl)-2-propylpyridine (400 mg, 2.26 mmol, 1.72 equiv) was added drop wise over 5 minutes. The temperature was raised to 120° C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 305

Preparation of 1-(8-chloro-1,2,3,4-tetrahydro-2-methylpyrido[4,3-b]indol-5-yl)-2-(3,4-difluorophenyl)propan-2-ol (Compound 498)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stiffing. The reaction mixture was cooled to 0 deg C. and 2-(3,4-difluorophenyl)-2-methyloxirane (400 mg, 2.4 mmol, 1.8 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dihydrate.

Example 306

Preparation of 1-(8-chloro-1,2,3,4-tetrahydro-2-methylpyrido[4,3-b]indol-5-yl)-2-(4-chlorophenyl)propan-2-ol (Compound 499)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120° C. for 1 hour with stiffing. The reaction mixture was cooled to 0° C. and 2-(4-chlorophenyl)-2-methyloxirane (400 mg, 2.4 mmol, 1.8 equiv) was added drop wise over 5 minutes. The temperature was raised to 120° C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 307

Preparation of 1-(8-chloro-1,2,3,4-tetrahydro-2-methylpyrido[4,3-b]indol-5-yl)-2-(4-chloro-3-fluorophenyl)propan-2-ol (Compound 500)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(4-chloro-3-fluorophenyl)-2-methyloxirane (400 mg, 2.15 mmol, 1.6 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 308

Preparation of 1-(8-chloro-1,2,3,4-tetrahydro-2-methylpyrido[4,3-b]indol-5-yl)-2-(3,4-dichlorophenyl)propan-2-ol (Compound 501)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(3,4-dichlorophenyl)-2-methyloxirane (400 mg, 1.97 mmol, 1.5 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 309

Preparation of 1-(8-chloro-1,2,3,4-tetrahydro-2-methylpyrido[4,3-b]indol-5-yl)-2-(3-chloro-4-fluorophenyl)propan-2-ol (Compound 502)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(3-chloro-4-fluorophenyl)-2-methyloxirane (400 mg, 2.14 mmol, 1.6 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 310

Preparation of 1-(8-chloro-1,2,3,4-tetrahydro-2-methylpyrido[4,3-b]indol-5-yl)-2-(2,4-difluorophenyl)propan-2-ol (Compound 503)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(2,4-difluorophenyl)-2-methyloxirane (400 mg, 2.4 mmol, 1.8 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 311

Preparation of 1-(8-fluoro-1,2,3,4-tetrahydro-2-methylpyrido[4,3-b]indol-5-yl)-2-(4-fluorophenyl)propan-2-ol (Compound 504)

Sodium hydride (38 mg, 1.6 mmol, 1.2 equiv.) was added to a solution of 8-fluoro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stiffing. The reaction mixture was cooled to 0 deg C. and 2-(4-fluorophenyl)-2-methyloxirane (400 mg, 2.63 mmol, 2.0 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 312

Preparation of 1-(8-chloro-2-cyclopropyl-1,2,3,4-tetrahydropyrido[4,3-b]indol-5-yl)-2-(4-fluorophenyl)propan-2-ol (Compound 505)

Sodium hydride (38 mg, 1.6 mmol, 1.36 equiv.) was added to a solution of 8-chloro-2-cyclopropyl-2,3,4,5-tetrahydro-1H-pyrido[4,3-b]indole (290 mg, 1.18 mmol, 1.0 equiv.) in DMF (6 ml), and heated to 120° C. for 1 hour with stirring. The reaction mixture was cooled to 0 deg C. and 2-(4-fluorophenyl)-2-methyloxirane (400 mg, 2.63 mmol, 2.2 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dihydrate Example 313

Preparation of 1-(8-chloro-1,2,3,4-tetrahydro-2-methylpyrido[4,3-b]indol-5-yl)-2-phenylpropan-2-ol (Compound 506)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-methyl-2-phenyloxirane (400 mg, 2.98 mmol, 2.3 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dihydrate Example 314

Preparation of 1-(8-chloro-1,2,3,4-tetrahydro-2-methylpyrido[4,3-b]indol-5-yl)-2-(2,4,6-trifluorophenyl)propan-2-ol (Compound 507)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0° C. and 2-(2,4,6-trifluorophenyl)-2-methyloxirane (400 mg, 2.1 mmol, 1.6 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 315

Preparation of 3-(8-chloro-1,2,3,4-tetrahydro-2-methylpyrido[4,3-b]indol-5-yl)-2-(4-fluorophenyl)butan-2-ol (Compound 508)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(4-fluorophenyl)-2,3-dimethyloxirane (400 mg, 2.4 mmol, 1.8 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 316

Preparation of 1-(8-chloro-1,2,3,4-tetrahydro-2-methylpyrido[4,3-b]indol-5-yl)-2-(2,4-dichlorophenyl)propan-2-ol (Compound 509)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(2,4-dichlorophenyl)-2-methyloxirane (400 mg, 1.96 mmol, 1.5 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 317

Preparation of 1-(8-chloro-1,2,3,4-tetrahydro-2-methylpyrido[4,3-b]indol-5-yl)-2-(4-fluorophenyl)butan-2-ol (Compound 510)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120° C. for 1 hour with stiffing. The reaction mixture was cooled to 0° C. and 2-ethyl-2-(4-fluorophenyl)oxirane (400 mg, 2.4 mmol, 1.8 equiv) was added drop wise over 5 minutes. The temperature was raised to 120° C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 318

Preparation of 3-(8-chloro-1,2,3,4-tetrahydro-2-methylpyrido[4,3-b]indol-5-yl)-1,1,1-trifluoro-2-(4-fluorophenyl)propan-2-ol (Compound 511)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-(trifluoromethyl)-2-(4-fluorophenyl)oxirane (400 mg, 1.94 mmol, 1.48 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 319

Preparation of 2-(8-chloro-1,2,3,4-tetrahydro-2-methylpyrido[4,3-b]indol-5-yl)-1-cyclopropyl-1-(4-fluorophenyl)ethanol (Compound 512)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 2-cyclopropyl-2-(4-fluorophenyl)oxirane (400 mg, 2.2 mmol, 1.71 equiv) was added drop wise over 5 minutes. The temperature was raised to 120 deg C. and stirred for 2 hours. The reaction mixture was cooled to RT and partitioned between ethyl acetate (60 ml) and water (15 ml). The organic layer was separated and the aqueous layer was extracted with ethyl acetate (1×20 ml). The combined organic layer was washed with water and followed by brine, dried over sodium sulphate and concentrated under vacuum to provide the crude product. The product was purified by flash column chromatography over silica gel (230-400 mesh, deactivated with 1% triethylamine/hexane) using a gradient of 5 to 15% methanol/ethyl acetate to yield the free base. Pure compound was converted to its oxalate salt. The analytical sample was prepared by dissolving free base in 10 mL THF and treatment with 1 equiv. of oxalic acid dehydrate.

Example 320

Preparation of 2-(8-bromo-2-methyl-3,4-dihydro-1H-pyrido[4,3-b]indol-5(2H)-yl)-1-(piperidin-1-yl)ethanone (Compound 516)

Sodium hydride (0.6 g, 15 mmol) washed with hexane for removal of oil and dried under vacuum. Then sodium hydride was taken in THF. To this solution 8-bromo-2-methyl-2,3,4,5-tetrahydro-1H-pyrido[4,3-b]indole (2 g, 7.5 mmol) in THF was added drop wise at 0° C. Then reaction mixture stirred for 0.5 h. The solution of 2-chloro-1-(piperidin-1-yl)ethanone (1.8 g, 11.3 mmol) in THF was added drop wise in reaction mixture. Then reaction mixture stirred at rt for 2 h. Reaction was monitored by TLC. After completion of the reaction, reaction mixture quench with ice-water. THF was evaporated and aqueous layer was extracted with ethyl acetate. Organic layer was dried over anhydrous sodium sulphate. The crude compound was washed with hexane and diethyl ether for removal of color impurities then recrystallized by using methanol to gives 1.5 g of desired compound then out of that 0.8 g compound was stirred in ethanolic HCl to give HCl salt of 2-(8-bromo-2-methyl-3,4-dihydro-1H-pyrido[4,3-b]indol-5(2H)-yl)-1-(piperidin-1-yl)ethanone.

Example 321

Preparation of 8-methyl-5-(2-(6-methylpyridin-3-yl)ethyl)-3,4-dihydro-1H-pyrido[4,3-b]indole-2(5H)-carbaldehyde (Compound 517)

The title compound is prepared from a mixture of 3,4-dihydro-8-methyl-1H-pyrido[4,3-b]indole-2(5H)-carbaldehyde, 2-methyl-5-vinylpyridine and KOH (5-7 equiv) in NMP at a temperature ranging between 25 deg C. to 100 deg C. The product obtained is isolated by preparative HPLC.

Example 322

Preparation of 2-butyl-8-methyl-5-(2-(6-methylpyridin-3-yl)ethyl)-2,3,4,5-tetrahydro-1H-pyrido[4,3-b]indole (Compound 518)

The title compound is prepared from a mixture of 2-butyl-2,3,4,5-tetrahydro-8-methyl-1H-pyrido[4,3-b]indole, 2-methyl-5-vinylpyridine and KOH (5-7 equiv) in NMP at a temperature ranging between 25 deg C. to 100 deg C. The product obtained is isolated by preparative HPLC.

Example 323

Preparation of 3,4-dihydro-3-hydroxy-2,8-dimethyl-5-(2-(6-methylpyridin-3-yl)ethyl)-2H-pyrido[4,3-b]indol-1(5H)-one (Compound 316)

The title compound is prepared from a mixture of 3,4-dihydro-3-hydroxy-2,8-dimethyl-2H-pyrido[4,3-b]indol-1(5H)-one, 2-methyl-5-vinylpyridine and KOH (5-7 equiv) in NMP at a temperature ranging between 25 deg C. to 100 deg C. The product obtained is isolated by preparative HPLC.

Example 324

Preparation of 1,2,4-oxadiazoles G6-a-f 1,2,4-Oxadiazoles (G6) were prepared using synthetic route shown in Scheme I. Pyrido[4,3-b]indoles (3), prepared by Fischer reaction, were alkylated to afford (4) by standard methods. Nitriles (4) were converted to their corresponding hydroxyamidines (5). Cyclization of 5 with ethyl carboxylate in the presence of NaOEt gave G6.

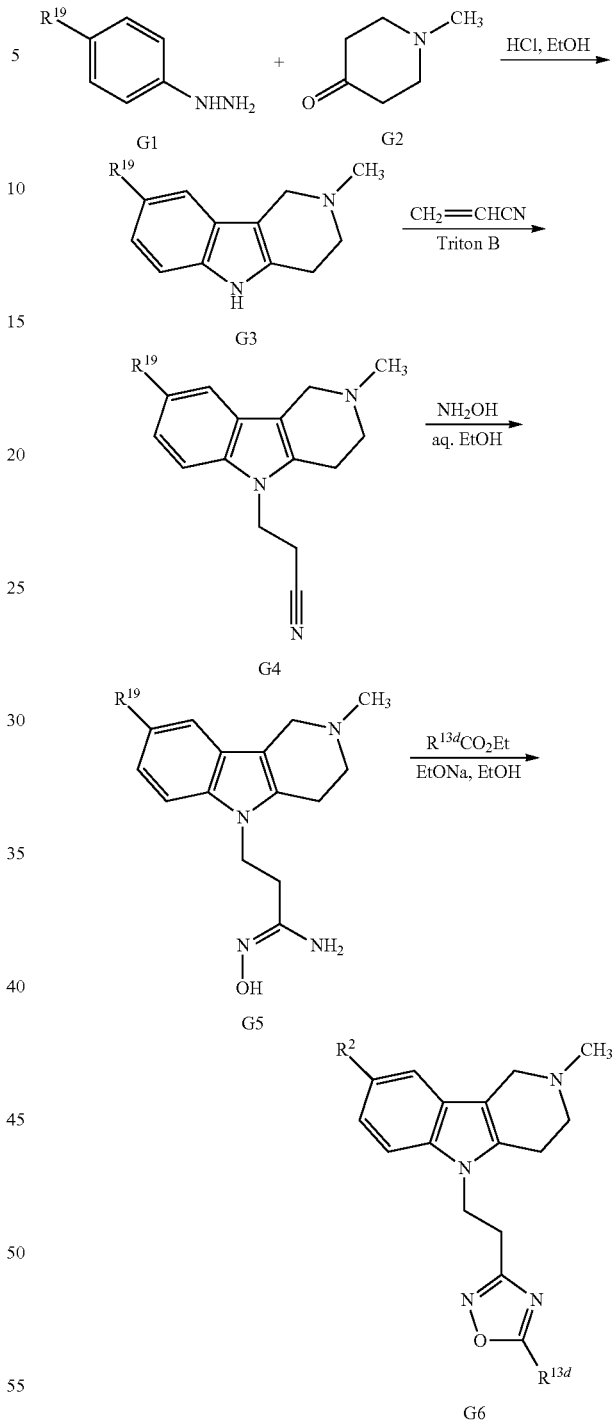

Scheme I

Preparation of Hydroxyamidines (G5) from the Corresponding Nitriles (G4)

Sodium hydroxide (1 equiv.) dissolved in water was added to a solution of hydroxylamine hydrochloride (1 equiv.) dissolved in 95% ethanol. The appropriate nitrile (0.5 equiv.) in 95% ethanol was added to the above solution. The mixture was heated under reflux for 6-7 h, cooled and diluted with water. The solid was isolated by filtration, washed with water, ethanol and ether and recrystallized from MeOH.

Preparation of 1,2,4-oxadiazoles (G6) from the Corresponding Hydroxyamidines (G5)

A solution of appropriate hydroxyamidine (0.6-1 equiv), of ethyl benzoate (1 equiv.) and of sodium ethoxide (1 equiv.) was heated under reflux for 7-15 h in anhydrous ethanol. The solvent was removed under reduced pressure and the residue was partitioned between CHCl$_3$ and water. The organic layer was washed with water, dried (Na$_2$SO$_4$) and evaporated. The residue was purified by chromatography on neutral aluminum oxide (EtOAc/Et$_3$N, 8:1).

3-(2-Methyl-2,3,4,5-tetrahydro-1H-pyrido[4,3-b] indol-5-yl)propionitrile (G4-a)

To a solution of Pyrido[4,3-b]indole G3-a (R$^{19}$=H) (2.108 g, 11.3 mmol) in mixture benzene (30 mL) and acrylonitrile (10 mL) was added benzyltrimethylammonium hydroxide solution (40% wt. % in methanol, 0.7 mL). The mixture was heated under reflux for 1 h, cooled, washed with water, dried over Na$_2$SO$_4$ and concentrated. Purification by column chromatography on silica gel (benzene/Et$_3$N, 9:1) gave 2.174 g (80%) of the title compound, mp 108-110° C. (acetone, −12° C.). $^1$H NMR (Acetone-d$_6$): 2.46 (3H, s), 2.73-3.01 (6H, m), 3.56 (2H, s), 4.48 (2H, t), 6.97-7.16 (2H, m), 7.38 (1H, d), 7.45 (1H, d).

3-(8-Chloro-2-methyl-2,3,4,5-tetrahydro-1H-pyrido[4,3-b]indol-5-yl)propionitrile (G4-b) was prepared from Pyrido[4,3-b]indole G3-b (R$^{19}$=Cl) in 76% yield, mp 127-129° C. (acetone, −12° C.). $^1$H NMR (Acetone-d$_6$): 2.50 (3H, s), 2.75-3.06 (6H, m), 3.58 (2H, s), 4.54 (2H, t), 7.12 (1H, dd), 7.43 (1H, d), 7.53 (1H, d).

N-Hydroxy-3-(2-methyl-2,3,4,5-tetrahydro-1H-pyrido[4,3-b]indol-5-yl) propionamidine (G5-a) was prepared in 72% yield, mp 218-219.5° C. (dec). $^1$H NMR (DMSO-d$_6$/CDCl$_3$, 2:1): 2.34 (2H, t), 2.48 (3H, s), 2.70-2.92 (4H, m), 3.52 (2H, s), 4.22 (2H, t), 5.48 (2H, s), 6.90-7.10 (2H, m), 7.28 (1H, d), 7.40 (1H, d), 8.90 (1H, s).

N-Hydroxy-3-(8-methoxy-2-methyl-2,3,4,5-tetrahydro-1H-pyrido[4,3-b]indol-5-yl) propionamidine (G5-b) was resulted in 65% yield, mp 211-213° C. (dec). $^1$H NMR (DMSO-d$_6$/CDCl$_3$, 2:1): 2.36 (2H, t), 2.48 (3H, s), 2.68-2.84 (4H, m), 3.52 (2H, s), 3.79 (3H, s), 4.21 (2H, t), 5.39 (2H, s), 6.67 (1H, dd), 6.77 (1H, d), 7.27 (1H, d), 8.90 (1H, s).

3-(2,8-Dimethyl-2,3,4,5-tetrahydro-1H-pyrido[4,3-b]indol-5-yl)-N-hydroxypropionamidine (G5-c) was prepared in 75% yield, mp 218-220° C. (dec). $^1$H NMR (DMSO-d$_6$/CDCl$_3$, 2:1): 2.36 (5H, m), 2.46 (3H, s), 2.68-2.88 (4H, m), 3.49 (2H, s), 4.22 (2H, t), 5.48 (2H, s), 6.90 (1H, d), 7.10 (1H, s), 7.30 (1H, d), 8.92 (1H, s).

3-(8-Chloro-2-methyl-2,3,4,5-tetrahydro-1H-pyrido[4,3-b]indol-5-yl)-N-hydroxypropionamidine (G5-d) was prepared in 68% yield, mp 222-224° C. (dec). $^1$H NMR (DMSO-d$_6$/CCl$_4$, 3:1): 2.32 (2H, t), 2.47 (3H, s), 2.73-2.92 (4H, m), 3.54 (2H, s), 4.23 (2H, t), 5.50 (2H, s), 7.03 (1H, dd), 7.32 (1H, d), 7.46 (1H, d), 8.87 (1H, s).

3-(8-Fluoro-2-methyl-2,3,4,5-tetrahydro-1H-pyrido[4,3-b]indol-5-yl)-N-hydroxypropionamidine (G5-f) was prepared in 71% yield, mp 222-224° C. (dec). $^1$H NMR (DMSO-d$_6$/CCl$_4$, 3:1): 2.35 (2H, t), 2.45 (3H, s), 2.72-2.92 (4H, m), 3.53 (2H, s), 4.25 (2H, t), 5.55 (2H, s), 6.89 (1H, td), 7.08 (1H, dd), 7.44 (1H, d), 8.89 (1H, s).

2-Methyl-5-[2-(5-phenyl-1,2,4-oxadiazol-3-yl)ethyl]-2,3,4,5-tetrahydro-1H-pyrido[4,3-b]indole (G6-a) was prepared on a 1.0-equiv scale. Chromatographic purification gave 60% (G6-a), mp 111-112° C. (acetone/pentane). $^1$H NMR (DMSO-d$_6$/CDCl$_3$, 1:2): 2.48 (3H, s), 2.70-2.88 (4H, m), 3.15 (2H, t), 3.55 (2H, s), 4.48 (2H, t), 6.90-7.08 (2H, m), 7.30 (2H, d), 7.48-7.65 (3H, m), 8.80 (2H, d). Hydrochloride (G6-a), mp softening 218° C., 226-228° C. (dec) (H$_2$O).

8-Methoxy-2-methyl-5-[2-(5-phenyl-1,2,4-oxadiazol-3-yl)ethyl]-2,3,4,5-tetrahydro-1H-pyrido[4,3-b]indole (G6-b) was prepared on a 1.0-equiv scale. Chromatographic purification gave 50.6% (G6-b), mp 77.5-79° C. (Et$_3$N, −12° C.). $^1$H NMR (CDCl$_3$): 2.60 (3H, s), 2.82-2.95 (4H, m), 3.22 (2H, t), 3.68 (2H, s), 3.88 (3H, s), 4.50 (2H, t), 6.78-6.94 (2H, m), 7.28 (1H, d), 7.52-7.70 (3H, m), 8.18 (2H, d). Hydrochloride (G6-b), mp 137-138° C. (H$_2$O).

2,8-Dimethyl-5-[2-(5-phenyl-1,2,4-oxadiazol-3-yl) ethyl]-2,3,4,5-tetrahydro-1H-pyrido[4,3-b]-indole (G6-c) was prepared on a 1.0-equiv. scale. Chromatographic purification gave 48% (G6-c), mp 120-120.5° C. (EtOAc/pentane). $^1$H NMR (DMSO-d$_6$/CDCl$_3$, 1:2): 2.40 (3H, s), 2.48 (3H, s), 2.72-2.90 (4H, m), 3.17 (2H, t), 3.57 (2H, s), 4.50 (2H, t), 6.92 (1H, d), 7.13 (1H, s), 7.22 (1H, d), 7.52-7.71 (3H, m), 8.11 (2H, d). Hydrochloride (G6-c), mp softening 213° C., 220-223° C. (dec) (H$_2$O).

8-Chloro-2-methyl-5-[2-(5-phenyl-1,2,4-oxadiazol-3-yl) ethyl]-2,3,4,5-tetrahydro-1H-pyrido-[4,3-b]indole (G6-d) was prepared on a 0.6-equiv. scale. Chromatographic purification gave 64% (G6-d), mp 122-123° C. (EtOAc/pentane). $^1$H NMR (CDCl$_3$): 2.58 (3H, s), 2.83-2.98 (4H, m), 3.23 (2H, t), 3.66 (2H, s), 4.52 (2H, t), 7.13 (1H, dd), 7.31 (1H, m), 7.42 (1H, d), 7.53-7.70 (3H, m), 8.17 (2H, d). Hydrochloride (G6-d), mp softening 214° C., 227-229° C. (dec) (H$_2$O).

2-Methyl-5-[2-(5-pyridin-4-yl-1,2,4-oxadiazol-3-yl) ethyl]-2,3,4,5-tetrahydro-1H-pyrido[4,3-b]indole (G6-e)

To sodium ethoxide (from 0.188 g of Na and 25 mL of anhydrous ethanol) was added ethyl isonicotinate (1.249 g, 8.3 mmol) and 5-a (1.336 g, 4.9 mmol). The mixture was heated under reflux for 7 h. Solvent was removed under reduced pressure and the residue partitioned between ethyl acetate and water. The organic layer was washed with water, dried over Na$_2$SO$_4$ and evaporated. The residue was purified by chromatography on silica gel (benzene/Et$_3$N, 9:1) to yield 1.145 g (64.9%) of G6-e, mp 110.5-111.5° C. (i-PrOH, −12° C.). $^1$H NMR (DMSO-d$_6$/CDCl$_3$, 2:1): 2.42 (3H, s), 2.64-2.90 (4H, m), 3.25 (2H, t), 3.51 (2H, s), 4.53 (2H, t), 6.90-7.12 (2H, m), 7.26-7.42 (2H, m), 7.98 (2H, d), 8.87 (2H, d).

8-Fluoro-2-methyl-5-[2-(5-phenyl-1,2,4-oxadiazol-3-yl) ethyl]-2,3,4,5-tetrahydro-1H-pyrido-[4,3-b]indole (G6-f) was prepared on a 0.6-equiv. scale. Chromatographic purification gave 76% (G6-f), mp 121.5-122.5° C. (EtOAc/pentane). $^1$H NMR (DMSO-d$_6$/CDCl$_3$, 1:2): 2.47 (3H, s), 2.73-2.92 (4H, m), 3.20 (2H, t), 3.55 (2H, s), 4.51 (2H, t), 6.82 (1H, td), 7.00 (1H, dd), 7.29 (1H, dd), 7.50-7.71 (3H, m), 8.11 (2H, d). Hydrochloride (G6-f), mp 187° C., 222-224° C. (dec) (H$_2$O).

Example 325

Preparation of Thiazoles G8-a-f

Thiazoles (G8) were prepared using synthetic route shown in Scheme II. Nitriles (G4) were converted to their corresponding thiopropionamides (7). Cyclization of 7 with 2-bromoketone (R$^{14a}$—COCH$_2$Br) gave G8.

Scheme II

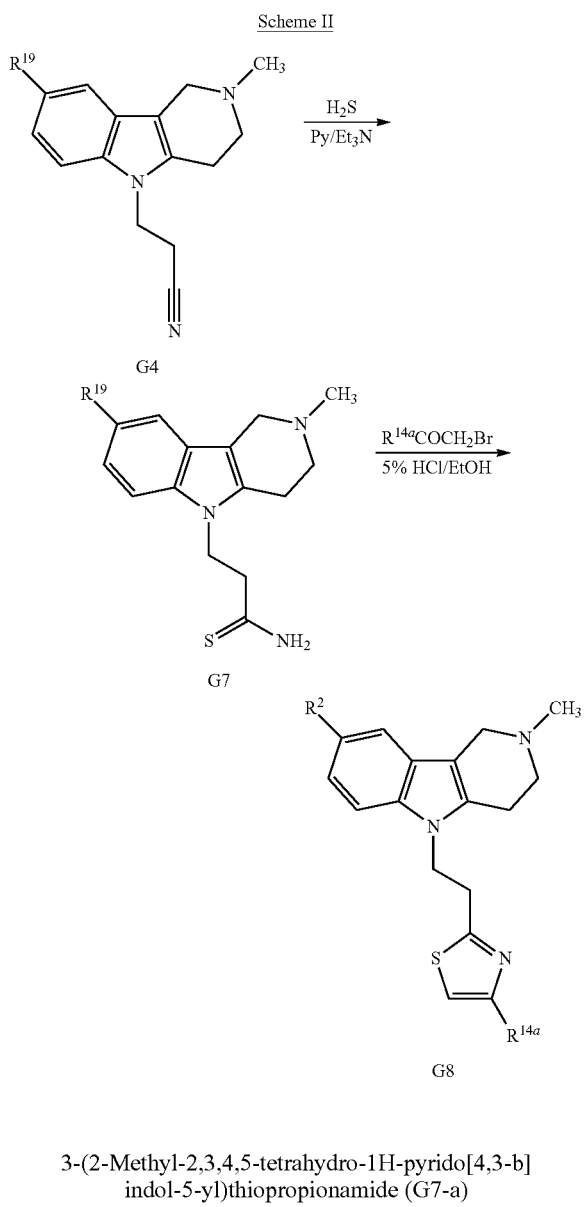

3-(2-Methyl-2,3,4,5-tetrahydro-1H-pyrido[4,3-b]indol-5-yl)thiopropionamide (G7-a)

Solution of G4-a (3.0 g, 12.5 mmol) in pyridine (25 mL) and triethylamine (3.5 mL) was saturated with H$_2$S for 15 min. The reaction mixture was concentrated in vacuo after 72 h at ambient temperature. The solid residue was washed with aqueous NaOH solution and with water. After drying in vacuo to yield 3.3 g (96%) of G7-a, mp 149-151° C. $^1$H NMR (DMSO-d$_6$/CDCl$_3$, 1:2): 2.53 (3H, s), 2.75-3.01 (6H, m), 3.60 (2H, s), 4.46 (2H, t), 6.94-7.16 (2H, m), 7.34 (1H, d), 7.43 (1H, d), 9.12 (2H, s).

Other thiopropionamides 7 were prepared by the above method for G7-a.

3-(8-Methoxy-2-methyl-2,3,4,5-tetrahydro-1H-pyrido[4,3-b]indol-5-yl)thiopropionamide (G7-b) was prepared in 89% yield, mp 145-147° C. $^1$H NMR (DMSO-d$_6$/CDCl$_3$, 1:2): 2.51 (3H, s), 2.74-2.98 (6H, m), 3.56 (2H, s), 3.80 (3H, s), 4.41 (2H, t), 6.72 (1H, d), 6.80 (1H, s), 7.31 (1H, d), 9.09 (2H, s).

3-(2,8-Dimethyl-2,3,4,5-tetrahydro-1H-pyrido[4,3-b]indol-5-yl)thiopropionamide (7G-c) was prepared in 91% yield, mp 161-164° C. $^1$H NMR (DMSO-d$_6$/CDCl$_3$, 1:2): 2.40 (3H, s), 2.52 (3H, s), 2.75-2.99 (6H, m), 3.57 (2H, s), 4.42 (2H, t), 6.92 (1H, d), 7.13 (1H, s), 7.31 (1H, d), 9.10 (2H, s).

3-(8-Chloro-2-methyl-2,3,4,5-tetrahydro-1H-pyrido[4,3-b]indol-5-yl)thiopropionamide (G7-e) was prepared in 91% yield, mp 156-158° C. $^1$H NMR (DMSO-d$_6$): 2.41 (3H, s), 2.66-2.94 (6H, m), 3.47 (2H, s), 4.41 (2H, t), 7.06 (1H, d), 7.38 (1H, s), 7.46 (1H, d), 9.30 (1H, s), 9.51 (1H, s).

3-(8-Fluoro-2-methyl-2,3,4,5-tetrahydro-1H-pyrido[4,3-b]indol-5-yl)thiopropionamide (G7-f) was prepared in 94% yield, mp 165-167° C. $^1$H NMR (DMSO-d$_6$/CDCl$_3$, 1:2): 2.52 (3H, s), 2.75-3.00 (6H, m), 3.55 (2H, s), 4.44 (2H, t), 6.84 (1H, td), 6.99 (1H, dd), 7.38 (1H, dd), 9.13 (2H, s).

2-Methyl-5-[2-(4-phenylthiazol-2-yl)ethyl]-2,3,4,5-tetrahydro-1H-pyrido[4,3-b]indole (G8-a)

A mixture of G7-a (1.62 g, 5.9 mmol), 2-bromoacetophenone (1.18 g, 5.9 mmol) and 5% HCl in ethanol (22 mL) was heated at reflux for 20 min. The reaction mixture was cooled to room temperature and concentrated in vacuo. The residue was partitioned between CH$_2$Cl$_2$ and aqueous NaOH solution. The organic layer was washed with water, dried (Na$_2$SO$_4$) and evaporated. Purification by column chromatography on silica gel (benzene/Et$_3$N, 13:1) gave 1.79 g (80.9%) of the title compound, mp 142-143 (i-PrOH). $^1$H NMR (DMSO-d$_6$/CDCl$_3$, 1:2): 2.48 (3H, s), 2.73 (4H, s), 3.43 (2H, t), 3.58 (2H, s), 4.53 (2H, t), 6.95-7.15 (2H, m), 7.27-7.53 (6H, m), 7.90 (2H, d). Hydrochloride (G8-a), mp 128-130° C. (H$_2$O).

Other substituted thiazoles 8 were prepared by the above method for G8-a.

8-Methoxy-2-methyl-5-[2-(4-phenylthiazol-2-yl)ethyl]-2,3,4,5-tetrahydro-1H-pyrido[4,3-b]indole (G8-b) was prepared in 62.8% yield, mp 135-136.5° C. (heptane). H NMR (Acetone-d$_6$): 2.43 (3H, s), 2.61-2.77 (4H, m), 3.45-3.57 (4H, m), 3.82 (3H, s), 4.58 (2H, t), 6.75 (1H, dd), 6.93 (1H, d), 7.30-7.53 (4H, m), 7.74 (1H, s), 8.04 (2H, d). Hydrochloride (G8-b), mp 162-163° C. (H$_2$O).

2,8-Dimethyl-5-[2-(4-phenylthiazol-2-yl)ethyl]-2,3,4,5-tetrahydro-1H-pyrido[4,3-b]indole (G8-c) was prepared in 72% yield, mp 148.5-149° C. (EtOAc). $^1$H NMR (DMSO-d$_6$/CDCl$_3$, 1:2): 2.41 (3H, s), 2.45 (3H, s), 2.69 (4H, s), 3.39 (2H, t), 3.53 (2H, s), 4.49 (2H, t), 6.87 (1H, d), 7.06-7.20 (2H, m), 7.24-7.45 (4H, m), 7.88 (2H, d). Hydrochloride (G8-c), mp 127-129° C. (H$_2$O).

2-Methyl-5-[2-(4-pyridin-4-yl-thiazol-2-yl)ethyl]-2,3,4,5-tetrahydro-1H-pyrido[4,3-b]indole (G8-d)

A mixture of 7-a (1.0 g, 3.7 mmol), 2-bromo-1-pyridin-4-yl-ethanone hydrobromide (1.029 g, 3.7 mmol) and 5% HCl in ethanol (44 mL) was heated at reflux for 20 min. The reaction mixture was cooled to room temperature and concentrated in vacuo. The residue partitioned between CH$_2$Cl$_2$ and aqueous NaOH solution. The organic layer was washed with water, dried over Na$_2$SO$_4$ and evaporated. The solid residue was washed with acetone. Recrystallization from 2-propanol afforded G8-d (0.42 g, 30.6%), mp 158.5-159.5° C. $^1$H NMR (DMSO-d$_6$/CCl$_4$, 1:1): 2.42 (3H, s), 2.67 (4H, s), 3.44 (2H, t), 3.53 (2H, s), 4.52 (2H, t), 6.90-7.09 (2H, m), 7.27-7.40 (2H, m), 7.86 (2H, d), 8.17 (1H, s), 8.58 (2H, d).

8-Chloro-2-methyl-5-[2-(4-phenylthiazol-2-yl)ethyl]-2,3,4,5-tetrahydro-1H-pyrido[4,3-b]indole (G8-e)

A mixture of 7-e (1.033 g, 3.4 mmol), 2-bromoacetophenone (0.67 g, 3.4 mmol) and 5% HCl in ethanol (20 mL) was heated at reflux for 20 min. The reaction mixture was cooled to room temperature and concentrated in vacuo. The residue partitioned between $CH_2Cl_2$ and aqueous NaOH solution. The organic layer was washed with water, dried over $Na_2SO_4$ and evaporated. Purification by column chromatography on silica gel (benzene/$Et_3N$, 9:1) gave 1.019 g (74%) of G8-e, mp 140-142° C. (i-PrOH). $^1H$ NMR (Acetone-$d_6$): 2.42 (3H, s), 2.56-2.81 (4H, m), 3.39-3.60 (4H, m), 4.60 (2H, t), 7.04 (1H, d), 7.27-7.51 (5H, m), 7.71 (1H, s), 7.98 (2H, d).

8-Fluoro-2-methyl-5-[2-(4-phenylthiazol-2-yl)ethyl]-2,3,4,5-tetrahydro-1H-pyrido[4,3-b]indole (G8-f) was prepared in 77% yield, mp 136.5-137° C. (EtOAc). $^1H$ NMR (DMSO-$d_6$/$CDCl_3$, 1:2): 2.49 (3H, s), 2.74 (4H, s), 3.42 (2H, t), 3.55 (2H, s), 4.53 (2H, t), 6.82 (1H, td), 7.01 (1H, dd), 7.20-7.53 (5H, m), 7.90 (2H, d). Hydrochloride (G8-f), mp 135-137° C. ($H_2O$).

Example 326

Preparation of 5-Substituted-2,4-dihydro-1,2,4-triazole-3-thiones G11-a-d

5-Substituted-2,4-dihydro-1,2,4-triazole-3-thiones (G11) were prepared using synthetic route shown in Scheme III. Pyrido[4,3-b]indole (3) were alkylated to afford the ester (G9), which was converted to its corresponding hydrazide (G10). Reaction of carboxylic acid hydrazides (G10) and methyl isothiocyanate afforded the 2,4-dihydro-1,2,4-triazole-3-thione (G11).

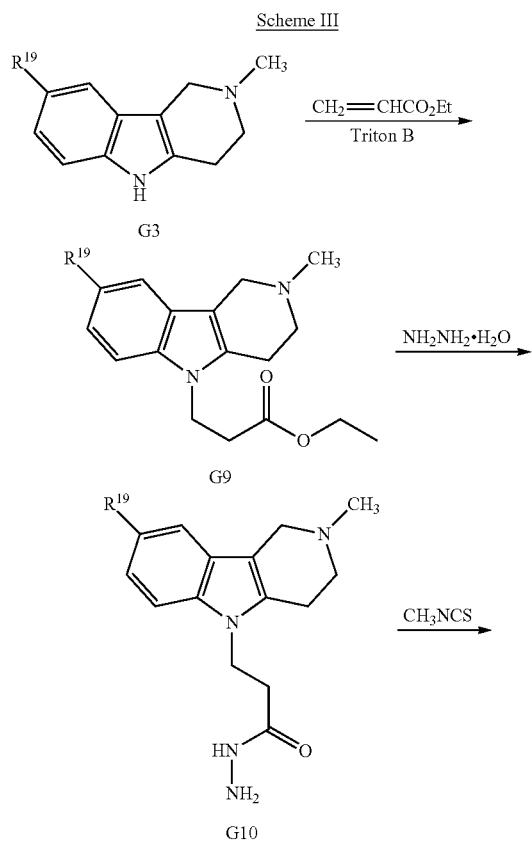

Scheme III

3-(2-Methyl-2,3,4,5-tetrahydro-1H-pyrido[4,3-b]indol-5-yl)propionic acid ethyl ester (G9-a)

The benzyltrimethylammonium hydroxide solution (40% wt. in methanol, 3.5 mL) was added to a solution of G3-a (17,114 g, 92 mmol) in mixture benzene (170 mL) and ethyl acrylate (75 mL). The mixture was heated under reflux for 7 h, cooled, washed with water, and extracted with 2M HCl. The acidic solution was extracted with benzene, basified with 10% NaOH, and extracted with benzene. The combined extracts were washed with water, dried and evaporated to an oil (21.18 g, 80%). $^1H$ NMR (Acetone-$d_6$): 1.13 (3H, t), 2.49 (3H, s), 2.70-2.96 (6H, m), 3.60 (2H, s), 4.05 (2H, q), 4.37 (2H, t), 6.94-7.15 (2H, m), 7.32-7.43 (2H, m).

Other esters 9 were prepared by the above method for 9-a.

3-(8-Chloro-2-methyl-2,3,4,5-tetrahydro-1H-pyrido[4,3-b]indol-5-yl)propionic acid ethyl ester (G9-b) was prepared in 88% yield, oil. $^1H$ NMR (Acetone-$d_6$): 1.13 (3H, t), 2.45 (3H, s), 2.69-2.98 (6H, m), 3.52 (2H, s), 4.03 (2H, q), 4.39 (2H, t), 7.06 (1H, dd), 7.36 (1H, d), 7.40 (1H, d).

3-(8-Fluoro-2-methyl-2,3,4,5-tetrahydro-1H-pyrido[4,3-b]indol-5-yl)propionic acid ethyl ester (G9-c) was prepared in 89% yield, oil. $^1H$ NMR (Acetone-$d_6$): 1.13 (3H, t), 2.45 (3H, s), 2.68-2.94 (6H, m), 3.51 (2H, s), 4.03 (2H, q), 4.38 (2H, t), 6.86 (1H, td), 7.06 (1H, dd), 7.37 (1H, dd).

3-(8-Methoxy-2-methyl-2,3,4,5-tetrahydro-1H-pyrido[4,3-b]indol-5-yl)propionic acid ethyl ester (G9-d) was prepared in 80% yield, oil. $^1H$ NMR (Acetone-$d_6$): 1.15 (3H, t), 2.46 (3H, s), 2.65-2.94 (6H, m), 3.51 (2H, s), 3.78 (3H, s), 4.05 (2H, q), 4.34 (2H, t), 6.73 (1H, d), 6.89 (1H, s), 7.28 (1H, d).

3-(2-Methyl-2,3,4,5-tetrahydro-1H-pyrido[4,3-b]indol-5-yl)propionic acid hydrazide (G10-a)

To a solution of G9-a (20.356 g, 74.8 mmol) in ethanol (50 mL) was added hydrazine monohydrate (20 mL, 0.41 mol), and the mixture was heated under reflux for 2 h 30 min. After 72 h storage at −12° C., the resulting crystals were collected, washed with 2-propanol, and dried to give 12.7 g (65.6%) of G10-a, mp 123-124° C. $^1H$ NMR (DMSO-$d_6$/$CCl_4$, 3:1): 2.32-2.47 (5H, m), 2.63-2.92 (4H, m), 3.50 (2H, s), 4.11 (2H, br s), 4.26 (2H, t), 6.89-7.12 (2H, m), 7.24-7.42 (2H, m), 9.03 (1H, br s).

Other acid hydrazides G10 were prepared by the above method for G10-a.

3-(8-Chloro-2-methyl-2,3,4,5-tetrahydro-1H-pyrido[4,3-b]indol-5-yl)propionic acid hydrazide (G10-b) was prepared in 74% yield, mp 172-173° C. $^1H$ NMR (DMSO-$d_6$/$CDCl_3$, 1:1): 2.38-2.50 (5H, m), 2.68-2.94 (4H, m), 3.50 (2H, s), 4.00 (2H, br s), 4.28 (2H, t), 7.01 (1H, dd), 7.28 (1H, d), 7.32 (1H, d), 9.05 (1H, br s).

3-(8-Fluoro-2-methyl-2,3,4,5-tetrahydro-1H-pyrido[4,3-b]indol-5-yl)propionic acid hydrazide (G10-c) was prepared in 72% yield, mp 158-159° C. $^1$H NMR (DMSO-$d_6$/CCl$_4$, 2:1): 2.30-2.45 (5H, m), 2.67-2.92 (4H, m), 3.48 (2H, s), 3.91 (2H, br s), 4.25 (2H, t), 6.82 (1H, td), 7.00 (1H, dd), 7.32 (1H, dd), 9.01 (1H, br s).

3-(8-Methoxy-2-methyl-2,3,4,5-tetrahydro-1H-pyrido[4,3-b]indol-5-yl)propionic acid hydrazide (G10-d)

The solution of 9-d (20.872 g, 66 mmol) in ethanol (50 mL) and hydrazine monohydrate (20 mL, 0.41 mol) was heated under reflux for 2 h 15 min and then evaporated in vacuo. The residue was crystallized from ethanol (−12° C.) to yield 8.9 g (44.6%) of G10-d, mp 126.5-127.5° C. $^1$H NMR (DMSO-$d_6$/CDCl$_3$, 1:1): 2.36-2.49 (5H, m), 2.67-2.94 (4H, m), 3.52 (2H, s), 3.77 (3H, s), 4.00 (2H, br s), 4.26 (2H, t), 6.69 (1H, d), 6.78 (1H, s), 7.22 (1H, d), 9.04 (1H, br s).

4-Methyl-5-[2-(2-methyl-2,3,4,5-tetrahydro-1H-pyrido[4,3-b]indol-5-yl)ethyl]-2,4-dihydro-1,2,4-triazole-3-thione (G11-a)

A mixture of G10-a (2.187 g, 8 mmol), methyl isothiocyanate (0.587 g, 8 mmol) and 55 mL of ethanol was heated under reflux for 6 h 30 min and then allowed to stand for 48 h at ambient temperature. The resulting crystals were collected by filtration, washed with ethanol, and dried to give 2.268 g (86%) of G11-a, mp 216-219° C. (EtOH). $^1$H NMR (DMSO-$d_6$/CDCl$_3$, 1:1): 2.45 (3H, s), 2.72 (4H, s), 3.05 (2H, t), 3.16 (3H, s), 3.53 (2H, s), 4.42 (2H, t), 6.88-7.13 (2H, m), 7.22-7.38 (2H, m), 13.52 (1H, br s); MS, m/z 327 (M$^+$).

Other 2,4-dihydro-1,2,4-triazole-3-thiones G11 were prepared by the above method for G11-a.

5-[2-(8-Chloro-2-methyl-2,3,4,5-tetrahydro-1H-pyrido[4,3-b]indol-5-yl)ethyl]-4-methyl-2,4-dihydro-1,2,4-triazole-3-thione (G11-b) was prepared in 88% yield, mp 216-219° C. (EtOH). $^1$H NMR (DMSO-$d_6$): 2.41 (3H, s), 2.70 (4H, s), 3.06 (2H, t), 3.20 (3H, s), 3.49 (2H, s), 4.42 (2H, t), 7.05 (1H, d), 7.30-7.47 (2H, m), 13.55 (1H, br s); MS, m/z 361 (M$^+$).

5-[2-(8-Fluoro-2-methyl-2,3,4,5-tetrahydro-1H-pyrido[4,3-b]indol-5-yl)ethyl]-4-methyl-2,4-dihydro-1,2,4-triazole-3-thione (G11-c) was prepared in 83% yield, mp 215-218° C. (EtOH). $^1$H NMR (DMSO-$d_6$/CDCl$_3$, 2:1): 2.43 (3H, s), 2.71 (4H, s), 3.04 (2H, t), 3.16 (3H, s), 3.48 (2H s), 4.41 (2H, t), 6.83 (1H, td), 7.03 (1H, dd), 7.29 (1H, dd), 13.52 (1H, br s); MS, m/z 345 (M$^+$).

5-[2-(8-Methoxy-2-methyl-2,3,4,5-tetrahydro-1H-pyrido[4,3-b]indol-5-yl)ethyl]-4-methyl-2,4-dihydro-1,2,4-triazole-3-thione (G11-d) was prepared in 93% yield, mp 219-222° C. (EtOH). $^1$H NMR (DMSO-$d_6$): 2.43 (3H, s), 2.69 (4H, s), 3.05 (2H, t), 3.17 (3H, s), 3.50 (2H, s), 3.77 (3H, s), 4.39 (2H, t), 6.72 (1H, dd), 6.89 (1H, d), 7.27 (1H, d), 13.49 (1H, br s); MS, m/z 357 (M$^+$).

The compounds prepared according to the Examples are further detailed in Table 4.

TABLE 4

| | | | | | | | | |
|---|---|---|---|---|---|---|---|---|
| Synthetic Data | | | | | | | | |
| Ex. No. | Comp. No. | Salt | MW | NMR Solvent | NMR Data | MS observed | HPLC Method[2] | HPLC Rt (min) |
| 9 | 25 | TFA Salt | 432.48 | CDCl$_3$ | 13.3 (bs, 1H), 7.4-7.0 (m, 5H), 6.80-6.70 (d, 2H), 4.7-4.6 (d, 1H), 4.40-4.22 (m, 1H), 4.20-4.10 (m, 1H), 4.10-4.0 (d, 1H), 3.5-3.4 (t, 1H), 3.20-3.17 (t, 1H), 3.0 (t, 2H), 2.80 (s, 3H), 2.7-2.61 (m, 1H), 2.40 (s, 3H), 2.23 (s, 3H), 2.2-2.1 (m, 1H) | 319 | 1 | 6.06 |
| 10 | 18 | Free Base | 442.35 | CDCl$_3$ | 8.10-8.0 (m, 1H), 7.60-6.80 (m, 5H), 4.50 (s, 2H), 4.2-4.0 (m, 4H), 3.60 (s, 2H), 2.90-2.80 (t, 2H), 2.30 (s, 3H), 2.30-2.24 (m, 2H), 1.20 (t, 3H) | 442 | 1 | 5.617 |
| 39 | 19 | Free Base | 440.54 | CDCl$_3$ | 7.83 (d, 1H), 7.60-7.18 (m 9H), 4.60 (s, 2H), 4.20-4.10 (t, 2H), 4.10-4.0 (q, 2H), 3.60-3.50 (m, 2H), 3.00-2.95 (m, 2H), 2.90-2.89 (m, 2H), 2.45 (s, 3H), 1.24-1.10 (t, 3H) | 441 | 1 | 4.01 |
| 11 | 24 | Free Base | 362.46 | CDCl$_3$ | 7.4-6.9 (m, 8H,), 4.65-4.60 (s, 2H), 4.3-4.2 (m, 4H), 3.7-3.6 (m, 2H), 3.0-2.99 (t, 2H), 2.4-2.3 (m, 1H), 2.29-2.20 (m, 1H), 2.15 (s, 3H), 0.9 (t, 3H) | 363 | 2 | 6.813 |

TABLE 4-continued

Synthetic Data

| 40 | 20 | Oxalate Salt | 394.46 | CDCl₃ | 13.2 (s, 1H), 7.4-7.2 (m, 6H), 6.98-6.80 (t, 2H), 4.80-4.60 (m, 1H), 4.40-4.00 (m, 3H), 3.60-3.40 (m, 2H), 3.20-3.00 (m, 3H), 2.80 (s, 3H), 2.6-2.4 (m, 1H) 2.50 (s, 3H) | 305 | 1 | 5.7 |
|---|---|---|---|---|---|---|---|---|
| 29 | 139 | TFA salt | 419.44 | CDCl₃ | 8.78 (s, 1H), 7.41-7.39 (d, 2H), 7.30-7.20 (m, 1H), 7.10-7.00 (d, 2H), 5.55-5.20 (dd, 2H), 4.80-4.70 (d, 1H), 4.20-4.10 (d, 1H), 3.90-3.80 (s, 1H), 3.40-3.30 (m, 2H), 3.10 (s, 3H), 2.90 (s, 1H), 2.75 (s, 3H), 2.40 (s, 3H) | 306 | 1 | 3.8 |
| 20 | 21 | Free Base | 305.42 | CDCl₃ | 8.6 (d, 1H), 7.9 (t, 1H), 7.58-7.50 (m, 1H), 7.1 (s, 1H), 7.05-6.90 (m, 3H), 4.8-4.6 (m, 2H), 4.42-4.38 (m, 1H), 4.0 (m, 1H), 3.8 (m, 1H), 3.60-3.4 (m, 2H), 3.20-3.10 (m, 1H), 3.0 (s, 3H), 3.0-2.8 (m, 2H), 2.42 (s, 3H) | 306 | 1 | 3.81 |
| 21 | 22 | Free Base | 305.42 | CDCl₃ | 8.5 (s, 2H), 7.20-7.15 (d, 2H), 7.14-7.06 (d, 1H), 6.90-6.85 (d, 2H), 4.30-4.22 (t, 2H), 4.20 (bs, 2H), 3.20 (bs, 2H), 3.05 (t, 2H), 2.8 (s, 3H), 2.6 (bs, 2H), 2.45 (s, 3H) | 306 | 1 | 1.5, 3.77 |
| 22 | 23 | TFA Salt | 433.47 | CDCl₃ | 8.70 (s, 1H), 7.85-7.80 (t, 1H), 7.6-7.5 (t, 1H), 7.1-6.9 (m, 4H), 4.7 (t, 2H), 4.50-4.40 (t, 1H), 4.0 (d, 1H), 3.8 (m, 1H), 3.60-3.2 (m, 5H), 2.9 (m, 2H), 2.4 (s, 3H), 1.5 (t, 3H) | 320 | 1 | 3.92 |
| 12 | 37 | TFA Salt | 432.48 | CDCl₃ | 7.5-7.1 (m, 6H), 6.93-6.90 (m, 2H), 4.8-4.4 (m, 4H), 4.0-3.2 (m, 4H), 3.2-3.0 (m, 4H), 2.5 (s, 3H), 1.4-1.3 (t, 3H) | 319 | 1 | 5.78 |
| 13 | 26 | TFA Salt | 446.51 | CDCl₃ | 7.4-7.2 (m, 1H,), 7.2-7.1 (d, 2H), 7.06-7.0 (d, 2H), 6.8-6.75 (d, 2H), 4.6-4.2 (m, 4H), 4.2-3.2 (m, 4H), 3.20-3.15 (m, 2H), 3.10-3.0 (m, 2H), 2.45 (s, 3H), 2.3 (s, 3H), 1.42-1.3 (t, 3H) | 333 | 1 | 6.04 |
| 23 | 27 | TFA Salt | 433.47 | CDCl₃ | 8.5 (d, 2H), 7.25 (d, 2H), 7.1 (s, 1H), 7.0 (d, 1H), 6.9 (d, 1H), 4.75-4.65 (d, 1H), 4.4-4.3 (m, 2H), 4.1-4.0 (d, 1H), 3.94-3.82 (m, 1H), 3.4-3.3 (m, 1H), 3.2-3.1 (m, 3H), 2.72-2.60 | 320 | 1 | 3.84 |

TABLE 4-continued

| | | | | | Synthetic Data | | | |
|---|---|---|---|---|---|---|---|---|
| | | | | | (m, 1H), 2.58-2.42 (m, 5H), 1.58-1.50 (t, 3H) | | | |
| 14 | 1 | TFA Salt | 418.45 | CDCl₃ | 7.45-7.40 (d, 2H), 7.25-7.16 (m, 2H), 7.1-6.9 (d, 2H), 6.8-6.7 (d, 2H), 4.7 (d, 1H), 4.4-4.3 (m, 1H), 4.20-4.03 (m, 2H), 3.55-3.40 (m, 1H), 3.22-3.10 (m, 1H), 3.09-2.90 (m, 2H), 2.83 (s, 3H), 2.65 (m, 1H), 2.35 (s, 3H), 2.2 (m, 1H). | 305 | 1 | 5.7 |
| 15 | 2 | TFA Salt | 404.43 | CDCl₃ | 7.5-7.10 (m, 7H), 6.9-6.8 (m, 2H), 4.6 (d, 1H), 4.30-4.19 (m, 2H), 4.05 (d, 1H), 3.62-3.40 (m, 1H), 3.20-3.0 (m, 3H), 2.9 (s, 3H), 2.7-2.6 (t, 1H), 2.2-2.1 (t, 1H) | 291 | 1 | 5.422 |
| 32 | 137 | TFA Salt | 404.43 | CDCl₃ | 9.6 (1H), 7.5-7.19 (m, 6H), 7.0-6.9 (d, 2H), 3.79 (s, 2H), 3.6 (s, 2H), 3.1-3.0 (m, 2H), 2.8-2.70 (t, 2H), 2.3 (s, 3H), 2.3 (s, 3H) | 291 | 1 | 5.28 |
| 30 | 138 | Free Base | 319.44 | CDCl₃ | 8.40-8.38 (s, 1H), 7.4-7.0 (m, 5H), 5.2 (s, 2H), 4.07-3.9 (bs, 1H), 3.1 (bs, 1H), 2.9 (bs, 2H), 2.5 (s, 3H), 2.42 (s, 3H), 2.0 (b, 2H), 1.4-1.3 (t, 3H) | 320 | 1 | 3.89 |
| 33 | 140 | TFA Salt | 418.45 | CDCl₃ | 12.0 (s, 1H), 7.5-7.0 (m, 8H), 4.10 (s, 2H), 3.61-3.5 (m, 2H), 3.0-2.8 (t, 4H), 2.45 (s, 3H), 2.4-1.7 (m, 2H), 1.5 (t, 3H) | 305 | 1 | 5.86 |
| 16 | 4 | TFA Salt | 418.45 | CDCl₃ | 7.40-7.38 (m, 3H), 7.25-7.18 (m, 4H), 6.9-6.8 (m, 2H), 4.70-4.60 (d, 1H), 4.40-4.36 (m, 1H), 4.23-4.10 (m, 2H), 3.56-3.42 (m, 1H), 3.21-3.19 (m, 1H), 3.10-3.0 (m, 4H), 2.67-2.58 (m, 1H), 2.1-2.0 (m, 1H), 1.4-1.3 (t, 3H) | 305 | 1 | 5.52 |
| 17 | 3 | TFA Salt | 432.48 | CDCl₃ | 7.41-7.15 (m, 4H), 7.1-7.0 (m, 2H), 6.8-6.7 (m, 2H), 4.70-4.60 (d, 1H), 4.40-4.30 (m, 1H), 4.20-4.10 (q, 2H), 3.60-3.50 (m, 1H), 3.30-3.20 (m, 1H), 3.15-3.0 (m, 4H), 2.6 (m, 1H), 2.30 (s, 3H), 2.1 (m, 1H), 1.38 (t, 3H) | 319 | 1 | 5.78 |
| 24 | 5 | TFA Salt | 419.44 | CDCl₃ | 8.60-8.50 (d, 2H), 7.4-7.0 (m, 6H), 4.80 (d, 1H), 4.40 (t, 2H), 4.10 (d, 1H), 3.9 (m, 1H), 3.60-3.40 (m, 2H), 3.30-3.17 (m, 4H), 2.80-2.70 (d, 1H), 1.60-1.50 (t, 3H) | 306 | 1 | 3.63 |

TABLE 4-continued

Synthetic Data

| | | | | | | | | |
|---|---|---|---|---|---|---|---|---|
| 25 | 6 | TFA Salt | 419.44 | CDCl$_3$ | 8.7 (d, 1H), 7.90-7.80 (t, 1H), 7.60-7.50 (m, 1H), 7.40-7.0 (m, 5H), 4.80-4.70 (d, 1H), 4.60-4.50 (m, 1H), 4.1-4.0 (d, 1H), 3.90-3.80 (m, 1H), 3.60-2.8 (m, 8H), 1.5 (t, 3H) | 306 | 1 | 3.64 |
| 35 | 28 | HCl salt | 370.92 | DMSO | 10.30 (s, 1H), 7.42-7.0 (m, 7H), 5.6 (m, 1H), 4.90-4.80 (m, 1H), 4.60-4.55 (d, 1H), 4.30-4.00 (m, 3H), 3.70 (s, 1H), 3.4 (m, 1H), 3.22-3.10 (d, 1H), 3.00-2.90 (m, 3H), 2.80-2.60 (d, 1H), 2.40 (s, 3H), 2.30 (s, 3H) | 335 | 1 | 5.35 |
| 36 | 29 | TFA salt | 462.5 | CDCl$_3$ | 13.20 (bs, 1H), 7.4-7.0 (m, 7H), 5.05-4.97 (m, 1H), 4.70 (t, 1H), 4.25-4.10 (m, 3H), 3.70-3.60 (m, 1H), 3.40-3.10 (m, 5H), , 2.5 (s, 3H), 2.38 (S, 3H), 1.41 (t, 3H) | 349 | 1 | 5.48 |
| 34 | 16 | TFA salt | 404.43 | CDCl$_3$ | 10.7 (s, 1H), 7.6-7.0 (m, 9H) 4.60-4.2 (m, 4H), 3.55-3.40 (m, 2H), 3.30-3.20 (dd, 2H), 3.0 (bs, 2H), 1.50-1.40 (t, 3H) | 291 | 1 | 5.14 |
| 37 | 7 | TFA salt | 434.45 | CDCl$_3$ | 13.45-13.20 (bs, 1H), 7.40-7.05 (m, 8H), 5.0-4.9 (t, 1H), 4.8-4.6 (t, 1H), 4.25-4.05 (m, 3H), 3.70-3.60 (m, 1H), 3.40-3.30 (m, 2H), 3.05 (m, 1H)3.00-2.91 (m, 3H), 2.3 (s, 3H) | 321 | 1 | 5.09 |
| 38 | 8 | TFA salt | 448.48 | CDCl$_3$ | 13.40-13.10 (bs, 1H), 7.40-7.30 (t, 2H), 7.29-7.10 (m, 6H), 5.07-4.95 (m, 1H), 4.75-4.60 (t, 1H), 4.25-4.02 (m, 3H), 3.75-3.65 (m, 1H), 3.40-3.0 (m, 5H), 2.35 (S, 3H), 1.47-1.40 (t, 3H) | 335 | 1 | 5.29 |
| 26 | 9 | TFA salt | 405.41 | CDCl$_3$ | 13.5 (bs, 1H), 8.7 (d, 1H), 7.9-7.8 (m, 1H), 7.6-7.5 (m, 1H), 7.40-6.95 (m, 5H), 4.80-4.65 (d, 2H), 4.50-4.40 (m, 1H), 4.10-4.0 (d, 1H), 3.80-3.70 (m, 1H), 3.40-3.30 (m, 2H), 3.28-3.18 (m, 1H), 3.10 (s, 3H), 2.95 (m, 2H). | 292 | 1 | 3.5 |
| 27 | 30 | Free Base | 325.84 | CDCl$_3$ | 8.63-5.58 (d, 1H), 7.5-7.4 (t, 2H), 7.18-7.1 (m, 4H), 4.42-4.38 (t, 2H), 3.6 (S, 2H), 3.2-3.17 (t, 2H), 2.78-2.7 (t, 2H), 2.65-2.60 (t, 2H), 2.5 (t, 2H) | 326 | 1 | 3.9 |

TABLE 4-continued

| | | | | Synthetic Data | | | | |
|---|---|---|---|---|---|---|---|---|
| 28 | 10 | TFA salt | 405.41 | CDCl₃ | 8.6-8.54 (d, 2H), 7.4-7.36 (d, 1H), 7.34-7.29 (d, 2H), 7.18-7.13 (m, 2H), 7.06-7.02 (d, 1H), 4.80-4.70 (d, 1H), 4.4 (m, 2H), 4.20-4.05 (d, 1H), 3.95 (m, 1H), 3.30-3.20 (m, 4H), 3.1 (s, 3H), 2.78-2.75 (d, 1H) | 292 | 1 | 3.5 |
| 18 | 31 | TFA salt | 447.49 | CDCl₃ | 8.22 (s, 1H), 7.24-7.20 (d, 2H), 7.20-7.18 (d, 1H), 7.05-6.80 (m, 2H), 4.20-4.18 (t, 2H), 3.70 (s, 2H), 3.0-2.9 (m, 2H), 2.82-2.78 (t, 2H), 2.70-2.60 (t, 2H), 2.58-2.50 (bs, 5H), 2.48-2.40 (s, 3H), 1.3 (t, 3H) | 334 | 1 | 4.13 |
| 31 | 17 | Free Base | 291.39 | CDCl₃ | 8.4 (s, 1H), 7.46-7.43 (dd, 1H), 7.23-7.19 (dd, 1H), 7.15-7.02 (m, 4H), 5.20 (s, 2H), 3.70 (s, 2H), 2.85-2.75 (m, 4H), 2.55 (s, 3H), 2.45 (s, 3H) | 292 | 1 | 3.55 |
| 41 | 34 | Oxalate Salt | 412.45 | DMSO | 7.40-6.90 (m, 7H), 4.30-4.20 (t, 2H), 3.4 (S, 2H), 3.06-2.95 (t, 2H), 2.80 (s, 3H), 2.60-2.4 (m, 4H), 2.40 (s, 3H). | 323 | 1 | 5.77 |
| 19 | 32 | TFA salt | 452.9 | CDCl₃ | 7.30-7.08 (m, 5H), 6.85-6.78 (d, 2H), 4.70-4.60 (d, 1H), 4.40-4.20 (m, 1H), 4.20-4.0 (m, 2H), 3.65-3.50 (m, 1H), 3.10-3.00 (m, 3H), 2.85 (s, 3H), 2.80 (m, 1H), 2.45 (s, 3H), 2.2 (m, 1H). | 339 | 1 | 6.03 |
| 42 | 163 | Free Base | 310.48 | CDCl₃ | 7.38-7.18 (m, 3H,), 4.05-3.98 (m, 2H), 3.70-3.60 (t, 2H), 2.88-2.80 (t, 4H), 2.6 (s, 3H), 2.40 (s, 3H,), 1.8-0.8 (m, 13H) | 311 | 1 | 6.55 |
| 43 | 33 | Oxalate Salt | 412.45 | CD₃OD | 7.30-7.25 (d, 1H), 7.22-7.20 (s, 1H), 7.10-7.0 (d, 1H), 6.9-6.98 (m, 4H), 4.8-4.2 (m, 4H), 3.6-3.2 (m, 2H), 3.0 (t, 2H), 2.98 (S, 3H), 2.65 (bs, 2H)2.4 (s, 3H) | 323 | 1 | 5.78 |
| 44 | 35 | Oxalate Salt | 420.5 | DMSO | 7.39-7.30 (d, 1H), 7.26-7.12 (m, 4H), 7.1-6.9 (d, 3H), 4.4-4.3 (s, 2H,), 4.3-4.2 (t, 2H), 4.0-3.3 (m, 2H), 2.95-2.90 (t, 2H), 2.80-2.60 (m, 2H,), 2.3 (s, 3H), 1.75 (S, 1H), 1.0-0.8 (m, 4H) | 331 | 1 | 5.96 |
| 45 | 36 | TFA salt | 438.87 | CDCl₃ | 7.40-7.35 (d, 1H), 7.34-7.30 (s, 1H), 7.23-7.15 (m, 4H), 6.92-6.68 (m, 2H), 4.6 (d, 1H), 4.4 (m, 1H), 4.20 (m, 1H), | 325 | 1 | 5.73 |

TABLE 4-continued

Synthetic Data

| | | | | | | | | |
|---|---|---|---|---|---|---|---|---|
| | | | | | 4.0 (d, 1H), 3.60-3.45 (m, 1H), 3.10 (bs, 3H), 2.90 (s, 3H), 2.70-2.60 (m, 1H), 2.10 (m, 1H). | | | |
| 50 | 216 | Free Base | 333.43 | CDCl₃ | 8.3 (s, 1H), 8.04 (s, 1H), 7.24-7.22 (m, 1H), 7.09-7.06 (d, 1H), 6.96-6.93 (d, 1H), 6.81-6.79 (dd, 1H), 4.26-4.23 (t, 2H), 3.40-3.30 (t, 2H), 3.09-3.03 (m, 5H), 2.43-2.39 (t, 2H), 2.5 (S, 3H), 2.48 (S, 3H) | 334 | 1 | 4.3 |
| 46 | 186 | Dioxalate Salt | 513.93 | D₂O | 7.55 (s, 1H), 7.43-7.40 (t, 1H), 7.30-7.20 (t, 1H), 4.8-4.2 (m, 4H), 4.2-3.8 (m, 4H), 3.6-3.2 (m, 10H), 3.05 (s, 3H). | 334 | 3 | 4.15 |
| 47 | 164 | Oxalate Salt | 420.93 | DMSO | 7.55 (s, 1H), 7.50-7.40 (d, 1H), 7.20-7.10 (d, 1H), 4.30 (t, 2H), 4.20-4.10 (t, 2H), 3.50 (t, 2H), 3.10 (s, 2H), 2.90 (s, 3H), 1.8-0.8 (m, 13H). | 331 | 3 | 7.33 |
| 48 | 187 | Oxalate Salt | 420.93 | DMSO | 7.40 (d, 1H), 7.12 (t, 1H), 7.02 (d, 1H), 4.70 (s, 2H), 4.20-4.10 (t, 2H), 3.60-3.50 (d, 2H), 3.20-3.08 (d, 2H), 2.90 (s, 3H), 1.8-0.8 (m, 13H). | 331 | 3 | 7.28 |
| 48 | 188 | Oxalate Salt | 420 | DMSO | 7.60 (s, 1H), 7.50-7.40 (d, 1H), 7.10-7.0 (d, 1H), 4.20 (t, 2H), 3.6 (bs, 2H), 3.10-3.0 (d, 2H), 2.90-2.80 (d, 2H), 2.60-2.50 (s, 3H), 1.8-0.8 (m, 13H). | 331 | 3 | 8.38 |
| 49 | 221 | Dioxalate Salt | 477.21 | D₂O | 7.50-7.45 (d, 1H), 7.40 (s, 1H), 7.30-7.20 (d, 1H), 4.80-4.70 (d, 1H), 4.60-4.50 (d, 2H), 4.40-4.30 (d, 1H), 4.0-3.90 (d, 1H), 3.70-3.60 (m, 6H), 3.30-3.20 (m, 1H), 3.19 (s, 3H)3.05 (m, 2H), 2.42 (s, 3H), 2.20-2.11 (d, 2H), 2.10-1.90 (d, 2H) | 298 | 3 | 3.99 |
| 50 | 215 | Free Base | 334.41 | CDCl₃/D₂O | 7.55-7.50 (m, 2H), 7.18-7.0 (m, 6H), 6.22-6.17 (d, 1H), 4.5 (s, 2H), 4.42-4.36 (t, 2H), 3.2-3.0 (m, 5H), 2.5 (s, 3H) | 305 (M-CHO) | 1 | 6.54 |
| 52 | 224 | Dioxalate Salt | 491.5459 | D₂O | 7.45 (d, 1H), 7.4 (s, 1H), 7.2 (d, 1H), 4.6 (bs, 2H), 4.4 (d, 1H), 3.9 (m, 1H), 3.6 (m, 4H), 3.45 (t, 2H), 3.4-3.2 (m, 2H), 3.15 (s, 3H), 3.05 (t, 2H), 2.45 (s, 3H), 2.05-1.4 (m, 6H). | 312 | 3 | 4.11 |
| 53 | 225 | TFA Salt | 453.89 | CDCl₃ | FREE BASE 8.2 (s, 1H), 7.4 (s, 1H), 7.1-6.9 (m, 6H), 4.2 (t, 2H), 3.6 (s, 2H), 3.0 | 340 | 3 | 4.25 |

TABLE 4-continued

Synthetic Data

| | | | | | | | | |
|---|---|---|---|---|---|---|---|---|
| 54 | 226 | TFA Salt | 568.63 | CDCl$_3$ | (t, 2H), 2.7 (t, 2H), 2.5 (s, 6H), 2.6-2.4 (m, 2H) 8.15 (s, 1H), 7.4-7.0 (m, 5H), 4.8-2.6 (m, 15H), 3.05 and 3.0 (s, 3H), 2.55 and 2.4 (s, 3H), 2.0-1.8 (m, 4H), 1.4 (s, 9H) | 455 | 3 | 5.89 |
| 55 | 227 | Free Base | 465.83 | CDCl$_3$ | 7.4-7.2 (m, 5H), 7.05 (d, 1H), 7.0-6.9 (m, 2H), 4.85-4.7 (2H), 4.2 (t, 2H), 3.7 (m, 2H), 3.5 (m, 1H), 3.0 (t, 2H), 2.5 (s, 3H), 2.4-2.2 (m, 2H), 1.8 (m, 1H) | 465 | 3 | 10.46 |
| 56 | 228 | Free Base | 290.4 | CDCl$_3$ | 8.4 (s, 1H), 7.4-7.2 (m, 5H), 7.05 (d, 1H), 6.9 (m, 2H), 4.2 (m, 4H), 3.2 (t, 2H), 3.0 (t, 2H), 2.45 (s, 3H), 2.4 (m, 2H) | 291 | 3 | 6.33 |
| 57 | 229 | Free Base | 335.44 | CDCl3 | 8.4 (s, 1H), 7.45 (d, 1H), 7.4 (s, 1H), 7.3 (d, 1H), 7.1 (d, 1H), 6.65 (d, 1H), 3.7 (m, 2H), 3.2 (m, 1H), 2.95 (t, 2H), 2.8 (m, 1H), 2.55 (s, 3H), 2.5 (t, 2H), 2.4 (bs, 2H), 2.3 (s, 3H), 2.05 (s, 3H) | 336 | 3 | 4.01 |
| 58 | 230 | Oxalate Salt | 467.57001 | DMSO | 9.2 (bs, 1H), 8.2 (s, 1H), 7.5 (d, 1H), 7.4 (d, 1H), 7.25 (s, 1H), 7.15 (s, 1H), 6.95 (s, 1H), 4.25 (m, 4H), 3.4 (m, 2H), 3.0-2.8 (m, 4H), 2.4 (s, 3H), 2.35 (s, 3H). | 306 | 3 | 4.06 |
| 59 | 231 | TFA Salt | 468.52372 | DMSO | 10.05 (bs, 1H), 7.9 (bs, 2H), 7.35 (d, 1H), 7.2 (s, 1H), 7.0 (d, 1H), 4.6-4.2 (m, 6H), 3.9-3.7 (m, 2H), 3.6-3.3 (m, 4H), 3.2 (m, 2H), 3.0 (s, 3H), 2.8 (m, 1H), 2.6-2.4 (m, 2H), 2.4 (s, 1H), 1.85 (m, 2H), 1.4-1.2 (m, 2H). | 355 | 3 | 3.98 |
| 60 | 232 | TFA Salt | 526.35726 | CDCl$_3$ | | 412 | 3 | 5.08 |
| 61 | 233 | DiHCl Salt | 392.37544 | DMSO | 8.5 (d, 1H), 8.1 (t, 1H), 7.65-7.5 (d, 2H), 7.3 (d, 1H), 7.2 (s, 1H), 7.0 (d, 1H), 4.5 (d, 1H), 4.2 (d, 1H), 4.1 (t, 2H), 3.1 (m, 2H), 3.0 (s, 3H), 2.9 (t, 2H), 2.6-2.4 (m, 2H), 2.35 (s, 3H), 2.1 (quint 2H) | 320 | 3 | 4.14 |
| 62 | 234 | TFA Salt | 548.32287 | CDCl$_3$ | 7.7 (s, 1H), 7.5 (d, 1H), 7.25 (m, 1H), 7.1 (d, 1H), 7.05 (t, 1H), 6.95 (t, 1H), 6.7 (t, 1H), 4.6 (d, 1H), 4.25 (m, 2H), 4.0 (d, 1H), 3.65 (m, 1H), 3.1 (m, 1H), 3.05 (m, 2H), 2.9 (m, 1H), 2.85 (s, 3H), 2.5 (m, 1H) | 435 | 3 | 5.08 |
| 67 | 236 | TFA Salt | 459.9 | CDC13 | 7.35 (s, 1H), 7.2 (d, 1H), 7.1 (d, 1H), 4.9 (d, 1H), 4.65 (m, 2H), 4.1 (d, 1H), 3.8 | 346 | 1 | 5.57 |

TABLE 4-continued

Synthetic Data

| | | | | | | | | |
|---|---|---|---|---|---|---|---|---|
| 68 | 237 | Free Base | 359.89 | CDC13 | (m, 1H), 3.5 (dt, 4H), 3.4-3.2 (m, 2H), 3.0 (s, 3H), 3.0-2.95 (m, 1H), 1.8-1.5 (m, 6H). 7.4 (s, 1H), 7.15 (s, 2H), 4.75 (s, 2H), 4.5 (d, 1H), 3.8 (m, 1H), 3.65 (m, 2H), 3.05 (m, 1H), 2.9-2.7 (m, 4H), 2.6 (m, 1H), 2.5 (s, 3H), 1.8-1.0 (m, 5H), 0.95 (d, 3H). | 360 | 1 | 5.94 |
| 69 | 238 | Oxalate Salt | 437.88 | DMSO | 7.5 (s, 1H), 7.35 (d, 1H), 7.1 (d, 1H), 5.05 (s, 2H), 4.35 (s, 2H), 3.75 (t, 2H), 3.65 (m, 1H), 3.65 (m, 5H), 3.4 (m, 1H), 3.05 (t, 2H), 2.95 (m, 1H), 2.9 (s, 3H). | 348 | 1 | 4.87 |
| 70 | 239 | Oxalate Salt | 453.94 | DMSO | 7.5 (s, 1H), 7.45 (d, 1H), 7.1 (d, 1H), 5.15 (s, 2H), 4.3 (s, 2H), 3.8 (m, 2H), 3.6 (m, 1H), 3.6-3.4 (m, 2H), 2.95 (bs, 2H), 2.9 (s, 3H), 2.75 (bs, 2H), 2.6 (bs, 2H). | 364 | 1 | 5.42 |

[2]Method-1 Column: YMC ODS-A 150 mm × 4.6 mm × 5μ, ID: E-AC-1/06/COL/013
  Mobile Phase: A: 0.05% TFA in Water/B: 0.05% TFA in Acetonitrile
  Inj. Vol: 10 μL, Col. Temp.: 30° C., Flow rate: 1.2 mL/min
  Gradient: 10% B to 80% B in 5 min, Hold for 2 min, 7.01-10 min 10% B
Method-2 Column: YMC ODS-A 150 mm × 4.6 mm × 5μ, ID: E-AC-1/06/COL/013
  Mobile Phase: A: 0.05% TFA in Water/B: 0.05% TFA in Acetonitrile
  Inj. Vol: 10 μL, Col. Temp.: 30° C., Flow rate: 1.2 mL/min
  Gradient: 50% B to 100% B in 5 min, Hold for 2 min, 7.01-10 min 50% B
Method-3 Column: YMC ODS-A 150 mm × 4.6 mm × 5μ, ID: E-AC-1/06/COL/013
  Mobile Phase: A: 0.05% TFA in Water/B: 0.05% TFA in Acetonitrile
  Inj. Vol: 10 μL, Col. Temp.: 30° C., Flow rate: 1.4 mL/min
  Gradient: 5% B to 95% B in 8 min, Hold for 1.5 min, 9.51-12 min 5% B Example 60

Determination of the Ability of Compounds of the Invention to Bind a Histamine Receptor To evaluate in radioligand binding assays the activity of compounds of the invention, human recombinant histamine H1 receptor expressed in Chinese hamster ovary (CHO) cells (De Backer M D et al. Biochem. Biophys. Res Comm. 197 (3):1601, 1993) in a modified Tris-HCl buffer (50 mM Tris-HCl, pH 7.4, 2 mM $MgCl_2$, 100 mM NaCl, 250 mM Sucrose) were used. Compounds of invention were incubated with 1.2 nM [$^3$H]Pyrilamine for 180 minutes at 25° C. Non-specific binding was estimated in the presence of 1 μM pyrilamine. Receptor proteins were filtered and washed, the filters were then counted to determine [$^3$H]Pyrilamine specifically bound. Compounds were screened at 1 μM or lower, using 1% DMSO as vehicle. Biochemical assay results are presented as the percent inhibition of specific binding in Table 5.

To evaluate in radioligand binding assays the activity of compounds of the invention, human recombinant histamine H2 receptor expressed in Chinese hamster ovary (CHO) K1 cells (Ruat M. Proc Natl Acad Sci USA. 87(5):1658, 1990) in a 50 mM Phosphate buffer, pH 7.4 were used. Compounds of invention were incubated with 0.1 nM [$^{125}$I]Aminopotentidine for 120 minutes at 25° C. Non-specific binding was estimated in the presence of 3 μM Tiotidine. Receptor proteins were filtered and washed, the filters were then counted to determine [$^{125}$I]Aminopotentidine specifically bound. Compounds were screened at 1 μM or lower, using 1% DMSO as vehicle. Biochemical assay results are presented as the percent inhibition of specific binding in Table 5.

TABLE 5

Binding data.

| Example No. | Compd. No. | Histamine Binding | |
|---|---|---|---|
| | | H1 | H2 |
| 9 | 25 | 97 (1 μM) | 96 (1 μM) |
| | | 89 (0.1 μM) | 75 (0.3 μM) |
| | | 71 (0.03 μM) | 54 (0.1 μM) |
| 10 | 18 | −14 (1 μM) | 1 (1 μM) |
| 39 | 19 | −3 (1 μM) | 10 (1 μM) |
| 11 | 24 | −4 (1 μM) | 13 (1 μM) |
| 40 | 20 | 97 (1 μM) | 72 (1 μM) |
| | | 93 (0.1 μM) | 51 (0.3 μM) |
| | | 73 (0.02 μM) | 33 (0.1 μM) |
| | | 34 (4 nM) | |
| 29 | 139 | Lot 1: 81 (1 μM) | Lot 1: 18 (1 μM) |
| | | Lot 2: 74 (1 μM) | Lot 2: 7 (1 μM) |
| 20 | 21 | 79 (1 μM) | 45 (1 μM) |
| 21 | 22 | 100 (1 μM) | 49 (1 μM) |
| | | 91 (0.3 μM) | 29 (0.3 μM) |
| | | 63 (0.03 μM) | |
| | | 36 (10 nM) | |
| 22 | 23 | 69 (1 μM) | 28 (1 μM) |
| 12 | 37 | 101 (1 μM) | 53 (1 μM) |
| | | 78 (0.1 μM) | 22 (0.3 μM) |
| | | 59 (0.03 μM) | |

TABLE 5-continued

Binding data.

| Example No. | Compd. No. | Histamine Binding H1 | H2 |
|---|---|---|---|
| 13 | 26 | 96 (1 µM) | 73 (1 µM) |
|  |  | 81 (0.1 µM) | 34 (0.3 µM) |
|  |  | 67 (0.03 µM) |  |
| 23 | 27 | 99 (1 µM) | 32 (1 µM) |
|  |  | 77 (0.1 µM) |  |
|  |  | 58 (0.03 µM) |  |
| 14 | 1 | 91 (1 µM) | 82 (1 µM) |
|  |  | 56 (0.1 µM) | 57 (0.3 µM) |
|  |  | 32 (0.03 µM) | 33 (0.1 µM) |
| 15 | 2 | 87 (1 µM) | 81 (1 µM) |
|  |  | 54 (0.1 µM) | 56 (0.3 µM) |
|  |  | 31 (0.03 µM) | 34 (0.1 µM) |
| 32 | 137 | 11 (1 µM) | 45 (1 µM) |
| 30 | 138 | 68 (1 µM) | 27 (1 µM) |
| 33 | 140 | 15 (1 µM) | 45 (1 µM) |
| 16 | 4 | 93 (1 µM) | 51 (1 µM) |
|  |  | 73 (0.1 µM) | 34 (0.3 µM) |
|  |  | 47 (0.03 µM) |  |
| 17 | 3 | 88 (1 µM) | 51 (1 µM) |
| 24 | 5 | 82 (1 µM) | 2 (1 µM) |
| 25 | 6 | 32 (1 µM) | −3 (1 µM) |
| 35 | 28 | 81 (1 µM) | 58 (1 µM) |
|  |  |  | 40 (0.3 µM) |
| 36 | 29 | 100 (1 µM) | 59 (1 µM) |
|  |  | 57 (0.1 µM) | 27 (0.3 µM) |
|  |  | 37 (0.03 µM) |  |
| 34 | 16 | 10 (1 µM) | 3 (1 µM) |
| 37 | 7 | 47 (1 µM) | 58 (1 µM) |
| 38 | 8 | 54 (1 µM) | 26 (1 µM) |
| 26 | 9 | 18 (1 µM) | 16 (1 µM) |
| 27 | 30 | 80 (1 µM) | 34 (1 µM) |
| 28 | 10 | 88 (1 µM) | 12 (1 µM) |
| 18 | 31 | 100 (1 µM) | 34 (1 µM) |
| 31 | 17 | 15 (1 µM) | −2 (1 µM) |
| 41 | 34 | 96 (1 µM) | 89 (1 µM) |
|  |  | 67 (0.1 µM) |  |
|  |  | 22 (10 nM) |  |
| 19 | 32 | 101 (1 µM) | 101 (1 µM) |
|  |  | 87 (0.1 µM) | 99 (0.3 µM) |
|  |  | 52 (10 nM) |  |
| 42 | 163 | 103 (1 µM) | 88 (1 µM) |
|  |  | 92 (0.1 µM) |  |
|  |  | 59 (10 nM) |  |
| 43 | 33 | 98 (1 µM) | 91 (1 µM) |
|  |  | 89 (0.1 µM) | 41 (0.1 µM) |
|  |  | 46 (10 nM) |  |
| 44 | 35 | 99 (1 µM) | 54 (1 µM) |
| 45 | 36 | 99 (1 µM) | 92 (1 µM) |
|  |  | 91 (0.1 µM) | 41 (0.1 µM) |
|  |  | 48 (10 nM) |  |
|  | 216 | 6 (1 µM) | 11 (1 µM) |
| 12 | 217 | −4 (1 µM) | 13 (1 µM) |
| 31 | 218 | 80 (1 µM) | 34 (1 µM) |
| 63 | 220 | 3 (1 µM) | 22 (1 µM) |
| 64 | 219 | 89 (1 µM) | 71 (1 µM) |
| 57 | 221 | 78 (1 µM) | 52 (1 µM) |
| 65 | 222 | 103 (1 µM) | 98 (1 µM) |
|  |  | 101 (0.1 µM) | 89 (0.1 µM) |
|  |  | 85 (0.01 µM) |  |
| 66 | 223 | 100 (1 µM) | 94 (1 µM) |
| 54 | 226 | 87 (1 µM) | 96 (1 µM) |
| 72 | 231 | −11 (1 µM) | 4 (1 µM) |
| 58 | 230 | 46 (1 µM) | 6 (1 µM) |
| 60 | 232 | −6 (1 µM) | 3 (1 µM) |
|  | 233 | 99 (1 µM) | 45 (1 µM) |
| 62 | 89 | 97 (1 µM) | 88 (1 µM) |
| 76 | 241 | 19 (1 µM) | 11 (1 µM) |
| 67 | 236 | 42 (1 µM) | 17 (1 µM) |
| 68 | 237 | 77 (1 µM) | 24 (1 µM) |
| 77 | 242 | 94 (1 µM) | 87 (1 µM) |
| 69 | 238 | 26 (1 µM) | 6 (1 µM) |
| 70 | 239 | 50 (1 µM) | 10 (1 µM) |
| 71 | 240 | 60 (1 µM) | 23 (1 µM) |
| 78 | 243 | 84 (1 µM) | 17 (1 µM) |
| 79 | 244 | 15 (1 µM) | 10 (1 µM) |
| 80 | 245 | 22 (1 µM) | 8 (1 µM) |
| 81 | 246 | 18 (1 µM) | 16 (1 µM) |
| 82 | 247 | 100 (1 µM) | 97 (1 µM) |
| 90 | 255 | 71 (1 µM) | −15 (1 µM) |
| 91 | 256 | −1 (2.5 µM) | −16 (2.5 µM) |

Example 1B

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 minutes at 25° C. Non-specific binding was estimated in the presence of 10 µM phentolamine. Receptor proteins were filtered and washed, the filters were then counted to determine [$^3$H]Prozosin specifically bound. Compounds of the invention were screened at 1 µM or lower, using 1% DMSO as vehicle. Compounds of the invention were tested in this biochemical assay and percent inhibition of specific binding was determined. Certain compounds showed inhibition of specific binding by at least about 80%.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. A. et al., Biochem. Biophys. Res. Commun. 186:760, 1992; Michel A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 minutes at 25° C. Non-specific binding was estimated in the presence of 10 µM phentolamine. Receptor proteins were filtered and washed, the filters were then counted to determine [$^3$H]Prozosin specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. A. et al. Br. J. Pharmacol. 115(6):981, 1995) in a 50 mM Tris-HCl buffer, pH 7.4, was used. Compounds of invention were incubated with 0.6 nM [$^3$H]Prozosin for 60 minutes at 25° C. Non-specific binding was estimated in the presence of 10 µM phentolamine. Receptor proteins were filtered and washed, the filters were then counted to determine [$^3$H]Prozosin specifically bound. Compounds were screened at 1 µM or lower, using 1% DMSO as vehicle. Biochemical assay results are presented as the percent inhibition of specific binding in Table 6.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM $MgCl_2$, 2 mM EDTA) was used. Compounds of invention were incubated with 1 nM [$^3$H]MK-912 for 60 minutes at 25° C. MK912 is (2S-trans)-1,3,4,5',6,6',7,12b-octahydro-1',3'-dimethyl-spiro[2H-benzofuro[2,3-a]quinolizine-2,4'(1'H)-pyrimidin]-2'(3'H)-one hydrochloride Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 6.

Adrenergic $\alpha_{2B}$

To evaluate in radioligand binding assays the activity of compounds of the invention, human recombinant adrenergic $\alpha_{2B}$ receptor expressed in Chinese hamster ovary (CHO-K1) cells (Uhlen S et al. Eur J Pharmacol. 343(1):93, 1998) in a modified Tris-HCl buffer (50 mM Tris-HCl, pH 7.4, 12.5 mM $MgCl_2$, 1 mM EDTA, 0.2% BSA) was used. Compounds of the invention were incubated with 2.5 nM [$^3$H]Rauwolscine for 60 minutes at 25° C. Non-specific binding was estimated in the presence of 10 µM Prozosin. Receptor proteins were filtered and washed, the filters were then counted to determine [$^3$H]Rauwolscine specifically bound. Compounds were screened at 1 µM or lower, using 1% DMSO as vehicle. Biochemical assay results are presented as the percent inhibition of specific binding in Table 6.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM $MgCl_2$, 2 mM EDTA) was used. Compounds of the invention were incubated with 1 nM [$^3$H]MK-912 for 60 minutes at 25° C. Non-specific binding was estimated in the presence of 10 µM WB-4101. Receptor proteins were filtered and washed, the filters were then counted to determine [$^3$H]MK-912 specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

Example 2B

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. K. et al. Proc. Natl. Acad. Sci. USA. 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H]Spiperone for 120 minutes at 25° C. Non-specific binding was estimated in the presence of 10 µM Haloperidol. Receptor proteins were filtered and washed, the filters were then counted to determine [$^3$H]Spiperone specifically bound. Compounds were screened at 1 µM or lower, using 1% DMSO as vehicle. Biochemical assay results are presented as the percent inhibition of specific binding in Table 6.

Example 3B

Determination of the Ability of Compounds of the Invention to Bind a Serotonin Receptor Serotonin (5-Hydroxytryptamine) 5-$HT_{1A}$ To evaluate in radioligand binding assays the activity of compounds of the invention, human recombinant serotonin (5-Hydroxytryptamine) 5-$HT_{1A}$ receptor expressed in Chinese hamster ovary (CHO-K1) cells (Martin G R and Humphrey P P A. Neuropharmacol. 33:261, 1994; May J A, et al. J Pharmacol Exp Ther. 306(1): 301, 2003) in a modified Tris-HCl buffer (50 mM Tris-HCl, pH 7.4, 0.1% Ascorbic Acid, 0.5 mM EDTA, 10 mM $MgSO_4$) was used. Compounds of invention were incubated with 1.5 nM [$^3$H]8-OH-DPAT for 60 minutes at 25° C. Non-specific binding was estimated in the presence of 10 µM Metergoline. Receptor proteins were filtered and washed, the filters were then counted to determine [$^3$H] 8-OH-DPAT specifically bound. Compounds were screened at 1 µM or lower, using 1% DMSO as vehicle. Compounds of the invention were tested in this biochemical assay and percent inhibition of specific binding was determined.

Serotonin (5-Hydroxytryptamine) 5-$HT_{1B}$

To evaluate in radioligand binding assays the activity of compounds of the invention, serotonin (5-Hydroxytryptamine) 5-$HT_{1B}$ receptor from Wistar Rat cerebral cortex (Hoyer et al. Eur J Pharmaco. 118: 1, 1985; Pazos et al. Eur J Pharmacol. 106: 531, 1985) in a modified Tris-HCl buffer (50 mM Tris-HCl, pH 7.4, 154 mM NaCl, 10 µM Pargyline, 30 µM Isoprenaline) was used. Compounds of invention were incubated with 10 pM [$^{125}$I]Cyanopindolol for 90 minutes at 37° C. Non-specific binding was estimated in the presence of 10 µM Serotonin (5-HT). Receptor proteins were filtered and washed, the filters were then counted to determine [$^{125}$I]Cyanopindolol specifically bound. Compounds were screened at 1 µM or lower, using 1% DMSO as vehicle. Compounds of the invention were tested in this biochemical assay and percent inhibition of specific binding was determined.

Serotonin (5-Hydroxytryptamine) 5-$HT_{2A}$

To evaluate in radioligand binding assays the activity of compounds of the invention, human recombinant serotonin (5-Hydroxytryptamine) 5-$HT_{2A}$ receptor expressed in Chinese hamster ovary (CHO-K1) cells (Bonhaus, D. W. et al. Br. J. Pharmacol. 115:622, 1995; Saucier, C. and Albert, P. R., J. Neurochem. 68:1998, 1997) in a 50 mM Tris-HCl buffer, pH 7.4, was used. Compounds of the invention were incubated with 0.5 nM [$^3$H]Ketanserin for 60 minutes at 25° C. Non-specific binding was estimated in the presence of 1 µM Mianserin. Receptor proteins were filtered and washed, the filters were then counted to determine [$^3$H]Ketanserin specifically bound. Compounds were screened at 1 µM or lower, using 1% DMSO as vehicle. Biochemical assay results are presented as the percent inhibition of specific binding in Table 6.

Serotonin (5-Hydroxytryptamine) 5-$HT_{2B}$

To evaluate in radioligand binding assays the activity of compounds of the invention, human recombinant serotonin (5-Hydroxytryptamine) 5-$HT_{2B}$ receptor expressed in Chinese hamster ovary (CHO-K1) cells (Bonhaus, D. W. et al., Br. J. Pharmacol. 115:622, 1995) in a modified Tris-HCl buffer (50 mM Tris-HCl, pH 7.4, 4 mM CaCl$_2$, 0.1% Ascorbic Acid) was used. Compounds of invention were incubated with 1.2 nM [$^3$H]Lysergic acid diethylamide (LSD) for 60 minutes at 37° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Compounds of the invention were tested in this biochemical assay and percent inhibition of specific binding was determined. Certain compounds showed inhibition of specific binding by at least about 80%.

Serotonin (5-Hydroxytryptamine) 5-HT$_{2C}$

To evaluate in radioligand binding assays the activity of compounds of the invention, human recombinant serotonin (5-Hydroxytryptamine) 5-HT$_{2C}$ receptor expressed in Chinese hamster ovary (CHO-K1) cells (Wolf, W. A. and Schutz, J. S., J. Neurochem. 69:1449, 1997) in a modified Tris-HCl buffer (50 mM Tris-HCl, pH 7.4, 0.1% Ascorbic Acid, 10 μM Pargyline) was used. Compounds of the invention were incubated with 1 nM [$^3$H]Mesulergine for 60 minutes at 25° C. Non-specific binding was estimated in the presence of 1 μM Mianserin. Receptor proteins were filtered and washed, the filters were then counted to determine [$^3$H]Mesulergine specifically bound. Compounds were screened at 1 μM or lower, using 1% DMSO as vehicle. Biochemical assay results are presented as the percent inhibition of specific binding in Table 6.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller K et al. Synapase. 11:58, 1992; Boess F G et al. Neuropharmacology. 36:637, 1997) in a modified Tris-HCl buffer (50 mM Tris-HCl, pH 7.4, 1 mM EDTA, 5 mM MgCl$_2$) was used. Compounds of invention were incubated with 0.69 nM [$^3$H]GR-65630 for 60 minutes at 25° C. Non-specific binding was estimated in the presence of 10 μM MDL-72222. Receptor proteins were filtered and washed, the filters were then counted to determine [$^3$]GR-65630 specifically bound. Compounds were screened at 1 μM or lower, using 1% DMSO as vehicle. Compounds of the invention were tested in this biochemical assay and percent inhibition of specific binding was determined. Certain compounds showed inhibition of specific binding by at least about 80%.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman C T et al. Br J Pharmacol. 109:618, 1993) in a 50 mM Tris-HCl, pH 7.4, was used. Compounds of invention were incubated with 0.7 nM [$^3$H]GR-113808 for 30 minutes at 25° C. Non-specific binding was estimated in the presence of 30 μM Serotonin (5-HT). Receptor proteins were filtered and washed, the filters were then counted to determine [$^3$H]GR-113808 specifically bound. Compounds were screened at 1 μM or lower, using 1% DMSO as vehicle. Compounds of the invention were tested in this biochemical assay and percent inhibition of specific binding was determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM MgCl$_2$, 0.5 mM EDTA) was used. Compounds of the invention were incubated with 1.7 nM [$^3$H]Lysergic acid diethylamide (LSD) for 60 minutes at 37° C. Non-specific binding was estimated in the presence of 100 μM Serotonin (5-HT). Receptor proteins were filtered and washed, the filters were then counted to determine [$^3$H]LSD specifically bound. Compounds were screened at 1 μM or lower, using 1% DMSO as vehicle. Compounds of the invention were tested in this biochemical assay and percent inhibition of specific binding was determined. Certain compounds showed inhibition of specific binding by at least about 80%.

Serotonin (5-Hydroxytryptamine) 5-HT$_6$

To evaluate in radioligand binding assays the activity of compounds of the invention, human recombinant serotonin (5-Hydroxytryptamine) 5-HT6 receptor expressed in human HeLa cells (Monsma, F. J. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 minutes at 37° C. Non-specific binding was estimated in the presence of 5 μM Serotonin (5-HT). Receptor proteins were filtered and washed, the filters were then counted to determine [3H]LSD specifically bound. Compounds were screened at 1 μM or lower, using 1% DMSO as vehicle. Biochemical assay results are presented as the percent inhibition of specific binding in Table 6.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. L. et al., J. Pharmacol. Exp. Ther. 268:1403, 1994; Shen, Y. et al., J. Biol. Chem. 268:18200, 1993) in a modified Tris-HCl buffer (50 mM Tris-HCl, pH 7.4, 10 mM MgCl$_2$, 0.5 mM EDTA) was used. Compounds of invention were incubated with 5.5 nM [$^3$H] Lysergic acid diethylamide (LSD) for 2 hours at 25° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Biochemical assay results are presented as the percent inhibition of specific binding in Table 6.

Example 4B

Determination of the Ability of Compounds of the Invention to Bind a Imidazoline I$_2$ Receptor Central Imidazoline I$_2$ To evaluate in radioligand binding assays the activity of compounds of the invention, rat central imidazoline I$_2$ receptor obtained from Wistar Rat cerebral cortex (Brown, C. M. et al., Br. J. Pharmacol. 99:803, 1990) in a modified Tris-HCl buffer (50 mM Tris-HCl buffer, pH 7.4, 0.5 mM EDTA) was used. Compounds of the invention were incubated with 2 nM [$^3$H]Idazoxan for 30 minutes at 25° C. Non-specific binding was estimated in the presence of 1 μM Idazoxan. Receptor proteins were filtered and washed, the filters were then counted to determine [$^3$H]Idazoxan specifically bound. Compounds were screened at 1 μM or lower, using 1% DMSO as vehicle. Compounds of the invention were tested in this biochemical assay and percent inhibition of specific binding was determined. Certain compounds showed inhibition of specific binding by at least about 80%.

Example 5B

Determination of the Ability of Compounds of the Invention to Bind a Histamine Receptor Histamine H1

To evaluate in radioligand binding assays the activity of compounds of the invention, human recombinant histamine H1 receptor expressed in Chinese hamster ovary (CHO) cells (De Backer, M. D. et al., Biochem. Biophys. Res. Comm. 197(3):1601, 1993) in a modified Tris-HCl buffer (50 mM Tris-HCl, pH 7.4, 2 mM $MgCl_2$, 100 mM NaCl, 250 mM Sucrose) was used. Compounds of the invention were incubated with 1.2 nM [$^3$H]Pyrilamine for 180 minutes at 25° C. Non-specific binding was estimated in the presence of 1 μM pyrilamine. Receptor proteins were filtered and washed, the filters were then counted to determine [$^3$H]Pyrilamine specifically bound. Compounds were screened at 1 μM, using 1% DMSO as vehicle. Biochemical assay results are presented as the percent inhibition of specific binding in Table 6.

Histamine H2

To evaluate in radioligand binding assays the activity of compounds of the invention, human recombinant histamine H2 receptor expressed in Chinese hamster ovary (CHO) K1 cells (Ruat, M., Proc. Natl. Acad. Sci. USA. 87(5):1658, 1990) in a 50 mM Phosphate buffer, pH 7.4 was used. Compounds of the invention were incubated with 0.1 nM [$^{125}$I] Aminopotentidine for 120 minutes at 25° C. Non-specific binding was estimated in the presence of 3 μM Tiotidine. Receptor proteins were filtered and washed, the filters were then counted to determine [$^{125}$I]Aminopotentidine specifically bound. Compounds were screened at 1 μM, using 1% DMSO as vehicle. Biochemical assay results are presented as the percent inhibition of specific binding in Table 6.

Histamine H3

To evaluate in radioligand binding assays the activity of compounds of the invention, human recombinant histamine $H_3$ receptor expressed in Chinese hamster ovary (CHO-K1) cells (Yanai K et al. Jpn J Pharmacol. 65(2): 107, 1994; Zhu Y et al. Mol Pharmacol. 59(3): 434, 2001) in a modified Tris-HCl buffer (50 mM Tris-HCl, pH 7.4, 5 mM $MgCl_2$, 0.04% BSA) was used. Compounds of invention were incubated with 3 nM [$^3$H]R(−)-α-Methylhistamine for 90 minutes at 25° C. Non-specific binding was estimated in the presence of 1 μM R(−)-α-Methylhistamine. Receptor proteins were filtered and washed, the filters were then counted to determine [$^3$H]R(−)-α-Methylhistamine specifically bound. Compounds were screened at 1 μM or lower, using 1% DMSO as vehicle. Compounds of the invention were tested in this biochemical assay and percent inhibition of specific binding was determined. Certain compounds showed inhibition of binding by at least about 80%.

TABLE 6

Inhibition of ligand binding to aminergic G protein-coupled receptors by compounds of the invention:

| Cmpd No. | Adren. alpha1D | Adren. alpha2A | Adren. alpha2B | Dop. D2L | Hist. H1 | Hist. H2 | Ser. 5-HT2A | Ser. 5-HT2C | Ser. 5-HT6 | Ser. 5-HT7 |
|---|---|---|---|---|---|---|---|---|---|---|
| Dimebon | 91 | 91 | 112 | 41 | 94 | 83 | 82 | 86 | 95 | |
| 1 | 76 | 99 | | 62 | 91 | 82 | 95 | 95 | 87 | 98 |
| 2 | 72 | 94 | | 70 | 87 | 81 | 96 | 97 | 95 | 100 |
| 3 | 48 | 86 | 102 | | 88 | 51 | 98 | 82 | 40 | 81 |
| 4 | 56 | 82 | 106 | | 93 | 51 | 102 | 94 | 82 | 88 |
| 5 | 21 | 20 | 78 | | 82 | 2 | 55 | 9 | 1 | 37 |
| 6 | 6 | 20 | 54 | | 32 | −3 | 74 | 34 | 7 | 39 |
| 7 | 55 | 93 | 114 | | 47 | 58 | 100 | 82 | 49 | 87 |
| 8 | 35 | 65 | 94 | | 54 | 26 | 80 | 36 | 9 | 42 |
| 10 | 19 | 33 | 92 | | 88 | 12 | 69 | 53 | 32 | 73 |
| 16 | 12 | 10 | 10 | | 10 | 3 | 14 | 5 | 6 | 14 |
| 17 | −7 | 56 | 9 | | 15 | −2 | −7 | 8 | 0 | 7 |
| 18 | −10 | −10 | −8 | −7 | −14 | 1 | 5 | −14 | 6 | 10 |
| 19 | −6 | −8 | −8 | −5 | −3 | 10 | 2 | −17 | −5 | 12 |
| 20 | 94 | 98 | 108 | 87 | 97 | 87 | 98 | 98 | 104 | |
| 21 | 76 | 82 | 114 | | 79 | 45 | 94 | 87 | 79 | 97 |
| 22 | 83 | 72 | 105 | 27 | 100 | 53 | 81 | 87 | 91 | 99 |
| 23 | 61 | 57 | 97 | | 69 | 28 | 78 | 53 | 47 | 94 |
| 24 | 6 | 7 | −1 | 3 | −4 | 13 | −2 | 1 | −4 | −2 |
| 25 | 98 | 99 | 108 | 94 | 97 | 96 | 93 | 99 | 103 | |
| 26 | 92 | 99 | 105 | 78 | 96 | 73 | 97 | 93 | 94 | 102 |
| 27 | 63 | 53 | 100 | | 99 | 32 | 63 | 29 | 38 | |
| 28 | 89 | 100 | 108 | 65 | 85 | 84 | 100 | 100 | 99 | 98 |
| 29 | 89 | 91 | 118 | | 100 | 59 | 102 | 84 | 83 | 91 |
| 30 | 68 | 84 | 102 | 29 | 80 | 34 | 91 | 90 | 90 | 99 |
| 31 | 70 | 66 | 91 | | 100 | 34 | 65 | 39 | 64 | 85 |
| 32 | 94 | 97 | 110 | 82 | 101 | 101 | 96 | 100 | 101 | 101 |
| 32 | 94 | 97 | 110 | 82 | 101 | 101 | 96 | 100 | 101 | 101 |
| 33 | 88 | 98 | 100 | 88 | 98 | 91 | 97 | 95 | 100 | 91 |
| 34 | 76 | 99 | 107 | 88 | 96 | 89 | 99 | 96 | 104 | 97 |
| 36 | 87 | 97 | 104 | 92 | 99 | 92 | 98 | 94 | 104 | 99 |
| 37 | 81 | 96 | 102 | 61 | 101 | 53 | 92 | 90 | 91 | 98 |
| 43 | 98 | 100 | 108 | | 110 | 100 | 99 | 100 | 102 | 92 |
| 45 | 92 | 100 | 102 | | 103 | 98 | 100 | 97 | 103 | 99 |
| 47 | 81 | 98 | 101 | | 81 | 78 | 92 | 89 | 99 | 92 |
| 51 | 22 | 26 | 10 | | 94 | 17 | 0 | 2 | 6 | 17 |
| 53 | 13 | 18 | 34 | | 43 | 4 | −1 | 12 | 18 | 49 |
| 55 | 84 | 86 | 90 | 29 | 101 | 62 | 86 | 87 | 94 | |

TABLE 6-continued

Inhibition of ligand binding to aminergic G protein-coupled receptors by compounds of the invention:

| Cmpd No. | Adren. alpha1D | Adren. alpha2A | Adren. alpha2B | Dop. D2L | Hist. H1 | Hist. H2 | Ser. 5-HT2A | Ser. 5-HT2C | Ser. 5-HT6 | Ser. 5-HT7 |
|---|---|---|---|---|---|---|---|---|---|---|
| 56 | 91 | 95 | 119 | 62 | 100 | 76 | 92 | 87 | 102 | 91 |
| 60 | 82 | 84 | 95 | 24 | 101 | 56 | 84 | 90 | 91 | |
| 62 | 51 | 51 | 90 | −3 | 93 | 15 | 85 | 88 | 83 | |
| 68 | 98 | 94 | 111 | 29 | 99 | 49 | 98 | 78 | 88 | 103 |
| 80 | 75 | 98 | 105 | | 89 | 71 | 88 | 90 | 101 | 92 |
| 81 | 47 | 96 | 90 | | 94 | 57 | 99 | 98 | 86 | 89 |
| 82 | 64 | 99 | 99 | | 99 | 99 | 99 | 95 | 103 | 100 |
| 83 | 92 | 100 | 96 | | 97 | 97 | 100 | 99 | 106 | 95 |
| 89 | 82 | 98 | 116 | | 97 | 88 | 90 | 97 | 103 | 100 |
| 110 | 61 | 89 | 109 | 35 | 65 | 94 | 99 | 95 | 94 | 92 |
| 119 | 82 | 81 | 106 | 7 | 33 | 48 | 84 | 81 | 39 | |
| 137 | 12 | 15 | 3 | | 11 | 45 | −2 | 10 | 12 | 15 |
| 138 | 33 | 31 | 19 | | 68 | 27 | 14 | 5 | 22 | 23 |
| 139 | 25 | 50 | 52 | | 74 | 7 | 2 | 0 | 39 | 74 |
| 140 | 14 | 17 | −4 | | 15 | 45 | −3 | −10 | 8 | 2 |
| 162 | 90 | 99 | 112 | | 100 | 94 | 98 | 94 | 99 | 94 |
| 163 | 49 | 93 | 104 | 36 | 103 | 88 | 92 | 99 | 99 | 95 |
| 164 | 32 | 95 | 93 | | 101 | 84 | 91 | 95 | 99 | 92 |
| 186 | 41 | 51 | 79 | | 97 | 25 | 84 | 89 | 83 | 57 |
| 187 | 15 | 90 | 57 | | 64 | 69 | 84 | 77 | 53 | 77 |
| 188 | 8 | 80 | 65 | | 97 | 72 | 58 | 66 | 67 | 41 |
| 189 | 28 | 76 | 72 | 0 | 94 | 87 | | 85 | 66 | |
| 195 | 15 | 4 | 7 | | 3 | 22 | −4 | −5 | 8 | 2 |
| 215 | −5 | 23 | −4 | | −2 | 16 | −6 | 2 | 8 | 10 |
| 216 | −7 | 15 | 3 | | 6 | 11 | 12 | −11 | −8 | 18 |
| 221 | 30 | 37 | 26 | | 78 | 52 | 46 | 69 | 29 | 36 |
| 224 | 22 | 57 | 46 | | 56 | 79 | 32 | 74 | 43 | 61 |
| 225 | 86 | 91 | 107 | 32 | 101 | 72 | 92 | 91 | 81 | |
| 227 | 11 | 0 | 0 | | −5 | 1 | −2 | 4 | 9 | −8 |
| 228 | 76 | 87 | 101 | | 81 | 15 | 77 | 82 | 89 | 95 |
| 230 | 75 | 56 | 104 | | 93 | 30 | 33 | 36 | 45 | |
| 231 | 21 | 29 | 11 | | −11 | 4 | 5 | 49 | 3 | 0 |
| 232 | 5 | 2 | 8 | | −6 | 3 | −10 | 2 | −7 | 6 |
| 233 | 49 | 90 | 96 | | 99 | 45 | 92 | 93 | 95 | 101 |
| 236 | 10 | 0 | 9 | 1 | 42 | 17 | | 54 | 18 | |
| 237 | 14 | 26 | 12 | −1 | 77 | 24 | | 36 | 20 | |
| 238 | 2 | −13 | 14 | −1 | 26 | 6 | | 20 | 5 | |
| 239 | 3 | 0 | 24 | −1 | 50 | 10 | | 65 | 8 | |
| 240 | 42 | 36 | 50 | 9 | 60 | 23 | | 27 | 25 | |
| 243 | 8 | 3 | 6 | 8 | 84 | 17 | | 33 | 12 | |
| 244 | 12 | 22 | 13 | 6 | 15 | 10 | | 22 | 13 | |
| 245 | 1 | 8 | 19 | 4 | 22 | 8 | | 20 | −2 | |
| 246 | 12 | 21 | 11 | 1 | 18 | 16 | | 59 | 2 | |
| 247 | 95 | 99 | 103 | 87 | 100 | 97 | 22$^a$ | 93 | 107 | |
| 248 | 26 | 27 | 75 | 2 | 85 | 7 | | 59 | 67 | |
| 249 | 65 | 97 | 109 | 64 | 100 | 88 | | 98 | 101 | |
| 250 | 93 | 91 | 108 | 21 | 102 | 54 | 101 | 79 | 84 | 93 |
| 251 | 14 | 2 | 8 | −7 | 55 | 21 | | 23 | 7 | |
| 253 | 81 | 93 | 104 | 96 | 97 | 73 | | 93 | 105 | 87 |
| 255 | 2 | −8 | 4 | | 71 | −15 | 1 | 11 | 2 | 11 |
| 256 | −10 | −7 | 4 | | −1 | −6 | 2 | 0 | 2 | |
| 257 | 3 | −4 | 20 | −7 | 64 | 1 | | 47 | 2 | |
| 262 | 3 | 8 | −2 | | 81 | −8 | 6 | 6 | −4 | 6 |
| 263 | 39 | 34 | 105 | −4 | 95 | 15 | 24 | 31 | 31 | |
| 266 | 45 | 83 | 100 | 8 | 93 | 47 | 73 | 67 | 59 | |
| 267 | 92 | 49 | 100 | 21 | 96 | 42 | 73 | 76 | 69 | |
| 274 | −16 | 7 | 9 | | 1 | −2 | 6 | −5 | −2 | −3 |
| 275 | 87 | 29 | 92 | 4 | 92 | 20 | 39 | 31 | 56 | |
| 295 | 4 | 26 | 18 | −7 | −3 | 10 | 0 | −19 | −1 | |
| 296 | 3 | 1 | −8 | 3 | 36 | −4 | 11 | 2 | 3 | |
| 297 | 15 | −2 | 7 | 0 | 43 | 3 | | 11 | 9 | |
| 321 | 4 | 12 | 25 | −1 | 50 | 25 | | 61 | 15 | |
| 322 | 66 | 44 | 115 | 5 | 89 | 20 | 64 | 69 | 75 | |
| 323 | 49 | 6 | 62 | 8 | 93 | 17 | 16 | 20 | 69 | |
| 324 | 53 | 60 | 98 | 28 | 101 | 63 | 86 | 57 | 93 | |
| 325 | 36 | 58 | 58 | −3 | 90 | 22 | 53 | 50 | 41 | |
| 326 | 40 | 55 | 52 | −5 | 47 | 12 | 27 | 31 | 26 | |
| 328 | 23 | 45 | 21 | 6 | 56 | 4 | 46 | 29 | 29 | |
| 329 | 4 | 37 | 68 | | 18 | 16 | 70 | 54 | 15 | 78 |
| 330 | 8 | 1 | 6 | −8 | 8 | 6 | 14 | 17 | 19 | |
| 331 | 63 | 50 | 105 | 20 | 102 | 73 | 93 | 72 | 100 | |
| 333 | 96 | 98 | 105 | 74 | 94 | 92 | 100 | 87 | 100 | 97 |
| 334 | 110 | 101 | 111 | 76 | 99 | 91 | 101 | 97 | 101 | |
| 335 | 91 | 31 | 104 | 44 | 96 | 77 | 97 | 72 | 9 | |

TABLE 6-continued

Inhibition of ligand binding to aminergic G protein-coupled receptors by compounds of the invention:

| Cmpd No. | Adren. alpha1D | Adren. alpha2A | Adren. alpha2B | Dop. D2L | Hist. H1 | Hist. H2 | Ser. 5-HT2A | Ser. 5-HT2C | Ser. 5-HT6 | Ser. 5-HT7 |
|---|---|---|---|---|---|---|---|---|---|---|
| 336 | 98 | 96 | 103 | 82 | 107 | 101 | 96 | 99 | 104 | |
| 337 | 97 | 97 | 117 | 81 | 99 | 92 | 101 | 94 | 104 | |
| 338 | 83 | 99 | 104 | 22 | 96 | 78 | 94 | 68 | 66 | |
| 341 | −3 | 36 | −1 | 8 | 28 | 15 | 39 | 16 | 17 | |
| 342 | 91 | 94 | 108 | 29 | 80 | 39 | 74 | 73 | 72 | |
| 343 | 61 | 90 | 117 | −7 | 98 | 29 | 89 | 69 | 57 | |
| 349 | 100 | 96 | 111 | 86 | 111 | 94 | 97 | 98 | 101 | 100 |
| 351 | 61 | 8 | 43 | 7 | 74 | −2 | 1 | 26 | −4 | |
| 353 | 11 | 8 | 11 | 5 | 10 | −2 | −1 | −15 | 0 | |
| 357 | 89 | 91 | 106 | 47 | 101 | 68 | 69 | 67 | 85 | |
| 358 | 95 | 96 | 109 | 38 | 94 | 47 | 95 | 78 | 65 | |
| 359 | 95 | 77 | 90 | 51 | 99 | 94 | 96 | 91 | 95 | |
| 360 | 96 | 101 | 115 | 37 | 101 | 75 | 97 | 83 | 91 | 91 |
| 361 | 87 | 30 | 94 | 31 | 106 | 25 | 60 | 58 | 76 | |
| 362 | 76 | 14 | 82 | 17 | 98 | 19 | 27 | 40 | 61 | |
| 363 | 73 | 59 | 104 | 24 | 95 | 31 | 75 | 66 | 83 | |
| 364 | 77 | 65 | 109 | 29 | 87 | 13 | 59 | 81 | 70 | |
| 369 | 51 | 25 | 105 | 1 | 39 | 6 | 10 | 57 | 23 | |
| 370 | 71 | 35 | 87 | 10 | 85 | 18 | 15 | 40 | 64 | |
| 371 | 88 | 89 | 98 | 40 | 99 | 74 | 93 | 87 | 88 | |
| 372 | 94 | 100 | 110 | 44 | 101 | 82 | 96 | 77 | 88 | 94 |
| 380 | 73 | 78 | 103 | −5 | 68 | 69 | 88 | 70 | 39 | |
| 387 | 47 | 12 | 95 | 1 | 97 | 11 | 54 | 76 | 79 | |
| 392 | 88 | 89 | 109 | 24 | 98 | 58 | 53 | 82 | 61 | |
| 393 | 16 | 98 | 28 | | 28 | 3 | 19 | 26 | 3 | 8 |
| 394 | 9 | 15 | 19 | | 30 | −2 | 3 | −8 | 5 | 7 |
| 395 | 9 | 4 | 2 | 2 | 20 | 4 | 16 | 50 | 0 | 24 |
| 396 | −20 | 22 | 7 | 12 | −11 | 26 | 26 | 40 | 46 | |
| 397 | 19 | 16 | 40 | 5 | 77 | 32 | 50 | 44 | −9 | |
| 398 | 17 | 23 | 50 | 8 | 76 | 24 | 85 | 69 | 15 | |
| 399 | 6 | 16 | 11 | 0 | 42 | 10 | 8 | 73 | −5 | |
| 401 | 1 | 3 | 3 | −12 | 36 | 14 | 17 | 39 | 1 | |
| 402 | −8 | 7 | −17 | −12 | 10 | 3 | −2 | 8 | −13 | |
| 403 | 19 | 30 | 46 | 2 | 54 | 10 | 32 | 35 | 0 | |
| 404 | 81 | 94 | 95 | 35 | 102 | 88 | 88 | 78 | 94 | |
| 417 | 1 | 28 | −1 | −12 | 10 | 19 | 23 | 29 | 5 | |
| 424 | 57 | 28 | 94 | 17 | 104 | 19 | 52 | 76 | 82 | |
| 425 | 65 | 49 | 99 | −1 | 100 | 85 | 84 | 72 | 64 | |
| 426 | 69 | 42 | 98 | −7 | 99 | 66 | 85 | 80 | 65 | |
| 429 | 69 | 67 | 115 | 23 | 100 | 68 | 76 | 84 | 79 | |
| 443 | 91 | 87 | 117 | 29 | 102 | 94 | 94 | 95 | 96 | |
| 444 | 91 | 89 | 113 | 32 | 101 | 80 | 95 | 95 | 96 | |
| 449 | 39 | 84 | 104 | 12 | 46 | 51 | 83 | 87 | 37 | |
| 452 | 82 | 92 | 104 | 52 | 109 | 92 | 97 | 93 | 93 | 96 |
| 453 | 15 | 39 | 103 | −4 | 68 | 5 | 42 | 22 | 31 | |
| 454 | 43 | 65 | 112 | 4 | 90 | 26 | 68 | 38 | 62 | |
| 455 | 81 | 93 | 120 | 88 | 80 | 91 | 99 | 97 | 99 | 98 |
| 456 | 96 | 106 | 110 | 76 | 99 | 98 | 104 | 99 | 98 | |
| 457 | 64 | 85 | 108 | 34 | 91 | 88 | 100 | 93 | 90 | |
| 459 | 0 | −9 | −20 | −7 | 0 | −4 | 1 | 3 | −10 | |
| 476 | 95 | 87 | 97 | 30 | 98 | 96 | 100 | 96 | 87 | |
| 481 | 3 | 3 | 19 | 16 | 4 | −17 | 27 | 20 | 14 | |
| 482 | 2 | −17 | 10 | 7 | −2 | −9 | −7 | 17 | 4 | |
| 483 | 3 | −7 | 12 | 0 | −5 | −7 | 2 | 9 | 13 | |
| 484 | 10 | 28 | 30 | 15 | 7 | −4 | 39 | 31 | 14 | |
| 485 | 69 | 86 | 98 | 43 | 105 | 71 | 69 | 91 | 94 | |
| 486 | 22 | 4 | 7 | 0 | 28 | 11 | 19 | 31 | 14 | |
| 487 | 90 | 88 | 100 | 42 | 98 | 80 | 87 | 84 | 94 | |
| 488 | 84 | 70 | 108 | 22 | 41 | 82 | 95 | 86 | 68 | |
| 493 | 84 | 74 | 101 | 17 | 46 | 53 | 95 | 95 | 73 | |
| 516 | 26 | 3 | 21 | −4 | 49 | 12 | 6 | 58 | 9 | |
| C4-1 | 60 | 95 | 94 | 14 | 93 | 47 | 96 | 91 | 51 | 88 |
| C4-4 | 92 | 96 | 102 | 46 | 101 | 68 | 100 | 98 | 103 | 96 |
| C4-5 | 56 | 56 | 73 | 18 | 82 | 22 | 89 | 81 | 73 | 66 |
| C4-6 | 84 | 96 | 94 | 36 | 100 | 68 | 99 | 94 | 105 | 90 |
| C4-7 | 62 | 86 | 86 | 22 | 98 | 46 | 101 | 90 | 88 | 90 |
| C1-1 | 64 | 93 | 110 | 18 | 101 | 57 | 94 | 84 | 77 | 89 |
| C1-5 | 92 | 92 | 113 | 36 | 100 | 73 | 97 | 93 | 101 | 93 |
| C1-6 | 72 | 55 | 110 | 29 | 104 | 21 | 84 | 90 | 84 | 57 |
| C1-7 | 66 | 88 | 113 | 25 | 99 | 55 | 96 | 91 | 91 | 90 |

[a]Percent Inhibition at 1 nM

Example 6B

Determination of Serotonin (5-Hydroxytryptamine) 5-HT$_{2A}$ Agonist/Antagonist of Compounds of the Invention To determine for agonist or antagonist activity of compounds of the invention in functional assays, human recombinant serotonin 5-HT$_{2A}$ receptor expressed in human embryonic kidney (HEK-293) cells (Jerman J C, Brough S J, Gager T, Wood M, Coldwell M C, Smart D and Middlemiss D N. Eur J Pharmacol, 414: 23-30, 2001) was used. Cells were suspended in DMEM buffer, and distributed in microplates. A cytoplasmic calcium fluorescent indicator which varies proportionally to the free cytosolic Ca$^{2+}$ ion concentration was mixed with probenicid in HBSS buffer complemented with 20 mM Hepes (pH 7.4), added into each well and equilibrated with the cells for 30 min at 37° C. followed by 30 min at 22° C.

To measure agonist effects, compounds of the invention, reference agonist or HBSS buffer (basal control) is added to the cells and changes in fluorescence intensity are measured using a microplate reader. For stimulated control measurements, 5-HT at 100 nM is added in separate assay wells.

The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the compounds of the invention, reference antagonist or HBSS buffer was followed by the addition of 3 nM 5-HT or HBSS buffer (basal control) prior the fluorescence measurements. The results were expressed as a percent inhibition of the control response to 3 nM 5-HT in Table 7. The standard reference antagonist was ketanserin, which was tested in each experiment at several concentrations to generate a concentration-response curve from which its IC$_{50}$ value was calculated. Compounds were screened at 3 μM or lower, using DMSO as vehicle.

TABLE 7

Serotonin 5-HT2A Antagonist Assay
Serotonin 5HT2A Antagonist Assay

| Test Concentration (M) | % of Control Agonist Response | | |
|---|---|---|---|
| | 1st Assay | 2nd Assay | Mean |
| Cmpd No. 36 | 3.00E−08 | 109 | 108 | 108.7 |
| Cmpd No. 36 | 1.00E−07 | 111 | 102 | 106.4 |
| Cmpd No. 36 | 1.00E−07 | 100 | 106 | 103 |
| Cmpd No. 36 | 1.00E−07 | 105 | 115 | 109.9 |
| Cmpd No. 36 | 3.00E−07 | 92 | 105 | 98.8 |
| Cmpd No. 36 | 3.00E−07 | 92 | 98 | 94.8 |
| Cmpd No. 36 | 3.00E−07 | 109 | 97 | 102.8 |
| Cmpd No. 36 | 1.00E−06 | 21 | 30 | 25.4 |
| Cmpd No. 36 | 1.00E−06 | 72 | 69 | 70.4 |
| Cmpd No. 36 | 1.00E−06 | 68 | 55 | 61.8 |
| Cmpd No. 36 | 3.00E−06 | 12 | −2 | 5.3 |
| Cmpd No. 36 | 3.00E−06 | −4 | 23 | 9.7 |
| Cmpd No. 36 | 3.00E−06 | 1 | 0 | 0.4 |
| Cmpd No. 253 | 3.00E−08 | 114 | 119 | 116.5 |
| Cmpd No. 253 | 1.00E−07 | 94 | 95 | 94.3 |
| Cmpd No. 253 | 3.00E−07 | 36 | 80 | 57.9 |
| Cmpd No. 253 | 1.00E−06 | 0 | 3 | 1.5 |
| Cmpd No. 253 | 3.00E−06 | −3 | −3 | −2.6 |
| Cmpd No. 247 | 3.00E−08 | 122 | 120 | 121.3 |
| Cmpd No. 247 | 3.00E−08 | 101 | 108 | 104.5 |
| Cmpd No. 247 | 3.00E−08 | 103 | 111 | 107 |
| Cmpd No. 247 | 1.00E−07 | 117 | 116 | 116.5 |
| Cmpd No. 247 | 1.00E−07 | 93 | 94 | 93.5 |
| Cmpd No. 247 | 1.00E−07 | 93 | 95 | 93.9 |
| Cmpd No. 247 | 3.00E−07 | 87 | 76 | 81.7 |
| Cmpd No. 247 | 3.00E−07 | 49 | 72 | 60.6 |
| Cmpd No. 247 | 3.00E−07 | 32 | 38 | 34.9 |
| Cmpd No. 247 | 1.00E−06 | −4 | 0 | −1.7 |
| Cmpd No. 247 | 1.00E−06 | −2 | 3 | 0.3 |
| Cmpd No. 247 | 1.00E−06 | 2 | 0 | 0.7 |
| Cmpd No. 247 | 3.00E−06 | −4 | −3 | −3.2 |

Example 7B

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M. W. Cloning, characterisation and chromosomal localization of a human 5-HT6 serotonin receptor, J. Neurochem., 66: 47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 μM IBMX, and then distributed in microplates and incubated for 45 min at 37° C. in the absence (control) or presence of compounds of the invention or the reference agonist or antagonist.

For agonist determinations, stimulated control measurement, separate assay wells contain 10 μM 5-HT. Following incubation, the cells are lysed and the fluorescence acceptor (D2-labeled cAMP) and fluorescence donor (anti-cAMP antibody labeled with europium cryptate) are added. After 60 min at room temperature, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 μM 5-HT. The standard reference agonist is 5-HT, which is tested in each experiment at several concentrations to generate a concentration-response curve from which its EC$_{50}$ value is calculated.

For antagonist determinations, the reference agonist 5-HT is added at a final concentration of 100 nM. For basal control measurements, separate assay wells do not contain 5-HT. Following 45 min incubation at 37° C., the cells are lysed and the fluorescence acceptor (D2-labeled cAMP) and fluorescence donor (anti-cAMP antibody labeled with europium cryptate) are added.

After 60 min at room temperature, the fluorescence transfer is measured as mentioned above. The results are expressed as a percent inhibition of the control response to 100 nM 5-HT. The standard reference antagonist is methiothepin

Example 8B

Determination of Dopamine $D_{2L}$ Antagonist Activity of Compounds

To determine for agonist or antagonist activity of compounds of the invention in functional assays, human recombinant dopamine $D_{2L}$ receptor stably expressed in Chinese hamster ovary (CHO) cells (Senogles S E et al. J Biol Chem. 265(8): 4507, 1990) was used. Compounds of invention were pre-incubated with the membranes (0.1 mg/ml) and 10 mM GDP in modified HEPES buffer (20 mM HEPES, pH 7.4, 100 mM NaCl, 10 mM $MgCl_2$, 1 mM DTT, 1 mM EDTA) for 20 minutes and Scintillation Proximity Assay (SPA) beads were added for another 60 minutes at 30° C. The reaction was initiated by 0.3 nM [$^{35}$S]GTPγS for an additional 15 minute incubation period. Increase of [$^{35}$S]GTPγS binding by 50 percent or more (≥50%) relative to the 1 mM dopamine response by compounds of the invention indicates possible dopamine $D_{2L}$ receptor agonists activity. Inhibition of a 10 µM dopamine-induced increase of [$^{35}$S]GTPγS binding response by 50 percent or more (≥50%) by compounds of the invention indicated receptor antagonist activity. Compounds were screened at 3 µM or lower, using 0.4% DMSO as vehicle. Assay results are presented as the percent response of specific binding in Table 8.

TABLE 8

Dopamine $D_{2L}$ antagonist activity of compounds of the invention

| | Antagonist Activity As Measured by % Inhibition D2L | | | | |
|---|---|---|---|---|---|
| | 0.03 uM | 0.1 uM | 0.3 uM | 1 uM | 3 uM |
| Cmpd No. 247 | 48, 52 | 66, 81 | 81, 83 | 89 | 91 |
| Cmpd No. 68 | not done | not done | 8 | 27 | 54 |
| Cmpd No. 253 | 36, 56 | 57, 77 | 81, 89 | not done | not done |
| Cmpd No. 36 | 48, 43 | 73, 57 | 83, 88 | 85 | 104 |

When two values are listed, this indicates the assay was run twice.

Example 9B

Determination of Dopamine $D_{2S}$ Antagonist Activity of Compounds of the Invention To determine for agonist or antagonist activity of compounds of the invention in functional assays, human recombinant dopamine $D_{2S}$ receptor stably expressed in Chinese hamster ovary (CHO) cells (Gilliland S L and Alper R H. Naunyn-Schmiedeberg's Archives of Pharmacology. 361: 498, 2000) was used. Compounds of invention were pre-incubated with the membranes (0.05 mg/ml) and 3 µM GDP in modified HEPES buffer (20 mM HEPES, pH 7.4, 100 mM NaCl, 10 mM $MgCl_2$, 1 mM DTT, 1 mM EDTA) for 20 minutes and Scintillation Proximity Assay (SPA) beads were then added for another 60 minutes at 30° C. The reaction was initiated by 0.3 nM [$^{35}$S]GTPγS for an additional 30 minute incubation period. Increase of [$^{35}$S]GTPγS binding by 50 percent or more (≥50%) relative to the 100 µM dopamine response by compounds of the invention indicates possible dopamine $D_{2S}$ receptor agonists activity. Inhibition of a 3 µM dopamine-induced increase of [$^{35}$S]GTPγS binding response by 50 percent or more (≥50%) by compounds of the invention indicated receptor antagonist activity. Compounds were screened at 3 µM or lower, using 0.4% DMSO as vehicle. Assay results are presented as the percent response of specific binding in Table 9.

TABLE 9

Dopamine $D_{2S}$ antagonist activity of compounds of the invention

| | Antagonist Activity As Measured by % Inhibition D2S | | | | |
|---|---|---|---|---|---|
| | 0.03 uM | 0.1 uM | 0.3 uM | 1 uM | 3 uM |
| Cmpd No. 247 | 67, 68 | 97, 89 | 81, 93 | 110 | 108 |
| Cmpd No. 68 | not done | not done | 42 | 70 | 93 |
| Cmpd No. 253 | 104, 80 | 94 | 96 | not done | not done |
| Cmpd No. 36 | 76, 85 | 97 | 98, 104 | 102 | 107 |

When two values are listed, this indicates the assay was run twice.

Example 10B

Determination for Agonist or Antagonist Activity of Compounds of the Invention in a Histamine H1 Functional Assay To determine for agonist or antagonist activity of compounds of the invention in functional assays, human recombinant Histamine $H_1$ receptor expressed in human embryonic kidney (HEK-293) cells (Miller, T. R., Witte, D. G., Ireland, L. M., Kang, C. H., Roch, J. M., Masters, J. N., Esbenshade, T. A And Hancock, A. A. J. Biomol. Screen., 4: 249-258, 1999) is used. Cells are suspended in DMEM buffer, and then distributed in microplates. A cytoplasmic calcium fluorescent indicator—which varies proportionally to the free cytosolic $Ca^{2+}$ ion concentration—is mixed with probenicid in HBSS buffer complemented with 20 mM Hepes (pH 7.4) and is then added into each well and equilibrated with the cells for 30 min at 37° C. and then for another 30 min at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example 11B

Increase of Neurite Outgrowth of Neurons that were Cultured with Compounds of the Invention Neurite Outgrowth in Cortical Neurons Compounds were tested to determine their ability to stimulate neurite outgrowth of cortical neurons. Standard methods were used to isolate cortical neurons. For the isolation of primary rat cortical neurons, the fetal brain from a pregnant rat at 17 days of gestation was prepared in Leibovitz's medium (L15; Gibco). The cortex was dissected out, and the meninges were removed. Trypsin (Gibco) was used to dissociate cortical C with DNAse I. The cells were triturated for 30 minutes with a pipette in Dulbecco's Modified Eagle Media ("DMEM"; Gibco) with 10% Fetal Bovine Serum ("FBS") (Gibco) and centrifuged at 350×g for 10 minutes at room temperature. The cells were suspended in Neurobasal medium supplemented with 2% B27 (Gibco) and 0.5 mM L-glutamine (Gibco). The cells were maintained at 30,000 cells per well of poly-L-lysine coated plates at 37° C. in 5% $CO_2$-95% air atmosphere. After adhesion, a vehicle control or compounds of the invention were added at different concentrations to the medium. BDNF (50 ng/mL) was used as a positive control for neurite growth. After treatment, cultures were washed in phosphate-buffered saline ("PBS"; Gibco) and fixed in glutaraldehyde 2.5% in PBS. Cells were fixed after 3 days growth. Several pictures (~80) of cells with neurites were taken per condition with a camera. The length measurements were made by analysis of the pictures using software from Image-Pro Plus (France). The results were expressed as mean (s.e.m.). Statistical analysis of the data was performed using one way analysis of variance (ANOVA). Results for compounds 395, 68, 250 and 20 are shown in FIGS. 1A-D.

Neurite Outgrowth in Rat Mixed Cortical Cultures

Cortical mixed cultures were prepared from E18 Wistar rat embryos. The cortices were dissected out and the tissue was cut to small pieces. The cells were separated by 15-min incubation with DNase and papain. The cells were collected by centrifugation (1500 rpm, 5 min). The tissue was triturated with a pipette and the cells were plated using the micro-islet protocol (20 000 cells in 25 μl medium) on poly-L-lysine coated 48 wells, in MEM supplemented with 2 mM glutamine, 0.1 μg/ml gentamicin, 10% heat-inactivated fetal bovine serum (FBS-HI) and 10% heat-inactivated horse serum (HS-HI). After the cells had attached to the well, 250 μl medium was added to the wells. Four hours after plating the medium was changed to fresh medium (MEM with supplements and 5% HS-HI) containing test compound at 0.5, 5 and 50 nM concentrations. As positive controls BDNF (50, 100 and/or 150 ng/ml), and/or NGF (50 ng/ml and/or 100 ng/ml) were used. After 2 days in vitro, the cell's conditioned media were collected from plates before fixing the cells. The media samples were centrifuged 13 000 rpm 3 min to get rid of cell debris. The samples were stored at −20 C for later analysis. Cells were formaldehyde-fixed and processed for immunocytochemistry. BDNF levels in the conditioned media were determined with a BDNF ELISA using the manufacturers (Promega, BDNF Emax® ImmunoAssay System, catalog number: G7610) instructions.

The cultures were fixed with 4% formaldehyde in 0.01 M PBS for 30 min and washed once with PBS. The fixed cells were first permeabilized and non-specific binding was blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) was used as a primary antibody. The cells were incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells were visualized by a fluorescence microscope equipped with appropriate filter set, and documented by a high resolution image capturing. The number of cells per field (4 field per well) were counted, and the neurite outgrowth was quantified using Image Pro Plus software.

Figure 1E:
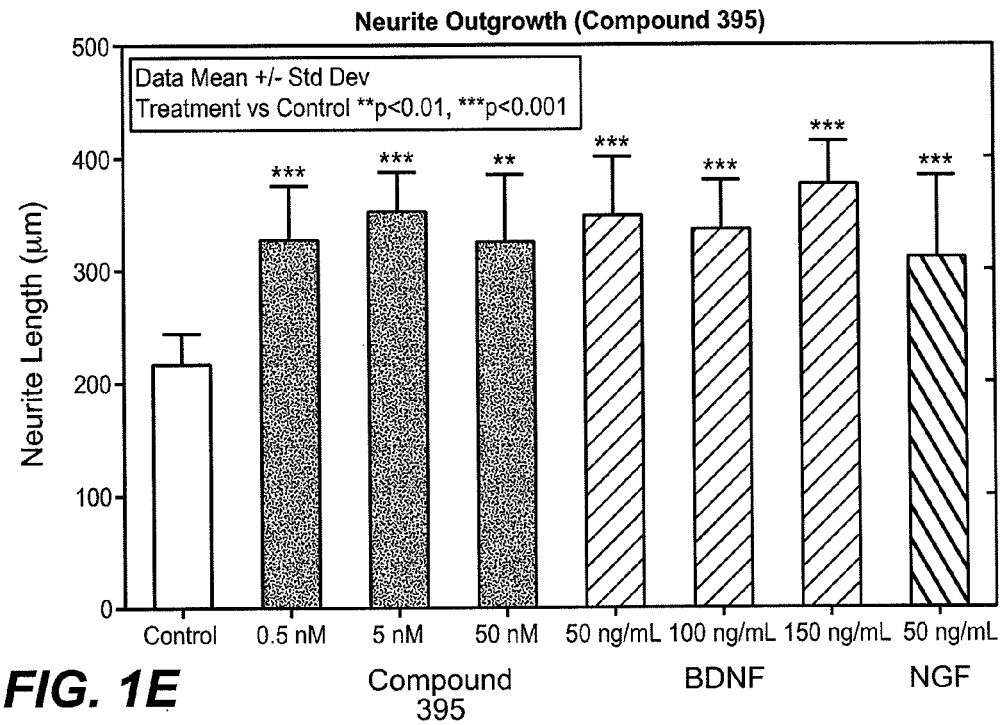
FIG. 1E shows the effect of compound 395 at different concentrations on neurite outgrowth using mixed cortical cultures.
Figure 2A:
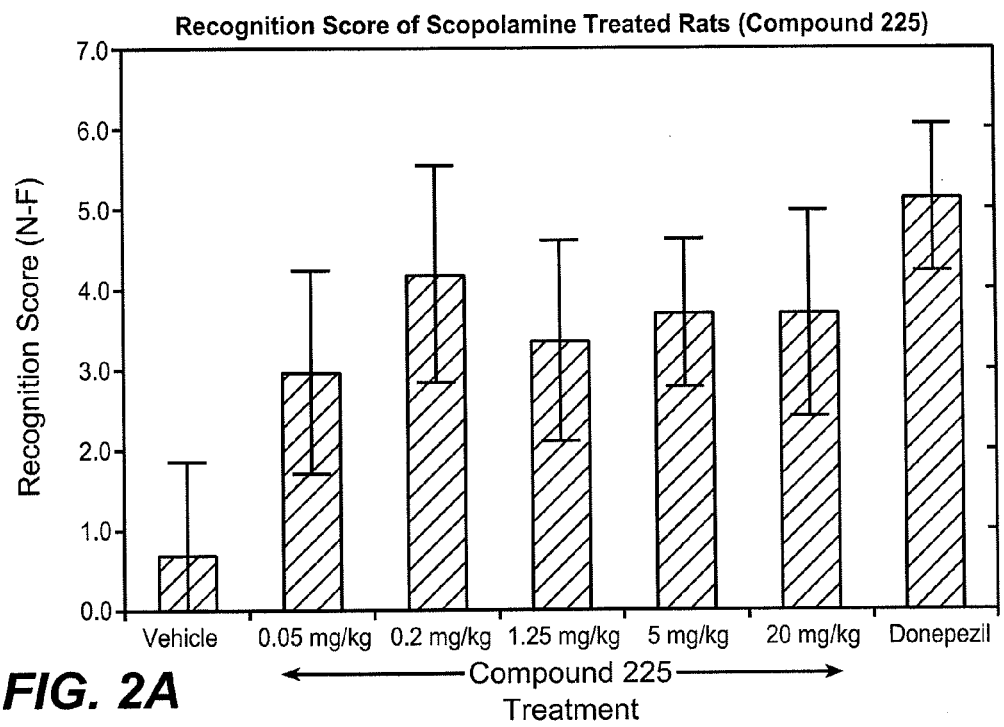
FIGS. 2A and 2B display the recognition score and the percentage of good learners in scopolamine treated rats treated with compound 225 at different concentrations.
Figure 2B:
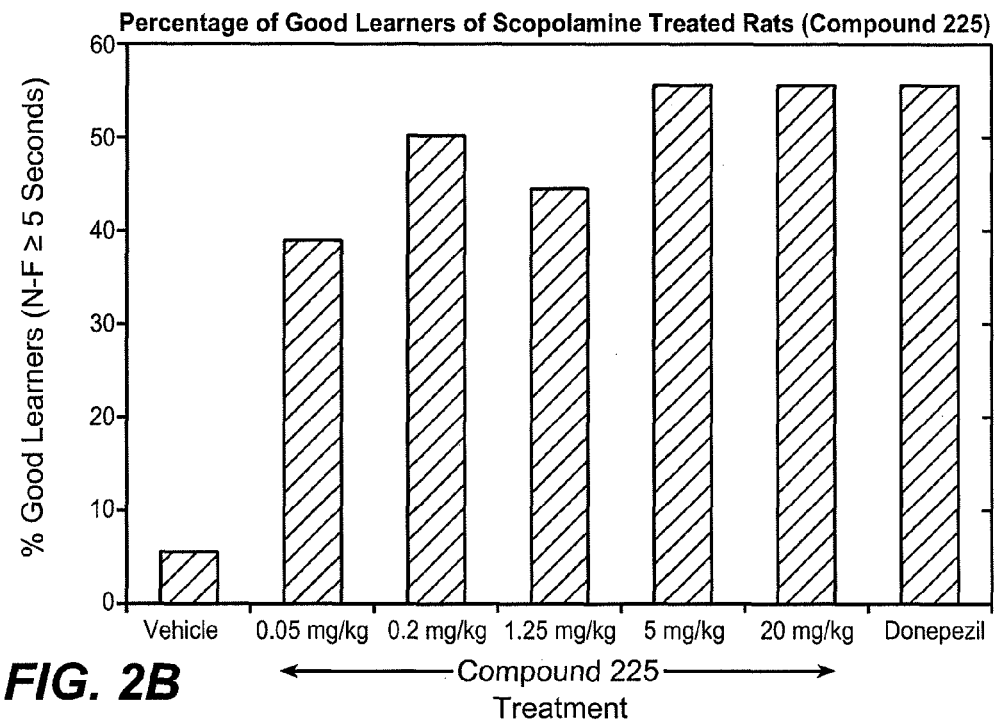
Figure 2C:
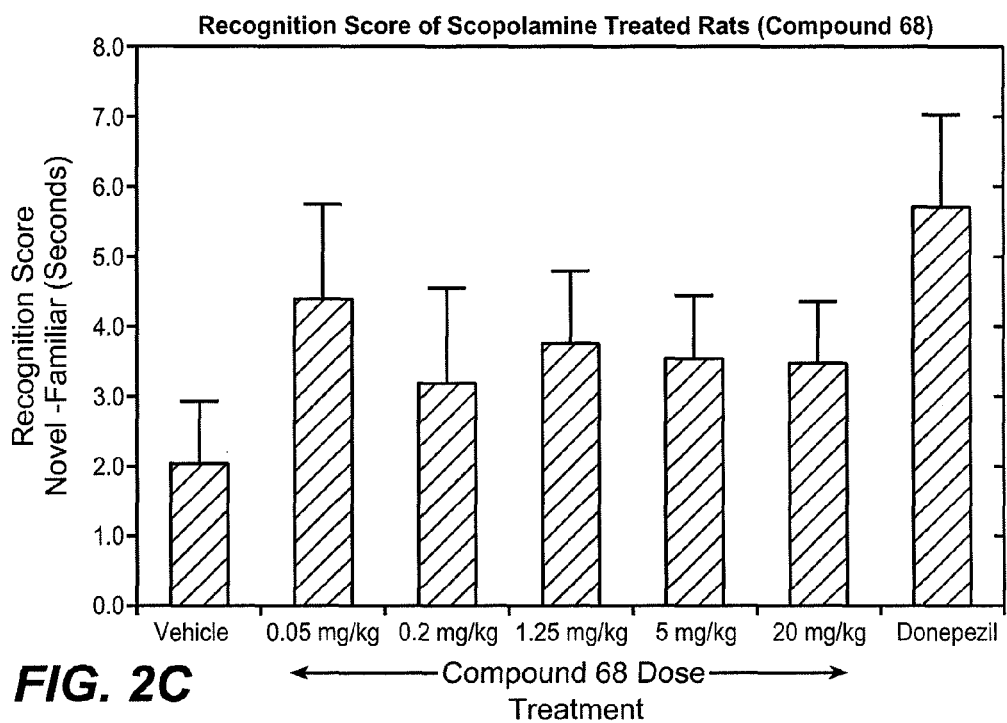
FIGS. 2C and 2D display the recognition score and the percentage of good learners in scopolamine treated rats treated with compound 68 at different concentrations.
Figure 2D:
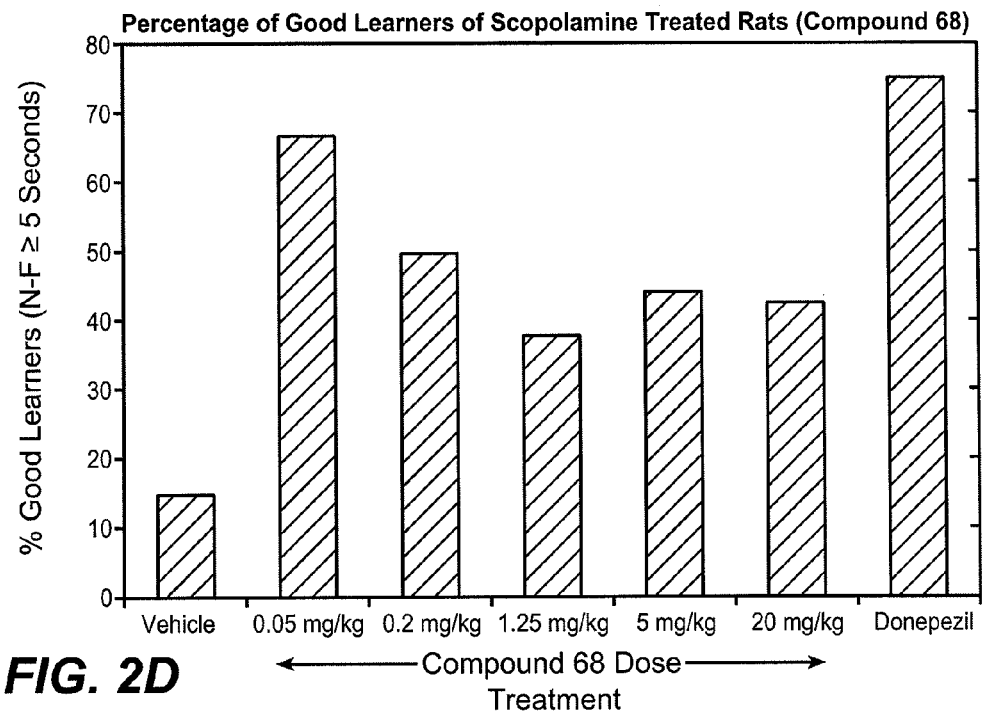
Figure 2E:
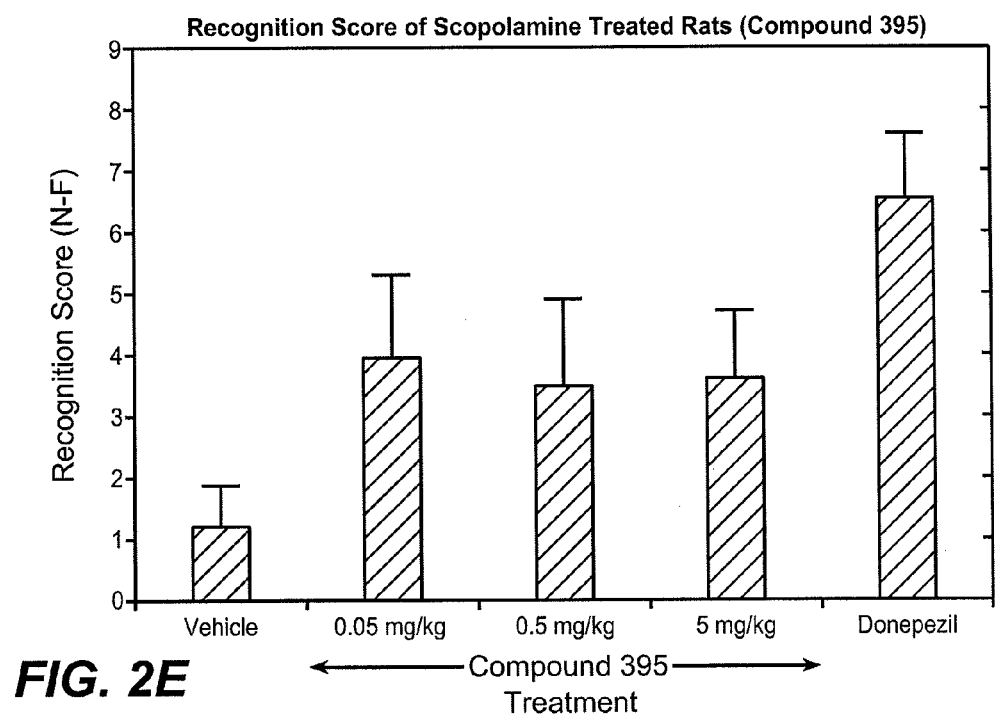
FIGS. 2E and 2F display the recognition score and the percentage of good learners in scopolamine treated rats treated with compound 395 at different concentrations.
Figure 2F:
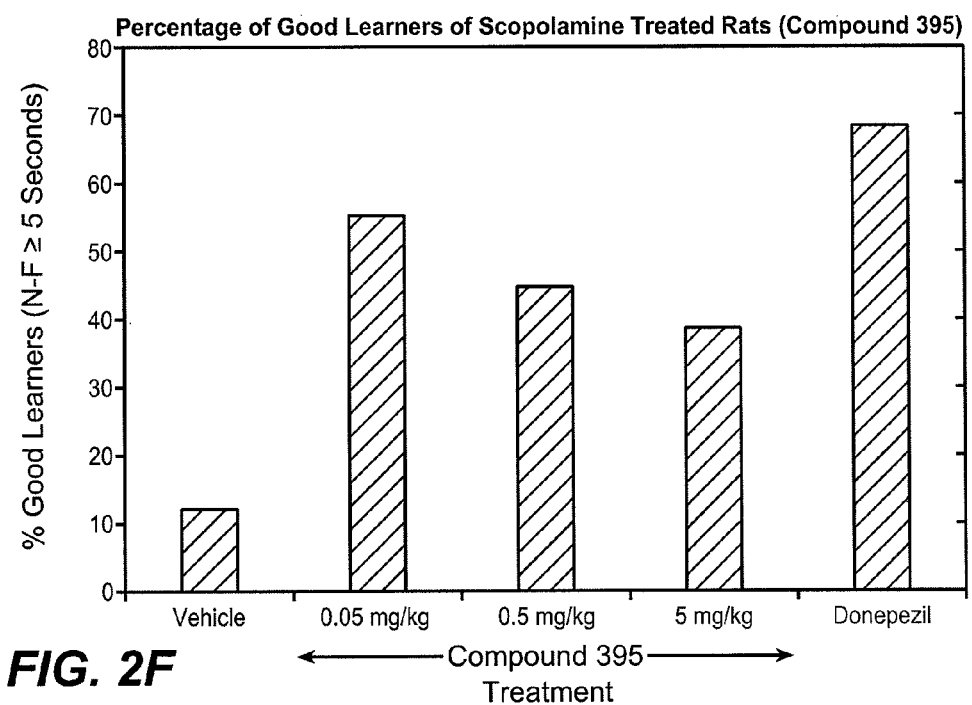
Figure 3A:
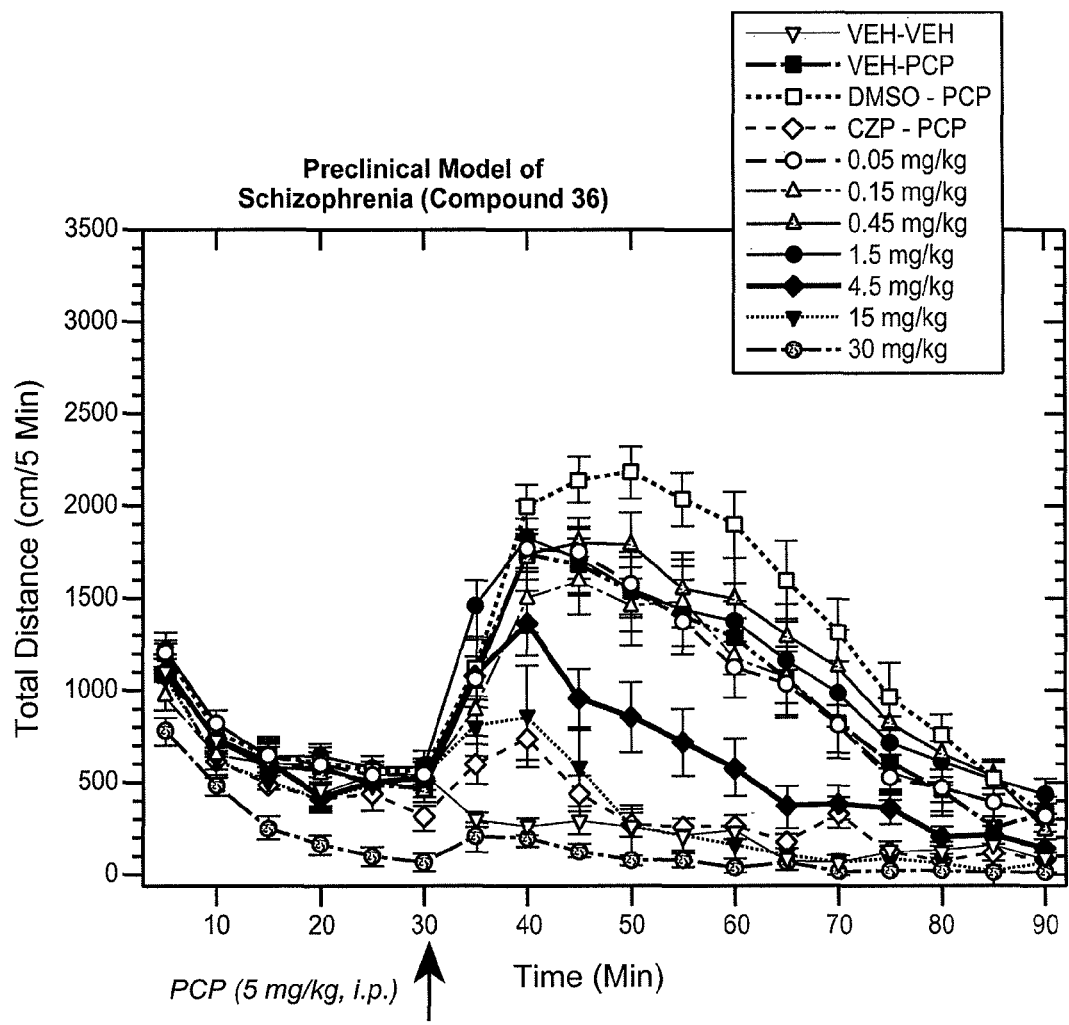
FIG. 3A displays a time course for the effects of clozapine and compound 36 on total distance traveled in the OF during the 90-min test period.
Figure 3B:
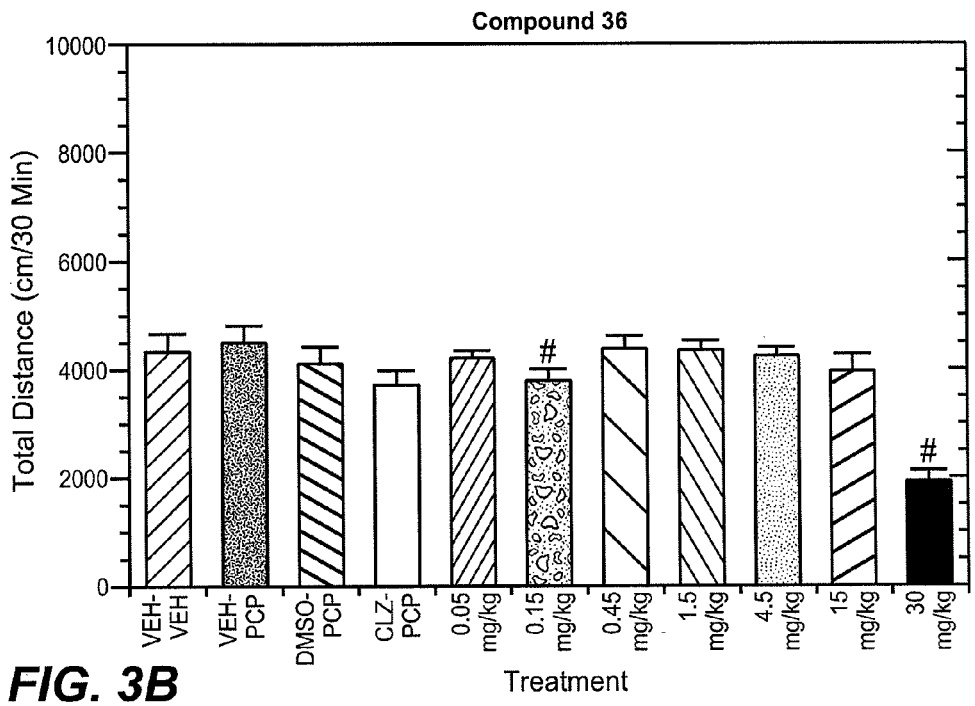
FIGS. 3B and 3C display the effect of clozapine and compound 36 on total distance traveled. Data were summed over the 30 min (B) prior to PCP injection (baseline) and during the 60 min post PCP injection (C) and represent mean±SEM. Asterisk ($*p<0.05$) indicates significant difference compared to DMSO-PCP. Pound sign ($\#p<0.05$) indicates significant difference compared to Vehicle-PCP.
Figure 3C:
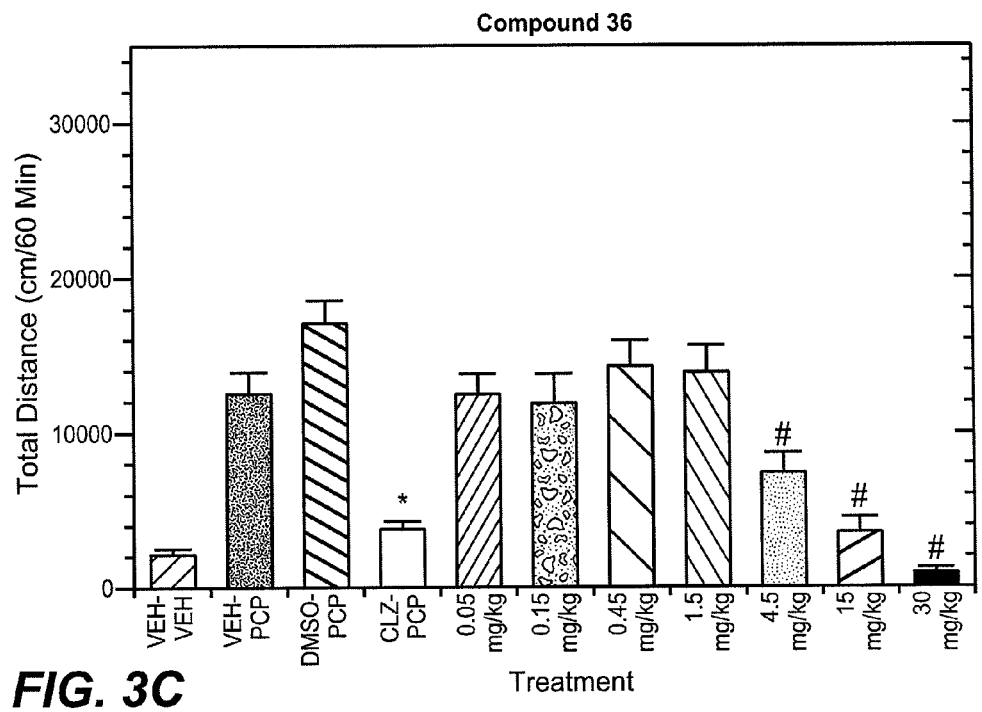
Figure 3D:
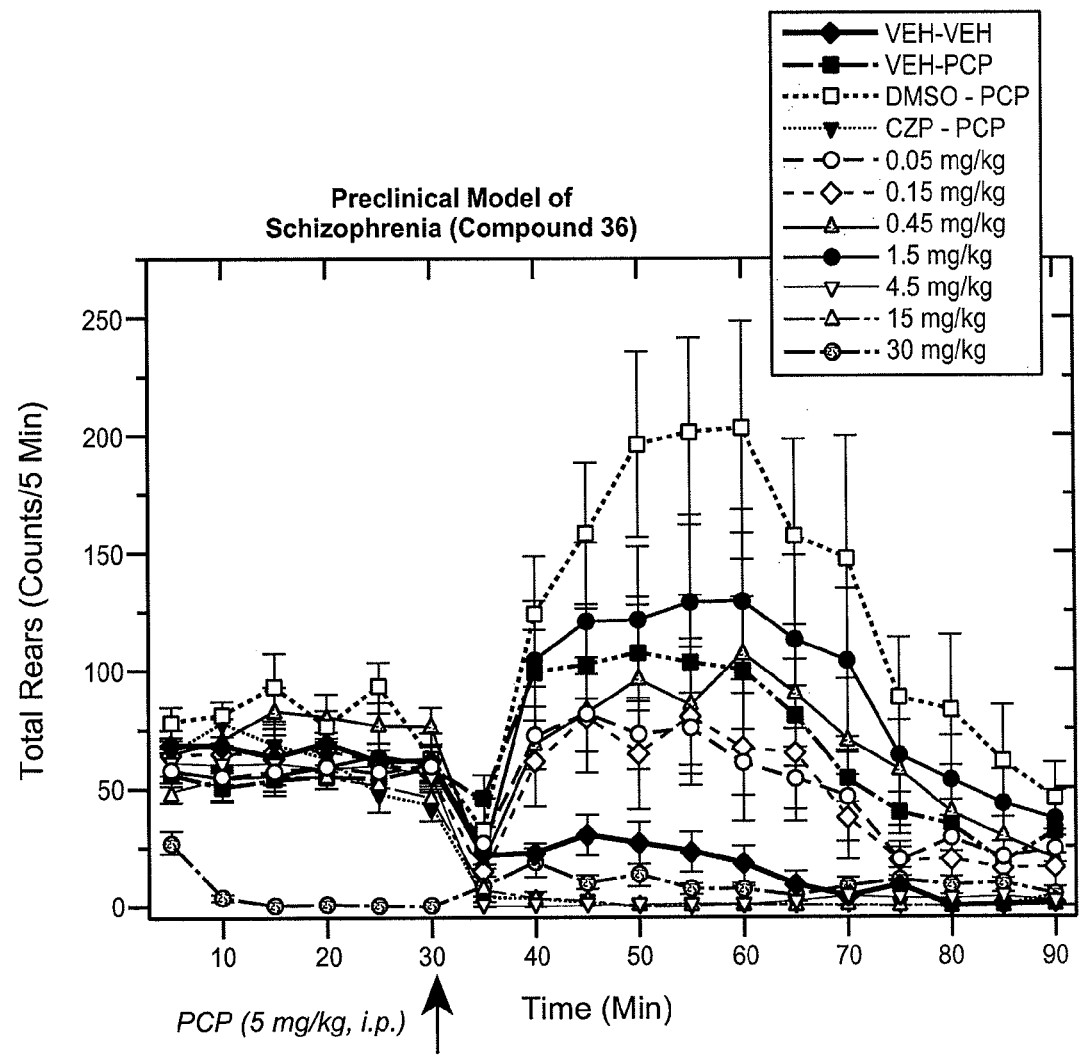
FIG. 3D displays a time course for the effects of clozapine and compound 36 on total rearing during the 90-min test period. Data represent mean±SEM.
Figure 3E:
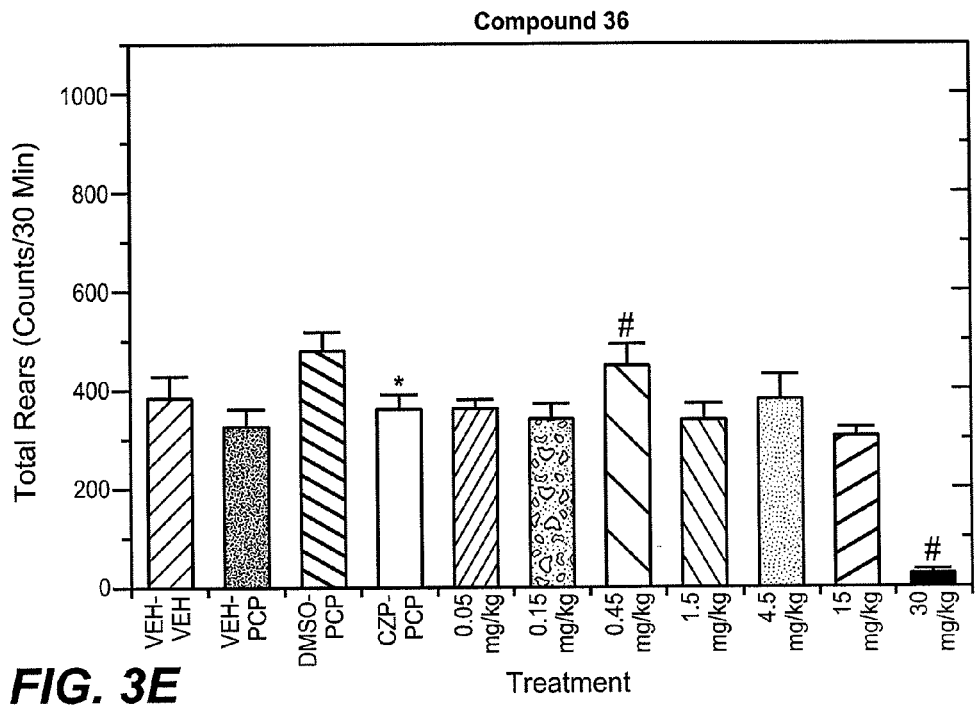
FIGS. 3E and 3F display the effects of clozapine and compound 36 on total rearing. Data were summed over the 30 min (E) prior to PCP injection (baseline) and during the 60 min post PCP injection (F) and represent mean±SEM. Asterisk ($*p<0.05$) indicates significant difference compared to DMSO-PCP. Pound sign ($\#p<0.05$) indicates significant difference compared to Vehicle-PCP.
Figure 3F:
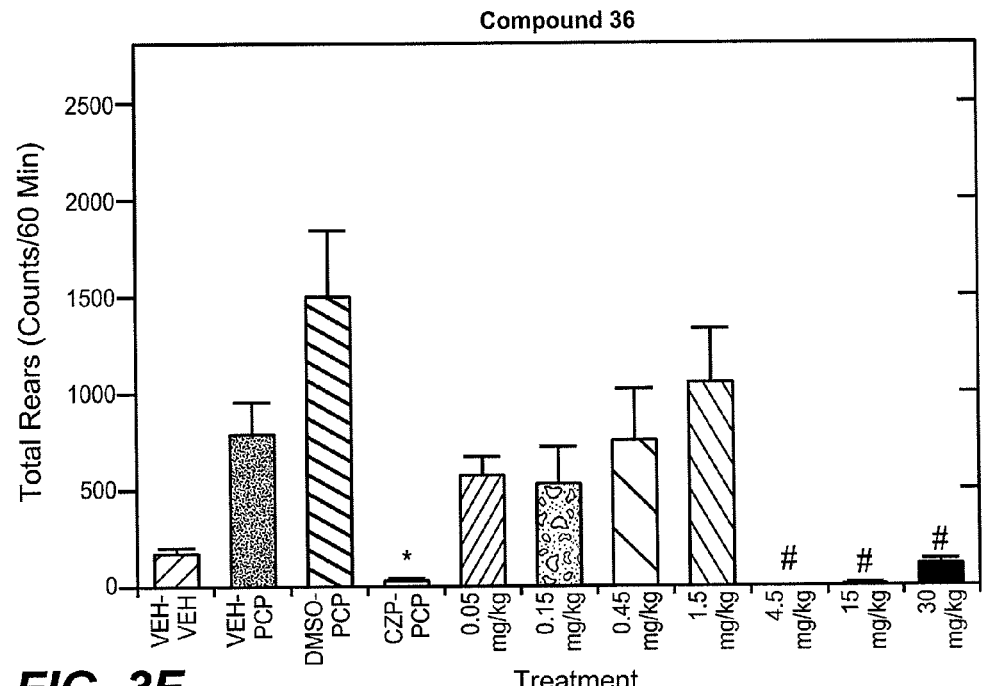

The number of wells per compound concentration used was 6 (n=6). All data are presented as mean±standard deviation (SD) or standard error of mean (SEM), and differences are considered to be statistically significant at the $p<0.05$ level. Statistical analysis was performed using StatsDirect statistical software. Differences between group means were analyzed by using 1-way-ANOVA followed by Dunnet's test (comparison to the vehicle treated group). Results for compound 395 are shown in FIG. 1E.

Example 12B

Use of an In Vivo Model to Evaluate the Ability of Compounds to Enhance Cognition, Learning and Memory in Scopolamine Treated Rats The two-trial object recognition paradigm developed by Ennaceur and Delacour in the rat was used as a model of episodic memory. Ennaceur, A., and Delacour, J. (1988), *Behav. Brain Res.* 31:47-59. The paradigm is based on spontaneous exploratory activity of rodents and does not involve rule learning or reinforcement. The object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem. Behav.* 53:277-283.

Male Sprague-Dawley rats between six and seven weeks old, weighing between 220-300 grams were obtained from Centre d'Elevage (Rue Janvier, B. P. 55, Le Genest-Saint-Isle 53940, France). The animals were housed in groups of 2 to 4 in polypropylene cages (with a floor area of 1032 $cm^2$) under standard conditions: at room temperature (22±2° C.), under a 12 hour light/12 hour dark cycle, with food and water provided ad libitum. Animals were permitted to acclimate to environmental conditions for at least 5 days before therapy began, and were numbered on their tails with indelible marker.

The experimental arena was a square wooden box (60 cm×60 cm×40 cm) painted dark blue, with 15 cm×15 cm black squares under a clear plexiglass floor. The arena and objects placed inside the arena were cleaned with water between each trial to eliminate any odor trails left by rats. The arena was placed in a dark room illuminated only by halogen lamps directed towards the ceiling in order to produce a uniformly dim light in the box of approximately 60 lux. The day before testing, animals were allowed to freely explore the experimental arena for three minutes in the presence of two objects (habituation). Animals to be tested were placed in the experimental room at least 30 minutes before testing.

On the day of the experiment, animals were submitted to two trials separated by an interval of 120 minutes. During the first, or acquisition, trial ($T_1$), rats were placed in the arena, which was prepared with two identical objects. The time required for each animal to complete 15 seconds of object exploration was determined, with a cut-off time of four minutes. Exploration was considered to be directing the nose at a distance less than 2 centimeters ("cm") from the object and/or touching the object. During the second, or testing, trial ($T_2$), one of the objects presented in the first trial was replaced with an unknown or novel object, while the second, familiar object was left in place. Rats were placed back in the arena for three minutes, and exploration of both objects was determined. Locomotor activity of rats (number of times rats cross grid lines visible under the clear plexiglass floor) was scored for during $T_1$ and $T_2$. At the conclusion of the experiments, the rats were sacrificed by an overdose of pentobarbital given intraperitoneally.

The following parameters were measured: (1) time required to achieve 15 seconds of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel} - T_{Familiar}$) was evaluated. The % of animals in each group with $T_{Novel} - T_{Familiar}$ greater than or equal to 5 seconds was also derived; described as % of good learners.

Animals not meeting a minimal level of object exploration were excluded from the study as having naturally low levels of spontaneous exploration. Thus, only rats exploring the objects for at least five seconds ($T_{Novel} + T_{Familiar} > 5$ seconds) were included in the study.

Animals were randomly assigned to groups of 14. Compounds of the invention and controls were administered to animals the groups as follows: Solutions of compounds were prepared freshly each day at a concentration of 0.25 mg/ml using purified water or saline as vehicle. Donepezil, used as a positive control, and scopolamine were administered simultaneously in a single solution of saline (5 mL/kg) prepared freshly each day. Scopolamine was purchased from Sigma Chemical Co. (Catalog No. S-1875; St. Quentin Fallavier, France) was dissolved in saline to a concentration of 0.06 mg/mL.

Donepezil or its vehicle and scopolamine were administered intraperitoneally forty minutes before the acquisition trial ($T_1$). Compounds or their vehicle were administered by gavage twenty-five minutes before the acquisition trial ($T_1$), i.e., five minutes after administration of scopolamine. The volume of administration was 5 ml/kg body weight for compounds administered intraperitoneally, and 10 ml/kg for compounds administered orally.

Recognition scores and % of good learners for compounds 225, 68 and 395 are shown in FIGS. 2 A-F.

Example 13B

Use of an In Vivo Model to Determine the Ability of Compounds to Treat, Prevent and/or Delay the Onset and/or the Development of Schizophrenia in PCP Treated Animals In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidene, which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci. 43(4):375-385). Standard experimental protocols may be employed in this or in other animal models. One protocol involves PCP-induced hyperactivity.

Male C57Bl/6J mice from Jackson Laboratories (Bar Harbor, Me.) were used. Mice were received at 6-weeks of age. Upon receipt, mice were assigned unique identification numbers (tail marked) and were group housed with 4 mice/cage in OPTI mouse ventilated cages. All animals remained housed in groups of four during the remainder of the study. All mice were acclimated to the colony room for at least two weeks prior to testing and were subsequently tested at an average age of 8 weeks of age. During the period of acclimation, mice were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Food and water were provided ad libitum for the duration of the study. In each test, animals were randomly assigned across treatment groups.

The open filed (OF) test assesses locomotor behavior. The open field chambers are Plexiglas square chambers (27.3× 27.3×20.3 cm; Med Associates Inc., St Albans, Vt.) surrounded by infrared photobeams (16×16×16) to measure horizontal and vertical activity. The analysis was configured to divide the open field into a center and periphery zone. Distance traveled was measured from horizontal beam breaks as the mouse moved whereas rearing activity was measured from vertical beam breaks.

Mice (10 to 12 animals per treatment group) were brought to the activity experimental room for at least 1 hr acclimation to the experimental room conditions prior to testing. Eight animals were tested in each run. Mice were administered vehicle (10% DMSO or 5% PEG200 and 1% Tween 80), compound of the invention, clozapine and placed in the OF chambers for 30 min following which they were injected with either water or PCP and placed back in the OF chambers for a 60-minute session. At the end of each OF test session the OF chambers were thoroughly cleaned.

Compound 36 in the PCP Hyperactivity Mouse Model of Schizophrenia

Compound 36 (doses tested include: 0.05, 0.15, 0.45, 1.5, 4.5, 15, 30) was dissolved in 5% PEG200, 1% Tween80 and administered orally 30 min prior to PCP injection. Clozapine (1 mg/kg) was dissolved in 10% DMSO and administered i.p. 30 min prior to PCP injection. PCP (5 mg/kg) was dissolved in sterile injectable water and administered i.p.

Data were analyzed by analysis of variance (ANOVA) followed by post-hoc comparisons with Fisher Tests when appropriate. Baseline activity was measured during the first 30 min of the test prior to PCP injection. PCP-induced activity was measured during the 60 min following PCP injection. Statistical outliers that fell above or below 2 standard deviations from the mean were removed from the final analyses. An effect was considered significant if $p<0.05$.

Total distances traveled and total rearing for compound 36 are shown in FIGS. 3A-F.

Compound 247 in the PCP Hyperactivity Mouse Model of Schizophrenia

Protocol was as described above with the exception of the treatment groups which were as follows: All injections were at a dose volume of 10 ml/kg. The following compounds were used for this study: Compound 247 (0.05, 0.15, 0.45, 1.5, 4.5, and 15.0 mg/kg) was dissolved in Phosphate Buffered Saline (PBS) and administered orally 30 min prior to PCP injection. Clozapine (0.5 and 1.0 mg/kg) was dissolved in 10% DMSO and administered i.p. 30 min prior to Phencyclidine (PCP) injection. PCP (5.0 mg/kg) was dissolved in sterile injectable water and administered i.p.

Figure 4A:
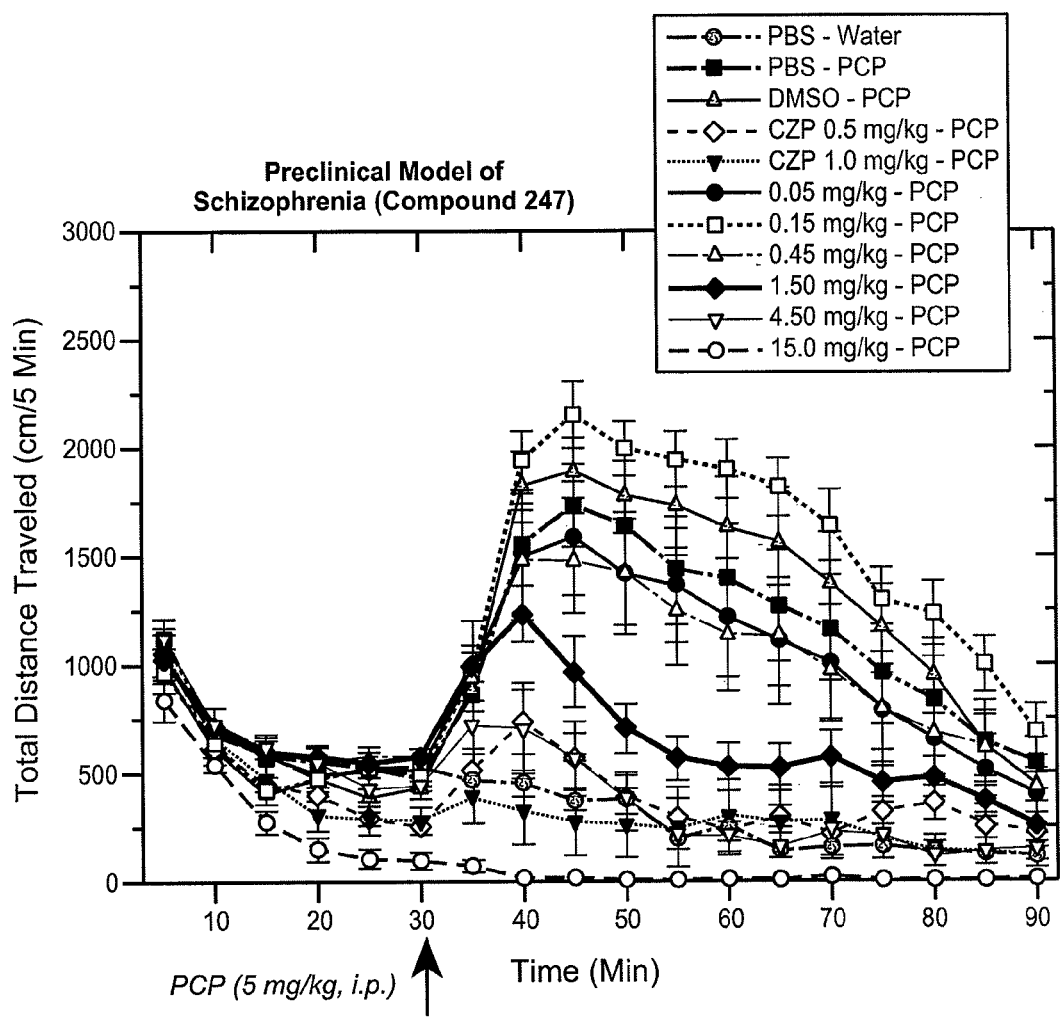
FIG. 4A displays a time course for the effects of clozapine and compound 247 on total distance traveled during the 90-min test period.
Figure 4B:
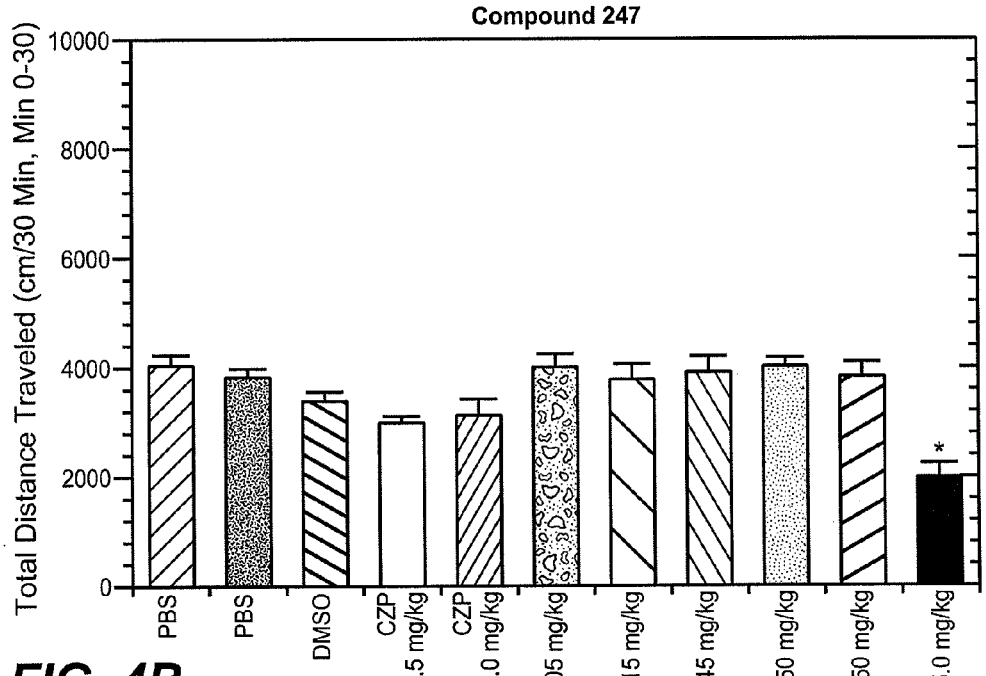
FIGS. 4B and 4C display the effects of clozapine and compound 247 on total distance traveled. Data were summed over the 30 minutes (B) prior to PCP injection (baseline) and during the 60 min post-PCP injection (C) and represent mean±SEM. Asterisk (*) indicates significant difference from PBS, $p<0.05$; Pound sign (#) indicates significant difference from DMSO, $p<0.05$.
Figure 4C:
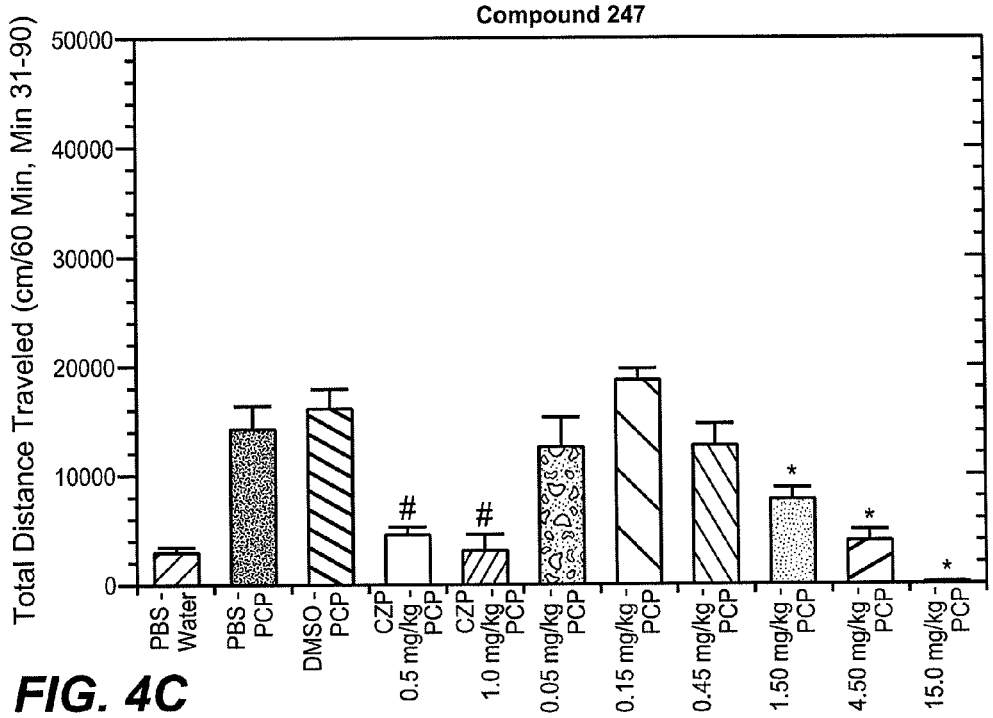

Total distances traveled for compound 247 are shown in FIGS. 4 A-C.

Example 14B

Use of an In Vivo Model to Determine the Ability of Compounds to Treat, Prevent and/or Delay the Onset and/or the Development of Schizophrenia in Amphetamine Treated Animals Male C57Bl/6J mice from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12/12 light/dark cycle. The room temperature is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglas square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 hr acclimation prior to start of treatment. Animals are administered with vehicle, clozapine or test compound and placed in the OF. The time of administration of client compound to each animal is recorded. Baseline activity is recorded for 30 min following which mice receive amphetamine (4 mg/kg) or water placed back in the OF chambers for a 60-minute session. At the end of each open field test session the OF chambers are thoroughly cleaned.

Typically ten to twelve mice are tested in each group. Test compound doses typically range from 0.01 mg/kg to 50 mg/kg.

Data are analyzed by analysis of variance (ANOVA) followed by post-hoc comparisons where appropriate. An effect is considered significant if p<0.05. Data are represented as the mean and standard error to the mean (s.e.m).

Example 15B

Determination of the Effect of Compounds of the Invention on Glutamate-Induced $^{45}Ca^{2\pm}$ Uptake into Synaptosomes of Cortex of Rat Brain Methods Synaptosomes were obtained from cerebral cortex of newborn (9-10 days) Wistar rats using standard Hajos method. The brain was homogenized with 10 volumes of cooled 0.32 M sucrose at 900 rpm. The homogenate was centrifuged at 1500 g for 10 min. and the resulted supernatant was centrifuged at 10000 g for 20 min. The radioactive label was accumulated by suspension of the synaptosomal $P_2$-fraction in the incubation buffer A having the following composition: 132 mM NaCl, 5 mM KCl, 5 mM HEPES, 10 mM glucose, pH 7.4 (protein concentration of approximately 1.5-2 mg/ml). The mixture was further incubated for 5 min with 200 µM glutamate at 37° C. and then $^{45}Ca^{2+}$ uptake was stopped by filtration through GF/B filters (Whatman, England) followed by three washes with cold buffer B (145 mM KCl, 10 mM Tris, 5.4 mM Trilon B, pH 7.4). The radioactivity probes were analyzed by fluid scintillation beta-analyzer (TriCarb, Perkin Elmer). All tests were performed in three parallel trials in 2-3 independent experiments. The amount of $^{45}Ca^{2+}$ uptake was estimated by calculating the difference of radioactive label during the stimulation with glutamate and without the stimulation with agonist. The result is presented as percents with respect to the control measurement which was 100%.

Specific $^{45}Ca^{2+}$ uptake was estimated using the following equation:

$$K_{(43/21)}=[(Ca_4-Ca_3)/(Ca_2-Ca_1)]100\%,$$

where $Ca_1$—$^{45}Ca^{2+}$ uptake for the Control (without glutamate and the compound tested), $Ca_2$—glutamate-induced $^{45}Ca^{2+}$ uptake (glutamate only), $Ca_3$—$^{45}Ca^{2+}$ uptake in the presence of the compound tested (without glutamate), $Ca_4$—$^{45}Ca^{2+}$ uptake in the presence of glutamate and the testing compound.

Statistical analysis of the results was performed using Student's t-test.

Results

Figure 5A:
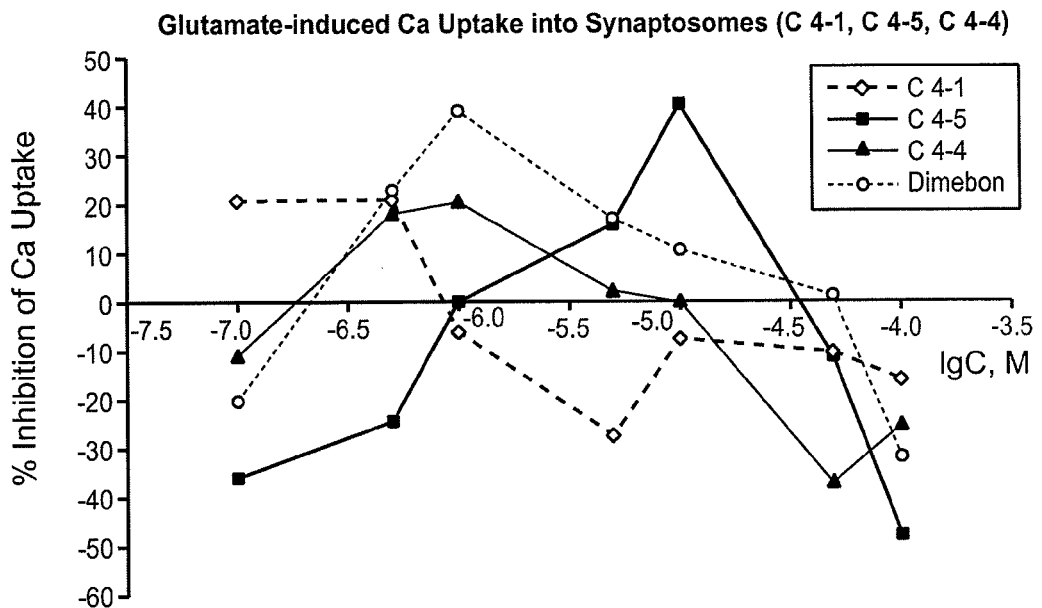
FIG. 5A indicates glutamate-induced Ca uptake into synaptosomes for compounds C 4-1, C 4-5, C 4-4).

The effect of dimebon on a glutamate-induced $^{45}Ca^{2+}$ uptake into synaptosomes of rat cortex was investigated. Dimebon inhibited $^{45}Ca^{2+}$ uptake into synaptosomes at a concentration of 0.25-10 µM. The maximal inhibition $^{45}Ca^{2+}$ uptake into synaptosomes was observed at a concentration of 1 µM dimebon (40%). At concentrations of 0.1 µM and 100 µM, dimebon caused an increase of glutamate-induced $^{45}Ca^{2+}$ uptake into synaptosomes of rat cortex (120.4% and 132%, accordingly) (Table 10, FIG. 5A).

The effect of compound C 4-1 on glutamate-induced $^{45}Ca^{2+}$ uptake into synaptosomes of rat cortex was investigated. Compound C 4-1 inhibited glutamate-induced $^{45}Ca^{2+}$ uptake into synaptosomes of rat cortex at a concentrations of 0.1-0.5 µM by about 20%. With increasing concentrations of C 4-1 glutamate-induced $^{45}Ca^{2+}$ uptake into synaptosomes increased. The maximal increase of glutamate-induced $^{45}Ca^{2+}$ uptake into synaptosomes was observed at a concentration of 5 µM C 4-1 (128% of the control) (Table 10, FIG. 5A).

The effect of compound C 4-4 on glutamate-induced $^{45}Ca^{2+}$ uptake into synaptosomes of rat cortex was investigated. Compound C 4-4 inhibited glutamate-induced $^{45}Ca^{2+}$ uptake into synaptosomes of rat cortex at a concentration of 0.5 µM. The maximal inhibition $^{45}Ca^{2+}$ uptake was observed at a concentration of 1 µM (20.5%). Increasing concentrations (50-100 µM) of C 4-4 caused an increase in glutamate-induced $^{45}Ca^{2+}$ uptake into synaptosomes of rat cortex. The maximal increase of glutamate-induced $^{45}Ca^{2+}$ uptake into synaptosomes was observed at a concentration of 50 µM C 4-1 (137.5% of the control) (Table 10, FIG. 5A).

The effect of compound C 4-5 on glutamate-induced $^{45}Ca^{2+}$ uptake into synaptosomes of rat cortex was investigated. Compound C 4-5 inhibited glutamate-induced $^{45}Ca^{2+}$ uptake into synaptosomes at a concentrations of 1-25 µM. The maximal inhibition (40%) was observed at a concentration of 10 µM C 4-5. At concentrations of 0.5-0.1 µM and at concentrations of 50-100 µM, compound C 4-5 caused an increase in glutamate-induced $^{45}Ca^{2+}$ uptake into synaptosomes of rat cortex. The maximal increase in glutamate-induced $^{45}Ca^{2+}$ uptake into synaptosomes was observed at concentrations of 100 μM and 0.1 μM C 4-5 (148.4% and 136.4%, accordingly) (Table 10, FIG. 5A).

TABLE 10

Effect of dimebon, C 4-1, C 4-4 and C 4-5 on glutamate-induced $^{45}Ca^{2+}$ uptake into synaptosomes of rat cortex.

| | % Ca of control (control - 100%) | | | |
|---|---|---|---|---|
| C, μM | Dimebon | C 4-1 | C 4-4 | C 4-5 |
| 0.1 | 120 ± 3.3 | 79.4 ± 6.1 | 111.2 ± 9.2 | 136.4 ± 11.8 |
| 0.25 | 77.2 ± 6.0 | — | — | — |
| 0.5 | 64.4 ± 12.4 | 79.2 ± 10 | 81.8 ± 14 | 124.6 ± 13.7 |
| 1.0 | 61.3 ± 8.1 | 106.1 ± 7.9 | 79.5 ± 11.1 | 99.8 ± 0.1 |
| 5.0 | 83.2 ± 4.1 | 128 ± 4.5 | 97.9 ± 4.3 | 84.2 ± 0.7 |
| 10 | 89.3 ± 1.2 | 107.6 ± 3.5 | 99.9 ± 11.7 | 59.9 ± 0.2 |
| 25 | 97.2 ± 8.5 | 114.3 ± 0.5 | 93.6 ± 15.7 | 98.6 ± 9.4 |
| 50 | 98.7 ± 8.8 | 110.1 ± 5.1 | 137.5 ± 5.4 | 111.7 ± 11.2 |
| 100 | 132 ± 2.9 | 115.9 ± 8.8 | 125.3 ± 11.2 | 148.4 ± 7.3 |

Figure 5B:
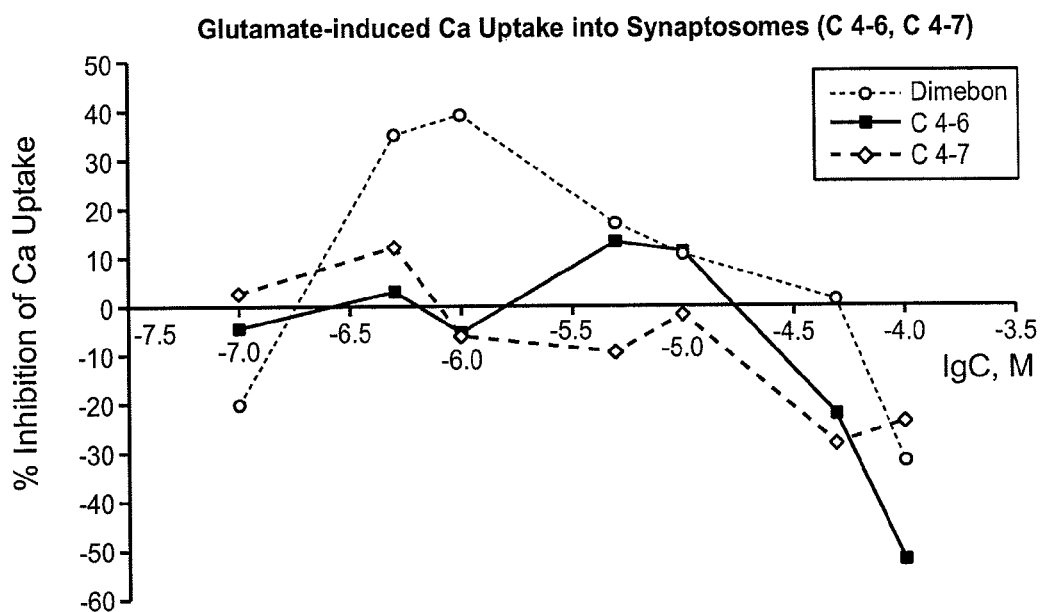
FIG. 5B indicates glutamate-induced Ca uptake into synaptosomes for compounds C 4-6, C 4-7.

The effect of compound C 4-6 on glutamate-induced $^{45}Ca^{2+}$ uptake into synaptosomes of rat cortex was investigated. C 4-6 inhibited glutamate-induced $^{45}Ca^{2+}$ uptake into synaptosomes at a concentration of 5-10 μM. With increasing concentrations (50-100 μM) compound C 4-6 caused an increase in glutamate-induced $^{45}Ca^{2+}$ uptake into synaptosomes of rat cortex. The maximal increase in glutamate-induced $^{45}Ca^{2+}$ uptake into synaptosomes was observed at a concentration of 100 μM (152.2% of the control) (Table 11, FIG. 5B).

TABLE 11

Effect of C 4-6, C 4-7, C 1-1, C 1-5, C 1-7 on glutamate-induced $^{45}Ca^{2+}$ uptake into synaptosomes of rat cortex.

| | % Ca of control (control - 100%) | | | | |
|---|---|---|---|---|---|
| C, μM | C 4-6 | C 4-7 | C 1-1 | C 1-5 | C 1-7 |
| 0.1 | 103.6 ± 11.4 | 97.2 ± 5.5 | 85.5 ± 5.8 | 96.3 ± 5.6 | 77.5 ± 2.4 |
| 0.5 | 96.9 ± 11.9 | 87.6 ± 3.9 | 86.9 ± 4.2 | 77.5 ± 0.8 | 72.7 ± 0.3 |
| 1.0 | 105.5 ± 5.2 | 105.3 ± 2.8 | 100.3 ± 6.5 | 94 ± 3.4 | 98.6 ± 2.4 |
| 5.0 | 86.5 ± 6.1 | 109.2 ± 10 | 98.8 ± 3.2 | 96 ± 1.5 | 131.8 ± 8.8 |
| 10 | 88.6 ± 2.8 | 101.6 ± 7.8 | 91 ± 11.9 | 117.2 ± 1.3 | 134.5 ± 9.2 |
| 50 | 122.1 ± 8.5 | 128.3 ± 8.1 | 126.9 ± 4.5 | 115.4 ± 4.8 | 126.7 ± 7.7 |
| 100 | 152.0 ± 6.7 | 123.6 ± 4.9 | 111.9 ± 11.3 | 130.1 ± 7.4 | 139.8 ± 6.5 |

The effect of compound C 4-7 on glutamate-induced $^{45}Ca^{2+}$ uptake into synaptosomes of rat cortex was investigated. C 4-7 did not affect glutamate-induced $^{45}Ca^{2+}$ uptake into synaptosomes at a concentration of 0.1-10 μM. At a concentration of 50-100 μM, compound C 4-7 caused an increase in glutamate-induced $^{45}Ca^{2+}$ uptake into synaptosomes of rat cortex (~128% of the control) (Table 11, FIG. 5B).

Figure 6A:
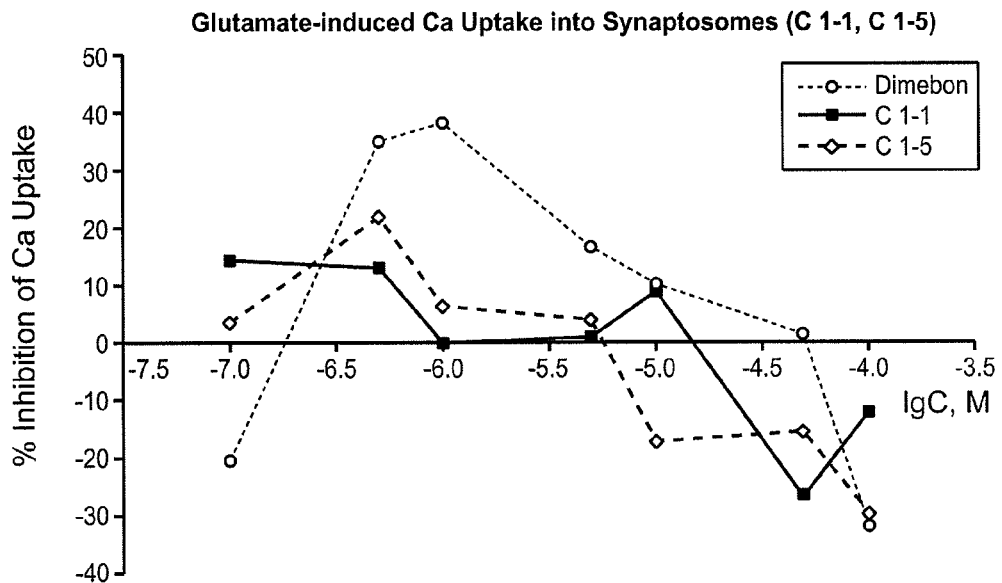
FIG. 6A indicates glutamate-induced Ca uptake into synaptosomes for compounds C 1-1, C 1-5.

The effect of compound C 1-1 on glutamate-induced $^{45}Ca^{2+}$ uptake into synaptosomes of rat cortex was investigated. C 1-1 inhibited glutamate-induced $^{45}Ca^{2+}$ uptake into synaptosomes (~13%) at a concentration of 0.1-0.5 μM. With increasing concentrations (50-100 μM) compound C 1-1 caused an increase in glutamate-induced $^{45}Ca^{2+}$ uptake into synaptosomes. The maximal increase in glutamate-induced $^{45}Ca^{2+}$ uptake into synaptosomes was observed at a concentration of 50 μM (126.9% of the control) (Table 11, FIG. 6A).

The effect of compound C 1-5 on glutamate-induced $^{45}Ca^{2+}$ uptake into synaptosomes of rat cortex was investigated. Compound C 1-5 inhibited glutamate-induced $^{45}Ca^{2+}$ uptake into synaptosomes: at a concentrations of 0.5 μM by about 22.5%. Compound C 1-5 caused an increase in glutamate-induced $^{45}Ca^{2+}$ uptake into synaptosomes of rat cortex at a concentration of 100 μM (130% of the control) (Table 11, FIG. 6A).

Figure 6B:
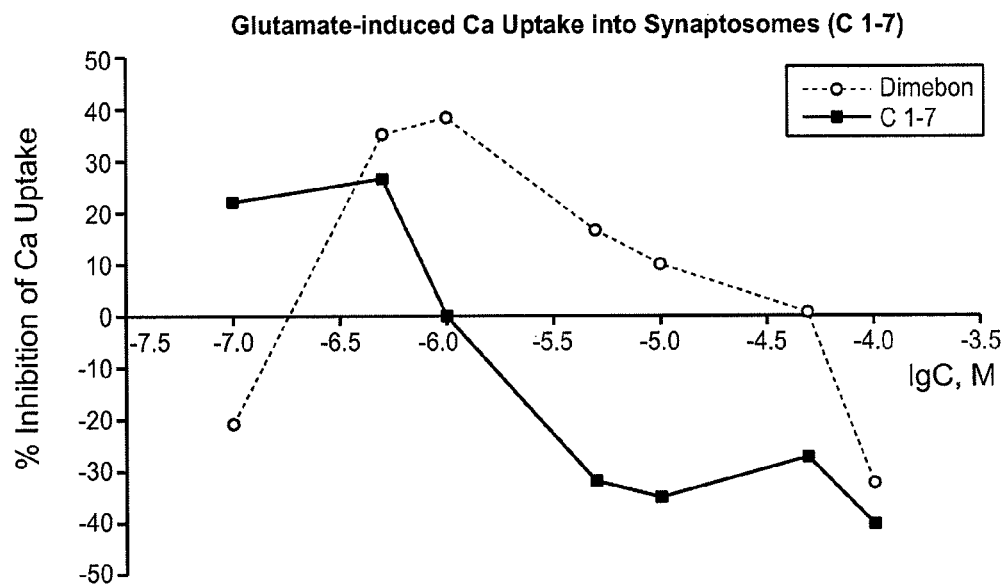
FIG. 6B indicates glutamate-induced Ca uptake into synaptosomes for compounds C 1-7.

The effect of compound C 1-7 on glutamate-induced $^{45}Ca^{2+}$ uptake into synaptosomes of rat cortex was investigated. Compound C 1-7 inhibited glutamate-induced $^{45}Ca^{2+}$ uptake into synaptosomes: at a concentration of 0.1-0.5 μM inhibition was ~27.3%. Compound C 1-7 caused an increase in glutamate-induced $^{45}Ca^{2+}$ uptake into synaptosomes of rat cortex at a concentration of 5-100 μM. The maximal increase in glutamate-induced $^{45}Ca^{2+}$ uptake into synaptosomes was observed at a concentration of 100 μM (139.8% of the control) (Table 11, FIG. 6B).

Figure 6C:
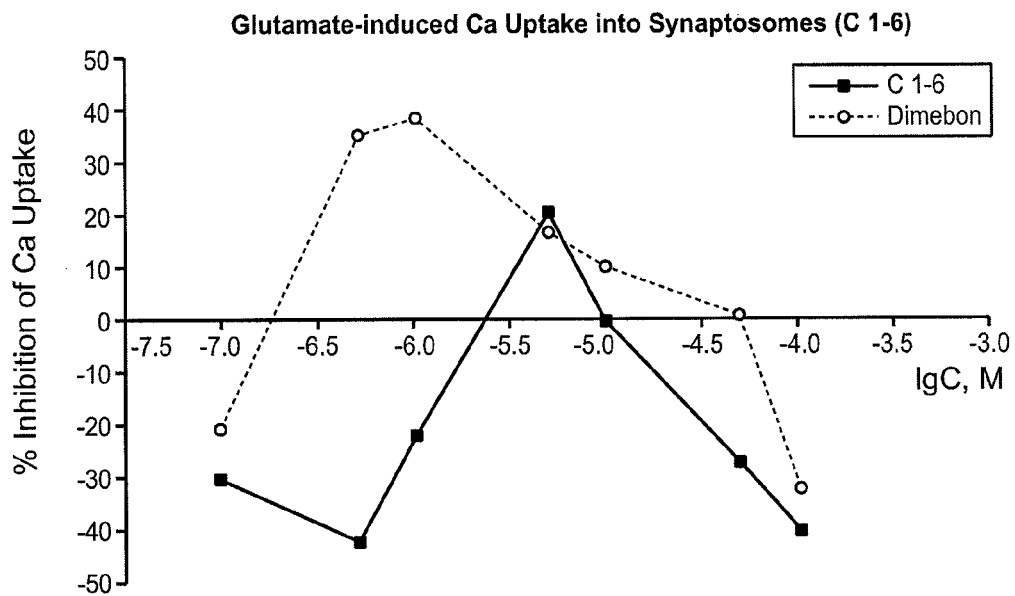
FIG. 6C indicates glutamate-induced Ca uptake into synaptosomes for compounds C 1-6.

The effect of compound C 1-6 on glutamate-induced $^{45}Ca^{2+}$ uptake into synaptosomes of rat cortex was investigated. C 1-6 inhibited glutamate-induced $^{45}Ca^{2+}$ uptake into synaptosomes (inhibition ~20%) at a concentration of 5 μM. At a concentration of 0.1-1 μM and 10-100 μM compound C 1-6 caused an increase in glutamate-induced $^{45}Ca^{2+}$ uptake into synaptosomes of rat cortex. The maximal increase in glutamate-induced $^{45}Ca^{2+}$ uptake into synaptosomes was observed at a concentration of 0.5 μM and 100 μM (142% and 140.8% of the control, accordingly) (Table 12, FIG. 6C).

Figure 6D:
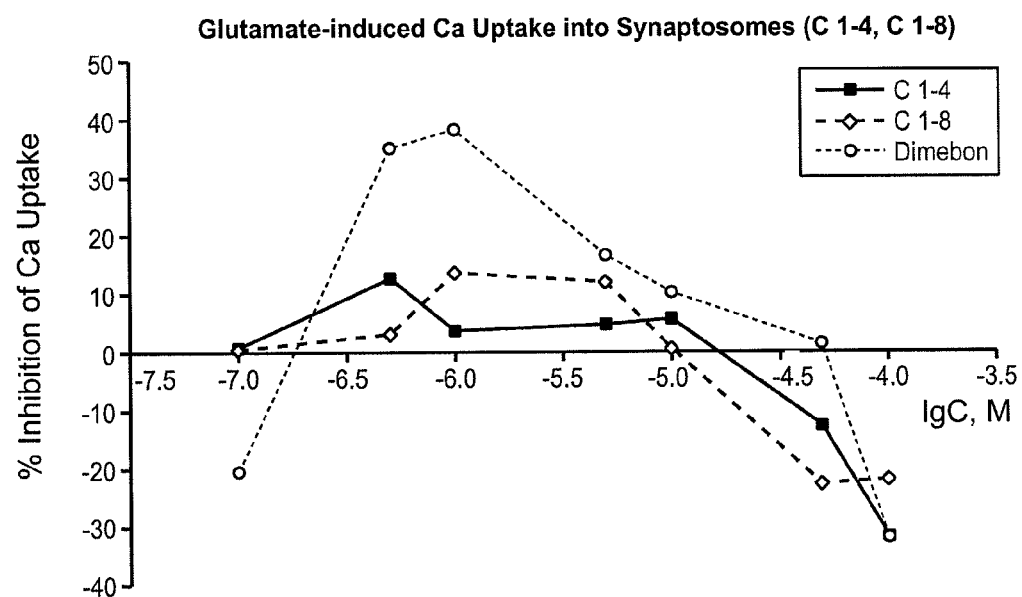
FIG. 6D indicates glutamate-induced Ca uptake into synaptosomes for compounds C 1-4, C 1-8.

The effect of compound C 1-8 on glutamate-induced $^{45}Ca^{2+}$ uptake into synaptosomes of rat cortex was investigated. C 1-8 inhibited glutamate-induced $^{45}Ca^{2+}$ uptake into synaptosomes (inhibition ~14%) at a concentration of 1-5 μM. At concentrations 50-100 μM, compound C 1-8 caused an increase in glutamate-induced $^{45}Ca^{2+}$ uptake into synaptosomes of rat cortex (~122% of control) (Table 12, FIG. 6D).

The effect of compound C 1-4 on glutamate-induced $^{45}Ca^{2+}$ uptake into synaptosomes of rat cortex was investigated. Compound C 1-4 inhibited glutamate-induced $^{45}Ca^{2+}$ uptake into synaptosomes (inhibition ~12.6%) at a concentration of 0.5 μM. At concentrations 50-100 μM, compound C 1-4 caused an increase in glutamate-induced $^{45}Ca^{2+}$ uptake into synaptosomes of rat cortex (~131% of control) (Table 12, FIG. 6D).

Figure 7:
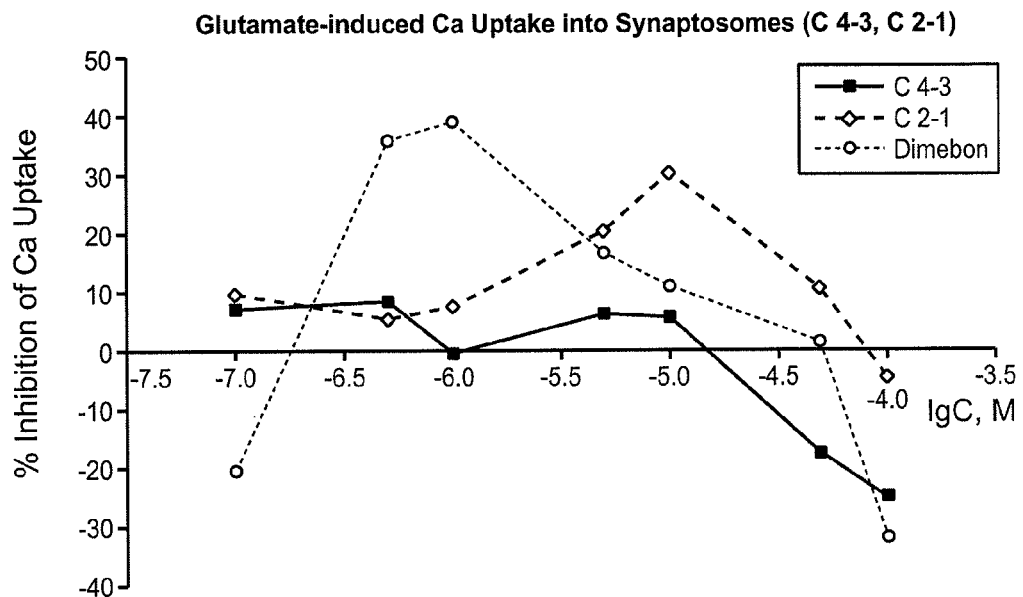
FIG. 7 indicates glutamate-induced Ca uptake into synaptosomes for compounds C 4-3, C 2-1.
Figure 8:
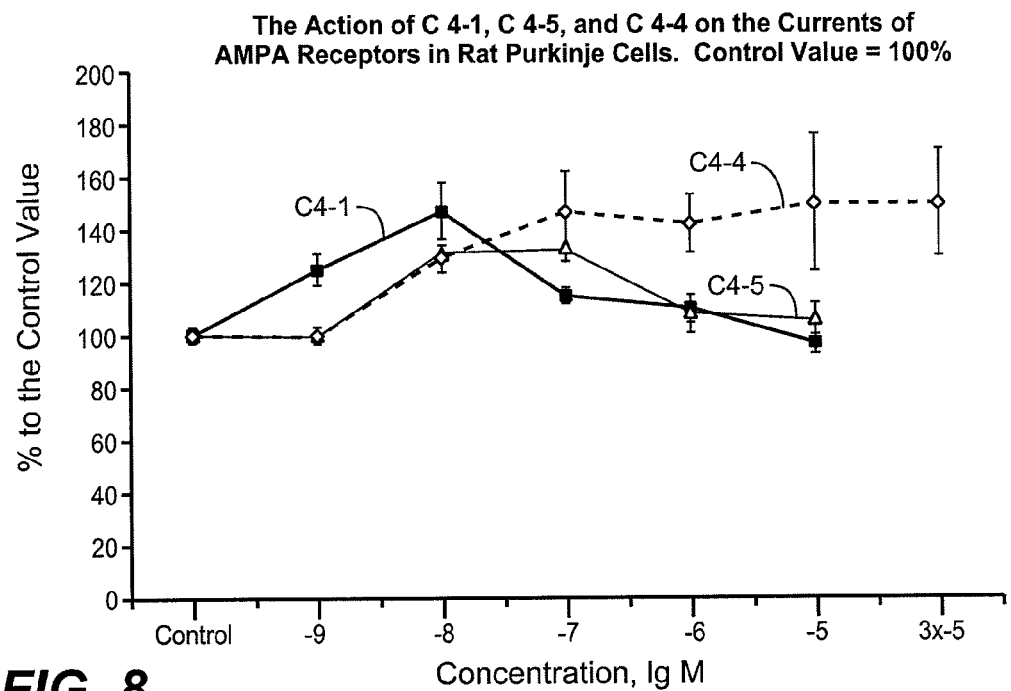
FIG. 8 displays the action of C 4-1, C 4-5, and C 4-4 on the currents of AMPA receptors in rat Purkinje cells.
Figure 9:
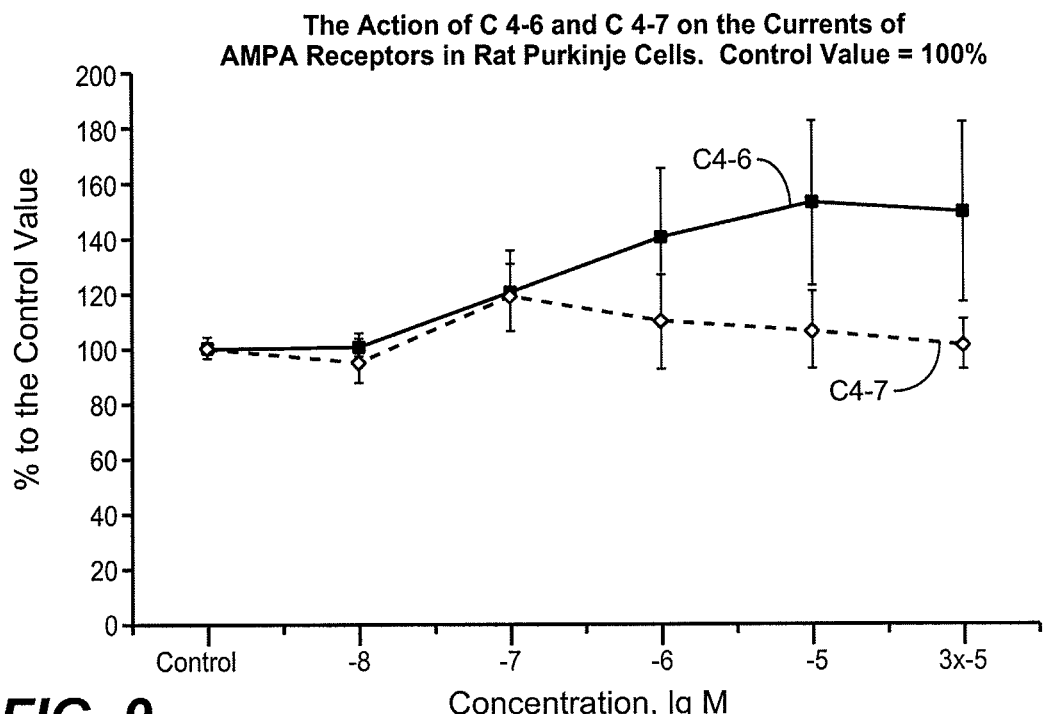
FIG. 9 displays the action of C 4-6 and C 4-7 on the currents of AMPA receptors in rat Purkinje cells.
Figure 10:
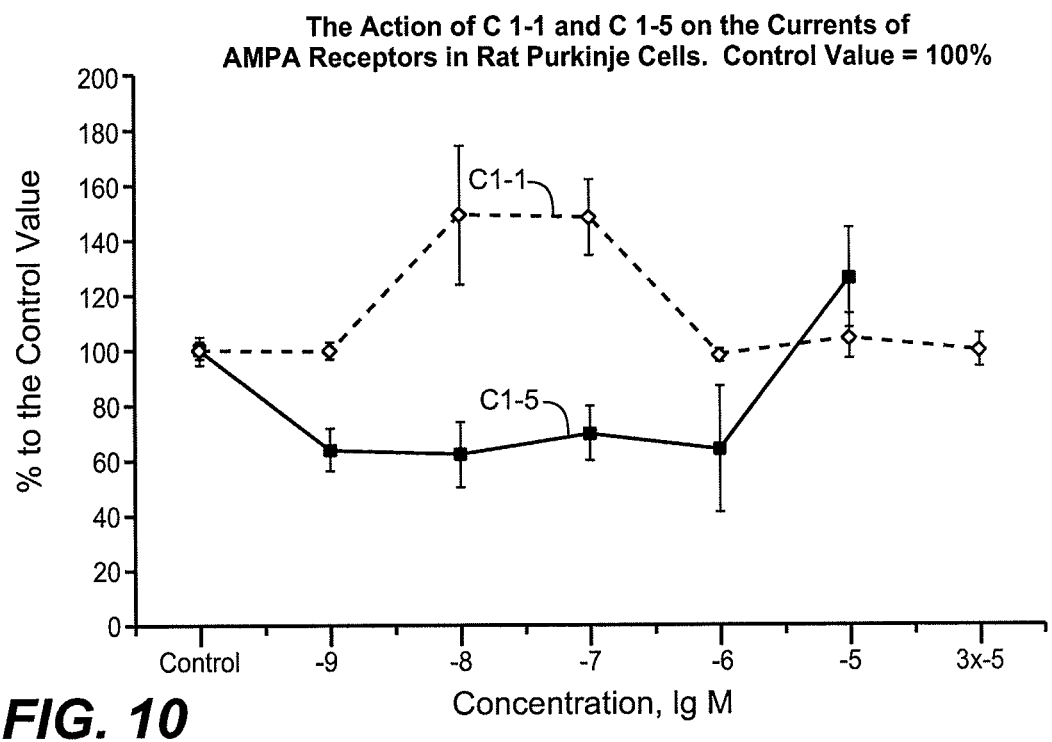
FIG. 10 displays the action of C 1-1 and C 1-5 on the currents of AMPA receptors in rat Purkinje cells.
Figure 11:
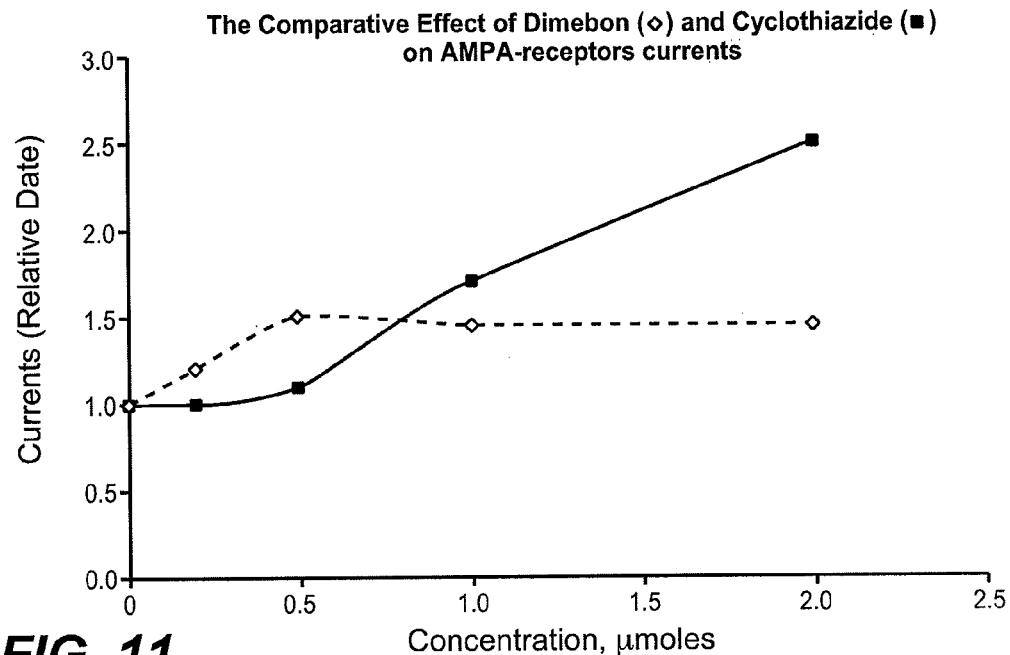
FIG. 11 shows the comparative effect of dimebon and cyclothiazide on AMPA-receptors currents.
Figure 12:
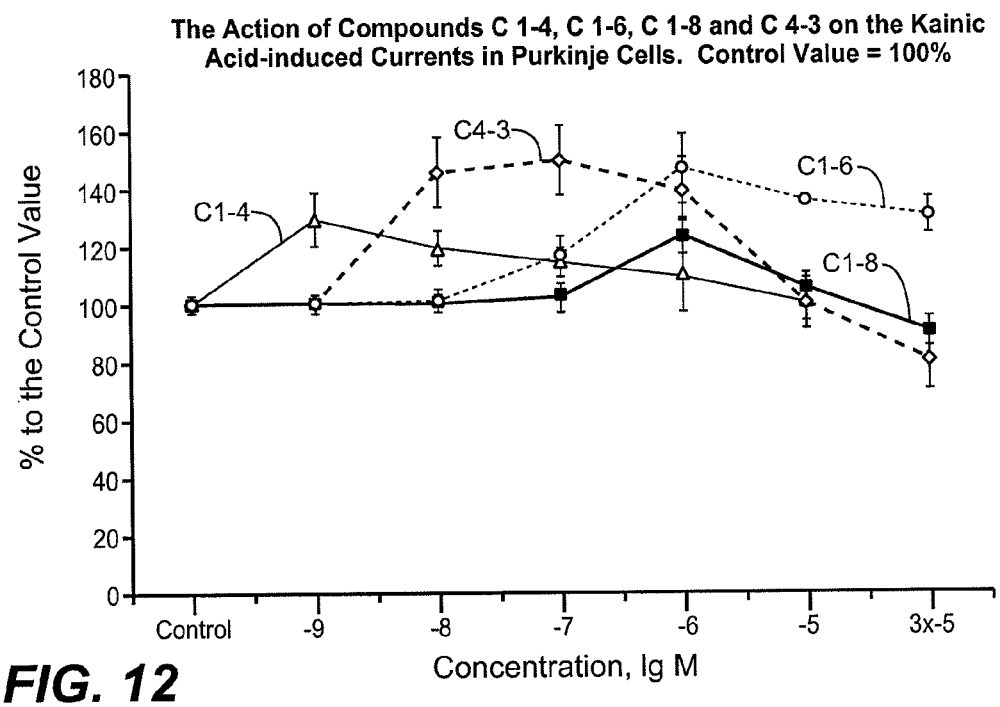
FIG. 12 displays the action of compounds C 1-4, C 1-6, C 1-8 and C 4-3 on the kainic acid-induced currents in Purkinje cells.

The effect of compound C 4-3 on glutamate-induced $^{45}Ca^{2+}$ uptake into synaptosomes of rat cortex was investigated. C 4-3 in did not affect glutamate-induced $^{45}Ca^{2+}$ uptake into synaptosomes at a concentration of 0.1-50 μM. At concentrations 50-100 μM compound, C 4-3 caused an increase in glutamate-induced $^{45}Ca^{2+}$ uptake into synaptosomes of rat cortex (~126% of control) (Table 12, FIG. 7).

The effect of compound C 2-1 on glutamate-induced $^{45}Ca^{2+}$ uptake into synaptosomes of rat cortex was investigated. C 2-1 did not affect glutamate-induced $^{45}Ca^{2+}$ uptake into synaptosomes at a concentration of 0.1-1 μM. At concentrations 5-50 μM, compound C 2-1 inhibited glutamate-induced $^{45}Ca^{2+}$ uptake into synaptosomes. The maximal inhibition of glutamate-induced $^{45}Ca^{2+}$ uptake into synaptosomes was 30% at a concentration of 10 μM (Table 12, FIG. 7).

TABLE 12

Effect of compounds C 1-6, C 1-8, C 1-4, C 2-1 on glutamate-induced $^{45}Ca^{2+}$ uptake into synaptosomes of rat cortex.

| | % Ca of control (control - 100%) | | | | |
|---|---|---|---|---|---|
| C, μM | C 1-6 | C 1-8 | C 1-4 | C 4-3 | C 2-1 |
| 0.1 | 130.1 ± 8.6 | 99.2 ± 1.4 | 99.1 ± 2.5 | 93.2 ± 3.0 | 90.5 ± 5.1 |
| 0.5 | 142 ± 6.4 | 96.7 ± 2.4 | 87.4 ± 3.7 | 92.1 ± 3.3 | 94.8 ± 3.0 |
| 1 | 121.8 ± 4.4 | 86.1 ± 0.1 | 96.2 ± 5.0 | 101.0 ± 1.0 | 94.5 ± 11.8 |
| 5 | 79.3 ± 11.8 | 87.7 ± 2.7 | 94.9 ± 5.7 | 93.7 ± 6.8 | 80 ± 3.0 |
| 10 | 100.2 ± 6.7 | 99.3 ± 3.0 | 94.3 ± 2.7 | 94.7 ± 6.9 | 69.9 ± 4.4 |
| 50 | 127.7 ± 0.7 | 122.4 ± 1.6 | 112.7 ± 10.1 | 117.9 ± 6.0 | 90 ± 6.1 |
| 100 | 140 ± 7.4 | 121.7 ± 13.9 | 131.5 ± 0.1 | 125.6 ± 3.9 | 104.2 ± 12.8 |

Example 16B

Determination of the Effect of Compounds of the Invention on AMPA-Receptor Activity Methods The analysis of effects of the testing compounds on AMPA receptors was carried out using an electrophysiological patch-clamp method in whole cell configuration (Hamill et al., 1980) of the Purkinje cell fresh isolated from the cerebellum of juvenile rats (12-15 days). The isolation was carried out using a modified method (Kaneda et al., 1988) in which cerebral 400-600 μm sections were incubated for 60 min in the temperature controlled chamber in 10 mL of buffer solution (150 mM NaCl, 5 mM KCl, 2 mM $CaCl_2$, 2 mM $MgSO_4.7H_2O$, 10 mM HEPES, 15 mM glucose, pH 7.42). The incubation solution was exchanged with the incubation buffer with pronase (2 mg/mL) and collagenase (1 mg/mL) for 70 min. After a 20 min wash with the original buffer, all sections were placed into the Petri dish and were separated using a Pasteur pipette. All solutions were constantly aerated with 100% $O_2$ at 34° C. The composition of extracellular saline was: 150 mM NaCl, 5 mM KCl, 2.6 mM $CaCl_2$, 2 mM $MgSO_4.7H_2O$, 10 mM HEPES, 15 mM glucose, pH 7.36. The transmembrane current was induced as a result of the activation of AMPA receptors by a superfusion with the agonist solution (kainic acid). The currents were measured using borosilicate microelectrodes (resistance 2.5-4.0 mOhms) filled with 100 mM KCl, 11 mM EGTA, 1 mM $CaCl_2$, 1 mM $MgCl_2$, 10 mM HEPES, 5 mM ATP, pH 7.2. The currents were registered using EPC-9 (HEKA, Germany) and recorded with Pulse software package which was also purchased from HEKA. The analysis of observations was carried out using Pulsefit (HEKA, Germany) and the statistical significance was analyzed using a Student's T-test criteria. Data are presented as mean±SEM in % of control values.

Results

Compounds of the invention were tested in 3-5 neurons. Every concentration of compound was repeated three-four times in every neuron. Data are presented as mean±SEM in % of Control values (Table 13+14, FIGS. 8-12). Control value=100%.

TABLE 13

The action of the new derivatives on the kainic acid-induced currents in Purkinje cells.

| Compounds | $10^{-9}$ M | $10^{-8}$ M | $10^{-7}$ M | $10^{-6}$ M | $10^{-5}$ M | $3 \times 10^{-5}$ M |
|---|---|---|---|---|---|---|
| C4-1 | 125 ± 6 | 147 ± 11 | 115 ± 3 | 110 ± 5 | 97 ± 4 | not tested |
| C4-5 | 100 | 131 ± 3 | 133 ± 5 | 108 ± 7 | 106 ± 6 | not tested |
| C4-4 | 100 | 129 ± 5 | 147 ± 15 | 142 ± 11 | 150 ± 26 | 150 ± 20 |
| C4-6 | not tested | 100 ± 3 | 120 ± 20 | 140 ± 25 | 152 ± 30 | 149 ± 33 |
| C4-7 | not tested | 95 ± 8 | 118 ± 12 | 109 ± 17 | 106 ± 14 | 101 ± 9 |
| C1-1 | 100 ± 3 | 149 ± 25 | 148 ± 14 | 98 ± 2 | 105 ± 8 | 95 ± 6 |
| C1-5 | 64 ± 8 | 62 ± 12 | 70 ± 23 | 64 ± 23 | 126 ± 18 | not tested |

TABLE 14

The action of the new derivative series C on the kainic acid-induced currents in Purkinjecells.

| Compounds | $10^{-9}$ M | $10^{-8}$ M | $10^{-7}$ M | $10^{-6}$ M | $10^{-5}$ M | $3 \times 10^{-5}$ M |
|---|---|---|---|---|---|---|
| C1-6 | 100 ± 3 | 101 ± 4 | 116 ± 7 | 146 ± 12 | 135 ± 1 | 130 ± 6 |
| C1-4 | 129 ± 9 | 119 ± 6 | 114 ± 5 | 109 ± 12 | 100 ± 9 | not tested |
| C1-8 | not tested | 100 ± 4 | 102 ± 3 | 123 ± 8 | 105 ± 8 | 90 ± 7 |
| C4-3 | 100 ± 3 | 145 ± 12 | 149 ± 15 | 139 ± 11 | 100 ± 6 | 80 ± 10 |

Example 17B

Influence of Compounds on Mitochondria

Methods

Rat liver and brain mitochondria were prepared from male Wistar rats. The rats were euthanized in a $CO_2$ chamber followed by decapitation the procedure being in compliance with the Guidelines for Animal Experiments at IPAC RAS.

Mitochondria from rat liver were isolated via the standard mannitol differential centrifugation protocol in sufficient buffer A, which contained 210 mM mannitol, 70 mM sucrose, 5 mM HEPES, 0.25 mM EDTA pH 7.4, at 4° C. and resuspended in buffer A without EDTA for the study of mPT.

Brain mitochondria were isolated from the pooled forebrains of two rats. The modified method of Sims was used to isolate and purify brain mitochondria in a Percoll gradient. The brain was homogenized in "buffer A" (225 mM mannitol, 75 mM sucrose, 5 mM HEPES, 1 mM EGTA, pH 7.4 [KOH]) and centrifuged for 10 min at 1300 g. The supernatant was centrifuged for 10 min at 10000 g, and then the pellet was suspended in 15% Percoll and layered on a discontinuous gradient consisting of 40 and 23% Percoll, respectively, which was then centrifuged for 10 min at 30000 g without using brakes. The mitochondria were collected from the interface of the lower two layers and after resuspension in "buffer A", the suspension was centrifuged at 16600 g for 10 min, then the pellet was resuspended in "buffer A", BSA (10 mg/mL) was added to bind free fatty acids; and the suspendions was centrifuged again at 6300 g for 10 min. Following centrifugation the pelleted mitochondria were re-suspended in isolation medium without EGTA to achieve a protein concentration of 15-20 mg/ml.

Swelling Assay.

Mitochondrial swelling caused by influx of solutes through open PT pores results in an increase in light transmission (i.e., a reduced turbidity). This turbidity change offers a convenient and frequently used assay of the MPT by measurement of absorbance in mitochondrial suspensions. In the present study, the MPT induced by $Ca^{2+}$ and inorganic phosphate (Ca/Pi) was monitored by absorbance changes at 540 nm in a cuvette in a Beckman DU 640 spectrophotometer in 1 ml of buffer A plus 0.8 µM rotenone, 5 mM succinate, 1 mM $KH_2PO_4$ and 0.5 mg or 0.2 mg protein of isolated liver or brain mitochondria, accordingly. Reaction was started by the addition of triggering agent ($Ca^{2+}$). Pre-treatment and reaction were performed at 30° C. Swelling rate was quantified as $\Delta A_{540}$/min/mg, calculated, in all cases, from a tangent to the steepest portion of the plot of $A_{540}$ versus time.

Measurement of Mitochondrial Membrane Potential.

The same experimental conditions were used for the assessment of alterations of the mitochondrial membrane potential, except that safranine was included in incubation medium at a final concentration of 10 mkM and succinate was added before the compounds of the invention. This concentration of safranine was determined before hand as the optimal compromise between signal/baseline ratio and interference of safranine itself with swelling induced by Ca/Pi (safranine tended to enhance Ca/Pi-induced swelling at concentrations above 20 mkM). Changes in the status of the mPT pore were assessed spectrophotometrically at 554 and 524 nm in a cuvette in a Beckman DU 640 spectrophotometer. $A_{554-524}$ represents the characteristics of mitochondrial potential and $A_{554}$-characteristics of mitochondrial swelling.

Measurement of Calcium Retention Capacity of Mitochondria.

Analyses of extramitochondrial $Ca^{2+}$ following a bolus dose of $Ca^{2+}$ were performed under energized conditions, in a sucrose based buffer (250 mM sucrose, 10 mM HEPES, 1 mM Pi (K), 1 mM $MgCl_2$, 10 µM EGTA, pH 7.2) containing 5 mkM Arsenazo III, 1 µg/ml oligomycin and 20 µM ADP with 5 mM malate and glutamate as respiratory substrates in a cuvette in a Beckman DU 640 spectrophotometer.

Results $Ca^{2+}$-induced Swelling of mitochondria was used as the primary screening test for compounds influence on MPT pore opening. $IC_{50}$ was estimated as the concentration of compound which reduces up to 50% the initial rate of turbidity fall after calcium addition. But the inhibition of swelling may be connected not only with direct inhibition of MPT pore opening but also with the impairment of respiratory function of mitochondria and with the compounds action on calcium transport into mitochondria. For the primary estimation of these possibilities the mitochondrial membrane potential and calcium retention capacity of mitochondria were measured. According to the experimental data (Table 15) it is suggested that at least particularly the inhibition of MPT by C 4-1, C 4-4, C 4-6 and C 1-5 was accompanied with impairment of mitochondrial respiratory functions. New synthesized compounds (except C-14 and C-43) alone induced an increase of brain mitochondria suspension turbidity. The mechanism of such effect needs additional investigations.

TABLE 15

Influence of compounds on functional characteristics of rat brain mitochondria.

| Compound | $IC_{50}$ µM, $Ca^{2+}$-induced (25-50 µM) swelling of brain mitochondria | $A_{540}$ increase in mitochondrial suspension after addition of 100 µM of compound (rel. units) | Depolarization of mitochondria |
|---|---|---|---|
| Dimebon | 66 ± 26 | 1 | – |
| C1-1 | 15 ± 16 | 16 | – |
| C1-4 | 93.9 ± 16.4 | 1 | – |
| C1-5 | 18 ± 16 | 30 | + |
| C1-6 | 12.7 ± 6.2 | 1.5 | C-16 react with safranine |
| C1-7 | 28 ± 6 | >30 | – |
| C1-8 | 6.25 ± 6.25 | 25 | C-18 react with safranine |
| C4-1 | 3.9 ± 1.6 | 10 | + |
| C4-3 | 76.0 ± 12.0 | 1 | – |
| C4-4 | 6.7 ± 1.2 | 14 | + |
| C4-5 | 28 ± 6 | 3 | – |
| C4-6 | 6.0 ± 1.2 | 28 | + |
| C4-7 | 9.9 ± 3.4 | 8 | – |

Compounds C-1-6 and C-1-8 decreased the calcium-induced swelling of brain mitochondria with $IC_{50}$ near 12 µM and 6 µM, respectively, but at higher concentrations a decrease of the effect (FIG. 13) and significant elevation of mitochondrial suspension absorbance after addition of 100 µM C-18 was observed (Table 15). Both compounds increased the calcium-retention capacity of mitochondria at concentrations near the $IC_{50}$.

In a safranine test, C-1-6 and C-1-8 revealed depolarizing activity, but both compounds did react with safranine in buffer without mitochondria.

Figure 13:
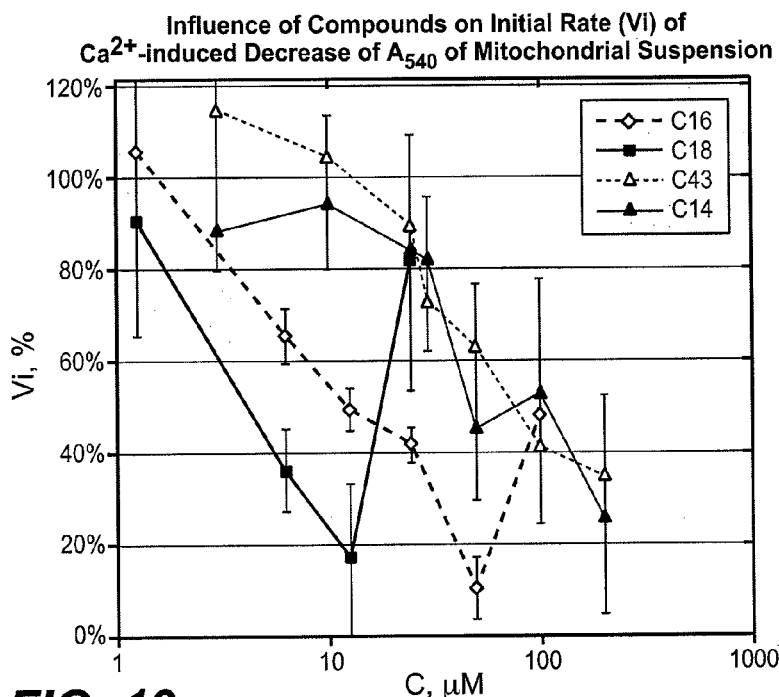
FIG. 13 displays the influence of compounds on initial rate (Vi) of $Ca^{2+}$-induced decrease of $A_{540}$ of mitochondrial suspension.

Compounds C-1-4 and C-4-3 decreased the calcium-induced swelling of brain mitochondria with an $IC_{50}$ near 94 µM and 76 µM, respectively (Table 15, FIG. 13). No depolarization of brain mitochondria by these compounds was observed at concentrations up to 100 mkM.

Example 18B

Influence of Compounds on Spatial Memory Performance and Performance on the Recognition Memory Task (Object Recognition Test)

The object recognition test is based on the fact that mice and rats spontaneously explore new object or location of a known object a lot longer than the know object or a known location of an object. This test was first used in rats (Ennaceur A., Delacour J., 1988). It was further shown by others that this type of memory testing is suitable for mice (Dodart J. et al. 1997, Messier C. 1997, Pittenger C. et al., 2002, Ryabinin A. et al., 2002, Sargolini F. et al., 2003). The method of recognition of an object is divided in two stages. The first one involves the recognition of a new location of a known object, which is used to assess spatial memory. The second one includes a test for recognition of a new in order to evaluate the non-spatial memory (Gaffan D., 1992, Kolb B. et al., 1994, Steckler T., 1998). Currently, both are widely used to determine the effectiveness of newly synthesized drugs on memory.

Materials and Methods

All experiments were carried out on 3-4 months old males (C57BL/6 line) 22-26 g weight with 10 animals in each group. All animals were kept in the animal facility (5 animals per cage) on the 12×12 hours light cycle (8 am-8 pm) with free access to food and water. The observation chamber was made of non-transparent white plastic 48×38×30 cm (18.9×14.9×11.8 inches). Brown glass vials were used as test objects which are 2.7 cm in diameter (1.1 inch) and 5.5 cm high (2.2 inch). All vials were treated with 85% ethanol 2-3 minutes before each testing. Animals were placed in the center of the chamber.

Dimebon and compounds of the invention were dissolved in distilled water and administered orally at 0.05 mL per 10 g of animal mass 1 hour before the training exercise. All animals in the control group were treated with the equivalent dose of vehicle. The testing was performed 48 hours after the training exercise because animals forget the location of the object during the 48-hour resting time.

Experimental Procedures

Recognition of a New Location of the Known Object (Spatial Memory Performance)

Habituation with the Testing Chamber

On the first day animals were brought in the testing room so that they could adapt to the testing environment for 20-30 min. Subsequently, each animal was placed in the empty testing chamber for 10 min, which was wiped with alcohol beforehand. After that animals were transferred back into the chamber and returned to the animal facility.

Training Exercise

The next day after habituation, the animals were brought back into the testing room where they were weighed and injected with the testing compound. An hour after injection, each animal was placed into the testing camber which had two identical objects that were positioned 14.5 cm (5.7 inches) from the corners on the diagonal. The training exercise lasted for 15 min for each animal. Subsequently, each animal was placed back into the cage and returned into the animal house.

Testing Procedure

The testing procedure was performed 48 hours after the training exercise. During the procedure two objects were used as in the training exercise. One object was left in the old position whereas another was placed in a new location. The amount of time that each animal spent on exploration each object was determined with 0.1 sec accuracy using two electronic stopwatches for total of 10 min. Animals were observed through minors. The survey of the object was counted as positive if the nose of an animal was pointed within 2 cm or if the animal was touching the objected directly with the nose.

Recognition of the New Object (Non-Spatial Performance on the Recognition Memory Task)

The following experiment was also performed on 3-4 months old males (C57BL/6 line) with 10 animals in each group. All animals were kept in the animal facility (5 animals per cage) on the 12×12 hours light cycle (8 am-8 pm) with free access to food and water. However, in this case a round bottom testing chamber 52 cm in diameter (20.5 inches) and 34 cm (13.4 inches) high was used. Similarly, brown glass vials were used as test objects which are 2.7 cm in diameter (1.1 inch) and 5.5 cm high (2.2 inch). The testing compounds were administered orally at 0.05 mL per 10 g of animal mass 1 hour before the training exercise. All animals in the control group were treated with the equivalent dose of vehicle. The testing was performed 48 hours after the training exercise because animals forget the location of the object during the 48-hour resting time.

The experimental procedure was identical to the previously described test (Recognition of a new location of a known object). The major difference is in the testing procedure which involved one known object (brown glass vial) and one unknown object. The second glass vial was substituted with metallic cylinder 3 cm (1.2 inches) in diameter and 4.5 cm (1.8 inches) high.

Statistical Data Analysis

Due to fair differences in the amount of time that each animal surveyed the object, the percentage of the survey time for each animal was determined using this formula: tNL/(tFL+tNL)×100 (where t is time, NL—new location (object), and FL—familiar location (object)). As 100% was taken the total amount of time that animals explored both objects. Subsequently, the statistical significance was analyzed using a Student's t-test criteria.

Results

Figure 14:
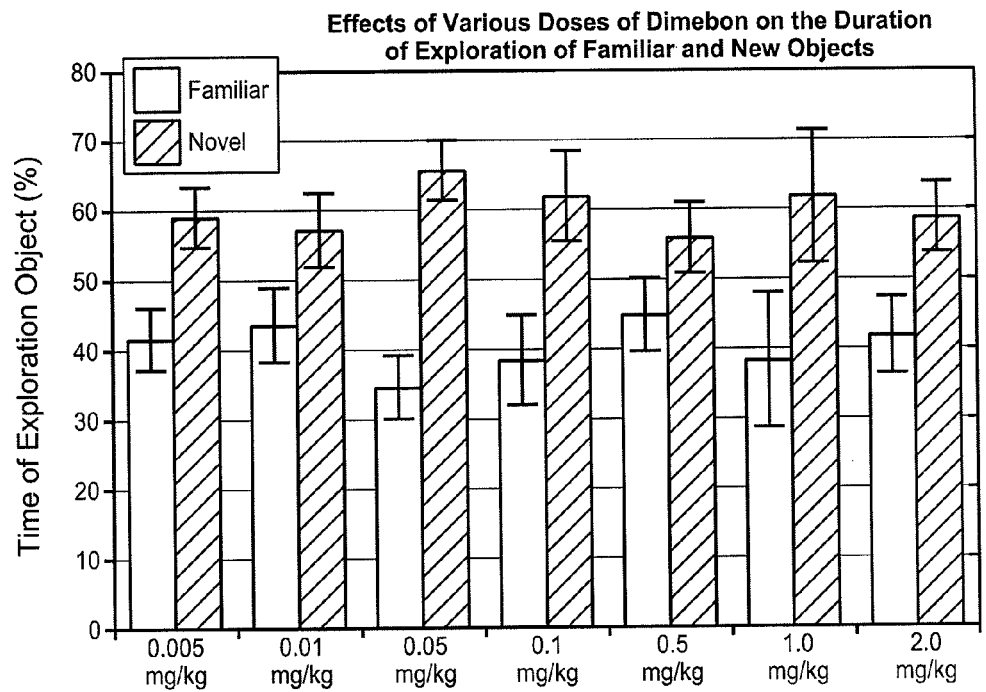
FIG. 14 displays the effects of various doses of dimebon on the duration of exploration of familiar and new objects.

Comparative Assessment of Dimebon Effect on Spatial and Non-Spatial Memory in Object Recognition Test 1. Effects of Dimebon on Memory in the New Object Recognition Test In this experiment dimebon was administered in a wide dose range (from 0.005 mg/kg to 2.0 mg/kg) 1 hour prior to training. As a result, it was found that at 0.005 mg/kg dimebon had a memory activating effect. The maximum effect was registered at 0.05 mg/kg. In this group animals spent 65.6±4.4% to recognize the new object, whereas 34.4±4.4% of the total time was spent to recognize the known object (P=0.0003). Further increase of the exposure dose resulted in the decrease of the stimulating effect. In addition, the results of the experiment at 0.5 mg/kg were not statistically significant. However, further increase of the exposure dose up to 1-2 mg/kg, the stimulating effect on memory returned (FIG. 14). Therefore, it was shown that dimebon has a two-phase activating effect on the non-spatial memory, which may be linked to at least two different mechanisms of its activating effect.

Figure 15:
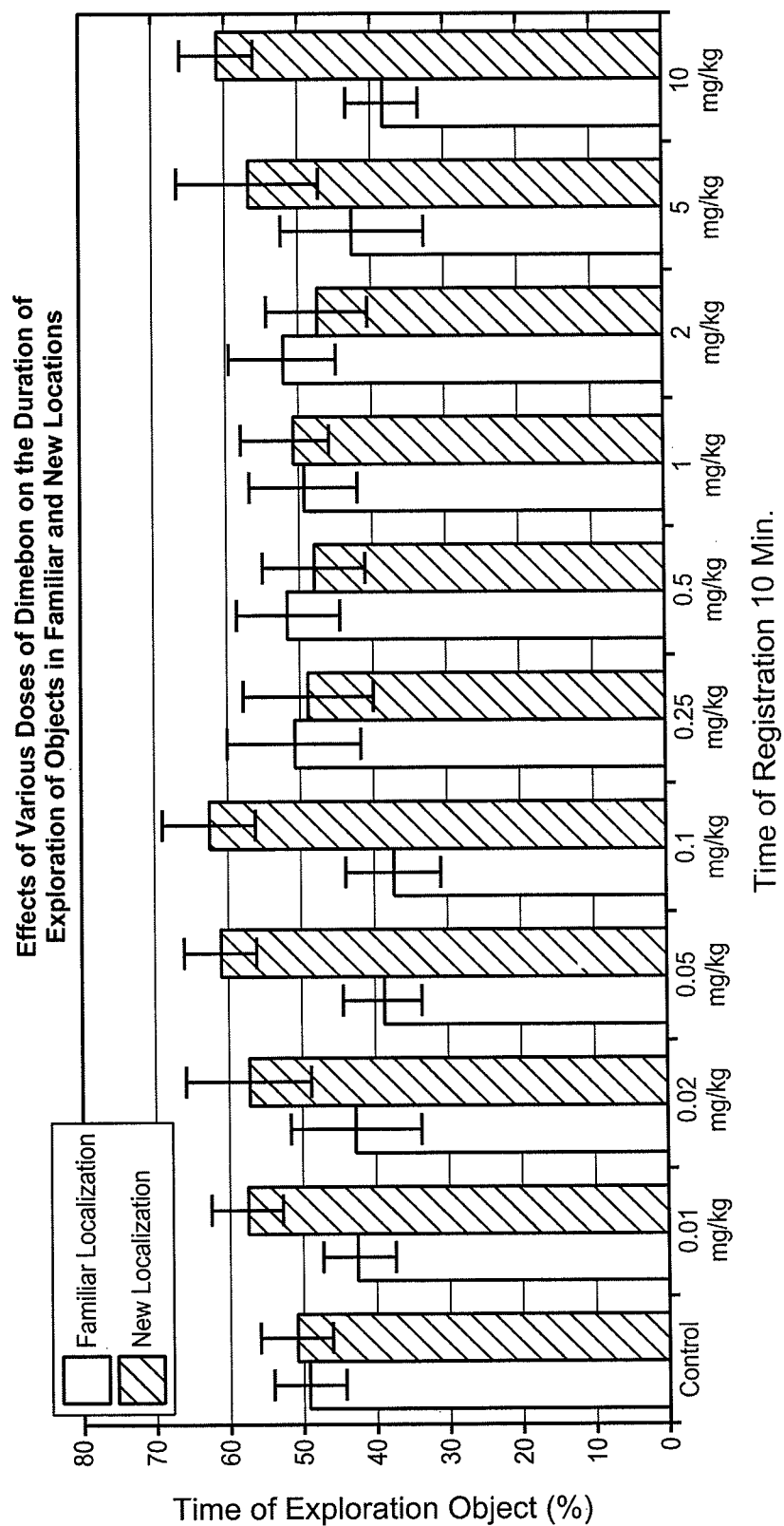
FIG. 15 displays the effects of various doses of dimebon on the duration of exploration of objects in familiar and new locations.

2. Effects of Dimebon on Memory in the Recognition Test of a Known Object in a New Location It was previously shown that dimebon at 0.01-0.1 mg/kg has a dose-dependent activating effect on memory in the test for recognition of a known object in a new location. However, this effect disappears at 0.25 mg/kg, and thus it was important to test whether the second phase of the activating wave would appear at higher doses of dimebon exposures. As a result, it was shown that only at 10 mg/kg dimebon had a pronounced stimulating effect on memory. Animals in this group spent 61.2±5% of the total time to explore the known object in a new location, and 38.8±5% in a known position (P=0.0003) (FIG. 15). Hence, it was concluded that dimebon also has a two-phase stimulating effect on the spatial memory (as shown in the recognition test of a known object in a new location); however much higher doses of this drug are required.

Effects of Compounds on Memory in the Recognition Test of a Known Object in a New Location A test was conducted to assess recognition of a new location of a familiar object to study the effects on memory of C 4-1, C 4-4, C 4-5, C 4-6, C 4-7, C 1-1 and C 1-5.

Figure 16:
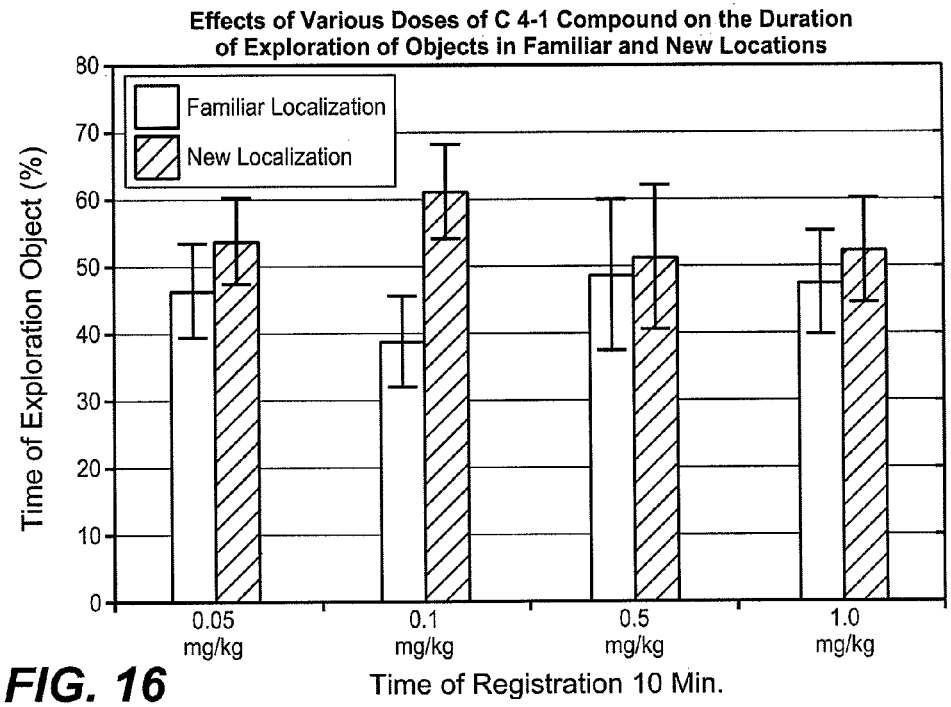
FIG. 16 displays the effects of various doses of C 4-1 compound on the duration of exploration of objects in familiar and new locations.

Control animals 48 hours after the training exercise explored objects approximately the same time in the known and new location. Thus, they forgot the location of the object during training. However, the C 4-1 treated animals (0.1 mg/kg) explored the object 61.3±6.9% of the total time in a new location and 38.7±6.9% in the known position (P=0.0004). Results in other groups (0.05 mg/kg, 0.5 mg/kg, and 1 mg/kg) were not significantly different from the control group (FIG. 16). Therefore, C 4-1 had an activating effect on memory only at 0.1 mg/kg.

Figure 17:
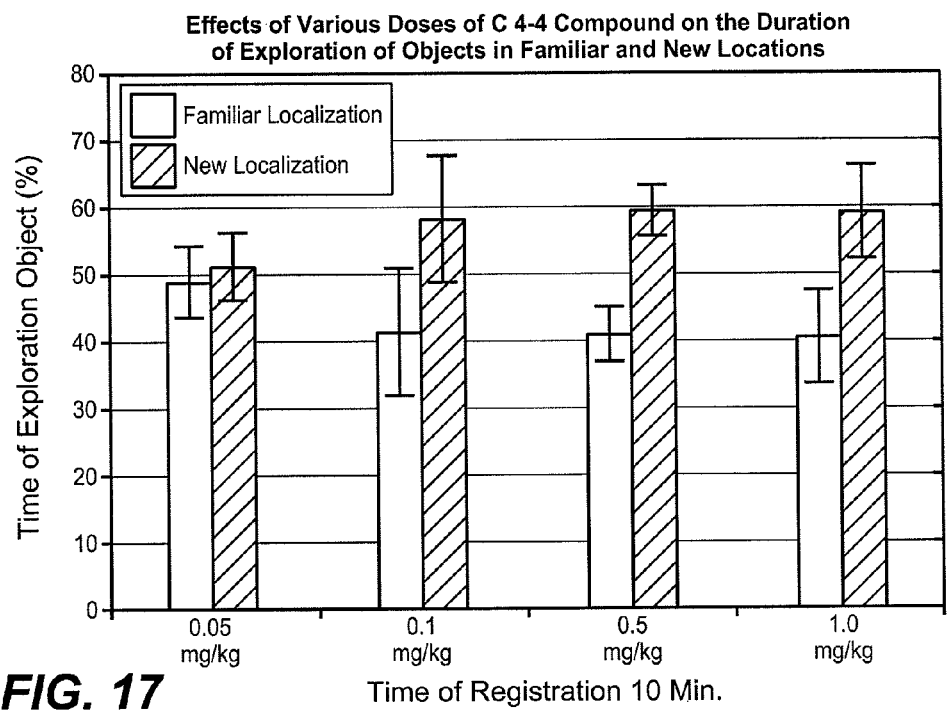
FIG. 17 displays the effects of various doses of C 4-4 compound on the duration of exploration of objects in familiar and new locations.

Studies with C 4-4 showed that at 0.05 mg/kg it had no effect on time that animals explore the object in a known or new location. However, the group of animals that was treated with 0.1 mg/kg of C 4-4 explored the object 58.5±9.6% of the total time in a new location and 41.5±9.6% in the known position (P=0.01). Mice that were treated with 0.5 mg/kg of C 4-4 explored the object 59.1±4.2% of the total time in a new location and 40.9±4.2% in the known position (P=0.0003). Similar results were obtained in mice that were treated with 1 mg/kg of C 4-4 (FIG. 17). C 4-4 had an activating effect on memory which is preserved for about 48 hours after training. This effect was similar to C 4-1, but C 4-4 had a wider range of effective doses.

Figure 18:
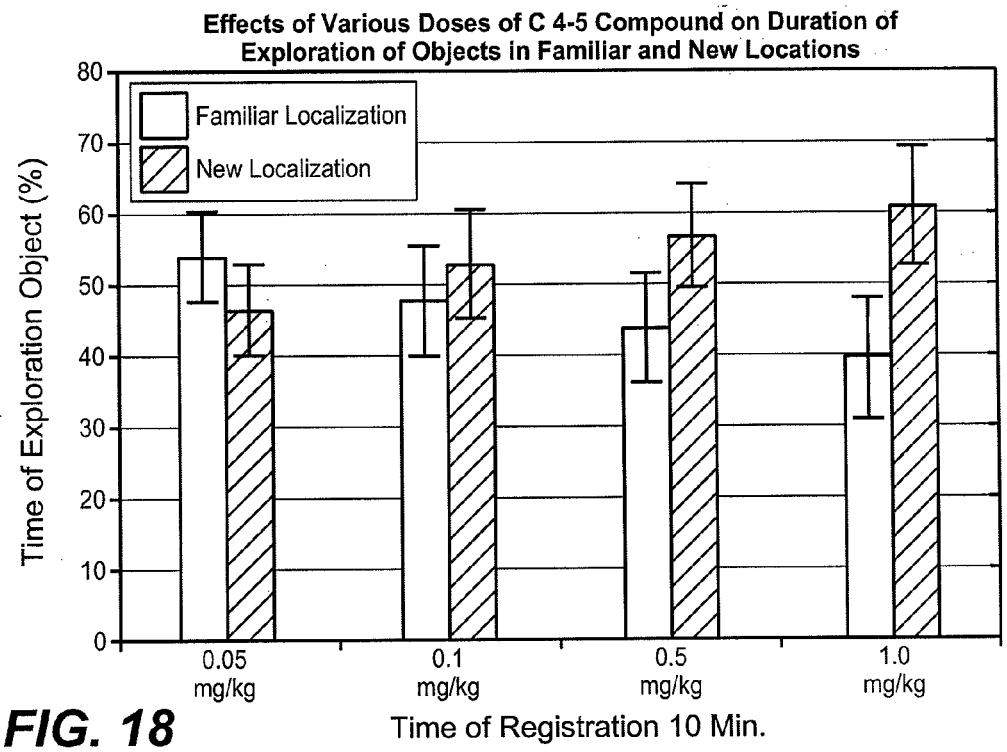
FIG. 18 displays the effects of various doses of C 4-5 compound on duration of exploration of objects in familiar and new locations.

The C 4-5 was tested at 0.05 mg/kg, 0.1 mg/kg, 0.5 mg/kg and 1 mg/kg in the recognition test of new location of a known object. The 0.5 mg/kg group explored the object in a new location for 56.2±7.6% of the total time and 43.8±7.6% in the known position (P=0.03). As dose was increased to 1 mg/kg animals explored the object in a new location for 60.6±8.4% of the total time and 39.4±8.4% in the known position (P=0.006). The 0.05 mg/kg and 0.1 mg/kg doses were not effective (FIG. 18). Therefore, C 4-5 stimulated memory, but its activity was approximately 10 times weaker than the one of C 4-1 and dimebon.

Figure 19:
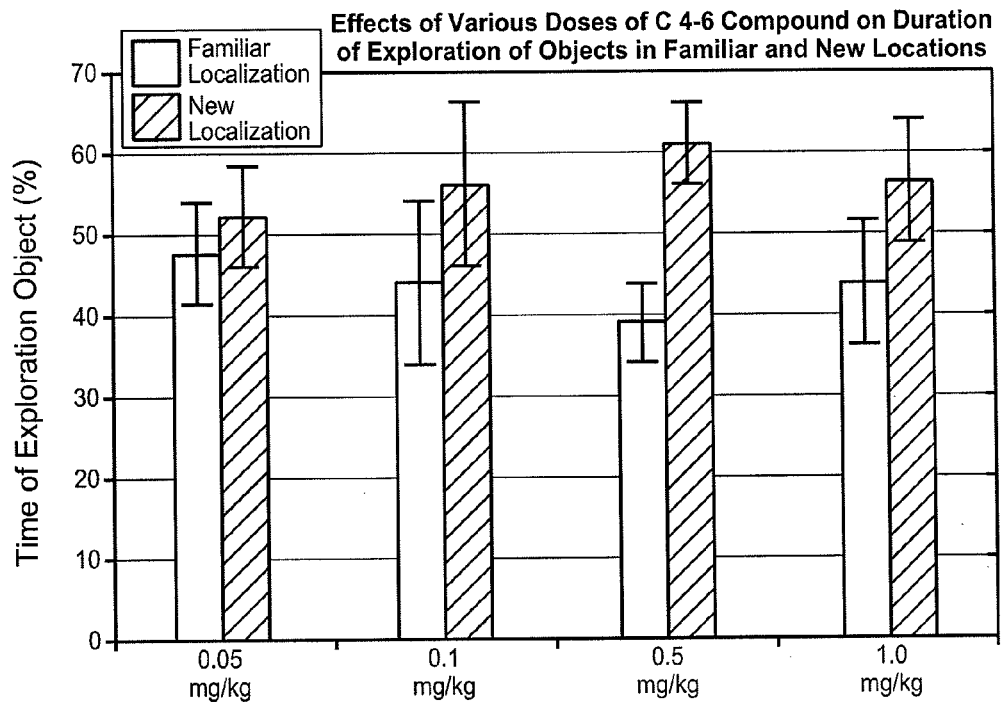
FIG. 19 displays the effects of various doses of C 4-6 compound on duration of exploration of objects in familiar and new locations.

Animals treated with compound C 4-6 at a concentration of 0.5 mg/kg explored the object in a new location for 61.0±4.8% of the total time and 39.0±4.8% in the known position (P=0.0007). As the dose was increased to 1 mg/kg, animals explored the object in a new location for 56.3±7.7% of the total time and 43.7±7.7% in the known position (P=0.03). The 0.05 mg/kg and 0.1 mg/kg doses were not effective (FIG. 19). Therefore, C 4-6 stimulated memory, but its activity was approximately 5 times weaker than the one of dimebon.

Figure 20:
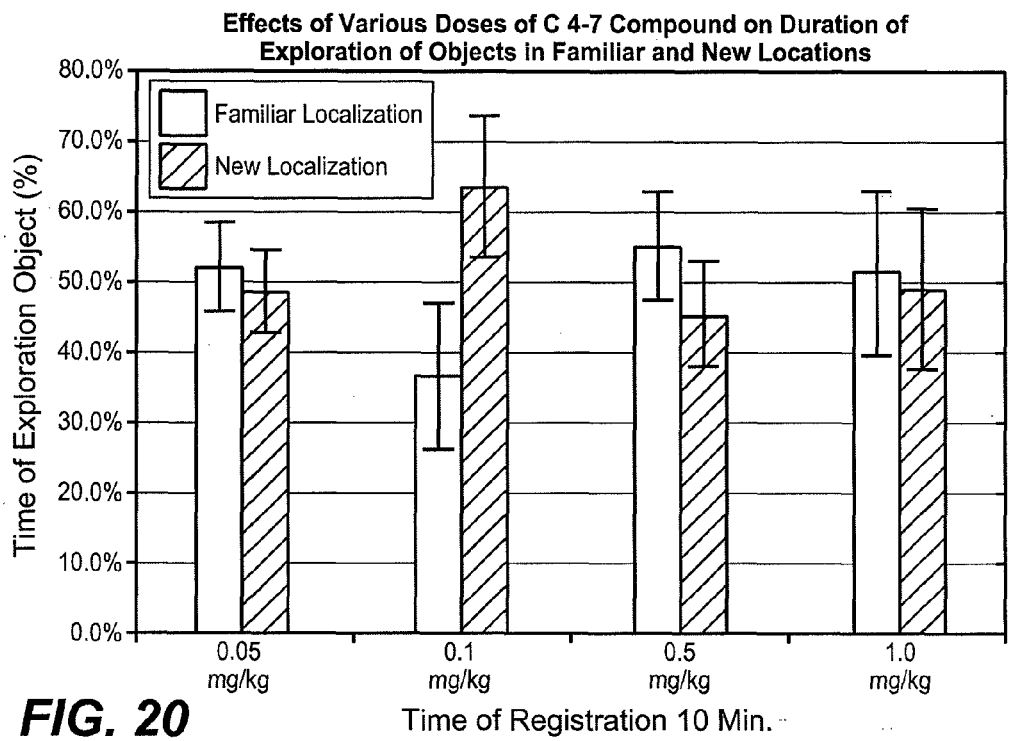
FIG. 20 displays the effects of various doses of C 4-7 compound on duration of exploration of objects in familiar and new locations.

The compound C 4-7 was tested at 0.05 mg/kg, 0.1 mg/kg, 0.5 mg/kg and 1 mg/kg in the recognition test of new location of a known object. It was determined that the 0.1 mg/kg group explored the object in a new location for 63.4±10.4% of the total time and 36.6±10.4% in the known position (P=0.01). The 0.05, 0.5 and 1 mg/kg doses were not effective (FIG. 20). Therefore, C 4-7 stimulated memory and has similar activity as dimebon, but it had a much more narrow range of the effective doses.

Figure 21:
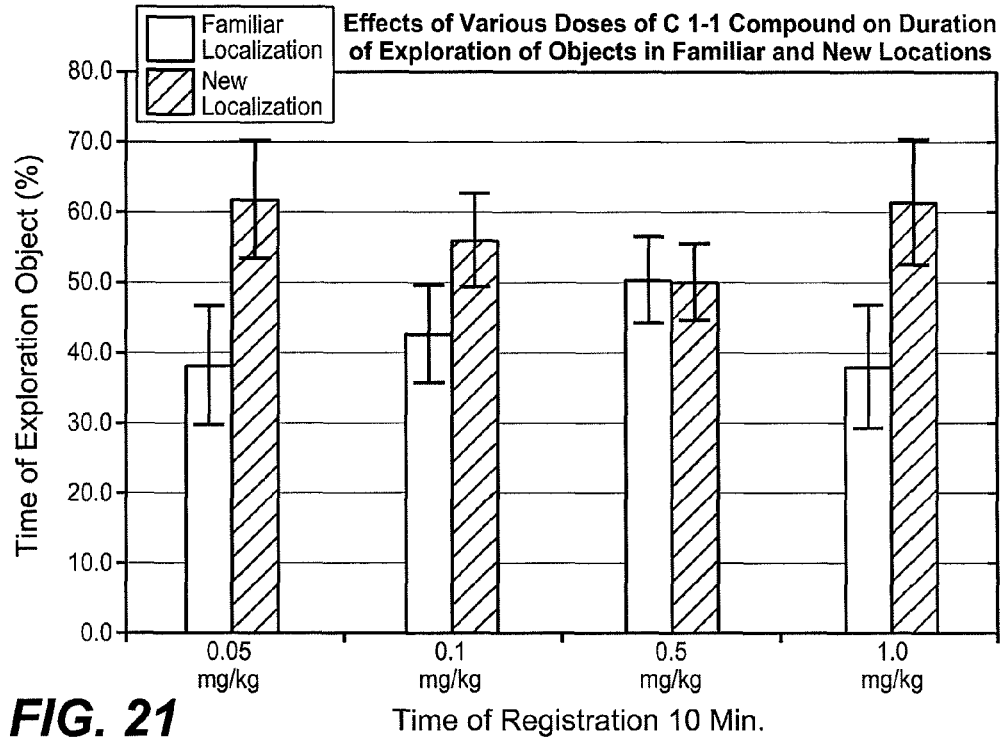
FIG. 21 displays the effects of various doses of C-1-1 compound on duration of exploration of objects in familiar and new locations.

A rather interesting memory activating effect of C 1-1 was discovered in case testing of a two phase effect of dimebon on spatial memory. Mice that were injected with 0.05 mg/kg of C 1-1 spent 61.8±8.4% of the total time and 38.2±8.4% in the known position (P=0.002). When the dose was increased up to 0.1 mg/kg, animals spent 56.0±6.9% of total time to locate the object in the new location and 42.7±6.9% in the known position (P=0.02). In addition, further increase to 0.5 mg/kg resulted in the disappearance of the stimulating effect on memory. However, a group of mice that was injected with C-1-1 at 1 mg/kg explored the object in the new location for 61.5±8.9% of total time and 37.8±8.9% in the known position (P=0.002). In other words, once again a stimulating effect was observed (FIG. 21). C 1-1 had a stimulating effect on memory. The activity of this compound was approximately two times higher than the one of dimebon, but in comparison C 1-1 had a two-phase response effect. Though, the second stimulating phase appeared at concentrations of C 1-1 10 times less than it was shown for dimebon. It is quite likely that the stimulating effect of this compound on spatial memory will be much higher than the one shown for dimebon.

Figure 22:
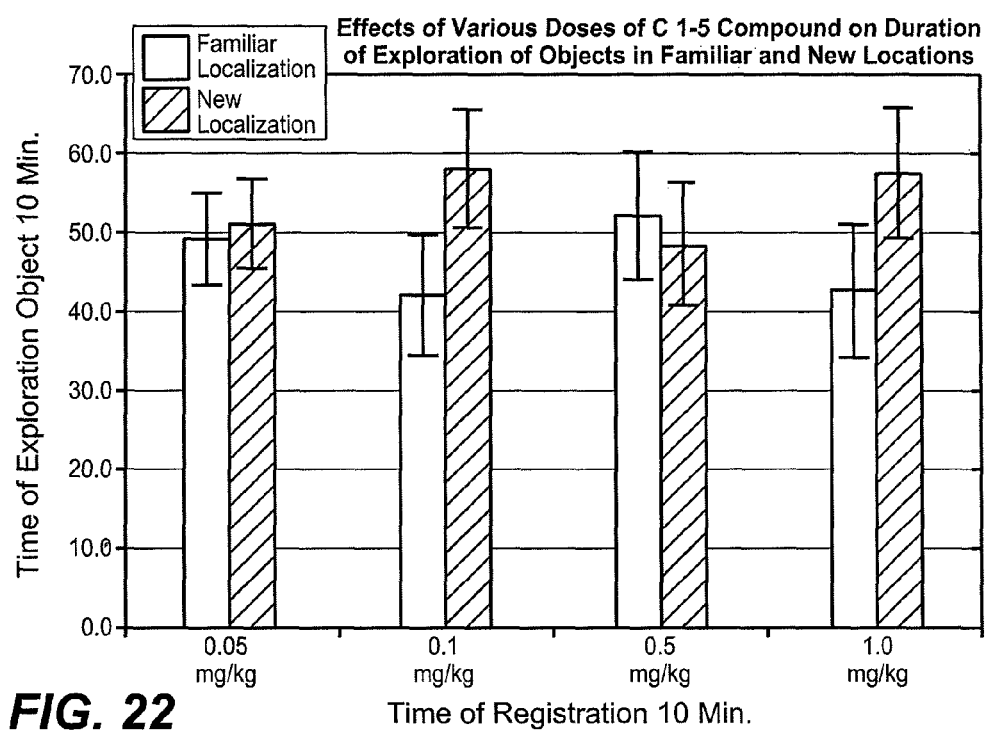
FIG. 22 displays the effects of various doses of C 1-5 compound on duration of exploration of objects in familiar and new locations.

Studies with C 1-5 showed that at 0.05 mg/kg it had no effect on the amount of time animals explore the object in a known or new location. However, the group of animals that was treated with 0.1 mg/kg of C 1-5 explored the object 57.9±7.5% of the total time in a new location and 42.1±7.5% in the familiar position (P=0.01). Treatment with 0.5 mg/kg of C 1-5 resulted in the disappearance of the stimulating effect on memory. However, at increasing dosages up to 1 mg/kg animals explored object in new localization 57.4±8.4% of time and in familiar—42.6±8.4% (P=0.03). On the basis of the received results the conclusion that C 1-5 had a stimulating effect on memory and on activity was at a level dimebon. Also as C 1-1 this compound had a two-phase stimulating effect (FIG. 22).

The results are summarized in Table 16.

TABLE 16

Influence of various doses of connections of series C on memory in the test recognition new localization of known object

| Compound | Dose of Compound in mg/kg | | | |
|---|---|---|---|---|
| | 0.05 | 0.1 | 0.5 | 1.0 |
| C 4-1 | − | + | − | − |
| C 4-4 | − | + | + | + |
| C 4-5 | − | − | + | + |
| C 4-6 | − | − | + | + |
| C 4-7 | − | + | − | − |
| C 1-1 | + | + | − | + |
| C 1-5 | − | + | − | + |
| Dimebon | + | + | − | − |

+ the dose has an activating effect on memory
− no activating effect on memory was discovered for the dose

REFERENCES

Dodart J. C., C. Mathis and A. Ungerer, Scopolamine-induced deficits in a two-trial object recognition task in mice. NeuroReport 8 (1997), pp. 1173-1178.

Ennaceur A. and J. Delacour, A new one-trial test for neurobiological studies of memory in rats. 1: behavioral data. Behav. Brain Res. 31 (1988), pp. 47-59.

Kolb B., K. Buhrmann, R. McDonald and R. Sutherland, Dissociation of the medial prefrontal, posterior parietal, and posterior temporal cortex for spatial navigation and recognition memory in the rat. Cereb. Cortex 6 (1994), pp. 664-680.

Messier C., Object recognition in mice: improvement of memory by glucose. Neurobiol. Learn. Mem. 67 (1997), pp. 172-175.

A. E. Ryabinin, M. N. Miller and S. Durrant, Effects of acute alcohol administration on object recognition learning in C57BL/6J mice. Pharmacol. Biochem. Behav. 71 (2002), pp. 307-312.

Sargolini F., P. Roullet, A. Oliverio and A. Mele, Effects of intra-accumbens focal administrations of glutamate antagonists on object recognition memory in mice. Behav. Brain Res. 138 (2003), pp. 153-163.

Sik A., van Nieuwehuyzen, J. Prickaerts, A. Blokland, Performance of different mouse strains in an object recognition task. Behav. Brain Res. 147 (2003), pp. 49-54.

Steckler T., W. H. I. M. Drinkenburgh, A. Sahgal and J. P. Aggleton, Recognition memory in rats. I. Concepts and classification. Prog. Neurobiol. 54 (1998), pp. 289-311.

Steckler T., W. H. I. M. Drinkenburgh, A. Sahgal and J. P. Aggleton, Recognition memory in rats II. Neuroanatomical substrates. Prog. Neurobiol. 54 (1998), pp. 313-332.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:
1. A compound of the Formula (E):

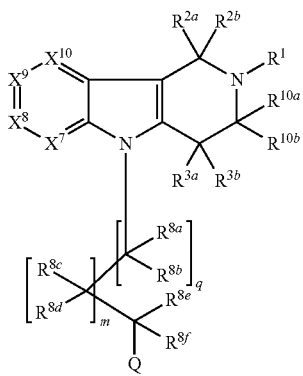

or a salt thereof,
wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
wherein acyl is selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—;
wherein sulfonylamino is selected from the group consisting of —$SO_2NH_2$, —$SO_2$NR-alkyl, —$SO_2$NR-substituted alkyl, —$SO_2$NR-alkenyl, —$SO_2$NR-substituted alkenyl, —$SO_2$NR-alkynyl, —$SO_2$NR-substituted alkynyl, —$SO_2$NR-aryl, —$SO_2$NR-substituted aryl, —$SO_2$NR-heteroaryl, —$SO_2$NR-substituted heteroaryl, —$SO_2$NR-heterocyclic, and —$SO_2$NR-substituted heterocyclic, where R is H or alkyl, or —$SO_2NR_2$, wherein the two R groups are taken together and with the nitrogen atom to which they are attached to form a heterocyclic or substituted heterocyclic ring;
wherein sulfonyl is selected from the group consisting of —$SO_2$-alkyl, —$SO_2$—substituted alkyl, —$SO_2$-alkenyl, —$SO_2$-substituted alkenyl, —$SO_2$-alkynyl, —$SO_2$-substituted alkynyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic;
each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together with the carbon to which they are attached to form a carbonyl moiety or $R^{2a}$ and $R^{2b}$ are taken together with the carbon to which they are attached to form a cycloalkyl moiety;
each $R^{3a}$ and $R^{3b}$ is independently H, substituted or unsubstituted $C_1$-$C_8$ alkyl, halo, hydroxyl, alkoxy, cyano, nitro or $R^{3a}$ and $R^{3b}$ are taken together with the carbon to which they are attached to form a carbonyl moiety or $R^{3a}$ and $R^{3b}$ are taken together with the carbon to which they are attached to form a cycloalkyl moiety;
each $X^7$, $X^8$, $X^9$ and $X^{10}$ is independently $CR^4$;
m and q are independently 0 or 1, provided that at least one of m and q is 1;
each $R^4$ is independently H, hydroxyl, nitro, cyano, halo, $C_1$-$C_8$ perhaloalkyl, carboxy, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
wherein acyl is selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—;
wherein sulfonylamino is selected from the group consisting of —$SO_2NH_2$, —$SO_2$NR-alkyl, —$SO_2$NR-substituted alkyl, —$SO_2$NR-alkenyl, —$SO_2$NR-substituted alkenyl, —$SO_2$NR-alkynyl, —$SO_2$NR-substituted alkynyl, —$SO_2$NR-aryl, —$SO_2$NR-substituted aryl, —$SO_2$NR-heteroaryl, —$SO_2$NR-substituted heteroaryl, —$SO_2$NR-heterocyclic, and —$SO_2$NR-substituted heterocyclic, where R is H or alkyl, or —$SO_2NR_2$, wherein the two R groups are taken together and with the nitrogen atom to which they are attached to form a heterocyclic or substituted heterocyclic ring;
wherein sulfonyl is selected from the group consisting of —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic;
each $R^{8a}$, $R^{8b}$, $R^{8c}$, $R^{8d}$, $R^{8e}$ and $R^{8f}$ is independently H, $C_1$-$C_8$ alkyl, carboxy, carbonylalkoxy, or is taken together with the carbon to which it is attached and a geminal $R^8$ to form a cycloalkyl moiety, provided that at least one of $R^{8a}$, $R^{8b}$, $R^{8c}$, $R^{8d}$, $R^{8e}$ and $R^{8f}$ is other than H;
each $R^{10a}$ and $R^{10b}$ is independently H, substituted or unsubstituted $C_1$-$C_8$ alkyl, halo, hydroxyl, alkoxy, cyano, nitro or $R^{10a}$ and $R^{10b}$ are taken together with the carbon to which they are attached to form a carbonyl moiety or $R^{10a}$ and $R^{10b}$ are taken together with the carbon to which they are attached to form a cycloalkyl moiety; and
Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl.

2. The compound of claim 1, or a salt thereof, wherein at least one of $R^{8c}$, $R^{8d}$, $R^{8e}$, and $R^{8f}$ is other than H.

3. The compound of claim 1, or a salt thereof, wherein at least one of $R^{8e}$ and $R^{8f}$ is other than H.

4. The compound of claim 3, or a salt thereof, wherein $X^7$, $X^8$ and $X^{10}$ are each $CR^4$ where $R^4$ is H, and $X^9$ is $CR^4$ where $R^4$ is substituted or unsubstituted $C_1$-$C_8$ alkyl, perhaloalkyl, or halo.

5. The compound of claim 4, or a salt thereof, wherein $X^9$ is $CR^4$ where $R^4$ is methyl, $CHF_2$, $CH_2F$, $CF_3$, chloro or fluoro.

6. The compound of claim 1, or a salt thereof, wherein at least one of $R^{8a}$, $R^{8b}$, $R^{8c}$, $R^{8d}$, $R^{8e}$ and $R^{8f}$ is $C_1$-$C_8$ alkyl.

7. The compound of claim 6, or a salt thereof, wherein the compound has one or more of the following structural features:
$R^1$ is methyl;
Q is a substituted or unsubstituted pyridyl; and
$X^9$ is $CR^4$ where $R^4$ is halo, a substituted or unsubstituted $C_1$-$C_8$ alkyl, or perhaloalkyl.

8. The compound of claim 1, or a salt thereof, wherein at least one of $R^{8a}$, $R^{8b}$, $R^{8c}$, $R^{8d}$, $R^{8e}$ and $R^{8f}$ is methyl.

9. The compound of claim 1, or a salt thereof, wherein —$R^{8c}R^{8d}$—$R^{8e}R^{8f}$— and the carbons to which they are attached are taken together to form a moiety selected from the group consisting of —CH$_2$—C(H)(CH$_3$)—, —C(H)(CH$_3$)—CH$_2$—, —CH$_2$—C(CH$_3$)(CH$_3$)—, —C(CH$_2$CH$_2$)—CH$_2$— and —CH$_2$—C(CH$_2$CH$_2$)—.

10. The compound of claim 1, or a salt thereof, wherein q is 0, and m is 1.

11. The compound of claim 1, or a salt thereof, wherein each $R^4$ is independently H, hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, thioalkyl, alkylsulfonylamino or acyl.

12. The compound of claim 1, or a salt thereof, wherein each $R^4$ is independently nitro, cyano, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, or carbonylalkylenealkoxy.

13. The compound of claim 1, or a salt thereof, wherein $X^7$, $X^8$ and $X^{10}$ are each $CR^4$ where $R^4$ is H, and $X^9$ is $CR^4$ where $R^4$ is substituted or unsubstituted $C_1$-$C_8$ alkyl, perhaloalkyl or halo.

14. The compound of claim 13, or a salt thereof, wherein $X^9$ is $CR^4$ where $R^4$ is methyl, $CF_3$, $CH_2F$, $CHF_2$, chloro or fluoro.

15. The compound of claim 1, or a salt thereof, wherein each $R^{2a}$, $R^{2b}$, $R^{3a}$, $R^{3b}$, $R^{10a}$ and $R^{10b}$ is independently H, substituted or unsubstituted $C_1$-$C_8$ alkyl, or halo.

16. The compound of claim 15, or a salt thereof, wherein each $R^{2a}$, $R^{2b}$, $R^{3a}$, $R^{3b}$, $R^{10a}$ and $R^{10b}$ is H.

17. The compound of claim 1, or a salt thereof, wherein Q is a substituted or unsubstituted aryl, or substituted or unsubstituted heteroaryl.

18. The compound of claim 17, or a salt thereof, wherein Q is selected from the group consisting of:

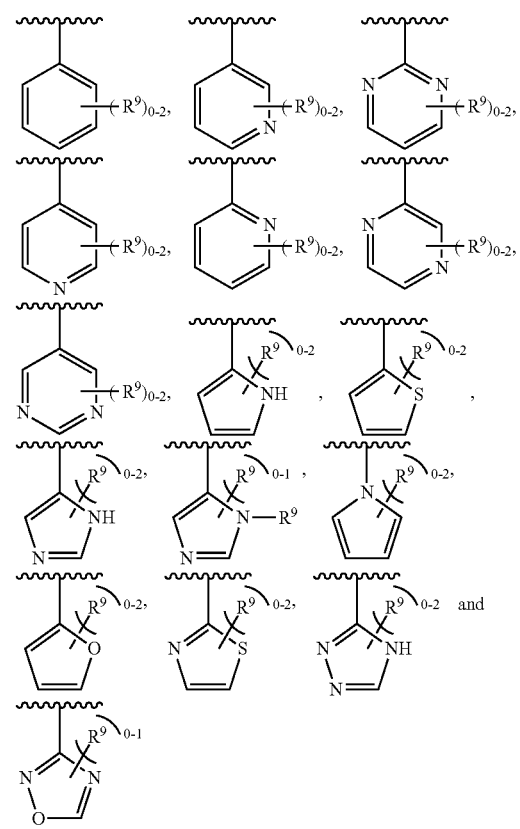

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino.

19. The compound of claim 1, or a salt thereof, wherein Q is substituted or unsubstituted pyridyl, substituted or unsubstituted phenyl, substituted or unsubstituted pyrimidinyl, or substituted or unsubstituted pyrazinyl.

20. The compound of claim 1, or a salt thereof, wherein Q is unsubstituted cycloalkyl, substituted or unsubstituted cycloalkenyl or substituted or unsubstituted heterocyclyl.

21. The compound of claim 20, or a salt thereof, wherein Q is selected from the group consisting of:

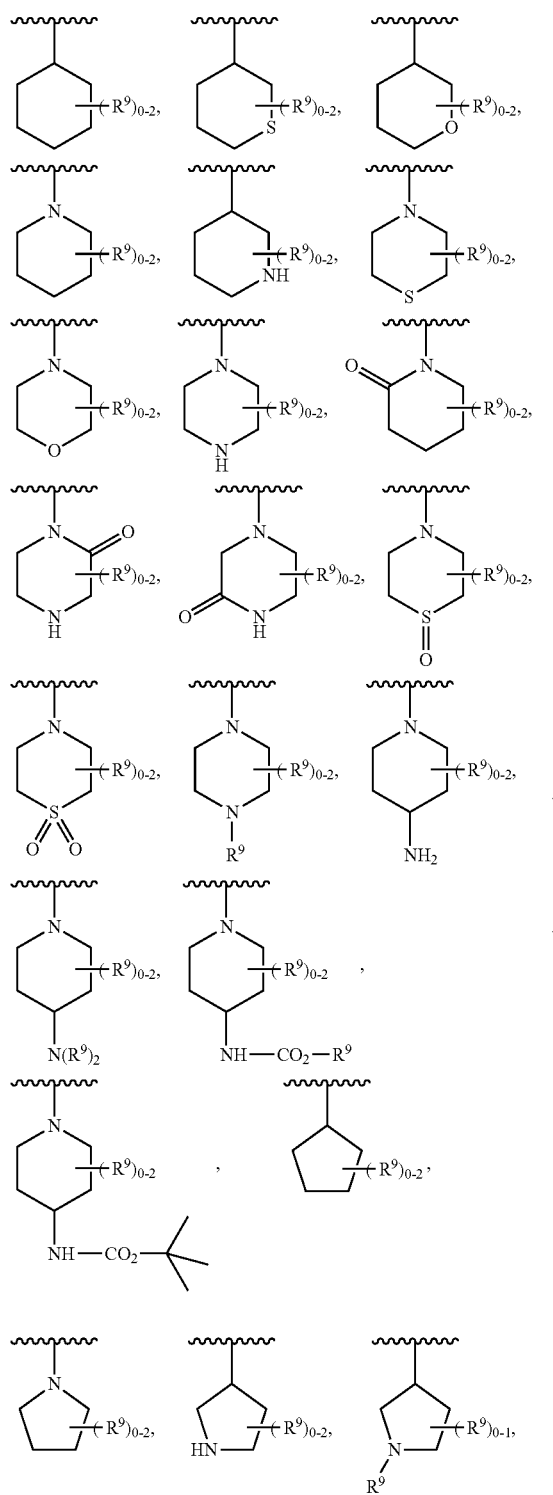

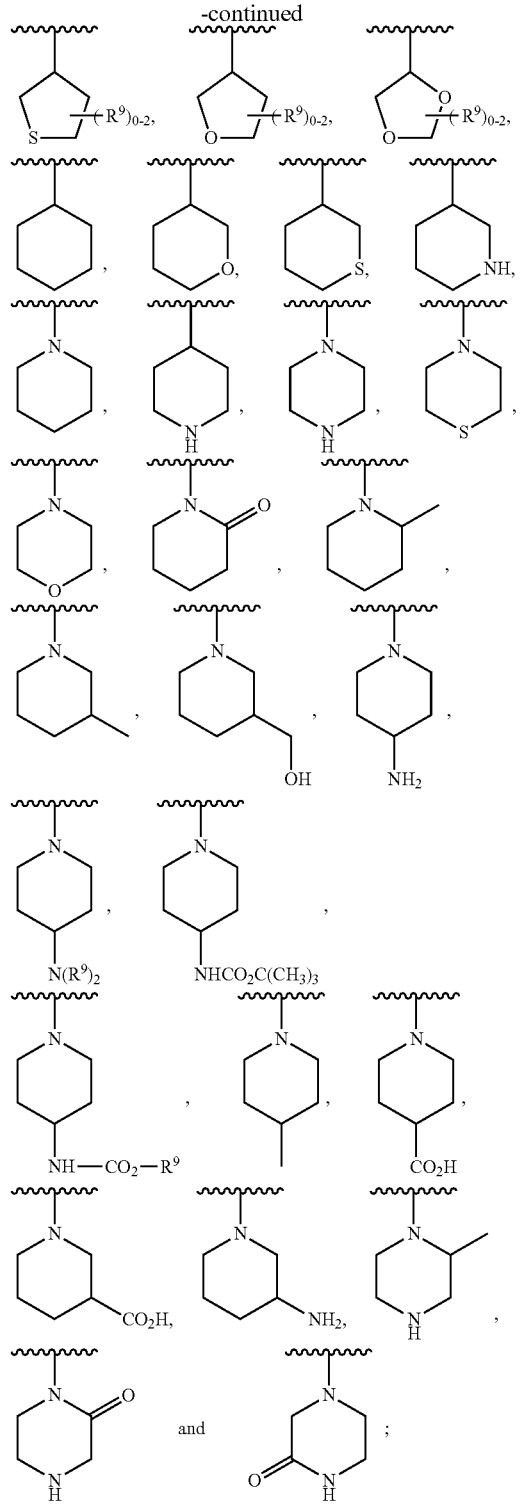

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino.

22. The compound of claim 1, or a salt thereof, wherein:
at least one of $R^{8c}$, $R^{8d}$, $R^{8e}$ and $R^{8f}$ is $C_1$-$C_8$ alkyl;
$X^7$, $X^8$ and $X^{10}$ are each $CR^4$ where $R^4$ is H;
$X^9$ is $CR^4$ where $R^4$ is substituted or unsubstituted $C_1$-$C_8$ alkyl, perhaloalkyl, or halo; and
$R^1$ is substituted or unsubstituted $C_1$-$C_8$ alkyl.

23. The compound of claim 1, or a salt thereof, wherein:
at least one of $R^{8c}$, $R^{8d}$, $R^{8e}$ and $R^{8f}$ is methyl, ethyl or cyclopropyl;
$X^7$, $X^8$ and $X^{10}$ are each $CR^4$ where $R^4$ is H;
$X^9$ is $CR^4$ where $R^4$ is methyl, $CHF_2$, $CH_2F$, $CF_3$, chloro or fluoro; and
$R^1$ is methyl or cyclopropyl.

24. The compound of claim 1, or a salt thereof, wherein the compound has one or more of the following structural features:
$R^1$ is methyl;
Q is a substituted or unsubstituted pyridyl; and
$X^9$ is $CR^4$ where $R^4$ is halo, a substituted or unsubstituted $C_1$-$C_8$ alkyl, or perhaloalkyl.

25. The compound of claim 1, or a salt thereof, wherein the compound has one or more of the following structural features:
$R^1$ is methyl;
Q is a substituted or unsubstituted phenyl; and
$X^9$ is $CR^4$ where $R^4$ is halo, a substituted or unsubstituted $C_1$-$C_8$ alkyl, or perhaloalkyl.

26. The compound of claim 1, or a salt thereof, wherein:
$R^1$ is methyl or ethyl;
each $R^{8c}$, $R^{8d}$, $R^{8e}$ and $R^{8f}$ is independently H or $C_1$-$C_8$ alkyl;
$X^7$ is $CR^4$ where $R^4$ is H;
$X^8$ and $X^{10}$ are independently $CR^4$ where $R^4$ is H or halo;
$X^9$ is $CR^4$ where $R^4$ is halo, methyl, trifluoromethyl or ethyl; and
Q is a substituted or unsubstituted phenyl or a substituted or unsubstituted pyridyl, provided that when $X^9$ is $CR^4$ where $R^4$ is halo, then only one of $X^8$ and $X^{10}$ is $CR^4$ where $R^4$ is halo.

27. The compound of claim 1, or a salt thereof, wherein:
$R^1$ is unsubstituted $C_1$-$C_8$ alkyl;
each of $R^{2a}$, $R^{2b}$, $R^{3a}$, $R^{3b}$, $R^{10a}$ and $R^{10b}$ is H; and
each $R^{8a}$, $R^{8b}$, $R^{8c}$, $R^{8d}$, $R^{8e}$ and $R^{8f}$ is independently H, $C_1$-$C_8$ alkyl, carboxy, carbonylalkoxy, or is taken together with the carbon to which it is attached and a geminal $R^{8(a-f)}$ to form a cycloalkyl moiety.

28. The compound of claim 27, or a salt thereof, wherein —$R^{8c}R^{8d}$—$R^{8e}R^{8f}$— and the carbons to which they are attached are taken together to form a moiety selected from the group consisting of —$CH_2$—$C(H)(CH_3)$—, —$C(H)(CH_3)$—$CH_2$—, —$CH_2$—$C(CH_3)(CH_3)$—, —$C(CH_2CH_2)$—$CH_2$— and —$CH_2$—$C(CH_2CH_2)$—.

29. The compound of claim 27, or a salt thereof, wherein Q is a substituted or unsubstituted aryl, or substituted or unsubstituted heteroaryl.

30. The compound of claim 1, or a salt thereof, wherein the compound is selected from the group consisting of:

| No. | Structure |
| --- | --- |
| 113 | 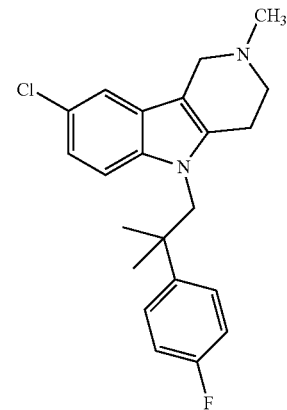 [SMILES: CN1CCc2c(c3cc(Cl)ccc3n2CC(C)(C)c2ccc(F)cc2)C1] |
| 114 | 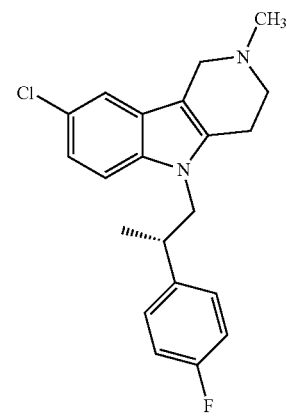 [SMILES: C[C@H](Cn1c2c(c3cc(Cl)ccc31)CN(C)CC2)c1ccc(F)cc1] |
| 115 | 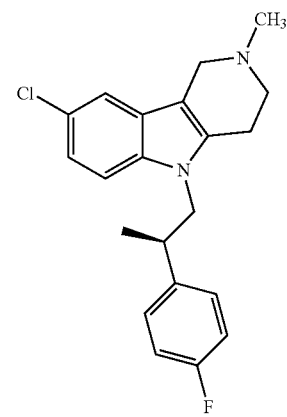 [SMILES: C[C@@H](Cn1c2c(c3cc(Cl)ccc31)CN(C)CC2)c1ccc(F)cc1] |

459
-continued
| No. | Structure |
|---|---|
| 116 | 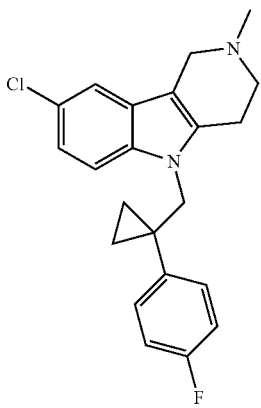 [SMILES: CN1CCc2c(c3cc(Cl)ccc3n2CC2(c3ccc(F)cc3)CC2)C1] |
| 117 | 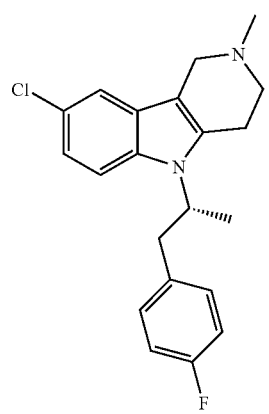 [SMILES: C[C@H](Cc1ccc(F)cc1)n1c2c(c3cc(Cl)ccc31)CN(C)CC2] |
| 118 | 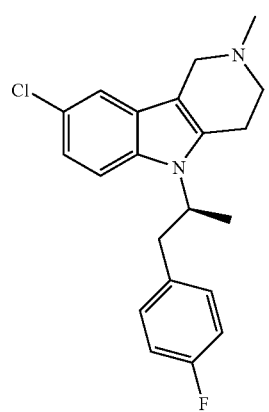 [SMILES: C[C@@H](Cc1ccc(F)cc1)n1c2c(c3cc(Cl)ccc31)CN(C)CC2] |
460
-continued
| No. | Structure |
|---|---|
| 122 | 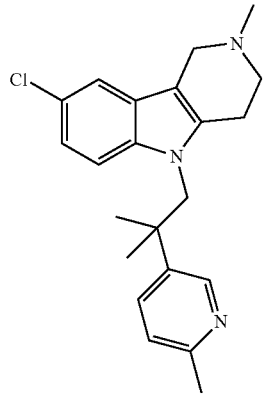 [SMILES: Cc1ccc(C(C)(C)Cn2c3c(c4cc(Cl)ccc42)CN(C)CC3)cn1] |
| 123 | 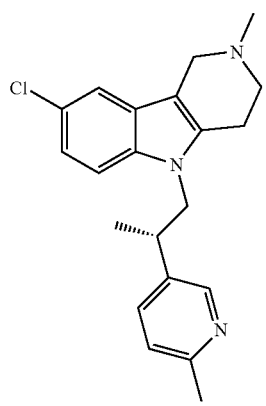 [SMILES: Cc1ccc([C@H](C)Cn2c3c(c4cc(Cl)ccc42)CN(C)CC3)cn1] |
| 124 | 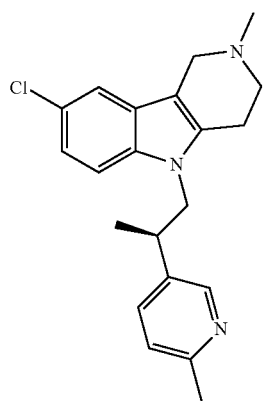 [SMILES: Cc1ccc([C@@H](C)Cn2c3c(c4cc(Cl)ccc42)CN(C)CC3)cn1] |
| 125 | 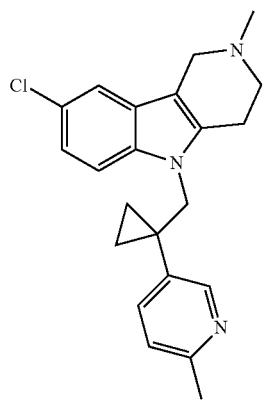 [SMILES: Cc1ccc(C2(Cn3c4c(c5cc(Cl)ccc53)CN(C)CC4)CC2)cn1] |

| No. | Structure |
|---|---|
| 126 | 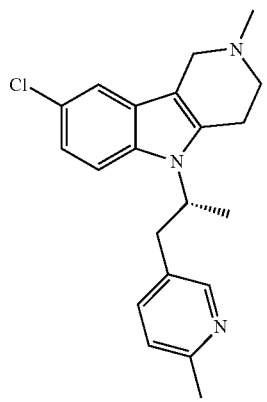 [SMILES: Cc1ccc(C[C@@H](C)n2c3c(c4cc(Cl)ccc42)CN(C)CC3)cn1] |
| 127 | 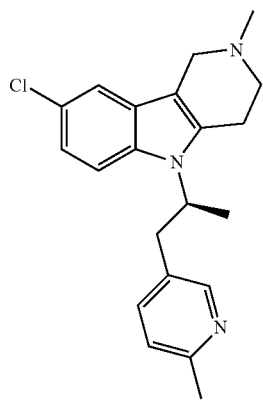 [SMILES: Cc1ccc(C[C@H](C)n2c3c(c4cc(Cl)ccc42)CN(C)CC3)cn1] |
| 131 | 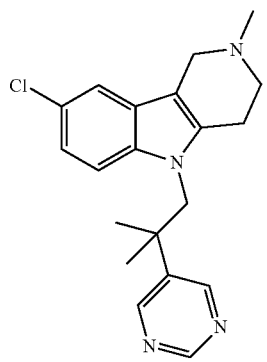 [SMILES: CN1CCc2c(c3cc(Cl)ccc3n2CC(C)(C)c2cncnc2)C1] |
| 132 | 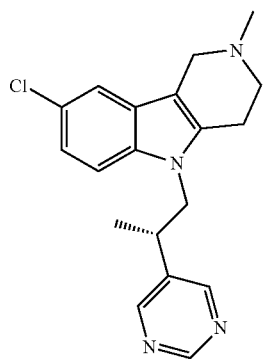 [SMILES: C[C@H](Cn1c2c(c3cc(Cl)ccc31)CN(C)CC2)c1cncnc1] |
| No. | Structure |
|---|---|
| 133 | 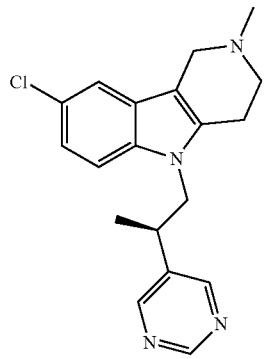 [SMILES: C[C@@H](Cn1c2c(c3cc(Cl)ccc31)CN(C)CC2)c1cncnc1] |
| 134 | 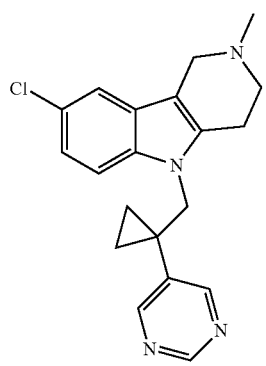 [SMILES: CN1CCc2c(c3cc(Cl)ccc3n2CC2(c3cncnc3)CC2)C1] |
| 135 | 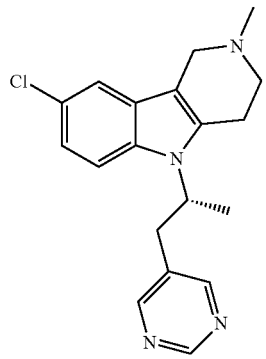 [SMILES: C[C@H](Cc1cncnc1)n1c2c(c3cc(Cl)ccc31)CN(C)CC2] |
| 136 | 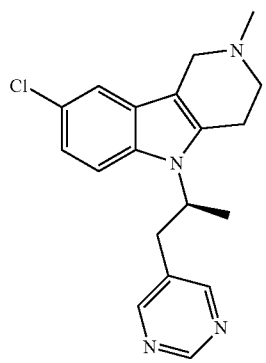 [SMILES: C[C@@H](Cc1cncnc1)n1c2c(c3cc(Cl)ccc31)CN(C)CC2] |

463
-continued
| No. | Structure |
|---|---|
| 381 | 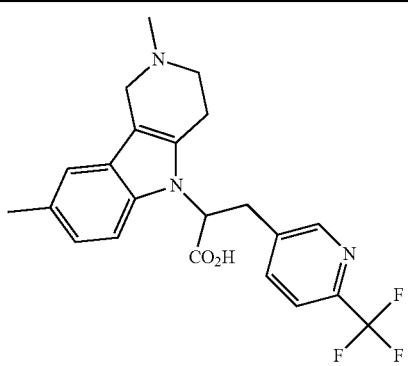 |
| 382 | 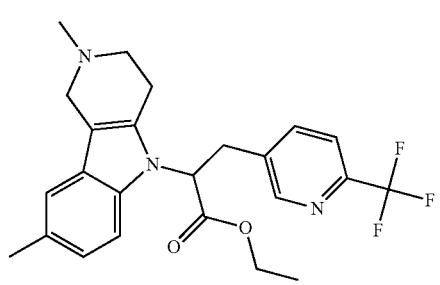 [SMILES: CCOC(=O)C(Cc1ccc(C(F)(F)F)nc1)n1c2c(c3cc(C)ccc31)CN(C)CC2] |
| 383 | 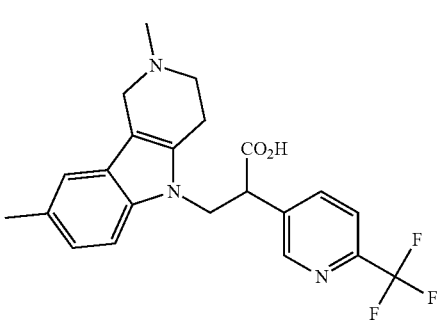 [SMILES: Cc1ccc2c(c1)c1c(n2CC(C(=O)O)c2ccc(C(F)(F)F)nc2)CCN(C)C1] |
| 384 | 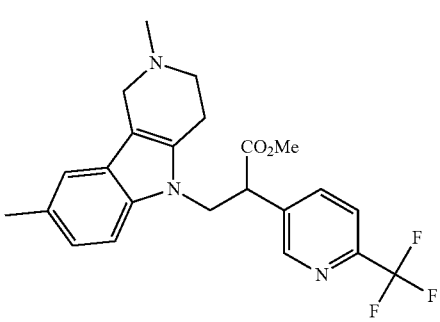 [SMILES: COC(=O)C(Cn1c2c(c3cc(C)ccc31)CN(C)CC2)c1ccc(C(F)(F)F)nc1] |
| 450 | 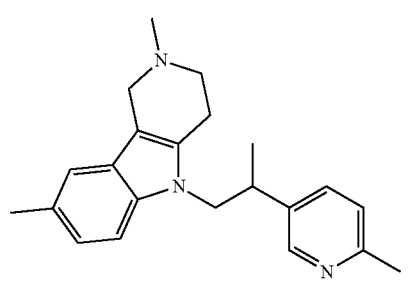 |
464
-continued
| No. | Structure |
|---|---|
| 451 | 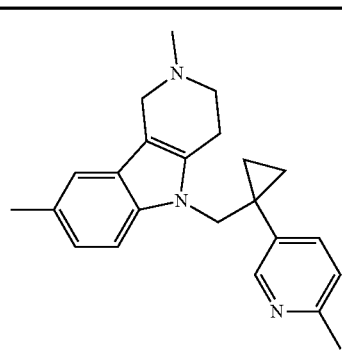 |
| 455 | 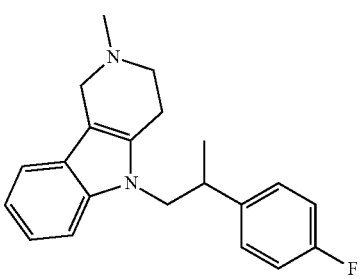 [SMILES: CC(Cn1c2c(c3ccccc31)CN(C)CC2)c1ccc(F)cc1] |
| 456 | 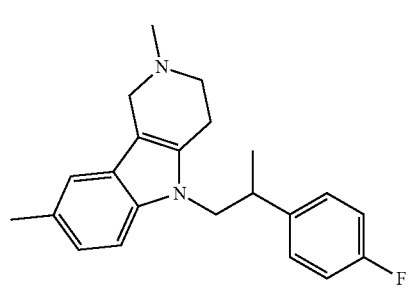 [SMILES: Cc1ccc2c(c1)c1c(n2CC(C)c2ccc(F)cc2)CCN(C)C1] |
| 477 | 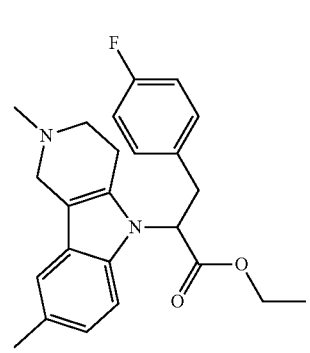 [SMILES: CCOC(=O)C(Cc1ccc(F)cc1)n1c2c(c3cc(C)ccc31)CN(C)CC2] |
| 478 | 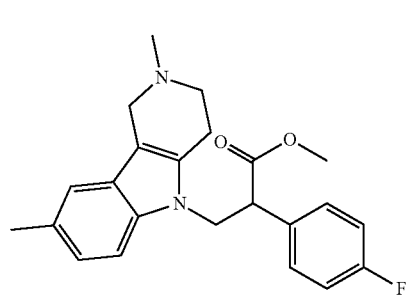 [SMILES: COC(=O)C(Cn1c2c(c3cc(C)ccc31)CN(C)CC2)c1ccc(F)cc1] |

| No. | Structure |
|---|---|
| 479 | 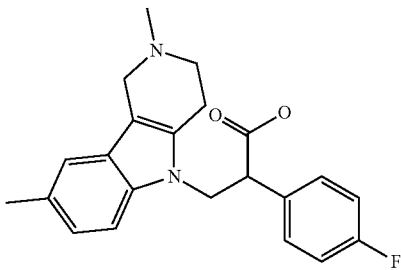 [SMILES: Cc1ccc2c(c1)c1c(n2CC(C(=O)O)c2ccc(F)cc2)CCN(C)C1] |
| 480 | 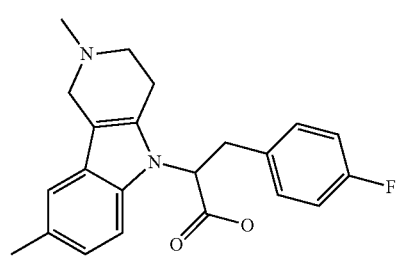 [SMILES: Cc1ccc2c(c1)c1c(n2C(Cc2ccc(F)cc2)C(=O)O)CCN(C)C1] |
| 521 | 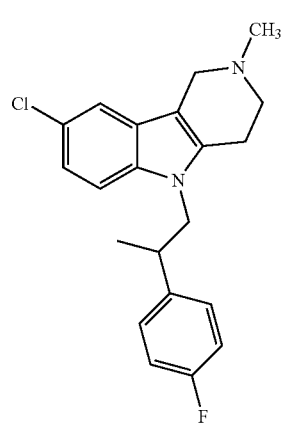 [SMILES: CC(Cn1c2c(c3cc(Cl)ccc31)CN(C)CC2)c1ccc(F)cc1] |
| 522 | 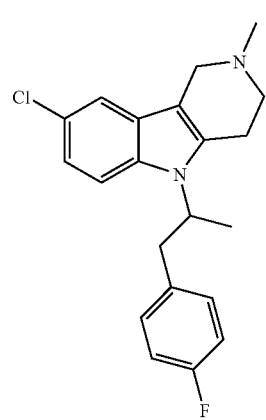 [SMILES: CC(Cc1ccc(F)cc1)n1c2c(c3cc(Cl)ccc31)CN(C)CC2] |
| No. | Structure |
|---|---|
| 524 | 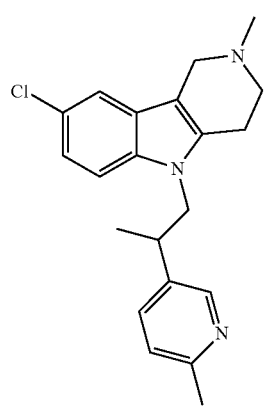 |
| 525 | 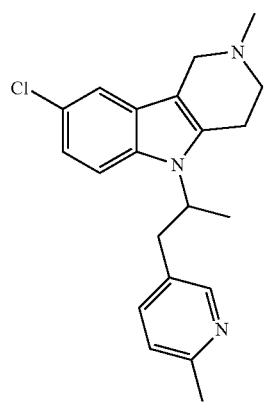 [SMILES: Cc1ccc(CC(C)n2c3c(c4cc(Cl)ccc42)CN(C)CC3)cn1] |
| 527 | 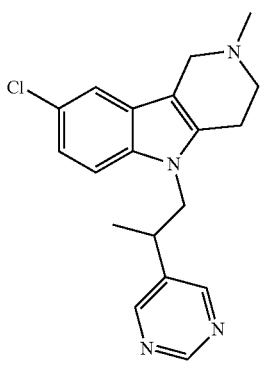 and |
| 528 | 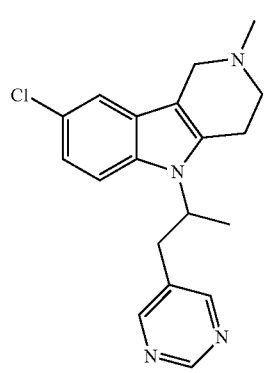 |

31. A compound of the formula (B):

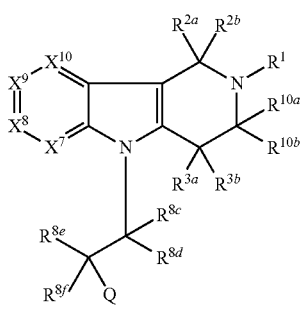

or a salt thereof,
wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
  wherein acyl is selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—;
  wherein sulfonylamino is selected from the group consisting of —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, wherein the two R groups are taken together and with the nitrogen atom to which they are attached to form a heterocyclic or substituted heterocyclic ring;
  wherein sulfonyl is selected from the group consisting of —SO$_2$-alkyl, —SO$_2$—substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic;
each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together with the carbon to which they are attached to form a carbonyl moiety;
each $R^{3a}$ and $R^{3b}$ is independently H, substituted or unsubstituted $C_1$-$C_8$ alkyl, halo, cyano or nitro or $R^{3a}$ and $R^{3b}$ are taken together with the carbon to which they are attached to form a carbonyl moiety;
each $X^7$, $X^8$, $X^9$ and $X^{10}$ is $CR^4$;
each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
  wherein acyl is selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—;
  wherein sulfonylamino is selected from the group consisting of —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, wherein the two R groups are taken together and with the nitrogen atom to which they are attached to form a heterocyclic or substituted heterocyclic ring;
  wherein sulfonyl is selected from the group consisting of —SO$_2$-alkyl, —SO$_2$—substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic;
each $R^{8c}$, $R^{8d}$, $R^{8e}$ and $R^{8f}$ is independently H, $C_1$-$C_8$ alkyl, $C_1$-$C_8$ perhaloalkyl, carboxy, carbonylalkoxy, or is taken together with the carbon to which it is attached and a geminal $R^8$ to form a cycloalkyl moiety, provided that at least one of $R^{8c}$, $R^{8d}$, $R^{8e}$ and $R^{8f}$ is other than H;
each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together with the carbon to which they are attached to form a carbonyl; and
Q is a substituted or unsubstituted aryl or a substituted or unsubstituted heteroaryl.

32. The compound of claim 31, or a salt thereof, wherein at least one of $R^{8e}$ and $R^{8f}$ is other than H.

33. The compound of claim 31, or a salt thereof, wherein at least one of $R^{8c}$, $R^{8d}$, $R^{8e}$ and $R^{8f}$ is $C_1$-$C_8$ alkyl.

34. The compound of claim 31, or a salt thereof, wherein —$R^{8c}R^{8d}$—$R^{8e}R^{8f}$— and the carbons to which they are attached are taken together to form a moiety selected from the group consisting of —CH$_2$—C(H)(CH$_3$)—, —C(H)(CH$_3$)—CH$_2$—, —CH$_2$—C(CH$_3$)(CH$_3$)—, —C(CH$_2$CH$_2$)—CH$_2$— and —CH$_2$—C(CH$_2$CH$_2$)—.

35. The compound of claim 31, or a salt thereof, wherein:
$R^1$ is substituted or unsubstituted $C_1$-$C_8$ alkyl;
$X^7$ is $CR^4$ where $R^4$ is H;
$X^8$ and $X^{10}$ are independently $CR^4$ where $R^4$ is H or halo;
$X^9$ is $CR^4$ where $R^4$ is halo, methyl, CHF$_2$, CH$_2$F, CF$_3$, or ethyl; and
Q is a substituted or unsubstituted phenyl or a substituted or unsubstituted pyridyl, provided that when $X^9$ is $CR^4$ where $R^4$ is halo, then only one of $X^8$ and $X^{10}$ is $CR^4$ where $R^4$ is halo.

36. The compound of claim 31, or a salt thereof, wherein:
$R^1$ is unsubstituted $C_1$-$C_8$ alkyl;
each of $R^{2a}$, $R^{2b}$, $R^{3a}$, $R^{3b}$, $R^{10a}$ and $R^{10b}$ is H; H and
each $R^{8c}$, $R^{8d}$, $R^{8e}$ and $R^{8f}$ is independently H, $C_1$-$C_8$ alkyl, or is taken together with the carbon to which it is attached and a geminal $R^{8(c-f)}$ to form a cycloalkyl moiety.

37. The compound of claim 31, or a salt thereof, wherein:
Q is 3-pyridyl, 4-pyridyl or 6-methyl-3-pyridyl; and
$X^9$ is $CR^4$ where $R^4$ is chloro, methyl, $CHF_2$, $CH_2F$, or $CF_3$.

38. The compound of claim 31, or a salt thereof, wherein
Q is an unsubstituted 3-pyridyl;
$X^9$ is $CR^4$ where $R^4$ is methyl, $CHF_2$, $CH_2F$ or $CF_3$; and
$R^1$ is methyl.

39. A pharmaceutical composition comprising a compound according to claim 1, or a salt thereof, and a pharmaceutically acceptable carrier.

40. A kit comprising a compound according to claim 1, or a salt thereof, and instructions.

41. A pharmaceutical composition comprising a compound according to claim 31, or a salt thereof, and a pharmaceutically acceptable carrier.

42. A kit comprising a compound according to claim 31, or a salt thereof, and instructions.

* * * * *

UNITED STATES PATENT AND TRADEMARK OFFICE
CERTIFICATE OF CORRECTION

PATENT NO.         : 9,034,880 B2
APPLICATION NO.    : 13/791750
DATED              : May 19, 2015
INVENTOR(S)        : David T. Hung et al.

Page 1 of 1

It is certified that error appears in the above-identified patent and that said Letters Patent is hereby corrected as shown below:

On the Title Page:

Under OTHER PUBLICATIONS:

References Cited

At column 2, line 3, delete "Ozadiazoles" and insert -- Oxadiazoles --, therefor.

In the Claims:

At column 453, line 29, in Claim 2, delete "$R^{8e}$," and insert -- $R^{8e}$ --, therefor.

At column 469, line 3, in Claim 36, delete "H; H" and insert -- H; --, therefor.

Signed and Sealed this
Twenty-ninth Day of December, 2015

Michelle K. Lee
*Director of the United States Patent and Trademark Office*